US007595166B2

(12) United States Patent
Zuker et al.

(10) Patent No.: US 7,595,166 B2
(45) Date of Patent: *Sep. 29, 2009

(54) METHODS OF SCREENING MODULATORS OF T2R TASTE RECEPTORS

(75) Inventors: Charles Zuker, San Diego, CA (US); Jon E. Adler, San Diego, CA (US); Nick Ryba, Bethesda, MD (US); Ken Mueller, San Diego, CA (US); Mark Hoon, Kensington, MD (US)

(73) Assignees: The Regents of the University of California, Oakland, CA (US); The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/978,088

(22) Filed: Oct. 25, 2007

(65) Prior Publication Data
US 2008/0108088 A1   May 8, 2008

Related U.S. Application Data

(63) Continuation of application No. 10/962,365, filed on Oct. 7, 2004, now Pat. No. 7,465,550, which is a continuation of application No. 09/510,332, filed on Feb. 22, 2000, now Pat. No. 7,244,584, which is a continuation-in-part of application No. 09/393,634, filed on Sep. 10, 1999, now Pat. No. 6,558,910.

(51) Int. Cl.
G01N 33/53    (2006.01)
G01N 33/567   (2006.01)
C07K 1/00     (2006.01)
C07K 14/00    (2006.01)
C07K 17/00    (2006.01)

(52) U.S. Cl. .................. 435/7.1; 435/7.2; 435/7.21; 530/350

(58) Field of Classification Search .................. None
See application file for complete search history.

(56) References Cited

FOREIGN PATENT DOCUMENTS

| WO | WO 93/16178 A2 | 8/1993 |
| WO | WO 98/13478 A2 | 4/1998 |
| WO | WO 99/42470 A1 | 8/1999 |
| WO | WO 00/38536 A2 | 7/2000 |

OTHER PUBLICATIONS

Adams, et al. "Use of a random human BAC End Sequence Database for Sequence-Ready Map Building; CITBI-E1-2530B8.TF CITBI-E1 *Homo sapiens* genomic clone 2530B8, genomic survey sequence" EMBL Database Entry AQ308694; Accession No. AQ308694 (Dec. 23, 1998).

Adler, et al. "A Novel Family of Mammalian Taste Receptors" Cell vol. 100, pp. 693-702, Mar. 17, 2000.
Brown et al.: "Cloning and characterization of an extracelluar Ca2+—sensing receptor from bovine parathyroid" Letters to Nature 366: 575-580 (Dec. 9, 1993).
Cao et al: "Cloning and localization of two multigene receptor families in goldfish olfactory epithelium" Proc. Natl. Acad. Sci. 95 11987-11992 (Sep. 1998).
Chandrashekar, et al. "T2Rs Function as Bitter Taste Receptors" Cell vol. 100, pp. 703-711, Mar. 17, 2000.
Chaudhari et al: "The Taste of Monosodium Glutamate: Membrane Receptors in Taste Buds" Journal of Neuroscience 16(12): 3817-3826 (Jun. 15, 1996).
Dulac and Axel: "A Novel Family of Genes Encoding Putative Pheromone Receptors in Mammals" Cell 83 195-206 (Oct. 20, 1995).
Herrada and Dulac: "A Novel Family of Putative Pheromone Receptors in Mammals with a Topographically Organized and Sexually Dimorphic Distribution," Cell 90: 763-773 (Aug. 22, 1997).
Hillier et al., "The DNA sequence of human chromosome 7", Nature, pp. 157-164, vol. 424 (2003).
Hoon et al.: "Putative Mammalian Taste Receptors: A Class of Taste-Specific GPCRs with Distinct Topographic Selectivity" Cell 96 541-551 (Feb. 19, 1999).
Hoon and Ryba: "Analysis and Comparison of Partial Sequences of Clones from a Taste-bud enriched cDNA Library," J. Dent Res. 76: 831-838 (Apr. 1997).
Kim et al., "Positional Cloning of the Human Quantitative Trait Locus Underlying Taste Sensitivity to Phenylthiocarbamide", Science, pp. 1221-1225, vol. 299 (2003).
Kinnamon and Margolskee: "Mechanisms of taste transduction" Current Opinion in Neurobiology 6 506-513 (1996).
Lush, I. : "The genetics of tasting mice" Genet. Res. Camb. 53 95-99 (1989).
Matsunami and Buck.: "A Multigene Family Encoding a Diverse Array of Putative Pheromone Receptors in Mammals," Cell 90: 775-784 (Aug. 22, 1997).
McLaughlin et al.: "Gustducin is a taste-cell-specific G protein closely related to the transducins" Letters to Nature 357 563-569 (Jun. 18, 1992).
Naito et al.: "Putative pheromone receptors Ca2+—sensing receptor in Fugu," Proc. Natl. Acad. Sci. 95: 5178-5181 (Apr. 1998).
Ogura, T., et al., *J. Neurosci.*, vol. 17(10), pp. 3580-3587 (1997).
Ryba and Tirindelli: "A New Multigene Family of Putative Pheromone Receptors," Neuron 19: 371-379 (Aug. 1997).
Sambrook, J., et al., "Molecular cloning: a laboratory manual," Second Ed. Cold Spring Harbor Laboratory Press, pp. 17.3-17.44 (1989).
Striem et al.: "Sweet tastants stimulate adenylate cyclase coupled to GTP-binding protein in rat tongue membranes," Biochem 260: 121-126 (1989).
Wamsley, et al. "Human BAC clone GS1-113H23 from 5p15.2, complete sequence" EMBL Database Entry AC003015, Accession No. AC003015 (Oct. 31, 1997).

(Continued)

*Primary Examiner*—Robert Landsman
(74) *Attorney, Agent, or Firm*—Townsend and Townsend and Crew LLP

(57) ABSTRACT

The invention provides nucleic acid and amino acid sequences for a novel family of taste transduction G-protein coupled receptors, antibodies to such receptors, methods of detecting such nucleic acids and receptors, and methods of screening for modulators of taste transduction G-protein coupled receptors.

21 Claims, 81 Drawing Sheets

OTHER PUBLICATIONS

Wong et al.: "Transduction of bitter and sweet taste by gustducin" Letters to Nature 381 796-800 (Jun. 27, 1996).

Adams, M., et al., "Sequence identification of 2,375 Human Brain Genes," *Nature*, vol. 355, pp. 632-634 (Feb. 13, 1992).

Bork, P., et al., "Go hunting in sequence database but watch out for traps," *Trends in Genetics*, vol. 12, pp. 425-427 (1996).

Bork, P., "Powers and pitfalls in sequence analysis: the 70% hurdle," *Genome Research*, vol. 10, pp. 398-400 (2000).

Brenner, S., "Errors in genome annotation," *Trends in Genetics*, vol. 15, pp. 132-133 (1999).

Doerks, T., et al., "Protein annotation: detective work for function prediction," *Trends in Genetics*, vol. 14, pp. 248-250 (1998).

Höfer, D., et al., "Taste receptor-like cells in the rat gut identified by expression of α-gustducin," *Proc. Nat'l. Acad. Sci. USA*, vol. 93, pp. 6631-6634 (Jun. 1996).

Ming, D., et al., "Characterization and solubilization of bitter-responsive receptors that couple to gustducin," *Proc. Nat'l. Acad. Sci. USA*, vol. 95, pp. 8933-8938 (Jul. 1998).

Ming, D., et al., "Blocking taste receptor activation of gustducin inhibits gustatory responses to bitter compounds," *Proc. Nat'l. Acad. Sci. USA*, vol. 96, pp. 9903-9908 (Aug. 2008).

Munzy, D., et al., Database GenEmbl; Accession No. AC006518 (May 1, 1999).

Skolnick and Fetrow, "From genes to protein structure and function: novel applications of computational approaches in the genomic era," *Trends in Biotech*, vol. 18, pp. 34-39 (2000).

Smith and Zhang, "The challenges of genome sequence annotation or The devil is in the details," *Nature Biotechnology*, vol. 15, pp. 1222-1223 (1997).

*Journal of Cookery Science of Japan*, vol. 30(2), pp. 68-73 (1997) (no translation available).

T2R ("GR") Family (hGR=human family members; mGR=mouse family members; rGR=rat family members)
aa=amino acid sequence
nt=nucleotide sequence

| | |
|---|---|
| SEQ ID NO: 1 - hGR01 aa<br><br>MLESHLIIYFLLAVIQFLLGIFTNGIIVVNGIDLIKHRKMAPLDL<br>LLSC<br>LAVSRIFLQLFIFYVNVIVIFFIEFIMCSANCAILLFINELELWLA<br>TWLG<br>VFYCAKVASVRHPLFIWLKMRISKLVPWMILGSLLYVSMICVFHSK<br>YAGF<br>MVPYFLRKFFSQNATIQKEDTLAIQIFSFVAEFSVPLLIFLFAVLL<br>LIFS<br>LGRHTRQMRNTVAGSRVPGRGAPISALLSILSFLILYFSHCMIKVF<br>LSSI<br>KFHIRRFIFLFFILVIGIYPSGHSLILILGNPKLKQNAKKFLLHSK<br>CCQ | SEQ ID NO: 2 - hGR01 nt<br><br>ATGCTAGAGTCTCACCTCATTATCTATTTCTTCTTGCAGTGATACAATT<br>TCTTCTTGGGATTTTCACAAATGGCATCATTGTGGTGAATGGCATTG<br>ACTTGATCAAGCACAGAAAAATGGCTCCGCTGATCTCCTTCTTCTTGT<br>CTGGCAGTTTCTAGAATTCTTCATAGAATTCATCATGTTCTGCAGTTGCAA<br>GATTGTTATCTCTCATAGAATTCATCATGTTCTGCAATGTGCAA<br>TTCTCTTATTTATAAATGAATTGGAACTTGGCTTGCCACATGGCTCGGC<br>GTTTTCTATTGTGCCAAGTTGCCAGCTCGCTCCAGCACCACTCTCATCTG<br>GTTGAAGATGAGGATATCCAAGCTGGTCCTGTTTTCCATAGCAAATATGCAGAGGTTT<br>TGCTATATGTATCTATGATTTGTGTTTTCCATAGCAAATATGCCACAATTCA<br>ATGGTCCCATACTTCCTAAGGAAATTTTCTCCAAAATGCCACAATTCA<br>AAAAGAAGATACACTGGCTATACAGATTTCTCTTTTGTTGCTGAGTTCT<br>CAGTGCCATTGCTTATCTTCCTTTTTGCTGTTTTCCATCTGAGTTTCT<br>CTGGGAGGCACACCCGGCAAATGAGAACACAGTGCCGGCAGCAGGGT<br>TCCTGGCAGGGTGCACCCATCAGCGCGTTGCTGCTATCCCTGTCCTCC<br>TGATCCTTCACTTCTCCACTGCATGATAAAAGTTTTCTCTTCTA<br>AAGTTTCACATCAGAAGGTTCATCTTCTGTTCTTCATCCTTGTGATTGG<br>TATATACCCTTCTGGACACTCTCATCTTAATTTAGGAAATCTAAAT<br>TGAAACAAAAATGCAAAAAGTTCCTCCCCCACAGTAAGTGCTGTCAGTGA |
| SEQ ID NO: 3 - hGR02 aa<br><br>MALSFSAILHIIMMSAEFFTGITVNGFLIIVNCNELIKHRKLMPIQ<br>ILLMCIGMSRFGLQMVLMVQSFFSVFFPLLYVKIIYGAAMMFLWMF<br>FSSISLWFATCLSVFYCLKIISGFTQSCFLWLKFRIPKLIPWLFWEA | SEQ ID NO: 4 - hGR02 nt<br><br>ATGGCCTTGTCTTTTTCAGCTATTCTTCATATTATCATGAGTCAGCAGA<br>ATTCTTCACAGGGATCACAGTAAATGAGTTCTTATCATTGTTAACTGTA<br>ATGAATTGATCAAACATGAGAAAGCTAATGCCAATTCAAATCCTCTTAATG |

FIG. 8

| FWPL*ALHLCVEVDYAKNVEEDALRNTILKKSKTKIKKISEVLLVN LALIFPLAIFVMCTSMLLISLYKHTHRMQHGSHGFRNANTEAHINA LKTVITFFCFFISYFAAFMTNMTFSLPYRSHQFFMLKDIMAAYPSG HSVIIILSNSKFQQSFRRILCLKKKL | TGCATAGGGATGTCTAGATTGGTCTGCAGATGTGTTAATGTACAAAG TTTTTCTCTGTGTTCTTTCCACTCCTTACGTCAGTCAAAATAATTATGGTG CAGCCAATGATGTTCCTTTGGATGTTTTTAGCTCTATCAGCCTATGGTTT GCCACTTGCCTTTCTGTATTTACTGCCTCAAGATTCAGGCTTCACTCA GTCCTGTTTCTTTGTTGAAATTCAGATCCTCTGAGCATTGCATCTGTGTCC TGCTTCGGGAAGCGTTCTGCCTCTGTGAAATGGAAGAGGATGCCCTCAGAAACACACAC GGTAGATTACGCTAAAAATGGAAGAGGATGCCCTCAGAAACACACAC TAAAAAGAGTAAACAAAGATAAAGAAAATTAGTGAAGTGCTTCTTGTC AACTTGGCATTAATATTCCTCAGCACACTCATCGGATGCAACATGGATCTC GTTACTCATCTCTTTACAAGCACACTCATCGGATGCAACATGGATCTC ATGGCTTTAGAAATGCCAACACAGAAGCCCATATAAATCATTAAAAACA GTGATAACATTCTTTTGCTCTTCTTATTCTTTATTTGCTGCCTTCATGAC AAATATGACATTAGTTACCTTACAGAAGTCACCAGTTCTTTATGCTGA AGGACATAATGGCAGCATATCCCTCGGCCACTCGGTTATAATAATCTTG AGTAATTCTAAGTTCCAACAATCATTTAGAAGAATTCTCTGCCTCAAAAA GAAACTATGA |
| SEQ ID NO: 5 - hGR03 aa MMGLTEGVFLILSGTQFTIGILVNCFIELVNGSSWFKTKRMSLSDF IITI LALLRIILLCIILTDSFLIEFSPNTHDSGIIMQIIDVSWTFTNHLS IWLA TCLGVLYCLKIASFSHPTFWLKWRVSRVWVMLLGALLLSCGSTA SLIN EFKLYSVFRGIEATRNVTEHFRKKRSEYLIHVLGTIMWYLPPLIVS LASY SLLIFSLGRHTRQMLQNGTSSRDPTTEAHKRAIRIILSFFLFLLY FLAF LIASFGNFLPKTKMAKMIGEVMTMFYPAGHSFILILGNSKLKQTFV VMLR CESGHLKPGSKGPIFS | SEQ ID NO: 6 - hGR03 nt ATGATGGGACTCACCGAGGGGTGTTCCTGATTCTGTCTGGCACTCAGTT CACACTGGGAATTCGTCAATGTTCATTGAGTGGTCAATGGTAGCA GCTGGTTCAAGACCAAGAGAATGTCTTGTCTGACTTCATCATCACCACC CTGGCACTCTTGAGGATCATTCGTGTGTATTATTCTTGACTGATAGTTT TTAATAGAATTCTCTCCAACACATGATTCAGGAGTAATAATGCAAA TTATTGATGTTTCCTGGACATTACAAACCATCTGAGCATTTGGCTTGCC ACCTGTCTTGGTGTCCTCTGCCTCAAGTGGAGAGTTTCTAGGGTGATGGATGC CACATTCCTCTGGCACTGCACTGCTTTACTCGTGGAGTACCGCATCTCTGATCAAT TGTGGGTGCACTGCACTGCTCTATTCTGTCTTTAGGGAATTGAGGCCACCAGGAATGT GAGTTAAGCTCATTCATTTCAGAAAGAGGAGTGAGTATTATCCATGTTC GACTTGAACACTTCAGAAAGAAGAGGAGTGAGTATTATCCATGTTC TTGGGACTCTGTGGATCCTGCCTCCCTAATTGTGTCCTGGCCTCCTAC TCTTTGCTCATCTTCCCCAGAGATCTTCCCGGGAGGCACACCAGGTGCAAAA TGGGACAAGCTCCAGAGATCTTCCCAACCACTGAGGCCCACAAGAGGGCCATCA |

FIG. 8

| | GAATCATCCTTCCTTCTTCTTCTCTTCTTCTTCTTACTTACTTCTTGCTTTC<br>TTAATTGCATCATTTGGTAATTCCTACCAAAAACCAAGATGCTAAGAT<br>GATTGGCGAAGTAATGACAATGTTTATCCTGCTGCCACTCATTTATTC<br>TCATTCGGGACAGTAAGCTGAAGCTGAAGCAGACATTTGTAGTGATGCTCCGG<br>TGTGAGTCTGGTCATCTGAAGCCTGGATCCAAGGGACCCATTTTCTCTTA<br>G |
|---|---|
| SEQ ID NO: 7 - hGR04 aa<br><br>MLRLFYFSAIIASVILNFVGIIMNLFITVVNCKTWVKSHRISSSDR<br>ILFS<br>LGITRFLMLGLFLVNTIYFVSSNTERSVYLSAFFVLCFMFLDSSSV<br>WFVT<br>LLNILYCVKITNFQHSVFLLLKRNISPKIPRLLLACVLISAFTTCL<br>YITL<br>SQASPFPELVITRNNTSFNISEGILSLVVSLVVSLQFIINVTSA<br>SLLI<br>HSLRRHIQKMQKNATGFWNPQTEAHVGAMKLMVFLLLYIPYSVAT<br>LVQY<br>LPFYAGMDMGTKSICLIFATLYSPGHSVLIIITHPKLKTTAKKILC<br>FKK | SEQ ID NO: 8 - hGR04 nt<br><br>ATGCTTCGGTTATTCTATTCTCTGCTATTATTGCCTCAGTTATTTTAAA<br>TTTGTAGGAATCATTATGAATCTGTTTATTACAGTGGTCAATTGCAAAA<br>CTTGGGTCAAAAGCCATAGAGAATCTCCTCTTCTGATAGGATTCTGTTCAGC<br>CTGGGCATCACCAGGTTCTTATGCTGGGACTATTTCTGGTGAACACCAT<br>CTACTTCGTCTCTTCAAATACGAAAGGTCAGTCTACCGTCTGCTTTT<br>TTGTGTGTGTTTCATGTTTTTGGACTGTGAAGATTACTAACTTCCAACACTCAGT<br>TTGCTCAATATCTTGTACTGTGAAGAATATCCCCAAAGATCCCCAGGCTGCTGC<br>GTTTCTCCTGCTGAAGCGGAATATCTCCTTCACCACTTGCTGACTACGAGAATAACACATC<br>TGGCCTGTGTGCTGATTTCTGCTTCCGACTTGTCTTAGTGGTTCTTTGGTCTTGA<br>AGCCAGGCATCACCTTTTCGAGGGCATCTGCATTAAGTGACTTCTGCTTCCTGCTAATA<br>ATTAATATCAGTGAGGGCATCTCATCATTAAGTGACTTCTGCTTCCTGCTAATA<br>GCTCATCTCTGAGGAGACATATACAGAAGATGCAGAAAAATGCCACTGGTTT<br>CACTCCTGAGGAGACATATACAGAAGATGCAGAAAAATGCCACTGGTTT<br>CTGGAATCCCAGACGGAAGCTCATGTAGGTGCTATGAAGCTGATGGTCT<br>ATTTCCTCATCCTCCTTTATTCCATATTCAGTTGCTACCCTGGTCCAGTAT<br>CTCCCCCTTTATTGCAGGAATGGATTGGGACCAAATCCATTTGTCTGAT<br>TTTTGCCACCCTTTACTCTCCAGGACATTCTGTTCTCATTATCACAC<br>ATCCTAAACTGAAAACAACAGCAAAGAAGATTCTTTGTTTCAAAAAATAG |
| SEQ ID NO: 9 - hGR05 aa<br><br>MLSAGLGLLMLVAVVEFLIGLIGNGSLVVWSFREWIRKFNWSSYNL<br>IILG<br>LAGCRFLLQWLIILDLSLFPLFQSSRWLRYLSIFWLVSQASLWFA<br>TFLS<br>VFYCKKITTFDRPAYLWLKQRAYNLSLWCLLGYFIINLLLTVQIGL | SEQ ID NO: 10 - hGR05 nt<br><br>ATGCTGAGCGCTGGCCTAGGACTGCTGATGCTGGTGGCAGTGGTTGAATT<br>TCTCATCGGTTTAATTGGAAATGGAAGCCTGGTGGTCTGGAGTTTAGAG<br>AATGGATCAGAAAATTCAACTGGTCCTCATATAACCTCATTATCCTGGGC<br>CTGGCTGGCTGCCGATTTCTCCTGCAGTGGCTGATCATTTGGACTTAAG<br>CTTGTTTCCACTTTTCCAGAGCAGCCGTTGGCTTCGCTATCTAGTATCT |

FIG. 8

| | |
|---|---|
| TFYH<br>PPQGNSSIRYPFESWQYLYAFQLNSGSYLPLVFLVSSGMLIVSLY<br>THHK<br>KMKVHSAGRRDVRAKAHITALKSLGCFLLLHLVYIMASPFSITSKT<br>YPPD<br>LISVFIWETLMAAYPSLHSLILIMGIPRVKQTCQKILWKIVCARRC<br>WGP | TCTGGGTCCTGGTAAGCCAGGCCAGTCAGCTTATGGTTTGCCACCTTCCTCAGT<br>GTCTTCTATTGCAAGAAGATCACGAACCTTCGATGCCCGCTACTTGTG<br>GCTGAAGCAGAGGGCCTATAACCTGAGTCCTGTGCCTTCTGGGCTACT<br>TTATAATCAATTTGTTACTTACAGTCCAAATTGGCTTAACATTCTATCAT<br>CCTCCCAAGGAAACAGCAGCATTCGGTATCCCTTGAAAGCTGGCAGTA<br>CCTGTATGCATTTCAGCTCAATTCAGGAAGTTATTTGCTTTAGTGGTGT<br>TTCTTGTTTCCTCTGGGATGCTGATTGTCTCTTTGTATACACACACAAG<br>AAGATGAAAGTCCATTCAGCTGGTAGGAGGATGTCCGGGCAAGGCTCA<br>CATCACTGCGCTGAAGTCCTTGGCGTCTTCCTCCTTACTTCACCTGTTT<br>ATATCATGGCCAGCCCCTTCTCCATCACCTCCAAGACTTATCCTCCTGAT<br>CTCACCAGTGTCTTCATCTGGGAGACACTCATGGCAGCCTATCCTTCTCT<br>TCATTCTCTCATATTGATCATGGGGATTCCTAGGGTGAAGCAGACTTGTC<br>AGAAGATCCTGTGGAAGACAGTGTGTCTCGGAGATGCTGGGGCCCATGA |
| SEQ ID NO: 11 - hGR06 aa<br>MLAAALGLIMPIAGAEFLIGLVGNGVPVVCSFRGWVKKM*GVPINS<br>HDSG<br>K*PLSPTQADHVGHKSVSTFPEQWLALLS*CLRVLVSQANM*FATF<br>FSGF<br>CCMEIMTFVXXXXXXXXXXXXXXXXXXXXLLVSFKITFYSALVGW<br>TL*KPLIGNSNILHPILNLLFI*IAVQ*RRLIAICDVSVPLVFL*R<br>HHRKMEDHTAVRRRLKPRXXXXXXXXXXXXXX<br>LYMVSALARHFSMTF*SPSDLTILAISATLMAVYTSFPSIVMVMRN<br>QTCQRIL*EMICTWKS | SEQ ID NO: 12 - hGR06 nt<br>ATGTTGGCGGCTGCCCTAGGATTGCTGATGCCCATTGCAGGGGCTGAATT<br>TCTCATTGGCCTGGTTGGAAATGGAGTCCCTGTGGTCTGCAGTTTTAGAG<br>GATGGGTCAAAAAATGTAAGGAGTCCCTATAAATTCTCATGATTCTGGT<br>AAGTAGCCACTTTCCTACTCAGGCCGATCATGTTGGCTTACTATCTTAATGTCTGT<br>TTCCACTTTCCCAGAGCAGTGGTTGGCTTGCCCACTTTCTTCAGTGGCTTC<br>TCCTGGTAAGCCAGGCCAACATGTAGTTTGCCGCTGACTTCTTGTAGCTGAAA<br>TGCTCATGGAGATCATGACCTTTGTCCAGTGGTCTTTAAAACCCTAACAGGAAACAGCA<br>AGACTGGGTTTTGTTTTTGCTGGACCCTTAAAACCCTAACAGGAAACAGCA<br>ACATCCTGCATCCCATTTAAATCTGTATTTTATAGATTGCTGTCCAG<br>TGAAGGAGACTGATTGCTATTTGTGATGTTTCTGTTCCACTTGTCTTTT<br>GTAAACATACCAAGGTGCTCATCGCTCGAAGATGGAGACCACCAGCTGTCAGGAGGAGGC<br>TCAAACCAAGGTGCTCATCGCTCGAACTTCCCCCTTTACATGGTTTCTG<br>CCTTGGCCAGACACTTTTCCATGACCTTCATGCGTGTTTATACTTCATTCCGTC<br>ATTCTTGCCATCCTCGCAACTCATGCTGTTTATACTTCATTCCGTC<br>TATTGTAATGTTATGAGAATCAGACTTGTCAGAGAATTCTGTAGGAGA<br>TGATATGTACATGGAAATCCTAG |

FIG. 8

| SEQ ID NO: 13 - hGR07 aa | SEQ ID NO: 14 - hGR07 nt |
|---|---|
| MADKVQTTLFLAVGEFSVGILGNAFIGLVNCMDWVKKRKIASIDL ILTS LAISRICLLCVILLDCFILVLYPDVYATGKEMRIIDFFWTLTNHLS IWFA TCLSIYYFFKIGNFFHPLFLMWKRIDRVISWILLGCVVLSVFISL PATE NLNADFRFCVKAKRKTNLTWSCRVNKTQHASTKLFLNLATLLPFCV CLMS FFLLILSLRRHIRRMQLSATGCRDPSTEAHVRALKAVISFLLLFIA YYLS FLIATSSYFMPETELAVIFGESIALIYPSSHSFILILGNNKLRHAS LKVI WKVMSILKGRKFQQHKQI | ATGGCAGATAAAGTGCAGACTACTTTATTGTTCTTAGCAGTTGGAGAGTT TTCAGTGGGATCTTAGGGAATGCATTCATTGGATTGGTAAACTGCATGG ACTGGGTCAAGAAGAGAAATGCCTCCATTGATTGATTAATCCTCACAAGT CTGGCCATATCCAGAATTGTCTATTGTGCGTAATACTATTAGATTGTTT TATATTGGTGCTATATCCAGAGTGCTATGCCACTGGTAAAGAAATGAGAA TCATTGACTTCTTCTGGACACTAACCAATCATTAAGTATCTGGTTTGCA ACCTGCCTCAGCATTACTATTTCTTCAAGATAGGTAATTTCTTTCACCC ACTTTCCTCTGGATGAAGTGGAGAATTGACAGGGTGATTCCTGGATTC TACTGGTCGTGGTTCTCTGTCTTTGTGTTTATTAGCCTTCCAGCCACTGAG AATTTGAACGCTGATTTCAGGTTTTGTGTGAAGCAAAGAAGAAAACAAA CTTAACTTGGAGTTGCAGAGTAAATAAAACTCAACATGCTTCTACCAAGT TATTTCTCCTTTGATCCTCCCCGGGAGACATATCAGGCAATGCAGCT CAGTGCCACAGGGTGCAGAGACCCAGCTCCTCCTCTTTATGCCCATGTGAGAGCCC TGAAAGCTGTCATTTCCTTGCCACCTCCAGCTACTTTATGCCAGAGACGAATTAGCTGT TTTCATTGCCACCTCCAGCTACTTTATGCCAGAGACGAATTAGCTGT GATTTTTGGTGAGTCCATAGCTCATACCCCTCAAGTCATCATTCATTTA TCCTAATACTGGGAACAATAAAATTAAGACATGCATCTCTAAAGGTGATT TGGAAAGTAATGTCTATTCTAAAGGAAGAAAATTCCAACAACATAAACA AATCTGA |
| SEQ ID NO: 15 - hGR08 aa | SEQ ID NO: 16 - hGR08 nt |
| MFSPADNIFILILTGEFILGILGNGYIALVNWIDWIKKKKISTVDY ILIN LVIARICLISVMVVNGIVIVLNPDVYITKNKQQIVIFTFWTFANYLN MWIT TCLNVFYFLKIASSSHPLFLWLKWKIDMVVHWILLGCFAISLLVSL IAAI VLSCDYRFHAIAKHKRNITEMEHVSKIPYFEPLTLFNLFAIVPFIV SLIS FFLLVRSLWRHTKQIKLYAIGSRDPSTEVHVRAIKTMTSFIFFFFL | ATGTTCAGTCCTGCAGATAACATCTTTATAATCCTAATAACTGGAGAATT CATACTAGGAATATTGGGAATGGAATGGATACATTGCACTAGTCAACTGGATTG ACTGGATTAAGAGAGAAAAAGATTTCCACAGTTGACTACATCCTTACCAAT TTAGTTATCGCCAGATTGTTTGATCAGTGAATGTTGAAATGGCAT TGTAATAGTACTGAACCCAGATGTTTATACAAAAAATAAACAACAGATAG TCATTTTTACCTTCTGGACATTGCCAACTACTTAAATATGGATTACC ACCTGCCTTAATGTCTTCTATTTTCTGAAGATAGCCAGTTCCTCCATCC ACTTTTTCTTGGCTGAAGTGGAAATTGATATGGTGGTCGACTGGATCC TGCTCGGGATGCTTTGCCATTCCTTGTTGGTGGTCAGCCTTATAGCAGCAATA |

FIG. 8

| YYIS | GTACTGAGTTGTGATTATAGTTTCATGCAATTGCCAATACATAAAGAAA |
| --- | --- |
| SILMTFSYLMTKYKLAVEFGEIAAILYPLGHSLILIVLNNKLRQTF | CATTACTGAAATGTTCATGTGAGTAAAATACCATACTTGAACCCTTGA |
| VRML | CTCTCTTAACCTGTTGCAATTGTCCCATTATTGTCACTGATATCA |
| TCRKIACMI | TTTTCCTTTAGTAAGATCTTTATGGAGACATACCAAGCAAATAAACT |
| | CTATGCTACCGGCAGTAGAGACCCCAGCACAGAAGTTCATGTGAGAGCCA |
| | TTAAAACTATGACTTCATTATCTTCTTTTTTTCCTATACTATATTCT |
| | TCTATTTTGATGACCTTTAGCTATCTTATGACAAAATACAAGTTAGCTGT |
| | GGAGTTGGAGAGATTGCAGCAATTCTCTACCCCTTGGGTCACTCACTTA |
| | TTTTAATTGTTTAAATAAACTGAGGCAGACATTTGTCAGAATGCTG |
| | ACATGTAGAAAAAATTGCCTGCATGATATGA |

SEQ ID NO: 18 - hGR09 nt

| SEQ ID NO: 17 - hGR09 aa | ATGCCAAGTGCAATAGAGGCAATATATATATATTTAATTGCTGGTGAATT |
| --- | --- |
| MPSAIEAIYILLIAGELTIGIWGNGFIVLVNCIDWLKRRDISLIDI | GACCATAGGGATTGGGGAAATGGATTCATTGTACTAGTTAACTGCATTG |
| ILIS | ACTGGCTCAAAAGAAGAGATATTTCCTTGATTGACATCATCCTGATCAGC |
| LAISRICLLCVISLDGFMLLFPGTYGNSVLVSIVNVVWTFANNSS | TTGGCCATCTCCAGAATCTGTCTGCTGTGTGTAATATCATTAGATGGCTT |
| LWFT | CTTTATGCTGCTCTTTCCAGGTACAATGGCAATAATGCGTGCTAGTAAGCA |
| SCLSIFYLLKIANISHPFFWLKLKINKVMLAILLGSFLISLIISV | TTGTGAATGTGTCTGGACATTTGCCAATAATTCAAGTCTCTGTTTACT |
| PKND | TCTTGCCTCAGTATCTTCTATTTACTCAAGATCAACAAGGTCATGCTTGCGCATTC |
| DMWYHLFKVSHEENITWKFKVSKIPGTFKQLTLNLGVMVPFILCLI | ATTTTCTTCTGGCTGAAGCTAAAGATCAACAAGGTCATGCTTGCGATTC |
| SFFL | TCTGGGGTCCTTCTTCCTTATCCTTTTCAAGTCAGTCATGTTCCAAAGAATGAT |
| LLFSLVRHTKQIRLHATGFRDPSTEAHMRAIKAVIIFLLLIVYYP | GATATGTGGTATCACCTTTTCAAGTCAGTCATGAAGAAAACATTACTTG |
| VFLV | GAAATTCAAAGTGAGTAAAATTCCAGTACTTCAAACAGTAACCCTGA |
| MTSSALIPQGKLVLMIGDIVTVIFPSSHSFILIMGNSKLREAFLKM | ACCTGGGGGTGATGGTCCCTAGTAGACACAGAGGCCACATGAGGCATGCTAC |
| LRFV | TTACTTTTCTCCCTAGTAGACACAGAGGCCACATGAGGCCATAAAGGCAG |
| KCFLRRRKPFVP | AGGGTTCAGAGACCCAGTGCCTCCTCCTCGATTCCTCAGGAAAATTAGTGTTTGATGATTGG |
| | TGATCATCTTTCTGCCTCCTCCTCGATTCCTCAGGAAAATTAGTGTTTGATGATTGG |
| | ATGACCTCTAGCGCTCAGTCATTTCCCATCAAGCCATTCATTCATTCTAATTA |
| | TGACATAGTAACGTCATTTCCCATCAAGCCATTCATTCATTCTAATTA |
| | TGGGAAATAGCAAGTTGAGGGAAGCTTTTCTGAAGATGTTAAGATTTGTG |
| | AAGTGTTTCCTTAGAAGAAGAGAAAGCCTTTGTTCCATAG |

FIG. 8

SEQ ID NO: 19 - hGR10 aa

MLRVEGIFIFVVVSESVFGVLGNGFIGIVNCIDCAKNKLSTIGFI
LTGL
AISRIFLLWLIITDGFIQIFSPNIYASGNLIEYISYFWVIGNQSSM
WFAT
SLSIFYFLKIANFSNYIFLMLKSRTNMVLPFMIVFLLISSLLNFAY
IAKI
LNDYKTIKNDIVWDLNMYKSEYFIKQILLNLGVIFFFTLSLITCIFL
IISL
WRHNRQMQSNVTGLRDSNTEAHVKAMKVLISFIILFILYFIGMAIE
ISCF
TVRENKLLLMFGMTTAIYPWGHSFILILGNSKLKQASLRVLQQLK
CCEK
RKNLRVT

SEQ ID NO: 20 - hGR10 nt

ATGCTACGTGTAGTGGAAGCCATCTTCATTTTTGTTGTAGTAGTGAGTC
AGTGTTTGGGGTTTGGGGAATGGATTATTGGACTTGTAAACTGCATTG
ACTGTGCCAAGAATAGTTATCTACGATTGGATAATAATTACAGATGGATTAT
GCTATTTCAAGAATATTCTCCAAATATATATGCCTCCGTAACCAAGTATGGTTTTGCCACC
ACAGATATTCTCCAAATATATATGCCTCCGTAACCAAGTATGGTTTTGCCACC
TTAGTTACTTTTGGGTAATTGTAATCAATCAAGATGTGTTTGCCACC
AGCCCTAGCATCTTCATTTCTGAAGATAGCAAATTTTTCCCTTCATGATAG
ATTTCTGGTTGAAGAGCAGAACAAATATGGTTTCTCCCTTCATGATAG
TATTCTTACTTATTTCATCGTTACTACTTAATTTGCATACATTGCGAAGATT
CTTAATGATTATAAAACGAAGAATGACACAGTCTGGGATCTCAACATGTA
TAAAAGTGAATACTTATATTAAACAGATTTTGCTAAATCTGGAGTCATTT
TCTTCTTTACACTATCCCTAATTACATGTATTTTTTTTAATCATTCCCTT
TGGAGACACACAGAAGCTCATGTGAAGGCAGATGCAATGCAATGTGAAGTGACGATTGAGAGACTC
CAACACAGAAGCTCATGTGAAGGCAATGAAAGTTTGATATCTTTCATCA
TCCTCTTATCTGTATTTATAGGCATGCCCATAGAAATATCATGTTTT
ACTGCGAGAAAACAAACTGCTGCTTATCTTATTCCTTAATTCTAGAAACAGCAAGC
CATCATCCCTGGGTCACTCATTTATCTCATTTCTTAGAAACAGCAAGC
TAAAGCAAGCCTCTTTGAGGGTACTGCAGCAATTGAAGTGCTGTGAGAAA
AGGAAAAAATCTCAGAGTCACATAG

SEQ ID NO: 21 - hGR12 aa

MSSIWETLFRILVV*FIMGTVGN*FIVIVNIID*IRN*KVSLIDF
ILNC
LAISRICFL*ITTLATSFNIGYEKMPDSKNLAVSFDILWTGSSYFC
LSCT
TCLSVFYFLKVANFSNPIFLWMKWKIHKVLLFIVLEATISFCTTSI
LKEI
IINSLI*ERVTIKGNLTFNYMDTMHDFTSLFLLQMFILPFVETLA
SILL
LILSLMWSHTRQMKLHGIYSRDPSTEAHVKPIKAIISFLLLFIVHYF
ISII

SEQ ID NO: 22 - hGR12 nt

ATGTCAAGCATTTGGGAGACACTGTTTATAAGAATTCTTGTAGTGTAATT
CATAATGGGACTGTGGGAAATTGATTCATTGTATTGGTTAATATCATTG
ACTGAATCAGGAACTGAAAGTCTCCCTGATTGATTTATTCTCAACTGC
TTGGCCATCTCAGGATATGTTCCTGAGATAACAATTTAGCTACCTC
TTTCAATATAGCTATGAGAAAATGCCTGATTCTAAGAATCTTGCAGTAA
GTTTTGACATTCTCTGGACAGATCCAGCTATTTCTGCCTGTCCTGTACC
ACTTGCCTCAGTCTCTTCTATTTCCTCAAGGTAGCCAACTTCTCCAATCC
CATTTTCCCTGGATGAAATGGAAAATTCACAAGGTGCTTCTTCTTTATTG
TACTAGAGGCAACGATCTCTTTCTGCCACACTTCCATTCCATTCCATTCCA
ATAATTAATAGTTAATCTAAGAACGGGTAACAATAAAAGGCAACTTGAC

FIG. 8

| *LTLACPLLDFVAARTFSSVLVFFHPSGHSFLLILRDSKLKQASLCV* | ATTTAATTATATGGATACCATGCATGATTTCACTTCTCTGTTTCTCCTTC |
| *LKKM* | AGATGATGTTCATCCTTCCTTATGGAGCCACACAGAAGCCCATGTGAAACACTGGCTTCCATTCTCTC |
| *KYAKKDIISHFYKHA* | TTAATCCTCCCTTATGGAGCCACACAGAAGCCCATGTGAAACACTGGCTTCCATTCTCTC |
| | TTATTCAGGGATCCCAGCACAGAAGCCCATGTGCATTAGTCTAAAACCTATAAAAGCTA |
| | TAATTTCATTTCTACTCCTCCTTTATTGTGCATTATTGTGTTCATCAGTATCATA |
| | CTAACATTGCTGCCTGTCCTCTTCTAGACTTGTTGTGCGCAAGGACTTTTAG |
| | TAGTGTGCTGGTATTTCCATCCATCTGGCCATTCATTTCTTCTAATTT |
| | TACGGACACAGCAAACTGAAGCAAGCTTCTCTCTGTCCTGAAGAAGATG |
| | AAGTATGCCAAAAGGACATAATCTCTCATTTTTATAAACATGCCTGA |

SEQ ID NO: 24 - hGR13 nt
ATGGAAAGTGCCCTGCCGAGTATCTTCACTCTTGTAATAATTGCAGAATT
CATAATTGGGAATTGAGCAATGAGTGCTGTCCAGTCGATCAACTGCATTG
ACTGGGTCAGTAGAGAGCTGTCCTCAGTCGATCGATAAACTCCTCATTATC
TGGCAATCTCCAGAATTGGGCTGATCTGGGAAATATTAGTAAGTTGGTT
TTTAGCTCTGCATTATCTAGCTGATAGTTTCTAATCACTTCAATCTCGGCTTGCT
TTATGATTTTAGCTGATAGTTTCTAATCACTTCAATCTCGGCTTGCT
ACAATCTTCAGCATCTTTATTGCTCAAAATAGCGAGTTCTCTAGCAC
TGCTTTTCTCTATTGAAGTGGAGAGTAAACAAGTGATTCTGATGATAC
TGCTAGGAACCTTGGTCTCTCTATTTTAAATCGATACAAATAAACATG
CATATAAAAGACTGGCTGGACCGATAGAAGAAACAACAACTTGGAATTT
CAGTATGAGTGACTTGACTTGAAACATTTCAGTGTGCCCTTCATCCTTTTTCCCTG
CTATGTTCAGTTCAGTCTAACACCATTTACTGTGCCCTTCATCCTTTTTCCCTG
TTAATTTCTCCCTGCAGAAACATCTCCAGAAAATGCAACTCAATTACAA
AGGACACAGAGACCCCAGGACCAAGGTCCATACAAATGCCTTGAAAATTG
TGATCCATTCCTTTATTCTATGCTAGTTTCTTAGTGTGTTCTCATA
TCATGGATTTCTGAGCTGTCTCCTTCAAGCCACTCCTTTTCTGATTCTAG
GACCATTGGAGTCTTCCTCCTTCAAGCCACTCCTTTTCTGATTCTAG
GAAACGCTAAGTTAAGACAGGCCTTTCTTTTGGTGGCAGCTAAGGTATGG
GCTAAACGATGA

SEQ ID NO: 23 - hGR13 aa
MESALPSIFTLVIIAEFIGNLSNGFIVLINCIDWVSKRELSSVDK
LLII
LAISRIGLIWEILVSWFLALHYLAIFVSGTGLRIMLFSWIVSNHFN
LWLA
TIFSIFYLLKIASFSSPAFLYLKWRVNKVIIMLLGTILVFLFLNLI
QINM
HIKDWLDRYERNTTWNFSMSDFETFSVSVKFTMTMFSLTPFTVAFI
SFLL
LIFSLQKHLQKMQLNYKGHRDPRTKVHTNALKIVISFLLFYASFFL
CVLI
SWISELYQNTVIVYMLCETIGVFSPSSHSFLLIGNAKLRQAFLL-
VAAKVWAKR

FIG. 8

| SEQ ID NO: 25 - hGR14 aa | SEQ ID NO: 26 - hGR14 nt |
|---|---|
| MGGVIKSIFTFVLIVEFIIGNLGNSFIALVNCIDWKGRKISSVDR<br>ILTALAISRISLVWLIFGSWCVSVFFPALFATEKMFRMLTNIWTVI<br>NHFSVWLATGLGTFYFLKIANFSNSIFYLKWRVKKVVLLLVTS<br>VFLFLNIALININIHNASINGYRRNKTCSSDSSNFTRFSSLIVLIST<br>VFIFIPFTLSLAMFLLLIFSMWKHRRKMQHTVKISGDASTKAHRGV<br>KSVITFFLLYAIFSLSFFISVWTSERLEENLIILSQVMGMAYPSCH<br>SCVLIIGNKKLRQASLSVLLWLRYMFKDGEPSGHKEFRESS | ATGGGTGGTGTCATAAAGAGCATATTTACATTCGTTTAATTGTGGAATT<br>TATAATTGGAAATTTAGGAAATAGTTTCATAGCACTGTGAACTGTATTG<br>ACTGGGTCAAGGAAGAAAGATCTCTTGGTTGATCGGATCCTCACTGCT<br>TTGGCAATCTCTGAATTAGCCTGGTTTGGTTAATATTCGAAGCTGGTG<br>TGTCTGTGTTTTCCCAGCTTATTTGCCACTGAAAAATGTTCAGAA<br>TGCTTACTAATATCTGGACAGTGATCAATCATTTAGTGTCTGGTTAGCT<br>ACAGGCCTCGGTACTTTTATTTCTGAGGGTTAAAAAGTGGTTTTGGTCTGC<br>TATTTTCTCACCTAAAGTGGAGGGTTAAAAATATTGCACTGATAAACATC<br>TTCTTGACTTCGGTCTCTTGTTTTTAAAATAATTGCACTGATAAACATC<br>CATATAAATGCCAGTATCAATGGATACAGAAGAAACAAGACTTGCAGTTC<br>TGATTCAAGTAACTTTACACGATTTTCCAGTCTTATTGTATTAACCAGCA<br>CTGTTCATTTTCATACCCTTTACTTTGTCCCTGGCAATGTTTCTTCTC<br>CTCATCTTCCATGTGGAAACATCGCAAGAAGATGCAGCACACTGTCAA<br>AATATCCGAGACGCCAGACAGCCCTCTCTTCTCTGTCTTTTTCATATCA<br>TCACTTCTTCTCCTACTCTATGCCATTTTCTCCTGTCTTTTTCATATCA<br>GTTTGGACCTCGAAAGGTTGGAAGAATCTAATTATTCTTTTCCCAGGT<br>GATGGGAATGGCTTATCCTCACTCATGTCACTCATGTGTTCTGATTCTTGGAA<br>ACAAGAGCTGAGACATGGGGAGCCCTCAGGTCACAAAGAATTTAGAGAATCATC<br>TTGA |
| SEQ ID NO: 27 - hGR15 aa | SEQ ID NO: 28 - hGR15 nt |
| MITFLPIIFSILVVTFVLGNFANGFIVLVNSIEWVKRQKISFADQ<br>ILTA<br>LAVSRVGLLWVILLHWYATVLNPGSYSLGVRITTINAWVTNHFSI<br>WVAT<br>SLSIFYFLKIANFSNFIFLHLKRRIKSVIPVILLGSLLFLVCHLVV<br>VNMD<br>ESMWTKEYEGNVSWEIKLSDPTHLSDMTVTTLANLIPFTLSLLSFL<br>LLIC<br>SLCKHLKKMQFHGKGSPDSNTKVHIKALQTVTSFLLLFAVYFLSLI | ATGATAACTTTTCTACCCATCATTTTTTCCATTCTAGTAGTTGTTACATT<br>TGTTCTCGGGAATTTGCTAATGGCTTCATAGTGTTGGTAAATTCCATTG<br>AGTGGGTCAAGAGACAAAAGATCTCCTTTGCTGACCAAATTCTCACTGCT<br>CTGGCAGTCTCCAGAGTTGGTTGCTCTGGTAATATTATTACATTGGTA<br>TGCAACTGTTTGAATCCAGGTTCATATAGTTAGGAGTAAGAATTACTA<br>CTATTAATGCCTGGGCTGTAACCAACCATTTCAGCATCTGGGTTGCTACT<br>AGCCTCAGCATATTTTATTTCCTCAAGATTGCCAATTTCTCCAACTTTAT<br>TTTTCTTCACTTAAAAGGAGAATTAAGAGTGTCATTCCAGTGATACTAT<br>TGGGGTCTTTGTTATTTTGGTTTGTCATCTGTGTGTGTAAACATGGAT |

FIG. 8

| TSIM<br>NFRRRL*NEPVLMLSQTTAIYPSFHSFILIWGSKKLKQTFLLLC<br>QIKC | GAGAGTATGTGGACAAAAGAATATGAAGAAGAAACGTGAGTGGAGATCAA<br>ATTGAGTGATCCGACGCACCTTCTGTCCCTGTTATCTTTCTGTCTTAATCTGT<br>ACTTAATACCCTTACTCTGCCCTGTTATCTTTCTGTCTTAATCTGT<br>TCTTTGTAAACATCTCAAGAAGATGCAGTTCAGTGCAAAGGATCTC<br>AGATTCCACACCAAGGTCCACATAAAAGCTTTGCAAACGTGACCTCCT<br>TCCTCTGTTATTGCTGTTTACTTTCTGTCCTAATCACATCGATTTGG<br>AATTTTAGGAGGAGCTGTAGAACGAACCTGTCTCATGCTCAGCAAAC<br>TACTGCAATTATATACCCTTCATTCATTCATTCCTAATTGGGGAA<br>GCAAGAAGCTGAAACAGACAGACCTTTCTTTTGATTTGTGTCAGATTAAGTGC<br>TGA |
|---|---|
| SEQ ID NO: 29 - hGR16 aa<br>MIPIQLTVFFMIIYVLESLITIVQSSLIVAVLGREWLQVRRLMPVD<br>MILI<br>SLGISRFCLQWASMLNNFCSYFNLNYVLCNLTITWEFFNILTFWLN<br>SLLT<br>VFYCIKVSSFTHHIFLWLRWRILRLFPWILLGSLMITCVTIIPSAI<br>GNYI<br>QIQLLTMEHLPRNSTVTDKLENFHQYQFQAHTVALVIPFILFLAST<br>IFLM<br>ASLIKQIQHHSTGHCNPSMKARFTALRSLAVLFIVFTSYFLTILIT<br>IIGT<br>LFDKRCWLWVWEAFVYAFILMHSTSLMLSSPTLKRILGKC | SEQ ID NO: 30 - hGR16 nt<br>ATGATACCCATCCAACTCACTGTCTCTTCTTCATGATCATCTATGTGCTTGA<br>GTCCTTGACAATTATTGTGCAGAGCAGCCTAATTGTTGCAGTGCTTGGGCA<br>GAGAATGCTGCAAGTCAGAAGGCTGATGCCTGTGACATGATTCTCATC<br>AGCCTGGGCATCTCGCTTCGTCTGTCTACAGTGGGCATCAAGCTGAACAA<br>TTTTGCCTGGGAATTTTTAATTTGAATTATGTACTTTGCAACTTAACAATCA<br>CCTGGGAATTTTTAATATCCTTACATTCTGGTTAAACAGCTTGCTTACC<br>GTGTTCACTGCATCAAGGTCTCTTCTTTCACCCATCACATCTTTCTG<br>GCTGAGGTGGAGAATTTGGTAACAATCATCCCTCAGCTATTGGGAATTACATT<br>CAATTCAGTTACTCACCATGGAGCATCTACCAAGAAACAGCACTGTAAC<br>TGACAAACTGAAAATTTTCATCAGTACAGTTCCAGGCTCATACAGTTG<br>CATTGGTTATTCCTTCATCCTGCCGCCTCCACCATCTTTCTCATG<br>GCATCACTGACCAAGCAGATACAACATCATAGCACACTGGTCACTGCAATCC<br>AAGCATGAAAAGCGCTTCACTGCCTTCTAACCATCATCCATTATAGTACT<br>TTGTGTTTACCTCTTACTTCTTCTAACCATCATCATCACCATTATAGTACT<br>CTATTGATAAGAGATGTTGGTTATGGCTCGGAAGCTTTTGTCTATGC<br>TTTCATCTTAATGCATTCCACTTCACTGATCGTGAGCAGCCCTACGTTGA<br>AAAGGATTCTAAAGGGAAAGTGCTAG |

FIG. 8

| | |
|---|---|
| SEQ ID NO: 31 - hGR17 aa<br>MCSAXLLIILSILVVFAFVLGNVANGFIALINVNDWVKTQKISSTD<br>QIVTALAFSRIGLIXTLIILLHWYATVFNSALYSLEVRIVPSNVSA<br>IINHFSIWLATSLSIFYLFKIANFSNFIFLHLKKRIKSVLIVILLG<br>SLVFLICNLAVVTMDDSVWTKEFEGNVTWKIELRNAIHLSNMTITN<br>HASKLHTVHSDSNIFSAVSLFSXTMLANFTLFLITLISFLLLVCSP<br>CKHLKMMQLHGKGSQDLSTKVHIKPLQTVISFRMLFAIYFLCIITS<br>TWNPRTQQSNLVFLLYQTLAIMYPSFHSFLIMRSRKLKQTSLSVL<br>CQVTCWVK | SEQ ID NO: 32 - hGR17 nt |
| SEQ ID NO: 33 - hGR18 aa<br>MFVGINIFFLVVATRGLIVLGMLGNGLIGLVNCIEWAKSWKVSSADF<br>ILTS<br>LAIVRIIRLYLILFDSFIMVLSPHLYTIRKLVKLFTIIWALINQLS<br>I*FA<br>TCLSIFYLLKIANFSHSLFLWLKWRMNGMIVMLLISLFLLIFDSL<br>VLEI<br>FIDISLNIIDKSNLTLYLDESKTLYDKLSILKTLLSLTYVIPFLLT<br>LTSL<br>LLLFISLVRHTKNLQLNSLGSRDSSTEAHKRAMKMVIAFLLLFIIN<br>FIST<br>LIGDWIFLEVENYQVMFIMMILLAFPSGHSFIIILGNNKLRQSSL<br>RLLW<br>HLIKFSLKKAKPLITS | SEQ ID NO: 34 - hGR18 nt<br>ATGTTCGTTGGAATTAATATTTCTTTCTGGTGGTGGCAACAAGAGACT<br>TGTCTTAGGAGGACTCTGGGAAACGGGCTCATTGGACTGGTAAACTGCATTG<br>AGTGGGCCAAGAGTTGGAAGTCTCATCAGCTGATTTCATCCTCACCAGC<br>TTGGCTATAGTCAGAATCATTCGACTGTATTTAATACTATTTGATTCATT<br>TATAATGGTATTGTCCCCTCATCATACCATCCGTAAACTAGTAATCATG<br>TGTTTACTATTCTTTGGCATTAATTAATCAGTTAAGTATCTAGTTTGCC<br>ACCTGCCTAAGCATTTTCTACTTGCTTAAGATAACGGAATGAATTGTATGCTTC<br>CCTTTTCCTCTGGCTGAAGTGGAGAATGAACGAGAATGATTGTTATGCTTC<br>TTATATGTCTTGTTCTTACTGATTTTGACAGTTAGTGCTAGAAATA<br>TTTATTGATATCTCACTCAATATAATAGATAAACTCTCTATTTAAAACTC<br>TTTAGATGAAAGTAAACTCTCAGTTATCCCTTTCTCCTTCTCTGACTCTGAAC<br>TTCTCAGCTTGACATACGTTATTCCCTTCTCCTTCTCTGACTCTGAGCTCTTTG<br>CTCTCGGCTCAAGGACTCCAGCACCAAGAATTTGCAGCTCAA<br>AAATGTGATAGCCTTCCTCCCTCCTTTTATTTATTAACTTATTTCCACT<br>TTAATAGGAGATTGGATCTTCCTTGAGGTAGAGAATTATCAGGTCATGAT<br>GTTTATTATGATGATTTACTTGCCTTTCCCTCAGGCACCACTCATTATTA<br>TAATTTTGGAAACAACAAGCTAAGACAAGAGCTCCTGAGACTACTGTGG<br>CATCTTAAATTCTCTGAAAAAGCAAAACCTTTAACTTAACTTCATAG |
| SEQ ID NO: 35 - hGR19 aa<br>VTTLANLIPFTLSLICFLLLICSLCKHLKMRLHSKGSQDPSTKVH | SEQ ID NO: 36 - hGR19 nt<br>CTGTAACTACTCTAGCAAACCTCATACCCTTTACTCTGAGCCTAATATGT |

```
AAGTATCAGATATCAATGCTCTTCTGCAATGTCTCATTGTNACATTATT
AATGATACANAGTATTAAAAACTTGGATTTNTGTCTGGAGATGGCC
ACCGAATCGGACACAAATCTTCTGATTCTGGCAATAGCAGAATTCATCAT
CAGCATGCTGGGAATGTGTTCTCAGCTGACTGGTAAACTGCTCTGAANGA
TCAAGAACCANAAGGTCTTCAACTTCATCCTCACTGCTTGGCT
ATCTCTCACAATGGACAACTGTTGGTGATACTGTTTGATTCATTTCTAGT
GGGACTTGCTTCCACATCTATATACCACATATAGACTANGAAAAAACTGTA
TTATGCTTTGGACATGACTAATCACTTGACACACTGCTTCGCACGTGCTA
GCATATTCTATTCTTAGATAGCCACTTCNCACTCCTTGTCTCTGCTGAAG
TGGGAT
```

SEQ ID NO: 42 - hGR23 nt
```
AGGGTTGAGTCGTCGTCTATCTTCACTTAACCTAGTATANAANTACAGCAT
ATAGCAAGGAGAGAATGTATATGAAGAGGAGTGAATTTGAGTCTGTTTGA
GAATAATGACCTTTCTATTTCTATAAAGACAGTTTGAATTCATCTATT
AGCATATGCTGGTGCTTGCCTGTTGACACTAGTCACTGAATTTAAAGGCA
GAAAATGTTATTGCACATTTAGTACTAATCAAGTGTTCATCGAAGTTAACATC
TGGATGTTAAAGGACTCAGAACAAGTGTTACTAAGCCTGCATTTTTTAT
CTGTTCAAACATGATGTTNTCTGCTCATCATTTCATCAATTCTGGTAG
AGTTGCATTIGTTCTTGAAATGTNGCCAATGGCTTCATAGCTCTAGTAA
ATGTCATTGACTGNGTTAACACACGAAAGATCTCCTCAGCTGACAAATT
CTCACTGCTCTGGTGTGTCCAGAATTGCAACATAGTTAATCTGCTCTGNGTCATAGTAT
TCCTTGAGATGCAACTAGATGTTAATCTGCTCTATAGGNTAGAAGTAA
GAATTGTTGCTTCTTCACTAAATGCTGAGCTGTACGAACCATT
```

SEQ ID NO: 44 - hGR24 nt
```
ATGGCCACCGAATTGGACAAAATCTTTCTGATTCTGGCAATAGCAGAATT
CATCATCAGCATGCTGGGAATGTGTTCATTGGACTGGTAAACTGCTCTG
AAGGGATCAAGAACCAAAAGGTCTTCTCAGCTGACTTCATCCTCACCTGC
TTGGCTATCTCCACAATTGGACAACTGTTGGTGATACTGTTTGATTCATT
TCTAGTGGACTTGCTTCCACATTTATATACCACATATAGACTAGGAAAAA
CTGTTATTATGCTTGGCACATGACTAATCACTTGACAACCTGGCTTGCC
ACCTGCCTAAGCATTTTCTATTTCTTTAAGATAGCCCACTTCCCCACTC
```

SEQ ID NO: 42 - hGR23 aa
VAFVLGNVANGFIALVNVIDXVNTRKISSAEQILTALVVSRIGXTL
XHSIP*DATRC*SALVRXEVRIVASN

SEQ ID NO: 43 - hGR24 aa
MATELDKIFLILAIAEFIISMLGNVFIGLVNCSEGIKNQKVFSADF
ILTCLAISTIGQLLVILFDSFLVGLASHLYTTYRLGKTVIMLWHMT
NHLTTWLATCLSIFYFFKIAHFPHSLFLWLRWRMNGMIVMLLILSL
FLLIFDSLVLEIFIDISLNIIDKSNLTIYLDESKTLYDKLSILKTL
LSLTSFIPFSLFITSLLFLFLSLVRHTRNLKLSSLGSRDSSTEAHR
RAMKMVMSFLFLFIVHFFSLQVANGIFFMLWNNKYIKFVMLALNAF
PSCHSFILILGNSKLRQTAVRLLWHLRNYTKITPNALPL

FIG. 8

| | CCTTTTCCTCTGCTGAGGTGAGGATGAACGAATGATTGTTATGCTTC |
|---|---|
| | TTATATTGTCTTTGTTCTTACTGATTTTGACAGTTTAGTGCTAGAAATA |
| | TTTATTGATATCTCACTCAATATATAGATAAAGTAATCTGACTTTATA |
| | TTTAGATGAAAGTAAAACTCTCTATGATAAACTCTCTATTTAAAACTC |
| | TTCTCAGCTTAACCAGTTTTATCCCCTTTTCTCTGTTCCTGACCTCCTG |
| | CTTTTTTATTCTGTCCCTGGTGAGACATACTAGAAATTGAAGCTCAG |
| | TTCCTGGGCTCTAGAGACTCCAGCACAGAGAGGCCCATAGAGGCCATGA |
| | AAATGGTGATGTCTTTCCTTTCCTCTTCATAGTTCATTTTTTTCCTTA |
| | CAAGTGGCCAATGGATATTTTTATGTTGTGAACAACAAGTACATAAA |
| | GTTTGTCATGTTAGCCTTAAATGCCTTTCCCTGCTGCCACTCATTATTC |
| | TCATTCTGGGAAACAGCAAGCTGCGACAGACAGCTGTGAGGCTACTGTGG |
| | CATCTTAGAAGAACTATACAAAAACACCAAATGCTTTACCTTTGTAG |
| SEQ ID NO: 46 - hGR25 nt | |
| SEQ ID NO: 48 - hGR26 nt | |
| SEQ ID NO: 45 - hGR25 aa<br>LSPFRMLFAIYFLCIITSTWNPRIQ<br>QSNLVFLLYQTLAIMYPSFHSFILI<br>MRSRKLKQTSLSVLCQVTCWVK | |
| SEQ ID NO: 47 - hGR26 aa<br>MPPGIGNTFLIVMGEFII*MLGNGFIVLVNCIDVRSQMILLDNCI<br>LTSL<br>AISTISQLMWILLDSFVTALWPHLYAFNKLIKFIHIFWALTNHLVT<br>WLACCLSVFYFFKIAYFSHPCFTWLRWRISRTLLELPIGSLLLLFF<br>NLALTGGLSDLWINIYTMYERNSTWSLDVSKILYCSLWILVSLIYL<br>ISFLLSLLISLLLLILSLMRHIRNLQLNTMGPRDLRMKAHKRAMKMK<br>MKMMVSFLLFFLVHFSSLLPTGWIFLIQQK | |

FIG. 8

| | |
|---|---|
| SEQ ID NO: 49 - hGR27 aa<br>LANLIDWAENQICLMDFILSSLAICRTLLLGCCVAIRCTYNDYPNI<br>DAVNHNLIKIITIFDILRLVSK*LGIWFASYLSIFYLLKVALFHHA<br>IFLWLKWRISRAVFTFLMIFLFFYISIISMIKIKLFLDQC*YKI*E<br>KLLEGRCE*SPPSC*PDAH*PGVVYSLYHPSYLMPLVCYLPKGKH<br>CTAVVIGDWLQRPRTEAYVRAMNIMIAFFFHLLYSLGTSLSSVSYF<br>LCKRKIVALGAVLSYPLSHSFILIMENNKVRKAL | |
| SEQ ID NO: 50 - hGR28 aa<br>NICVLLILSILVVSAFVLGNVANGFIALINVNDW | SEQ ID NO: 51 - hGR28 nt |
| SEQ ID NO: 52 - hGR29 aa<br>MQAALTAFFVLLFSLLSLLGIAANGFIVLLGKEWL | SEQ ID NO: 53 - hGR28 nt |
| SEQ ID NO: 54 - hGR30 aa<br>MITFLPIIFSILVVTFVLGNFSNGFIALVNSIEWKTRKISSADQ<br>ILTA<br>LVVSRVGLLMVILLHWYANVFNSALYSSHVGAVASNISAIINHFSI<br>WLAT<br>SLSIFYLLKIANFSNLIFLHLKKIRSVVLVLILLGPLVFLICNLAV<br>ITMD<br>DSVWTKEYEGNVTWKIKLRNAIHLSNMTVSTIANLIPFILTLICFL<br>LLIC<br>SLCKHLKKMQLHGKGSQDPSTKVHIKALQIVTSFLLLCAIYFLSMI<br>ISVC<br>NFGRLEKQPVFMFCQAIIFSYPSTHPFILLIGNKKLKQIFLSVLRH<br>VRYW<br>VKDRSLRLHRFTRGALCVF | SEQ ID NO: 55 - hGR30 nt<br>ATGATAACTTTTCTACCCATCATTTTTCCATTCTGTAGTGGTTACATT<br>TGTTCTTGGAAATTTTCCAATGGCTTCATAGCTCTAGTAAATTCCATTG<br>AGTGGGTCAAGACACGAGATCTCCTCAGCTGCCTGACCAAATCCTCACTGCT<br>CTGGTGGTCTCCAGAGTTGGTTTACTCTGGGTCATATTATTACATTGGTA<br>TGCAAATGTGTTTAATTCAGCTTTATATAGTTCAGAAGTAGGAGCTGTTG<br>CTTCTAATATCTCAGCAATAATCAACCATTTCAGCATTCAGCTTGCTACT<br>AGCCTCAGCATATTATTGCTCAAGATTGCCAATTCTCCAACCTTAT<br>TTTTCTCCACTTAAGAGAGAATTAGAGTGTTGTTCTGTGATAACTGT<br>TGGGTCCCTTGGTATTTTGATTTGTAATCTTGCTGTGATAACCATGGAT<br>GACAGTGTGTGACAAAAGAATATGAAGGAAATGACTGTAAGCACACTAGCAA<br>ATTGAGGAATGCAATACACCCTTTCAAAATATGACTGTTTCTGCTGTTAATCTGT<br>ACCTCATACCCTTCATTCTGACCCTAATATGTTTTCTGCTGTTAATCTGT<br>TCTCTGTGTAAACATCTCAAGAAGATGCAGCTCCATGCCAAACTGTGACCTCCT<br>AGATCCCAGCACCAAGGTCCATTACTTTCTGTCCATGATCATATCAGTTTGT<br>TCTTCTGTTATGTGCCATTACTTTCTGTCCATGATCATATCAGTTTGT<br>AATTTTGGAGGCTGGAAAAGCAACCTGTCTTCATGTTCTGCCAAGCTAT<br>TATATTCAGTCATCCTTCAACCCACCATTCAGTTTTGCGCATGTGAGGTACTGG<br>AGAAGCTAAAGCAGAGTTTTCTTTCAGTTTTCCGCATGTGAGGTACTGG<br>GTGAAAGACAGAGAAGCCTTCGTCTCCATAGATTCACAGAGAGGGCATTGTG |

FIG. 8

| SEQ ID NO: | Sequence |
|---|---|
| SEQ ID NO: 56 - hGR31 aa | MTTFIPIIFSSVVVLFVLIGNFANGFIALVNSIERVKRQKISFADQ<br>ILTA<br>LAVSRVGLLMVLLLNWYSTVFNPAFYSVEVRTTAYNWAVTGHFSN<br>WLAT<br>SLSIFYLLKIANFSNLIFLHLKRRVKSVILVMLLGPLLFLACQLFV<br>INMK<br>EIVRTKEFEGNMTWKIKLKSAMYFSXMTVTIGAXLVPFTLSLISFL<br>MLIC<br>SLCKHLKKMQLHGEGSQDLSTKVHIKALQTLISFLLCAIFFLFLI<br>VSVW<br>SPRRLRNDPVVMVSKAVGNIYLAFDSFILIWRTKKLIKHTFLLILCQ<br>IRC |
| SEQ ID NO: 57 - hGR31 nt | ATGACAACTTTTATACCCATCATTTTTTCCAGTGTGGTAGTGTTCATT<br>TGTTATTGGAAATTTTGCTAATGGCTTCATAGCATTGGTAAATTCATTG<br>AGCGGGTCAAGAGACAAAAGATCTCTTTTGCTGACCAGATTCTCACTGCT<br>CTGGCGGTCTCCAGAGTTGGTTTGCTCTGGGTATTATTATTAAATTGGTA<br>TTCAACTGTGTTTAATCCAGCTTTTATAGTGTAGAAGTAAGAACTACTG<br>CTTATAATGTCTGGGCAGTAACCGGCCATTTCAGCAACTGGCTTGCTACT<br>AGCCTCAGCATATTTATTTGCTCAAGAGAGTTAAGAGTGTCATTCTGATGCTGT<br>TTTCTTCACTTAAAGAGGAGTTGGCTTGTCAACTTTTTGTGATAAACATGAAA<br>TGGGGCCTTTACTATTTTGGCTTGTCAACTTTTTGTGATAAACATGAAA<br>GAGATTGTACGGACAAAAGAATTTGAAGGAACATGACTGAAGATCAA<br>ATTGAAGAGTGCAATGTACTTTTCANATATGACTGTAACCATTGGAGCAN<br>ACTTAGTACCCTTTCACTCTGTCCCTGATATCTTTTCTGATGCTAATCTGT<br>TCTCTGTGTAAACATCTCAAGAAGATCAGCTCCATGGAGAAGATGCCA<br>AGATCTCAGCACCAAGGTCCACATAAAGCTTTGCAAACTCTGATCTCCT<br>TCCTCTGTTATGTGCCATTTCTTCTTCTATTCCTAATCGTTTCGGTTTGG<br>AGTTCCTAGGAGCTGCGAATGACCCGGTTGTCATGCTTAGCAAGGCTGT<br>TGGAAACATATATCTTGCATTGGACTCATTCATCCTAATTGGAGAACCA<br>AGAAGCTAAAACACACCCTTTCTTTGATTTGTTGTCAGATTAGGTGCTGA. |
| SEQ ID NO: 58 - hGR32 aa | HSFMLIMGSRKPKQTFLSAL |
| SEQ ID NO: 59 - hGR33 aa | MVYFLPIIFSILVVFAFVLGNFSNGFIALVNVIDWVKRQKISSADQ<br>ILTA<br>LVVSRVGLLMVILLHWYANVFNSALYSLEVRIVASNISAVINHFSI<br>WLAA<br>SLSIFYLLKIANFSNLIFLHLKKRIKSVVIILLGPLVFLICNLAV<br>ITMD<br>ERVWTKEYEGNVTWKIKLRNATHLSSLTVTTLANLIPFTLSLICFL<br>LLIC |
| SEQ ID NO: 60 - hGR33 nt | ATGGTATATTTTCTGCCCATCATTTTTCCATTCTGGTAGTGTTTGCATT<br>TGTTCTTGGAAATTTTTCCAATGGCTTCATAGCTCTAGTAAATGTCATTG<br>ACTGGGTTAAGAGACAAAAGATCTCCAGCTGACCAGATTCTCACTGCT<br>CTGGTGGTCTCCAGAGTTGGTTTACTCTGGGTCATATTATTACATTGGTA<br>TGCAAATGTGTTTAATTCAGCTTTATAGTTAGAAGTAAGAATTGTTG<br>CTTCAATATCTCAGCAGTAATCAACCATTTCAGCATCGTTGCTGCT<br>AGCCTCAGCATATTTATTGCTCAAGATTGCCAATTCTCCAACCTTAT<br>TTTTCTTCCACTTAAAGAAGAATTAAGAGTGTTCTTCGATATACTGT |

FIG. 8

| | |
|---|---|
| SLCKHLKKMQLHSKGSQDPSTKVHIKALQTVISFLMLCAIYFLSIM ISVW NLRSLENKPVFMFCKAIRFSYPSIHPFILIWGNKKLKQTFLSVFWQ VRYW VKGEKPSSP | TGGGGCCCTTGGTATTTCTGATTTGTAATCTTGCTGTGATAACCATGGAT GAGAGAGTGTGGACAAAAGAATATGAAGGAAATGTGACTTGGAAGATCAA ATTGAGGAATGCAATACCCTTTACTCTGAGCCTAATATGTTTCTGCTGTTAATCTGT ACCTCATACCCTTTACTCTGAGCCTAATATGTTTCTGCTGTTAATCTGT TCTCTTTGTAAACATCTCAAGAGATGCAGCTCCATAGCAAAGGATCTCA AGATCCCAGCACCAAGGTCCACATAAAAAGCTTTGCAAACTGTGATCTCCT TCCTCATGTTATGTGCCATTTACTTTCTGCCATAATGATATCAGTTTGG AATCTTAGGAGTCTGGAAAACAAACCTGTCTTCATGTTCTGCAAAGCTAT TAGAATTCAGCTACTATCCTTCATCCACCATTCATCCTGATTGGGAAACA AGAAGCTAAAGCAGACTTTCTTTCAGTTTTTTGGCAAGTGAGGTACTGG GTGAAAGGAGAGAAGCCTTCATCTCCATAG |
| SEQ ID NO: 61 - hGR34 aa GSSRXKPPRIPHKKLCKLGPSFPHNNLPIYFLCXNHIVLEFLKMRP KKKC SLMLCQAFGIIYPSFHSFILXWGNKTLKQTFLSVXWQVTCWAKGQN QSTP | |
| SEQ ID NO: 62 - hGR35 aa NAIRPSKLWTVTEADKTSQPGTSANKI FSAGNLISHVNMSRRMQLHGKGSQHLS TRVHIKAXQTVISFLMLXAIYFLCLIT STWNPRTQQSKLIVFLLYQTLGFMYLLF HSFILIMGSRKPKQTFLSAL | |
| SEQ ID NO: 63 - hGR36 aa MICFLLIILSILVVFAFVLGNFSNGFIALVNVIDWVKRQKISSADQ ILTALVVSRVGLLMVILLHWYSNVLNSALYSSEVIIFISNAWAIIN HFSIWLATSLSIFYLLKIVNFSRLLFHHLKRKAKSVVLIVLGPLV FLVCHLVMKHTY INVWTKEYEGNVTWKIKLRNAIHLSNLTVSTLANLIPFTLTLISFL LLIYSLCKHLKKMQLHGKGSQDPSTKVHIKALQTVTSFLLLCAIYF | SEQ ID NO: 64 - hGR36 nt ATGATATGTTTCTGCTCATCATTTATCAATTCTGGTAGTGTTTGCATT TGTTCTTGGAAATTTTTCCAATGGCTTCATAGCTCTAGTAAATGTCATTG ACTGGGTCAAGAGACAAAAGATCTCCTCAGCTGACCAAATCCTCACTGCT CTGGTGGTCTCCAGAGTTGGTTTACTCGGTAATATTATACATTGGTA TTCAAATGTGTTGAATTCAGCTTTATATAGTTCAGAAGTAATAATTTTTA TTTCTAATGCTGGCAATAATCAACCATTTCAGCATTCTGGCTACTGCTACT |

FIG. 8

| LSMIISVCNFGRLEKQPVFMFCQAIIFSYPSTHPFILILGNKKLKQ<br>IFLSVFWQMRYWVKGEKPSSP | AGCCTCAGATATTTATTGCTCAAGATCGTCAATTTCTCCAGACTTAT<br>TTTTCATCATCTAAAAGGAAGGCTAAGAGTGTAGTTCTGATGATGT<br>TGGGTCCCTTGGTATTTTGGTTTGTCACCTTGTGATGAAACACGTAT<br>ATAAATGTGTGGACAAAAGAATATGAAGGAAATGTGACTTGGAAGATCAA<br>ACTGAGGAATGCAATACACCTTCAAACTTGACTGTAAGCACACTAGCAA<br>ACTTGATACCCTTCACTCTGACCCTGATATCTTTTCTGCTGTTAATCTAC<br>TCTCTGTAAACATCTCAAGAAGATGCAGCTCCATGGCAAAGATCTCA<br>AGATCCCAGCACCAAGGTCCACATAAAAGCTTTGCAAACTGTGACCTCCT<br>TTCTTCTGTTATGTGCCATTTACTTTCTGTCCATGATCATATCAGTTTGT<br>AATTTGGAGGCTGGAAAAGCAACCTGTCTCTTCATGTCTCTGCCAAGCTAT<br>TATATTCAGCTATCCTTCAACCCACCCATTCATTCTTTGTTTTTGGCAAATGAGGTACTGG<br>AGAAGCTAAAGCAGATTTTCTTTCAGTTTTTTGCAAATGAGGTACTGG<br>GTGAAAGGAGAAGCCTTCATCTCCATAG |
|---|---|
| SEQ ID NO: 65 - hGR37 aa<br>MITFLPIIFSLLIVVTFVIGNFANGFIALVNSIEWKRQKISSADQ<br>ISHC<br>SGGVQNWFTLGHIITLVCNCV*FGFI*IRSKNFWF*CLSNNQAFQH<br>VGVT<br>SLSIFHLLKTANFSNLIFLHLKKRIKSVGLIVILLGPLLFFICNLFV<br>INMD<br>ESVWTKEYEGNVTWKIKLRSAMYHSNMTLIMLANFVPFTLTLISFL<br>LLIC<br>SLCKHLLKKMQLHGKGSQDPSTKVHIKALQTVTSFLLLCAIYFLSMI<br>ISVC<br>NLGRLEKQPVFMFCEAIIFSYPSTHPFILILGNKKLKQIFLSVLRH<br>VRYW<br>VKGEKPSSS | SEQ ID NO: 66 - hGR37 nt<br>ATGATAACTTTTCTGCCCATCATTTTTCCATTCTAATAGTGGTTACATT<br>TGTGATTGGAAATTTGCTAATGGCTCTAGTACATCTAGTAAATTCCATTG<br>AGTGGGTTAAGACAAATTTGCTAATGGCTCATCAGCTGACCAAATTTCTCACTGC<br>TCTGGGTGTCCAGAATTGGTTTACTCTGGGTCATATTATTACATTGGT<br>ATGCAACTGTGTTAATTTGGCTCATATAGAATTCAGCATGTGTGTTACT<br>GGTTCTAATGTCTCAGCAATAACCAAGCATTTCAGCATGTGGGTGTTACT<br>AGCCTCAGCATATTCATTTGCTCAAGACTGCCAATTCTCCAACCTTAT<br>TTTTCTCCACCTAAAGAGAAGGATTAAGAGTGTTGTTTTGTGATAAACATGAT<br>TGGGGCCTTTGCTATTTTGCTATTTGTAATCTTTTTGTGAAGATCAA<br>GAGAGTGTATGGACAAAAGAATATGAAGGAAACGTGACTTGGAAGATCAA<br>ATTGAGGAGTGCAATGTACCATTCAAATATGACTTCTAACCATGCTAGCAA<br>ACTTTGTACCCTTCACTCTGACCCTGATATCTTTTCTGCTGTTAATCTGT<br>TCTCTGTGTAAACATCTCAAGAAGATGCAGCTCCATGGCAAAGATCTCA<br>AGATCCCAGCACCAAGGTCCACATAAAAGCTTTGCAAACTGTGACCTCCT<br>TTCTTCTGTTATGTGCCATTTACTTTCTGTCCATGATCATATCAGTTTGT<br>AATTTGGGAGGCTGAAAAGCAACCTGTCTCTTCATTCATCCTGATTTTGCGAAGCTAT<br>TATATTCAGCTATCCTTCAACCCACCCATTCATCCTGATTTTGGGAAACA |

FIG. 8

| | AGAAGCTAAAGCAGATTTTCTTTCAGTTTGCGGCATGTGAGTACTGG GTGAAAGGAGAGAAGCCTTCATCTTCATAG |
|---|---|
| SEQ ID NO: 67 - hGR38 aa<br>MLTLTIRTVSYEVRSTFLFISVLEFAVGFLTNAFVFLVNFWDVVK<br>RQPLSNSDCVLLCLSISRLIFLHGLLFLSAIQLITHFQKLSEPLNHSY<br>QAIMLWMIANQANLWLAACLSLLYCSKLIRFSHTFLICLASWSPG<br>RSPVPS | SEQ ID NO: 68 - hGR38 nt |
| SEQ ID NO: 69 - hGR39 aa<br>LRNAGLNDSNAKLVRNNDLLLINLLLLLPLSVFVMCTSMLFVSLYK<br>HMHWMQSESHKLSSARTEAHINALKTVTFFCFFVSYFAAFMANMT<br>FRIPYRSHQFFVKEIMAAYPAGHSVIIVLSNSKFKDLFRRMICLQ<br>KE | SEQ ID NO: 70 - hGR39 nt |
| SEQ ID NO: 71 - hGR40 aa<br>SQYSLGHSYVVIFGYGQMKKTFLGILWHLKCGLKGRALLATQVGLR<br>EKSTRSLGVIFLASSYSFFVYVLCH | SEQ ID NO: 72 - hGR40 nt |
| SEQ ID NO: 73 - hGR41 aa<br>MITFLLIILSILVVFAFVLGNFSNGFIALVNVIDWVNTRKISSADQ<br>ILTALAVSRVGLLMVILLHWYANVLNPALYSSEVIIFISNISAIIN<br>HFSIMLATSLSIFYLLKIVNFSRLIFHHLKRKAKSVVLIVLGPLV<br>FLVCHLVMKHTYINVWTKEYEGNVTWKIKLRNAIHLSNLTVSTLAN<br>LIPFTLTLISFLLLICSLCKHLKKMQLHSKGSQDPSTKVHIKALQI<br>VTSFLMLFAIYFLYLITSTWNL*TQQSKLVFMFCQTLGIMYPSFHS<br>FILLMGSRKLKQTFLSVLCQVTCLVKGQQPSTP | SEQ ID NO: 74 - hGR41 nt |
| SEQ ID NO: 75 - hGR42 aa<br>FIGLTDCIAWMRNQKLCMVGFILTRMALARINIL | |
| SEQ ID NO: 76 - hGR43 aa<br>LELIFS*KVVATRGLVLGMLGNGLIGLVNCIEWAKSWKVSSADFIL<br>TSLAIVRIIRLYLILFDSFIMVLSPHLYTXXXXXXXXXXXXXXXXX<br>XXXXXXXSLSIFHWFKTANFSNLIFLPLKEED*NVWLGDAVGALGIF<br>HL*SCSENHG*EVCGQKNMKEFCSGMIKLRNAIQLSNLTVTMPANV<br>TPCTLTLISFLLLIYSPCKHVKKMQLHGKGSQHLSTKVHIKVLQTV | |

FIG. 8

| | |
|---|---|
| ISFFLLCAIYFVSVIISVWSFKNLENKPVFMFCQAIGFSCSSAHPF ILTMGNKKLKQTYLSVLWQMR | |
| SEQ ID NO: 77 - hGR44 aa MITFLPIIFSILIVIFVIGNFANGFIALVNSIEWVKRQKISFVDQ ILTA LAVSRVGLLMVLLLHWYATQLNPAFYSVEVRITAYNVWAVTNHFSS WLAT SLSMFYLLRIANFSNLIFLRIKRRVKSVVLVILLGPLLFLVCHLFV INMD ETVWTKEVEGNVTWKIKLRSAMYHSNMTLTMLANFVPLTLTLISFL LLIC SLCKHLKKMQLHGKGSQDPSTKVHIKALQTVTSFLLLCAIYFLSMI ISVC NLGRLEKQPVFMFCQAIIFSYPSTHPFILIGNKKLKQIFLSVLRH VRYW VKDRSLRLHRFTRGALCVF | |
| SEQ ID NO: 78 - hGR45 aa MATELDKIFLILAIAEFIISMLGNVFIGLVNCSEGIKNQKVFSADF ILTCLAISTIGQLLVILFDSFLVGLAASHLYTTYRLGKTVIMLWHMT NHLTTWLATCLSIFYFFKIAHFPHSLFLWLRWRMNGMIVMLLILSL FLLIFDSIVLEIFIDISLNIIDKSNLITLYLDESKTTYDKLSILKTL LSLTSFIPFSLFLTSLLFLFSLVRHTRNLKLSSLGSRDSSTEAHR RAMKMVMSFLFLFIVHFFSLQVANWIFPMLWNNKCIKFVMLALNAF PSCHSFILIGNSKLQQTAVRLLWHLRNYTKTPNPLPL | |
| SEQ ID NO: 79 - hGR46 MSFLHIVFSILVVVAFILGNFANGFIALINFIAWVKKQKISSADQI IADKQSPELVCSG | |
| SEQ ID NO: 80 - hGR47 aa MLNALYSILIIINI*FLIGILGNGFTILVNGIDWVKM*KRSSILT ALTISRICLISVIMVRWFI | |

FIG. 8

| | |
|---|---|
| SEQ ID NO: 81 - hGR48 aa<br>VSRVGLLMVILLHWYSTVLNPTSSNLKVIIFISNAWAVTNHFSIWL<br>ATSLSIFYLLKIVN | |
| SEQ ID NO: 82 - hGR49 aa<br>TVTMLANLVPFTVTLISFLLLVCSLCKHLKKMHLHGKGSQDPSTKV<br>HIKVLQTVISFLLLCAIYFVSVIISS | |
| SEQ ID NO: 83 - hGR50 aa<br>MITFLPIIFSILVVTFVIGNFANGFIALVNSTEWVKRQKISFADQ<br>IVTA<br>LAVSRVGLLMVLLLNWYSTVLNPAFYSVELRTTAYNIWAVTGHFSN<br>WPAT<br>SLSIFYLLKIANFSNLIFLRLKRRVKSVILVVLLGPLLFLACHLFV<br>VNMN<br>QIVWTKEYEGNMTWKIKLRRAMYLSDTTVTMLANLVPFTVTLISFL<br>LLVC<br>SLCKHLKKMQLHGKGSQDPSTKVHIKVLQTVISFFLLCAIYFVSVI<br>ISVW<br>SFKNLENKPVFMFCQAIGFSCSSAHPFILIWGNKKLKQTYLSVLWQ<br>MRY | |

| |
|---|
| SEQ ID NO: 85 - rGR01 nt<br>CAGGAATCATAAATGGCTGAAACTGGGCAGAACTCTATGCATTATTAAA<br>GAAGTCATTGGTTTGTCATTCTTAAAATGATGAAGGCATATACTCTTC<br>TTCTTTTGGTTGTTGATGGTGCAGTTTGTCACTGGGTCTTGGCAAATGG<br>CCTCATTGTGGTTGTCCATGCTATTGACTTGACTTGATCATGTGAAGAAAATGG<br>CCCCGTTGATCTGCTTCTATTTGCCTGGCGACTTCTCGGATCATTCTG<br>CAGTTATGTATATTGAGGACAATGTGTCTATTCCTCTTGGTGAGACA<br>CACTTTATTGGTTGCTACACATGGCTCGGTGTTTTCATCTGCCAATGAACTGA<br>GTCTTTGGTTGCTACACATGGCTCGGTGTTTTCTACTGTGAAGATGCT<br>ACCATTCCTCACCCACTCTTTCTGTGGCTGAAGATGAGGATATCCAGGTT |

FIG. 8

| | |
|---|---|
| LSILSFLIIYLSHYMVAVLISTQVLYLGSRTFVFCLLIVIGMYPSIH SIVL ILGNPKLKRNAKMFIVHCKCCHCTRAWTSRSPRLSDLPVPPTHPS ANKT SCSEACIMPS | GGTACCATGGCTGATCCTGGGATCTGTGCTCTATGTAATTATTACTT TCATCCATAGCAGAGACTTCAGCAATCCTTAAACCAATTTTATAAGC CTTTTTCCTAAAAATGCAACTCAAGTCGGAACAGGCATGCCACACTACT CTCAGTCCTGGTCCTTGGGCTCACACTGCCGTTGTTCATCTTTACTGTTG CTGTTCTGCTCTTGATATACTCCCTGTGGAATTATAGCAGGATGAGG ACTATGGTAGGCACCAGGAGTATAGCGGACATGCTCACATCAGTGCAAT GCTGTCCATTCTATCATTCCTCATCCTCTATCTCTCCACTACATGGTGG CTGTTCTGATCTCTACTGGTTATTGGTATGTACCCCTCAATACACTGATTGTCTT TTCTGCTTACTGGTTATTGGTATGTACCCCTCAATACACTGATTGTCTT AATTTAGGAAATCCTAAGCTGAAACGAAATGCAAAAATGTTCATTGTC ATTGTAAGTGTTGTCATTGTCAAGAGCTTGGGTCACCTCAAGGAGCCCA AGACTCAGTGACTGCCAGTGCCTCCTACTCATCCTCAGCCAACAAGAC ATCCTGCTCAGAAGCCTGTATAATGCCATCCTAATTGTCCAGCCTGAGT TTAATCCTAGGTTTGGTACTATTCAAAGAGTAAAGTTGATCATTAAAGC ACAACATATGTTGGTGGATGACATCAAGTCCATATCCCAGTTGTCAATT GTAAACCTCACCTTGCAGATGATGACTTGCTGCAGTATATGTGAATCTATAATTT TCTCCAAAAAACAAAAAAAAAAAAAAAAA |
| | SEQ ID NO: 87 - rGR02 nt (3'UTR not pristine) ATTTGCTCCACTATTTGCTCTTCTGCAGTAACACAGACCACAAAACAA TGGAGCCAATGGGTCAAGACTGAAACTTCAGGAAGTGGGAGCCAAATTT TCTTTGTGATAGGTTGGCATATGAGAATTCATTATTTGATGCAGCTTCTG AAAACTGAGGATGTGAAATACTGGATGAAGCAGAGGTGATGACCCTTTGAA ATTAAAAAGCCAAGATGTTCATGGAGATGTTCATGGAGAATTATAAACAATATCGGAA ATTTGATGCTTCCAATGCGGTGTAAATGTAAAGTTTTAAACACAGAGACAT TGAATTTCCAATGACCATTATGTAAAGTTTTAAACAACTACAGCCATTGTTTA CATAAATTGAAGCATGTTCTCACAGAAAAATAGTAACAGGAAATCTTAGGAAAT CTTTTTCAATTATTTTTATGTGAAATATCATGGACTGGCTCAAGAGGAGGAT GGATTCATGACACTAGTGAATATCACTGCTTTGGCCCTTACCAGACTCATTT CTCTACTGGGTCTGTACTCATTGTATATTGTTACTATTTCTGTGCCACAT |

FIG. 8

| FVLILGNSKLRQATLSVLPCLRCRSKDMDTVVF | TTGTCTCATGAGAGACCAGAAATGTTTACAGGCGATAGTGTGTTATCTGGGTAGT |
| --- | --- |
| | GGATAACCACTTCAGACATCTGGCTTGCTACATGTCTTGTGTCTTTTATT |
| | TCCTCAAAATAGCCAGTTTTCTAACTCTTTGTTTCTTTACCTAAAGTGG |
| | AGAGTTAAAAAGTGGTTTAATGATAATACTGATATCACTGATTTCTT |
| | GATGTTAAACATTTCATCATTAGGGATGTATGATGGATTCAACACATTTCCC |
| | TTTATGAAGGTAATATGTCTTATATTTGGTGGATTCTTCTTAATGCCATTC |
| | AGAATTTCTTATTCACAAACTCATCTAAGGTCTTCTTCAGCTCATACCCTTCA |
| | ATCCCATGTTTTTCTTACCCATCAACTCACTCTTCAGCTCATACCCTTCA |
| | CAGTTTCCCTGGTAGCTTTTTCGTGCTCTTTTCTCCACTGTGGAAGCAT |
| | CACAAGAAGATGCAGGTCAATGCCAAAGGACCCAGAGATGCCAGCACCAT |
| | GGCCCACACAAAAGCCTTGCAAATTGGTTCTCCTCCTCCTGCTGTATG |
| | CAATATACTTACTTTCCATTATCACAGGAATTTGAACCTTGACTTGATG |
| | AGATGTATAGTAATACTTTATTTGACCACATATCTGGAGCAGTTTTTC |
| | TATAAGCCACTCATTGTCGTGATTCTGGGAAACAGTAAGCTGAGACAAG |
| | CCACTCTTTCTGTCTGCCCTTGTCTTAGGTGCCGGTCCAAAGATGGAC |
| | ACTGTCGTTTTCTAATAAATCCAGAGTACATTATGCAAAATCTTGAGG |
| | TGATCAGTTCATAGAAAAAGTAATCTTAGAGGGGAAAATAAAATATTGGG |
| | GCTTCAAATGTTGGATGGTAATACATAGGAAGGCAGGACAAGATGAAG |
| | GAGACTAGACATTATATAAGTGATTCACAGGGGAAATGGGAAAGAGGGCT |
| | TTTATATAATGAAGAAGAAGATAAATGATGAAGGATGAGGAAGAGTTAAA |
| | TATGTAAAATGACAATAGAGATGGCATCATGCCGTTTTAAGAAAATTTGGA |
| | ATGCATATGTATGTTTATATATTTTTAATTTTTATTGAATATATTATT |
| | TACATTTTAAAGTTATCCTGTTCCCCACCCCAACCCTCCCACCTCTTCC |
| | CACCTCCCTTGCCCCTGCCCATTCCCCCTGCACTGGGAATCCAGCCTTGACAG |
| | GACCAAGGGCTTCTCCCCCTTTGTTGCCAACAAGGCCATTCTTTGCTAC |
| | ATGTGCAGCAGGAGCCATGGATCTGTCTATGTGTCTCTTTGGATGGTGG |
| | TTTAGTCCCTGGGAGCTCTGTTGTTGGTTATTGTTGTTCTTATGGTGTT |
| | GCAACTCCCTTCAGCTCCTTCAATCTTCCTGTAACTCCTCCAATGTGGA |
| | CCCTGTTCTCAGTCGCACAGCTCCAATGGTTGACTATGAGCATTCACCTCTGATTGT |
| | CATGCACTTCATGCGATCAGCAATGTGTCTTCTGATTGGTCTGTATGT |
| | AGTGCACTCTGGCCACAGCTCTCAGAAGACAGCTACATCAGTCGTCTCCTATAAG |
| | ATATGGGCTGGATCCCAGGTGGGGCCAGGCGCTGAATGGTCATTCCTTCAG |

FIG. 8

| | |
|---|---|
| | TCTTTGCTCCAAACTTTGTCTTTATATCTCCTATGAATATTTGTTCCC<br>CCTTATAAGAATGACTGAAGTATCCACACTTGGCCATCCTTCTTCATGA<br>GCTTCATGTGGTCTGTGAATTGTACATTGTGCAGTTGCAGTTTGGGCT<br>AATATCCAATTATAGTGAGTGCATACCAAAAAAAAAAAAAAAAAAAA<br>AAAAAAAAAAAAAAAAAAAAAAAAAAAAAAAAAAAA |
| SEQ ID NO: 88 - rGR03 aa<br><br>MVPTQVTIFSIIMVLESLVIIVQSCTTVAVLFREWMHFQRLSPVE<br>IILI<br>SLGISHFCLQWTSMLYNFGTYSRPVLLFWKVSVVWEFMNVLTFWLT<br>SLLA<br>VLYCVKVSSFSHPVFLMWLRLKILKLVLWLLLGALIASCLSIIPSVV<br>KYHI<br>QMELLTLDHLPKNSSLILRLQMFEWYFSNPFKMIGFGVPFLVFLIS<br>IILL<br>TVSLVQHWGQMKHYSSSSSLRAQCTVLKSLATFFIFFTSYFLTIV<br>VSFI<br>GTVFDKKSWFWVCEAVIYGLVCIHFTSLMMSNPTLKKALRLQFWSP<br>ESS | SEQ ID NO: 89 - rGR03 nt (cds pristine; 3'UTR not so hot)<br>GCATGGTGCCAACCAAGTACCATTCCTATCATCATGTATGTCTT<br>GAGTCCTTAGTCATAATTGTGCAAAGTTGCACAACGGTTGCAGTGCTGTT<br>CAGAGAGTGGATGCACTTTCAAAGACTGTCGCCGGTGGAAATAATTCTCA<br>TCAGCCTGGGCATTTCACATTTCTGTCTACAGTGACATGGACATCGATGCTGTAC<br>AACTTTGGTACCTACTCTAGGCCTGCTTTCCTTTATTTGAAGGTATCGGT<br>CGTCTGGGAGTTCATGAACGTTTTGACATTCTGGCTAACCAGTTTGCTTG<br>CTGTCCTCACTGTGTCAAGTCTCTTCCTTCCTCTCACCCGTCTTCCTC<br>TGGCTGAGGTTGAAAATTTTGAAACTGGTTCTCTGTTGCTATTGGGCGC<br>TCTGATAGCTTCTGTTTGTTGTCAATCATCCCTTCTGTTGTTAAATATCATA<br>TCCAGATGAATTACTCACCTAGATCATTACCCAAAACAGTTCTTTG<br>ATTCTAAGACTGCAAATGTCGAGTGATGGTATTTCTAATCCTTTCAAAAT<br>GATTGGGTTTGGCGTTCCTTTCCTGCTGTTCCTGATTTCTATCATCTTAC<br>TCACAGTTCTCGCTGGTCCAGCATTGGGGGCAGAATGAAACACTACAGCAGC<br>AGCAGCTCCAGCTCAGACCTGAGAGCTTCAGTGCACTGTTCTGAAGTCTCTTGCCAC<br>CTTCTTCATCTTCTCACATCCTATTTCTGACTATAGTCGTCTCCTTTA<br>TTGGCACCGTGTTGATAAGAAGTCATGGTTCTGGGTCTGCGAAGCTGTC<br>ATCTATGTTTAGTCGTATTCTTCACTTCACTTCCTGATGATGAGCAACCC<br>TACACTGAAAAAAGCACTCAGGTTGCAGTTCTGGAGCCCAGAGTCTTCCT<br>AAGGCAGGAATTCAGTGAAGCCTCTGGGTAAGGAGGCTTTGCATTGGC<br>ACAGTTCCTAGAGTGAAATGCAAACGTGGACACGAACTTCATTCTCTTTC<br>ATGTCCACAGATGGATGGATCTATAAATCATCACCAATCTTCCCTGTATT<br>CTGACCCATCCTTTTCCTGCTCTATCCATAGTCCCCAGTTGGTTTTGAT<br>TTTTCTGATGATCACACCTTAGCTTTAGCCACCGTTGCAATATCAAACAT<br>GATCTATATATGTTACAGCCAAAATCATTCTCACAAATTGTCAATTGCTTCAC<br>AAATTCAGATAAATCCCCCTTCCTGTCAGGAATGATGTATTGTCTGTGCATTC |

```
AATGCTCACCATGCTAAGCCATTCATTCCCTTCCTAACTTGAGTTTAAGA
AGAAAATGTCTTACTGTGCCATGTCCTATTGTGCTTCTGGATGTT
TTATGCAGTGATTAGACACGCCCTTGCCTGTCTCTCCAAATACTGGCCC
TTTATTCCTTATAAGTCTAGTAGAAATGAACTCGTCTTTACTTCATTG
ACGAAGACATTGTATTCTCCCAAAATAGTGTTTAACTACTCTAGTCTC
ATCCATAATATCCTAAATATCAGTGATTCAGTGAGTAACCTGACAA
CAGTTATTGCTTTGACTCTTAATTCAATTGTGCTGTAACATAGAGGAAAC
ATTCTAGAACATTTCCATATTAATTGTGCTTGTGTAGCAAACCAAAATTCT
CCCCAGTTGGGTAAAAATATCAAAAGCACAGAGTAATCAATTTGAAATC
ACTCAGAAGACATCATTGTTCTATATGTTTTTTTAAACTTCCCTCTA
ACAAGTATCAGATCTTTGCCTTTACAGGGTCTGGTCTTACCATGACTATA
TTTTATCACCATGACCAAATATCCTAATTTCTCTTCATCTCTTTGTTTCACTAACTC
AGTAGCAACCAAACCAAATCACATTAATAGCTAACCTGGCACTTATTTCTC
AGCCTTTATCTATTCCAGACACTTTCAATGTATTCTGCTAAACACAATG
ACATCTCTTTGTGTTCTAACGACAAGGAATCATAACTTTCCAACTTTT
ATACATGGTAGACATATTTGGTGAACTTAACTTCTGACTCTTCTTTAGA
AGACTGAAACTACTCCCGAAAGCAAGCCTTCTGATGGAGAAATAGATACG
GGTATCGTGATTCATTGGAAAGTGAATTCCGGTGCCTGGAAAGAAATGG
ATATTTTTTTTCTCTGAGTGTGTCACTGAATGTAAGCATGTATGTAAG
ATCCATATTTGATACTGATAGCCATGAATGTAAGAACTTTCCTCAGCAGTATCCCTG
TAAAGACTGCTACCAAAACTTCGATTCAACTTTCAACTGTGTCCTACTTGAAGAAGGACGTG
ATATTGCATAAGAGAAAAAACACGCTGTCTCCTACTTGGCTCAACTGCAGCTG
TTCCATGCAATGTGGATGTGTCCCAGGCTACATGGCTCAACTGCAGCTG
AAGGTGGGATGGGAAATGGTATAGTTAGTAATGTCGTCGAGCTGTCTCA
CTGGAAAGGAATTCTGAGCAGGAGTAAATGTAAGCAATGGCCAAGGTCTC
CTAGGAATGGGTTGTAAGCTTGTAAGGAGTTGTAAGAGTTGGGA
TCCTTTCAGAATGGATTGAGCAAGAGCCACTGAAACTTGGACTATACCTT
TGTTATTGTATCTAAATCCAGAAGGGTCTTTGCATGTTCCAAAATCTCA
GATAGCTGAAGGAAGACCCCCTCACCCCGCCGTCACACAGGAATACT
AATGAGCTAAAAACTAGGGAGTATTTTAGTGTTCTCACTATTCCCTTTGAA
ATTCCAGAAAACTAGGGAGTATTATCCATGACATACATGAGTTGAGTTGATA
AAAAGTGCAATGGAAAACTTATCCATGACATACATGAGTTGAGTGATA
```

```
AAAACAGCTGAAGGAAGAGGAAGTCTGAAAAAAGATGGAAACAGCAATGA
TGCTTGTCTCCTATATGTGTGACACCCACTAGTTCCAAGGAAACCTTAC
ATCCATTATCTCATTTCAAGCTGGAAGGACAAGTCAGATCACTCAACCG
ACCCAGCTGGAAAACAGACTTAAGAATGTTAAACTCATACTGATGGTTAT
TTCTCACTCTAAAGTCAAATGCAAACAGGGGTTTCAATCTAGAATCAGAGAAACAAAGGGGCTATTTT
TTTAAGGACCAGAGGGTTTCAATCTAGAATCAGAGAAAGATAAAAAGG
GAGATGCTATAGAAAAACAATAGAGAAGATGTGGCCAAGAACAAGGAAAA
TCTCCAGTTAGCTTGGCACTTAGGGGCCAACATGTTTCTGTTGTTCGGTC
TTCAATACTGTATTGCATGTTGGGCTCACTATGTTTTAGTTGTGAGTGGG
TTGTGCTTCCTGGAATTAAGAAAGTCTGTTTCAGATTTCAGGTACAAA
TGTTTAGAAGCCCATTGGTAGCATCAGTGAAATTAGGAAAAAACTGTGAG
CACTGCTGGCTGGACTTGGCAAAGTCATTCACTATTTACACATCAAATTA
TTAGCAACTTGAAATGACTTGTAATACTGTGGAGACTGGCAACGACGGTGAATTC
CCTGGTGAATGACTTGTAATACTGTGGAGACTGGCAACGACGGTGAATTC
CTAGTAACACTTACCATAGAACATCTGTTCATAATTAGACTCGCCCAGATTT
TAGTTGCTAGAGAACAACAATCTTCCTTTACCCATTCCTACTGAGTAG
GATGCATAGGTTCGGAACCCCCATGCGAAACCATCGTTTGACTCCTCCTGGTAG
TCAAGAGAGTCCAGTCACCAGTTCCGAAACACCTGCCAAGTCCTAACTC
CCAACAGTCTACAGTGAAACCTCAGTGTTTGCATGAGGTTTATGTATCT
CCTTACCATTCCTAAATGTCAATACCCGTGCAGGATATTGCATAGG
CTGCCTCCAAGCCTGGGAAACACTCTCCTCCTGCCATTTGCTGGGTTTCA
CCTTTCCAATTCAGTGTGCCCTTTGAACATCAAATCACCAGGCACTGCTTTCTAGGCCCAC
CACTATTGCTGCTCACGCATGAACATCAAATCACCAGGCACTGCTTTCTAGGCCCAC
CTCAGAATTATTCTTCTTTCTACTACTTGTTTCATGCGTATCCATGAGAACTT
TGTCAATTGTCAATTCTACCTTGTTTTAATGnGCCTTTGTAATAG
nGACTATGCCCAGAAATTAATTATATAGTAAGATGGGTAACAAChTTCAA
TTnTGGAATTATATATTAATAAATATTATGTAATAATTATGACTTATTAT
AAnGTCAATCACTGTACCCTACTCCTACTTCACAAGATATCTCGATCATTTTTTTTT
CAATGTGATCAGCATGTGCTCTTTCACAAGATATCTCGATCATTTTTTTTT
GATGATGCCCACAGTGCCATCTATCAGAATAATCTGATCATTTTTTTTT
TTTGCTTTTGAGAAGCCCCGGTTGGTGCTGGGATGCTTCATAGCAGGTCC
ACCATAGACACATGCTTAGAGAGGAAAGCTGCCTCTCCTCCTTCATTCCCAA
```

FIG. 8

```
GGAACAGTAAAAGCAGAAAAGGCTCTTATGTTCTAAAGAACAGAAAATAG
CCTGCATTCAACTACCTCCTGTTCAGAAGGCACCGAAACACCACCAA
GCAAGACACCCCTTACTTTCTCCTGCTTCCCTGCCAATTGATGATCATTT
GGAAATAAGAAGAAAAGAAGAAAGATGGAAGCCAATTAAAACAGTCTTG
TCTATCTCCCTGGTGAGCTCTCAACTTCCTAGTCAGACCAAAGTAGGTGA
AAAATAATAATTTTAATTGGTATGAGAGTCATGTTAGGCTGAAAAT
CTTAAAAAATCTTAGCATAAAAACATTTCCCCTAGACCCATGAAATTTA
TAATATATCTGTGGTTGAGAAAGGCTAGTTATAGAAAAATGTTTAGAAT
CAGAATATTTGAGGGCTCTTTTTGTTTTGCCTAATCATTACATTTGT
TATAAGAAGTCTAAAAGTTGGTATGCTACAGGTCTTGTCATATTTCTCT
GAGGTTGAGTGCCAAGTAGTCTGCATTGTGTTTAAATCCTGCTTAAAATT
ATCCAAGACAATATAACTTCTCAGGAGCTAAGCCAAGGGCCCCTTTCAG
ACTACCTTAGTCCTCTCACCGTTGCACCGTGGCTCATACATCAGAAT
CCTGAGGGAGCATCATGAAATCTTTAACCTTGGGTTTTATTCTCATGCCATTCTGATG
CCTGGTAGAAATCTTTAACCTTGGTTTTTCATATGTTCTTGCATTCTATCG
CTCGTATTAAATTTATGTGTTTCAAATGCTTGTTATTTAAAAGGGAC
TTAAATTATGGTGACATACTTCAAATGCTTGTTATTTAAAAGGGAC
AAAGAGAAAGAAGCTATCAAAAGTATTTAGCAACAGAGGCTTGCCTAATACA
GTCAAGAAAGAAGCTATCAAAAGTATTAGCAACAACATTTATGATAT
ATTCATAACTGTTAACCATTTTAATATTCTAAAATTCACTTTGTTTC
AGAAATGTATATTAAGAGAATCGAGAAACATTTAAGTGATTGAAAATAAAA
GAAAAAACACAAAAATAAGGTATAACACATTTAAGTGATTGAAAATAAAA
ACAAAAGCTTGCAAACAGGAGGAAAAGTACATTGTAGGCTTTCGACATGG
AGCTGCTACTAGGACCCAGGACTTGTTATCATTATTGCCAAGTCCCA
CAAACTCAGGGCAATACATCTCGAGACAGTTTCCTATATTTAATAAAA
CTTCCAAAATTGATACTCAGTGAATTGGCTAGCTTTAATGGCAGTCAT
TGGATAAACAATTCCAATGCCAAATTCCCTAAGTTGATATATTGATTA
ATATGTATATTAAAACATCAGCTATCCATCGGTTGATCAAATACATTC
TTTAGGGATCCATTCTTTTTCCTAAATTTGACTTATATGTGGATTCTTTT
CACAATAAATAAGTAAATGAGCATTTATTTAAAACTATTTAGACGGAA
CTGAATTACAGCCAAGGTAGTCAAATGACTGAGAATAATCACTTACATA
TTTACAAGGGAAAGTGACTCTTCAGATTTAAGTTTAAAATTAGAAGAGAG
```

| SEQ ID NO: 90 rGR04 aa<br><br>MLSAAEGILLCVVTSEAVLGVLGDTFIALANCMEYAKNKKLSKIGF<br>ILIGLAISRIGVVWIIILQGYMQVFFPHILTFGNITEYITYIWFL<br>NHLSVWFATNLNILYFLKIANFSNSVFLWMLKSRVRVFIFLSGCLL<br>TSWLLCFPQFSKMLNNSKMYWGNTSWLQQQKNVFLINQSITNLGIF<br>FFIVSLITCFLLIVFLWRHIRQMHSDGSGLRDLNTEAHVKAMRVL<br>ISFAVLFILHFVGLSIQVLCFFLPQNNLLFITGLIATCLYPCGHSI<br>ILIGNKQLKQASLKALQHLITCCETKRNLSVT | SEQ ID NO: 91 rGR04 nt (pristine cds; 3'UTR not so hot) TGGTTCCATCACATGACACATAGGCTTGAAAAACTTGCAGATAGAG<br>AAGACATAACCCCTCCAACAAGAAGCCAACATATGGGACATTCTCCAGCA<br>GATAATTTATAACAGATGCAACGGAGCAACTTCGAGATCTGCAAAGATG<br>CTGAGTGCAGCAGGCATCCTCCTTTGTGTTGTCACTAGTGAGGCAGT<br>GCTGGGGGTTTAGGAGACAAGAAGCTCTCTAAGATTGGTTCATTCTCATTGGCTTG<br>ATGCCAAGAACAAGAAGCTCTCTAAGATTGGTTCATTCTCATTGGCTTG<br>GCGATTTCCAGATTTGGTGTCGTATGGATAATAATTTTACAGGGGTATAT<br>GCAAGTATTTTTCCACACATGGTGTTTCTCAATCACTTAGTGTCTGGTTTGCTACC<br>AACCTCAATATCCTGGCTGAAAAGTAGAGTCCGTGTGGTTTTTTATCTTTCTGTCAG<br>ATTTCTGGCTGAAAAGTAGAGTCCGTGTGGTTTTTTATCTTTCTGTCAG<br>GATGCTTACTTACCTCGTGGTTACTATGTTTTCCACAATTTCAAAGATG<br>CTTAACAACAGTAAAATGTACTGGGGAAACACGTCTTGGCTCCAGCAGCA<br>GAAAAATGTCTTCCTTATTAACCAAAGTTTAACCAATCTGGGAATCTTCT<br>TTTTCATTATTGTATCCCTGATTACCCTGCTCCTGTGATTGTTTCCTC<br>TGGAGACACATCAGGCAAATGCACTCAGATGTTCAGGACTCAGAGACCTT<br>CAACACAGAAGCTCATGTGAAAGCCATGAGAGTTCTAATATCTTTTGCGG<br>TACTCTTTATCCTGCATTTCGTAGGTCTTTCCATACAAGTGCTATGCTTT<br>TTTCTGCCACAAAACAACCTACTCTTTATAACTGGTTTGATAGCCACATG |
|---|---|

(top-left column, continued)

ATAAATTTCACAAGCTTTCACTCCTAAGGCTAAAGATAGGCTGTGTAGT<br>AGTTATTTCTGAGCACATTGGCACATCACCATTGTCAGTACTTGAGGGTT<br>TGAATGAAGCTCACTCAAGAACTTGGAAAGAAGGTGGTCTTCTGACATC<br>AATCAAGAAACAAGCTTTCCTCCTACTTCTCCCTAAATGCAACAACCT<br>AAGAATTATCCACAAGATGATGGCGAGGCCTATACTACACCGAAAAGAAGCGCATGGG<br>GATGTACATCAATGCGCAGCCTATACTACACCGAAAAGAAGCGCATGGG<br>TCTTAAAAAGTAAAGGGGATATCAAAAATTCGACAACAAACAAAAGTG<br>GCACACACATTAAGCTAGGTCTATGTTTGTCGAACACTGTCAGTCAGTTACACCTGAGAAGG<br>GGACATTTGGTCAGCTCATTCGAACACTGTCAGTCTCATCGAAAAAAAAAAAA<br>TCTATGCTATTACCCATTAAACCTCAGGTCTCATCGAAAAAAAAAAAA<br>AA

```
CCTCTATCCCTGTGGTCACTCAATCATCTTAATTCTAGGAAACAAGCAGC
TGAAGCAAGCCTCCTTGAAGGCACTGCAGCACTTAACGTGCTGTGAGACA
AAAAGAAATCTCAGTCACATAAATGGGTTTGCCAATTAATATCGCCA
TGTTATTCCACTGATTTTCACCTGTTAGTTTCTCTGTCTCTGTTAGT
TTCTGTTTCCATGATCTGTCCATTGATGAGCGTGGGGTGTTGAAATCTCC
GACTATTGTTGTGAGATTAGGTGCTTTTGCATTTGGTGCTTTAGTAAGATTT
CTTTTGTGAATGAGGTGCTTTTGCATTTGGTGCATAGATATTTAAGATT
GAGAGTTCAGCTTGGTGGTGGATTTTCCTTTGATGAACGTCAATTTATTGGATATTA
CTTATCTTTTTGATGATGACTTTTGATTGAACGTCAATTTATTGGATATTA
GATTGGCAACTCAAGATGCTTCTTGAGGTGTTCTGTCTTCTGAGGTGTT
TTTCAGCCATTACTCGAGTGTCCTCTTCACATATCCAGTTTGTTA
TCCTGCATTCAGCAAATGCTGGGTCCTCTTCACATATCCAGTTTGTTA
GTCTATGTCTTTTATTGGGAATTGAGTCCATTGAGTTGAGATGAGAGATAT
AATGAATAGTGATCATTGCTTCTCTCTTTGGTGTTTATTGTCAAGGAAATTATATACT
TATGTTGTTGTCTCTCTTTGGTGTTTATTGCAAGGAAATTATATACTT
GCTTTCTGATGGTGTAGTTTCTCTCTTGTGTTGCAGTTTCTCCTTCTAT
TATCCCTTGTAGGCTAGATGGTTTCAATATGTCTTAATTGCATAAGCTTGGTT
TGTCATGGAGATATCTTGGTTCTCTCATCTGTCCTATGAATCGGATG
GGATATAGTAGGCCTGGAATGACATTGTGTTCTCTTAGGGCTGTATGAC
ATCTGTCCAAAAATCTTCCGCTTTCATGTCTTCCTAGGGCTCTAGG
TAATTCTCATAGTCTGCCATTATATCTGTCACTGACCTTTTCCCTTATT
GCTTTTATTTATGTTCTTTCTTGTTTTGTGCATTGGTGTTCTGATTATTAT
GTGATGTGAGGTATCTCTTCTCTTGGCATCTCTTCTTAGTTATGGATGTTTTCT
CTTCTGTATGTTTATGGGCATCTCTTCTTAGTTATGGATGTTTTCT
TCTATAATTTGTTGAATATATCCTGTCCCTTAAGTTAGGAGCCTTC
ACTTTCTTCTATACCGTTATCCTTAGTTTAATCTTCTCACTGCATTC
CTCGATGTTTGACTAGGAACTTTTGCATTTACATTATCTTTGACAG
GTATTTCAATGTTTTCATGGTATCTTCTGCCACTGTGACTCCCTTCTTCT
AGCTCTTGTATAATGTTGGTGATGCTTGTACCTGTCTCCCTTGTGACTCTTATTG
CCTTAGGTTTCTATCTCAGGGTGTCTCCCTTGTGCTTTTTATTG
CTTCTATTCATTCAAATCCTGTAATTCTTTCAGGATTTCTTTCCTCT
CTTTGGTTGTTGTATTTCCTGTAATTCTTTCAGGATTTTCGTGTTCCTCT
```

SEQ ID NO: 92 rGR05
aa  MLGAMEGVLLSVATSEALLGIVGNTFIALVNCMDCTRNKNLYN
IGFILTGLAISRICLVWILITEAYIKIFSPQLLSPINIIELISYLW
IITSQLNVWFATSLSIFYFLKIANFSHHIFLWLKRRINIVFAFLIG
CLLMSWLFSFPVVVKMVKDKKMLYINSSWQIHMKKSELIINYVFTN
GGVFLLFIIMLIVCFLLIISLWRHSKWMQSNESGFRDLNTEVHVKT
IKVLLSFIILFIIHLIGITINVICLLVPENNLLFVFGLTIAFLYPC
CHSLILIANSRLKRCFVRILQQLMCSBEGKEFRNT

SEQ ID NO: 93 rGR05 nt
AAGAGATTCAGATACTACCACAAACATTTTTAAATATATGTAAGTCTT
TAAAGAAAGAAGGAAAGCCACTCCTTTATTGAGCAGCCAATAGATTGCC
ATCTTAAAATTCTGTGGCAGAAGCTATTTTAAAGATCGGAAGATGCTG
GGTGCAATGGAAGGTGTCCTCCTTTCAGTTGCAACTAGTGAGGCTTTGCT
TGGCATTGTAGGGAACATTCATTGCACTTGTGAACTGCATGACTGTA
CCAGGAACAAGAATCTCTATAATATTGGCTTCATTCTCACTGGCTTGGCA
ATTTCCAGAATCTGCCTGGTGATCTTAATCACAGAGCATAACATAAA
AATATTCTCTCCACAGTTGCTGTCTCCTATCAACATAATGAACTCATCA
GTTATCTATGGATAATTCCTCCAGTCAAGATCAATTGAATGTTTGGTTGCTACCAGC
CTCAGTATCTTTTATTTCCTCAAGATAGCAAATTTTTGCCTTCCACCATATT
TCTCTGGTTAAAAGAAGAATTAATATAGTTTTTGCCTTCCTGATAGGGT
GCTTACTTAGTCATGGCTATTTCTTTCCCAGTAGTTGTGAAGATGGTT

SEQ ID NO: 94 rGR06 aa (partial)
EALVGILGNAFIALVNFMGWMKNRKITAIDLLILSSLAMSRICLQCIILLD
CIILVQYPDTYNRGKEMRIIDFFWTLINHLSVWFATCLSIFYFFKIANFF
HPLFLMIKWRIDKLILRTLLACLILSLCFSLPVTENLADDFRRCVKTKER
INSTLRCKLNKAGYASVKVNLNLVMLFPFSVSLIVSFLLLILSLWRHTRQM
QLNVTGYNDPSTTAHVKATKAVISFIVLFIVYCLAFLIATSSYFMPESEL
AVIWGELIALIYPSSHSFILIGNSKLKQASVRVLCRVKTMLKGRKY AAAGATAAAAAAATGCTGTATATAAACTCATCTTGGCAAATCCACATGAA
GAAAAGTGAGTTAATCATTAACTATGTTTCACCAATGGGGAGTATTTT
TACTTTTTATATAATAAGTAATTGTATGTTTTCTTAATTAATTTCCCTT
TGGAGACACAGCAAGTGATGCAATCAAATGAATCAGGATTCAGAGATCT
CAACACAGAAGTTCATGTGAAAACAATAAAAGTTTTATTATCTTTATTA
TCCTTTTATATTGCATTTAATTGGTATTACCATCAATGTCATTGTCTG
TTAGTCCCAGAAAATAACTTGTTATTCGTGTTTGGTTTGACGATTGCATT
CCTCTATCCCTGCTGCACTCACTTACTCCTAATTCTAGACAAACAGCCGGC
TGAAACGATGCTTTGTAAGGATACTGCAACAATTAATGTGCTCTGAGGAA
GGAAAAGAATTCAGAAACACACATGACAGTCTGGAAGACAAACAATCAGAAA
TAGTAAGTGAAAAAAAAAAAAAAAAA SEQ ID NO: 95 rGR06 nt (5'-truncated)
GTGAGGCCTTAGTGGAATCTTAGGAAATGCATTCATTGGTAAAC
TTCATGGGCTGGATGAAGAATAGGAAGATCACTGCTATTGATTAATCCT
CTCAAGTCTGGCTATGTCCAGGATTTGTCTACAGTGTATAATTCTATTAG
ATTGTATTATATTGGTGCAGTATCCAGACGCTTACAACAGGGTAAAGAA
ATGAGGATCATTGATTTCTTCTGGACGCTTACCAACCATTAAGTGTCTG
GTTTGCCACCTGCCTCAGCATTTCTATTTCTTCAAGATAGCAAACTTCT
TCCATCCTCTTTTCCTCTGGATAAGTGGAGAATTGACAAGCTAATTCTG
AGGACTCTACTGGCATGCTTGATTCTCAGAGCGCTGTGTCAAGACAAAGAAA
CACTGAGAATTGGCTGATGATTCAGAATTGCAAATTAAATAAAGCTGGATATGCTTCT
GAATAAACTCTACTCTGAGGTGCAAATTGCAAATTAAATAAAGCTGGATATGCTTCT
GTCAAGTAAATCCAACTTGGTCATGCTGTTCCCCTTTCTGTCCCT
TGTCTCATTCCTTCTTCTTGATTCTCAATGGGTACAACGGTACCAGGCAGA
TGCAACTCAATGTAACAGGTACAATTCCTTCCAGTTCTGTTATTGTCTACTG
AAAGCCACAAAAGCAGTAATTTCTTCCAGCTACTTTATGCCAGAGAGTGAAT
CCTGGCCTTTCTTATAGCCACTTCCAGCTACTTTATGCCAGAGAGTGAAT
TAGCTGTAATTGGGGTGAGCTGATAGTCTAATATATCCTCAAGCCAT
TCATTATCCTGATCCTGGAACAGTAGTAAACTAAACAGCATCTGTAAG
GGTGCTTTGTAGAGTAAAGACTATGTTAAAGGGAAGAAATATTAGCATC

FIG. 8

| SEQ ID NO: 96 rGR07 aa<br><br>MGSSLYDILTIVMIAEFIFGNVTNGFIVLTINCIAWLSKRTLSFIGW<br>IQLFLAISRVVLIWEMLLAWLKYMKYSFSVLAGTELRVMMLTWVS<br>NHFSLWLATILSIFYLLKIASFSRPVFLYLKWRVKKVLLILLLGNL<br>IFLMFNLLQINTHIEDWDQYKRNITWDSRVNEFVGFSNLVLLEMI<br>MFSVTPFTVALVSFILLIFSLWKHLQKMHLSSRGERDPSTKAHVNA<br>LRIMVSFLLLYATYFISFFISLLIPMAHKKGLDLMFSLITVGLFYPSS<br>HSFILLLGHSNLRHSSCLVITYLRCKEKD | ATGGATATATTTGAAGAAAAACTATCACTGTCTAAAGAAAAAGGATGACA<br>AATCATTATCTTTCATTCTTATGAATATTGCTTTCATGCGGTAACATC<br>TTTAACAAACTTAAATCAAATGTTGGGAAATCTCATATACAGCAACTTT<br>GCATGTCTCTGTCTATTCCCTCCCTTGTACATAGTTGACATAAA<br>AAAGAATTTCATGACAAATTGTAATAAATAGCTACAGAGGCAGCA<br>TTTCATAGTAAGTTCTGAATCACTGTTCCAAATGCAAAGCTGCCTGACA<br>AATTCAAAAACAACTGTAACAGTATTCACTGCTGTTTGCATTCTTTGGAA<br>AAGCAGGTGGTTTGTTCCATGACCTGACTTGGAGTTTTCTTCTTACATC<br>ACTG<br><br>SEQ ID NO: 97 rGR07 nt<br><br>CAGTAGCAAAATTTACTATGTCATTGATATTAGTGCAnGnCACTACGT<br>AAGAAGGAAGACTTGAAAGAAGCTTATCTGAGTTTTAAGAATACATGG<br>ACATTTCAGCTTGGCAAATGACGAGCTGTGAATTTTGTCATCTGGACAT<br>GGGAAGCAGCCTGATGATATCTTAACTATTGTCATGATTGCAGAGTTTA<br>TATTCGGAAATGTGACCAATGGATTCATAGTGCTGACAAACTGTATTGCT<br>TGGCTCAGTAAAAGAACTCTTTCTTCATTGGGAAAATGTTACTAGCATGGCTGA<br>AATATATGAAGTATTCATTTCATATTGGCTGGCACAGAGAATTAAGGGTT<br>ATGATGTTGACCTGGGTAGTTTCCAATCACTTAGTCTCTGGCTTGCCAC<br>CATTCTTAAGCATCTTTATTCTGAAGTGGAGAGTAAAAAAGTGCTCCTGCTGATTCTT<br>TTTCCCTGTATCGAAGTGGAGAGTAAAAAAGTGCTCCTGCTGATTCTT<br>CTCGGAAATTTAAATCTCCTGATGTTCAATATATAAGAAATATAACGTGGGATTCCA<br>CATAGAAGACTGGATGGATCAATATAAGAAATATAACGTGGGATTCCA<br>GAGTGAATGAATTGTGGGGTTTTCAAATCTGGTTTTATTGGAGATGATT<br>ATGTTCTCTGTAACACCATTCACCGTGGCTCTGGTCTCCTTCATCCTGTT<br>AATCTTCTTTATGGAAACATCTCCAGAAGATGCATCTCAGTTCCAGAG<br>GGGAACGAGACCCTAGCACAAAAGCCCATGTGAATGCCCTGAGAATTATG<br>GTCTCCTTCCCTCTTACTCATGCCACTTACTTCATGAATCTTCATATCCTTTTTATATC<br>ATTAATTCCTATGGCACATAAAAAAGGACTAGACTTATGTTTTAGCCTAA<br>CTGTTGGACTTTTCTACCCTTCCAGTTGTCTGGTGATAACCTATCTGAGATG<br>CATTCTAATCTAAGGCATTCCAGTTGTCTGGTGATAACCTATCTGAGATG |

FIG. 8

```
TAAGGAAAAGGATTAGAAATTCACTATTCCATAAGGCAGTAAACCACAT
GCTATTAGTATACTCAGTGCTAGATCCCTAGGCAAGCATTAACATTAAA
AATATATAATTTCTAGATTCTTCTATTGTGATAAACCACTCACTTAGAA
TAATGCTAAAGTAGCGTGATGTTGTATATAAGTGTAAGAATAAAATGTAA
TTAATTAGTTAGGCACAATAACATATGCTACTAAGTAAAACTAGGC
AGGCTGCTACACGCATATTAGAATCCAGGCTGAGGTATATAGACTCAAGA
AATACTGTGGAATAAAGATTTAATTTCATTCTATTGTGAGTTATGTGA
AATCAATGCCATTAAAGCATACACAAGATTTCACACACTGAAACAACT
TCTTGCATTTGTCATATTGTATTGGAAGTAAATTGGAGATAAACTTAAT
ATCAATAAATTACAAATGTAAACATAAACAGGGTGATTAAAAATTAGCC
TCTAGGTCCTGGGAAATGATTCaAGTAAAGTGCTTTCTTTTCAAATAGG
AGAATCTGATTGTAAATCATCTAAAAGTCGGCATAAAATGTCAATGAAA
ATTGTATGTAAAATATAGCTATgGCmAAGACCACCmAAAGAAAGAAAATT
TTGCCTTTGAAACCCAGTAATTGATATCCTTTAAAAAAGCAGTTACATA
TTTTCTGTTTAAGATTTTGTCAAAGGGTAGCTTTGACAACTAATATAAG
CTGAGGAAGGTAGCAAGTGTGAAGTCAGCTAATGGGGTCAGTCAAGTGCT
GTTAGCAGCAGATGGAGGCCACTGCTGAATTAGCAGGCAATTTACAGGG
TGAGCACTGCTAGTGTGCTGACAGAGAAAAGAGAGAAAATCGCATATATATATATATA
AGGGTCTGGTGAGAAAGAAGAGAGAAAATCGCATATATATATATATA
TCTAACAAGTTGACTGAATTAGTGTGGTACACCAATATTTATGATGTTTTTAGGCCCTTTTATT
TTAATGTCAGTCAGTGAATTAGTGTGGTACACCAATATTGCTACTTTATAAATT
CAAAGCAGTTGTTTTATATATTATTCATTATATAACTTTAATATATAAGTTT
AAATCAAAAGTTGTTTATTTGTCCATGATTTACTTTATCATTGGCACACC
TGTGCTCTCATCCTGGGCTTGACCTAGAATGAAAGTTTATCCTTGATCA
TATGTCTGTCACAAGACTACTTCTCTTCCTATAGTAGTTATGTACTTAC
AATATACAAAAGTTTATTGAATTCCTTTTATCACTTATGCAGCCTTTTCT
TACTATTCTATTCTATTCTATTCTATTCTATTCTATTCTAGCAGCCCTTTCT
TTCTATTCTATTCTATTCTATTCTATTCTTAGAATCTCCTATACATTCA
TTTCTGCAAAACCTGAAGTTATTAAAACTAAATAAGGACTCTGTAAGTCAC
CTAACATCCGAAGTTATTAAAACTAAATAAGGACTCTGTAAGTCAC
AAATTTATTTATACTTCACAAAATTCATTATTTTATGGAACTGCAGCATT
```

FIG. 8

| SEQ ID NO: 98 rGR08 aa

MEPVIHVFATLLIHVEFIFGNLSNGLIVLSNFWDWVVKRKLSTIDK
ILLTLAISRITLIWEMYACFKIVYGSSSFIFGMKLQILYFAWILSS
HFSLMFATALSIFYLLRIANCSWKIFLYLKWRLKQVIVGMLLASLV | SEQ ID NO: 99 rGR08 nt

CTGCAGGTTGGTGATCCAGTAATGAGCAGCACTGTTATATCAGGCTTT
CTAAGATCATGAACCTGTCATTCACGTCTTTGCCACTCTACTAATACAT
GTGGAGTTCATTTTGGGAATCTGAGCAATGGATTAATGATTATGAAAAAAAGA
GCCTGGGCCAGAGAGTCACAAGAGTTCCAGAGTTGACTTATTGGCATCTG
CCTGGCTAACTGAAGGATCAGTTTCTGTGTACAATAATTTGTGTATCT
CTTTGATGCAAGATATGAAAAATAATTCAGTCTAAAGTGTCCTTAAA
TTTGAAACTCTCTGGCCAGAATCTAACTATTGATGACCAGTTTGCACCAT
GGACTCAGTGTCTTCTATTGCTTAAAATAAGCAACATCTTGAATGCTTT
TCTGTGTATTAGCCAAATAATTAACAACATGTTTCATGATGTCTCAA
TAACAATACTATTTCTCACAGTTTAATTTTATGCAAAGTTGCT
AATAAGAATTTTTTCAAATTATCAAACGTGAAGAAAACTTGACATTTA
TTTCAAATAAATCTAAATGTTTCTTAGCATATTGCCTTTTACTAACT
TGATTTTTATCATGTTTGGTAGTATTTCTAATTTTCCTTTTTCTAAG
TATGTTATGTAGTAACACCAGGAGAATGAAACAAATGACATTTATACTAA
GGATGTGACAAATAAGGCCAAAGAAGTTTGAAAAATCATGATCCATT
TCTATTCTTCTTTATTAAGTACATAAGCAAATTCTGATGGTGTCT
TGGCCCATATCTTTTGAACACAGTGTAGTGGTGAAGACTTTTCAAATATT
AATGTCATATTTGTACCATCCTGTACTATTCTCCGATTTCATGAGG
AAAAAATGAGGAAGGGTTGTCTGTTGTCGGTCGACTGAAGTGGACCA
AGGGCAGGAATTCCTCTGTTGTTCGGTCCTAGTGTGACTGATGCTCTC
ATTGAAAAACAGGAAGAGAAGAAGACTTTATATGCACCATTCACTCCT
TCCCCCTCCTACATTCCAAATCATTAAGTAGACCTGACTGGCTAAATCA
ATATAGCTATCCGAAATCATTAAGTAGACCTGACTGGCTAAATCA
CAGAAATTCACCTACCTTTCCAGACCTTTGCCAACTGTCTCTTCATTT
GACACTACTGAGAAGTATTACTTGAATTGGATAGAGAAATTTCACTTACAAGTG
AGTGGCTCTATATTACTTGAATTGGATAGAGAAATTTCACTTACAAGTG
ATATTGAAAATGGGAGGAGAATGTATTTTAGCATAAGCACCAGAACACAAA
GCAATTCTTGTTAAAACTTATCGATAATTGATAAATGTAAAAAAGA
AAAAATAAAATACGAACTATTATGAAAAAAAAAAAAAAAA |

FIG. 8

FLPGILMQRTLEERPYQYGGNTSEDSMETDFAKFTELILFNMTIFS
VIPFSLALISFLLLIFSLMWKHLQKMQLSSRGHGDPSTKAHRNALRI
MVSFLLLYTSYFLSLLISWIAQKHHSKLVDIIGIITELMYPSVHSF
ILILGNSKLKQTSLWILSHLKCRLKGENILTPSGKPIN

```
CTTCTGGGACTGGGTCGTTAAACGAAAACTTTCCACAATTGATAAAATTC
TTCTTACATTGGCAATTTCAAGAATCACTCTCCATCTGGGAAATGTATGCT
TGTTTAAAATTGTATATGTTCATCTCATTTATATTGGGATGAAGTT
ACAAATTCTTTATTTGCCTGATCCTTTCAGTCACTTCAGCCTCTGGT
TTGCCACAGCTCTCAGCATCTTTTACTTACTCAGAATAGCTAACTGCTCC
TGGAAGATCTTCCTGTATCTGAAATGGGAGACTAAACAAGTGATTGTGGG
GATGTTGCTGGCAAGCTTGGTGTTCTTGCCTGGAATCCTGATGCAAAGGA
CTCTTGAAGAGAGGCCCTATCAATATGGAGAAACACAAGTGAGGATTCC
ATGGAAAACTGACTTTGCAAAGTTTACAGAGCTGATTCTTTTCAACATGAC
TATATTCTCTGTAATACCATTTTCATTGGCCTTGATTCTTTTCTCCTGC
TAATCTTCTCTTTGTGGAAACATCTCCAGAAGATGCAGCTCAGTTCCAGA
GGACATGGAGACCCTAGCACCAAGGCCCACAGAAATGCTTTGAGAATTAT
GGTCTCCTTCCTCTTGCTCTACACTTCATATTTCCTGTCTCTTCTTATAT
CATGGATTGCTCAGAAGCATCACAGTAAACTGGTTGACATTATTGGTATT
ATTACTGAACTCATGTATCCTTCAGTCCACTCATTTATCCTGATTCTAGG
AAATTCTAAATTAAAGCAGACTTCTCTTTGGATACTCAGTCATTTGAAAT
GTAGACTGAAAGGAGAGAATATTTAACTCATCCATCTGGCAAACCAATTAAC
TAGCTGTTATATATTCTGTATTGCAAACAAATCAGTGAGTTAGTGTTCA
AGGATTCCATCCTTGACTATTGTATCATGGAAGTCATATAGGAGAGGC
TGAACAAGCTATCTTCTGTAAATTGCAAGGTTGCATATATAGTACTGGTA
CTGGGACACCATCCAACCATAAAACCTTCTAACCATAACCTACCTGACTG
CAAGATATGTGGGACAATGGTGGCTCAGAGATTTTGGGACTGGCCAACC
AATGTCTATTCTTTCTTGAGGCTCACTCAATAAGGAGGCCATGCCCAACT
CGTCcCTGGATGGCCAGGAACCAGAATCTCTGATGGsCCAATGATCTATGG
nAGAACCCAGCATTACTGGGAAAAAAGAATAATCACTTTGATGAATGGTC
AAATATTCCTAAATATATTCTGATACACTTGACATCATTTCTCTTTCC
CAATCATCATCACAGGGACTTCTCCCCAGCACCTGATGGAACAGATACC
AAAATTACAGCCAAATACTAAATGCAGGTGGGAACTCCACACTAGGAGAACA
TGGAAGGAAGTACTGTGAGAGCAGAGTGTCCAGAACACTAGAGAACAA
CAGAACATCGAATTAACTAAGCAGCACTCATAGGGTTAATGTAAAATAAA
GCAGCAGTCACATAGACTGCACAGTGTACTCTAGATCCTCTGCATATAT
GTTGTGGTTGTCAAACTTGGGAGTTTTTGTTGGACTAATAACAATGTGAAT
```

FIG. 8

| | |
|---|---|
| SEQ ID NO: 100 rGR09 aa<br><br>MLSAAEGILLSIATVEAGLGVLGNTFIALVNCMDWAKNKKLSKIGF<br>LLFGLATSRIFIVWILILDAYAKLFFPGKYLSKSLIEIISCIWMTV<br>NHMTVWFATSLSIFYFLKIANFSHYIFLMLKRRIDKVFAFLLWCLL<br>ISWAISFSFTVKVMKSNPKNHGNRTSGTHWEKREFTSNYVLINIGV<br>ISLLIMLTACFLLIISLWKHSRQMQSNVSGFRDLNTEAHVKAIKF<br>LISFIILFILYFIGVAVEIICMFIPENKLLFIFGLITASVYPCCHS<br>VILILTNSQLKQAFVKVLEGLKFSENGKDLRAT | SEQ ID NO: 101 rGR09 nt<br><br>GGACACTGCAGCAGATCTGCTATAGAATAACAGATACAAACATAGCAACC<br>TGCAGAGATGCTCAGTGCAGCAGAAGGCATCCTTCTTTCCATTGCAACTG<br>TTGAAGCTGGGCTGGGAGTTTAGGGAACACATTATCGCCCTGGTTAAC<br>TGCATGGATTGGGCCAAGAACAAGAGAGTCTCTAAGATTGTTTCCTTCT<br>CTTGGCTTAGCAACTTCCAGAATTTTATTGTATGGATATTAATTTTAG<br>ACGCATATGCAAAGCTATTCTTTCCGGGAAGTATTGTCTAAGAGTCTG<br>ACTGAAATCATCTCTGTATATGGATGACTGTGAATCACATGACAAATTTT<br>GTTTGCCACCAGCTCAGCATCTTCTATTTCCTAAAATAGCAAATTTTT<br>CCCACTATATTCTCTGGTTAATTCATGGAGAACTGATAAAGTATTTGCC<br>TTTCTTGTGGTGTTTATTAATTCATGGCAATCTCCTTCTCATTCAC<br>TGTGAAAGTGATGAAGAGCAATCCAAAGAATCATGGAAACAGGACCAGTG<br>GGACACATTGGGAGAAGAGAATTCACAAGTAACTATGTTTAATCAAT<br>ATTGGAGTCATTTCACTTGTCTCTTGATCATGACCTTAACTGCATGTTTCTTGTT<br>AATTATTTCACTTGCTGAAACACAGCAGGCAGTCTCATGTTCTAAGTTTCAG<br>GATTCAGAGATCTCAACACTACTGAAGCTCATGTGAAAGCCATAAAAATTTTA<br>ATTTCATTTATCATCCTTTTCATCTTGTACTTTATAGGTGTTGCAGTAGA<br>AATCATCTGCATGTTTATCCCAGAAAACAAACTGCTATTATTTTGGTT<br>TGACAACTGCATCCGTCTATCCCTGCTCACTCAGTCATTCAATTCTA<br>ACAAACAGCCAGCTGAAGCTGAAGCAAGCCTTTGTAAGGTACTGAGGGATTAAA<br>GTTCTCTGAGAACGGAAAAGATCTCAGGGCCACATGAGTCTGAACAGAA<br>ATGGGTAGTCTGGAATAATTGTAAGGAAGTCGTAGAAGGTCTTTTTCATT<br>TGTACAGTGCTCTTACCTTGTTTTTGAGGAGATGTAAACTTTTTATTTT<br>TATTTTTATCCTATGTGAATAAGTGTGTGTGTGTGTGTTAGGTTTATG<br>TGTGTGTATATATGTCTATGTGTGTTTAACATGGATATTCACAGGCAAGG<br>GGGAATAGAGGTAGTTGTTGTTTACCTTAGGGTAGTGTCCTTTGTGTCACT<br>AACTTGTTCTCTCCTTTTACCTTAGGGTAGTGTCCTTTGTGCTGTCACT<br>CTGACAGTCTACACTAGTTGAACTAAGAGCTTTTAGCCAGTTCACTTGTC<br>AAGTAAGTCTCTGACACTTATTCCGCCTCTTGAACCCCTTTTCCACATTT<br>TGTATTGCTTACCACCTTGATATGAAGGTTTCTGAATAGTCCAAAAAAA<br>AAAAAAAAAAAAAAAAAAAAAAAAAAAAAA |

FIG. 8

| SEQ ID NO: 102 rGR10 aa (partial) | SEQ ID NO: 103 rGR10 nt (3'-truncated?) |
|---|---|
| MFLHTIKQRDIFTLIIFFVEITMGILGNGFIALVNIVDWIKRRRI SSVDKILTTLALTRLIYAWSMLIFILLFILGPHLIMRSEILTSMGV IWVNNHFSIWLATCLGVFYFLKIANFSNSLFLYLKWRVKKVVLM | CCCGGGCTGCAGGATTCGGCACGAGAATGAAAACTTTGCTCTACTATTT TGCTGTTCTGTGATACCACAGACCATAAAACAATCGAGCCAAGGATCAA GAGCTGAAACTTCAGAAAGTGGAATCATCTTATTCAACTTCAACAATTTCCTTCCTGATAGGTTAG CTTATGAGAATTCAGCATCTTATTCAACTTCAACTTGATAAGAT ACAGTGTCTGGATGAAGCCGAATTGATCTATTTGGGAGAGAAAACGCCA
TAAACCTCCCTTCTCATGGTAGCAGTGTTCTGATTACAGAATCATGCTGT CACATACAGCTTTTAACAGGTTCCCATAGACAGAATTCATGTCAAACG GAATGCACAGCTGTCACTCTTACCCACGATCTCTCTGCCAGCCATTC CTATTGACTTAAACTGTAGTATTAAACTTTACTGAAATCTCTGCAACC AGTCTGACTATGTCTCTTGAAATCACATGATGATGGTGGAATTTTAATGCC ATGTGAAAATTGTTGTTGTTCAGTTAGTTTCCTACTCTGCCAAATCATTCT CTTACACTTGGCAGAAAAAACCATCAACTGTAGACTATTTGTGTAAAG ACTAATACAGATAGAATAAGTATCTTAATCAAGATGTCATTGTGATTATC CTAATTTCCCAGAGCACTGGTTCCCTTTCCCAGAAAGACTCACAAAGG AACTGAGGCAAACAGTTGTGGTCACTCTTGATATTTACCAGTTGAAACTG AAGAACAGTGTTCCTTTCGTTCAGTTTACTTACTTACAGTTACTTAT TTCATCCATTAAATCCCAAAGTGCTTATTAATAGTAGATATTTGATGAAG CAACAATGGTTATAAGAGTGGATGTGGATCTATGACAAAGATCTAGAGAA ACAGACTATTTGTGAAAGATGGATGAAAGCCCTGATGAAGAAGGATTCTTCA TGGTCTTTGACCCCAGGGAGTTTTGAAATCAAGCAGCCACAGATCAAAGA GAGCTGAGAAGAGGTTCTCTGAACAGAAAATATCCAAGACATGGTGCCAG CCAAAGCAGAAAAATAGTGGACAATTCAGTCAGGACCTGAATGAGGTAGA CAATGTCCTGTTAAGGGTTGGAACAAATATAGATATGGTTCTCAGTAATCAATC ACAGAAACCTACAGGCCGTGTTGAACTCTTGGTTTCTCAGTAATCATAT TTAAATCTTTTTAGAATGGATTTTTATCATCATCATGATCTCCAGC AGAGTCTGCAGGGGCTAAGAGACACTAAGATCATATATAACAATACAAATTC GTCTTCCTGCTGCTCTATCAACCCCTAAAGTCATATTTTATTAAATGGGTATTCT CACATTAGTTAAGTTCTTTTTTTTTACATCTTTATTCCTGGTTTCCAGCGCCGAATTC CCCTAACCCTCCCCCCTTCCTATGCTGGGTATTCCCCTGTGCGCCAATATCC CGAATTC |

| | ACATTATAATAAGGTTTATGAGACAGTTCCTGGGAAATTTGGATATTT |
|---|---|
| | CCTAGTTAGTAGTGTAAATGGGATTTTAAAACATGATTATTTGTATT |
| | TTTAACAACCAACATGAGGAGCTTTTTAAATGCCACTTAGACATTATAAA |
| | CTGAAGCATGTTCTTACACACAATAAAGCAACGTGATATTTTACTTTGA |
| | TAATCATATTTTTGTGGAAATAACAATGGGAATCTTAGGAAATGGATTC |
| | ATAGCACTAGTGAACATTGTGACTGGATCAAGAGAAGGATTCTTC |
| | AGTGGATAAGATTCTCACTACCTTGGCCCTTACCACCAGACTCATTATGCGT |
| | GGTCTATGCTCATTTTATATTGTTATTCATACTGGGCCCGCATTTGATT |
| | ATGAGATCAGAAATACTTACATCAATGGTGTTATCTGGTGTGAACAA |
| | TCACTTCAGCATCGGCTTGCTACATGCCTCGGTGTCTTTATTTTCTCA |
| | AGATAGCCAATTTTCTAACTCTTGTTTCTTTACCTAAAGTGGAGAGTT |
| | AAAAAGTGGTTTTAATG |

SEQ ID NO: 104 rGR11 aa

GSGNGFIVSVNGSSHWFKSKKISLSDFIITSLALFRIFLLWIIFTDS
LIIV
FSYHAHDSGIRMQLIDVFWIFTTHFSIWLISCLSVFYCLKIATFSH
PSFL
*LKSR

... poly(dA) ???

SEQ ID NO: 105 rGR11 nt

GGATCCGAAACGGTTTATCGTCAGTCAGCAGCCATTGGTTCAA
GAGCAAGAAGATTTCTTTGCTGACTTCATCATTACCAGCTTGCCCTCT
TCAGGATCTTTCTGCTGTGATCATCTTACTGATAGCTCATAATAGTG
TTCTTACCACGCCCACGACTCAGGATAAGATGCAACTTATTGATGT
TTTCTGGACATTTACAACCCACTTCAGTATTTGGCTTATCTCCTGTCTCA
GTGTTTCTACTGCCTGAAAATAGCCACTTTCTCCCACCCCTCATTCCTG
TAGCTCAAATCTAGA

SEQ ID NO: 106 rGR12 aa

MLSTVSVFFMSIFVLLCFLGILANGFIVLMLSREWLMRGRLLPSDM
ILLSLGTSRFCQQCVGLVNSFYYSLHIVEYSRSLARQLISLHMDFL
NSAIFWFGIWLSVLFCIKIANFSHPAFLWLKWRFPALVPWLLLGSI
LVSFIVILMFWGNHTVYQAPLRRKFSGNTTFKEWNRRLEIDYFMP
LKLVTTSIPCSLFLVSILLLINSLRRHSQRMQHNAHSLQDPNTQAH
SRALKLSLISFLVLYALSYVSMVIDATVVISSDNVWYMPWQIILYLC
MSVHPFILITNNLKFRGTFRQLLLLARGFWVT

SEQ ID NO: 107 rGR12 nt

GTGTGAGGGACTGTGGGTAGGGCGTGGGAGGAGGCCAGGAACCAAGGCAA
CCAGTGTGACAGGAGGGCTGAAATGCTATCAACTGTATCAGTTTCTT
CATGTCGATCTTTGTTCTGCTCTGTTCCTGGGAATCCTGGCAAACGGCT
TCATTGTGCTGATGCTGAGCAGGAATGCTATGGCCACCCTCCGGATCCTGCTC
CCCTCAGACATGATCCTCCAGTTTGGGCACTTCTACTATTCCTCACCTTGAGT
GTGGTTGGGCTGGTGTGCCCGTCAACTCAGGGTCTATCAGTTCTTG
ACTCCAGGAGCCTTGCCCACTTTGGCACCTGGCTCAGCGTCCTGTTCTGTAT
AACTCAGCCACTTTCTGGTTTGGCACCTGGCTCAGCGTCCTGTTCTGTAT

FIG. 8

| CAAGATTGCTAACTTCTCCCATCCTGCCTTCCTGTGTTGAAGTGGAGAT |
| TCCCAGCATTGGTGCCTGGCTCTTTTGGGAACCACACTTTAAGGACCATT |
| ATCGTAACTCTGATGTTCTTTTCGGGAACACAACCTTTAAGGAGTGGAACAGAA |
| CTTAAGGAGAAATAGACTATTTCATGCCTCTGAAACTTGTCACCAGTCAATT |
| GGCTGGAAATAGACTATTTCATGCCTCTGAAACTTGTCACCAGTCAATT |
| CCTTGCTCTCTTTTTCAGTCTGTTTTGCTGTTGATCAATTCTCAG |
| AAGGCATTCACAAAGAATGCAGCACAATGCTCACAGCTTCACAGACCCCA |
| ACACCCAGGCTCACAGCAGAGCCCTGAAGTCACTCATCTCATTCTGGTT |
| CTTTACGCGCTGTCCATGTGTCCATGGTCATTGACGCTACAGTTGTCAT |
| CTCCTCAGATAACGTGGTATTGGCCCTGCAAATTACTAAATAATCTCAAGTTCCGA |
| GCATGTCCGTACATCCATTATTCCTTATCACTACTAATAATCTCAAGTTCCGA |
| GGCACCTTCAGGCAGCTACTCCTGTTGGCCAGGGATTCTGGGTGACCTA |
| GAAGGTTTGGTCTCTTTATCTGTACCCTTTGAAGAGACTTAGGTGAGGGT |
| GACTTCCCTTGGAAGTGATCTCATCTACAGTGGAGAGGAGAAAATGGAC |
| ACAGGAGGTCATACATGCGGTTCTTCCCTTCTGTTCTGGATATATGAAAATGGAC |
| ACAGGAGGATTCTGAGCGTTCTTCCCTTCTGTTCTGGGAAATGCAAGTACAATATGCC |
| ATTCGAATCTGAACCAGTATTGATCGAACTCGTGAAAATGCAAGTACAATATGCC |
| TGTTCCCTCATGCTCGCTATCCTCTGGTACTTATTAATTCCCT |

... approximately 500 bp to end

SEQ ID NO: 109 rGR13 nt
GGGATTCAGTTGGATAAGAAAAGTCAAAACCCTAAGACTAAGAATTTC
CTTAAGTAGATATCAATTTCTATCCATTGGAAGGAGTTTCCAATCACACT
GAAATTACAATAAAAAAGGAGCAAGATAACTATGGAAGGATGATTTTC
GGTGGAGTGTTTGAGAACTGAGCAGCAAGCAAATTGATAGATGTGGAT
TCCCTCTTTCTATTCAACTGCTTACCTGGATTGGTTCAAATGTACGTGATA
TTGATAATAGCAGTGTTTACACCTGGGTAAAAACAAGAAAATCACCTTCATCA
ACTGGTAAACTACTCTGACTGTTGGCAGCGTCCAGAACTAACTCCATGTCTATCATTC
ACTTCATCCTGATCGTTTGGCAGCGTCCAGAACTAACTCCATGTCTATCATTC
GTATTATTGATGCAATCATCCTAGAACTAGATATATATTCGGTTATAACTGACCAGC
TTACAGTCGAGTGAAATGCTCTGATATATTCGGTTATAACTGACCAGC

SEQ ID NO: 108 rGR13 aa
MCCGFPLSIQLLTGLVQMYVILIAVFTPGMLGNVFIGLVNYSDWVK
NKKI
TFINFLLICLAASRISSVLVVFIDAILELTPHVYHSYSRVKCSDI
FWVI
TDQLSTWLATCLSIFYLLKIAHFSHPLFLWLKWRLRGVIVGFLLFS
LFSL
IVYPLLELLSIWGDIYVIPKSNLTLYSETIKTLAFQKIIVFDMLY
LVPF
LVSLASLLLLFLSLVKHSQNLDRISTTSEDSRAKIHKKAMKMLLSF
LVLF

FIG. 8

| | |
|---|---|
| IIHIFCMQLSRWLFFLFPNNRSTNFLLLTLNIFPLSHTFIIILGNS<br>KLRQ<br>RAMRVLQHLKSQLQELILSLHRLSRVFTMEIA | TGTCAACGTGGCTGCCACCTGCCTCAGCATTTCTACTTACTCAAAATA<br>GCCCACTTCCCCATCCCCTTTCCTTTGTTGAAGTGGAGATTGAGAGG<br>AGTGCTTGTGTTTCTTCTATTTCTTGTTCTCATTGATTGTTTATT<br>TTCTACTCCTGGAATTACTGTCTATTTCAGAAACAATTAGTCCCATTTCTGCTTTTCA<br>AAAAGCAATCGACTTTATATTCAGAAACAATTAAGACCCTTGCTTTTCA<br>AAAGATAATGTTTTTGATATGCTATATTTTATCCTTGGTGAAGCACTCCAAAAC<br>TAGCCTCATTGCTCCTTTTATTTTATCCTTGGTGAAGCACTCCAAAAC<br>CTTGACAGATTTCACCACCTCTGAAGATTCCAGAGCCAAGATCCACAA<br>GAAGGCCATGAAAATGCTATTATCTTTCCTCGTTCTCTTTATAATTCACA<br>TTTTTGCATGCAGTTGTCACGGTGGTTATTCTTTTTGTTTCCAAACAAC<br>AGTCAACTAATTTCTTTGTTAACATTAAACATCTTCCCATTATCTCA<br>TACATTCATTATCATCCTGGGAAACAGCAGCAAGCTTCGACAAAGAGCAATGA<br>GGGTCCTGCAACATCTTAAAAGCCAACTTCAAGAGTTGATCCTCCCTT<br>CATAGATTGTCCAGAGTCTTCACTATGAAAATAGCTAAAGGGGAGACTT<br>GGAAGGTCACTGGTAACTGTTCTTCCGCTGAGTTCTGTTAAGTAATGCT<br>GGACATATGAACTATCCCTAGTGCATACTGATATT<br>... approximately 1500 bp to end? |
| SEQ ID NO: 110 rGR14 aa (partial)<br>VANIMDWVKRRKLSAVDQLLTVLAISRITLLWSLYILKSTFSMVPN<br>FEVA<br>IPSTRLTNLVWIISNHFN | SEQ ID NO: 111 rGR14 nt (oligo sequence removed)<br>CTGTGGCAAACATAATGGATTGGGTCAAGAGAAGAAGCTCTCTCAGTG<br>GATCAGCTCCTCACTGTGCTGGCCATCTCCAGAATCACTCTGTTGTGTC<br>ATTGTACATACGAAATCAACATTTCAATGTGCCAAACTTTGAGGTAG<br>CTATACCGTCAACAAGACTAACTAATCTGTCTGATAATTCTAACCAT<br>TTTAAT |

| |
|---|
| SEQ ID NO: 113 mGR01 nt<br>AGCTGTGCCTGAGCAAGCATTTCTTGTCTGCCACTTCTGAGCTGTGTGA<br>GGAGACACATTATCACGGAAAGAGATTCAGACTCTGTCGCTGTCAAACCT<br>GTATGTTTGCTCCTCTTTACTGTGAAGGCAGAGTTACGAAAAAAATGT |

| |
|---|
| SEQ ID NO: 112 mGR01 aa (notional)<br>MQHLLKTIFVICHSTLAIIIFELIIGILGNGFMALVHCMDWVKRK<br>KMSLVNKLITALAISRIFHLSLLLISLVIFFSYSDIPMTSRMTQVS<br>NNVWIIVANHFSIWLSTCLSVLYFLKISNFSNSFFLYKWRVEKVVS |

FIG. 8

| SEQ ID NO: 114 mGR02 aa | TATGAGAACCAACTCAGAAATTGACAAAAATTTCTAAATGTCATTTTTA |
|---|---|
| VTLLVSLLLLLNLLINLELSICIKECQRNISCSFSSHYAKCHR QVIRLHIFLSVPVVLSLSTFLLLIFSLWTLHQRMQQHVQGGRDAR TTAHFKALQTVIAFFLLYSIPFILSVLIQNELIKKNLFVVFCEVVYI APFTFHSYILIVGDMKLRQACLPLCIIAAEIQTTLCRNFRSLKYFR LCCIF | AAAATTATATTCAAATGGAAATGTGAGCAAATCTTTATACTAATATAT AAAATGCAGCATCTTTAAAGACAATATTGTTATCTGCCATAGCACACT TGCAATCATTTAATCTTTGAATTAATAATAATGGAATTTAGGAAATGGT TCATGGCCCTGGTGCACTGTATGGACTGGGTTAAGAGAAGAAAATGTCC TTAGTTAATAAAATCCTCACTGCTTTGGCAATCTCCAGAATTTTCATCT CAGTTATTGCTTATAAGTTAGTCATATTCTTTCATATTCTGATATTC CTATGACTTCAAGGATGACACAAGTCAGTAATAATGTTTGGATTATAGTC AATCATTTCAGTATCTGGCTTTCTACATGCCTCAGTGCTCTTTATTTCT CAAGATATCCAATTTTCTAACTCTTTTTCTTTATCTAAAGTGGAGAG TTGAAAAGTAGTTTCAGTTACACTGTTGGTGTCATTGCTCCTCCTGATT TTAAATATTTTATTAATTAACTTGGAAATTAGCATATGCATAAGGAATG TCAAAGAAACATATCAGCTTCAGTTCTCATTATTTCCTGTCTGTCCCGTTGTT ACAGGCAGGTGATAAGGCTTCAACTTTTCTCCTGCTCATCTTCCCCGTGGACACTTCA CCAGAGATGCAGCAGCATGTTCAGGGAGGCAGAGATGCCAGAACCACGG CCCACTTCAAAGCCCTACAACAAACTGTGATTGCATTTTCCTACTATATTCC ATTTTATTCTGTCTGTCTAATACAAATATGAATTACTGAAGAAAAATC TTTCGTTGTATTTGTGAGGTTGTATATACAAGCTTTTCCGACATTCCAT CTGCATGAAATTGATTTCTGCTTGCAATTATCACTGATTAAAACTATTAA TAATTAACTAGTTGTATACAAGG |

| SEQ ID NO: 115 mGR02 nt |
|---|
| CAGCACAGTGAAAAACTCATGGGCCACTTGGTCACCCAGGACAGGCGAC GCTGTTATATGCCAAGCTTTCTATGAACATGGAGTTTATTTTGGAATTGAGCAAT TGCCACTGCTACTAATATACGTGGAGTTTATTTTGGAATTGAGCAAT GGATTCATAGTGTTGTCAAACTTCTTGACTGGGTCATTAAACAAAGCT TTCCTTAATAGATAAAATTCTTCTTACATTGCAATTCAAGAATCACTC |

| MESVLHNFATVLIYEFIFGNLSNGFIVLSNFLDWVIKQKLSLIDK ILLTLAISRITLIWEIYAWFKSLYDPSSFLIGIEFQIIYFSWVLSS HFSLWLATTLSVFYLLRIANCSWQIFLYLKQLIVGMLLGSLV FLLGNLMQSMLEERFYQYGRNTSVNTMSNDLAMWTELIFFNMAMFS VIPFTLALISFLLIFSLMKHLQKMQLISRRHRDPSTKAHMNALRI |

FIG. 8

```
MVSFLLLYTMHFLSLLISWIAQKHQSELADIIGMITELMYPSVHSC
ILILGNSKLKQTSLCMLRHLRCRLKGENITIAYSNQITSFCVFCVA
NKSMR
```

```
TCATCTGGAAATATGCTTGGTTTAAAAGTTTATATGATCCATCTTCC
TTTTTAATTGGAATAGAATTCAAATTATTATTTTAGCTGGGTCCTTTC
TAGTCACTTCAGCCTCTGCCTTGCCACAACTCTCAGCGTCTTTATTAC
TCAGAATAGCTAACTGCTCCTGCGGCAGATCTTCTCTATTGAAATGGAGA
CTTAAACAACTGATTGTGGGGATGTTGCTGGGAAGCTTGGTGTTCTTGCT
TGGAAATCTGATGCAAAGCATGCTTGAAGAGAGGTTCTATCAATATGGAA
GGAACACAAGTGTGAATACCATGAGCAATGACCTTGCAATGTGGACCGAG
CTGATCTTTTTCAACATGGCTATGTTCTCTGTAATACCATTACATTGGC
CTTGATTCTTTTCTCCTGCTAATCTTCTCTTTGTGGAAACATCTCCAGA
AGATGCAGCTCATTTCAGAAGACACAGAGACCCTAGCACCAAGGCCCAC
ATGAATGCCTTGAGAATTATGGTGTCCTTCCTTGCTCTATACCATGCA
TTTCCTGTCTCTTCTTATATCATGGATTGCTCAAAAGCATCAGAGTGAAC
TGGCTGATATTATTGGTATGATAACTGAACTCATGTATCCTTCAGTCCAT
TCATGTATCCTGATTCTAGGAGATGTAGGCTTGAAAGGAGAATATCTTTG
TATGCTGAGGCATTTGAGATGTAGGCTTTGTATTCTGTGTTGCAAACAAA
CATATAGCAACCAAATAACTAGCTTTGTATTCTGTGTTGCAAACAAA
TCTATGAGGTAGTTGTTCAAGGAATCTTCCTTGACTTATTGTATCATGG
AAGTCATATATGGGGGCTGGGAGTCTGAAAGAGCTGTCTTCTGTAAGGTTTGT
ATACACTAGTGGGCTGCAGGATATGCTGGAACAATGGTGGCTTGGAAATGTG
CCTATCCTGGCTGCAAAGCAATAGCTAGTCTAACTTGAGGCCCATTCCACAGCAGG
GGACTGGCAAAGCAATAGCTAGTCTAACTTGAGGCCCATTCCACAGCAGG
AAGCTCATGCCCACCCTGCCTGATGGCCAGGAAGCAAAATCTTGATGG
CCCCAAGACCTATGGTAAACTGAACACTACTGGAAAAGAAAGACTCGTG
TTAATGATCTATCAAATATTTCCTAATGATATTCTGATAAACTCATATAT
TAGTCCCTGTCCTAATCATCATCGGGACTTCCTTCCCAGCACCTGATG
GGAGCAGATAGAGATCTACATCCAAATAGTAAGTGTATCTTGGGAACTC
CACTTAAGAATAGAAGGAACAATTATGAGAGCCAGAGTGATCCAGAACAC
TAGGATCACAGAATCAACTAAGCAGCATGCATAGGTCTACTAGGGGTAATGGAGACTG
AAGTGGCAATCACAGAGCCTGCATAGGTCTACTAAGTCCTCTGTGTAT
ATACTGTGCGTGTTAGCTTAGCTTAGGAATTTGTTGACTCCTAACAATGGAT
AAGGAATTC
```

FIG. 8

SEQ ID NO: 116 mGR03 aa
MVLTIRAILWTLTITISLEFIIGILGNVFIALVNIIDWVKRGKIS
AVDKTYMALAISRTAFLLSLLTGFLVSLLDPALLGMRTMVRLLTIS
WMVTNHFSVWFAICLSIFYFLKIANFSNSIFIVLKWEAKKVVSVTL
VVSVILIMNIIVINKFTDRLQVNTLQNCSTSNTLKDYGLFIST
GFTLTPFAVSLTMFLLLIFSLWRHLKNMCHSATGSRDVSTVAHIKG
LQTVVTFLLLYTAFVMSLLSESLNINIQHTNLLSHFLRSIGVAFPT
GHSCVLILGNSKLRQASLSVILWLRYKYKHIENWGP

SEQ ID NO: 117 mGR03 nt
CTTAATAGCAGGGTGTGAATATTTAAATTTCTTTCTGCAGCAACTACT
GAGGGCTTCAGACTGCTGTATACAGGGCATGAAGCATCGATGAAGTTC
AGCTGTGCTGCCTTTGACACAATTTTTGTGTATGTGTGAGAACATAA
ACCATTCATTAGTGAAATTGGCTTTTGGGTGACATTGTCTATGATAGT
TCTGAAAGTGATTATGTTAACAGAAATCAGACACAGCCGTCTAGAACAGATTGTA
TTAACACATCTTGGTAGTTCAGAAGAAATTAGATCATCATGGTGTTGAC
AATAAGGGCTATTTTATGCGGAAATTGATTATTCATAGCTCTGAACATCATA
TTATCATAGGAATTTAGGAAATGTATTCATAGCTCTGTGAACATCATA
GACTGGGTTAAAAGAGGAAAGATCTCTGCAGTGGATAGACCTATATGGC
CCTGGCCATCTCCAGACTGCTTTTTATTGTCACTAATCACAGGGTTCT
TGGTATCATTATTGGACCCAGCTTATTGGAATGAGAACGATGGTAAGG
CTCCTTACTATTTCCTGGATGGTGACCAATCATTTCAGTGTCTGGTTGC
AACATGCCTCAGTATCTTTTATTTTCTCAAGATAGCTAATTCTCAAATT
CTATTTCCTTGTTCTGATATCGGAAAGCTAAAAAAGTGTATCAGTGACA
TTGGTGGTATCTGTGATAATCTTGATCATGAAACATTATAGTCATAAACAA
ATTCACTGACAGACTTCAAGTAAACACACTCCAGAACTTGTAGTACAAGTA
ACACTTTAAAAGATTATGGGCTCTTTTATTCATTAGCACTGGGTTACA
CTCACCCCATTCGCTGTGTCTTGACAATGTTTCTTCTGCTCATCTCTC
CCTGTGGAGACATCTGAAGAATATGTGTCACAGTGCCACAGGCTCCAGAG
ATGTCAGCAGCAGTGGCCACATAAAAGGCTTGCAAACTGTGGTAACCTTC
CTGTTACTATACTGCTTTGTATGTCACTTCTTTCAGAGTCTTTGAA
TATTAACATTCAACATACAAATCTTCTTTCTCATTTTTACGGATATAG
GAGTAGCTTTTCCCACAGGCCACTCCTGTGTACTGTACTGATTCTTGAAACAGT
AAGCTGAGGCAAGCCTCTCTTCTGTGATATTGTGGCTGAGGTATAAGTA
CAAACATATAGAGAAAAAAATCAGTTAATAAGAACAGAATTTAGGAAGGAATC
ACATTCTAGAAAAAATCAGTTAATAGCCATGAACCTTCAGACAAGATCATTA
TGAAATTGAATCTCATAGCCATGAACCTTCAGACAAGAATCATTA
GAGAGATAGAGAGAAATAAATCAGTCTGTAATGAAAGCAAACATGCTATA
AGATTATGAAATAAATCAGTCTGTAATGAAAGCAAACATGCTATA
TTTTATTAATTGGTTTTGGTTTAAGGTCGGGATA

SEQ ID NO: 118 mGR04 aa
MLSALESILLSVATSEAMLGVLGNTFIVLVNYTDWRNKKLSKINF
MLTGLAISRIFTIWITLDAYTKVFLLTMLMPSSLHECMSYIWVII
NHLSVWFSTSLGIFYFLKIANFSHYIFLWMKRRADKVFVFLIVFLI
ITWLASFPLAVKVIKDVKIYQSNTSWLIHLEKSELLINYVFANMGP
ISLFIVAIIACFLLTISLWRHSRQMQSIGSSFRDLNTEAHMKAMKV
LIAFIILFILYFLGILIETLCLFLTNNKLLFIFGFTLSAMYPCCHS
FILILTSRELKQDTMRALQRLKCCET

SEQ ID NO: 119 mGR04 nt
CTGCAGCAGTAAATCACACCAGATCCAGCAGAAGAAGCCTTCTGGAAATTG
GCAGAGATGCTGAGTGCACTGGAGTTTAGGAACATCCTCCTTTCTGTTGCCACTAG
TGAAGCCATGCTGGGAGTTTAGGGAACACATTCTCAAGATTAACTTATTCTC
ACACAGACTGGGTCAGGAATAAGAAACTCCTCAAGATTAACTTATTCTC
ACTGGCTAGACAAAAGGTTTCCTTCGACTATGCCTATGCCGAGCAGTCTAC
TGCATATACAAAGGTTTCCTTCGACTATGCCTATGCCGAGCAGTCTAC
ATGAATGCATGAGTTACATATGGTAATTATTAACCATCTGAGCGTTTGG
TTTAGACCAGCCTCGGCATCTTTATTTTCTGAAGATAGCAAATTTTC
CCACTACATATTCTCTGGATGAAGAGAGAGCTGATAAAGTTTTGTCT
TTCTAATTGTATTCTTAATTATAACGTGGCTAGCTTCCTTCCGCTAGCT
GTGAAGGTCATTAAAGATGTTAAAATATACAGACAACACATCCTGGCT
GATCCACCTGGAGAAGAGTGAGTTACTTATAAACTATGTTTTTGCCAATA
TGGGCCATTCCCTCTTTGGAGACACAGCAGGCAGATGCAATCCATTGGATCAGG
ACCATTCCCTTGGAGACACAGCAAGCTCACATGAAAGCCATTGAAAGTTTAA
ATTCAGAGATCTCAACACAGAAGCTCACATGAAAGCCATTGAAAGTTTAA
TTGCATTTATCATCCTGTTTCTTACAAACATAACTCTTAATCCTAATTCTAA
ACATTATGCTTGTTCTTACAAACATAACTCTCTTATTTTGGCTT
CACTTTGCAGCCATGTATCCCTGTTGCCATTCCTTATCCTAATTCTAA
CAAGCAGGAGCTGAAGCAAGACACTATGAGGGCACTGCAGAGATTAAAA
TGCTGTGAGACTTGACAGAAATGAATGTTCTGGCACAGTTCAGCAGGG
AATCCCTGGAGCCCTTTCCATTCCCACTATGTTCTCACACTGTCTTTAGT
TGAATTGTTAAAAGTTTTGAAACCTTTGGCAACTGATTGACTGCAGCTA
CGCCAGTGTAAGATTTTCATAGTAAGAGCAAACATTGAAAATAAGACTTC
TCAGTCTTATTCATTGAGTTTCTAAAGCATTGACACCATTCACCAGAA
AAACCAAAGGCGAAGAGAGAGAGTTTCAGACATGTGTGATGAATCTGAT
ATTTAGGACATGGAATTGAGGAG~CCAGAGGGATGCTACCGTGTGTCTAC
AGCTTGTTGTTAAATAGCTACTTTCCTTCCAGTTAGTAAAGTAG
ATGCTTGGAGTAGTGGTGAGCAGGCTGTTTCTGAACAGGCGTAGATGGATCTGTGGAA
GTGGTTGAGGAGCTGAAGCAGGCTGTTTCTGAACAAGATAGCAAGGATCTGTGGAA
GAACTGGTCATTGTCATGTGTATCAAAATAGTGATTTCAGATGAAGCCAAGT
TGTAGAGCAAAGATATCTGAGGAAGAATTC

SEQ ID NO: 120 mGR05 aa

MLSAAEGILLSIATVEAGLGVLGNTFIALVNCMDWAKNNKLSMTGF
LLIGLATSRIFIVWLLTLDAYKLFYPSKYFSSSLIEIISYIWMTV
NHLTVWFATSLSLFYFLKIANFSDCVFLWLKRRTDKAFVFLLGCLL
TSWVISFSFVVKMDGKVNHRNRTSEMYWEKRQFTINVVFLNIGV
ISLFMMTLTACFLLIMSLWRHSRQMSGVSGFRDLNTEAHVKAIKF
LISFILFVLYFIGVSIEIICIFIPENKLLFIFGFTTASIYPCCHS
FILILSNSQLKQAFVKVLQGLKFF

SEQ ID NO: 121 mGR05 nt

ATGCTGAGTGCGGCAGAAGGCATCCTCCTTTCCATTGCAACTGTTGAAGC
TGGGCTGGGAGTTTTAGGGAACACATTTATTGCACTGGTAAACTGCATGG
ACTGGGCCAAGAACAATAAGCTTCTATGACTGGCTTCCTCTTCATCGGC
TTAGCAACTTCCAGGATTTTCATTGTGTGGCTATTAACTTAGATGCATA
TGCAAAGCTATTCTATCCAAGTAAGTATTTTCTAGTAGTCTGATTGAAA
TCATCTCTTATATATGGATGACTGTGAATCACCTGACTGTCTGGTTGCC
ACCAGCCTAAGCATCTTCTATTCCTGAAGATAGCCAATTTTCGACTG
TGTATTTCTCTGGTTGCTAACTTCATGGGGTAATCTCCTTCCATTGTGAAG
TGGGGTGTTTGCTAACTTCATGGGTAATCATAGAAACCTTGTGAAG
GTGATGAAGGACGGTAAAGTGAATCATAGAAACACGGACCTCGGAGATGTA
CTGGGAGAAAAAGCAATTCACTATTAACTACGTTTTCCTCAATATTGGAG
TCATTCTCTCTTATGATGACCTTAACTGCATGTTTCTTGTTCAGATTCAG
TCACTTTGGAGACACAGCAGGCAGATGCAGTCTGGTGTTTCAGGATTCAG
AGACCTCAACACAGAAGCTCATGTGAAAGCCATAAATTTTTAATTCAT
TTATCATCCTTTTCGTCTTGTATTTATAGGTGTTTCAATAGAAATTATC
TGCATATTTATACCAGAAAAACAACTGCTATTTATTTTTCTAATTCTAATCTAACA
GCCAGCTAAAGCAAGCCTTTGTAAAGGTACTGCAAGGATTAAAGTTCTTT
TAG

SEQ ID NO: 122 mGR06 aa

MLITVAEGILLCVTSGSVLGVLGNGFILHANYINCVRKKFSTAGFI
LIGLAICRIFVICIIISDGYLKLFSPHMVASDAHIIVISYIWVIIN
HTSIWFATSLNLFYLLKIANFSHYIFFCLKRRINTVFIFLLGCLFI
SWSIAFPQIVKIFNVKKQHRNVSWQVYLYKNEFIVSHILLLNLGVIF
FFMVAIITCFLIIISLWKHNRKMQLYASRFKSLNTEVHVKVMKVLI
SFIILLLHFIGLLIETLSFLKYENKLLLIGLIISCMYPCCHSFI
LILANSQLKQASLKALKQLKCHKKDKDVRVTW

SEQ ID NO: 123 mGR06 nt

TATAGTTGCAGCAGAAGCAACGTTAGGGATCCTGTAGAGATGCTGACTGT
AGCAGAAGGAATCCTCCTTGTTTGTAACTAGTGGTTCAGTCCTGGA
GTTCTAGGAAATGGAATTTATCCTGCATGGCAAACTAACTAACTGTGTCA
GAAAGAAGTTCTCCACAGCTGGCTTATTCTCACAGGCTTGGCTATTG
CAGAATCTTTGTCATATGTATAATAATCTCTGATGCCACATTAGTGATTCTT
TTTTCTCCACATAGGTAATTATCAATCATCAAAGTATCAGTATGGTTGCCACCAGCCT
ACATATGGGTAATTATCAATCATCAAGTATCAGTATGGTTGCCACCAGCCT
CAACCTCTTCTATCTCCTGAAGATAGCAAATTTTCACTACATCTTC
TTCTGCTTGAAGAAGAATCAATACAGTATTATCTTTCCTGGAT
GCTTATTTATATCATGTCAATTGCTTTCCCACAAACAGTGAAGATATT

FIG. 8

| SEQ ID NO: 124 mGR07 aa

MLNSAEGILLCVVTSEAVLGVLGDTYIALFNCMDYAKNKKLSKIGF
ILIGLAISRIGVVWIIILQGYIQVFFPHMLTSGNITEYITYIWFL
NHLSWFVTNLNILYFLKIANFSNSVFLWLKRRVNAVFIFLSGCLL
TSWLLCFPQMTKILQNSKMHQRNTSWVHQRKNYFLINQSVTNLGIF
FFIIVSLITCFLLIVFLWRHVRQMHSDVSGFRDHSTKVHVKAMKFL
ISFMVFFILHFVGLSIEVLCFILPQNKLLFITGLTATCLYPCGHSI
IVILGNKQLKQASLKALQQLKCCETKGNFRVK | TAATGTTAAAAAGCAGCACAGAAaTGTTTCCTGGCAGGTTACCTCTAT
AAGAATGAGTTCATtGTAAGCCACATTCTTCTCAACCTGGAGTTATAT
TCTTCTTATGGTGGCTATCATTACATGCTTCCTATTAATTATTCACT
TTGGAAACATAACAGAAAAGATGCAGTTGTATGCCTCAAGATTCAAAAGC
CTTAACACAGAAGTACATGTGAAAGTCATAGGGATTTGATAGAAACATTGAG
TTATCCTGTTAATCTGTCATTTCATAGGGATTTGATAGAAACATTGAG
CTTTTTAAAATATGAAAATAAACTGCTACTTATTTTGGGTTGATAATT
TCATGCATGTATCCTGCTGTCATTCATTTATCCTAATTCTAGCAAACA
GTCAGCTGAAGCAGGCTTCTTTGAAGGCACTGAAGCAATTAAAATGCCA
TAAGAAAGACAAGGACGTCAGAGTGACATGTAGACATGTGAGAAATG
AATGGTCACAAGAAATAGCCTGGTCTGTGTGAGATGTTGATATCTCTAAGA
CCGTTCACTTCACTTCTGCAATTCTTGCAATTATTTAAAAAAAAGTCTTGCT
GATATCATGGAATCATGGGAAATGTTGCAATTGTGTTTGGGACAGGG
TGACCAGTGAAGGTATGGTTAAGCAGCGAAACACTCATACGTCGTTC
GTTCTTTTTTGTATTTATTTGTGTTGGTGGCCTTCAAGACATGATTT
CTCTATGTAAGTTTTGG |
| SEQ ID NO: 125 mGR07 nt

| TTCATAATGAAGAGGAGGCAGGGCAATGTTGGTTCTCTGTTGTCTGACCAG
TGTATTTGACAGTGAGATACTACACATTTGGTTCTCTGACCAG
AAAGGAACAAGTAATTTATGAAATAGAAGCTTCTATTGCTTATTAAC
AACTGCAAGCAACATTAGTCTGCACACATTTATAGACAAGTAAATC
TTCAAAGCAATAAAAAAGAGCACCCATAAGTTCTGACTCATCACATG
ACAATAGGCTTGAAAGATTGTCTATGTAGATAAGAAGATGCATAACT
TCTCCATCAAGAACCAGTATATGGGACATTCTCCAGCAGATAATTACA
ATAGATGCAGCAGAAGTAACCTTAGAGATCTGTCACTAGTGAGATCTGAATTCAG
CAGAAGGCATCCTCCCTCTTGTTGTTGTCACTTTTAACTGCATGAACAA
TTAGGGGACACATATATTGCACTTTTAACTGCATGGACTATGCTAAGAA
CAAGAAGCTCTCAAGATCGGTTCATTCTCATTGGCTTGGCGATTTCCA
GAATTGGTGTGTGATAATAATTTACAAGGGATTACAAGTATTT
TTCCACACAGCTTACCCTGTGGATAAAATAACTGAAGTATATTACTACAT
ATGGGTATTTTCAATCACTTAAGTGTCTGGTTTGTCACCAACCTCAACA |

FIG. 8

| | |
|---|---|
| SEQ ID NO: 126 mGR08 aa<br>MLWELYVFVFAASVFLNFPVGIIANLFIIVIIIKTWNSRRIASPDR<br>ILFS<br>LAITRFLTLGLFLLNSVVIATNTGRSVYFSTFFLCWKFLDANSLW<br>LVTI<br>LNSLYCVKITNFQHPVFLLKRTISMKTTSLLLACLLISALTTLLY<br>YMLS<br>QISRFPEHIIGRNDTSFDLSDGILTLVASLVLNSLLQFMLNVTFAS<br>LLIH | TCCTCTACTTTCTAAAGATAGCTAATTTTCCAACTCTGTATTTCTCTGG<br>CTGAAAAGGAGAGTCAATGCAGTTTTTATCTTTCTGTCAGGATGCTTACT<br>TACCTCATGGTTACTATGTTTTCCACAAATGACAAAGATACTTCAAAATA<br>GTAAAATGCACCAGAGAAACACATCTGGGTCCACCAGCGGAAAAATTAC<br>TTTCTTATTAACCAAAGTGTGACCAATCTGGGAATCTTTTTCTTCATTAT<br>TGTATCCCTGATTACCTGCTTTCTGTGATGTTTCCCTCGGAGACATG<br>TCAGACAAATGCACTCAGATGTTTCAGGATTCAGAGACCACAGCACAAAA<br>GTACATGTGAAAGTATGAAAATTCTAATATCTTTATGGTCTTCTTTAT<br>TCTGCATTTTGTAGGCCTTTCTATAACTGGTTTGACAGCCACATGCCTCTATCCC<br>AAATAAACTGCTCTTTATAACTGGTTTGACAGCCACATGCCTCTATCCC<br>TGCGGTCACTCAATCATCGTAATTTTAGGAAATAAGCAGTTAAAGCAAGC<br>CTCTTTGAAGGCACTGCAGCAACTAAAATGCTGTGAGACAAAGGAAATT<br>TCAGAGTCAAATAAATAGGTTTGCAAATAAATAGCTGCCTGTTCTTCCA<br>CTGGTTTTACCCTGTTAGTTGATGTTATGAAAAGTTCTGCTATGGTTG<br>ATGACATCTCAAGGAATCTATTTTCTGGTGGCATGTAAGTCCACGTGA<br>AGCCTCACTTCATACTGTGACTATGCAAATTCTTTCCACAAATA<br>ACCAGATAACATTCAGCCTGGAGATAAATTCATTTAAAGCTTTTATGGT<br>GAGGATAAACAAAAAAAAATCATTTTCTGATTCACTGTAACTCC<br>CAGGATGAGTAAAGAAGAAGACAAGACAAGTTGATGCTTGTGTGTGTTGAG<br>GTCTAGACAGAGCTAGGACCAGAGTTGCCTCTCTGCCATTCGGTATTCCTCAGGTGAGA<br>TTCTTTAAGAGTTATTGCCTCTCTGCCATTCGGTATTCCTCAGGTGAGA<br>ATTC |
| | SEQ ID NO: 127 mGR08 nt<br>AAGCTTGTTGTTGTAATTAGGCATTCCTAAGAAATAAGAACAGGAGTGAAG<br>AAATAGTAATTTAATCCTTGAAAGATTTGCATCTCAGTAAAAGCAGCTGC<br>CTCTTAGACCAGAAATGTGTTTGCCATGCTGGAAAATAAAAGGAGACC<br>TCTTTCCAGGCTGCATCCTGTCGTCGCTTACTATTTCAGTTGTTTTCA<br>TCGGCACCAAACCAGGAAAGATGCTCTGGGAACTGTATGTATTTGTGTTT<br>GCTGCCTCGGTTTTTTAAATTTGTAGGAATCATTGCAAATCTATTAT<br>TATAGTGATAATATTATTAAGACTTGGTCAACAGTCGCAGAATTGCCTCTC<br>CGGATAGGATCCGTTCAGCTTGGCCATCACTACTAGATTCCTGACTTGGGG |

FIG. 8

| SLRRHIQKMQRNRTSFWNPQTEAHMGAMRLMICFLVLYIPYSIATL<br>LYLP<br>SYMRKNLRAQAICMIITAAYPPGHSVLLIITHHKLKAKAKIFCFY<br>K | TTGTTTCTACTGAACAGTGTCTACACATTGCTACAAATACTGGAAGGTCAGT<br>CTACTTTTCCACATTTTCTATTGTGTTGGAAGTTTCTGGATGCAAACA<br>GTCTCTGGTTAGTGACCATTCTGAACAGCTTGTATTGTGTGAAGATTACT<br>AATTTCAACACCCAGTGTTTCTCCCTGTTGAAACGGACTATCTCATGAA<br>GACCACCAGCCTGCTGTTGGCCTGTCTTCTGATTCAGCCTCCACCACTC<br>TCCTATATTATATGCTCACAGATATCACGTTTTCCTGAACACATAATT<br>GGGAGAAATGACACGTCATTTGACCTCAGTGATGTATCTTGACGTTAGT<br>AGCCTCTTTGGTCCTGAACTCACTTCTACAGTTTATGCTCAATGTGACTT<br>TTGCTTCCTTGTTAATACATTCCTTGAGAAGACATATACAGAAGATGCAG<br>AGAAACAGGACCAGCTTTGGAATCCCCAGACGGAGGCTCACATGGGTGC<br>TATGAGGCTGATGATCTGTTTCCTCGTGCTCTACATTCCATATTCAATTG<br>CTACCCTGCTCTATCTTCCTTCCTATATGAGGAAGAATCTGAGAGCCCAG<br>GCCATTTGCATGATTATTACTGCTGCTACCCTGCTAGTAACCTCTGTCCT<br>CCTCATTATCACACATCATAAACTGAAAGCTAAAGCTAAAGAAGATTTTCT<br>GTTTCTACAAGTAGCAGAATTTCATTAGTAGTTAACAGCATCAATTCATG<br>GTTTGGTTGCATTAGAAATGTCTCAGTGACCTGAGACTGATCTAAGGTGTGA<br>TCTTGTATCGGCATCCTGACCCTGAGACTGAGATTAAAGTAAATCACATTCGTCA<br>ATACAGCATCTTTGGCTAATATTTAAAGTAAATCACATTCCATAAGAA<br>ATTGTTAAGGATTACGTATTTTCGCTAGCTACTGAAGTCCTAGACAA<br>TGGAAATCACCATACTGTTTCGCTAGCTACTGAAGTCCTAGACAA<br>CATGAATGAAGGCCACATTGTGATGTTCTTGGTTAGCACAGATTAGAGAA<br>TTTGGCCTCAACTGAGCAAGATATC |
| --- | --- |
| | SEQ ID NO: 129 mGR09 nt<br>GAATTCAGAAATCATCAAAAATCTTCAAAACTACATGTTTAAAATAGCCA<br>CTTCAAATGAATACATTTGCAAATCTTTACAACTTTACACTAATACATAAATGGAG<br>CATCTTTTGAAGAGAACATTTGATATCACCGAGAACATACTTCAATTAT<br>TTATTCATTGAATTAATAATTGGACTTATAGGAAACGGATTCACAGCCT<br>TGGTGCACTGCATGACTGGGTTAAGAGAAAAAATGTCATTAGTTAAT<br>AAAATCCTCACCGCTTTGGCAACTTCAGCTCACTGTACCCATATTAGTTACTACTA<br>GCTAGTAGTTTCCAATTAGCTCACTGTACCCATATTAGTTACTACTA<br>GACTGATGATACAGTTCACTAGTACTCTATGGACTATAGCTATAACCATATT |
| SEQ ID NO: 128 mGR09 aa<br>MEHLLKRTFDITENILLIILFIELIIGLIGNGFTALVHCMDWVKRK<br>KMSLVNKILILALATSRIFLLWFMLVGFPISSLYPYLVTTRLMIQFT<br>STLWTIANHISVWFATCLSVFYFLKIANFSNSPFLYLKRRVEKVVS<br>VTLLVSLVLFLNILLNLEINMCINEYHQINISYIFISYYHLSCQ<br>IQVLGSHIIFLSVPVVLSLSTFLLLIFSLWTLHKRMQQHVQGGRDA<br>RTTAHFKALQAVIAFLLLYSIFILSLLLQFWIHGLRKKPPFIAFCQ<br>VVDTAFPSFHSYVLILRDRKLRHASLSVLSWLKCRPNYVK | |

FIG. 8

| | |
|---|---|
| SEQ ID NO: 130 mGR10 aa<br><br>MFSQIISTSDIFTFTIILFVELVIGILGNGFIALVNIMDWTKRRSI<br>SSADQILTALAITRFLYVWFMIICILLFMLCPHLLITRSEIVTSIGI<br>INIVNNHFSVWLATCLGVFYFLKIANFSNSLFLYLKWRVKKVLMI<br>IQVSMIFLIINLLSLSMYDQFSIDVYEGNTSYNLGDSTPFPTISLF<br>INSSKVFVITNSSHIFLPINSLFMLIPFTVSLIVAFLMLIFSLWKHH<br>KKMQVNAKPPRDASTMAHIKALQTGFSFLLLYAVYLLFIVIGMLSL<br>RLIGGKLILLFDHISGLGFPISHSFVLILGNNKLRQASLSVLHCLR<br>CRSKDMDTMGP | AGTGTCTGGTTGCTACATGCCTCAGTGTCTTTATTTCTCAAGATAGC<br>CAATTTTCTAATTCTCCTTTCTCTATCTAAAGAGGAGAGTTGAAAAG<br>TAGTTTCAGTTACATTACTGGTGTCTCTGGTCTCCTTGTTTTAAATATT<br>TTACTACTTAATTGGAAATTAACATGTGTAAATGAATATCATCAAAT<br>AAACATATCATACATCTTCATTTCTTATTACCATTTAAGTTGTCAAATTC<br>AGGTGTTAGGAAGTCACATTATTTCCTGTCGTCCCGTTGTTTTGTCC<br>CTGTCAACTTTCTCCTGCTCATCTTCCCTGTCCTGGACACTTCACAAGAG<br>GATGCAGCAGCATGTCAAGCAGTGATTGCCTTTCTCCTACTATCCATTTT<br>TCAAAGCCTTGCAAGCAGTGATTGCCTTTCTCCTACTATCCATTTT<br>ATCCTGTCACTGTTACTACAATTTGGATCCATTGGAGATATACACAGTCTTTCCTTCATTCC<br>TCCTTTCATTGCATTTTGTCAGTTGTAGATACAGCTTTTCCTTCATTCC<br>ATTCATATGTCTTGATTCTGAGAGACAGGAAGCTGAGACACGCCTCTC<br>TCTGTGTGTCGTGGCTGAAATGCAGGCCAAATTATGTGAAATAATATTT<br>CTTTGTATTTCATTTCAATTTAAAATATTCTTAGAATTGACTGCAT<br>GTATTTCATCTTTTATTTGAAACAACCACTAATTAAAGCTATTACTAATT<br>TAGCAAGTCGTATACAAGGTTATTTTTAATACACATATCAAAAACTGAC<br>ATGTTTATGTTCTACAAAAACTGAATATATCAAAATTATATAAATTTTG<br>TATCAACGATTAACAATGGAGTTTTTTATTTGACCTGTCACGGGACT<br>CCGGTGAGTCAGCTTGTCAGATGAAGTCTGAAAGCTT<br><br>SEQ ID NO: 131 mGR10 nt<br>GAATTCAACATCTTATTCAACTTCAGAAAACTGATATTAGACACAGTGT<br>CTGGATGAAGCAGCAGAGGTGATCTCTTGGGAATAAAAGCCAAGTAGTCATA<br>AAGAATTATGAAACAATTCCTGGGATTGTTTATTGTTGTTACAACAAA<br>TTTATATGTTTGTTAGTCAGTAATGTATAAGTGTATAGTGGATTTAAAGCATGAT<br>TATCTTGAATTTTAACAAAAAACATGTAGTGCTTTTAAATGTAGCAGA<br>AACATTAAAATTGAAGCATGTTCTCACAGATAATAAGCACCAGTGATAT<br>TTTTACTTTACAATAATATTATTTGTGAATTAGTAATCATGGACTGGAAGAAGA<br>GAAATGGATTCATAGCACTAGTGAATATCATGACTGGACCAAGAAGA<br>AGCATTCATCAGCGGATCAGATTCTCACTGCTTTGGCCATTACCAGATT<br>TCTCTATGTGTGTTACAAGATCAGATCAGAAATATCAGAAATATCAACAATCAATTGGTATTATTGG<br>CACATTGCTTACAAGATCAGATCAGAAATAGTAACATCAATCAATTGGTATTATTGG |

```
SEQ ID NO: 132 mGR11 aa (notional!)
MEHPLRRTFDFSQSILLTILFIELIIGLIRNGLMVLVHCIDWVKRK
KFHL
LIKSSPLWQTSRICLLWFMLIHLLITLVADLASTRTMMQFASNPW
TISN
HISIWLATCLGVFYFLKIANFSNSTFLYLKWRVQFLLLNILLVKFE
INMW
INEYHQININIPYSFISYYQXCQIQVLSLHIIFLSVPFILSLSTFLLL
IFSL
WTLHQRMQQHVQGYRDASTMAHFKALQAVIAFLLIHSIFILSLLLQ
LWKH
ELRKKPPFVVFCQVAVIAFPSSHSYVFILGDRKLRQACLSVLWRLIK
CRPN
YVG
```

```
ATAGTGAATAACCATTTCAGCGTTTGGCTTGCACATGCCTCGGTGTCTT
TTATTTCTGAAGATAGCCAATTTTCTAACTCTTTGTTCTTTACCTAA
AGTGGAGAGTTAAAAAGTAGTTTTAATGATAATACAGGTATCAATGATT
TCTTGATTTAAACCTGTTATCTCTAAGCATGTATGATCAGTTCTCAAT
TGATGTTTATGAAGGAAATACATCTTATAATTTAGGGGATTCAACCCAT
TTCCCACAATTCCTATTCTTACTTCATCAATTCATCAAAAGTTTCGTAATCACC
AACTCATCATCCCATATTTTCTTACCATCCATCAACTCCCTGTTCAGTCTCATACC
CTTCACAGTGCCCCTGGTAGCCTTTCTCATGCTCATCTTCTCACTGTGGA
AGCATCACAAAAAGATGCAGGTCAATGCCAAACCACCTAGAGATGCCAGC
ACCATGGCCCCACATTAAAGCCTTGCAAACAGGGTTCTCCTTCCTGCTCT
GTATGCAGTATACTTACTTTTTATTGTCATAGGAATGTTGAGCCTTAGT
TGATAGGAGGAAATTAATACTTTTATTGACCACATTTCTGGAATAGGT
TTTCCTATAAGCCACTCATTGTGCTGATTGTCTGGGAGTGCCGATCAAGATA
ACAAGCCAGTCTTCAGTGTTGCATTCAGAGGTCATTGGGAAACATTTT
TGGACACCATGGTCCATAAAAAAATTTCAGAGGTCATTGGGAAACATTTT
GAGATCTTATAGGGAAAAAGAAAAATGTGGGCTTCAAGCTGGTAGGAG
TAATATAGAAGGATAGGAG

SEQ ID NO: 133 mGR11 nt
AATAATGTATGTGGAAGAGTTAAGTATAAATGTGTATGAGAATGAACTC
AGAAATCATCAAAATCTTTAAAACTGCATGTTAAAAATCACACTTCAAA
TGAATATATTTGTAATTCTTTAGAACTAATAATAAAATGGAGCATCCTT
TGAGGAGAACATTTGATTTCTCCCAGAGCATACTTCTAACCATTTATTC
ATTGAATTAATAATTGGACTTATAAGAAATGGATTAATGGTATTGGTGCA
CTGCATAGATTGGGTAAGAGAAAAAAATTCATTGTTAATCAAATCCT
CACCACTTTGGCAAACTTCCAGAATTTGTCTGCTCGGTTCATGCTAATA
CATCTCCTGATTACTTTATTGTATGCAGATTAGCTAGTACTAGAACGAT
GATGCAATTCGCTAGCAATCCATGGTCTTTATTTCTCAAGATAGCCATCT
GGCTTGCTACATGCCTTGGTGTCTTCTATCTAAAATGGCGAGTTCAGTTCCTCTGTT
TCTAACTCTACTTTCTCTATCTAAATTTGAGATTAACATGTGGATAAATGAATATC
AAATATTTTACTGGTTAAATTTGAGATTAACATGTGGATAAATGAATATC
ATCAAATAACATACCATACCTTCATTCTTATTCAAGTTGTCAAA
```

| | |
|---|---|
| SEQ ID NO: 134 mGR12 aa (partial)<br>GAIVNVDFLIGNVGNGFIVANIMDLVKRRKLSSVDQLLTALAVSR<br>ITLLWYLYIMKRTFLVDPNIGAIMQSTRLTNVIWIISNHFSIWLAT<br>TLSIFYFLKIANFSNSIFCYLRWRFEKVILMALLVSLVLLFIDILV<br>TNMYINIWTDEF | TACAGGTGTTAAGTCTTCACATTATTTCCTGTCTGTCCCTTATTTG<br>TCCCTGTCAACTTTTCTCCTGCTCATCTTCCCTGTGACACTTCACCA<br>GAGGATGCAGCAGCATGTTCAAGGATACAGAGATGCCAGCAATGGCCC<br>ACTTCAAAGCCTTGCAAGCAGTGATTGCCTTTCTCTAATACACTCCATT<br>TTTATCCTGTCACTGTTACTACAACTTTGGAAACATGAATTAAGGAAGAA<br>ACCTCCTTTTGTTGTATTTGTCAGTTGCATATATAGCTTTCCTTCAT<br>CCCATTCATATGTCTTCATTCTGGGAGACAGAAGCTGAGACAGGCTTGT<br>CTCTCTGTGTTGTGAGGCTGAAATGCAGGCCAAATATGTGGGATAAAA<br>TCTCTTTGTGCTTCATTCCAATTCTTAAATATTCTTTGATTTGACTG<br>CATAAATT |
| SEQ ID NO: 135 mGR12 nt (truncated)<br>TTTTCAGCAGTGACTTTGGGAAGCAGAACGTCTCCTCTAGAGACAGTGGGT<br>GCTGCTATCCTAGTTAATGTGGAGCAATAGTTAATGTGGATTTCCTAATT<br>GGAAATGTTGGGAATGGATTCATTGTTGTGGCAAACATAATGGACTTGGT<br>CAAGAGAAGAAGCTTTCTTGCTGTGGATCAGCTGCTACTGCACTGGCCG<br>TCTCCAGAATCACTTTGCTGTGTGACCTGTACATATGAAACGAACATTT<br>TTAGTGGATCCAAACATTGGTGCAATATGCAATCAACAGACTGACTAA<br>TGTTATCTGGATAATTTCTAACCATTTAGTAGCTAATGGCTGGCCACCACCC<br>TCAGCATCTTTTATTTTCTCAAGATAGCAAATTTTTCTAACTCTATTTC<br>TGTTACCTGAGGTGGAGATTTGAAAAGGTGATTTGATGGCATTGCTGGT<br>GTCCCTGGTCCTCCTGTTATAGATATTTTAGTAACAACATGTACATTA<br>ATATTTGGACTGATGAATTC | |
| SEQ ID NO: 136 mGR13 aa<br>MVAVLQSTLPIIFSMEFIMGTLGNGFIFLIVCIDWVQRRKISLVDQ<br>IRTALAISRIALIWLIFLDWWVSVHYPALHETGKMLSTYLISWTVI<br>NHCNFWLTANLSILYFLKIANFSNIIFLYLKFRSKNVVLVTLLVSL<br>FFLFLNTVIIKIFSDVCFDSVQRNVSQIFIMYNHEQICKFLSFTNP<br>MFTFIPFVMSTVMFSLLIFSLWRHLKNMQHTAKGCRDISTTVHIRA<br>LQIIVSVVLYTIFFLSFFVKVWSFVSPERYLIFLFVWALGNAVFS<br>AHPFVMILVNRRLRLASLSLLIFWLWYRFKNIEV | SEQ ID NO: 137 mGR13 nt<br>AAGCTTGTTGTTTGTTTTGGATGAATTCTATTTATGTCATCATCAATTAAGAT<br>TTTCATATGAATCATTAAGAAATCTTGATAGTTGTTGTGAGATATCACT<br>TCTGCAATTTTAAATGAAATTACACTCATATTTGAAGGAACAATATGT<br>TTTAAAGGAATATATTAACAAATCTTCAGCAGTTACCTCAGAAGTTTGGG<br>TATTGTTTTACAGAAAATGTGGCAGTTCTACAGAGCACACTTCCAATAA<br>TTTTCAGTATGGAATTCATAATGGGAACTTAGGAACTTGATTCATTTTT<br>CTGATAGTCTGCATAGACTGGGTCCAAAGAAGAAAAAATCTTAGTGGA |

FIG. 8

SEQ ID NO: 138 mGR14 aa
MLSTMEGVLLSVSTSEAVLGIVGNTFIALVNCMDYNRNKKLSNIGF
ILIGLAISRICLVLLITEAYIKIFYPQLLSPVNIIELISYLMII
CQLNVWFATSLSIFYFLKIANFSHYIFWLKRRIDLVFFLIGCLL
ISWLFSFPVVAKMVKDNKMLYINTSWQIHMKKSELIINYVFTNGGV
FLFFMIMLIVCFLLIISLMRHRRQMESNKLGFRDLNTEVHVRTIKV
LLSFIILFILHFMGITINVICLLIPESNLLFMFGLTTAFIYPGCHS
LILILANSRLKQCSVMIIQLLKCCENGKELRDT

TCAAATCCGCACTGCTCTGGCAATTAGCAGAATCGCTCTAATTGGTTGA
TATTCCTAGATTGGTGGGTGTCTGTTCATTACCCAGCATTACATGAAACT
GGTAAGATGTTATCAACATGATTGATTCCTGGACGGTGATCAATCATTG
TAACTTTTGGCTTACTGCAAACTGAGCATCCTTATTTCTCAAGATAG
CCAACTTTCTAACATTATTTTCTTATCAAGTTTAGATCTAAAAAT
GTGGTATTAGTGACCCTGTTAGTGTCTTAGTTTTCTTGTTCTTAAATAC
TGTAATTATAAAATATTTTCATAATGTATAACCATGAACAAATTGTAAATTT
ATGTGCTCAAATTTCATAACCTAGTTCACATTCATACCTTTTGTTATGTCCAC
CTTTCCTTTACTAACCTATGTTCATCTTCTCCCTGTGAGACATCTGAAGAATA
GGTAATGTTTTCTTTGCTCATCTTCTCCCTGTGAGACATCTGAAGAATA
TGCAGCACACCGCCAAAGGATGCAGAGACATCAGCACCACAGTGCACATC
AGAGCCCTGCAAACCATCATTGTCTGTAGTGCTATACACTATTTTTT
TCTATCATTTTTGTTAAAGTTGGAGTTTTGTGTCACCAGAGATACC
TGATCTTTTTGTTGTCTCGGCTCTGGTAAACAGAAGATTGACATGGCTTCTCTC
CCATTGTCATGATTTTGGTAATACAGAGATTAAAAATATAGACTATAGGGTC
TCTGATTTTTGGCTCTGGTACAGTTTAAAAATATAGAACATAAGGGTC
CAAAGACCACCAAGGAATCATTTTCCTTATCCTAAAGAAAAATCAGGAG

SEQ ID NO: 139 mGR14 nt
CTGCAGTGTATATACCTACCCTGAAGGCTTCATCTAGAGTAAACAAAGTAG
TCTGTATAGTCTGCCATTCCTCAGATTCTCCTCAACTTCCCACCCTCCAG
TGACCTTTCTCCTTTTCTACAGTCAAACTATGGACCTCACAACCTGACAC
TTCTTCAGATGCAAAATATTCTCACAGAGACAAGTAAAACATACAAAACA
AATACTTAATTGCCTATTAACAAATGCAAGAAAGATTCAGGCTTGA
ACATCCTGTAGACAAGCTAAGGACAGGAGCAACTGAAGGGATCTCATGA
AGACCTTTCAGATTCTACCAAAGTAATTTTTATTGAACAGCAATAGATTGGAA
TAAAGAAAGATAAAGCCACTCTCTTTTATTGAACAGCAATAGCTGAA
TCTTAAACAACTGCAACAGAAGCCATTTAAAGATCAACAAAGATGCTGA
GCACAATGGAAGGTGTCCTCCTTTCAGTTGCACTTGGCTTTCAACTGACTATAA
GGCATTGTAGGGAACACATTCATTGCTTTATTCTCACTGGCTTGGCAA
CAGGAACAAGAAGCTCTAATAATTGGCTTATTCTCACTGGCTTGGCAA
TTTCCAGAATTTGCCTTGTGTTGATCTTAATCACAGAGGCATACATAAAA

FIG. 8

| |
|---|
| SEQ ID NO: 140 mGR15 aa<br><br>MCAVLRSILTIFILEFFIGNLGNGFIALVQCMDLRKRRTFPSADH<br>FLTALAISRLALIWVLFLDSFLFIQSPLLMTRNTLRLIQTAWNISN<br>HFSIWFAISLSIFYLFKIAIFSNVLFFYIKRRVKRVLVILLLSMI<br>LLFFNIFLEIKHIDVWIYGTKRNITNGLSSNSFSEFSRLILPSLM<br>FTLVPFGVSLIAFLLLIFSLMKHVRKMQYYTKGCKDVRTMAHTTAL<br>QTVVAFLLLYTTFFISLVVEVSTLEMDESLMLLFAKVTIMIFPSIH<br>SCIFIIKHNKLRQDLLSVLKWLQYWCKREKTLDS |
| SEQ ID NO: 141 mGR15 nt<br><br>AATAATAGAATTTTTAATATCAGAATTTTTAAGTAATGAGTATTGTTA<br>GCAGCATAGCTTATAGCAAAGTTCCAAGTAATTTGATTTGTAATTCT<br>GATTCCCCAAATCAAGTATCAAGTTTACCTGCACAGACAAGGAAGAAG<br>TGCAAAATGTGCAAATGAGAGCAACTTTATTGACTGTCAGTACGTTGA<br>AATTCAGTGTTCCTTAATCTCAGTTATGGATTGACATTTATGTGCACAGAA<br>CCTGGAAGAATTTCAGCCAAGCTGGAGGTAAAATCTCTTATTTTCTTTTAA<br>TAAAACCAAAAGTAAATCACAGGTAAATCTCTTATTTTTCTTTTTAA<br>TACTGTATATGACAAATTTTTAATACAGCATATTTTTTTGAAATTTA<br>GAAAAAACCACTAAGAAATATTCACCAATGGAATAGACTTAAAGTCAC<br>TTAGAATGTGTGCTGTTCACGTAGCATACTGACAATCATTTCATTT<br>TGGAGTTCTTCATTGGAAATCTGGGAATGGATTCATAGTCTGGTACAA<br>TGCATGGACTTACGAAAGAGAAGAACGTTCCCTTCAGCAGATCATTCCT |
| ATATTCTATCCACAGTTGCTGCTCCTGTCAACATAATTGAGCTCATCAG<br>TTATCTATGATAATTATCGTCAATTGAATGTCTGGTTTGCCACTAGTC<br>TCAGTATTTTTTATTCCTGAAGATAGCAAATTTTTTCCCACTACATATT<br>GTCTGGTTAAAAGAAGAATTGATTAGTTTTTTTCTTCCTGATAGGGTG<br>CTTGCTTATCTCATGCGCTATTTCTTTCCCAGTTGTTGCAGATCCACATGAAG<br>AAGATAATAAAATGCTATATAAACACATCTTGGCAATCCACATGAAG<br>AAAAGTGAGTTAATCATTAATGTATGTTTCCTGTTAATCATTCACTTT<br>ATTTTTATGATAATGTTAATTGTATGTTTCCTGTTAATCATTCACTTT<br>GGGAGACATCGCAGGCAGATGGAATCAAATAAATTAGGATTCAGAGATCTC<br>AACACAGAAGTTCATGTGAGAACAATAAAAGTTTTATTGTCTTTTATTAT<br>CCTTTTATATTGCATTCATGGGTATTACCATAAATGTAATTGTCTGT<br>TAATCCCAGAAAGCAACTGTTATTCATGTTGGTTGACAACTGCATTC<br>ATCTATCCCGGCTGCCACTCACTTATCTGCAACTATTACAGCAGACAGTCGGCT<br>GAAGCAGTGCTCTGTAATGATACTGCAACTATTAAAGTGCTGTGAGAATG<br>GTAAAGAACTCAGAGACACATGACAGTCTGGAACACATGCACTATGCTCTTT<br>TGTCAGTGGAAGATACTGAGAGATCTTTTCACTTGCACTATGCTCTTT<br>TATTGATTTGGCATCATTATCAACACACTGTTGGAGCCTTGTGAACTCTTG<br>TTCAGAGTCTTCTGCCCTCCAAGGAATCACACTCC |

FIG. 8

| | |
|---|---|
| | CACTGCTCTGGCCATCTCCAGGCTTGCTCTGATATGGGTTTATTTCTAG<br>ATTCATTCTGTTTATACAATCCCATTACTGATGACTAGAAATACATTA<br>AGACTGATTCAGACTGCCTGAATATAAGCAATCATTCAGTATATGGTT<br>TGCTACCAGCCTCAGCATCTTTATCTCTTCAAGATAGCCATTTTTCTA<br>ACTATCTTTCTTCTACCTGAAGCGGAGAGTTAAAAGGGTGGTTTTGGTG<br>ATATGCTGTCTATCCATGATCCTTTGTTTTTAAATATTTTTAGAAAT<br>CAAACATATTGATGTCTGGATCTATGGAACCAAAAGAAACATAACTAATG<br>GTTTGAGTTCAAACAGTTTTCAGAGTTTTCCAGGCTTATTTTAATTCCA<br>AGTTAAATGTTCACATTAGTACCCTTTGGTGTATCCTTGATAGCTTCCT<br>CCTCCAATCTTTTTCCCTTATGAAACATGTAAGGAAGATGCAGTACTACA<br>CCAAAGGATGCAAAGATGTCAGAACCATGGCCCACACCACAGCCCTGCAG<br>ACTGTGGTTGCCTTCCTCCTATTATATACTTTCTTCTGTCTCTAGT<br>TGTGGAAGTTCAACACTTGAAATGATGAAAGTCTGATGCTTCTGTTTG<br>CAAAAGTTACTATAATAAGTTGAGACAGGACTTGCTTTCAGTACTACAGA<br>TTGAAACATAATAAGTTGGCAAGCGTGAGAGGGTGTAGTTCATATAGAGA<br>ACAGTATTGGTGCAAGCGTGAGAAACCTTGGATTCATAGAAGTATTGA<br>GCATCACCTGAATATTCTAGAGGGGTGTAGTTCATATAGAAGTATTGA<br>ATTTTAAATTGAGCCTTTTGTATATTTCT<br><br>SEQ ID NO: 142 mGR16 nt<br>TTTATGATGGAAAGAATAAAAACCATTAGCAAGGCTTAATGGCTTGTTTGG<br>TATTAGACCTGTACATTGTTTATGGAACATGATATGGAGCTTTGTTTATT<br>GAATATGCACAATATTTTAGAAGCATGTTTCAAGAATCTTAAGTAATTA<br>CAATAGAAATTGAAGCATCCAAGTGAAGATGAATTATAATTGGCAAT<br>CATTTATAGTCATTTGAGTGTGGAACATAAAGGACTTGGTCAAGGAAGAAGAT<br>GGATTCATAGCGGTGGTGAACATAAAGGACTTGGTCAAGGAAGAAGAT<br>CTCTTCAGTGGTTAATATTAGTAAGTTGGTGGATATTGTGCTTTACCAGGA<br>TGCTGTGGTTAATATTAGTAAGTTGGTGGATATTGTGCTTTACCAGGA<br>CAATGGATGACTTAGATAGAAGAGTTAGCATAAGATCACAGTATATGGACAAC<br>ATTCAACCAGAGTAGTCTCTGGTTTGCTACAAGTCTCAGCATCTTTATT<br>TTTCAAGATAGCAAATTTTCCAACCCTATTTTCTTATTTAAAGGTC<br>AGACTAAAAAGTCATGATAGGGACATTGATAATGCTTTAATTGATTCTTT<br><br>SEQ ID NO: 141 mGR16 aa<br>MNGVLQVTFIVILSVEFIIGLFGNGFIAVVNIKDLVKGRKISSVDQ<br>ILITALAISRIALLWLILVSWWIFVLYPGQWMTDRRVSIMHSIWTTF<br>NQSSLWFATSLSIFYFFKIANFSNPIFLYLKVRLKKVMIGTLIMSL<br>ILFCLNIIIMNAPENILITEYNVSMSYSLILNNTQLSMLFPFANTM<br>FGFIPFAVSLVTFVLLVFSLMKHQRKMQHSAHGCRDASTKAHIRAL<br>QTLIASLLLYSIFFLSHVMKVWSALLLERTLLLLITQVARTAFPSV<br>HSWVLILGNAKMRKASLYVFLMLRCRHKE |

SEQ ID NO: 143 mGR17 aa

MKHFWKILSVISQSTLSVILIVELVIGIIGNGFMVLVHCMDWVKKK
KMSLVNQILTALSISRIFQLCLLFISLVINFSYTDLITSSRMIQVM
YNAWILANHFSIWIATCLTVLYFLKIANFSNSFFLYLKWRVEKVVS
VTLLVSLLLLILNLILTNLETDMWTNEYQRNISCSFSSHYYAKCHR
QVLRLHIIFLSVPVVLSLSTFLLLIFSLWTHHKRMQQHVQGGRDAR
TTAHFKALQTVIAFFLLYSIFILSVLIQIWKYELLKKNLFVVFCEV
VYIAFPTFHSYILIVGDMKLRQACLPLCIIAAEIQTTLCRNFRSLK
YFRLCCIF

SEQ ID NO: 144 mGR17 nt

GAATTCTGGTCTCGGCACCCCTGAGCTGTGAGTAGACACATTATCATGG
AAAGAGATTCAGAATCTGTCACTGTCAAAACTGCATGTTGCTCCTCTGT
TAGTGTGTTGGGGAAAGTTAAGAAAATACATTTATGAGAATCAACTCA
GAGGTTGTCAGAAATTGTCGAAACAGCATTTTAAAAATTACATCTCAAC
TGGATATATGACCAAGTCTTTATACTGATATAAAATGAAGCACTTTT
GGAAGATATATCTGTTATCTCCCAGAGCACACTTCAGTCATTTAATC
GTGGAATTAGTAGTAATTGGAATTATAGAAAAAGAAAATGTGGTTCATGTCCTGGTCCA
CTGTATGGACTGGGTTAAGAAAAACAAAATGTCCCTAGTTAATCAAATTC
TTACTGCTTGTCAATCTCAGCTTTCAGCTCTGTTTATTGTTATA
AGTTTAGTAATCAACTTTCATATACAGATTAACTACAAGTTCAAGGAT
GATACAAGTCATGTACAATGCTTGGATTTTAGCCAACCATTTCAGCATCT
GGATTGCTACATGCCTCACTGTCCTTATTTCTAAAGTGGAGAGTTGAAAAAGTAGTTTC
TCTAACTCTTTTTTCTTTATCTAAAGTGGAGAGTTGAAAAAGTAGTTTC
AGTTACACTGTTGGTGTCATTGCTCCTCCTGATTTAAATATTTTACTAA
CTAACTTGGAAACCGACATGTGGACAAATGAAATCAAAGAAACATATCA
TATGTAAAAACATGT

| | TGCAGCTTCAGTTCTCATTACTATGCAAAGTGTCACAGGCAGGTGTTAAG<br>GCTTCACATTATTTCCGTCGTCCCCGTTGTTGTTTGTCCCTGTCAACTT<br>TTCTCCCTGCTCATCTTCCCCTGTGACACATCACAAGAGGATGCAGCAG<br>CATGTTCAGGGAGGCAGAGATGCCAGAAACCACGGCCCACTTCAAAGCCCT<br>ACAAACTGTGATTGCATTTTCCTACTATATTCCATTTTTATTCTGTCTG<br>TCTTAATACAAATTGGAAATATGAATTACTGAAGAAAAATCTTTTCGTT<br>GTATTTGTGAGGTTGTATATATGCTTTCCGACATTCCATTATAT<br>TCTGATTGTAGGAGACATGAAGCTGAGACTACACTATGTAGAACAGGCCTGCCCTCTGTA<br>TTATCGCAGCTGAAATTCAGACTACACTATGTAGACAAAATTAACTGATACAA<br>AAGTACTTTAGATTATGTTGTATATTCTAGACAAAATTAACTGATACAA<br>AATGTCTTTTGTATTTTCATTTAAATATCCTTTAATTTGACTGCATGA<br>AATTGATTTCTGCTTGCAATTATCACTGATTAAAACTATTAATAATTTAA<br>CTAG |
|---|---|
| SEQ ID NO: 145 mGR18 aa<br><br>MVPTQVTIFSLIMVYLESLVIIVQSCTTVAVLFREWMHFQRLSPVE<br>TILISLGISHFCLQWTSMLYNFGTYSRPVLLFWKVSVVWEFMNILI<br>FWLTSWLAVLYCVKVSSFTHPIFLMLRMKILKLVLMLLIGALIASC<br>LSIIPSVVKYHIQMELVTLDNLPKNNSLILRLQQFEWYFSNPLKMI<br>GFGIPFFVFLASIILLITVSLVQHWVQMKHYSSSNSSLKAQFTVLKS<br>LAIFFTFFTSYFLITIVISFIGTVFDKKSWFWVCEAVIYGLVCIHFT<br>SLMMSNPALKKALKLQFWSPEPS | SEQ ID NO: 146 mGR18 nt<br><br>GCGTGCTTCAGAGAGCAGTATACTACAAAGCAAATGTCATTGCTGCCATT<br>GTATATTTCCTAAAGACATTTCACATTTTATCTCCCTGTCCATTGTGT<br>GCAGAGCCCACACTTCAATCAATCAATTCCTAATTATAAGCTATTGTTT<br>CATTATTCATTTCCTACGTTTTTTGCATTTTACTAGTAGAATTTAAAACTCCAAAGC<br>AGAGATTTCTAATTATAATCCTACATGTAGTTAGAATTTAAAATTAT<br>ATACTATTTCTTTGCACCACTGAGTTCAGTAGATTATTCCTGCCTTCCTTATCTTGA<br>TTAACAATTGAACATTTCATGTTAGATTATTCCTGCCTTCCTTATCTTGA<br>ATAATTAAATGTCCATCCACTATCTCAGCCTTAGAATTCACAGAGTCAACAGCTTTCA<br>CCTTGATTCTCTCACTATCTATCAATGACTAGAATCTGTCTGTCACTTTT<br>GAAACCGCTAATTAAAATGTATTTCTTCCTAGATGCTTGTCCTTTAAAGGCCCATGCCA<br>AGAGAAAATGATTTCTCTTCCTAGATGCTTGTCCTTTACAAGTTACAT<br>GCTTTACTGATGTGAATTGGTTTCTTCCAGTTCATCTGGGTTAAGTGA<br>CCTAAGAACCTAGCCATGGAAGGAGAAACAGAAGCAAATATAACGATAC<br>AAGAACAAGTTCCAGAACATTGGAAAGTACTTAGTAAAGGCATTGGAATT<br>AGCAAAAGAATAGTAGCGAAGCAAAAATACTTCATCTCCATTGGGAGGT<br>CAAGAAAGACTATGCAGTGTTTTGATGCAACTTGTCATCTCTGAGTTAG<br>ACGATTCAGCAGCACACACTTTGAACTTGAACTTGAATTGAACAGGTGGAGCCAGCA |

FIG. 8

```
GACCTGAGCTTAGGAATGATGGTGGAATTCCAACCAAAGACTTCCGTT
ACTTTTGATGTCCCTAACAATTCGGTTGCAATGCTCACACGCCCAA
CTGTTGAAATGCTTGGGAAAAGGATTCTGAGACTGGCATTAGTATGTCA
TTTGACAGAATGGGAAACATTGCCCAGGGCATTAATTGCACAGTAAAGGATT
CACCTTTTCTAAGTGCTCAAATTTTAAATTTGnATATTTTAGAAGACAT
TATTTAAAAGAAAGGTGGAGAGAAATAATCCAAACAGCAGCACCTGAGCAGATA
AAGAGGTGAAGAAGAAAAAACAACATGCGTACATGATGGATTTCTCTTTA
TGAAAATGATCAAATGATCTTAGGATCAAGAATCCACACCTGAATGAGAT
TTGCTTGTATCCCTGTGTGAATTGACCTAACAAGCAAAGCACAGACAAA
TGCTGTAGATAGGGAAATGTCTATGTCAAATGTGTGTAAGGAGGATTTGC
ATCCACAAGAAGTGCCCTCTTATACTGAGAGTGCTAAGAACACATGTCC
GTTTCATATTTCGGAAAGTGTATAGAGCTGTTGAGTCTTGGCTAGGAAG
AGACTTCAGAGTGGAAGCATGGTCCAACGCAAGTCACCATTCTCTCCAT
CATCATGTATGTGCTTGAGTCTATTCAGAGAGTGGATGCACTTCAAAGTTGCACAA
CGGTTGCAGTGCGATTCTCATCAGCCTGGGCATCTCACATTTCTGTCTACAGTG
GTGGAGACGAGCTGCATGGTTGCTCTGGGAGTTGTACTTGGTCCCTGTCCTCCTTCAC (corrected)
```

FIG. 8

| | |
|---|---|
| SEQ ID NO: 147 mGR19 aa<br><br>MMEGHMLFFLIVVVQFLIGVLANGLIVVNAIDLIMWKKMAPLDL<br>LLFCLATSRIILQLCILFAQLGLSLVRHTLFADNVTFVYIINELS<br>LMFATWLGVFYCAKIATIPHPLFLWLKMRISRLVPWLILASVVYVT<br>VTTFIHSRETSELPKQIFISFFSKNTTRVRPAHATLLSVFVFGLTI<br>PFLIFTVAVLLLLSSLWNHSRQMRTMVGTREPSRHALVSAMLSILS<br>FLILYLSHDMVAVLICTQGLHFGSRTFAFCLLVIGMYPSLHSIVLI<br>LGNPKLKRNAKTFIVHCKCCHCARAMVTSRNPRLSDLPVPATHHSA<br>NKITSCSSEACIMPS | AACTTCATCCCTTTCACATCCACAAATGGCTGCATCTATACATCATCAC<br>CAGTCTTCCCTGTATTCTGATTTTCTGACCATTCTCTTCCGTCCTATCCATAGTCC<br>CCAGGTTGGTTTGATTTTCTCATGATCACCACCAACTCTGCTTAGCTTT<br>TGCCACCACTGTAATAGTAAACATGGGTGTTCTATATATTACAGTCAAA<br>ATCATTCACATTGTTGATTGCTCACGAAATCATATAAATCCCCCTTC<br>CTGTCAGGAATTTATTGTCTGCTCACTTGAGTTTAAGAAGAAAATGTCTTACCA<br>CATTAATTCCCCTTCCTACCTTGAGTTTAAGAAGAAAATGTCTTACCA<br>TTGCCCACAACCTATTCTGCTGCTTCTAGACTTTATGCAAGTGATTTAT<br>ACACACACACACACACACATACAAACAAC<br><br>SEQ ID NO: 148 mGR19 nt<br>CTGCAGCTAGAGAACTAATGCATAGGAAACTTATATTCCCACCTCCGTG<br>AGTCACTCTGACAGAAGTGAACTTATATTCCCACCTCGTGACGTCACT<br>CTGACAGAAGTGACTTGTTTTGTATGATGCTCCAGGATGCCTATTAGC<br>ATTGAGGACAATCATAATTAAGTAAGCAAGGCATGAAGGTGTCCTCAC<br>TAGTACCTGGAGGCTTCTGGGTTGCATGATTTACTTGTGATGACTCTGAC<br>ACTTAAGAAGACCTGAAAATGCAAAGCTGTCATAAGGCACAGTTCGTT<br>TCTATGGTATCTTCCTTATTTGACTGACATTGAGTTGAGAAGGCAGCA<br>CTATAAACAAATGGGCCCCACCTTGGTCTCAGTTGAAGAAGCCAGAAATCATACA<br>TCATCTCCAAAGGAACCTTGGTCTCAGTTGAAGAAGCCAGAAATCATACA<br>TGGCTGAGACTGTGCATAACTCTATGTATCATTCATTTAAAGAAGTCATTGGTT<br>CTTCTTATTTTAAAATGATGGAAGGTCATATGCTCTTCTTCCTTCTGGTC<br>GTGGTAGTGCAGTTTTAACTGGGTCTTGGCAAATGCCCCACTGGATC<br>TGTCAATGCCATGCACTTGATCATCGTGGAAGAAAATGGCCCACTGGATC<br>TGCTTCTTTTTGCCTGGCGACTTCTCGGATCATTCTTCAATTGTGTATA<br>TTGTTTGCACAGCTGGGTCTATCCTGTTGGTGAGACACACGTTATTTGC<br>TGACAATGTTACCTTTGGTGTTTTCTACTGTGCCAAGAATTGCTACCATCCCTCAC<br>CCACATGGCTTGGTGTTTTCTACTGTGCCAAGAATTGCTACCATCCCTCAC<br>CCACTCTTTCTGTGGCATCTGTGTCTGAAGATGAGGATATCCAGGTTGGTGCCATGGCT<br>GATCCTGGCATCTGTGCTTGAAGATGAGGATATCCAGGTTGGTGCCATGGCT<br>GAGAGACTTCAGAACTTCCTAAGCAACTTCTACTGTTATAAGCTTTTTTCTAAA<br>AATACAACTCGGGTCAGACCAGCCATGCCACCACTACTCCAGTCTTTGT |

FIG. 8

| | |
|---|---|
| SEQ ID NO: 149 mGR20 aa<br><br>MNLVEWIVTIIMMTEFLLGNCANVFITIVNFIDCVKRRKISSADRI<br>ITAIAIFRIGLLWAMLTNWHSHVFTPDTDNLQMRVFGGITWAITNH<br>FTTWLGTILSMFYLFKIANFSNSLFLHLKRKLDNVLLVIFLGSSLF<br>LVAYLGMVNIKKIAWMSIHEGNVTTKSKLIKHVTSINMLFSLINI<br>VPFGISLNCVLLIYSLSKHLKNMKFYGKGCQDQSTMVHLKALQTV<br>VSFLLLYATYSSCVIISGWSLQNAPVFLFCVTIGSFYPAGHSCILI<br>WGNQKLKQVFLLLLRQMRC | CTTTGGGCTCACACTACCATTTCTCATCTTCACTGTGTGCTCTGCTCT<br>TGTTGTCCTCCCCTGTGGAACCACAGCCGGCAGATGAGGACTATGTGGGA<br>ACTAGGGAACCTAGCAGACATGCCCTCGTCAGTGCGATGCTCTCCATTCT<br>GTCATTCCTGCATCCTCTATCTCCATGACAGAACATGGTAGCTGTTCTGATCT<br>GTACCCAAGGCCTCCACTTTGGAAGCAGAACCTTTGCATTCTGCTATTG<br>GTTATTGGTATGTACCCCTCCTTACACTGATTGTCTTAATTTAGGAAA<br>CCCTAAGCTGAAAACGAAAATGCAAAAACGTTCATTGTCCATTGTAAGTGTT<br>GTCATTGTGCAAGAGCTTGGGTCACCTCACTCAAGGAACCCAAGACATCCTGCTCAGA<br>TTGCCAGTGCCTGCTACTCATCATCTTAATTGTCCAACCTGAGCTTAATCATTTCA<br>AGCCTGTATAATGCCATCTTAATTGTCCAACCTGAGCTTAATCATTTCA<br>AAGGGTAAATTGATGATCAAAGCCCAACACATGATACATCAAGGTCC<br>ATATCCCAGTAGTCATGTGGAAATACCACCTTGCAAAATGATGTCATTGA<br>GAAACCAGGGCAAATGGAGTCTAGGTCTTTCAGTATGATTTGCTCAG |
| | SEQ ID NO: 150 mGR20 nt<br><br>CTAGATGGGCTGTTTCATATAATGACTGGAACTCCCACTGTCCACGT<br>CTTGAGTTCTAAAATTTCACTAACAATTTTGACTGCCATAATAATGA<br>AGTTTAAGAAGAACAATCATTTGAAGCAATGACCAGAATTCCTCTTT<br>ATTTGACTTAGCAATGCAATGGCAGAGAGTAAAAAGTATGCAATGAGACAT<br>AAATATACCAGTCAATGGCAGAGAGTAAAAAGTATGCAATTGAGACAT<br>TATGGTAATATAATTTCCATTAAAAATGAGACTGCATTCACCTATTACA<br>ACACATTGCTATTCTGCTCAACACAGAGTTAAAAGAAACAAGAACTCTT<br>GTATACATTCAGTAGTCACAAGTATAATTATGTTCACATATTTAAAAA<br>AATGAATCATGATCTGTGAATTGAGCCTGCCTTTTTTGTCTCTCTTT<br>TTATTCTTTTCCTTTAGACAGACAGAATTTCTTTAGGAAACTGTGCCAATGTCTT<br>ACCATCATAATGATGACACTTCATCGACTGTGTGAAGAGACACTG<br>CATAACCATAGTGAATTATAACTGCTATTCGACTGTGTGAAGAGACACTG<br>CAGCTGATCGAATTATAACTGCTATTCGACTGTGCCATCTGTGAAGAGAAGAATCCCT<br>TGGGCAATGTTAACGAACTGGCATTCACATGTTACCTCCAGACACAGA<br>CAATTACAAATGAGAGTTTTCGGTGGACCATATACCTGGGCTATAACCACC<br>ATTTTACCACTTGGCTGGGGACCATACTGAGCATGTTTATTATTCAAG<br>ATAGCCAATTTTCCAACAGTCTATTCTTCATCTGAGTATAAAAGAAAAACTTGA |

FIG. 8

| SEQ ID NO: 151 mGR21 aa | CAATGTTCTACTTGTGATTTCCTGGATCGTCTCTGTTTTGGTTGAT |
| --- | --- |
| | ATCTTGGGATGGTGAACATCAAAGAGCAAACTGAAGAAGATTGAA |
| | GGAAATGACCACAAAGAGCAAACTGAAGCATGTAACAAGCATCACAAA |
| | TATGCTTCTCTCAGCCTGATAAACATTGTACCATTGTATATCACTGA |
| | ACTGTGTTCTGCTCTTAATCTATTCCCTGAGATCAGAGACATCTCAAGATATG |
| | AAATTCTATGGCAAACTGTGGTCTCTTTTCTCTTGTTATATGCCACATACTCTT |
| | GGCCTGCAAACTGTGGTCTCTTTTCTCTTGTTATATGCCACATACTCTT |
| | CCTGTCATTATATCAGGTTGGATCCTTCTACCCAGCAGGTCTTCATTCTTGTATCTT |
| | TTTTGTGTGACAATTGGATCCTTCTACCCAGCAGGTCTTCATTCTTGTATCTT |
| | GATTGGGGAAACCAGAAACTTAAACAGGTCTTTCTTGTTGTTGCTGAGGC |
| | AGATGAGATGCTGACTGAAAAAATGAAAGTCCCCCTGTCTCTAG |
| SEQ ID NO: 152 mGR21 nt | |
| | CTCTTTGAAGACAATAGTTGTTCTACTAGCTATTGATAGCATGTTACA |
| | TTTGTCATTTCAAGTATGTTCAGAAACAAAGCTACATATTGTGGGAGT |
| | ATATAAAAATGAAAGCATGCCATTCCCAGGCATCCAAGATCCCTGTGT |
| | ATTAAAAGGCAACAACAAGCAGAACCAAATGTTCTGTTTTGACATGAGCTT |
| | CTTCCAATTCAACTGCTGAAAAATTGGATAACTACATAAAACTAAGA |
| | ACACAGAGTGTCACAGAGCAGTCTCATTAGTAACATAAGCTGATAACATAT |
| | ATTGACAGACCCAACCTTTGTGCTCTAGAACATAAGCTGATAACATAT |
| | TGTTGTCCACCTTTGTGCTCTAGAACATAAGCTGATGAATCAAATTTCT |
| | TTAGCAGGAACAGCAATTGTGATACACAGTGAAAGAGAATATATCTTT |
| | ATTTGCATGTAGCAACAGCTGGATGCACTTCATGATTTTCTGCAA |
| | TCTAGTTCAGTCTTTAGATATATATATATAAACCTTAGTGTTGACATGAGCTT |
| | TATATATATATATATAAACCTTAGTGTTGACATGAGCTT |
| | AGAAGGATTTCACAAGAATGTACAGAGCCATTAGCACATAAGAACTAAGA |
| | TCATCGACATTAGGTCAGTCACTACATACAGGACATTTCACCTTGCCAAATGAGAAGC |
| | AGTGAGTCTCTTTCTGTCTGTCTGGACATGGAAGCAATGTGTATGTATCTTAA |
| | CTATGGTTATGCAGAGTTGTATTTGGGTCAGGAAGCAATGATTC |
| | CATTGGTTGGATCCTGCTTTTCTTGCTTGATTGGGTCAGGCCATTTCAAGAACTGGTTGAATAT |
| SEQ ID NO: 151 mGR21 aa | |
| MGSNVVYGLLTMWMLAEFVFGNMSNGFIVLLINCIDWVRKGTLSSIGW | |
| ILLFLAISRMVLIWEMLITWIKYMKYSFSFVTGTELRGIMFTWVIS | |
| NHFSLWLATILSIFYLLKIASFSKPVFLYLKWREKKVLLIVLLGNL | |
| IFLMLNLQINKHIEHWMYQYERNITWSSRVSDFAGFSNLVLLEMI | |
| VFSVTPFTVALVSFILLIFSLWKHLQKMHLNSRGERDPSTKAHVNA | |
| LRIMVSFLLLYATYFISFFLSLIPMAHKTRLGLMFSITVGLFYPSS | |
| HSFILLLGHSNLRQASLWMTYLKCGQKH | |

FIG. 8

```
GGGAAATGTTAATAACATGGATAAAATATATGAAGTATTCATTT
GTGACTGGAACAGAATTACGGGTATCATGTTTACCTGGTAATTTCCAA
TCACTTCAGTCTCTGGCTTGCCACTATTCTCAGCATCTTTATTTGCTCA
AAATAGCCAGTTCTCCAAACCGGTTTTTCTCTATTTGAAGTGGAGAGAG
AAGAAAGTGCTTCTGATTGTCCTTCTGGAAATTGATCTTCTTGATGCT
CAACATATTACAAATAAACAACATATAGAACACTGGATGTATCAATATG
AGAGAAATATAACTTGGAGTTCTAGAGTGATGAGTTTGCAGGGTTTTCA
AATCTGGTCTTATTGGAGATGATTGTGTTCTCTGTAACCATTCACAGT
GGCCCTGGTCTCTCCTCCTTGTTAATCTTCTCCTTGTGGAAACATCTAC
AGAAAATGCATCTCAATTCTAGAGGGGAACGAGACCCCAGCACTAAAGCC
CATGTGAATGCCTTGAGAATTATGGTCTCCTTCCCTTACTCTATGCCAC
TTACTTCATATCTTTTTCTATCATTGATTCCCATGTTGGGCTTTTCTACCCTTCAAGC
GACTGGGTCTTATGTTTAGCATAACTGTTGGGCATTCTAATTAAGGCAAGCCAGTCT
CACTCATTTATCTTAATTTTGGGACATTCTAATTAAGGCATTAGAATTCACTA
TTGGGTGATGACATATCTTAAATGTGGGCAAAAGCATTAGAATTCACTA
TTCCATAAGGCAGCCAAACCACGTGCTACTAGGTATATGATACTACTCAG
TGGTAAAGCCCTAGGCAGCCAAACATTAACCTTAGAAAATATATAATTTGTGA
CTCTTCGTATTTGATAAATCACTCACATATTTAGAAGAATGCTACAGTA
GTGTGATCTTGTACATGATTGTAACAATTCAATTTATTAATATAGTTCA
GGCATGATAACATACCCCTGATAACTGAAAAGTAGGATGCTACATA
TATATTAGATCTAGATTTAATTTCATCCTGTTGTGAGTTATCTGAAATCTAIG
GCAATAAAGATTTAATTTCATCCTGTTGTGAGTTATCTGAAATCTTATGC
TCACTGAAGGCATAACCAAGATTTTCACACACTGAAAATTAATAAACTTAAATG
TTTCTTATATGTTTTAAAAGTAACACATGTAAAGTCTTTGTTATTAGACT
GCAATTGAAATTACAAAGCTAAACACATGTAAAGTCTTTGTTATTAGACT
GTATGTAGGTCCTAGGGATGGCTTAGTAAAGTGCTTGTTGCAAGCTTC
AGGATATGATTCAAATCCCTAGATTCAATTAAAATCTGGCATAAATAG
CCAAATGTAAAATTTGTCTGTAAAATGTAACCAGTGCTAAGAGTACCAAGA
CAACAAAATGTTTACTTTTAAACCATTTATTGATATTCTTTAAAAATA
GGTAGTATTTTACTATTTAAATAAGATTTGTCAAAGCTAGTCTTGAC
ACCTTAGTAAACATAGGAAGGCAACAAGTTGAAGTCAGCTACTAGA
CAGTGCTGCTAGCAGTCGACAGAGAGCCACTGCTGACTGCTACAGCAGATCATT
```

FIG. 8

| | |
|---|---|
| SEQ ID NO: 153 mGR22 aa<br>MSSLLEIFFVIISVVEFIIGTLGNGFIVLINSTSWFKNQKISVIDF<br>ILTW<br>LAISRMCVLWTTIAGASLRKFYKILSYSKNFKFCFDIIWTGSNYLC<br>IACT<br>TCISVFYLFKIANFSNSIFFWIKQRIHAVLIAIVLGTLMYFILFLI<br>FMKM<br>IANNFIYKWTKLEQNTTFPVLDTLSGFLVHSLYNGILIFFFIVSL<br>TSFL<br>LLIFSLWSHLRRMKLQGIHTKDISTEAHIKAMKTMMSFLLFFIIYY<br>ISNI<br>MLIVASSILDNVVAQIFSYNLIFLYLSVHPFLLVLWNSKLKWTFQH<br>VLRK<br>LVCHCGGYS | TACAGGTTCAGCACTAG<br>SEQ ID NO: 154 mGR22 nt<br>AAATGAATAATTTCATGCAAAGATACCATTAGAATGATCACTATTA<br>AATTTAGCAAATACATATTCAAATACCAGCACACAATGTTTCAAATTTAAA<br>ATATAAACATTATAAAACCAGCAGAGAACAAAATGATAGCCTTGATAAT<br>TGTTGGTTTGCTCAAGAAAAATGGTGTATACTTTAACATTTAATTGGGA<br>ACTCAGTTGAGAGCATACATTTAGGGTTTTACAGAGGTATTCATTGCCCA<br>TTTAAGATTTGGATTCACACATCTACATCAATGGGCTGTAATCATTT<br>CCCATGATGAAATAAGGTAGAGACTGCCTATTAAACGACATGTGAGCCT<br>ACTGGAGATTTCTTTGTGATCATTTCGGTTGTAGAATTCATAATAGGAA<br>CTTTGGGAAATGGATTATTGTCCTGATAAACAGTACTTCTTGGTTCAAG<br>AATCAGAAAATCTCTGTAATTGATTTCATTCTTACTTGGTGCCATCTC<br>CAGAAATGTGTTCTATGGACAACAATTGCTGGTGCCTCTCTCAGGAAAT<br>TCTACAAGACGTTAAGTTACTCTAAGAATTTCAAATTTGTTTTGACATT<br>ATCTGGACAGGATCCAACTATTTATGCATAGCCTGTACAACGTGCATCAG<br>TGTCTTCTACTTGTTCAAGAATTGCCAACTTTTCTAATTCCATTTCTTCT<br>GGATTAAACAGAGAATTCATGCAGTACTTCTGGCTATTGTCCAGGCACA<br>CTCAGTATTTCATTTATTTCTCATTTTATGAAAATGATAGCTAATAA<br>TTTTATCTACAAATGGACAAAATTGGAACAAAACAACATTCCTGTTT<br>TAGATACTCTAAGTGTGTTTTATAGTGTCTCTAGCTACCATAGCCTCATT<br>CTCATTCTCTTTTTCATTTGAAGTGCCACCTTAGGAGGATGAAAACTACAGGGCATACATACCA<br>AAGACATAAGCACAGAAGCACACATATATTATATTAGCAACATTATGCTTATTGT<br>TTCCTTTTGTTCTTCATCATATATATATATTAGCAACATTATGCTTATTGT<br>GGCAAGCTCCATTCTTGACAATGTGGTTGCACAAATTTCTCTATAACC<br>TAATATTTCTGTATTTATCTGTTCATCCTTTTCTTCTGGTTTATGGAAC<br>AGCAAATTGAAATGGACATTCCAGCATGTATTGAGAAAGCTGGTGTGTCA<br>TGTGGAGGTTATTCTTGATTTCAGTAAATAACTCAATATAACTGATGG<br>ATTTCTAAGGTAAGAAAATGGAACAAGGAATAAAGAGGAATATATT<br>CCTTTTCAGATCATCTGCTCTGTCATTCTGTCCTTAGCATGCTATTAAGA<br>ATTGTTGACTAAATCCAGTCATTTTTAACATGAGGAAGATGTTTCAAT |

FIG. 8

| SEQ ID NO: 155 mGR23 aa | CCAACTTAGAGAGGGTACAAAATAGTCCTAGGAGCAG |
|---|---|
| MFSQKINYSHLFTFSITLYVEIVTGILGHGFIALVNIMDWVKRRRI SSVDQIITALALTRFIYVLSMLICILLFMLCPHLPRRSEMLSAMGI FWVVNSHFSIMLTTCLGVFYFLKIANFSNSFFLYLKWRVKKVILLI ILASLIFLILHLSLGIYDQFSIAAYVGNMSYSLITDLTQFSSTFLF SNSSNVFLITNSSHVFLPINSLFMLIPFTVSLVAFLMLIPSLMKHH KKMQVNAKQPRDVSTMAHIKALQTVFSFLLLYAIYLLFLIIGILNL GLMEKIVLILIFDHISGAVFPISHSFVLILGNSKLRQASLSVLPCLR CQSKDMDTMGL | SEQ ID NO: 156 mGR23 nt<br>AATTTTCAGCAACCAATATGTTCTCAGAGACTTAGACTCTTAAATGCATCAGAAACATTAT AAATTGAAGCATGTTTCACAGAAAATAACTGCTTAAATCTACAGCCATTGTTACTT TTTCAATCACCTTGTATGTGAACATGGAAATAGTAACGGAATCTTAGGACATGGA TTCATAGCATTAGTGAACATCATGGACTGCTTGGCCCTTACCAGATTCATTTATG TTCAGTGGATCAGATTCCACTGCTTGCATATTGTATTCATGCTGTGCCCACATTTG TCTTGTCTATGCTGATTGCATATTGTATTCATGGTATTCTCGGTAGTCAA CCTAGGAGATCAGAAATGCTTTCAGCAATGTTTCTTCAGCAATGGTATTTCTCGGTAGTCAA CAGCCATTTAGCATCGGCTTACTACATGCCTCGGTGTCTTTATTTTC TCAAGATAGCCAATTTTCTAACTCTTTTTCTTATCTAAAGTGGAGA GTTAAAAAAGTGATTTTAATAATAATCCTGGCATCACTGATTTCTTGAC TTTACACATTTATCTTTAGGGATATATGACAGATTCAGTTCTCAATTGCTGCTT ATGTAGGAAATATGTCTATAGTTTGACAGATTTAACACAATTTCCAGT ACTTTCTTATTCTCCAACTCATCCATCAATGTTTCTTAATCACCAACTCATC CCATGTTTCCTTACCATCCATCAACTCCCTGTTCATGCTCATACCCTCACAG TGTCCCTGGTAGCCTTTCCATGCTCATCTTCTCACTGTGAAGCATCAC ATGTAGGAGAGATGCAGGTCAATGCCAAAACTGTGTTCTCCTTCCTCAGAGATGTCAGTACTATGGC AAAAAGATGCAGGTCAATGCCAAACCTGTGTTCTCCTTCCTCAGAGATGTCAGTACTATGGC CCACATTAAGCCTTGCAAACTCATCAGGAATTTTGAACCTTGGATTGATGGAG TATACTTACTTTTCCTTATCATAGGAATTTTGAACCTTGGATTGATGGAG AAAATAGTGATACTGATATTTGACCACATTCTGGAGCAGTCAGCTGAGACAAGCCA AAGCCACTGTCTCATTGTACTGATTCTGTAAGGTGCCAGTCGAAACAGTAAGCTGAGACACC GTCTTCTGTGTTGCCCTGTCGTAAGGTGCCAGTCCAAAGATATGGGATG ATGGGTCTCTAGTAAATTCCAGAGTACATTTGTAAAAATCTTGAGGATG ATCAGTTCATAGAAAAGATACCTTATGGGGAAATAAAAAGTGGGGC TTCAATCCTGGGAGTAATAATACACAGGAGGGTAGACAGCATGAAGAG ACTAGCACTATATAAGTGGTCTCATACAGGATATGGGAAAGAAGAATTT ATGCAATAAAGAGGGAGATCATATTGGAGGATGAGGAGCATTACATATG TAAAATGACTATAGAATGAATCATGCTAATCTAAAAAAATCTGTAATG CATTCATTCAGTACTATACATATTTTAAAAGAAACTTTCTTATATAG TATATATTCTATACATATTTTAAAAGAAACTTTCTTATATAG |

FIG. 8

| SEQ ID NO: 157 mGR24 aa | SEQ ID NO: 158 mGR24 nt |
|---|---|
| MVPVLHSLSTILLIAEFVWGNLSNGLIVLKNCIDWINKKELSTVDQ ILIV LAISRISLIIWETLIIWVKDQLISSITIEELKIIVFSFILSSHFSLW LATPA LSIFYLFRIPNCYWQIFLYLKWRIKQLIVHMLLGSLVFLVANMIQI TITL EERFYQVGGNTSVNSMETEFSILIELMLFNWTMFSIIPFSLALISF LLLI FSLMKHLQKMPLNSRGDRDPSATAHRNALRIIVSFLLLYTIYFLSL LISW VAQKNQSELVHIICMITSLVYPSFHSYILLGNYKLKQTSLWVMRQ LGCR MKRQNTPTT | CAAAGAGGAGAAATATTAGTACACAGTGTACCACATACAAGCCGTTCA ATCAGTATAAGGGGAGCAGTCATATAGAATTGGGCTTTCTTTCTTTTAA TATGGTACCTGTTCTGCACAGTCTCTCCACCATCATACTAATTGCAGAGT TTGTTTGGGAAATTGAGCAATGGTTTGATAGTGTTGAAGAACTGCATT GACTGGATCAATAAAAAAGAGCTCTCCACAGTTGATCAAATACTCATTGT CTTGGCAATTCAAGAATTAGTCTCATCTGGGAAACACTAATTATATGGG TTAAAGATCAACTAATTTCATCTATTACTATTGAAGAATTAAAAATAATT GTGTTCAGCTTTATACTATCTAGCCACTTCAGTCTCTGGCTTGCTACAGC TCTCTACTTGAAATGGAGAATAAAGCAACTGATTGTCCACATGCTTCTG TTCTCTACTTGAAATGGAGAATAAAGCAACTGATTGTCCACATGCTTCTG GGAAGCTTGGTCGTTCTTGGTTGCAAATATGATACAGATAACCATCACTCT ATAGAGACCCTAGTGCTACGGCCCACAGAAATGCCTTGAGAATTTGGTC TCCTTCCTCTTGCTCTATACTATAATTCCTGTCTCTTCTTATATCATG GGTTGCTCAGAAGAATCAAAGTGAACTGGTTCACATTATTGTATGATAA CTTCACTCGTGTATCCTCATTCCACTCATATATCCTGATTCTGGGAAAT TATAAATTAAAGCAGAACAGATCTCTCTTGGGTAATGAGGCAGCTGGGATGTAG GATGAAAAGACAGAATACACCAACTACATAAGGCAGCCAAACAGTCTATT GGGTTTTAGATAACAAATCTAAATCTATGAGGAAGTAGTTCAATAACATT TTTCCCCTTGACATGGAGTAGCAGGTTTTTTTTTATTAGATATTTCTT TACTTACATTTCAAATGCTATCCGAAAATTCCCTGTACCCCTCCCCGT CCTGTCCCCTACCCACCCACTCCCACTCTTGGCCCTGCATTCCCCTG GAGTATCAGTTTTTATTAGTCAAACTATCCACTGACTAAGGGTCATAA AACAAGTATTTTAACACTAATTCAATTAAATCAAGGTAAAGTGTCAG CACATGCCTTAATCACACAACAATTCATCAAATTCAGCACTCAGGAGGG TGATCTCTGGAATTCCAGCACACTGGCGCCGTTACTAGTGGATCCGAG CTCGGTACCAAGCTT |

FIG. 8

| SEQ ID NO: 159 mGR25 aa<br>MMGIAIDILWAAIIVQFIIGNIANGFIALVNIIDWVKRRKISLMD<br>KIIT<br>ALAISRIYLLWSTPLITLTSSLDPDIKMAVKIIRISNNTWIIANHF<br>SIWF<br>ATCLSIFYFLKIANFSNYIFLYLRWRFKVVSVTLLISLIFLLLNI<br>LLMN<br>MHIDIWSDKSKRNLSFSVRSNNCTQFPRLVLLINIMFTSIPFTVSL<br>LAFL<br>LLIFSLWRHLKTMQYYAKGSEDTTAAHIKALHMVAFLLFYTVFF<br>LSLA<br>IQYWISGSQENNNLFYATIVITFPSVHSCILIRNSQLRQASLLVL<br>WWLL<br>CKSKDVRMLVP | SEQ ID NO: 160 mGR25 nt<br>AAAACTATTCGAATTGAACACAGTAACCAATTCTTCAGCGGACTTACACA<br>AATCAAGCTATTATCTTATGGATGATGGGTATTGCCATAGATATCTTATG<br>GGCAGCTATTATCATTGTGCAATTCATAATTGGGAATATTGCAAATGGAT<br>TCATAGCATTGGTGAACATCATAGACTGCTTTGGCAATCTCTAGATTATCTGCT<br>TTAATGATAAGATCATTACTGCTTTGGCAATCTCTAGATTATCTGCT<br>GTGGTCTACATTCTTAATTACACTAACATCTTCACTGGATCCAGATATTA<br>AAATGGCTGTGAAAATCATTAGAATAAGCAATAACACCTGGATTATTGCA<br>AATCATTTCAGCATTTGGTTTGCTACATGTCTCAGCATCTTTATTTCT<br>CAAGATAGCCAATTTCTAACTATATATTTCTCTACTTAAGTGGAGAT<br>TTAAGAAGTGGTTTCAGTGACATTGCTAATCTCTCTTATCTTCCTGCTT<br>TTAAATATTTACTGATGAACATGCATATTGATATCTGGAGTGATAAGTC<br>CAAAAGAAACCTTTCTTTTAGTGTCAGATCAAATAATTGCACTCAGTTTC<br>CCAGACTTGTCTCCTTTAATCAACACAATGTTCACATCACATCCCCTTCACT<br>GTGTCCCCTGTTGGCTTTCTGCTTCTCATCTCTCCCTGTGGAGACACCT<br>GAAAACCATGCAATACTATGCTAAAGGCTCAAGTGTAGTGGCCTTTCTCACACA<br>CACATATAAAGGCCTTGCACATGTAGTGGCCTTTCTCCTGTTCACACA<br>GTTTCTTTTTGTCTCTTGCCATACAATATTGTAATTACTTTCCCTCAGTCC<br>GAATAACAACCTGTTTATGCCACAGAAACAGCCAGCTGAGGCAGGCATCCTG<br>ATTCATGTATCCGATTCTGAGAAACAGCCAGCTGAGGCAGGCATCCTG<br>TTGGTGCTGTGGTGGCTGCTGTGCAAGTCCAAAGATGTACGGATGTTGGT<br>TCCCTGAAATACTCGTCAAGCTCTTTAGTAGTGAAGAAGAAATAGCT<br>TAGTTAAGGAAATTCTTGTTCATTACCGAAGTATACTTTCAAGTTTATGT<br>ATC |
| SEQ ID NO: 161 mGR26 aa<br>MLPTLSVFFMLTFVLLCFLGILANGFIVLMLSREWLLRGRLLPSDM<br>ILFS<br>LGTSRFFQQCVGLVNSFYYFLHLVEYSGSLARQLISLHWDFLNSAT<br>FWFC<br>TWLSVLFCIKIANFSHPAFLWLKWRFPALVPWFLLGSILVSVIVTL<br>LFFW | SEQ ID NO: 162 mGR26 nt<br>GAATTCTAGACAGGAAAGACACCACACTAAATGACTTTACTTGTGGACC<br>TAAATAACCAAATAAGTCAAAATCACGTGATGTTACTAGGGATCTAG<br>GATAAGGGAATGAAGAGAAGAATGTTGGTCATAGAGTACAAAAATTCAGC<br>TAAGAACTCAGTCCTGGAGGCTGAATGTATAGCTGTGTGACAGACAGCAG<br>CTAGCCATACCAGAGTATACACTTGCCTCTTGCTGAAGAGTAGATCTTA<br>TGTGTCCTTGTCACCATAAAAGTAATTGAAAAGTAACTCTCGAGATG |

FIG. 8

| | |
|---|---|
| GNHTIYQAFLRRKFTGNTTFKEWNRRLEIDYFMPLKVVTMSIPCSL<br>FLVS<br>ILLLISSLRRHSLRMQHNTHSLQDPNVQAHSRALKSLISFLVLYAV<br>SFVS<br>MIIDATVFISSDNVWWPWQIILYFCMSVHPFILITNNLRFRGTFR<br>QLLL<br>LARGFWVA | ACAGATACGTTAAAATGGTTTACTTTTCAACCTGCTCCAGTAGGGTCC<br>CTTTAATGTTTGTGCTAGTAGATGGGGACTCTCAAGTATCTTTGTGGTA<br>GACAAATCTAAGGTGGCCTTCATGAATACCAACCCAGACTTTTGTGACTT<br>TGTGATCCCCACTTTTGAAGTGCATAAGAACCTGTGACTTGACTCTAATC<br>AAAGGAGTCCAACGTGTTGTTTATTCTGTAACAGTGCTTTGTGTTTCTAG<br>TTAATAACAGGCAAAGAAGGCTAGGTGACATTCCTAGATGTGTTA<br>TTTCTATCTTGCTCATGCCTCCCTCGTCTGTCTAATGAAATAAGTCAGT<br>GGCCATATTTAAATATGACTACGTGGCAAATACTGATGATAGCCTGTGTG<br>TTCCAACAAATATCCAGTAGGAGACCTAGGCATTCAGTCCTGCAGCCACA<br>AGGAAATAGTTCTTTCACTGGAAAAGAGCAGTTAGAGATGGTTATAAAT<br>TACTTAATCCATAGAAGCCATAGGGCTTTATGTAGAGATTGGGTAGAG<br>AGGTAGACCTAGATATTGACTTAGGAGTGCTATTCCTGAGTGGGGTAG<br>ATATATGGCAGGAAACTCAGATAAGAAAGACTTCTTTAGTGTCAGATT<br>TTTCCTAGGTATCTCCTTGTGCCAGATATCTATGCGTCTAGTACCTACC<br>TACCTACCTACCTACCTACCTGCAATGATGGGATAAGAATGATGAACTC<br>AGAGGCAAGTGGTCACAACCTGCACAACCTTCCCACTGATGTTATTGCAAGCATGGC<br>AGTTACCAAGATTAAAATACCTTCCCACTGATGTTATTGCAAGCATGGC<br>AGCATGTAGGCACAACTGAGAGAAGCAATCAGATCATGAGCAGCTGCTGCCCA<br>TGGTACCCGAGCCGGACAAATCAGAGAAATATTTGCATATCTGAGCCAAAAGCACA<br>CCTTTATCTACTGCCTGACCATTTTCACATTGAAGTTCGGCTCACAT<br>GCAGAATCAACCATTATCCTGTCTCAGAAGGGAGTGTCAGGGACT<br>GTGGGTAGGGCCAGGGAGGAGGCCAGGAACCAAGGCAATCAGTGGTGACA<br>GGAGGAGGGACTGAAATGCTACCAACATTATCAGTTTTCTTCATGTTGAC<br>CTTTGTTCTGCTCGTTTCTGGGGATCCTGCGTGTAGGCTTGGCCAACGGCTGCCTCCCTGGAC<br>TGATGCTGAGCAGGAATGGCTACTGCACCTCCGATTCTTCCAGCAGTGTGTGGG<br>ATGATCCTCCAGTTTGGGCACCTCCGATTCTTCCAGCAGTGTGTGGG<br>ATTGGTCAACAGTTCTATTACTTCCTCCATCCTGGTTGAGACTTCCGGGA<br>GCCTTGCCCGGCAGCTCAGTTGTACCTGGCTCAGCCTTCTGTTCTGTTCTGAACTCAGCC<br>ACTTTCTGGTTTGTACCTGGCTCAGCCGTCCTGTTCTGTTGAAGTGGAGATTCCCAGCGT<br>TAACTTCTCCATCCTGCCTTCTGTGGGCTCTATCTTGGTGTCCGTCATTGTAACT<br>TGGTGCCCTGTTCTTGGGCTCTATCTTGGTGTCCGTCATTCTTAACT<br>CTGCTGTTCTTTGGGGAAACCACACTATATATCAGGCATTCTTAAGGAG |

FIG. 8

```
AAAGTTTACTGGGAACACAACCTTTAAGGAGTGGAACAGAAGGCTGGAAA
TAGACTATTTCATGCCTCTGAAAGTTGTCACCATGTCAATTCCTTGTTCT
CTTTTTCTGGTCTCAATTTGCTGTTGATCAGTTCTCTCAGAAGGCATTC
GCTAAGAATGCAGCACAATACCCACAGCTTGCAAGACCCCAACGTCCAGG
CTCACACCAGAGCCCTGAAGTCACTCATCCATTCCTGGTTCTTTATGCG
GTGTCCTTTGTGTCCATGATCATTGATGCTACAGTCTTCATCTCCTCAGA
TAATGTGTGGTATTGGCCCTGCAAATATACTTTACTTTGCATGTCTG
TACATCCATTTATCCTCATCACCAATAATCTCAGGTTCCGCGGCACCTTC
AGGCAGCTACTCCTGTTGCCAGGGATTCGGGTGGCCTAGAAGGCTTG
GTCTCTTTATCTAGAGCCTTTGAAGAGACTCAGGTGAGGGTAACTTCACT
TGGAAGTGAGCTCATCTACGTGGAAATGTCTTTGTAGGCAGGCATGGGGT
CATACTGTGAGGTTCCTCATTGGAAGAGGAGAAGAAATACAGAGTGT
CCTTCCTTACCTTAGGATATTATGAAAGTGAAATTCGAATCCTGACC
AGTATTGATCTAAGTGCAAAGTACAATATGTCCTGTTCTTTCATGTCTG
TTTTCCTTTGTTACTGATTCATTCTCTAGGAATAGTCTTGATCAACTG
AATCATCTCATCTGGCTGCCACTGGGTGGGAACCAAGTGTCCTGAGGCAGAG
TGCTGCATTGGGATATACATGGGAGACCTCAAGAGCAGGTGGCTGTGTGGACC
TAGCACTCAGTAGATGAGTCCTGATCACTCTTCACTGTATGGGATTATTTGTCT
CTGGGCAAGAATTGGAGACTTTGGCTTTAGTTTTGTGAAGATGACTGGAA
CTTGCCAAAATTTGGAGACTTTGGCTTTAGTTTTGTGAAGATGACTGGAA
AAATCTTAATGCTACCCGTATCATTTCTCAATAATATTTCCTTTTCC
TGCCTTTAATTTTCTCCTATCTGCAGCGCCCCTTGCTTGTTATCCGTAAA
TAAATAAATAAATAAATAAAATAAGCCCAATCCTCATTTCCTGTCTTTGG
GAACCCTTTACTTCCCCAGGTATACGCTACAAAGCCACTTCTGCATTGA
ATAAACATTATATCTTTCATTCAGAAAAAGACTTAAGAATCTCACCTTTACA
AAAAAAAAAAAAAGAATCTCACTATTTTATATTCAAATTCCATTTT
AAAAAGAAAAGCACAGCATTAATTATACAAAGTTTGAAAGGTAACTTTGAAAATAA
CTTGCTCTAAGAATATACAAGATGTTTGTAAGACAGAACAAAGAGCTCTTGGAAG
GTGTGATTAGACATGACATGGTCTTTCATTGGTCTTGCCTTCAGTAGACGGCTGTCTGAATCCTG
TCCATGCCAGCTCATTGGTCTTGCCTTCAGTAGAGCCTGTCTGAATCCTG
TAACCTCTTATGCCCTTTGTAGCTTTTCTGCAGATC
```

FIG. 8

| SEQ ID NO: 163 mGR27 aa | SEQ ID NO: 164 mGR27 nt |
|---|---|
| GREWLRYGRLLPLDMILISLGASRFCLQLVGTVHNFYYSAQKVEYS GGLGRQFFHLHWHFLNSATFWFCSWLSVLFCVKIAN | GAATTCGCCCTTGCGGGATCCGGGAACGGATTCATAGCACTGTAAACTT CATGGGCTGATGAAGAATAGAAGAATTGCCTCCATTGATTAATCCTCA CAAGTCTGGCCATATCCAGAATTGTCTATTGCGTAATACTATTAGAT TGTTTTATATTGTGTCATATCCAGATGTCTATGCCACTGGTAAAGAAAT GAGAATCATTGACTTCTTCTGGACACTACTATTCTTCAAGATACTGGT TTGCAACCTGCCTCAGCATTACTATTTCTTCAAGATAGTAATTTCTTT CACCCCACTTTTCCTATGCCTCAAGTCTAGACGCCAAGGGC |
| SEQ ID NO: 165 mGR28 aa | SEQ ID NO: 166 mGR28 nt |
|  | GAATTCGCCCTTGCGGGATCCGGGAACGGGTTTATTGTGCTGGTGGG CAGGGAGTGGCTGCGATATGGCAGGTTGCTGCCCTTGGATATGATCCTCA TTAGCTTGGGTGCCTCCCGCTTCTGCCTGCAGAGGTCGAGTACTTCGGGACGGTGCAC AACTTCTACTACTCTGCCCAGAAGGTCGAGTACTCTGGGGGTCTCGGCCG ACAGTTCTTCCATCTACACTGGCACTTCCTGAACTCAGCCACCTTCTGT TTTGCAGCTGGCTCAGTGTCCTGTTCTGTGTGAAGATTGCTAACATCACA CACTCCACCTTCCTGTGTCTCAAGTCTAGACGCCAAGGGCG |
| SEQ ID NO: 167 mGR29 aa | SEQ ID NO: 168 mGR29 nt |
| MDGIVQNMFTFIVIVEIIIGWIGNGFIALVNCIHWYKRRKISALNQ ILTA LAFSRIYLLLITVFTVIAVSTLYTHVLVTRRVVKLINFHLLFSNHFS MWLA ACLGLYYFLKIAHFPNSIFVYLKMRINQVVSGTLLMSLGLLFLNTL LINS YIDTKIDDYREHLLYDFTSNNTASFYRVILVINNCIFTSIPFTLSQ STFL LLIFSIWRHYKKMQQHAQRCRDVLADAHIRVLQTMVTYVLLCAIFF LSLS MQILRSELLKNILYVRFCEIVAAVFPSGHSCVLICRDTNLRGTFLS VLSW LKQRFTSWIPNINCRSSCIF | AGCTTGATATTCCTATTGTTACTGCACAGAGTTTTTTTAAAAATTGA GTTTGTTAGTGGATTCAATACTCAGATAGAGCTCTTTAATTTTTTACA GTGACCTCATGAATCATAACTGCCTTACAGACAATGGATGGAATCGTAC AGAACATGTTTACTTCATTGTAATTGTGGAAATAATAGGATGGATT GGAAATGGATTCATAGCTCTGGTGAACTGCATACACTGGTACAAGAGAAG AAAGATCTCGCACTGAATCAAATACTCACTGTTATAGCAGTGTCTACGCTATAC TCTACCTTCTTTTAACAGTATTCACTGTTATAGCAGTGTCTACGCTATAC ACACACGTGTTGGTAACTAGAGAGTGGTAAAACTGATTAATTTCCATTT GCTTTCAGCAATCATTTTAGCATGTGGCTTGCTGCATGCCTTGGCCTTT ATTATTTCTTAAAATAGCTCATTTTCCTAACTCTATTTTGTTTACTTA AAGATGAGAATTAACCAGGTGGTTCAGGAGATAAACTCATACATTGATACCAAGA CCTCTTGTTTTCTAAACACTCTGCTGATAAACTACTGTATGATTTCGAATTAATACT TAGATGACTACAGAGAACATCTACGTATGATTCACTTCACATCTCACTCACATC GCTTCATTTTACAGGTTATTTAGTCATTAACAACTGTATTTCACATC |

FIG. 8

| | |
|---|---|
| SEQ ID NO: 169 mGR30 aa<br><br>MTYETDTTLMLVAVGEALVGILGNAFIALVNFMGWMKNRKIASIDL<br>ILSS<br>VAMSRICLQCIILLDCIILVQYPDTYNRGKEMRIVDFFWTLTNHLS<br>VWFA<br>TCLSIFYLFKIANFFHPLFLWIKWRIDKLILRTLLACVIISLCFSL<br>PVTE<br>NLSDDFRRCVKTKERINSTLRCKVNKAGHASVKVNLNLVMLFPFSV<br>SLVS<br>FLLLILSLWRHTRQIQLSVTGYKDPSTTAHVKAMKAVISFLALFVV<br>YCLA<br>FLIATSSYFMPESELAVIWGELIALIYPSSHSFILLGSSKLKQAS<br>VRVLCRVKTMLKGKKY | TATACCCTTTACACTTTCCCAGTCCACTTTCTCCTGCTCATCTTCTCCC<br>TGTGGAGACATTACAAGAGAATGCAACAGCATGCAAAGATGCAGAGAT<br>GTCCTTGAGATGCCCACATTGCTCTTGCAAACCATGGTCACCTATGT<br>CCTACTCTGTGCCATTTCTTTCTGTCCTTTCCATGCAAATTTTGAGGA<br>GTGAGTTGTTGAAGAACATTCTTTACGTTAGGTTCTGCGAGATTGTTGCA<br>GCAGTTTTCCTTCAGGACACTCCTGTCTTAATCTGTAGAGACACAAA<br>CCTGAGAGGGACCCTTTCTTTCTGCTCATCGTGGCTGAAGCAGAGGTTTA<br>CATCATGGATTCCTAACATAAATTGCAGATCATCTTGCATATTCTAAAG<br>AAACTGAG<br><br>SEQ ID NO: 170 mGR30 nt<br><br>AAAAATGTTCATTGTTTATCTAAAATTCAAATTAACTGAGTGCCCTACA<br>TTTTTATTTATTCAATCTAGTAGCTGTACTGAGGTTATTAGTGTGATTTC<br>TGAAGCCCAAATTGTAAAACTTAGCCTCAGATAAACAGCTTGAGACCAT<br>GGAAAGTAATTTGGTAGAAAGAATGACCTGCGGAGAGATAAATGACATA<br>ATTAACTGTGTGTAGAAAGAATGACCTGCGGAGAGATAAATGACATA<br>CAATATCCAGGCTAAGGATTGCCAAACACACTGTTTTTAAGACTAATTGA<br>GATTTAGATAAACTATCTACAGTCTTCATGTATAATTCTCATCTTCATCA<br>CAAGACAGACTTCAACTTAAGGAGGTAAAGACAAGACAGCGAACCCTAA<br>ACAGCCAAGTGTAGAAACTGTCATCAAATCAGCAGAAACATACTAATTG<br>GATACTTCTCTACTTTAAAATGACATAGAGAACAGATACTACCTTAATGC<br>TTGTAGCTGTTGGTGAGGCTAGTGGGCTGGATGAAGAATAGGAAATGCATTCATT<br>GCACTGTGTAAACTTCATGGTGCCATGTCCAGAATTTGTCTACAGTGTA<br>TGATTTAATCCTCCAAGTTGTATTATATGGTGACTCTTCTGGACACTTACCAACCA<br>AGAGGTAAGAAATGAGGACCGTTGCACTGCCTGCTCAGCATTTTCTATTATTCAAGA<br>TTTAAGTGTCTGGTTTGCCACCTGCCTGCTCAGCATTTTCTATTATTCAAGA<br>TAGCAAACTTCTTCCACCCTCTTTTCCCTGGATAAAGTGGAGAATTGAC<br>AAGCTAATTCTCAGAACTCTACTGGCATGTGTGATTATCTCCTGTTT<br>TAGCCCTCCCAGTCACTGCAGGAGAATCTGAGTGATGATTTCAGACGTTGTTA<br>AGACAAAGGAGAGAATAAACTCTACTTTGAGATGCAAAGTAAAATAAGCT<br>GGACATGCCTCGTCAAGGTAAATCTCAACTTGGTCATGCTGTCCCCTT |

```
TTCTGTGTCTCTGGTCTCCTTTCTCCCTCTTGATCCTCTCCCTGTGGAGAC
ACACCAGGCAGATACAACTCAGTGTAACAGGGTACAAAGATCCAGCACA
ACAGCTCATGTGAAAGCCATGAGTAATTCCTTCCTGCCCTGTT
TGTTGTCTACTGCCTAGCTCTTTCTCATAGCCACCTCCAGCTACTTATGC
CAGAGAGTGAATTAGCTGTAATATGGGGTGAGCTGATAGCTCTAATCTAT
CCTTCAAGCCATTCATTATCCTCATCCTGGGGAGTAGTAAAACTAAAACA
AGCATCGTGAGGGTGCTTTGTAGAGTAAAGACCATGTTAAAGGGAAAAA
AATATTAGCATCATGAGCATATCGAAGAAAAACTATCACTTTCTAAGAG
AAAGGAAGACACGATCATTATCCGTCCTTTTCACATGAATATTGATTTCA
TGCAGTGACATCCTCTTAACAAACTAAATTGAACCTTGAGAAATCTCAT
ATACAGCAACTTGCATGTCTCTATCTCTGCTTTTCTCCTTTTCAAT
ATGAGTTGACATAAAAATAATTTCAGAACAAATTATAACAGAAGAAAG
GGCATTTCATAATCAGTTCTGAATCACTCTCCAAATGCAAAGTGCCT
GACAAATTCAAAACAATTGTAACAGACATCTCACTGTCGTTTGCATTCTTT
GGAAAAGCAGGTGGTTTGTCTTGGAGCCTGGCTTAGAGTTTTCTTCTTA
GACCATTGAATTATGTTCATGATTGGAGAAGAGTCAAGTACCAAGTAACA
ATTTTATTGTGAAGATGGTGTTCATCATGTGATTTGCTGGCCTGGA
ACTTGTTATGTAGACTAGTCTGTCATCAAACACAAAGATCTGCCTGCC
TCACCTGCCAGTTCTAGGATTCAAGGAATGCACCACACAGCTTGTTCAA
GTGACAATTCTTACAAATGTTTAGAAATAAATAATAATTATGATTAAATGTTATAGT
CACTGAATGTAAGTGCTGTTTAGGTATAGATCAGTGATGAAAATATTCTAGAATAA
TAGAAATTATTTAAGATTATAGATCAGTGATGAAAATATTCTAGAATAA
GTTTATGAAGAAACTTTTATAAAGAAACTGAAAAAATCTTGATTG
CATATTGAAACAAATTTCTCCAAAAGAACTACAACTTGCTCTAGA
CATCTAGACTGTATCAAACAGTGAATATGAAATATCATAACAGGATATA
GCCTTTAGTATTGAAGACAGGTTCATCTATAACCTGCATACATACC
TAAAGACTAGTCAATATCCCACAACATATTTGCACTATCATGTCTAT
TGAAACACTATTCATAGTAGCTAAAAGCAAATGTACATACACAAGATGAAATTGTAT
CAATAGATGAATCAATAAAGCAGTCATTAGCACATACACACAAAACAGA
TCAGGCATAAGAAGAATGCAGTCAGTCATTGAAATAACCAGACCTGCAAAAACAAA
ATTGGAGGTCATTGTGATAATTGAAATAAAACCAGACCTGCAAAAACAAA
ACCTGTGTAATTTTCTGAAGTAGAGAATATACTCTGATGGATAGATG
```

| SEQ ID NO: 171 mGR31 aa<br><br>MYMLLVRAVFITGMLGNMFIGLANCSDWVKNQKITFINFIMVCLAA<br>SRISSVLMLFIDATIQELAPHFYYSYRLIVKCSDIFWVITDQLSTWL<br>AICLSIFYLFKVAHISHPLFLWLKWRLRGVLVVFLVFSLFLLISYF<br>LLLETLPIWGDIYVTLKNNLITLFSGTIKTTAFQKIIVEDIIYLVPF<br>LVSLASLLLFLSIVKHSRSLDLISTTSEDSRTKIHKKAMKMLVSF<br>LILFIIHIFFMQLARWLLFLFPMSRPINFILTLNIFALTHSFILIL<br>GNSNLRQRAMRILQHIKSQIQELILSLHRFSSLY | GGTACTGTTATAGTATAAAATGTGTGTGTGTGTGTGTGTG<br>TATTTCATGAAAGCAAGAATGGGACTGCTTAGACAAAGGACAAAC<br>AGGTGAAGGGGTCGAAAGAAAAGGCAATGACAAGGAGTAATGATATGAGC<br>AAAGTACCATTATTAAACATGTGACAATATAATTTTAAAATGTATCATTAAAA<br>TGTGTGCCTACCAAAACTGGATAATAATTTTAAAATGTATCATTAAAA<br>GGAAAGAAAAGAAAGTGCAAGCCAGGAAGTGAAGGGAGAAAGAAACAATGA<br>GAGAGAAAAATGGAAAATGGTGAAGAGATCTCAGCTACAAAAGAAATGGAGT<br>AAGTGTGGCCAGGAATGAAGGATCTCAGCTACTAGTTATCCAGTACGGTA<br>ATACAAATCTGTGACTCCAGCACTGCAATGCTAGTTAGCAAGGCTGAGATGTGAGAGAG<br>GGCCAGTTAACAACCAGTCTGGGCTTATTCCAAGAGATAACAAGATTGGG<br>GGAAAGTATGTAGAAGGGTTTGGAAGGAAGAGGAAGAGGAAATGAT<br>GTAATGATAGTAGTACAAATCAAAAGTTATTTTTCTAAAAAACAATGGAC<br>AGGAAACCAACTAACACTAACAAGTAAAGTGCTTGGTTCACAAGACCAGCAACC<br>TGAGTGCATCCTTGCTAGAATGAAATTGGCCTTACTCTGGAAAGCTTACT<br>TCCTCAGTGTATTCATTGTTAAAATTCATGTGAGATTTAAAGAAAAA<br>GGAAAAAAAGTTAAATGTAGATTTGTGTAGGGAATATTCCCCTAAT<br>TAATTGATTAGATAATAAAGATGACAAGCAAATGCTGTGCAAAAAGGAA<br>GACAAGGTCTAAGAGGGGAAGAGGGGAGTGGAGCACGGGACCAGGGG<br>TTTTAAAGCAAGTCGGTGCCAGCTTCTGCACCTGAAGATTTCAACATAGTATA<br>GTTAGACCTGGTGCCAGCTTCTGCACCTGAAGATTTCAACATAGTATA<br>GTTCATGAGTTTAGGAACTAAGATTGTCTGTGTTTCCATTGCGGAGACTCAAG<br>TTGATTTTAAACTAAGATTGTCTGTGTTTCCATTGCGGAGACTCAAG<br>TAGACCAAAGGGAAAGAATGAATTC |
|---|---|
| | SEQ ID NO: 172 mGR31 nt<br><br>CTGCAGCTTTCTCAGAAATCTCACCAGAATGTCTTTGTCAGCTTAATAG<br>TTCCTCGGTTATACCTTGTCACATTAGATAAAGCTAAGACATCTTGGTGCCAC<br>AATATACTCTCACTAATCAGAGAGATTAGACAGAAAATAAGTTCTTAA<br>CAACTGTTTTAGATAGGGTCATGAAATGACATAAAACACCAATGCTAAGG<br>CAATCCATTATGTTTCTCATGAGGAGCCCATATGTACACTTGAGTGTGT<br>CTTATTATTTCCCTGAGTGATTTGTAATTTATTAAACTTAACTGTG<br>ATTCATACTAGTAGTTCTGAAATTCTTTTTCATCAAGCCATTAATC |

FIG. 8

```
CTGGGGTTTTTTAAATGGAGAACCCCAAAAACAAAGTGAAATGTTGTGTGT
GGAGCAGGCTGTCTTCCCACACTACCATGAGATGCTCATTCTGTAATT
GTTCCCCGGAATAGGAAATGCCCTGAATTCAGGCACACAAGAGCTAGTCT
GTGCACCATGTCTGGTTCTTGCATTAATAACACTTTGTCAGAAGCTT
CATTGATTCGCATCTTCAGAAGCTGGTATCATTATTAGTTCTTCCTCA
GGTGACTCTGnCCAAAATATTAnGGGCCCTTAAAAAGTAAAACTAC
AAAATTTCTTATAATTTCTTTAAGTTGTTATATATAGCATGACCTA
CACACACACACACACACACACACACACACACACACACAAGTATGCCTC
TCCTTTCCTTCTAAAAATCTCACTTAAAGCAATTGTTAGCTGTCTTCGA
AGTCTAGACTGCCACTGTCGTGTCTTCAGCCAAAACAAATGCAACACATA
AAATGATAGAGCTCAAAACTTAGGAATCTATTTAACCTGTGAAGATCACGC
AAGCAAACCTGAGAAATCTAGAAGGAAACCACACAGCAAATCACTGGAGA
GAAGGTGTTAATCTAGTAAGAATAGTTTTATTTGGGTATCCTTTTGTA
GATTGGTTAGTTCATCCAAAATCCAACTTGTTAGTTCTTCATAAATTGTA
AGTGTCTCCAACATCAAAGCACCACTTCTCTCTTTCCCCTGTAATTAAAAA
TGCTTTAAGTACAGAGTTACTCTTTTTGGTGTGTTATTCTGTTCTCAATGT
AATTGTTCACTCATTCTTTTCAAAACTTTCTTTATAAAAGTCATACACATAGCA
TATCTTTTTTTTTTTCAAAACTTTCTTTATAAAAGTCATACACATAGCA
AATGCAGTGCATGTTTATGGAATCCATAACAAGATATCGTTATTGAGACTTCTCC
TAGTACTTTCTTTGAACAGTAACAAATATTATACAAATCAGTAGAGTGCAG
TGTTTCAGGTGAGGAGGAACATATTAATATATTGACTTTATCACTTCAGATATTAC
GATTCAAATTGTATTTAATATATTGACTTTATCACTTCAGATATTAC
ATCAATGGAATTTGAAGCACACAAGTGATGATGTGGGCATAGAGACT
GTCTGTACTAGAATTAATATTTCTTTAAATATCTTTAATAAAATAT
GATGCTGTATTCATAAACAGATCTTTATAGATTAAGTATGAGATTAAAGT
TGGAAAAACAAAAGACAAAACTAGGACTAAGAATTCCTTAAGTATGT
GTGAATATCAACCTAATGGAGGAAGTTTCCATCAAAGCTGAAATTACAG
TAAAAGGAGGAACTAATGAAGATAAATATGAAAAGGATGATTTCTGTGGAAGTTT
GTTTGAGAACTGATCCACGAGACTAGGACTGGAATGCTGGGAATGCTAGAAGTGCTAGAAGTGCTAG
TACTATTCAACTGCTTATAACTGGAATGCTGGGAAATGTTCATTGGACTGGCA
GAGCAGTATTTATAACTGGAATGCTGGGAAATGTTCATTGGACTGGCA
AACTGCTCTGACTGGGTCAAGAACCAGAAAATCACCTTCATCAACTTCAT
```

FIG. 8

```
CATGGCTCTGTTTGGCAGCTTCCAGAATCAGCTCTGTGCTGATGTTATTTA
TTGATGCAACCATACAAGAACTAGCGCCTCATTTCTATTATTCTTACCGT
CTAGTAAAAATGCTCTGATATATTCTGGTTATAACTGATCAACTATCAAC
ATGGCTGCCACCTGCCTTTCCTCTGGTTGAAGTGGAGATTGAGAGGTGCTT
TTTCCATCCCCTTTTCCTCTGGTTGAAGTGGAGATTGAGAGGTGCTT
GTGTTTTCTTGTATTTCTTGTTCTTATTGATTCTTATTTCTACT
GCTTGAAACACTTCCTATTTGGGAGATATTTATGTAACCCTAAAAACA
ATCTGACCTTATTTTCAGGTACAATTAAGACCACTGCTTTTCAAAAGATA
ATGTTTTTGATATAATATATTAGTCCCATTTCTGTCCCTAGCATC
ATTGCTCCCTTTATTTTGTCCTTGGTGAAACACTCCCGAAGCCTTGACC
TGATTTCTACCACTTCTGAAGATTCCAGAACCAAGATTCATAAGAAGGCC
ATGAAAAATGCTGGTGTCTTCCTCATTCTCTTTATAATTCACATTTTTT
CATGCAGTTAGCACGGTTGGTTATTATTTTGTTTCCAATGAGCAGGCCAA
TTAATTTCATCTTAACATTAAATATCTTTGCCTTAACTCACTCATTTATT
CTCATCCTGGGAAATAGCAATCTTCGACAGAGACAATGAGGATCCTGCA
ACATCTTAAAAGCCAGTTCAAGAGACTTGATCCTCTCCCTTGAAGGTCACTG
CCAGTCTTACTAGAGGAACAGCTAACAGGGAGACTTGAAGTCACTG
GCAAATTATTCTTCTTTGATTTCTTTAAGTACTGCTGAACATATATGAA
CTGTCCCAGAGACATAGTGCTATCTTATGAGAAGAATCATCTCACAGT
CTGGTTATAAACACAAACCAATCTTTTATAATTCTTTACAGCATTGC
TAATAAAGACTTGTAGTCTCAAATATTTAAAGAGAATAATTAATTTTA
TAGGCAAAAGGTATGAAATTACAATTCACAGGAAGTTCATGACTCCTT
AGATATTAAAGTTAATTGTAAGCCACAATAGCCAGAAGATGAGCAAATG
TTGATAGGAAGATAAATAATTAAAGTTACGAGAAAAAAACATCAAC
TTGCCTTTAGATTACTTTAAAGCTCTCTCTGCTCTCTGCTCTCTCTGTA
TCTACTTACTTTATATATACAAATGTTTGTCTGCATGTATTTCTTTGCA
CCATATAAAATGTCTAAGTATCCAGAANGTCAGCAGAGGCATCAAATTCT
CTGGAAGAGAGTTACAAATGCTGTGGGTAACACTGGGTGCTGGGAACT
AACCTGAGTCCTTGCCACAGCAACTGCTCTTCCCTGCTAGTCATGTTT
TAAGTCTCCACAACTTAAGTTTGTATCATAGTTGTTGATGGTAGGAGGGCTGGTTTTAATC
GAATTTACATTCTAAGGTTCTTATACAAACCCAGTTTTGTAAGAGACTGTATTCT
ATATTCTAATGTTCTTATACAAACCCAGTTTGTAAGAGACTGTATTCT
```

FIG. 8

```
ATCATGAGACTCTTTCCCCACACCGCCAATGTAACATTTTATTAATTTT
GAGGGGAATTTATACAGTGTACCCTGATCACCCTTGCTTCCACTCCTT
GCAGGTCTACCCTCCCACCATTGCTCAATCCCCCCTAAAAGAGAGAAA
CAAACCATGTCCAATTGTGTTGGACACATACTCAGTGGAACATGCCAA
ACCCCTAGTGAGCAGTTCCTTAAAGAAAACTAAGCTGCCTCCCCACCACT
ACCACCATAGGGCATTAACTGTGAAGAGCTACACTTTAGCTATTTTATCA
CCAATTTAAAAGACTGTCTTCAATAGCTTCCTCTATGGACTGTTTCTGGT
TTTAGTGGGACAGGGAGAAGGGGTCAAGAGGTTGTCACAGAAACTTTTGA
TGTCTCTTATTCTCCACTGCTAAAGTCCACTGCAAAAGAAGTCTGCTGCTCT
AATAAAGCTTGCAACAGCATGGGCCAGTGACATCATCATGATTTCTGGCA
ACAATATGGACCACAAATATCATGGCTCAGTGGCATTACGACCACAGA
CATCAACATGTCTCTGCAGCAAGAACCAGAATCTTTGAGGAGGCTTC
ATTCAGAAAATGAATTTTCTTCATCCAGATATACTGATGTTGCTCAAT
CAGAGTATTAGTATGCTGTGGGCACCATATTGGGACAGACCTTCAATA
TTTCCAGGCTGCTGTGTAACACATTATCTTTAGTGTCAGGTGCCCTTAGT
GTCAGGACATGACCATCATGTATGCGCCTGTGGCAGAGAATACATCTTTG
TACTTTCTTACACCTGGGCAGGGTGAGTAGCAGGAGCAGGGCATTAATAC
TTCCATACCCTGGGCAGCTATCAGTATCATCTAGGCAAGGTAAGCCC
AGTAGTGGCCCAAGGCTCCTGTGTCTGGTTCTCCACATGTCTGCTTCT
GTCTGCACTGCCATATCTATGGCTGGTTCTCCACATTCTATTTTCCATGA
CTCCAGGTTTTATACGACTCTATTCCACATTCTATTTTCCAGTTCCATGA
AACCAGTGTTTAAAAGTATCATCCCATAAGACCGGCCTTTTAAAGGTTAT
TCTGGAGATATTGCAGAGTCTGCAG
```

FIG. 8

SEQUENCE LISTING

```
<160> NUMBER OF SEQ ID NOS: 172

<210> SEQ ID NO 1
<211> LENGTH: 299
<212> TYPE: PRT
<213> ORGANISM: Homo sapiens
<220> FEATURE:
<223> OTHER INFORMATION: human T2R01 (hGR01)

<400> SEQUENCE: 1

Met Leu Glu Ser His Leu Ile Ile Tyr Phe Leu Leu Ala Val Ile Gln
 1               5                  10                  15

Phe Leu Leu Gly Ile Phe Thr Asn Gly Ile Ile Val Val Val Asn Gly
                20                  25                  30

Ile Asp Leu Ile Lys His Arg Lys Met Ala Pro Leu Asp Leu Leu Leu
            35                  40                  45

Ser Cys Leu Ala Val Ser Arg Ile Phe Leu Gln Leu Phe Ile Phe Tyr
        50                  55                  60

Val Asn Val Ile Val Ile Phe Phe Ile Glu Phe Ile Met Cys Ser Ala
    65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
               100                 105                 110

Pro Leu Phe Ile Trp Leu Lys Met Arg Ile Ser Lys Leu Val Pro Trp
            115                 120                 125

Met Ile Leu Gly Ser Leu Leu Tyr Val Ser Met Ile Cys Val Phe His
        130                 135                 140
```

```
Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
            165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
        210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
            245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
    290                 295

<210> SEQ ID NO 2
<211> LENGTH: 900
<212> TYPE: DNA
<213> ORGANISM: Homo sapiens
<220> FEATURE:
<223> OTHER INFORMATION: human T2R01 (hGR01)

<400> SEQUENCE: 2
atgctagagt ctcacctcat tatctatttt cttcttgcag tgatacaatt tcttcttggg      60
attttcacaa atggcatcat tgtggtggtg aatggcattg acttgatcaa gcacagaaaa     120
atggctccgc tggatctcct tctttcttgt ctggcagttt ctagaatttt tctgcagttg     180
ttcatcttct acgttaatgt gattgttatc ttcttcatag aattcatcat gtgttctgcg     240
aattgtgcaa ttctcttatt tataaatgaa ttggaacttt ggcttgccac atggctcggc     300
gttttctatt gtgccaaggt tgccagcgtc cgtcacccac tcttcatctg gttgaagatg     360
aggatatcca agctggtccc atggatgatc ctggggtctc tgctatatgt atctatgatt     420
tgtgttttcc atagcaaata tgcagggttt atggtcccat acttcctaag gaaatttttc     480
tcccaaaatg ccacaattca aaagaagat acactggcta tacagatttt ctcttttgtt      540
gctgagttct cagtgccatt gcttatcttc cttttgctg ttttgctctt gattttctct      600
ctggggaggc acacccggca aatgagaaac acagtggccg gcagcagggt tcctggcagg     660
ggtgcaccca tcagcgcgtt gctgtctatc ctgtccttcc tgatcctcta cttctcccac     720
tgcatgataa agtttttct ctcttctcta agtttcaca tcagaaggtt catctttctg       780
ttcttcatcc ttgtgattgg tatataccct tctggacact ctctcatctt aattttagga     840
aatcctaaat tgaaacaaaa tgcaaaaaag ttcctcctcc acagtaagtg ctgtcagtga     900

<210> SEQ ID NO 3
<211> LENGTH: 302
<212> TYPE: PRT
<213> ORGANISM: Homo sapiens
<220> FEATURE:
<221> NAME/KEY: MOD_RES
<222> LOCATION: (143)
<223> OTHER INFORMATION: human T2R02 (hGR02)
```

<223> OTHER INFORMATION: Xaa = any amino acid

<400> SEQUENCE: 3

```
Met Ala Leu Ser Phe Ser Ala Ile Leu His Ile Ile Met Met Ser Ala
 1               5                   10                  15
Glu Phe Phe Thr Gly Ile Thr Val Asn Gly Phe Leu Ile Ile Val Asn
                20                  25                  30
Cys Asn Glu Leu Ile Lys His Arg Lys Leu Met Pro Ile Gln Ile Leu
            35                  40                  45
Leu Met Cys Ile Gly Met Ser Arg Phe Gly Leu Gln Met Val Leu Met
        50                  55                  60
Val Gln Ser Phe Phe Ser Val Phe Pro Leu Leu Tyr Val Lys Ile
 65                  70                  75                  80
Ile Tyr Gly Ala Ala Met Met Phe Leu Trp Met Phe Phe Ser Ser Ile
                85                  90                  95
Ser Leu Trp Phe Ala Thr Cys Leu Ser Val Phe Tyr Cys Leu Lys Ile
            100                 105                 110
Ser Gly Phe Thr Gln Ser Cys Phe Leu Trp Leu Lys Phe Arg Ile Pro
        115                 120                 125
Lys Leu Ile Pro Trp Leu Phe Trp Glu Ala Phe Trp Pro Leu Xaa Ala
    130                 135                 140
Leu His Leu Cys Val Glu Val Asp Tyr Ala Lys Asn Val Glu Glu Asp
145                 150                 155                 160
Ala Leu Arg Asn Thr Thr Leu Lys Lys Ser Lys Thr Lys Ile Lys Lys
                165                 170                 175
Ile Ser Glu Val Leu Leu Val Asn Leu Ala Leu Ile Phe Pro Leu Ala
            180                 185                 190
Ile Phe Val Met Cys Thr Ser Met Leu Leu Ile Ser Leu Tyr Lys His
        195                 200                 205
Thr His Arg Met Gln His Gly Ser His Gly Phe Arg Asn Ala Asn Thr
    210                 215                 220
Glu Ala His Ile Asn Ala Leu Lys Thr Val Ile Thr Phe Phe Cys Phe
225                 230                 235                 240
Phe Ile Ser Tyr Phe Ala Ala Phe Met Thr Asn Met Thr Phe Ser Leu
                245                 250                 255
Pro Tyr Arg Ser His Gln Phe Phe Met Leu Lys Asp Ile Met Ala Ala
            260                 265                 270
Tyr Pro Ser Gly His Ser Val Ile Ile Leu Ser Asn Ser Lys Phe
        275                 280                 285
Gln Gln Ser Phe Arg Arg Ile Leu Cys Leu Lys Lys Leu
    290                 295                 300
```

<210> SEQ ID NO 4
<211> LENGTH: 910
<212> TYPE: DNA
<213> ORGANISM: Homo sapiens
<220> FEATURE:
<223> OTHER INFORMATION: human T2R02 (hGR02)
<223> OTHER INFORMATION: human T2R02 (hGR02)

<400> SEQUENCE: 4

```
atggccttgt cttttcagc tattcttcat attatcatga tgtcagcaga attcttcaca      60
gggatcacag taaatggatt tctatcatt gttaactgta atgaattgat caaacataga    120
aagctaatgc caattcaaat cctcttaatg tgcataggga tgtctagatt tggtctgcag    180
atggtgttaa tggtacaaag ttttttctct gtgttctttc cactccttta cgtcaaaata    240
```

-continued

```
atttatggtg cagcaatgat gttcctttgg atgttttta gctctatcag cctatggttt      300
gccacttgcc tttctgtatt ttactgcctc aagatttcag gcttcactca gtcctgtttt      360
ctttggttga aattcaggat cccaaagtta ataccttggc tgcttctggg aagcgttctg      420
gcctctgtga gcattgcatc tgtgtgtcga ggtagattac gctaaaaatg tggaagagga      480
tgccctcaga acaccacac taaaaagag taaacaaag ataagaaaa ttagtgaagt          540 gcttcttgtc aacttggcat taatatttcc tctagccata tttgtgatgt gcacttctat      600
gttactcatc tctctttaca agcacactca tcggatgcaa catggatctc atggctttag      660
aaatgccaac acagaagccc atataaatgc attaaaaaca gtgataacat tcttttgctt      720
ctttatttct tattttgctg ccttcatgac aaatatgaca tttagtttac cttacagaag      780
tcaccagttc tttatgctga aggacataat ggcagcatat ccctctggcc actcggttat      840
aataatcttg agtaattcta agttccaaca atcatttaga agaattctct gcctcaaaaa      900
gaaactatga                                                             910
```

<210> SEQ ID NO 5
<211> LENGTH: 316
<212> TYPE: PRT
<213> ORGANISM: Homo sapiens
<220> FEATURE:
<223> OTHER INFORMATION: human T2R03 (hGR03)

<400> SEQUENCE: 5

```
Met Met Gly Leu Thr Glu Gly Val Phe Leu Ile Leu Ser Gly Thr Gln
  1               5                  10                  15

Phe Thr Leu Gly Ile Leu Val Asn Cys Phe Ile Glu Leu Val Asn Gly
             20                  25                  30

Ser Ser Trp Phe Lys Thr Lys Arg Met Ser Leu Ser Asp Phe Ile Ile
         35                  40                  45

Thr Thr Leu Ala Leu Leu Arg Ile Ile Leu Leu Cys Ile Ile Leu Thr
     50                  55                  60

Asp Ser Phe Leu Ile Glu Phe Ser Pro Asn Thr His Asp Ser Gly Ile
 65                  70                  75                  80

Ile Met Gln Ile Ile Asp Val Ser Trp Thr Phe Thr Asn His Leu Ser
                 85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
    210                 215                 220

Thr Thr Glu Ala His Lys Arg Ala Ile Arg Ile Ile Leu Ser Phe Phe
225                 230                 235                 240
```

```
Phe Leu Phe Leu Leu Tyr Phe Leu Ala Phe Leu Ile Ala Ser Phe Gly
                245                 250                 255

Asn Phe Leu Pro Lys Thr Lys Met Ala Lys Met Ile Gly Glu Val Met
            260                 265                 270

Thr Met Phe Tyr Pro Ala Gly His Ser Phe Ile Leu Ile Leu Gly Asn
        275                 280                 285

Ser Lys Leu Lys Gln Thr Phe Val Val Met Leu Arg Cys Glu Ser Gly
    290                 295                 300

His Leu Lys Pro Gly Ser Lys Gly Pro Ile Phe Ser
305                 310                 315

<210> SEQ ID NO 6
<211> LENGTH: 951
<212> TYPE: DNA
<213> ORGANISM: Homo sapiens
<220> FEATURE:
<223> OTHER INFORMATION: human T2R03 (hGR03)

<400> SEQUENCE: 6
atgatgggac tcaccgaggg ggtgttcctg attctgtctg gcactcagtt cacactggga      60
attctggtca attgtttcat tgagttggtc aatggtagca gctggttcaa gaccaagaga     120
atgtctttgt ctgacttcat catcaccacc ctggcactct tgaggatcat tctgctgtgt     180
attatcttga ctgatagttt tttaatagaa ttctctccca acacacatga ttcagggata     240
ataatgcaaa ttattgatgt ttcctggaca tttacaaacc atctgagcat ttggcttgcc     300
acctgtcttg gtgtcctcta ctgcctgaaa tcgccagtt tctctcaccc cacattcctc      360
tggctcaagt ggagagtttc tagggtgatg gtatggatgc tgttgggtgc actgctctta     420
tcctgtggta gtaccgcatc tctgatcaat gagtttaagc tctattctgt ctttagggga     480
attgaggcca ccaggaatgt gactgaacac ttcagaaaga agaggagtga gtattatctg     540
atccatgttc ttgggactct gtggtacctg cctcccttaa ttgtgtccct ggcctcctac     600
tctttgctca tcttctccct ggggaggcac acacggcaga tgctgcaaaa tgggacaagc     660
tccagagatc caaccactga ggcccacaag agggccatca gaatcatcct tccttcttc      720
tttctcttct actttactt tcttgctttc ttaattgcat catttggtaa tttcctacca      780
aaaaccaaga tggctaagat gattggcgaa gtaatgacaa tgttttatcc tgctggccac     840
tcatttattc tcattctggg aacagtaagc ctgaagcaga catttgtagt gatgctccgg     900
tgtgagtctg gtcatctgaa gcctggatcc aagggaccca ttttctctta g              951

<210> SEQ ID NO 7
<211> LENGTH: 299
<212> TYPE: PRT
<213> ORGANISM: Homo sapiens
<220> FEATURE:
<223> OTHER INFORMATION: human T2R04 (hGR04)

<400> SEQUENCE: 7

Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Ser Asp Arg Ile Leu
        35                  40                  45

Phe Ser Leu Gly Ile Thr Arg Phe Leu Met Leu Gly Leu Phe Leu Val
    50                  55                  60
```

```
Asn Thr Ile Tyr Phe Val Ser Ser Asn Thr Glu Arg Ser Val Tyr Leu
 65                  70                  75                  80

Ser Ala Phe Phe Val Leu Cys Phe Met Phe Leu Asp Ser Ser Val
                 85                  90                  95

Trp Phe Val Thr Leu Leu Asn Ile Leu Tyr Cys Val Lys Ile Thr Asn
                100                 105                 110

Phe Gln His Ser Val Phe Leu Leu Lys Arg Asn Ile Ser Pro Lys
            115                 120                 125

Ile Pro Arg Leu Leu Leu Ala Cys Val Leu Ile Ser Ala Phe Thr Thr
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
                180                 185                 190

Val Thr Ser Ala Ser Leu Leu Ile His Ser Leu Arg Arg His Ile Gln
                195                 200                 205

Lys Met Gln Lys Asn Ala Thr Gly Phe Trp Asn Pro Gln Thr Glu Ala
    210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
                260                 265                 270

Ser Pro Gly His Ser Val Leu Ile Ile Thr His Pro Lys Leu Lys
            275                 280                 285

Thr Thr Ala Lys Lys Ile Leu Cys Phe Lys Lys
    290                 295

<210> SEQ ID NO 8
<211> LENGTH: 900
<212> TYPE: DNA
<213> ORGANISM: Homo sapiens
<220> FEATURE:
<223> OTHER INFORMATION: human T2R04 (hGR04)

<400> SEQUENCE: 8
atgcttcggt tattctattt ctctgctatt attgcctcag ttattttaaa ttttgtagga      60
atcattatga atctgtttat tacagtggtc aattgcaaaa cttgggtcaa aagccataga     120
atctcctctt ctgataggat tctgttcagc ctgggcatca ccaggtttct tatgctggga     180
ctatttctgg tgaacaccat ctacttcgtc tcttcaaata cggaaaggtc agtctacctg     240
tctgcttttt ttgtgttgtg tttcatgttt ttggactcga gcagtgtctg gtttgtgacc     300
ttgctcaata tcttgtactg tgtgaagatt actaacttcc aacactcagt gtttctcctg     360
ctgaagcgga atatctcccc aaagatcccc aggctgctgc tggcctgtgt gctgatttct     420
gctttcacca cttgcctgta catcacgctt agccaggcat cacctttttcc tgaacttgtg    480 actacgagaa ataacacatc atttaatatc agtgagggca tcttgtcttt agtggtttct     540
ttggtcttga gctcatctct ccagttcatc attaatgtga cttctgcttc cttgctaata     600
cactccttga ggagacatat acagaagatg cagaaaaatg ccactggttt ctggaatccc     660
cagacggaag ctcatgtagg tgctatgaag ctgatggtct atttcctcat cctctacatt     720
```

```
ccatattcag ttgctaccct ggtccagtat ctccccttt  atgcagggat ggatatgggg    780
accaaatcca tttgtctgat ttttgccacc ctttactctc caggacattc tgttctcatt    840
attatcacac atcctaaact gaaaacaaca gcaaagaaga ttctttgttt caaaaaatag    900
```

<210> SEQ ID NO 9
<211> LENGTH: 299
<212> TYPE: PRT
<213> ORGANISM: Homo sapiens
<220> FEATURE:
<223> OTHER INFORMATION: human T2R05 (hGR05)

<400> SEQUENCE: 9

```
Met Leu Ser Ala Gly Leu Gly Leu Leu Met Leu Val Ala Val Glu
 1               5                  10                  15

Phe Leu Ile Gly Leu Ile Gly Asn Gly Ser Leu Val Val Trp Ser Phe
                20                  25                  30

Arg Glu Trp Ile Arg Lys Phe Asn Trp Ser Ser Tyr Asn Leu Ile Ile
             35                  40                  45

Leu Gly Leu Ala Gly Cys Arg Phe Leu Leu Gln Trp Leu Ile Ile Leu
         50                  55                  60

Asp Leu Ser Leu Phe Pro Leu Phe Gln Ser Ser Arg Trp Leu Arg Tyr
 65                  70                  75                  80

Leu Ser Ile Phe Trp Val Leu Val Ser Gln Ala Ser Leu Trp Phe Ala
                 85                  90                  95

Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
        115                 120                 125

Cys Leu Leu Gly Tyr Phe Ile Ile Asn Leu Leu Leu Thr Val Gln Ile
    130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
                165                 170                 175

Ser Tyr Leu Pro Leu Val Val Phe Leu Val Ser Ser Gly Met Leu Ile
            180                 185                 190

Val Ser Leu Tyr Thr His His Lys Met Lys Val His Ser Ala Gly
        195                 200                 205

Arg Arg Asp Val Arg Ala Lys Ala His Ile Thr Ala Leu Lys Ser Leu
    210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
                245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
        275                 280                 285

Lys Thr Val Cys Ala Arg Arg Cys Trp Gly Pro
    290                 295
```

<210> SEQ ID NO 10
<211> LENGTH: 900
<212> TYPE: DNA
<213> ORGANISM: Homo sapiens
<220> FEATURE:
<223> OTHER INFORMATION: human T2R05 (hGR05)

<400> SEQUENCE: 10

| | | | | | |
|---|---|---|---|---|---|
| atgctgagcg | ctggcctagg | actgctgatg | ctggtggcag | tggttgaatt | tctcatcggt | 60 |
| ttaattggaa | atggaagcct | ggtggtctgg | agttttagag | aatggatcag | aaaattcaac | 120 |
| tggtcctcat | ataacctcat | tatcctgggc | ctggctggct | gccgatttct | cctgcagtgg | 180 |
| ctgatcattt | tggacttaag | cttgtttcca | cttttccaga | gcagccgttg | gcttcgctat | 240 |
| cttagtatct | tctgggtcct | ggtaagccag | gccagcttat | ggtttgccac | cttcctcagt | 300 |
| gtcttctatt | gcaagaagat | cacgaccttc | gatcgcccgg | cctacttgtg | gctgaagcag | 360 |
| agggcctata | acctgagtct | ctggtgcctt | ctgggctact | ttataatcaa | tttgttactt | 420 |
| acagtccaaa | ttggcttaac | attctatcat | cctccccaag | gaaacagcag | cattcggtat | 480 |
| ccctttgaaa | gctggcagta | cctgtatgca | tttcagctca | attcaggaag | ttatttgcct | 540 |
| ttagtggtgt | tcttgtttc | ctctgggatg | ctgattgtct | ctttgtatac | acaccacaag | 600 |
| aagatgaagg | tccattcagc | tggtaggagg | gatgtccggg | ccaaggctca | catcactgcg | 660 |
| ctgaagtcct | tgggctgctt | cctcttactt | cacctggttt | atatcatggc | cagccccttc | 720 |
| tccatcacct | ccaagactta | tcctcctgat | ctcaccagtg | tcttcatctg | ggagacactc | 780 |
| atggcagcct | atccttctct | tcattctctc | atattgatca | tggggattcc | tagggtgaag | 840 |
| cagacttgtc | agaagatcct | gtggaagaca | gtgtgtgctc | ggagatgctg | ggcccatga | 900 |

<210> SEQ ID NO 11
<211> LENGTH: 287
<212> TYPE: PRT
<213> ORGANISM: Homo sapiens
<220> FEATURE:
<221> NAME/KEY: MOD_RES
<222> LOCATION: (1)..(287)
<223> OTHER INFORMATION: human T2R06 (hGR06)
<223> OTHER INFORMATION: Xaa = any amino acid

<400> SEQUENCE: 11

Met Leu Ala Ala Ala Leu Gly Leu Leu Met Pro Ile Ala Gly Ala Glu
 1               5                  10                  15

Phe Leu Ile Gly Leu Val Gly Asn Gly Val Pro Val Val Cys Ser Phe
             20                  25                  30

Arg Gly Trp Val Lys Lys Met Xaa Gly Val Pro Ile Asn Ser His Asp
         35                  40                  45

Ser Gly Lys Xaa Pro Leu Ser Pro Thr Gln Ala Asp His Val Gly His
     50                  55                  60

Lys Ser Val Ser Thr Phe Pro Glu Gln Trp Leu Ala Leu Leu Ser Xaa
 65                  70                  75                  80

Cys Leu Arg Val Leu Val Ser Gln Ala Asn Met Xaa Phe Ala Thr Phe
                 85                  90                  95

Phe Ser Gly Phe Cys Cys Met Glu Ile Met Thr Phe Val Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Leu Leu Val Ser Phe Lys Ile Thr Phe Tyr Phe Ser Ala Leu Val
    130                 135                 140

Gly Trp Thr Leu Xaa Lys Pro Leu Thr Gly Asn Ser Asn Ile Leu His
145                 150                 155                 160

Pro Ile Leu Asn Leu Leu Phe Leu Xaa Ile Ala Val Gln Xaa Arg Arg

-continued

```
                165                 170                 175
Leu Ile Ala Ile Cys Asp Val Ser Val Pro Leu Val Phe Leu Xaa Arg
            180                 185                 190
His His Arg Lys Met Glu Asp His Thr Ala Val Arg Arg Arg Leu Lys
        195                 200                 205
Pro Arg Xaa Xaa Xaa Xaa Xaa Xaa Xaa Xaa Xaa Xaa Xaa Xaa Xaa Xaa
    210                 215                 220
Xaa Leu Tyr Met Val Ser Ala Leu Ala Arg His Phe Ser Met Thr Phe
225                 230                 235                 240
Xaa Ser Pro Ser Asp Leu Thr Ile Leu Ala Ile Ser Ala Thr Leu Met
                245                 250                 255
Ala Val Tyr Thr Ser Phe Pro Ser Ile Val Met Val Met Arg Asn Gln
            260                 265                 270
Thr Cys Gln Arg Ile Leu Xaa Glu Met Ile Cys Thr Trp Lys Ser
        275                 280                 285
```

<210> SEQ ID NO 12
<211> LENGTH: 823
<212> TYPE: DNA
<213> ORGANISM: Homo sapiens
<220> FEATURE:
<223> OTHER INFORMATION: human T2R06 (hGR06)
<223> OTHER INFORMATION: human T2R07 (hGR07)

<400> SEQUENCE: 12

```
atgttggcgg ctgccctagg attgctgatg cccattgcag gggctgaatt tctcattggc    60
ctggttggaa atggagtccc tgtggtctgc agttttagag gatgggtcaa aaaaatgtaa   120
ggagtcccta taaattctca tgattctggt aagtagccac tttctcctac tcaggccgat   180
catgttggac ataagtctgt ttccactttc ccagagcagt ggttggcttt actatcttaa   240
tgtcttcgag tcctggtaag ccaggccaac atgtagtttg ccactttctt cagtggcttc   300
tgctgcatgg agatcatgac ctttgtcccg ctgacttctt gtagctgaaa agactgggtt   360
tttgtttttt gctagtgtct ttcaagatca cttttattt ctcagctctt gttggctgga   420
ccctttaaaa acccttaaca ggaaacagca acatcctgca tcccatttta aatctgttat   480
ttttatagat tgctgtccag tgaaggagac tgattgctat tgtgatgtt tctgttccac   540
ttgtcttttt gtaaagacat cacaggaaga tggaggacca cacagctgtc aggaggaggc   600
tcaaaccaag gtgctcatcg ctctgaactt cccccttta c atggtttctg ccttggccag   660
acacttttcc atgaccttct aatctccctc tgatctcacc attcttgcca tctctgcaac   720
actcatggct gtttatactt catttccgtc tattgtaatg ttatgagga atcagacttg   780
tcagagaatt ctgtaggaga tgatatgtac atggaaatcc tag                      823
```

<210> SEQ ID NO 13
<211> LENGTH: 318
<212> TYPE: PRT
<213> ORGANISM: Homo sapiens
<220> FEATURE:
<223> OTHER INFORMATION: human T2R07 (hGR07)

<400> SEQUENCE: 13

```
Met Ala Asp Lys Val Gln Thr Thr Leu Leu Phe Leu Ala Val Gly Glu
  1                 5                  10                 15
Phe Ser Val Gly Ile Leu Gly Asn Ala Phe Ile Gly Leu Val Asn Cys
             20                  25                  30
Met Asp Trp Val Lys Lys Arg Lys Ile Ala Ser Ile Asp Leu Ile Leu
```

```
                    35                  40                  45
Thr Ser Leu Ala Ile Ser Arg Ile Cys Leu Leu Cys Val Ile Leu Leu
 50                  55                  60

Asp Cys Phe Ile Leu Val Leu Tyr Pro Asp Val Tyr Ala Thr Gly Lys
 65                  70                  75                  80

Glu Met Arg Ile Ile Asp Phe Phe Trp Thr Leu Thr Asn His Leu Ser
                 85                  90                  95

Ile Trp Phe Ala Thr Cys Leu Ser Ile Tyr Tyr Phe Phe Lys Ile Gly
                100                 105                 110

Asn Phe Phe His Pro Leu Phe Leu Trp Met Lys Trp Arg Ile Asp Arg
            115                 120                 125

Val Ile Ser Trp Ile Leu Leu Gly Cys Val Val Leu Ser Val Phe Ile
130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
        275                 280                 285

Asn Asn Lys Leu Arg His Ala Ser Leu Lys Val Ile Trp Lys Val Met
290                 295                 300

Ser Ile Leu Lys Gly Arg Lys Phe Gln Gln His Lys Gln Ile
305                 310                 315

<210> SEQ ID NO 14
<211> LENGTH: 957
<212> TYPE: DNA
<213> ORGANISM: Homo sapiens
<220> FEATURE:
<223> OTHER INFORMATION: human T2R07 (hGR07)

<400> SEQUENCE: 14
atggcagata aagtgcagac tactttattg ttcttagcag ttggagagtt ttcagtgggg      60
atcttaggga atgcattcat tggattggta aactgcatgg actgggtcaa gaagaggaaa     120
attgcctcca ttgatttaat cctcacaagt ctggccatat ccagaatttg tctattgtgc     180
gtaatactat tagattgttt tatattggtg ctatatccag atgtctatgc cactggtaaa     240
gaaatgagaa tcattgactt cttctggaca ctaaccaatc atttaagtat ctggtttgca     300
acctgcctca gcatttacta tttcttcaag ataggtaatt tctttcaccc acttttcctc     360
tggatgaagt ggagaattga cagggtgatt cctggattc tactggggtg cgtggttctc      420
tctgtgttta ttagccttcc agccactgag aatttgaacg ctgatttcag gttttgtgtg     480
```

```
aaggcaaaga ggaaaacaaa cttaacttgg agttgcagag taaataaaac tcaacatgct    540
tctaccaagt tatttctcaa cctggcaacg ctgctcccct tttgtgtgtg cctaatgtcc    600 ttttctct tgatcctctc cctgcggaga catatcaggc gaatgcagct cagtgccaca      660
```
*(ttttcctct above as shown)*

```
gggtgcagag accccagcac agaagcccat gtgagagccc tgaaagctgt catttccttc    720
cttctcctct ttattgccta ctatttgtcc tttctcattg ccacctccag ctactttatg    780
ccagagacgg aattagctgt gattttggt gagtccatag ctctaatcta cccctcaagt    840
```

```
cattcattta tcctaatact ggggaacaat aaattaagac atgcatctct aaaggtgatt    900
tggaaagtaa tgtctattct aaaaggaaga aaattccaac aacataaaca aatctga      957
```

<210> SEQ ID NO 15
<211> LENGTH: 309
<212> TYPE: PRT
<213> ORGANISM: Homo sapiens
<220> FEATURE:
<223> OTHER INFORMATION: human T2R08 (hGR08)

<400> SEQUENCE: 15

```
Met Phe Ser Pro Ala Asp Asn Ile Phe Ile Ile Leu Ile Thr Gly Glu
  1               5                  10                  15

Phe Ile Leu Gly Ile Leu Gly Asn Gly Tyr Ile Ala Leu Val Asn Trp
             20                  25                  30

Ile Asp Trp Ile Lys Lys Lys Ile Ser Thr Val Asp Tyr Ile Leu
         35                  40                  45

Thr Asn Leu Val Ile Ala Arg Ile Cys Leu Ile Ser Val Met Val Val
 50                  55                  60

Asn Gly Ile Val Ile Val Leu Asn Pro Asp Val Tyr Thr Lys Asn Lys
 65                  70                  75                  80

Gln Gln Ile Val Ile Phe Thr Phe Trp Thr Phe Ala Asn Tyr Leu Asn
                 85                  90                  95

Met Trp Ile Thr Thr Cys Leu Asn Val Phe Tyr Phe Leu Lys Ile Ala
            100                 105                 110

Ser Ser His Pro Leu Phe Leu Trp Leu Lys Trp Lys Ile Asp Met
            115                 120                 125

Val Val His Trp Ile Leu Leu Gly Cys Phe Ala Ile Ser Leu Leu Val
        130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
                165                 170                 175

Ile Pro Tyr Phe Glu Pro Leu Thr Leu Phe Asn Leu Phe Ala Ile Val
            180                 185                 190

Pro Phe Ile Val Ser Leu Ile Ser Phe Phe Leu Leu Val Arg Ser Leu
        195                 200                 205

Trp Arg His Thr Lys Gln Ile Lys Leu Tyr Ala Thr Gly Ser Arg Asp
    210                 215                 220

Pro Ser Thr Glu Val His Val Arg Ala Ile Lys Thr Met Thr Ser Phe
225                 230                 235                 240

Ile Phe Phe Phe Leu Tyr Tyr Ile Ser Ser Ile Leu Met Thr Phe
                245                 250                 255

Ser Tyr Leu Met Thr Lys Tyr Lys Leu Ala Val Glu Phe Gly Glu Ile
            260                 265                 270

Ala Ala Ile Leu Tyr Pro Leu Gly His Ser Leu Ile Leu Ile Val Leu
        275                 280                 285
```

Asn Asn Lys Leu Arg Gln Thr Phe Val Arg Met Leu Thr Cys Arg Lys
    290                 295                 300

Ile Ala Cys Met Ile
305

<210> SEQ ID NO 16
<211> LENGTH: 930
<212> TYPE: DNA
<213> ORGANISM: Homo sapiens
<220> FEATURE:
<223> OTHER INFORMATION: human T2R08 (hGR08)

<400> SEQUENCE: 16

| | | | | | |
|---|---|---|---|---|---|
| atgttcagtc | ctgcagataa | catctttata | atcctaataa | ctggagaatt | catactagga | 60 |
| atattgggga | atggatacat | tgcactagtc | aactggattg | actggattaa | gaagaaaaag | 120 |
| atttccacag | ttgactacat | ccttaccaat | ttagttatcg | ccagaatttg | tttgatcagt | 180 |
| gtaatggttg | taaatggcat | tgtaatagta | ctgaacccag | atgtttatac | aaaaaataaa | 240 |
| caacagatag | tcattttttac | cttctggaca | tttgccaact | acttaaatat | gtggattacc | 300 |
| acctgcctta | atgtcttcta | ttttctgaag | atagccagtt | cctctcatcc | acttttttctc | 360 |
| tggctgaagt | ggaaaattga | tatggtggtg | cactggatcc | tgctgggatg | ctttgccatt | 420 |
| tccttgttgg | tcagccttat | agcagcaata | gtactgagtt | gtgattatag | gtttcatgca | 480 |
| attgccaaac | ataaaagaaa | cattactgaa | atgttccatg | tgagtaaaat | accatacttt | 540 |
| gaaccccttga | ctctctttaa | cctgtttgca | attgtcccat | ttattgtgtc | actgatatca | 600 |
| ttttttccttt | tagtaagatc | tttatggaga | cataccaagc | aaataaaaact | ctatgctacc | 660 |
| ggcagtagag | accccagcac | agaagttcat | gtgagagcca | ttaaaactat | gacttcattt | 720 |
| atcttctttt | ttttcctata | ctatatttct | tctattttga | tgacctttag | ctatcttatg | 780 |
| acaaaataca | agttagctgt | ggagtttgga | gagattgcag | caattctcta | ccccttgggt | 840 |
| cactcactta | ttttaattgt | tttaaataat | aaactgaggc | agacatttgt | cagaatgctg | 900 |
| acatgtagaa | aaattgcctg | catgatatga | | | | 930 |

<210> SEQ ID NO 17
<211> LENGTH: 312
<212> TYPE: PRT
<213> ORGANISM: Homo sapiens
<220> FEATURE:
<223> OTHER INFORMATION: human T2R09 (hGR09)

<400> SEQUENCE: 17

Met Pro Ser Ala Ile Glu Ala Ile Tyr Ile Ile Leu Ile Ala Gly Glu
  1               5                  10                  15

Leu Thr Ile Gly Ile Trp Gly Asn Gly Phe Ile Val Leu Val Asn Cys
             20                  25                  30

Ile Asp Trp Leu Lys Arg Arg Asp Ile Ser Leu Ile Asp Ile Ile Leu
         35                  40                  45

Ile Ser Leu Ala Ile Ser Arg Ile Cys Leu Leu Cys Val Ile Ser Leu
     50                  55                  60

Asp Gly Phe Phe Met Leu Leu Phe Pro Gly Thr Tyr Gly Asn Ser Val
 65                  70                  75                  80

Leu Val Ser Ile Val Asn Val Val Trp Thr Phe Ala Asn Asn Ser Ser
                 85                  90                  95

Leu Trp Phe Thr Ser Cys Leu Ser Ile Phe Tyr Leu Leu Lys Ile Ala
            100                 105                 110

```
Asn Ile Ser His Pro Phe Phe Phe Trp Leu Lys Leu Lys Ile Asn Lys
        115                 120                 125

Val Met Leu Ala Ile Leu Leu Gly Ser Phe Leu Ile Ser Leu Ile Ile
130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
        195                 200                 205

Thr Lys Gln Ile Arg Leu His Ala Thr Gly Phe Arg Asp Pro Ser Thr
        210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Ile Leu Ile Met Gly Asn Ser Lys
        275                 280                 285

Leu Arg Glu Ala Phe Leu Lys Met Leu Arg Phe Val Lys Cys Phe Leu
        290                 295                 300

Arg Arg Arg Lys Pro Phe Val Pro
305                 310

<210> SEQ ID NO 18
<211> LENGTH: 939
<212> TYPE: DNA
<213> ORGANISM: Homo sapiens
<220> FEATURE:
<223> OTHER INFORMATION: human T2R09 (hGR09)

<400> SEQUENCE: 18
atgccaagtg caatagaggc aatatatatt attttaattg ctggtgaatt gaccataggg      60
atttggggaa atggattcat tgtactagtt aactgcattg actggctcaa aagaagagat     120
atttccttga ttgacatcat cctgatcagc ttggccatct ccagaatctg tctgctgtgt     180
gtaatatcat tagatggctt cttttatgctg ctctttccag gtacatatgg caatagcgtg     240
ctagtaagca ttgtgaatgt tgtctggaca tttgccaata attcaagtct ctggtttact     300
tcttgcctca gtatcttcta tttactcaag atagccaata tatcgcaccc attttcttc     360 tggctgaagc taaagatcaa caaggtcatg cttgcgattc ttctggggtc ctttcttatc     420
tctttaatta ttagtgttcc aaagaatgat gatatgtggt atcaccttt caaagtcagt     480 catgaagaaa acattacttg gaaattcaaa gtgagtaaaa ttccaggtac tttcaaacag     540
ttaaccctga acctgggggt gatggttccc tttatccttt gcctgatctc attttttcttg     600 ttactttttct ccctagttag acacaccaag cagattcgac tgcatgctac agggttcaga     660
gaccccagta cagaggccca catgagggcc ataaaggcag tgatcatctt ctgctcctc     720 ctcatcgtgt actacccagt cttctcttgtt atgacctcta gcgctctgat tcctcaggga     780
aaattagtgt tgatgattgg tgacatagta actgtcattt tcccatcaag ccattcattc     840
attctaatta tgggaaatag caagttgagg gaagcttttc tgaagatgtt aagatttgtg     900
```

<210> SEQ ID NO 19
<211> LENGTH: 307
<212> TYPE: PRT
<213> ORGANISM: Homo sapiens
<220> FEATURE:
<223> OTHER INFORMATION: human T2R10 (hGR10)

<400> SEQUENCE: 19

```
Met Leu Arg Val Val Glu Gly Ile Phe Ile Phe Val Val Ser Glu
 1               5                  10                  15

Ser Val Phe Gly Val Leu Gly Asn Gly Phe Ile Gly Leu Val Asn Cys
                 20                  25                  30

Ile Asp Cys Ala Lys Asn Lys Leu Ser Thr Ile Gly Phe Ile Leu Thr
             35                  40                  45

Gly Leu Ala Ile Ser Arg Ile Phe Leu Ile Trp Ile Ile Ile Thr Asp
 50                  55                  60

Gly Phe Ile Gln Ile Phe Ser Pro Asn Ile Tyr Ala Ser Gly Asn Leu
 65                  70                  75                  80

Ile Glu Tyr Ile Ser Tyr Phe Trp Val Ile Gly Asn Gln Ser Ser Met
                 85                  90                  95

Trp Phe Ala Thr Ser Leu Ser Ile Phe Tyr Phe Leu Lys Ile Ala Asn
                100                 105                 110

Phe Ser Asn Tyr Ile Phe Leu Trp Leu Lys Ser Arg Thr Asn Met Val
            115                 120                 125

Leu Pro Phe Met Ile Val Phe Leu Leu Ile Ser Ser Leu Leu Asn Phe
130                 135                 140

Ala Tyr Ile Ala Lys Ile Leu Asn Asp Tyr Lys Thr Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
    210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Gln Leu Lys Cys Cys Glu Lys Arg Lys Asn Leu
    290                 295                 300

Arg Val Thr
305
```

<210> SEQ ID NO 20
<211> LENGTH: 924
<212> TYPE: DNA
<213> ORGANISM: Homo sapiens
<220> FEATURE:

aagtgtttcc ttagaagaag aaagcctttt gttccatag                                  939

<223> OTHER INFORMATION: human T2R10 (hGR10)

<400> SEQUENCE: 20

```
atgctacgtg tagtggaagg catcttcatt tttgttgtag ttagtgagtc agtgtttggg      60
gttttgggga atggatttat tggacttgta aactgcattg actgtgccaa gaataagtta     120
tctacgattg ctttattct caccggctta gctatttcaa gaattttct gatatggata      180
ataattacag atggatttat acagatattc tctccaaata tatatgcctc cggtaaccta     240
attgaatata ttagttactt tgggtaatt ggtaatcaat caagtatgtg gtttgccacc      300
agcctcagca tcttctattt cctgaagata gcaaattttt ccaactacat atttctctgg     360
ttgaagagca gaacaaatat ggttcttccc ttcatgatag tattcttact tatttcatcg     420
ttacttaatt ttgcatacat tgcgaagatt cttaatgatt ataaaacgaa gaatgacaca     480
gtctgggatc tcaacatgta taaaagtgaa tactttatta aacagatttt gctaaatctg     540
ggagtcattt tcttctttac actatcccta attacatga ttttttttaat catttcccctt   600
tggagacaca acaggcagat gcaatcgaat gtgacaggat tgagagactc caacacagaa     660
gctcatgtga aggcaatgaa agttttgata tctttcatca tcctcttat cttgtatttt      720
ataggcatgg ccatagaaat atcatgtttt actgtgcgag aaaacaaact gctgcttatg     780
tttggaatga caaccacagc catctatccc tggggtcact catttatctt aattctagga     840
aacagcaagc taaagcaagc ctctttgagg gtactgcagc aattgaagtg ctgtgagaaa     900
aggaaaaatc tcagagtcac atag                                            924
```

<210> SEQ ID NO 21
<211> LENGTH: 245
<212> TYPE: PRT
<213> ORGANISM: Homo sapiens
<220> FEATURE:
<221> NAME/KEY: MOD_RES
<222> LOCATION: (1)..(245)
<223> OTHER INFORMATION: human T2R11 (hGR11)
<223> OTHER INFORMATION: Xaa = any amino acid

<400> SEQUENCE: 21

```
Met Ala Asn Met Leu Lys Asn Met Leu Thr Met Ile Ser Ala Ile Asp
  1               5                  10                  15

Phe Ile Met Gly Ile Gln Arg Ser Arg Val Met Val Leu Val His Cys
                 20                  25                  30

Ile Asp Trp Ile Arg Arg Trp Lys Leu Ser Leu Ile Asp Phe Ile Leu
             35                  40                  45

Thr Cys Trp Ala Ile Ser Arg Ile Phe Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Asn His Leu Cys Thr Xaa Phe
                 85                  90                  95

Ala Thr Cys Leu Ala Val Phe Tyr Phe Leu Lys Ile Val Asn Phe Ser
                100                 105                 110

Tyr Leu Phe Tyr Phe Trp Leu Lys Trp Arg Ile Asn Lys Val Ala Phe
            115                 120                 125

Ile Leu Pro Leu Val Ser Ala Phe Ser Val Tyr Gln Leu Ser Phe Asp
        130                 135                 140

Val His Phe Xaa Cys Leu Leu Val Ser Cys Pro Lys Lys Tyr Glu Arg
145                 150                 155                 160
```

His Met Thr Gly Leu Leu Asn Val Ser Asn Asn Lys Asn Val Asn Asn
                165                 170                 175

Ile Ile Ile Phe Phe Ile Gly Ser Leu Ser Ser Phe Ser Ile Ser Ser
            180                 185                 190

Ile Phe Phe Leu Leu Leu Leu Ser Ser Xaa Arg His Met Lys His
            195                 200                 205

Ile Arg Phe Asn Phe Arg Asp Cys Arg Thr Pro Val Tyr Gly Pro Ile
        210                 215                 220

Ser Glu Pro Arg Lys Arg Phe Ser Phe Phe Val Leu Leu Leu Tyr Lys
225                 230                 235                 240

Asn Leu Pro Phe Ser
                245

<210> SEQ ID NO 22
<211> LENGTH: 315
<212> TYPE: PRT
<213> ORGANISM: Homo sapiens
<220> FEATURE:
<221> NAME/KEY: MOD_RES
<222> LOCATION: (1)..(315)
<223> OTHER INFORMATION: human T2R12 (hGR12)
<223> OTHER INFORMATION: Xaa = any amino acid

<400> SEQUENCE: 22

Met Ser Ser Ile Trp Glu Thr Leu Phe Ile Arg Ile Leu Val Val Xaa
1               5                   10                  15

Phe Ile Met Gly Thr Val Gly Asn Xaa Phe Ile Val Leu Val Asn Ile
            20                  25                  30

Ile Asp Xaa Ile Arg Asn Xaa Lys Val Ser Leu Ile Asp Phe Ile Leu
        35                  40                  45

Asn Cys Leu Ala Ile Ser Arg Ile Cys Phe Leu Xaa Ile Thr Ile Leu
    50                  55                  60

Ala Thr Ser Phe Asn Ile Gly Tyr Glu Lys Met Pro Asp Ser Lys Asn
65                  70                  75                  80

Leu Ala Val Ser Phe Asp Ile Leu Trp Thr Gly Ser Ser Tyr Phe Cys
                85                  90                  95

Leu Ser Cys Thr Thr Cys Leu Ser Val Phe Tyr Phe Leu Lys Val Ala
            100                 105                 110

Asn Phe Ser Asn Pro Ile Phe Leu Trp Met Lys Trp Lys Ile His Lys
        115                 120                 125

Val Leu Leu Phe Ile Val Leu Glu Ala Thr Ile Ser Phe Cys Thr Thr
130                 135                 140

Ser Ile Leu Lys Glu Ile Ile Asn Ser Leu Ile Xaa Glu Arg Val
145                 150                 155                 160

Thr Ile Lys Gly Asn Leu Thr Phe Asn Tyr Met Asp Thr Met His Asp
                165                 170                 175

Phe Thr Ser Leu Phe Leu Leu Gln Met Met Phe Ile Leu Pro Phe Val
            180                 185                 190

Glu Thr Leu Ala Ser Ile Leu Leu Ile Leu Ser Leu Trp Ser His
            195                 200                 205

Thr Arg Gln Met Lys Leu His Gly Ile Tyr Ser Arg Asp Pro Ser Thr
        210                 215                 220

Glu Ala His Val Lys Pro Ile Lys Ala Ile Ile Ser Phe Leu Leu Leu
225                 230                 235                 240

Phe Ile Val His Tyr Phe Ile Ser Ile Ile Leu Thr Leu Ala Cys Pro
                245                 250                 255

Leu Leu Asp Phe Val Ala Ala Arg Thr Phe Ser Ser Val Leu Val Phe
             260                 265                 270

Phe His Pro Ser Gly His Ser Phe Leu Leu Ile Leu Arg Asp Ser Lys
     275                 280                 285

Leu Lys Gln Ala Ser Leu Cys Val Leu Lys Lys Met Lys Tyr Ala Lys
     290                 295                 300

Lys Asp Ile Ile Ser His Phe Tyr Lys His Ala
305                 310                 315

<210> SEQ ID NO 23
<211> LENGTH: 948
<212> TYPE: DNA
<213> ORGANISM: Homo sapiens
<220> FEATURE:
<223> OTHER INFORMATION: human T2R12 (hGR12)

<400> SEQUENCE: 23

```
atgtcaagca tttgggagac actgtttata agaattcttg tagtgtaatt cataatgggg      60
actgtgggaa attgattcat tgtattggtt aatatcattg actgaatcag gaactgaaag     120
gtctccctga ttgattttat tctcaactgc ttggccatct ccaggatatg tttcctgtag     180
ataacaattt tagctacctc tttcaatata ggctatgaga aaatgcctga ttctaagaat     240
cttgcagtaa gttttgacat tctctggaca ggatccagct attctgcct gtcctgtacc      300
acttgcctca gtgtcttcta tttcctcaag gtagccaact tctccaatcc cattttcctc     360
tggatgaaat ggaaaattca caaggtgctt ctctttattg tactagaggc aacgatctct     420
ttctgcacaa cttccattct gaaggaaata ataattaata gtttaatcta agaacgggta     480
acaataaaag gcaacttgac atttaattat atggatacca tgcatgattt cacttctctg     540
tttctccttc agatgatgtt catccttcct tttgtggaaa cactggcttc cattcttctc     600
ttaatcctct ccttatggag ccacaccagg cagatgaagc tacatggtat ttattccagg     660
gatcccagca cagaagccca tgtaaaacct ataaaagcta aatttcatt tctactcctc      720
tttattgtgc attatttcat cagtatcata ctaacattgg cctgtcctct tctagacttc     780
gttgcggcaa ggacttttag tagtgtgctg gtatttttcc atccatctgg ccattcattt     840
cttctaattt tacgggacag caaactgaag caagcttctc tctgtgtcct gaagaagatg     900
aagtatgcca aaaggacat aatctctcat ttttataaac atgcctga                   948
```

<210> SEQ ID NO 24
<211> LENGTH: 303
<212> TYPE: PRT
<213> ORGANISM: Homo sapiens
<220> FEATURE:
<223> OTHER INFORMATION: human T2R13 (hGR13)

<400> SEQUENCE: 24

Met Glu Ser Ala Leu Pro Ser Ile Phe Thr Leu Val Ile Ile Ala Glu
 1               5                  10                  15

Phe Ile Ile Gly Asn Leu Ser Asn Gly Phe Ile Val Leu Ile Asn Cys
             20                  25                  30

Ile Asp Trp Val Ser Lys Arg Glu Leu Ser Ser Val Asp Lys Leu Leu
         35                  40                  45

Ile Ile Leu Ala Ile Ser Arg Ile Gly Leu Ile Trp Glu Ile Leu Val
     50                  55                  60

Ser Trp Phe Leu Ala Leu His Tyr Leu Ala Ile Phe Val Ser Gly Thr
65                  70                  75                  80

```
Gly Leu Arg Ile Met Ile Phe Ser Trp Ile Val Ser Asn His Phe Asn
                85                  90                  95
Leu Trp Leu Ala Thr Ile Phe Ser Ile Phe Tyr Leu Leu Lys Ile Ala
            100                 105                 110
Ser Phe Ser Ser Pro Ala Phe Leu Tyr Leu Lys Trp Arg Val Asn Lys
        115                 120                 125
Val Ile Leu Met Ile Leu Leu Gly Thr Leu Val Phe Leu Phe Leu Asn
    130                 135                 140
Leu Ile Gln Ile Asn Met His Ile Lys Asp Trp Leu Asp Arg Tyr Glu
145                 150                 155                 160
Arg Asn Thr Thr Trp Asn Phe Ser Met Ser Asp Phe Glu Thr Phe Ser
                165                 170                 175
Val Ser Val Lys Phe Thr Met Thr Met Phe Ser Leu Thr Pro Phe Thr
            180                 185                 190
Val Ala Phe Ile Ser Phe Leu Leu Leu Ile Phe Ser Leu Gln Lys His
        195                 200                 205
Leu Gln Lys Met Gln Leu Asn Tyr Lys Gly His Arg Asp Pro Arg Thr
    210                 215                 220
Lys Val His Thr Asn Ala Leu Lys Ile Val Ile Ser Phe Leu Leu Phe
225                 230                 235                 240
Tyr Ala Ser Phe Phe Leu Cys Val Leu Ile Ser Trp Ile Ser Glu Leu
                245                 250                 255
Tyr Gln Asn Thr Val Ile Tyr Met Leu Cys Glu Thr Ile Gly Val Phe
            260                 265                 270
Ser Pro Ser Ser His Ser Phe Leu Leu Ile Leu Gly Asn Ala Lys Leu
        275                 280                 285
Arg Gln Ala Phe Leu Leu Val Ala Ala Lys Val Trp Ala Lys Arg
    290                 295                 300

<210> SEQ ID NO 25
<211> LENGTH: 912
<212> TYPE: DNA
<213> ORGANISM: Homo sapiens
<220> FEATURE:
<223> OTHER INFORMATION: human T2R13 (hGR13)

<400> SEQUENCE: 25
atggaaagtg ccctgccgag tatcttcact cttgtaataa ttgcagaatt cataattggg      60
aatttgagca atggatttat agtactgatc aactgcattg actgggtcag taaaagagag     120
ctgtcctcag tcgataaact cctcattatc ttggcaatct ccagaattgg gctgatctgg     180
gaaatattag taagttggtt tttagctctg cattatctag ccatatttgt gtctggaaca     240
ggattaagaa ttatgatttt tagctggata gtttctaatc acttcaatct ctggcttgct     300
acaatcttca gcatctttta tttgctcaaa atagcgagtt tctctagccc tgcttttctc     360
tatttgaagt ggagagtaaa caaagtgatt ctgatgatac tgctaggaac cttggtcttc     420
ttatttttaa atctgataca aataaacatg catataaaag actggctgga ccgatatgaa     480
agaaacacaa cttggaattt cagtatgagt gactttgaaa cattttcagt gtcggtcaaa     540
ttcactatga ctatgttcag tctaacacca tttactgtgg ccttcatctc ttttctcctg     600
ttaattttct ccctgcagaa acatctccag aaaatgcaac tcaattacaa aggcacagag     660 accccagga ccaaggtcca tacaaatgcc ttgaaaattg tgatctcatt ccttttattc      720
tatgctagtt tctttctatg tgttctcata tcatggattt ctgagctgta tcagaacaca     780
gtgatctaca tgctttgtga gacgattgga gtcttctctc cttcaagcca ctcctttctt     840
```
ctgattctag gaaacgctaa gttaagacag gcctttcttt tggtggcagc taaggtatgg    900
gctaaacgat ga    912

<210> SEQ ID NO 26
<211> LENGTH: 317
<212> TYPE: PRT
<213> ORGANISM: Homo sapiens
<220> FEATURE:
<223> OTHER INFORMATION: human T2R14 (hGR14)

<400> SEQUENCE: 26

Met Gly Gly Val Ile Lys Ser Ile Phe Thr Phe Val Leu Ile Val Glu
 1               5                  10                  15

Phe Ile Ile Gly Asn Leu Gly Asn Ser Phe Ile Ala Leu Val Asn Cys
                20                  25                  30

Ile Asp Trp Val Lys Gly Arg Lys Ile Ser Ser Val Asp Arg Ile Leu
            35                  40                  45

Thr Ala Leu Ala Ile Ser Arg Ile Ser Leu Val Trp Leu Ile Phe Gly
    50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95

Val Trp Leu Ala Thr Gly Leu Gly Thr Phe Tyr Phe Leu Lys Ile Ala
            100                 105                 110

Asn Phe Ser Asn Ser Ile Phe Leu Tyr Leu Lys Trp Arg Val Lys Lys
        115                 120                 125

Val Val Leu Val Leu Leu Leu Val Thr Ser Val Phe Leu Phe Leu Asn
    130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190

Leu Ser Leu Ala Met Phe Leu Leu Leu Ile Phe Ser Met Trp Lys His
        195                 200                 205

Arg Lys Lys Met Gln His Thr Val Lys Ile Ser Gly Asp Ala Ser Thr
    210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
            260                 265                 270

Pro Ser Cys His Ser Cys Val Leu Ile Leu Gly Asn Lys Lys Leu Arg
        275                 280                 285

Gln Ala Ser Leu Ser Val Leu Leu Trp Leu Arg Tyr Met Phe Lys Asp
    290                 295                 300

Gly Glu Pro Ser Gly His Lys Glu Phe Arg Glu Ser Ser
305                 310                 315

<210> SEQ ID NO 27
<211> LENGTH: 954
<212> TYPE: DNA

<213> ORGANISM: Homo sapiens
<220> FEATURE:
<223> OTHER INFORMATION: huamn T2R14 (hGR14)

<400> SEQUENCE: 27

```
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg ttttttccag ctttatttgc cactgaaaaa     240
atgttcagaa tgcttactaa tatctggaca gtgatcaatc attttagtgt ctggttagct     300
acaggcctcg gtactttta ttttctcaag atagccaatt tttctaactc tatttttctc     360
tacctaaagt ggagggttaa aaaggtggtt ttggtgctgc ttcttgtgac ttcggtcttc     420
ttgtttttaa atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcatacccc tttactttgt ccctggcaat gtttcttctc     600
ctcatcttct ccatgtggaa acatcgcaag aagatgcagc acactgtcaa aatatccgga     660
gacgccagca ccaaagccca cagaggagtt aaaagtgtga tcactttctt cctactctat     720
gccattttct ctctgtcttt tttcatatca gtttggaccct ctgaaaggtt ggaggaaaat     780
ctaattattc tttcccaggt gatgggaatg cttatcctt catgtcactc atgtgttctg     840
attcttggaa caagaagct gagacaggcc tctctgtcag tgctactgtg gctgaggtac     900
atgttcaaag atggggagcc ctcaggtcac aaagaattta gagaatcatc ttga           954
```

<210> SEQ ID NO 28
<211> LENGTH: 300
<212> TYPE: PRT
<213> ORGANISM: Homo sapiens
<220> FEATURE:
<221> NAME/KEY: MOD_RES
<222> LOCATION: (257)
<223> OTHER INFORMATION: human T2R15 (hGR15)
<223> OTHER INFORMATION: Xaa = any amino acid

<400> SEQUENCE: 28

```
Met Ile Thr Phe Leu Pro Ile Ile Phe Ser Ile Leu Val Val Thr
  1               5                  10                  15

Phe Val Leu Gly Asn Phe Ala Asn Gly Phe Ile Val Leu Val Asn Ser
                 20                  25                  30

Ile Glu Trp Val Lys Arg Gln Lys Ile Ser Phe Ala Asp Gln Ile Leu
             35                  40                  45

Thr Ala Leu Ala Val Ser Arg Val Gly Leu Leu Trp Val Ile Leu Leu
         50                  55                  60

His Trp Tyr Ala Thr Val Leu Asn Pro Gly Ser Tyr Ser Leu Gly Val
 65                  70                  75                  80

Arg Ile Thr Thr Ile Asn Ala Trp Ala Val Thr Asn His Phe Ser Ile
                 85                  90                  95

Trp Val Ala Thr Ser Leu Ser Ile Phe Tyr Phe Leu Lys Ile Ala Asn
                100                 105                 110

Phe Ser Asn Phe Ile Phe Leu His Leu Lys Arg Arg Ile Lys Ser Val
            115                 120                 125

Ile Pro Val Ile Leu Leu Gly Ser Leu Leu Phe Leu Val Cys His Leu
        130                 135                 140

Val Val Val Asn Met Asp Glu Ser Met Trp Thr Lys Glu Tyr Glu Gly
```

```
                145                 150                 155                 160
Asn Val Ser Trp Glu Ile Lys Leu Ser Asp Pro Thr His Leu Ser Asp
                    165                 170                 175
Met Thr Val Thr Thr Leu Ala Asn Leu Ile Pro Phe Thr Leu Ser Leu
                180                 185                 190
Leu Ser Phe Leu Leu Leu Ile Cys Ser Leu Cys Lys His Leu Lys Lys
            195                 200                 205
Met Gln Phe His Gly Lys Gly Ser Pro Asp Ser Asn Thr Lys Val His
        210                 215                 220
Ile Lys Ala Leu Gln Thr Val Thr Ser Phe Leu Leu Phe Ala Val
225                 230                 235                 240
Tyr Phe Leu Ser Leu Ile Thr Ser Ile Trp Asn Phe Arg Arg Arg Leu
                245                 250                 255
Xaa Asn Glu Pro Val Leu Met Leu Ser Gln Thr Thr Ala Ile Ile Tyr
                260                 265                 270
Pro Ser Phe His Ser Phe Ile Leu Ile Trp Gly Ser Lys Lys Leu Lys
                275                 280                 285
Gln Thr Phe Leu Leu Ile Leu Cys Gln Ile Lys Cys
        290                 295                 300

<210> SEQ ID NO 29
<211> LENGTH: 903
<212> TYPE: DNA
<213> ORGANISM: Homo sapiens
<220> FEATURE:
<223> OTHER INFORMATION: human T2R15 (hGR15)

<400> SEQUENCE: 29
atgataactt ttctacccat cattttttcc attctagtag tggttacatt tgttcttggg      60
aattttgcta atggcttcat agtgttggta aattccattg agtgggtcaa gagacaaaag     120
atctccttttg ctgaccaaat tctcactgct ctggcagtct ccagagttgg tttgctctgg    180
gtaatattat tacattggta tgcaactgtt ttgaatccag ttcatatag tttaggagta      240
agaattacta ctattaatgc ctgggctgta accaaccatt tcagcatctg ggttgctact     300
agcctcagca tattttattt cctcaagatt gccaatttct ccaactttat ttttcttcac     360
ttaaaaagga gaattaagag tgtcattcca gtgatactat gggggtctttt gttattttg    420
gtttgtcatc ttgttgtggt aaacatggat gagagtatgt ggacaaaaga atatgaagga    480
aacgtgagtt gggagatcaa attgagtgat ccgacgcacc tttcagatat gactgtaacc    540
acgcttgcaa acttaatacc ctttactctg tccctgttat cttttctgct cttaatctgt    600
tctttgtgta acatctcaa gaagatgcag ttccatggca aaggatctcc agattccaac     660
accaaggtcc acataaaagc tttgcaaacg gtgacctcct tcctcttgtt atttgctgtt    720
tactttctgt ccctaatcac atcgatttgg aattttagga ggaggctgta gaacgaacct    780
gtcctcatgc tcagccaaac tactgcaatt atatacccttt catttcattc attcatccta   840
atttggggaa gcaagaagct gaaacagacc tttcttttga ttttgtgtca gattaagtgc    900
tga                                                                   903

<210> SEQ ID NO 30
<211> LENGTH: 291
<212> TYPE: PRT
<213> ORGANISM: Homo sapiens
<220> FEATURE:
<223> OTHER INFORMATION: human T2R16 (hGR16)
```

<400> SEQUENCE: 30

```
Met Ile Pro Ile Gln Leu Thr Val Phe Phe Met Ile Ile Tyr Val Leu
  1               5                  10                  15
Glu Ser Leu Thr Ile Ile Val Gln Ser Ser Leu Ile Val Ala Val Leu
             20                  25                  30
Gly Arg Glu Trp Leu Gln Val Arg Arg Leu Met Pro Val Asp Met Ile
         35                  40                  45
Leu Ile Ser Leu Gly Ile Ser Arg Phe Cys Leu Gln Trp Ala Ser Met
     50                  55                  60
Leu Asn Asn Phe Cys Ser Tyr Phe Asn Leu Asn Tyr Val Leu Cys Asn
 65                  70                  75                  80
Leu Thr Ile Thr Trp Glu Phe Phe Asn Ile Leu Thr Phe Trp Leu Asn
                 85                  90                  95
Ser Leu Leu Thr Val Phe Tyr Cys Ile Lys Val Ser Ser Phe Thr His
            100                 105                 110
His Ile Phe Leu Trp Leu Arg Trp Arg Ile Leu Arg Leu Phe Pro Trp
        115                 120                 125
Ile Leu Leu Gly Ser Leu Met Ile Thr Cys Val Thr Ile Ile Pro Ser
    130                 135                 140
Ala Ile Gly Asn Tyr Ile Gln Ile Gln Leu Leu Thr Met Glu His Leu
145                 150                 155                 160
Pro Arg Asn Ser Thr Val Thr Asp Lys Leu Glu Asn Phe His Gln Tyr
                165                 170                 175
Gln Phe Gln Ala His Thr Val Ala Leu Val Ile Pro Phe Ile Leu Phe
            180                 185                 190
Leu Ala Ser Thr Ile Phe Leu Met Ala Ser Leu Thr Lys Gln Ile Gln
        195                 200                 205
His His Ser Thr Gly His Cys Asn Pro Ser Met Lys Ala Arg Phe Thr
    210                 215                 220
Ala Leu Arg Ser Leu Ala Val Leu Phe Ile Val Phe Thr Ser Tyr Phe
225                 230                 235                 240
Leu Thr Ile Leu Ile Thr Ile Gly Thr Leu Phe Asp Lys Arg Cys
                245                 250                 255
Trp Leu Trp Val Trp Glu Ala Phe Val Tyr Ala Phe Ile Leu Met His
            260                 265                 270
Ser Thr Ser Leu Met Leu Ser Ser Pro Thr Leu Lys Arg Ile Leu Lys
        275                 280                 285
Gly Lys Cys
    290
```

<210> SEQ ID NO 31
<211> LENGTH: 876
<212> TYPE: DNA
<213> ORGANISM: Homo sapiens
<220> FEATURE:
<223> OTHER INFORMATION: human T2R16 (hGR16)

<400> SEQUENCE: 31

```
atgataccca tccaactcac tgtcttcttc atgatcatct atgtgcttga gtccttgaca      60
attattgtgc agagcagcct aattgttgca gtgctgggca gagaatggct gcaagtcaga     120
aggctgatgc ctgtggacat gattctcatc agcctgggca tctctcgctt ctgtctacag     180
tgggcatcaa tgctgaacaa ttttgctcc tattttaatt tgaattatgt actttgcaac      240
ttaacaatca cctgggaatt ttttaatatc cttacattct ggttaaacag cttgcttacc     300
```

```
gtgttctact gcatcaaggt ctcttctttc acccatcaca tctttctctg gctgaggtgg    360
agaattttga ggttgttccc ctggatatta ctgggttctc tgatgattac ttgtgtaaca    420
atcatccctt cagctattgg gaattacatt caaattcagt tactcaccat ggagcatcta    480
ccaagaaaca gcactgtaac tgacaaactt gaaaattttc atcagtatca gttccaggct    540
catacagttg cattggttat tcctttcatc ctgttcctgg cctccaccat ctttctcatg    600
gcatcactga ccaagcagat acaacatcat agcactggtc actgcaatcc aagcatgaaa    660
gcgcgcttca ctgccctgag gtcccttgcc gtcttattta ttgtgtttac ctcttacttt    720
ctaaccatac tcatcaccat tataggtact ctatttgata agagatgttg gttatgggtc    780
tgggaagctt ttgtctatgc tttcatctta atgcattcca cttcactgat gctgagcagc    840
cctacgttga aaaggattct aaagggaaag tgctag                               876
```

<210> SEQ ID NO 32
<211> LENGTH: 330
<212> TYPE: PRT
<213> ORGANISM: Homo sapiens
<220> FEATURE:
<221> NAME/KEY: MOD_RES
<222> LOCATION: (1)..(330)
<223> OTHER INFORMATION: human T2R17 (hGR17)
<223> OTHER INFORMATION: Xaa = any amino acid

<400> SEQUENCE: 32

```
Met Cys Ser Ala Xaa Leu Leu Ile Ile Leu Ser Ile Leu Val Val Phe
  1               5                  10                  15

Ala Phe Val Leu Gly Asn Val Ala Asn Gly Phe Ile Ala Leu Ile Asn
                 20                  25                  30

Val Asn Asp Trp Val Lys Thr Gln Lys Ile Ser Ser Thr Asp Gln Ile
             35                  40                  45

Val Thr Ala Leu Ala Phe Ser Arg Ile Gly Leu Leu Xaa Thr Leu Ile
         50                  55                  60

Ile Leu Leu His Trp Tyr Ala Thr Val Phe Asn Ser Ala Leu Tyr Ser
 65                  70                  75                  80

Leu Glu Val Arg Ile Val Pro Ser Asn Val Ser Ala Ile Ile Asn His
                 85                  90                  95

Phe Ser Ile Trp Leu Ala Thr Ser Leu Ser Ile Phe Tyr Leu Phe Lys
                100                 105                 110

Ile Ala Asn Phe Ser Asn Phe Ile Phe Leu His Leu Lys Lys Arg Ile
            115                 120                 125

Lys Ser Val Leu Leu Val Ile Leu Leu Gly Ser Leu Val Phe Leu Ile
        130                 135                 140

Cys Asn Leu Ala Val Val Thr Met Asp Asp Ser Val Trp Thr Lys Glu
145                 150                 155                 160

Phe Glu Gly Asn Val Thr Trp Lys Ile Glu Leu Arg Asn Ala Ile His
                165                 170                 175

Leu Ser Asn Met Thr Ile Thr Asn His Ala Ser Lys Leu His Thr Val
            180                 185                 190

His Ser Asp Ser Asn Ile Phe Ser Ala Val Ser Leu Phe Ser Xaa Thr
        195                 200                 205

Met Leu Ala Asn Phe Thr Leu Phe Ile Leu Thr Leu Ile Ser Phe Leu
    210                 215                 220

Leu Leu Val Cys Ser Pro Cys Lys His Leu Lys Met Met Gln Leu His
225                 230                 235                 240

Gly Lys Gly Ser Gln Asp Leu Ser Thr Lys Val His Ile Lys Pro Leu
```

-continued

```
                245                 250                 255
Gln Thr Val Ile Ser Phe Arg Met Leu Phe Ala Ile Tyr Phe Leu Cys
                260                 265                 270

Ile Ile Thr Ser Thr Trp Asn Pro Arg Thr Gln Gln Ser Asn Leu Val
            275                 280                 285

Phe Leu Leu Tyr Gln Thr Leu Ala Ile Met Tyr Pro Ser Phe His Ser
        290                 295                 300

Phe Ile Leu Ile Met Arg Ser Arg Lys Leu Lys Gln Thr Ser Leu Ser
305                 310                 315                 320

Val Leu Cys Gln Val Thr Cys Trp Val Lys
                325                 330

<210> SEQ ID NO 33
<211> LENGTH: 314
<212> TYPE: PRT
<213> ORGANISM: Homo sapiens
<220> FEATURE:
<221> NAME/KEY: MOD_RES
<222> LOCATION: (98)
<223> OTHER INFORMATION: human T2R18 (hGR18)
<223> OTHER INFORMATION: Xaa = any amino acid

<400> SEQUENCE: 33

Met Phe Val Gly Ile Asn Ile Phe Phe Leu Val Val Ala Thr Arg Gly
1               5                   10                  15

Leu Val Leu Gly Met Leu Gly Asn Gly Leu Ile Gly Leu Val Asn Cys
            20                  25                  30

Ile Glu Trp Ala Lys Ser Trp Lys Val Ser Ser Ala Asp Phe Ile Leu
        35                  40                  45

Thr Ser Leu Ala Ile Val Arg Ile Ile Arg Leu Tyr Leu Ile Leu Phe
    50                  55                  60

Asp Ser Phe Ile Met Val Leu Ser Pro His Leu Tyr Thr Ile Arg Lys
65                  70                  75                  80

Leu Val Lys Leu Phe Thr Ile Leu Trp Ala Leu Ile Asn Gln Leu Ser
                85                  90                  95

Ile Xaa Phe Ala Thr Cys Leu Ser Ile Phe Tyr Leu Leu Lys Ile Ala
            100                 105                 110

Asn Phe Ser His Ser Leu Phe Leu Trp Leu Lys Trp Arg Met Asn Gly
        115                 120                 125

Met Ile Val Met Leu Leu Ile Leu Ser Leu Phe Leu Leu Ile Phe Asp
    130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                165                 170                 175

Lys Leu Ser Ile Leu Lys Thr Leu Leu Ser Leu Thr Tyr Val Ile Pro
            180                 185                 190

Phe Leu Leu Thr Leu Thr Ser Leu Leu Leu Phe Ile Ser Leu Val
        195                 200                 205

Arg His Thr Lys Asn Leu Gln Leu Asn Ser Leu Gly Ser Arg Asp Ser
    210                 215                 220

Ser Thr Glu Ala His Lys Arg Ala Met Lys Met Val Ile Ala Phe Leu
225                 230                 235                 240

Leu Leu Phe Ile Ile Asn Phe Ile Ser Thr Leu Ile Gly Asp Trp Ile
                245                 250                 255

Phe Leu Glu Val Glu Asn Tyr Gln Val Met Met Phe Ile Met Met Ile
```

```
                260             265             270
Leu Leu Ala Phe Pro Ser Gly His Ser Phe Ile Ile Leu Gly Asn
        275                 280             285

Asn Lys Leu Arg Gln Ser Ser Leu Arg Leu Leu Trp His Leu Lys Phe
    290                 295                 300

Ser Leu Lys Lys Ala Lys Pro Leu Thr Ser
305                 310
```

<210> SEQ ID NO 34
<211> LENGTH: 945
<212> TYPE: DNA
<213> ORGANISM: Homo sapiens
<220> FEATURE:
<223> OTHER INFORMATION: human T2R18 (hGR18)

<400> SEQUENCE: 34

```
atgttcgttg gaattaatat tttctttctg gtggtggcaa caagaggact tgtcttagga      60
atgctgggaa acgggctcat tggactggta aactgcattg agtgggccaa gagttggaag    120
gtctcatcag ctgatttcat cctcaccagc ttggctatag tcagaatcat tcgactgtat    180
ttaatactat ttgattcatt tataatggta ttgtcccctc atctatatac catccgtaaa    240
ctagtaaaac tgtttactat tctttgggca ttaattaatc agttaagtat ctagtttgcc    300
acctgcctaa gcatttttcta cttgcttaag atagccaatt tctcccactc ccttttcctc    360
tggctgaagt ggagaatgaa cggaatgatt gttatgcttc ttatattgtc tttgttctta    420
ctgatttttg acagtttagt gctagaaata tttattgata tctcactcaa tataatagat    480
aaaagtaatc tgactttata tttagatgaa agtaaaactc tctatgataa actctctatt    540
ttaaaaactc ttctcagctt gacatacgtt attccctttc ttctgactct gacctctttg    600
ctccttttat ttatatcctt agtgagacac accaagaatt tgcagctcaa ctctctgggc    660
tcaagggact ccagcacaga ggcccataaa agggccatga aaatggtgat agccttcctc    720
ctccttttta ttattaactt tatttccact ttaataggag attggatctt ccttgaggta    780
gagaattatc aggtcatgat gtttattatg atgattttac ttgcctttcc ctcaggccac    840
tcatttatta aattttggg aaacaacaag ctaagacaga gctccttgag actactgtgg    900
catcttaaat tctctctgaa aaagcaaaa cctttaactt catag                      945
```

<210> SEQ ID NO 35
<211> LENGTH: 121
<212> TYPE: PRT
<213> ORGANISM: Homo sapiens
<220> FEATURE:
<223> OTHER INFORMATION: human T2R19 (hGR19)

<400> SEQUENCE: 35

```
Val Thr Thr Leu Ala Asn Leu Ile Pro Phe Thr Leu Ser Leu Ile Cys
  1               5                  10                  15

Phe Leu Leu Leu Ile Cys Ser Leu Cys Lys His Leu Lys Lys Met Arg
                 20                  25                  30

Leu His Ser Lys Gly Ser Gln Asp Pro Ser Thr Lys Val His Ile Lys
             35                  40                  45

Ala Leu Gln Thr Val Thr Ser Phe Leu Met Leu Phe Ala Ile Tyr Phe
         50                  55                  60

Leu Cys Ile Ile Thr Ser Thr Trp Asn Leu Arg Thr Gln Gln Ser Lys
 65                  70                  75                  80

Leu Val Leu Leu Leu Cys Gln Thr Val Ala Ile Met Tyr Pro Ser Phe
```

```
                    85                  90                  95
His Ser Phe Ile Leu Ile Met Gly Ser Arg Lys Leu Lys Gln Thr Phe
            100                 105                 110

Leu Ser Val Leu Trp Gln Met Thr Cys
        115                 120

<210> SEQ ID NO 36
<211> LENGTH: 466
<212> TYPE: DNA
<213> ORGANISM: Homo sapiens
<220> FEATURE:
<223> OTHER INFORMATION: human T2R19 (hGR19)

<400> SEQUENCE: 36
ctgtaactac tctagcaaac ctcatacact ttactctgag cctaatatgt tttctgctgt     60
taatctgttc tctttgtaaa catctcaaga agatgcggct ccatagcaaa ggatctcaag    120
atcccagcac caaggtccat ataaaagctt tgcaaactgt gacctccttc ctcatgttat    180
ttgccattta ctttctgtgt ataatcacat caacttggaa tcttaggaca cagcagagca    240
aacttgtact cctgctttgc caaactgttg caatcatgta tccttcattc cactcattca    300
tcctgattat gggaagtagg aagctaaaac agacctttct ttcagttttg tggcagatga    360
catgctgagt gaaagaagag aaaccctcaa ctccatagat tcacaagggg agcatcgtgg    420
gtcttctagc agaaaacaaa ctgatggtgt ctggaacatt ttatat                   466

<210> SEQ ID NO 37
<211> LENGTH: 129
<212> TYPE: PRT
<213> ORGANISM: Homo sapiens
<220> FEATURE:
<221> NAME/KEY: MOD_RES
<222> LOCATION: (3)
<223> OTHER INFORMATION: human T2R20 (hGR20)
<223> OTHER INFORMATION: Xaa = any amino acid

<400> SEQUENCE: 37

His Leu Xaa Arg Lys Ala Lys Ser Val Val Leu Val Ile Val Leu Gly
1               5                   10                  15

Ser Leu Phe Phe Leu Val Cys Gln Leu Val Met Lys Asn Thr Tyr Ile
            20                  25                  30

Asn Val Trp Thr Glu Glu Cys Glu Gly Asn Val Thr Trp Lys Ile Lys
        35                  40                  45

Leu Arg Asn Ala Met His Leu Ser Asn Leu Thr Val Ala Met Leu Ala
    50                  55                  60

Asn Leu Ile Pro Phe Thr Leu Thr Val Ile Ser Phe Leu Leu Leu Ile
65                  70                  75                  80

Tyr Ser Leu Cys Lys His Leu Lys Lys Met Gln Leu His Gly Lys Gly
                85                  90                  95

Ser Gln Asp Pro Ser Thr Lys Ile His Ile Lys Ala Leu Gln Thr Val
            100                 105                 110

Thr Ser Phe Leu Val Leu Leu Ala Ile Tyr Phe Leu Cys Leu Ile Ile
        115                 120                 125

Ser

<210> SEQ ID NO 38
<211> LENGTH: 397
<212> TYPE: DNA
<213> ORGANISM: Homo sapiens
<220> FEATURE:
```

-continued

```
<221> NAME/KEY: modified_base
<222> LOCATION: (12)
<223> OTHER INFORMATION: human T2R20 (hGR20)
<223> OTHER INFORMATION: n = g, a, c or t

<400> SEQUENCE: 38
ttcatcactt anaaaggaag gctaagagtg tagttctggt gatagtgttg gggtctttgt    60
tctttttggt tgtcaacttt gtgatgaaaa acacgtatat aaatgtgtgg acagaagaat   120
gtgaaggaaa cgtaacttgg aagatcaaac tgaggaatgc aatgcacctt ccaacttga    180 ctgtagccat gctagcaaac ttgataccat tcactctgac cgtgatatct tttctgctgt   240
taatctactc tctgtgtaaa catctgaaga agatgcagct ccatggcaaa ggatctcaag   300
atcccagcac caagatccac ataaaagctc tgcaaactgt gacctccttc ctcgtattac   360
ttgccattta ctttctgtgt ctaatcatat cctttg                              397

<210> SEQ ID NO 39
<211> LENGTH: 312
<212> TYPE: PRT
<213> ORGANISM: Homo sapiens
<220> FEATURE:
<221> NAME/KEY: MOD_RES
<222> LOCATION: (1)..(312)
<223> OTHER INFORMATION: human T2R21 (hGR21)
<223> OTHER INFORMATION: Xaa = any amino acid

<400> SEQUENCE: 39
```

Met Pro Pro Gly Ile Gly Asn Thr Phe Leu Ile Val Met Met Gly Glu
 1               5                  10                  15

Phe Ile Ile Xaa Met Leu Gly Asn Gly Phe Ile Val Leu Val Asn Cys
                20                  25                  30

Ile Asp Trp Xaa Gly Val Lys Xaa Ser Tyr Xaa Thr Ala Ser Ser
            35                  40                  45

Pro Ala Trp Leu Ser Pro Gln Ser Val Asn Phe Gly Xaa Tyr Tyr Leu
    50                  55                  60

Ile His Leu Xaa Gln His Tyr Gly His Ile Tyr Met Pro Ser Ile Asn
 65                 70                  75                  80

Xaa Xaa Asn Leu Phe Ile Phe Phe Gly His Xaa Pro Ile Thr Xaa Leu
                85                  90                  95

Pro Gly Leu Leu Pro Xaa Cys Phe Leu Leu Leu Xaa Asn Thr Tyr Phe
            100                 105                 110

Ser His Pro Cys Phe Ile Trp Leu Arg Trp Arg Ile Ser Arg Thr Leu
        115                 120                 125

Leu Glu Leu Pro Leu Gly Ser Leu Leu Leu Leu Phe Phe Asn Leu Ala
    130                 135                 140

Leu Thr Gly Gly Leu Ser Asp Leu Trp Ile Asn Ile Tyr Thr Ile Tyr
145                 150                 155                 160

Glu Arg Asn Ser Thr Trp Ser Leu Asp Val Ser Lys Ile Leu Tyr Cys
                165                 170                 175

Ser Leu Trp Ile Leu Val Ser Leu Ile Tyr Leu Ile Ser Phe Leu Leu
            180                 185                 190

Ser Leu Ile Ser Leu Leu Leu Ile Leu Ser Leu Met Arg His Ile
        195                 200                 205

Arg Asn Leu Gln Leu Asn Thr Met Gly Pro Arg Asp Leu Arg Met Lys
    210                 215                 220

Ala His Lys Arg Ala Met Lys Met Lys Met Lys Met Met Val Ser Phe
225                 230                 235                 240

Leu Leu Phe Phe Leu Val His Phe Ser Ser Leu Leu Pro Thr Gly Trp
                245                 250                 255

Ile Phe Leu Ile Gln Gln Lys Xaa Gln Ala Asn Phe Phe Val Leu Leu
            260                 265                 270

Thr Ser Ile Ile Phe Pro Ser Ser His Ser Phe Val Leu Ile Leu Glu
        275                 280                 285

Asn Cys Lys Leu Arg Gln Thr Ala Val Gly Pro Leu Trp His Leu Lys
    290                 295                 300

Cys His Leu Lys Arg Val Lys Leu
305                 310

<210> SEQ ID NO 40
<211> LENGTH: 90
<212> TYPE: PRT
<213> ORGANISM: Homo sapiens
<220> FEATURE:
<221> NAME/KEY: MOD_RES
<222> LOCATION: (1)..(90)
<223> OTHER INFORMATION: human T2R22 (hGR22)
<223> OTHER INFORMATION: Xaa = any amino acid

<400> SEQUENCE: 40

Met Ala Thr Glu Ser Asp Thr Asn Leu Leu Ile Leu Ala Ile Ala Glu
 1               5                  10                  15

Phe Ile Ile Ser Met Leu Gly Asn Val Phe Ile Gly Leu Val Asn Cys
            20                  25                  30

Ser Glu Xaa Ile Lys Asn Xaa Lys Val Phe Ser Ala Asp Phe Ile Leu
        35                  40                  45

Thr Cys Leu Ala Ile Ser His Asn Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Xaa Lys Asn Cys Ile Met Leu Trp Thr
            85                  90

<210> SEQ ID NO 41
<211> LENGTH: 656
<212> TYPE: DNA
<213> ORGANISM: Homo sapiens
<220> FEATURE:
<221> NAME/KEY: modified_base
<222> LOCATION: (1)..(656)
<223> OTHER INFORMATION: human T2R22 (hGR22)
<223> OTHER INFORMATION: n = g, a, c or t

<400> SEQUENCE: 41
tatagggacn gtgatgcttc gtacactctc caagaagaaa cactccgtga ggtatgtgag      60
actgcatncc ttagtagatc tnttgggata tatattcata atatagaaaa anaggcaaag     120
acttncttaa gtatatgaga ctctatccaa cagcagaagg ttctgatcaa gactggaagt     180
gcaatanaag caatgaagat aagtatcaga tatgaatgct cttctgcaat ggtctgattg     240
tnacattatt aatgatacan agtattaaaa acttggattt tnttgtctct ggagatggcc     300
accgaatcgg acacaaatct tctgattctg caatagcag aattcatcat cagcatgctg      360
gggaatgtgt tcattggact ggtaaactgc tctgaagga tcaagaacca naaggtcttc      420
tcagctgact tcatcctcac ctgcttggct atctctcaca atggacaact gttggtgata     480
ctgtttgatt catttctagt gggacttgct tcacatctat ataccacata tagactanga     540
aaaaactgta ttatgctttg acatgactaa atcacttgac acactgcttc gcacgtgcta     600
gcatattcta ttcttagata gccacttcnc actccttgtc tctgctgaag tgggat    656

<210> SEQ ID NO 42
<211> LENGTH: 72
<212> TYPE: PRT
<213> ORGANISM: Homo sapiens
<220> FEATURE:
<221> NAME/KEY: MOD_RES
<222> LOCATION: (1)..(72)
<223> OTHER INFORMATION: human T2R23 (hGR23)
<223> OTHER INFORMATION: Xaa = any amino acid

<400> SEQUENCE: 42

Val Ala Phe Val Leu Gly Asn Val Ala Asn Gly Phe Ile Ala Leu Val
 1               5                  10                  15

Asn Val Ile Asp Xaa Val Asn Thr Arg Lys Ile Ser Ser Ala Glu Gln
            20                  25                  30

Ile Leu Thr Ala Leu Val Val Ser Arg Ile Gly Xaa Thr Leu Xaa His
        35                  40                  45

Ser Ile Pro Xaa Asp Ala Thr Arg Cys Xaa Ser Ala Leu Tyr Arg Xaa
    50                  55                  60

Glu Val Arg Ile Val Ala Ser Asn
 65                  70

<210> SEQ ID NO 43
<211> LENGTH: 589
<212> TYPE: DNA
<213> ORGANISM: Homo sapiens
<220> FEATURE:
<221> NAME/KEY: modified_base
<222> LOCATION: (1)..(589)
<223> OTHER INFORMATION: human T2R23 (hGR23)
<223> OTHER INFORMATION: n = g, a, c or t

<400> SEQUENCE: 43
agggttgagt cgtgcttatc ttcacttaac ctagtatana antacagcat atagcaagga    60
gagaatgtat atgaagagga gtgaatttga gtctgtttga gaataatgac cttttctatt   120
tctataaaga cagttttgaa ttcatctatt agcatatgct ggtgcttgcc tgttgacact   180
agtcactgaa tttaaaggca gaaaatgtta ttgcacattt agtaatcaag tgttcatcga   240
agttaacatc tggatgttaa aggactcaga acaagtgtta ctaagcctgc attttttat    300 ctgttcaaac atgatgtgtt nctgctcat catttcatca attctggtag agttgcattt   360
gttcttggaa atgtngccaa tggcttcata gctctagtaa atgtcattga ctgngttaac   420
acacgaaaga tctcctcagc tgagcaaatt ctcactgctc tggtggtctc cagaattggt   480
nntactctgn gtcatagtat tccttgagat gcaactagat gttaatctgc tctatatagg   540
ntagaagtaa gaattgttgc ttctaatgcc tgagctcgta cgaaccatt               589

<210> SEQ ID NO 44
<211> LENGTH: 314
<212> TYPE: PRT
<213> ORGANISM: Homo sapiens
<220> FEATURE:
<223> OTHER INFORMATION: human T2R24 (hGR24)

<400> SEQUENCE: 44

Met Ala Thr Glu Leu Asp Lys Ile Phe Leu Ile Leu Ala Ile Ala Glu
 1               5                  10                  15

Phe Ile Ile Ser Met Leu Gly Asn Val Phe Ile Gly Leu Val Asn Cys
            20                  25                  30

```
Ser Glu Gly Ile Lys Asn Gln Lys Val Phe Ser Ala Asp Phe Ile Leu
         35                  40                  45

Thr Cys Leu Ala Ile Ser Thr Ile Gly Gln Leu Leu Val Ile Leu Phe
         50                  55                  60

Asp Ser Phe Leu Val Gly Leu Ala Ser His Leu Tyr Thr Thr Tyr Arg
 65                  70                  75                  80

Leu Gly Lys Thr Val Ile Met Leu Trp His Met Thr Asn His Leu Thr
                 85                  90                  95

Thr Trp Leu Ala Thr Cys Leu Ser Ile Phe Tyr Phe Lys Ile Ala
                 100                 105                 110

His Phe Pro His Ser Leu Phe Leu Trp Leu Arg Trp Arg Met Asn Gly
             115                 120                 125

Met Ile Val Met Leu Leu Ile Leu Ser Leu Phe Leu Leu Ile Phe Asp
         130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                 165                 170                 175

Lys Leu Ser Ile Leu Lys Thr Leu Leu Ser Leu Thr Ser Phe Ile Pro
             180                 185                 190

Phe Ser Leu Phe Leu Thr Ser Leu Leu Phe Leu Phe Leu Ser Leu Val
         195                 200                 205

Arg His Thr Arg Asn Leu Lys Leu Ser Ser Leu Gly Ser Arg Asp Ser
         210                 215                 220

Ser Thr Glu Ala His Arg Arg Ala Met Lys Met Val Met Ser Phe Leu
225                 230                 235                 240

Phe Leu Phe Ile Val His Phe Ser Leu Gln Val Ala Asn Gly Ile
                 245                 250                 255

Phe Phe Met Leu Trp Asn Asn Lys Tyr Ile Lys Phe Val Met Leu Ala
                 260                 265                 270

Leu Asn Ala Phe Pro Ser Cys His Ser Phe Ile Leu Ile Leu Gly Asn
             275                 280                 285

Ser Lys Leu Arg Gln Thr Ala Val Arg Leu Leu Trp His Leu Arg Asn
         290                 295                 300

Tyr Thr Lys Thr Pro Asn Ala Leu Pro Leu
305                 310

<210> SEQ ID NO 45
<211> LENGTH: 945
<212> TYPE: DNA
<213> ORGANISM: Homo sapiens
<220> FEATURE:
<223> OTHER INFORMATION: human T2R24 (hGR24)

<400> SEQUENCE: 45
atggccaccg aattggacaa aatctttctg attctggcaa tagcagaatt catcatcagc      60
atgctgggga atgtgttcat tggactggta aactgctctg aagggatcaa gaaccaaaag     120
gtcttctcag ctgacttcat cctcacctgc ttggctatct ccacaattgg acaactgttg     180
gtgatactgt ttgattcatt tctagtggga cttgcttcac atttatatac cacatataga     240
ctaggaaaaa ctgttattat gctttggcac atgactaatc acttgacaac ctggcttgcc     300
acctgcctaa gcattttcta tttctttaag atagcccact ccccccactc cctttttcctc    360 tggctgaggt ggaggatgaa cggaatgatt gttatgcttc ttatattgtc tttgttctta    420 ctgattttg acagtttagt gctagaaata tttattgata tctcactcaa tataatagat    480
```

-continued

```
aaaagtaatc tgactttata tttagatgaa agtaaaactc tctatgataa actctctatt    540
ttaaaaactc ttctcagctt aaccagtttt atcccctttt ctctgttcct gacctccttg    600 cttttttat ttctgtcctt ggtgagacat actagaaatt tgaagctcag ttccttgggc     660
tctagagact ccagcacaga ggcccatagg agggccatga aaatggtgat gtctttcctt    720
ttcctcttca tagttcattt ttttccctta caagtggcca atgggatatt ttttatgttg    780
tggaacaaca agtacataaa gtttgtcatg ttagccttaa atgcctttcc ctcgtgccac    840
tcatttattc tcattctggg aaacagcaag ctgcgacaga cagctgtgag gctactgtgg    900
catcttagga actatacaaa aacaccaaat gctttacctt tgtag                    945
```

<210> SEQ ID NO 46
<211> LENGTH: 72
<212> TYPE: PRT
<213> ORGANISM: Homo sapiens
<220> FEATURE:
<223> OTHER INFORMATION: human T2R25 (hGR25)

<400> SEQUENCE: 46

```
Leu Ser Pro Phe Arg Met Leu Phe Ala Ile Tyr Phe Leu Cys Ile Ile
  1               5                  10                  15

Thr Ser Thr Trp Asn Pro Arg Thr Gln Gln Ser Asn Leu Val Phe Leu
             20                  25                  30

Leu Tyr Gln Thr Leu Ala Ile Met Tyr Pro Ser Phe His Ser Phe Ile
         35                  40                  45

Leu Ile Met Arg Ser Arg Lys Leu Lys Gln Thr Ser Leu Ser Val Leu
     50                  55                  60

Cys Gln Val Thr Cys Trp Val Lys
 65                  70
```

<210> SEQ ID NO 47
<211> LENGTH: 264
<212> TYPE: PRT
<213> ORGANISM: Homo sapiens
<220> FEATURE:
<221> NAME/KEY: MOD_RES
<222> LOCATION: (20)
<223> OTHER INFORMATION: human T2R26 (hGR26)
<223> OTHER INFORMATION: Xaa = any amino acid

<400> SEQUENCE: 47

```
Met Pro Pro Gly Ile Gly Asn Thr Phe Leu Ile Val Met Met Gly Glu
  1               5                  10                  15

Phe Ile Ile Xaa Met Leu Gly Asn Gly Phe Ile Val Leu Val Asn Cys
             20                  25                  30

Ile Asp Val Arg Ser Gln Met Ile Leu Leu Asp Asn Cys Ile Leu Thr
         35                  40                  45

Ser Leu Ala Ile Ser Thr Ile Ser Gln Leu Trp Ile Ile Leu Leu Asp
     50                  55                  60

Ser Phe Val Thr Ala Leu Trp Pro His Leu Tyr Ala Phe Asn Lys Leu
 65                  70                  75                  80

Ile Lys Phe Ile His Ile Phe Trp Ala Leu Thr Asn His Leu Val Thr
                 85                  90                  95

Trp Leu Ala Cys Cys Leu Ser Val Phe Tyr Phe Lys Ile Ala Tyr
                100                 105                 110

Phe Ser His Pro Cys Phe Ile Trp Leu Arg Trp Arg Ile Ser Arg Thr
            115                 120                 125
```

-continued

```
Leu Leu Glu Leu Pro Leu Gly Ser Leu Leu Leu Phe Asn Leu
    130                 135                 140

Ala Leu Thr Gly Gly Leu Ser Asp Leu Trp Ile Asn Ile Tyr Thr Met
145                 150                 155                 160

Tyr Glu Arg Asn Ser Thr Trp Ser Leu Asp Val Ser Lys Ile Leu Tyr
                165                 170                 175

Cys Ser Leu Trp Ile Leu Val Ser Leu Ile Tyr Leu Ile Ser Phe Leu
                180                 185                 190

Leu Ser Leu Ile Ser Leu Leu Leu Ile Leu Ser Leu Met Arg His
                195                 200                 205

Ile Arg Asn Leu Gln Leu Asn Thr Met Gly Pro Arg Asp Leu Arg Met
    210                 215                 220

Lys Ala His Lys Arg Ala Met Lys Met Lys Met Lys Met Met Val Ser
225                 230                 235                 240

Phe Leu Leu Phe Phe Leu Val His Phe Ser Ser Leu Leu Pro Thr Gly
                245                 250                 255

Trp Ile Phe Leu Ile Gln Gln Lys
                260
```

<210> SEQ ID NO 48
<211> LENGTH: 264
<212> TYPE: PRT
<213> ORGANISM: Homo sapiens
<220> FEATURE:
<221> NAME/KEY: MOD_RES
<222> LOCATION: (1)..(264)
<223> OTHER INFORMATION: human T2R27 (hGR27)
<223> OTHER INFORMATION: Xaa = any amino acid

<400> SEQUENCE: 48

```
Leu Ala Asn Leu Ile Asp Trp Ala Glu Asn Gln Ile Cys Leu Met Asp
1               5                   10                  15

Phe Ile Leu Ser Ser Leu Ala Ile Cys Arg Thr Leu Leu Leu Gly Cys
                20                  25                  30

Cys Val Ala Ile Arg Cys Thr Tyr Asn Asp Tyr Pro Asn Ile Asp Ala
                35                  40                  45

Val Asn His Asn Leu Ile Lys Ile Ile Thr Ile Phe Asp Ile Leu Arg
    50                  55                  60

Leu Val Ser Lys Xaa Leu Gly Ile Trp Phe Ala Ser Tyr Leu Ser Ile
65                  70                  75                  80

Phe Tyr Leu Leu Lys Val Ala Leu Phe His His Ala Ile Phe Leu Trp
                85                  90                  95

Leu Lys Trp Arg Ile Ser Arg Ala Val Phe Thr Phe Leu Met Ile Phe
                100                 105                 110

Leu Phe Phe Tyr Ile Ser Ile Ile Ser Met Ile Lys Ile Lys Leu Phe
                115                 120                 125

Leu Asp Gln Cys Xaa Tyr Lys Ile Xaa Glu Lys Leu Leu Leu Glu Gly
    130                 135                 140

Arg Cys Glu Xaa Ser Pro Pro Ser Cys Xaa Pro Asp Ala His Xaa Pro
145                 150                 155                 160

Gly Val Val Tyr Ser Leu Tyr His Phe Ser Tyr Leu Met Phe Leu Val
                165                 170                 175

Cys Tyr Leu Pro Lys Gly Lys His Cys Thr Ala Val Val Ile Gly Asp
                180                 185                 190

Trp Leu Gln Arg Pro Arg Thr Glu Ala Tyr Val Arg Ala Met Asn Ile
                195                 200                 205
```

```
Met Ile Ala Phe Phe His Leu Leu Tyr Ser Leu Gly Thr Ser Leu
            210                 215                 220

Ser Ser Val Ser Tyr Phe Leu Cys Lys Arg Lys Ile Val Ala Leu Gly
225                 230                 235                 240

Ala Tyr Leu Ser Tyr Pro Leu Ser His Ser Phe Ile Leu Met Glu
                245                 250                 255

Asn Asn Lys Val Arg Lys Ala Leu
            260

<210> SEQ ID NO 49
<211> LENGTH: 35
<212> TYPE: PRT
<213> ORGANISM: Homo sapiens
<220> FEATURE:
<223> OTHER INFORMATION: human T2R28 (hGR28)

<400> SEQUENCE: 49

Asn Ile Cys Val Leu Leu Ile Ile Leu Ser Ile Leu Val Val Ser Ala
1               5                   10                  15

Phe Val Leu Gly Asn Val Ala Asn Gly Phe Ile Ala Leu Ile Asn Val
            20                  25                  30

Asn Asp Trp
        35

<210> SEQ ID NO 50
<211> LENGTH: 36
<212> TYPE: PRT
<213> ORGANISM: Homo sapiens
<220> FEATURE:
<223> OTHER INFORMATION: human T2R29 (hGR29)

<400> SEQUENCE: 50

Met Gln Ala Ala Leu Thr Ala Phe Phe Val Leu Leu Phe Ser Leu Leu
1               5                   10                  15

Ser Leu Leu Gly Ile Ala Ala Asn Gly Phe Ile Val Leu Val Leu Gly
            20                  25                  30

Lys Glu Trp Leu
        35

<210> SEQ ID NO 51
<211> LENGTH: 319
<212> TYPE: PRT
<213> ORGANISM: Homo sapiens
<220> FEATURE:
<223> OTHER INFORMATION: human T2R30 (hGR30)

<400> SEQUENCE: 51

Met Ile Thr Phe Leu Pro Ile Ile Phe Ser Ile Leu Val Val Val Thr
1               5                   10                  15

Phe Val Leu Gly Asn Phe Ser Asn Gly Phe Ile Ala Leu Val Asn Ser
            20                  25                  30

Ile Glu Trp Val Lys Thr Arg Lys Ile Ser Ser Ala Asp Gln Ile Leu
        35                  40                  45

Thr Ala Leu Val Val Ser Arg Val Gly Leu Leu Trp Val Ile Leu Leu
    50                  55                  60

His Trp Tyr Ala Asn Val Phe Asn Ser Ala Leu Tyr Ser Ser Glu Val
65                  70                  75                  80

Gly Ala Val Ala Ser Asn Ile Ser Ala Ile Ile Asn His Phe Ser Ile
                85                  90                  95

Trp Leu Ala Thr Ser Leu Ser Ile Phe Tyr Leu Leu Lys Ile Ala Asn
```

```
                 100                 105                 110
Phe Ser Asn Leu Ile Phe Leu His Leu Lys Lys Arg Ile Arg Ser Val
            115                 120                 125

Val Leu Val Ile Leu Leu Gly Pro Leu Val Phe Leu Ile Cys Asn Leu
130                 135                 140

Ala Val Ile Thr Met Asp Asp Ser Val Trp Thr Lys Glu Tyr Glu Gly
145                 150                 155                 160

Asn Val Thr Trp Lys Ile Lys Leu Arg Asn Ala Ile His Leu Ser Asn
                165                 170                 175

Met Thr Val Ser Thr Leu Ala Asn Leu Ile Pro Phe Ile Leu Thr Leu
            180                 185                 190

Ile Cys Phe Leu Leu Leu Ile Cys Ser Leu Cys Lys His Leu Lys Lys
                195                 200                 205

Met Gln Leu His Gly Lys Gly Ser Gln Asp Pro Ser Thr Lys Val His
            210                 215                 220

Ile Lys Ala Leu Gln Thr Val Thr Ser Phe Leu Leu Cys Ala Ile
225                 230                 235                 240

Tyr Phe Leu Ser Met Ile Ile Ser Val Cys Asn Phe Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
                275                 280                 285

Ile Phe Leu Ser Val Leu Arg His Val Arg Tyr Trp Val Lys Asp Arg
            290                 295                 300

Ser Leu Arg Leu His Arg Phe Thr Arg Gly Ala Leu Cys Val Phe
305                 310                 315

<210> SEQ ID NO 52
<211> LENGTH: 960
<212> TYPE: DNA
<213> ORGANISM: Homo sapiens
<220> FEATURE:
<223> OTHER INFORMATION: human T2R30 (hGR30)

<400> SEQUENCE: 52
atgataactt ttctacccat cattttttcc attctggtag tggttacatt tgttcttgga      60 aattttttcca atggcttcat agctctagta aattccattg agtgggtcaa gacacgaaag    120
atctcctcag ctgaccaaat cctcactgct ctggtggtct ccagagttgg tttactctgg    180
gtcatattat tacattggta tgcaaatgtg tttaattcag ctttatatag ttcagaagta    240
ggagctgttg cttctaatat ctcagcaata atcaaccatt tcagcatctg gcttgctact    300
agcctcagca tattttattt gctcaagatt gccaatttct ccaaccttat ttttctccac    360
ttaaagaaga gaattaggag tgttgttctg tgatactgt tgggtccctt ggtattttg      420 atttgtaatc ttgctgtgat aaccatggat gacagtgtgt ggacaaaaga atatgaagga    480
aatgtgactt ggaagatcaa attgaggaat gcaatacacc tttcaaatat gactgtaagc    540
acactagcaa acctcatacc cttcattctg accctaatat gttttctgct gttaatctgt    600
tctctgtgta aacatctcaa gaagatgcag ctccatggca aaggatctca agatcccagc    660
accaaggtcc acataaaagc tttgcaaact gtgacctcct tcttctgtt atgtgccatt    720 tactttctgt ccatgatcat atcagtttgt aattttggga ggctggaaaa gcaacctgtc    780
ttcatgttct gccaagctat tatattcagc tatccttcaa cccacccatt catcctgatt    840
```

```
ttgggaaaca agaagctaaa gcagatttt  ctttcagttt tgcggcatgt gaggtactgg      900
gtgaaagaca gaagccttcg tctccataga ttcacaagag gggcattgtg tgtcttctag      960
```

<210> SEQ ID NO 53
<211> LENGTH: 299
<212> TYPE: PRT
<213> ORGANISM: Homo sapiens
<220> FEATURE:
<221> NAME/KEY: MOD_RES
<222> LOCATION: (1)..(299)
<223> OTHER INFORMATION: human T2R31 (hGR31)
<223> OTHER INFORMATION: Xaa = any amino acid

<400> SEQUENCE: 53

```
Met Thr Thr Phe Ile Pro Ile Ile Phe Ser Ser Val Val Val Leu
 1               5                  10                  15

Phe Val Ile Gly Asn Phe Ala Asn Gly Phe Ile Ala Leu Val Asn Ser
            20                  25                  30

Ile Glu Arg Val Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Ile Leu Val Met Leu Leu Gly Pro Leu Leu Phe Leu Ala Cys Gln Leu
    130                 135                 140

Phe Val Ile Asn Met Lys Glu Ile Val Arg Thr Lys Glu Phe Glu Gly
145                 150                 155                 160

Asn Met Thr Trp Lys Ile Lys Leu Lys Ser Ala Met Tyr Phe Ser Xaa
                165                 170                 175

Met Thr Val Thr Ile Gly Ala Xaa Leu Val Pro Phe Thr Leu Ser Leu
            180                 185                 190

Ile Ser Phe Leu Met Leu Ile Cys Ser Leu Cys Lys His Leu Lys Lys
        195                 200                 205

Met Gln Leu His Gly Glu Gly Ser Gln Asp Leu Ser Thr Lys Val His
    210                 215                 220

Ile Lys Ala Leu Gln Thr Leu Ile Ser Phe Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
            260                 265                 270

Ala Phe Asp Ser Phe Ile Leu Ile Trp Arg Thr Lys Lys Leu Lys His
        275                 280                 285

Thr Phe Leu Leu Ile Leu Cys Gln Ile Arg Cys
    290                 295
```

<210> SEQ ID NO 54
<211> LENGTH: 900
<212> TYPE: DNA
<213> ORGANISM: Homo sapiens
<220> FEATURE:
<221> NAME/KEY: modified_base
<222> LOCATION: (1)..(900)
<223> OTHER INFORMATION: human T2R31 (hGR31)
<223> OTHER INFORMATION: n = g, a, c or t

<400> SEQUENCE: 54

```
atgacaactt ttatacccat catttttcc agtgtggtag tggttctatt tgttattgga      60
aattttgcta atggcttcat agcattggta aattccattg agcgggtcaa gagacaaaag     120
atctcttttg ctgaccagat tctcactgct ctggcggtct ccagagttgg tttgctctgg     180
gtattattat taaattggta ttcaactgtg tttaatccag cttttttatag tgtagaagta    240
agaactactg cttataatgt ctgggcagta accggccatt tcagcaactg gcttgctact    300
agcctcagca tattttatt gctcaagatt gccaatttct ccaaccttat ttttcttcac    360
ttaaagagga gagttaagag tgtcattctg gtgatgctgt tgggccttt actattttg    420
gcttgtcaac ttttttgtgat aaacatgaaa gagattgtac ggacaaaaga atttgaagga    480
aacatgactt ggaagatcaa attgaagagt gcaatgtact tttcanatat gactgtaacc    540
attggagcan acttagtacc ctttactctg tccctgatat cttttctgat gctaatctgt    600
tctctgtgta aacatctcaa gaagatgcag ctccatggag aaggatcgca agatctcagc    660
accaaggtcc acataaaagc tttgcaaact ctgatctcct tcctcttgtt atgtgccatt    720
ttctttctat tcctaatcgt ttcggtttgg agtcctagga ggctgcggaa tgacccggtt    780
gtcatggtta gcaaggctgt tggaaacata tatcttgcat tcgactcatt catcctaatt    840
tggagaacca agaagctaaa acacaccttt cttttgattt tgtgtcagat taggtgctga    900
```

<210> SEQ ID NO 55
<211> LENGTH: 20
<212> TYPE: PRT
<213> ORGANISM: Homo sapiens
<220> FEATURE:
<223> OTHER INFORMATION: human T2R32 (hGR32)

<400> SEQUENCE: 55

```
His Ser Phe Met Leu Thr Met Gly Ser Arg Lys Pro Lys Gln Thr Phe
1               5                   10                  15
Leu Ser Ala Leu
            20
```

<210> SEQ ID NO 56
<211> LENGTH: 309
<212> TYPE: PRT
<213> ORGANISM: Homo sapiens
<220> FEATURE:
<223> OTHER INFORMATION: human T2R33 (hGR33)

<400> SEQUENCE: 56

```
Met Val Tyr Phe Leu Pro Ile Ile Phe Ser Ile Leu Val Val Phe Ala
1               5                   10                  15

Phe Val Leu Gly Asn Phe Ser Asn Gly Phe Ile Ala Leu Val Asn Val
            20                  25                  30

Ile Asp Trp Val Lys Arg Gln Lys Ile Ser Ser Ala Asp Gln Ile Leu
        35                  40                  45

Thr Ala Leu Val Val Ser Arg Val Gly Leu Leu Trp Val Ile Leu Leu
    50                  55                  60

His Trp Tyr Ala Asn Val Phe Asn Ser Ala Leu Tyr Ser Leu Glu Val
65                  70                  75                  80
```

```
Arg Ile Val Ala Ser Asn Ile Ser Ala Val Ile Asn His Phe Ser Ile
                 85                  90                  95

Trp Leu Ala Ala Ser Leu Ser Ile Phe Tyr Leu Leu Lys Ile Ala Asn
            100                 105                 110

Phe Ser Asn Leu Ile Phe Leu His Leu Lys Lys Arg Ile Lys Ser Val
        115                 120                 125

Val Leu Val Ile Leu Leu Gly Pro Leu Val Phe Leu Ile Cys Asn Leu
130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Gln Leu His Ser Lys Gly Ser Gln Asp Pro Ser Thr Lys Val His
210                 215                 220

Ile Lys Ala Leu Gln Thr Val Ile Ser Phe Leu Met Leu Cys Ala Ile
225                 230                 235                 240

Tyr Phe Leu Ser Ile Met Ile Ser Val Trp Asn Leu Arg Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Val Arg Tyr Trp Val Lys Gly Glu
    290                 295                 300

Lys Pro Ser Ser Pro
305

<210> SEQ ID NO 57
<211> LENGTH: 930
<212> TYPE: DNA
<213> ORGANISM: Homo sapiens
<220> FEATURE:
<223> OTHER INFORMATION: human T2R33 (hGR33)

<400> SEQUENCE: 57
atggtatatt ttctgcccat cattttttcc attctggtag tgtttgcatt tgttcttgga     60 aattttttcca atggcttcat agctctagta aatgtcattg actgggttaa gagacaaaag    120
atctcctcag ctgaccaaat tctcactgct ctggtggtct ccagagttgg tttactctgg    180
gtcatattat tacattggta tgcaaatgtg tttaattcag ctttatatag tttagaagta    240
agaattgttg cttctaatat ctcagcagta atcaaccatt tcagcatctg gcttgctgct    300
agcctcagca tattttattt gctcaagatt gccaatttct ccaaccttat tttttctccac    360 ctaaagaaga gaattaagag tgttgttctg tgatactgt tggggccctt ggtatttctg     420
atttgtaatc ttgctgtgat aaccatggat gagagagtgt ggacaaaaga atatgaagga    480
aatgtgactt ggaagatcaa attgaggaat gcaatacacc ttcaagctt gactgtaact    540 actctagcaa acctcatacc ctttactctg agcctaatat gttttctgct gttaatctgt    600
tctctttgta acatctcaa gaagatgcag ctccatagca aaggatctca agatcccagc    660
accaaggtcc acataaaagc tttgcaaact gtgatctcct cctcatgtt atgtgccatt    720
```

```
tactttctgt ccataatgat atcagtttgg aatcttagga gtctggaaaa caaacctgtc    780
ttcatgttct gcaaagctat tagattcagc tatccttcaa tccacccatt catcctgatt    840
tggggaaaca agaagctaaa gcagactttt ctttcagttt tttggcaagt gaggtactgg    900
gtgaaaggag agaagccttc atctccatag                                    930
```

```
<210> SEQ ID NO 58
<211> LENGTH: 100
<212> TYPE: PRT
<213> ORGANISM: Homo sapiens
<220> FEATURE:
<221> NAME/KEY: MOD_RES
<222> LOCATION: (1)..(100)
<223> OTHER INFORMATION: human T2R34 (hGR34)
<223> OTHER INFORMATION: Xaa = any amino acid

<400> SEQUENCE: 58
```

```
Gly Ser Ser Arg Xaa Lys Pro Pro Arg Ile Pro His Lys Lys Leu Cys
  1               5                  10                  15

Lys Leu Gly Pro Ser Phe Pro His Asn Asn Leu Pro Ile Tyr Phe Leu
             20                  25                  30

Cys Xaa Asn His Ile Val Leu Glu Phe Leu Lys Met Arg Pro Lys Lys
         35                  40                  45

Lys Cys Ser Leu Met Leu Cys Gln Ala Phe Gly Ile Ile Tyr Pro Ser
     50                  55                  60

Phe His Ser Phe Ile Leu Xaa Trp Gly Asn Lys Thr Leu Lys Gln Thr
 65                  70                  75                  80

Phe Leu Ser Val Xaa Trp Gln Val Thr Cys Trp Ala Lys Gly Gln Asn
                 85                  90                  95

Gln Ser Thr Pro
            100
```

```
<210> SEQ ID NO 59
<211> LENGTH: 128
<212> TYPE: PRT
<213> ORGANISM: Homo sapiens
<220> FEATURE:
<221> NAME/KEY: MOD_RES
<222> LOCATION: (1)..(128)
<223> OTHER INFORMATION: human T2R35 (hGR35)
<223> OTHER INFORMATION: Xaa = any amino acid

<400> SEQUENCE: 59
```

```
Asn Ala Ile Arg Pro Ser Lys Leu Trp Thr Val Thr Glu Ala Asp Lys
  1               5                  10                  15

Thr Ser Gln Pro Gly Thr Ser Ala Asn Lys Ile Phe Ser Ala Gly Asn
             20                  25                  30

Leu Ile Ser His Val Asn Met Ser Arg Arg Met Gln Leu His Gly Lys
         35                  40                  45

Gly Ser Gln His Leu Ser Thr Arg Val His Ile Lys Ala Xaa Gln Thr
     50                  55                  60

Val Ile Ser Phe Leu Met Leu Xaa Ala Ile Tyr Phe Leu Cys Leu Ile
 65                  70                  75                  80

Thr Ser Thr Trp Asn Pro Arg Thr Gln Gln Ser Lys Leu Val Phe Leu
                 85                  90                  95

Leu Tyr Gln Thr Leu Gly Phe Met Tyr Leu Phe His Ser Phe Ile
            100                 105                 110

Leu Thr Met Gly Ser Arg Lys Pro Lys Gln Thr Phe Leu Ser Ala Leu
            115                 120                 125
```

<210> SEQ ID NO 60
<211> LENGTH: 309
<212> TYPE: PRT
<213> ORGANISM: Homo sapiens
<220> FEATURE:
<223> OTHER INFORMATION: human T2R36 (hGR36)

<400> SEQUENCE: 60

```
Met Ile Cys Phe Leu Leu Ile Ile Leu Ser Ile Leu Val Val Phe Ala
  1               5                  10                  15

Phe Val Leu Gly Asn Phe Ser Asn Gly Phe Ile Ala Leu Val Asn Val
             20                  25                  30

Ile Asp Trp Val Lys Arg Gln Lys Ile Ser Ser Ala Asp Gln Ile Leu
         35                  40                  45

Thr Ala Leu Val Val Ser Arg Val Gly Leu Leu Trp Val Ile Leu Leu
     50                  55                  60

His Trp Tyr Ser Asn Val Leu Asn Ser Ala Leu Tyr Ser Ser Glu Val
 65                  70                  75                  80

Ile Ile Phe Ile Ser Asn Ala Trp Ala Ile Ile Asn His Phe Ser Ile
                 85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Pro Leu Val Phe Leu Val Cys His Leu
    130                 135                 140

Val Met Lys His Thr Tyr Ile Asn Val Trp Thr Lys Glu Tyr Glu Gly
145                 150                 155                 160

Asn Val Thr Trp Lys Ile Lys Leu Arg Asn Ala Ile His Leu Ser Asn
                165                 170                 175

Leu Thr Val Ser Thr Leu Ala Asn Leu Ile Pro Phe Thr Leu Thr Leu
            180                 185                 190

Ile Ser Phe Leu Leu Leu Ile Tyr Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Phe Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Phe Trp Gln Met Arg Tyr Trp Val Lys Gly Glu
    290                 295                 300

Lys Pro Ser Ser Pro
305
```

<210> SEQ ID NO 61
<211> LENGTH: 930
<212> TYPE: DNA
<213> ORGANISM: Homo sapiens
<220> FEATURE:
<223> OTHER INFORMATION: human T2R36 (hGR36)

<400> SEQUENCE: 61

```
atgatatgtt ttctgctcat cattttatca attctggtag tgtttgcatt tgttcttgga      60 aattttttcca atggcttcat agctctagta aatgtcattg actgggtcaa gagacaaaag     120
atctcctcag ctgaccaaat cctcactgct ctggtggtct ccagagttgg tttactctgg     180
gtaatattat tacattggta ttcaaatgtg ttgaattcag ctttatatag ttcagaagta     240
ataattttta tttctaatgc ctgggcaata atcaaccatt tcagcatctg gcttgctact     300
agcctcagca tattttattt gctcaagatc gtcaatttct ccagacttat ttttcatcac     360
ttaaaaagga aggctaagag tgtagttctg tgatagtgt tgggtccctt ggtattttg       420 gtttgtcacc ttgtgatgaa acacacgtat ataaatgtgt ggacaaaaga atatgaagga     480
aatgtgactt ggaagatcaa actgaggaat gcaatacacc tttcaaactt gactgtaagc     540
acactagcaa acttgatacc cttcactctg accctgatat cttttctgct gttaatctac     600
tctctgtgta acatctcaa gaagatgcag ctccatggca aaggatctca agatcccagc     660
accaaggtcc acataaaagc tttgcaaact gtgacctcct ttcttctgtt atgtgccatt     720
tactttctgt ccatgatcat atcagtttgt aattttggga ggctgaaaa gcaacctgtc     780 ttcatgttct gccaagctat tatattcagc tatccttcaa cccacccatt catcctgatt     840
ttgggaaaca agaagctaaa gcagattttt ctttcagttt tttggcaaat gaggtactgg     900
gtgaaaggag agaagccttc atctccatag                                      930
```

<210> SEQ ID NO 62
<211> LENGTH: 309
<212> TYPE: PRT
<213> ORGANISM: Homo sapiens
<220> FEATURE:
<221> NAME/KEY: MOD_RES
<222> LOCATION: (1)..(309)
<223> OTHER INFORMATION: human T2R37 (hGR37)
<223> OTHER INFORMATION: Xaa = any amino acid

<400> SEQUENCE: 62

Met Ile Thr Phe Leu Pro Ile Ile Phe Ser Ile Leu Ile Val Val Thr
 1               5                  10                  15

Phe Val Ile Gly Asn Phe Ala Asn Gly Phe Ile Ala Leu Val Asn Ser
                20                  25                  30

Ile Glu Trp Val Lys Arg Gln Lys Ile Ser Ser Ala Asp Gln Ile Ser
            35                  40                  45

His Cys Ser Gly Gly Val Gln Asn Trp Phe Thr Leu Gly His Ile Ile
        50                  55                  60

Thr Leu Val Cys Asn Cys Val Xaa Phe Gly Phe Ile Xaa Ile Arg Ser
 65                  70                  75                  80

Lys Asn Phe Trp Phe Xaa Cys Leu Ser Asn Asn Gln Ala Phe Gln His
                85                  90                  95

Val Gly Val Thr Ser Leu Ser Ile Phe His Leu Leu Lys Thr Ala Asn
            100                 105                 110

Phe Ser Asn Leu Ile Phe Leu His Leu Lys Lys Arg Ile Lys Ser Val
        115                 120                 125

Gly Leu Val Ile Leu Leu Gly Pro Leu Leu Phe Phe Ile Cys Asn Leu
    130                 135                 140

Phe Val Ile Asn Met Asp Glu Ser Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

```
Met Thr Leu Thr Met Leu Ala Asn Phe Val Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Cys Ala Ile
225                 230                 235                 240

Tyr Phe Leu Ser Met Ile Ile Ser Val Cys Asn Leu Gly Arg Leu Glu
                245                 250                 255

Lys Gln Pro Val Phe Met Phe Cys Glu Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Gly Glu
    290                 295                 300

Lys Pro Ser Ser Ser
305

<210> SEQ ID NO 63
<211> LENGTH: 930
<212> TYPE: DNA
<213> ORGANISM: Homo sapiens
<220> FEATURE:
<223> OTHER INFORMATION: human T2R37 (hGR37)

<400> SEQUENCE: 63
atgataactt ttctgcccat cattttttcc attctaatag tggttacatt tgtgattgga      60
aattttgcta atggcttcat agctctagta aattccattg agtgggttaa gagacaaaag     120
atctcatcag ctgaccaaat ttctcactgc tctggtggtg tccagaattg gtttactctg     180
ggtcatatta ttacattggt atgcaactgt gtttaatttg gcttcatata gattagaagt     240
aagaattttt ggttctaatg tctcagcaat aaccaagcat tcagcatgt gggtgttact      300 agcctcagca tatttcattt gctcaagact gccaatttct ccaaccttat ttttctccac     360
ctaaagaaga ggattaagag tgttggtttg gtgatactat tggggccttt gctattttc     420 atttgtaatc ttttttgtgat aaacatggat gagagtgtat ggacaaaaga atatgaagga     480
aacgtgactt ggaagatcaa attgaggagt gcaatgtacc attcaaatat gactctaacc     540
atgctagcaa actttgtacc cttcactctg accctgatat cttttctgct gttaatctgt     600
tctctgtgta acatctcaa gaagatgcag ctccatggca aaggatctca agatcccagc      660
accaaggtcc acataaaagc tttgcaaact gtgacctcct ttcttctgtt atgtgccatt     720
tactttctgt ccatgatcat atcagtttgt aatttgggga ggctggaaaa gcaacctgtc     780
ttcatgttct gcgaagctat tatattcagc tatccttcaa cccacccatt catcctgatt     840
tgggaaaaca gaagctaaa gcagattttt ctttcagttt tgcggcatgt gaggtactgg     900
gtgaaaggag agaagccttc atcttcatag                                      930

<210> SEQ ID NO 64
<211> LENGTH: 144
<212> TYPE: PRT
<213> ORGANISM: Homo sapiens
<220> FEATURE:
<223> OTHER INFORMATION: human T2R38 (hGR38)

<400> SEQUENCE: 64
```

-continued

```
Met Leu Thr Leu Thr Arg Ile Arg Thr Val Ser Tyr Glu Val Arg Ser
 1               5                  10                  15

Thr Phe Leu Phe Ile Ser Val Leu Glu Phe Ala Val Gly Phe Leu Thr
                20                  25                  30

Asn Ala Phe Val Phe Leu Val Asn Phe Trp Asp Val Val Lys Arg Gln
            35                  40                  45

Pro Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Ser Pro Gly Arg Ser Pro Val Pro Ser
    130                 135                 140
```

<210> SEQ ID NO 65
<211> LENGTH: 140
<212> TYPE: PRT
<213> ORGANISM: Homo sapiens
<220> FEATURE:
<223> OTHER INFORMATION: human T2R39 (hGR39)

<400> SEQUENCE: 65

```
Leu Arg Asn Ala Gly Leu Asn Asp Ser Asn Ala Lys Leu Val Arg Asn
 1               5                  10                  15

Asn Asp Leu Leu Leu Ile Asn Leu Ile Leu Leu Pro Leu Ser Val
                20                  25                  30

Phe Val Met Cys Thr Ser Met Leu Phe Val Ser Leu Tyr Lys His Met
            35                  40                  45

His Trp Met Gln Ser Glu Ser His Lys Leu Ser Ser Ala Arg Thr Glu
    50                  55                  60

Ala His Ile Asn Ala Leu Lys Thr Val Thr Thr Phe Phe Cys Phe Phe
65                  70                  75                  80

Val Ser Tyr Phe Ala Ala Phe Met Ala Asn Met Thr Phe Arg Ile Pro
                85                  90                  95

Tyr Arg Ser His Gln Phe Phe Val Val Lys Glu Ile Met Ala Ala Tyr
            100                 105                 110

Pro Ala Gly His Ser Val Ile Ile Val Leu Ser Asn Ser Lys Phe Lys
        115                 120                 125

Asp Leu Phe Arg Arg Met Ile Cys Leu Gln Lys Glu
    130                 135                 140
```

<210> SEQ ID NO 66
<211> LENGTH: 71
<212> TYPE: PRT
<213> ORGANISM: Homo sapiens
<220> FEATURE:
<223> OTHER INFORMATION: human T2R40 (hGR40)

<400> SEQUENCE: 66

```
Ser Gln Tyr Ser Leu Gly His Ser Tyr Val Val Ile Phe Gly Tyr Gly
 1               5                  10                  15

Gln Met Lys Lys Thr Phe Leu Gly Ile Leu Trp His Leu Lys Cys Gly
                20                  25                  30
```

```
Leu Lys Gly Arg Ala Leu Leu Ala Thr Gln Val Gly Leu Arg Glu Lys
            35                  40                  45

Ser Thr Arg Ser Leu Gly Val Ile Phe Leu Ala Ser Ser Tyr Ser Phe
        50                  55                  60

Phe Val Tyr Val Leu Cys His
 65                  70

<210> SEQ ID NO 67
<211> LENGTH: 309
<212> TYPE: PRT
<213> ORGANISM: Homo sapiens
<220> FEATURE:
<221> NAME/KEY: MOD_RES
<222> LOCATION: (253)
<223> OTHER INFORMATION: human T2R41 (hGR41)
<223> OTHER INFORMATION: Xaa = any amino acid

<400> SEQUENCE: 67

Met Ile Thr Phe Leu Leu Ile Ile Leu Ser Ile Leu Val Val Phe Ala
  1               5                  10                  15

Phe Val Leu Gly Asn Phe Ser Asn Gly Phe Ile Ala Leu Val Asn Val
                 20                  25                  30

Ile Asp Trp Val Asn Thr Arg Lys Ile Ser Ser Ala Asp Gln Ile Leu
             35                  40                  45

Thr Ala Leu Ala Val Ser Arg Val Gly Leu Leu Trp Val Ile Leu Leu
     50                  55                  60

His Trp Tyr Ala Asn Val Leu Asn Pro Ala Leu Tyr Ser Ser Glu Val
 65                  70                  75                  80

Ile Ile Phe Ile Ser Asn Ile Ser Ala Ile Ile Asn His Phe Ser Ile
                 85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Pro Leu Val Phe Leu Val Cys His Leu
    130                 135                 140

Val Met Lys His Thr Tyr Ile Asn Val Trp Thr Lys Glu Tyr Glu Gly
145                 150                 155                 160

Asn Val Thr Trp Lys Ile Lys Leu Arg Asn Ala Ile His Leu Ser Asn
                165                 170                 175

Leu Thr Val Ser Thr Leu Ala Asn Leu Ile Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Tyr Leu Ile Thr Ser Thr Trp Asn Leu Xaa Thr Gln Gln
                245                 250                 255

Ser Lys Leu Val Phe Met Phe Cys Gln Thr Leu Gly Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Cys Gln Val Thr Cys Leu Val Lys Gly Gln
    290                 295                 300
```

Gln Pro Ser Thr Pro
305

<210> SEQ ID NO 68
<211> LENGTH: 34
<212> TYPE: PRT
<213> ORGANISM: Homo sapiens
<220> FEATURE:
<223> OTHER INFORMATION: human T2R42 (hGR42)

<400> SEQUENCE: 68

Phe Ile Gly Leu Thr Asp Cys Ile Ala Trp Met Arg Asn Gln Lys Leu
 1               5                  10                  15

Cys Met Val Gly Phe Ile Leu Thr Arg Met Ala Leu Ala Arg Ile Asn
                20                  25                  30

Ile Leu

<210> SEQ ID NO 69
<211> LENGTH: 297
<212> TYPE: PRT
<213> ORGANISM: Homo sapiens
<220> FEATURE:
<221> NAME/KEY: MOD_RES
<222> LOCATION: (1)..(297)
<223> OTHER INFORMATION: human T2R43 (hGR43)
<223> OTHER INFORMATION: Xaa = any amino acid

<400> SEQUENCE: 69

Leu Glu Leu Ile Phe Ser Xaa Lys Val Val Ala Thr Arg Gly Leu Val
 1               5                  10                  15

Leu Gly Met Leu Gly Asn Gly Leu Ile Gly Leu Val Asn Cys Ile Glu
                20                  25                  30

Trp Ala Lys Ser Trp Lys Val Ser Ser Ala Asp Phe Ile Leu Thr Ser
            35                  40                  45

Leu Ala Ile Val Arg Ile Ile Arg Leu Tyr Leu Ile Leu Phe Asp Ser
        50                  55                  60

Phe Ile Met Val Leu Ser Pro His Leu Tyr Thr Xaa Xaa Xaa Xaa Xaa
 65              70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Ser Leu Ser Ile Phe His Trp Phe Lys Thr Ala Asn Phe Ser
            100                 105                 110

Asn Leu Ile Phe Leu Pro Leu Lys Glu Glu Asp Xaa Asn Val Trp Leu
        115                 120                 125

Gly Asp Ala Val Gly Ala Leu Gly Ile Phe His Leu Xaa Ser Cys Ser
    130                 135                 140

Glu Asn His Gly Xaa Glu Val Cys Gly Gln Lys Asn Met Lys Glu Phe
145                 150                 155                 160

Cys Ser Gly Met Ile Lys Leu Arg Asn Ala Ile Gln Leu Ser Asn Leu
                165                 170                 175

Thr Val Thr Met Pro Ala Asn Val Thr Pro Cys Thr Leu Thr Leu Ile
            180                 185                 190

Ser Phe Leu Leu Leu Ile Tyr Ser Pro Cys Lys His Val Lys Lys Met
        195                 200                 205

Gln Leu His Gly Lys Gly Ser Gln His Leu Ser Thr Lys Val His Ile
    210                 215                 220

Lys Val Leu Gln Thr Val Ile Ser Phe Phe Leu Leu Cys Ala Ile Tyr
225                 230                 235                 240

```
Phe Val Ser Val Ile Ile Ser Val Trp Ser Phe Lys Asn Leu Glu Asn
                245                 250                 255

Lys Pro Val Phe Met Phe Cys Gln Ala Ile Gly Phe Ser Cys Ser Ser
            260                 265                 270

Ala His Pro Phe Ile Leu Thr Met Gly Asn Lys Lys Leu Lys Gln Thr
        275                 280                 285

Tyr Leu Ser Val Leu Trp Gln Met Arg
    290                 295

<210> SEQ ID NO 70
<211> LENGTH: 319
<212> TYPE: PRT
<213> ORGANISM: Homo sapiens
<220> FEATURE:
<223> OTHER INFORMATION: human T2R44 (hGR44)

<400> SEQUENCE: 70

Met Ile Thr Phe Leu Pro Ile Ile Phe Ser Ile Leu Ile Val Val Ile
 1               5                  10                  15

Phe Val Ile Gly Asn Phe Ala Asn Gly Phe Ile Ala Leu Val Asn Ser
                20                  25                  30

Ile Glu Trp Val Lys Arg Gln Lys Ile Ser Phe Val Asp Gln Ile Leu
            35                  40                  45

Thr Ala Leu Ala Val Ser Arg Val Gly Leu Leu Trp Val Leu Leu Leu
        50                  55                  60

His Trp Tyr Ala Thr Gln Leu Asn Pro Ala Phe Tyr Ser Val Glu Val
 65                  70                  75                  80

Arg Ile Thr Ala Tyr Asn Val Trp Ala Val Thr Asn His Phe Ser Ser
                85                  90                  95

Trp Leu Ala Thr Ser Leu Ser Met Phe Tyr Leu Leu Arg Ile Ala Asn
                100                 105                 110

Phe Ser Asn Leu Ile Phe Leu Arg Ile Lys Arg Arg Val Lys Ser Val
            115                 120                 125

Val Leu Val Ile Leu Leu Gly Pro Leu Leu Phe Leu Val Cys His Leu
        130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Leu Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
    290                 295                 300
```

-continued

```
Ser Leu Arg Leu His Arg Phe Thr Arg Gly Ala Leu Cys Val Phe
305                 310                 315

<210> SEQ ID NO 71
<211> LENGTH: 314
<212> TYPE: PRT
<213> ORGANISM: Homo sapiens
<220> FEATURE:
<223> OTHER INFORMATION: human T2R45 (hGR45)

<400> SEQUENCE: 71

Met Ala Thr Glu Leu Asp Lys Ile Phe Leu Ile Leu Ala Ile Ala Glu
 1               5                  10                  15

Phe Ile Ile Ser Met Leu Gly Asn Val Phe Ile Gly Leu Val Asn Cys
                20                  25                  30

Ser Glu Gly Ile Lys Asn Gln Lys Val Phe Ser Ala Asp Phe Ile Leu
            35                  40                  45

Thr Cys Leu Ala Ile Ser Thr Ile Gly Gln Leu Val Ile Leu Phe
 50                  55                  60

Asp Ser Phe Leu Val Gly Leu Ala Ser His Leu Tyr Thr Thr Tyr Arg
 65                  70                  75                  80

Leu Gly Lys Thr Val Ile Met Leu Trp His Met Thr Asn His Leu Thr
                85                  90                  95

Thr Trp Leu Ala Thr Cys Leu Ser Ile Phe Tyr Phe Phe Lys Ile Ala
            100                 105                 110

His Phe Pro His Ser Leu Phe Leu Trp Leu Arg Trp Arg Met Asn Gly
        115                 120                 125

Met Ile Val Met Leu Leu Ile Leu Ser Leu Phe Leu Leu Ile Phe Asp
130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                165                 170                 175

Lys Leu Ser Ile Leu Lys Thr Leu Leu Ser Leu Thr Ser Phe Ile Pro
            180                 185                 190

Phe Ser Leu Phe Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
210                 215                 220

Ser Thr Glu Ala His Arg Arg Ala Met Lys Met Val Met Ser Phe Leu
225                 230                 235                 240

Phe Leu Phe Ile Val His Phe Ser Leu Gln Val Ala Asn Trp Ile
                245                 250                 255

Phe Phe Met Leu Trp Asn Asn Lys Cys Ile Lys Phe Val Met Leu Ala
            260                 265                 270

Leu Asn Ala Phe Pro Ser Cys His Ser Phe Ile Leu Ile Leu Gly Asn
        275                 280                 285

Ser Lys Leu Gln Gln Thr Ala Val Arg Leu Leu Trp His Leu Arg Asn
    290                 295                 300

Tyr Thr Lys Thr Pro Asn Pro Leu Pro Leu
305                 310

<210> SEQ ID NO 72
<211> LENGTH: 59
<212> TYPE: PRT
<213> ORGANISM: Homo sapiens
```

```
<220> FEATURE:
<223> OTHER INFORMATION: human T2R46 (hGR46)

<400> SEQUENCE: 72

Met Ser Phe Leu His Ile Val Phe Ser Ile Leu Val Val Ala Phe
 1               5                  10                  15

Ile Leu Gly Asn Phe Ala Asn Gly Phe Ile Ala Leu Ile Asn Phe Ile
            20                  25                  30

Ala Trp Val Lys Lys Gln Lys Ile Ser Ser Ala Asp Gln Ile Ile Ala
            35                  40                  45

Asp Lys Gln Ser Pro Glu Leu Val Cys Ser Gly
        50                  55

<210> SEQ ID NO 73
<211> LENGTH: 65
<212> TYPE: PRT
<213> ORGANISM: Homo sapiens
<220> FEATURE:
<221> NAME/KEY: MOD_RES
<222> LOCATION: (1)..(65)
<223> OTHER INFORMATION: human T2R47 (hGR47)
<223> OTHER INFORMATION: Xaa = any amino acid

<400> SEQUENCE: 73

Met Leu Asn Ala Leu Tyr Ser Ile Leu Ile Ile Ile Asn Ile Xaa
 1               5                  10                  15

Phe Leu Ile Gly Ile Leu Gly Asn Gly Phe Ile Thr Leu Val Asn Gly
            20                  25                  30

Ile Asp Trp Val Lys Met Xaa Lys Arg Ser Ser Ile Leu Thr Ala Leu
            35                  40                  45

Thr Ile Ser Arg Ile Cys Leu Ile Ser Val Ile Met Val Arg Trp Phe
        50                  55                  60

Ile
 65

<210> SEQ ID NO 74
<211> LENGTH: 60
<212> TYPE: PRT
<213> ORGANISM: Homo sapiens
<220> FEATURE:
<223> OTHER INFORMATION: human T2R48 (hGR48)

<400> SEQUENCE: 74

Val Ser Arg Val Gly Leu Leu Trp Val Ile Leu Leu His Trp Tyr Ser
 1               5                  10                  15

Thr Val Leu Asn Pro Thr Ser Ser Asn Leu Lys Val Ile Ile Phe Ile
            20                  25                  30

Ser Asn Ala Trp Ala Val Thr Asn His Phe Ser Ile Trp Leu Ala Thr
            35                  40                  45

Ser Leu Ser Ile Phe Tyr Leu Leu Lys Ile Val Asn
        50                  55                  60

<210> SEQ ID NO 75
<211> LENGTH: 72
<212> TYPE: PRT
<213> ORGANISM: Homo sapiens
<220> FEATURE:
<223> OTHER INFORMATION: human T2R49 (hGR49)

<400> SEQUENCE: 75

Thr Val Thr Met Leu Ala Asn Leu Val Pro Phe Thr Val Thr Leu Ile
 1               5                  10                  15
```

-continued

Ser Phe Leu Leu Leu Val Cys Ser Leu Cys Lys His Leu Lys Lys Met
                20                  25                  30

His Leu His Gly Lys Gly Ser Gln Asp Pro Ser Thr Lys Val His Ile
         35                  40                  45

Lys Val Leu Gln Thr Val Ile Ser Phe Leu Leu Cys Ala Ile Tyr
    50                  55                  60

Phe Val Ser Val Ile Ile Ser Ser
 65                  70

<210> SEQ ID NO 76
<211> LENGTH: 299
<212> TYPE: PRT
<213> ORGANISM: Homo sapiens
<220> FEATURE:
<223> OTHER INFORMATION: human T2R50 (hGR50)

<400> SEQUENCE: 76

Met Ile Thr Phe Leu Pro Ile Ile Phe Ser Ile Leu Val Val Val Thr
 1               5                  10                  15

Phe Val Ile Gly Asn Phe Ala Asn Gly Phe Ile Ala Leu Val Asn Ser
                20                  25                  30

Thr Glu Trp Val Lys Arg Gln Lys Ile Ser Phe Ala Asp Gln Ile Val
         35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Tyr Ser Val Glu Leu
 65                  70                  75                  80

Arg Thr Thr Ala Tyr Asn Ile Trp Ala Val Thr Gly His Phe Ser Asn
                85                  90                  95

Trp Pro Ala Thr Ser Leu Ser Ile Phe Tyr Leu Leu Lys Ile Ala Asn
                100                 105                 110

Phe Ser Asn Leu Ile Phe Leu Arg Leu Lys Arg Arg Val Lys Ser Val
            115                 120                 125

Ile Leu Val Val Leu Leu Gly Pro Leu Leu Phe Leu Ala Cys His Leu
130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
            195                 200                 205

Met Gln Leu His Gly Lys Gly Ser Gln Asp Pro Ser Thr Lys Val His
        210                 215                 220

Ile Lys Val Leu Gln Thr Val Ile Ser Phe Leu Leu Cys Ala Ile
225                 230                 235                 240

Tyr Phe Val Ser Val Ile Ile Ser Val Trp Ser Phe Lys Asn Leu Glu
                245                 250                 255

Asn Lys Pro Val Phe Met Phe Cys Gln Ala Ile Gly Phe Ser Cys Ser
            260                 265                 270

Ser Ala His Pro Phe Ile Leu Ile Trp Gly Asn Lys Lys Leu Lys Gln
        275                 280                 285

Thr Tyr Leu Ser Val Leu Trp Gln Met Arg Tyr
        290                 295

<210> SEQ ID NO 77
<211> LENGTH: 335
<212> TYPE: PRT
<213> ORGANISM: Rattus sp.
<220> FEATURE:
<223> OTHER INFORMATION: rat T2R01 (rGR01)

<400> SEQUENCE: 77

```
Met Met Glu Gly His Ile Leu Phe Phe Leu Val Val Met Val Gln
 1               5                  10                  15

Phe Val Thr Gly Val Leu Ala Asn Gly Leu Ile Val Val His Ala
                20                  25                  30

Ile Asp Leu Ile Met Trp Lys Lys Met Ala Pro Leu Asp Leu Leu
            35                  40                  45

Phe Cys Leu Ala Thr Ser Arg Ile Ile Leu Gln Leu Cys Ile Leu Phe
        50                  55                  60

Ala Gln Leu Cys Leu Phe Ser Leu Val Arg His Thr Leu Phe Glu Asp
 65                  70                  75                  80

Asn Ile Thr Phe Val Phe Ile Ile Asn Glu Leu Ser Leu Trp Phe Ala
                85                  90                  95

Thr Trp Leu Gly Val Phe Tyr Cys Ala Lys Ile Ala Thr Ile Pro His
                100                 105                 110

Pro Leu Phe Leu Trp Leu Lys Met Arg Ile Ser Arg Leu Val Pro Trp
            115                 120                 125

Leu Ile Leu Gly Ser Val Leu Tyr Val Ile Thr Thr Phe Ile His
            130                 135                 140

Ser Arg Glu Thr Ser Ala Ile Leu Lys Pro Ile Phe Ile Ser Leu Phe
145                 150                 155                 160

Pro Lys Asn Ala Thr Gln Val Gly Thr Gly His Ala Thr Leu Leu Ser
                165                 170                 175

Val Leu Val Leu Gly Leu Thr Leu Pro Leu Phe Ile Phe Thr Val Ala
                180                 185                 190

Val Leu Leu Leu Ile Tyr Ser Leu Trp Asn Tyr Ser Arg Gln Met Arg
            195                 200                 205

Thr Met Val Gly Thr Arg Glu Tyr Ser Gly His Ala His Ile Ser Ala
210                 215                 220

Met Leu Ser Ile Leu Ser Phe Leu Ile Leu Tyr Leu Ser His Tyr Met
225                 230                 235                 240

Val Ala Val Leu Ile Ser Thr Gln Val Leu Tyr Leu Gly Ser Arg Thr
                245                 250                 255

Phe Val Phe Cys Leu Leu Val Ile Gly Met Tyr Pro Ser Ile His Ser
                260                 265                 270

Ile Val Leu Ile Leu Gly Asn Pro Lys Leu Lys Arg Asn Ala Lys Met
            275                 280                 285

Phe Ile Val His Cys Lys Cys Cys His Cys Thr Arg Ala Trp Val Thr
            290                 295                 300

Ser Arg Ser Pro Arg Leu Ser Asp Leu Pro Val Pro Thr His Pro
305                 310                 315                 320

Ser Ala Asn Lys Thr Ser Cys Ser Glu Ala Cys Ile Met Pro Ser
                325                 330                 335
```

<210> SEQ ID NO 78
<211> LENGTH: 1331
<212> TYPE: DNA
<213> ORGANISM: Rattus sp.

<220> FEATURE:
<223> OTHER INFORMATION: rat T2R01 (rGR01)

<400> SEQUENCE: 78

```
caggaatcat aaatggctga aactgggcag aactctatgc attatttaaa gaagtcattg     60
gtttgtcatt cttaaaatga tggaagggca tatactcttc ttcttttttgg ttgtgatggt    120
gcagtttgtc actggggtct tggcaaatgg cctcattgtg gttgtccatg ctattgactt    180
gatcatgtgg aagaaaatgg ccccgttgga tctgcttcta ttttgcctgg cgacttctcg    240
gatcattctg cagttatgta tattgtttgc acaattgtgt ctattctctt tggtgagaca    300
cactttattt gaggacaata ttacctttgt cttcatcata aatgaactga gtctttggtt    360
tgctacatgg ctcggtgttt tctactgtgc caagattgct accattcctc acccactctt    420
tctgtggctg aagatgagga tatccaggtt ggtaccatgg ctgatcctgg gatctgtgct    480
ctatgtaatt attactactt tcatccatag cagagagact tcagcaatcc ttaaaccaat    540
ttttataagc ctttttccta aaaatgcaac tcaagtcgga acagggcatg ccacactact    600
ctcagtcctg gtccttgggc tcacactgcc gttgttcatc tttactgttg ctgttctgct    660
cttgatatac tccctgtgga attatagcag gcagatgagg actatggtag caccaggga    720
gtatagcgga catgctcaca tcagtgcaat gctgtccatt ctatcattcc tcatcctcta    780
tctctcccac tacatggtgg ctgttctgat ctctactcaa gtcctctacc ttggaagcag    840
aacctttgta ttctgcttac tggttattgg tatgtacccc tcaatacact cgattgtctt    900
aattttagga atcctaagc tgaaacgaaa tgcaaaaatg ttcattgtcc attgtaagtg    960
ttgtcattgt acaagagctt gggtcacctc aaggagccca agactcagtg acttgccagt    1020
gcctcctact catccctcag ccaacaagac atcctgctca gaagcctgta taatgccatc    1080
ctaattgtcc agcctgaggt ttaatcctag gtttggtact atttcaaaga gtaaagttga    1140
tcattaaagc acaacatatg ttggtggatg acatcaaggt ccatatccca gttgtcaatt    1200
gtaaacctca ccttgcaaga tgatgtcact gagaaagcag gacaaatgga gtctaggtcc    1260
ttctgtatga cttgctgcag tatatgtgaa tctataattt tctccaaaaa aacaaaaaaa    1320
aaaaaaaaaa a                                                         1331
```

<210> SEQ ID NO 79
<211> LENGTH: 333
<212> TYPE: PRT
<213> ORGANISM: Rattus sp.
<220> FEATURE:
<223> OTHER INFORMATION: rat T2R02 (rGR02)

<400> SEQUENCE: 79

```
Met Phe Ser Gln Lys Thr Asn Tyr Ser His Leu Phe Thr Phe Ser Ile
  1               5                  10                  15

Ile Phe Tyr Val Glu Ile Val Thr Gly Ile Leu Gly Asn Gly Phe Ile
                 20                  25                  30

Ala Leu Val Asn Ile Met Asp Trp Leu Lys Arg Arg Arg Ile Ser Thr
             35                  40                  45

Ala Asp Gln Ile Leu Thr Ala Leu Ala Leu Thr Arg Leu Ile Tyr Val
         50                  55                  60

Trp Ser Val Leu Ile Cys Ile Leu Leu Leu Phe Leu Cys Pro His Leu
 65                  70                  75                  80

Ser Met Arg Pro Glu Met Phe Thr Ala Ile Gly Val Ile Trp Val Val
                 85                  90                  95
```

```
Asp Asn His Phe Ser Ile Trp Leu Ala Thr Cys Leu Gly Val Phe Tyr
                100                 105                 110

Phe Leu Lys Ile Ala Ser Phe Ser Asn Ser Leu Phe Leu Tyr Leu Lys
            115                 120                 125

Trp Arg Val Lys Lys Val Val Leu Met Ile Ile Leu Ile Ser Leu Ile
        130                 135                 140

Phe Leu Met Leu Asn Ile Ser Ser Leu Gly Met Tyr Asp His Phe Ser
145                 150                 155                 160

Ile Asp Val Tyr Glu Gly Asn Met Ser Tyr Asn Leu Val Asp Ser Thr
                165                 170                 175

His Phe Pro Arg Ile Phe Leu Phe Thr Asn Ser Ser Lys Val Phe Leu
            180                 185                 190

Ile Ala Asn Ser Ser His Val Phe Leu Pro Ile Asn Ser Leu Phe Met
        195                 200                 205

Leu Ile Pro Phe Thr Val Ser Leu Val Ala Phe Phe Val Leu Phe Leu
    210                 215                 220

Ser Leu Trp Lys His His Lys Lys Met Gln Val Asn Ala Lys Gly Pro
225                 230                 235                 240

Arg Asp Ala Ser Thr Met Ala His Thr Lys Ala Leu Gln Ile Gly Phe
                245                 250                 255

Ser Phe Leu Leu Leu Tyr Ala Ile Tyr Leu Leu Phe Ile Ile Thr Gly
            260                 265                 270

Ile Leu Asn Leu Asp Leu Met Arg Cys Ile Val Ile Leu Leu Phe Asp
        275                 280                 285

His Ile Ser Gly Ala Val Phe Ser Ile Ser His Ser Phe Val Leu Ile
    290                 295                 300

Leu Gly Asn Ser Lys Leu Arg Gln Ala Thr Leu Ser Val Leu Pro Cys
305                 310                 315                 320

Leu Arg Cys Arg Ser Lys Asp Met Asp Thr Val Val Phe
                325                 330

<210> SEQ ID NO 80
<211> LENGTH: 2438
<212> TYPE: DNA
<213> ORGANISM: Rattus sp.
<220> FEATURE:
<223> OTHER INFORMATION: rat T2R02 (rGR02)

<400> SEQUENCE: 80
attttgctcc actattttgc tcttctgcag taacacagac cacaaaacaa tggagccaat      60
gggtcaagag ctgaaacttc aggaagtggg agccaaattt tctttgtgat aggttggcat     120
atgagaattc attatttgat gcagcttctg aaaactggat gtgaaatact ggatgaagca     180
gaggtgatga cccctttgaa attaaaaagc caagatgttc atggagaaat tataaaacaa     240
tatctgggaa atttgatgct tcctaatcgg gtgtaaatgg gattttaaat gatgaacatt     300
ttgaatttcc aatgaccatt atgtaaagtt tttaaacaca gtagagacat cataaattga     360
agcatgttct cacagaaaac aaactacagc catttgttta ctttttcaat tattttttat     420
gtggaaatag taacaggaat cttaggaaat ggattcatag cactagtgaa tatcatggac     480
tggctcaaga ggaggaggat ctctactgca gatcagattc tcactgcttt ggcccttacc     540
agactcattt atgtgtggtc tgtactcatt tgtatattgt tactatttct gtgcccacat     600
ttgtctatga gaccagaaat gtttacagcg ataggtgtta tctgggtagt ggataaccac     660
ttcagcatct ggcttgctac atgtcttggt gtctttatt cctcaaaat agccagtttt      720
```

-continued

```
tctaactctt tgtttctttta cctaaagtgg agagttaaaa aagtggtttt aatgataata        780
ctgatatcac tgattttctt gatgttaaac atttcatcat tagggatgta tgatcatttc        840
tcaattgatg tttatgaagg taatatgtct tataatttgg tggattcaac acattttccc        900
agaattttct tattcacaaa ctcatctaag gtcttcttaa tcgccaattc atcccatgtt        960
ttcttaccca tcaactcact cttcatgctc atacccttca cagtttccct ggtagctttt       1020
ttcgtgctct ttctctcact gtggaagcat cacaagaaga tgcaggtcaa tgccaaagga       1080
cccagagatg ccagcaccat ggcccacaca aaagccttgc aaattgggtt ctccttcctc       1140
ctgctgtatg caatatactt actttctcatt atcacaggaa ttttgaacct tgacttgatg       1200
agatgtatag taatactttt atttgaccac atatctggag cagttttttc tataagccac       1260
tcatttgtgc tgattctggg aaacagtaag ctgagacaag ccactctttc tgtgctgcct       1320
tgtcttaggt gccggtccaa agatatggac actgtcgttt tctaataaat tccagagtac       1380
attatgcaaa tcttgaggg tgatcagttc atagaaaaag taatcttaga ggggaaaata       1440
aaatattggg gcttcaaatg ttggatgggt aatacatagg aaggcaggac aaggatgaag       1500
gagactagca ttatataagt gatttcacag ggaatggg aaagagggct tttatataat        1560
gaagaagaag ataaatgatg aaggatgagg aagagttaaa tatgtaaaat gacaatagag       1620
atggcatcat gccgttttaa gaaatttgga atgcatatgt atgtttatat atttttaat        1680
ttttattgaa tatatttatt tacattttaa atgttatcct gtttccccca cccaacctcc       1740
cacctcttcc cacctccttg ccctgacatt cccctgcact ggggaatcca gccttgacag       1800
gaccaagggc ttctcctccc tttgttgcca acaaggccat tctttgctac atgtgcagca       1860
ggagccatgg atctgtctat gtgtactctt tggatggtgg tttagtccct gggagctctt       1920
gttggttggt attgttgttc ttatggtgtt gcaactccct tcagctcctt caatccttcc       1980
tgtaactcct ccaatgtgga ccctgttctc agtccaatgg ttgactatga gcattcacct       2040
ctgtgattgt catgctctgg cacagcttct cagaagacag ctacatcagt ctcctataag       2100
agtgcacttc atggcatcag caatgttgtc ttgatttggt gtctgtatgt atatgggctg       2160
gatcccaggt ggggcaggcg ctgaatggtc attccttcag tctttgctcc aaactttgtc       2220
tttatatctc ctatgaatat ttttgttccc ccttataaga atgactgaag tatccacact       2280
ttggccatcc ttcttcatga gcttcatgtg gtctgtgaat tgtacattgt gtaatccaag       2340
cttttgggct aatatccaat tatagtgagt gcataccaaa aaaaaaaaa aaaaaaaaa        2400
aaaaaaaaa aaaaaaaaa aaaaaaaaa aaaaaaa                                   2438
```

<210> SEQ ID NO 81
<211> LENGTH: 299
<212> TYPE: PRT
<213> ORGANISM: Rattus sp.
<220> FEATURE:
<223> OTHER INFORMATION: rat T2R03 (rGR03)

<400> SEQUENCE: 81

```
Met Val Pro Thr Gln Val Thr Ile Phe Ser Ile Ile Met Tyr Val Leu
  1               5                  10                  15

Glu Ser Leu Val Ile Val Gln Ser Cys Thr Thr Val Ala Val Leu
             20                  25                  30

Phe Arg Glu Trp Met His Phe Gln Arg Leu Ser Pro Val Glu Ile Ile
         35                  40                  45

Leu Ile Ser Leu Gly Ile Ser His Phe Cys Leu Gln Trp Thr Ser Met
     50                  55                  60
```

```
Leu Tyr Asn Phe Gly Thr Tyr Ser Arg Pro Val Leu Phe Trp Lys
 65                  70                  75                  80

Val Ser Val Val Trp Glu Phe Met Asn Val Leu Thr Phe Trp Leu Thr
                 85                  90                  95

Ser Leu Leu Ala Val Leu Tyr Cys Val Lys Val Ser Ser Phe Ser His
            100                 105                 110

Pro Val Phe Leu Trp Leu Arg Leu Lys Ile Leu Lys Leu Val Leu Trp
        115                 120                 125

Leu Leu Leu Gly Ala Leu Ile Ala Ser Cys Leu Ser Ile Ile Pro Ser
130                 135                 140

Val Val Lys Tyr His Ile Gln Met Glu Leu Leu Thr Leu Asp His Leu
145                 150                 155                 160

Pro Lys Asn Ser Ser Leu Ile Leu Arg Leu Gln Met Phe Glu Trp Tyr
                165                 170                 175

Phe Ser Asn Pro Phe Lys Met Ile Gly Phe Gly Val Pro Phe Leu Val
            180                 185                 190

Phe Leu Ile Ser Ile Ile Leu Leu Thr Val Ser Leu Val Gln His Trp
        195                 200                 205

Gly Gln Met Lys His Tyr Ser Ser Ser Ser Ser Leu Arg Ala Gln
    210                 215                 220

Cys Thr Val Leu Lys Ser Leu Ala Thr Phe Phe Ile Phe Phe Thr Ser
225                 230                 235                 240

Tyr Phe Leu Thr Ile Val Val Ser Phe Ile Gly Thr Val Phe Asp Lys
                245                 250                 255

Lys Ser Trp Phe Trp Val Cys Glu Ala Val Ile Tyr Gly Leu Val Cys
            260                 265                 270

Ile His Phe Thr Ser Leu Met Met Ser Asn Pro Thr Leu Lys Lys Ala
        275                 280                 285

Leu Arg Leu Gln Phe Trp Ser Pro Glu Ser Ser
    290                 295

<210> SEQ ID NO 82
<211> LENGTH: 6552
<212> TYPE: DNA
<213> ORGANISM: Rattus sp.
<220> FEATURE:
<221> NAME/KEY: modified_base
<222> LOCATION: (1)..(6552)
<223> OTHER INFORMATION: rat T2R03 (rGR03)
<223> OTHER INFORMATION: n = g, a, c or t

<400> SEQUENCE: 82
gcatggtgcc aacccaagtc accatcttct ctatcatcat gtatgtgctt gagtccttag    60
tcataattgt gcaaagttgc acaacggttg cagtgctgtt cagagagtgg atgcactttc   120
aaagactgtc gccggtggaa ataattctca tcagcctggg catttcacat ttctgtctac   180
agtggacatc gatgctgtac aactttggta cctactctag gcctgtcctt ttattttgga   240
aggtatcggt cgtctgggag ttcatgaacg ttttgacatt ctggctaacc agtttgcttg   300
ctgtcctcta ctgtgtcaag gtctcttcct tctctcaccc cgtcttcctc tggctgaggt   360
tgaaaatttt gaaactggtt ctctggttgc tattgggcgc tctgatagct tcttgtttgt   420
caatcatccc ttctgttgtt aaatatcata tccagatgga attactcacc ctagatcatt   480
tacccaaaaa cagttctttg attctaagac tgcaaatgtt cgagtggtat ttttctaatc   540
ctttcaaaat gattgggttt ggcgttcctt tcctcgtgtt cctgatttct atcatcttac   600
```

```
tcacagtctc gctggtccag cattgggggc agatgaaaca ctacagcagc agcagctcca    660
gcctgagagc tcagtgcact gttctgaagt ctcttgccac cttcttcatc ttcttcacat    720
cctattttct gactatagtc gtctccttta ttggcaccgt gtttgataag aagtcatggt    780
tctgggtctg cgaagctgtc atctatggtt tagtctgtat tcacttcact tccctgatga    840
tgagcaaccc tacactgaaa aaagcactca ggttgcagtt ctggagccca gagtcttcct    900
aaggcaggga attcagtgaa gcctctgggg taaggaggct ttgcattggc acagttctta    960
gagtgaaatg caaacgtgga cacgaacttc attctctttc atgtccacag atggatggat   1020
ctataaatca tcaccaatct tccctgtatt ctgacccatc cttttcctgt cctatccata   1080
gtccccaggt tggttttgat ttttctcatg atcacacctt agctttagcc accgttgcaa   1140
tatcaaacat gatctatatg ttacagccaa aatcattctc acaattgtca attgcttcac   1200
aaattcagat aaatcccccct tcctgtcagg aatgtattgt ctgtgcattc aatgctcacc   1260
atgctaagcc attcattccc ttcctaactt gagtttaaga agaaaatgtc ttactgttgc   1320
ccatgtccta ttgtgctgct tctggatgtt ttatgcagtg atttagacac acgcccttgc   1380
ctgtctccaa atactggccc tttattcctt ataagtctta gtagaaaatg aactcgtctt   1440
tacttcattg acgaagacat tgtattcttc cccaaaatag tgtttaacta ctctagtctc   1500
atccataata tccctaaata tcagtgattt cagtgagtaa aacctgacaa cagttattgc   1560
tttgactctt aattcaattg tgctgtaaca tagaggaaac attctagaac atttccatat   1620
taatttgtgc ttgtagcaaa ccaaaattct ccccagttgg gtaaaaatat caaaagcaca   1680
gagtaatcaa ttttgaaatc actcagaaga catcattgtt ctatatatgt ttttttttaaa   1740 cttccctcta acaagtatca gatctttgcc tttacagggt ctggtcttac catgactata   1800
ttttatcacc atgacctatt ttctcttcat ctctttgttt tcactaactc agtagcaacc   1860
aaatatcaca ttaatagcta actctgggca cttatttctc agcctttatc tattccagac   1920
actttcaatg tatttctgct aaacacaatg acatctcttt ttgtgttcta acgacaagga   1980
atcataactt tccaactttt atacatggta gacatatttg gtgaacttaa cttctgactc   2040
tttctttaga agactgaaac tactccggaa agcaagcctt ctgatggaga aatagatacg   2100
ggtatcgtga ttcattgtga aagtgaattc cggtgcctgg aaagaaatgg atattttttt   2160
ttctcttgag tgtgtcactc tgacatatgt tccatgttga atccatattt gatactgata   2220
gcatgaatgt aagtaaagca tgtatgtaag taaagactgc taccaaaact tcgattcaac   2280
tttcctcagc agtatccctg atattgcata agaaagaaaa aacacgctgt cctacttgaa   2340
gaaggacgtg ttccatgcaa tgtggatgtg tcccaggcta cattggctca actgcagctg   2400
aaggtgggat gggaaatggt atagttagta atgtctgctg agctgtctca ctggaaagga   2460
ttctgagcag agtaaatgta agcaatgtgg ccaaggtctc ctaggaatgg gttgtaagct   2520
tgtaaggagt tgggttgtaa gagtttggga tcctttcaga atggattgag caagagccac   2580
tgaaacttgg actataccTT tgttatttgt atctaaatcc agaagggtct ttgcatgttc   2640
caaaatctca gatagctgga aggaagaagg actgttctct ttacaagtat ataaatagag   2700
aatgagctaa aaaggacccc ctcaccccccg ccgtcacaca caggaatact attccagaaa   2760
ctagggagta tttttagtgt tctcactatt tcccctttgaa aaaagtgcaa tggaaaactt   2820
atccatgaca tacatgaggt tggagtgata aaaacagctg aaggaagagg aagtctgaaa   2880
aaagatggaa acagcaatga tgcttgtcct atatatgtgt gacacccact agttcccaag   2940
gaaaccttac atccattatc tcatttcaag ctggaaggac aagtcaagat cactcaaccg   3000
```

```
acccagctgg aaaacagacc taagaatgtt aaactcatac tgatggttat ttctcactct   3060
aaagtcaatg caaatggata gcaaacaaag gggctatttt tttaagggac cagagggttt   3120
caatctagaa tcagagaaaa gataaaaagg gagatgctat agaaaaacaa tagagaagat   3180
gtggccaaga acaaggaaaa tctccagtta gcttggcact taggggccaa catgtttctg   3240
ttgttcggtc ttcaatactg tattgcatgt tgggctcact atgttttagt tgtgagtggg   3300
ttgtgcttcc tggaattaag aaaggtctgt ttctagattt caggtacaaa tgtttagaag   3360
cccattggta gcatcagtga aattaggaaa aaactgtgag cactgctggc tggacttggc   3420
aaagtcattc actatttaca catcaaatta ttagcaactt gaaagtaaat ctttgctcat   3480
catccagtgg cccccatgat cctggtgaat gacttgtaat actgtggaga ctggcaacga   3540
cggtgaattc ctagtaacac ttaccataga atctgttcat aattagactc gcccagattt   3600
tagttgctag agaacaatct ttctccttta cccacattcc tactgagtag gatgcatagg   3660
ttcggaaacc cccatggcat cgtttgactc ctcctggtag tcaagagagt ccagtcacca   3720
gtctccgaaa cacctgccaa gtcctaactc ccaacagtct acagtgtaaa cctcagtgtt   3780
tgcatgaggt ttatgtatct ccttaccatt tcctaaatgt caatacccgt gcacaggata   3840
tttgcatagg ctgcctccaa gcctgggaaa cactctcctc ctcgcatttg ctgggtttca   3900
cctttccaat tcagtgtgcc cttaaaagg cactgctttt ctaggcccac cactattgct   3960
gctcacgcat gaacatcaaa tctaccacag gcttttgcct ctcagaatta ttcttctttc   4020
tactatgcaa tgtggtatcc atgagaactt tgtcacattg tcaaattcta cctttgtttt   4080
aatgngngcc tttgtaatag ngactatgcc cagaaattaa attatagtaa gatgggtaac   4140
aacncttcaa ttntggaatt tataattaaa taaatattat gtaatattat gacttattat   4200
aangtcaatc tactgtaccc tactcctact aggaatgcaa agacaaatag caatgtgatc   4260
agcatgtgct ctttcacaag atcatattgt gcatgttgct gatgatgccc acagtgcatc   4320
tatcagaata tctctgatca ttttttttt tttgcttttg agaagccccg gttggtgctg   4380
ggatgcttca tagcaggtcc accatagaca catgcttaga ggaaagctgc ctctctctct   4440
tcattcccaa ggaacagtaa aagcagaaaa ggctcttatg ttctaaagaa cagaaaatag   4500
cctgcatttc aactacctcc tgttcagaag gcaccgaaac acaccaccaa gcaagacacc   4560
cctttacttt ctcctgcttc cctcaatttg atgatcattt ggaataaga agaaagaaaa   4620
agatgtggaa gccaattaaa aacagtcttg tctatctccc tggtgagctc tcaacttctt   4680
agtcagacca aagtaggtga aaaaataata atttttaatt tggtatgaga gtcatgttta   4740
ggctgaaaat cttaaaaaat cttagcataa aaacattttc ccctagaccc atgaaattta   4800
taatattatc tgtggttgag aaaggctagt tatagaaaaa tgtttagaat cagaatattt   4860
tgagggctct ttttttgttt tgcctaatca ttacatttgt tataagaagt ctaaagttg    4920
gtatgctaca ggtcttgtca tattttctct gaggttgagt gccaagtagt ctgcattgtg   4980
tttaaatcct gcttaaaatt atcccaagac aatataactt ctcaggagct aagccaaggg   5040
cccctttcag actaccttag tcctctctca ccgttgtcac cgtggctcat acatcagaat   5100
cctgagggag catcatgaaa tctaaggctt acaacagaa tctttctatc cctggtagaa    5160
atctttaac cttgggtttt attctcatgc cattctgatg ctcgtattta aattttatgt    5220
gttttttcat atgttcttgc atttctatcg ttaaattatg gtgacatact ttcaaatgct   5280
ttgttatttt aaaagggac aaagagagat agaaagacag ggaaagatag acagaggctt    5340
```

```
gcctaataca gtcaagaaag aagctatcaa aagtatttag caatacaaca tttatgatat    5400
attcataact gttaaccatt tttaatattc taaaatttca cttttgtttc agaaatgtat    5460
attaagagaa tctgagaaac attttttttct catagatgta gaaaaacaca caaataagg    5520 tataacacat ttaagtgatt gaaaataaaa acaaaagctt gcaaacagga ggaaaagtac    5580
attgtaggct ttcgacatgg agctgctact aggacccagg acttgtttat catttatttg    5640
ccaagtccca caaactcagg gcaatacatc tctgagacag tttcctatat tttaataaaa    5700
cttccaaaat tgatactcag tgtgaattgg ctagctttaa tggcagtcat tggataaaca    5760
attccaatgc caaatttccc taagttgata tatttgatta atatgtatat taaaacatca    5820
ggctatccat cggttggatc aaatacattc tttagggatc cattctttc cttaaatttg     5880 acttatatgt ggattctttt cacaataaat aagtaaatga gcatttattt taaaactatt    5940
ttagacggaa ctgaattaca gccaaggtag tcaaaatgac tgagaataat cacttacata    6000
tttacaaggg aaagtgactc ttcagattta agtttaaaat tagaagagag ataaatttca    6060
caagctttca ctcctaaggc taaagatagg ctgtgtaggt agttatttct gagcacattg    6120
gcacatcacc attgtcagta cttgagggtt tgaatgaagc tcactcaaag aacttggaaa    6180
gaaggtggtc ttctgacatc aatcaagaaa caagctttcc tccctacttc ttccctaaat    6240
gcaacaacct aagaattatc cacaagatgg atggcgcaag ggttcctcaa tcaatttcag    6300
gatgtacatc aatgcgcagc ctatactaca ccgaaaagga agcgcatggg tcttaaaaag    6360 taaagggat atcaaaaaat tcgcaaccaa acaaaaagtg gcacacattt aagctaggtc      6420
tatgtttggt cagttacacc tggagaaggg ggacatttgg tcagctcatt cgaacactgt    6480
caagtcctac caacaattcc tctatgctat tacccattaa acctcaggtc tcatcgaaaa    6540 aaaaaaaaa aa                                                         6552

<210> SEQ ID NO 83
<211> LENGTH: 308
<212> TYPE: PRT
<213> ORGANISM: Rattus sp.
<220> FEATURE:
<223> OTHER INFORMATION: rat T2R04 (rGR04)

<400> SEQUENCE: 83

Met Leu Ser Ala Ala Glu Gly Ile Leu Leu Cys Val Val Thr Ser Glu
  1               5                  10                  15

Ala Val Leu Gly Val Leu Gly Asp Thr Phe Ile Ala Leu Ala Asn Cys
             20                  25                  30

Met Glu Tyr Ala Lys Asn Lys Lys Leu Ser Lys Ile Gly Phe Ile Leu
         35                  40                  45

Ile Gly Leu Ala Ile Ser Arg Ile Gly Val Val Trp Ile Ile Ile Leu
     50                  55                  60

Gln Gly Tyr Met Gln Val Phe Phe Pro His Ile Leu Thr Phe Gly Asn
 65                  70                  75                  80

Ile Thr Glu Tyr Ile Thr Tyr Ile Trp Val Phe Leu Asn His Leu Ser
                 85                  90                  95

Val Trp Phe Ala Thr Asn Leu Asn Ile Leu Tyr Phe Leu Lys Ile Ala
            100                 105                 110

Asn Phe Ser Asn Ser Val Phe Leu Trp Leu Lys Ser Arg Val Arg Val
        115                 120                 125

Val Phe Ile Phe Leu Ser Gly Cys Leu Leu Thr Ser Trp Leu Leu Cys
    130                 135                 140
```

Phe Pro Gln Phe Ser Lys Met Leu Asn Asn Ser Lys Met Tyr Trp Gly
145                 150                 155                 160

Asn Thr Ser Trp Leu Gln Gln Lys Asn Val Phe Leu Ile Asn Gln
            165                 170                 175

Ser Leu Thr Asn Leu Gly Ile Phe Phe Ile Ile Val Ser Leu Ile
        180                 185                 190

Thr Cys Phe Leu Leu Ile Val Phe Leu Trp Arg His Ile Arg Gln Met
    195                 200                 205

His Ser Asp Gly Ser Gly Leu Arg Asp Leu Asn Thr Glu Ala His Val
    210                 215                 220

Lys Ala Met Arg Val Leu Ile Ser Phe Ala Val Leu Phe Ile Leu His
225                 230                 235                 240

Phe Val Gly Leu Ser Ile Gln Val Leu Cys Phe Phe Leu Pro Gln Asn
                245                 250                 255

Asn Leu Leu Phe Ile Thr Gly Leu Ile Ala Thr Cys Leu Tyr Pro Cys
            260                 265                 270

Gly His Ser Ile Ile Leu Ile Leu Gly Asn Lys Gln Leu Lys Gln Ala
        275                 280                 285

Ser Leu Lys Ala Leu Gln His Leu Thr Cys Cys Glu Thr Lys Arg Asn
    290                 295                 300

Leu Ser Val Thr
305

<210> SEQ ID NO 84
<211> LENGTH: 3449
<212> TYPE: DNA
<213> ORGANISM: Rattus sp.
<220> FEATURE:
<223> OTHER INFORMATION: rat T2R04 (rGR04)

<400> SEQUENCE: 84
tggttccatc acatgacaat aggcttgaaa aacttgcaga tagagaagac ataacccctc      60
caacaagaag ccaacatatg ggacattctc cagcagataa tttataacag atgcaacggg     120
agcaacttcg agatctgcaa agatgctgag tgcagcagaa ggcatcctcc tttgtgttgt     180
cactagtgag gcagtgctgg gggttttagg agacacattc attgcacttg caaactgcat     240
ggagtatgcc aagaacaaga agctctctaa gattggtttc attctcattg cttggcgat     300 ttccagaatt ggtgtcgtat ggataataat tttacagggg tatatgcaag tattttttcc     360
acacatactt acctttggaa acataactga atatattact tacatatggg tgtttctcaa     420
tcacttaagt gtctggtttg ctaccaacct caatatcctc tactttctaa agatagcaaa     480
tttttccaac tctgtatttc tctggctgaa aagtagagtc cgtgtggttt ttatctttct     540
gtcaggatgc ttacttacct cgtggttact atgttttcca caattttcaa agatgcttaa     600
caacagtaaa atgtactggg gaaacacgtc ttggctccag cagcagaaaa atgtcttcct     660
tattaaccaa agtttaacca atctgggaat cttcttttc attattgtat ccctgattac     720
ctgcttcctg ttgattgttt tcctctggag acacatcagg caaatgcact cagatggttc     780
aggactcaga gacctcaaca cagaagctca tgtgaaagcc atgagagttc taatatcttt     840
tgcggtactc tttatcctgc atttcgtagg tcttttccata caagtgctat gcttttttct     900
gccacaaaac aacctactct ttataactgg tttgatagcc acatgcctct atccctgtgg     960
tcactcaatc atcttaattc taggaaacaa gcagctgaag caagcctcct tgaaggcact    1020
gcagcactta acgtgctgtg agacaaaaag aaatctctca gtcacataaa tgggtttgcc    1080

```
aattaatatc tgccatgtta ttccactgat ttttacctgt tagtttctct gtgtctctgt    1140
ttagtttctg tttccatgat ctgtccattg atgagcgtgg ggtgttgaaa tctccgacta    1200
ttgttgtgtg agatgaaatg tgtgctttga gctttagtaa gatttctttt gtgaatgtag    1260
gtgcttttgc atttggtgca tagatattta agattgagag ttcagcttgg tggatttttc    1320
ctttgatgaa tatgaagtgt ccttgcttat cttttttgat gacttttgat tgaacgtcaa    1380
ttttattgga tattagattg gcaactcaag attgcttctt gaggtcattt gcttggaaag    1440 ttgttttttca gccatttact ctgaggtagt gtctgtcttt gtctctgagg tgtgtttcct    1500
gcattcagca aaatgctggg tcctctttac atatccagtt tgttagtcta tgtcttttta    1560
ttggggaatt gagtccattg atgttgagag atattaatga atagtgatca ttgcttcctg    1620
ttattttcgt tgttagatgt ggaattatgt ttgtttgtct ctcttttggt tttattgcaa    1680
ggaaattata tacttgcttt ctgtatggtg tagtttctct ccttgtgttg cagttttcct    1740
tctattatcc tttgtagggc tagatttgaa gaaagatatt gcataagctt ggttttgtca    1800
tgggatatct tggtttctcc atctatgtta attgagagtt ttgcaggata tagtagcctg    1860
ggatgacatt tgtgttctct tagggtctgt atgacatctg tccaaaatct tctggctttc    1920
atagtctctg gtgagaaatc ggatgtaatt ctcataagtc tgccattata tgtcacttga    1980 ccttttttccc ttattgcttt ttatgttctt tctttgtttt gtgcatttgg tgttctgatt    2040
attatgtgat gtgaggtatt tctcttctgg tcaaatctat ttggagttct gtaggcttct    2100
tgtatgttta tgggcatctc tttctttagg ttatggatgt tttcttctat aattttgttg    2160
aatatatcta ctgtcccttt aagttaggag ccttcacttt cttctatacc tgttatcctt    2220
aggtttaatc ttctcactgg atttcctcga tgttttggac taggaacttt ttgcattta    2280 cattatcttt gacaggtatt tcaatgtttt ctatggtatc ttctgccact gagattctct    2340
cttctagctc ttgtataatg ttggtgatgc ttgtacctgt gactccttgt ttcttcctta    2400
ggttttctat ctccagggtt gtctcccttt gtgcttttt tattgcttct atttccattc    2460
taaatcctgg atggttttgt tcaattcctt cacctctttg gttgtatttt cctgtaattc    2520
tttcagggat ttttgtgttt cctctttaag ggcttctact tgtttacttg tgttgtcctg    2580
tatttcttta aggtagttat ttatgtcctt cttgaagtcc tccatcatta tcaaaaaatg    2640
tgatttttaa atataaacct tgcttttctg gtgtgtttgg atgtcaagta ttttctttgc    2700
tgggagaact gggctctgat aatgccaagt tgtttgattt ctgttgctta gtttcctgtt    2760
cttgcctctc gccattgggt tttctctggt gtttgcttat cttgctgttt ctgagagtgg    2820
cttgacactc ttgtaggcat ctgtgtcagg cctcctgtag aactgtttcc ctgttttctt    2880 tcagccttttt ctgagaacag gtgctctgat ctcaggtgtg taggcattcc tggtgactat    2940
ctttcagctt taggagcagg caggaatcag aagggtcctg tccctgactg ctcctagatc    3000
cttgcaccca gggggcacag ttagcactag gcaattccct cttgtgtagg gaatgtgggg    3060
agaggatagt cgcctctgat ttctcaggaa tgtctgcact tctgaaagtc cagccctctc    3120
ccccacagga tttaggtgca gggagctgtt tgaccacttc aattcagtcc tgggtgtaga    3180
ccagaaccac aggtaaaaaa gaatgacttc attaaattag cagacaaatg ggtggaacta    3240
gaaaatgtca tcctgggctg gagagatggc tcagtggttc agaccactgg ctgctcttcc    3300
agaggtcctg agttcaattc ccaacaacta tatggtggct accaaccatt acaatgagat    3360
cagatgccct cctcttgtgt atctgaagag agtgacagtg tacttacata cataaaataa    3420
ataaataaat ctaaaaaaat gttaaaaaa                                      3449
```

<210> SEQ ID NO 85
<211> LENGTH: 309
<212> TYPE: PRT
<213> ORGANISM: Rattus sp.
<220> FEATURE:
<223> OTHER INFORMATION: rat T2R05 (rGR05)

<400> SEQUENCE: 85

Met Leu Gly Ala Met Glu Gly Val Leu Leu Ser Val Ala Thr Ser Glu
1               5                   10                  15

Ala Leu Leu Gly Ile Val Gly Asn Thr Phe Ile Ala Leu Val Asn Cys
            20                  25                  30

Met Asp Cys Thr Arg Asn Lys Asn Leu Tyr Asn Ile Gly Phe Ile Leu
        35                  40                  45

Thr Gly Leu Ala Ile Ser Arg Ile Cys Leu Val Trp Ile Leu Ile Thr
    50                  55                  60

Glu Ala Tyr Ile Lys Ile Phe Ser Pro Gln Leu Ser Pro Ile Asn
65                  70                  75                  80

Ile Ile Glu Leu Ile Ser Tyr Leu Trp Ile Ile Thr Ser Gln Leu Asn
                85                  90                  95

Val Trp Phe Ala Thr Ser Leu Ser Ile Phe Tyr Phe Leu Lys Ile Ala
            100                 105                 110

Asn Phe Ser His His Ile Phe Leu Trp Leu Lys Arg Arg Ile Asn Ile
        115                 120                 125

Val Phe Ala Phe Leu Ile Gly Cys Leu Leu Met Ser Trp Leu Phe Ser
    130                 135                 140

Phe Pro Val Val Val Lys Met Val Lys Asp Lys Lys Met Leu Tyr Ile
145                 150                 155                 160

Asn Ser Ser Trp Gln Ile His Met Lys Lys Ser Glu Leu Ile Ile Asn
                165                 170                 175

Tyr Val Phe Thr Asn Gly Gly Val Phe Leu Leu Phe Ile Ile Met Leu
            180                 185                 190

Ile Val Cys Phe Leu Leu Ile Ile Ser Leu Trp Arg His Ser Lys Trp
    195                 200                 205

Met Gln Ser Asn Glu Ser Gly Phe Arg Asp Leu Asn Thr Glu Val His
210                 215                 220

Val Lys Thr Ile Lys Val Leu Leu Ser Phe Ile Ile Leu Phe Ile Leu
225                 230                 235                 240

His Leu Ile Gly Ile Thr Ile Asn Val Ile Cys Leu Leu Val Pro Glu
                245                 250                 255

Asn Asn Leu Leu Phe Val Phe Gly Leu Thr Ile Ala Phe Leu Tyr Pro
            260                 265                 270

Cys Cys His Ser Leu Ile Leu Ile Leu Ala Asn Ser Arg Leu Lys Arg
        275                 280                 285

Cys Phe Val Arg Ile Leu Gln Gln Leu Met Cys Ser Glu Glu Gly Lys
    290                 295                 300

Glu Phe Arg Asn Thr
305

<210> SEQ ID NO 86
<211> LENGTH: 1127
<212> TYPE: DNA
<213> ORGANISM: Rattus sp.
<220> FEATURE:
<223> OTHER INFORMATION: rat T2R05 (rGR05)

<400> SEQUENCE: 86

```
aagagatttc agatactacc acaaacattt tttaaatata tgtaagtctt taagaaaga        60
agggaaagcc actcctttat tgagcagcca atagattgcc atcttaaaat tctgtggcag      120
aagctatttt aaagatctgc gaagatgctg ggtgcaatgg aaggtgtcct cctttcagtt      180
gcaactagtg aggctttgct tggcattgta gggaacacat tcattgcact tgtgaactgc      240
atggactgta ccaggaacaa gaatctctat aatattggct tcattctcac tggcttggca      300
atttccagaa tctgcctcgt gtggatctta atcacagagg catacataaa atattctct       360
ccacagttgc tgtctcctat caacataatt gaactcatca gttatctatg gataattacc      420
agtcaattga atgtttggtt tgctaccagc ctcagtatct tttatttcct caagatagca      480
aattttccc accacatatt tctctggtta aaagaagaa ttaatatagt ttttgccttc        540
ctgatagggt gcttacttat gtcatggcta ttttctttcc cagtagttgt gaagatggtt      600
aaagataaaa aaatgctgta tataaactca tcttggcaaa tccacatgaa gaaagtgag       660
ttaatcatta actatgtttt caccaatggg ggagtatttt tacttttat aataatgtta       720
attgtatgtt ttctcttaat tatttcccctt tggagacaca gcaagtggat gcaatcaaat     780
gaatcaggat tcagagatct caacacagaa gttcatgtga aaacaataaa agttttatta      840
tcttttatta tccttttttat attgcattta attggtatta ccatcaatgt catttgtctg     900
ttagtcccag aaaataactt gttattcgtg tttggtttga cgattgcatt cctctatccc      960
tgctgccact cacttatcct aattctagca aacagccggc tgaaacgatg ctttgtaagg     1020
atactgcaac aattaatgtg ctctgaggaa ggaaaagaat tcagaaacac atgacagtct     1080
ggaagacaaa caatcagaaa tagtaagtga aaaaaaaaa aaaaaaa                    1127
```

<210> SEQ ID NO 87
<211> LENGTH: 297
<212> TYPE: PRT
<213> ORGANISM: Rattus sp.
<220> FEATURE:
<223> OTHER INFORMATION: rat T2R06 (rGR06)

<400> SEQUENCE: 87

```
Glu Ala Leu Val Gly Ile Leu Gly Asn Ala Phe Ile Ala Leu Val Asn
 1               5                  10                  15

Phe Met Gly Trp Met Lys Asn Arg Lys Ile Thr Ala Ile Asp Leu Ile
                20                  25                  30

Leu Ser Ser Leu Ala Met Ser Arg Ile Cys Leu Gln Cys Ile Ile Leu
            35                  40                  45

Leu Asp Cys Ile Ile Leu Val Gln Tyr Pro Asp Thr Tyr Asn Arg Gly
        50                  55                  60

Lys Glu Met Arg Ile Ile Asp Phe Phe Trp Thr Leu Thr Asn His Leu
 65                 70                  75                  80

Ser Val Trp Phe Ala Thr Cys Leu Ser Ile Phe Tyr Phe Phe Lys Ile
                85                  90                  95

Ala Asn Phe Phe His Pro Leu Pro Leu Trp Ile Lys Trp Arg Ile Asp
                100                 105                 110

Lys Leu Ile Leu Arg Thr Leu Leu Ala Cys Leu Ile Leu Ser Leu Cys
            115                 120                 125

Phe Ser Leu Pro Val Thr Glu Asn Leu Ala Asp Asp Phe Arg Arg Cys
        130                 135                 140

Val Lys Thr Lys Glu Arg Ile Asn Ser Thr Leu Arg Cys Lys Leu Asn
145                 150                 155                 160
```

```
Lys Ala Gly Tyr Ala Ser Val Lys Val Asn Leu Asn Leu Val Met Leu
                165                 170                 175
Phe Pro Phe Ser Val Ser Leu Val Ser Phe Leu Leu Ile Leu Ser
            180                 185                 190
Leu Trp Arg His Thr Arg Gln Met Gln Leu Asn Val Thr Gly Tyr Asn
            195                 200                 205
Asp Pro Ser Thr Thr Ala His Val Lys Ala Thr Lys Ala Val Ile Ser
        210                 215                 220
Phe Leu Val Leu Phe Ile Val Tyr Cys Leu Ala Phe Leu Ile Ala Thr
225                 230                 235                 240
Ser Ser Tyr Phe Met Pro Glu Ser Glu Leu Ala Val Ile Trp Gly Glu
                245                 250                 255
Leu Ile Ala Leu Ile Tyr Pro Ser Ser His Ser Phe Ile Leu Ile Leu
                260                 265                 270
Gly Asn Ser Lys Leu Lys Gln Ala Ser Val Arg Val Leu Cys Arg Val
                275                 280                 285
Lys Thr Met Leu Lys Gly Arg Lys Tyr
        290                 295

<210> SEQ ID NO 88
<211> LENGTH: 1304
<212> TYPE: DNA
<213> ORGANISM: Rattus sp.
<220> FEATURE:
<223> OTHER INFORMATION: rat T2R06 (rGR06)

<400> SEQUENCE: 88
gtgaggcctt agtaggaatc ttaggaaatg cattcattgc attggtaaac ttcatgggct      60
ggatgaagaa taggaagatc actgctattg atttaatcct ctcaagtctg ctatgtcca     120
ggatttgtct acagtgtata attctattag attgtattat attggtgcag tatccagaca    180
cttacaacag gggtaaagaa atgaggatca ttgatttctt ctggacgctt accaaccatt    240
taagtgtctg gtttgccacc tgcctcagca ttttctattt cttcaagata gcaaacttct    300
tccatcctct tttcctctgg ataaagtgga gaattgacaa gctaattctg aggactctac    360
tggcatgctt gattctctcc ctatgcttta gcctcccagt cactgagaat ttggctgatg    420
atttcagacg ctgtgtcaag acaaagaaa gaataaactc tactctgagg tgcaaattaa     480
ataaagctgg atatgcttct gtcaaggtaa atctcaactt ggtcatgctg ttccccttt     540
ctgtgtccct tgtctcattc cttctcttga ttctctccct atggagacac accaggcaga    600
tgcaactcaa tgtaacaggg tacaatgatc ccagcacaac agctcatgtg aaagccacaa    660
aagcagtaat ttccttccta gttctgttta ttgtctactg cctggccttt cttatagcca    720
cttccagcta ctttatgcca gagagtgaat tagctgtaat ttggggtgag ctgatagctc    780
taatatatcc ctcaagccat tcatttatcc tgatccttgg gaacagtaaa ctaaaacagg    840
catctgtaag ggtgctttgt agagtaaaga ctatgttaaa gggaagaaaa tattagcatc    900
atggatatat ttgaagaaaa actatcactg tctaaagaaa aaggatgaca aatcattatc    960
tttcattctt atatgaatat tgctttcatg cggtaacatc ttttaacaaa cttaaatcaa   1020
atgttgggaa atctcatata cagcaacttt gcatgtctct ctgtctattt ccctctccct   1080
ttgtacatag ttgacataaa aaagaatttt tcatgacaaa attgtaataa atagctacag   1140
aggcagcaca ttttcatagt aagttctgaa tcactcttcc aaatgcaaag ctgcctgaca   1200
aattcaaaac aactgtaaca gtatttcact gctgtttgca ttctttggaa aagcaggtgg   1260
```

```
tttgttccta tgacctgact tggagttttc ttcttacatc actg                        1304
```

<210> SEQ ID NO 89
<211> LENGTH: 305
<212> TYPE: PRT
<213> ORGANISM: Rattus sp.
<220> FEATURE:
<223> OTHER INFORMATION: rat T2R07 (rGR07)

<400> SEQUENCE: 89

```
Met Gly Ser Ser Leu Tyr Asp Ile Leu Thr Ile Val Met Ile Ala Glu
  1               5                  10                  15

Phe Ile Phe Gly Asn Val Thr Asn Gly Phe Ile Val Leu Thr Asn Cys
             20                  25                  30

Ile Ala Trp Leu Ser Lys Arg Thr Leu Ser Phe Ile Gly Trp Ile Gln
         35                  40                  45

Leu Phe Leu Ala Ile Ser Arg Val Val Leu Ile Trp Glu Met Leu Leu
     50                  55                  60

Ala Trp Leu Lys Tyr Met Lys Tyr Ser Phe Ser Tyr Leu Ala Gly Thr
 65                  70                  75                  80

Glu Leu Arg Val Met Met Leu Thr Trp Val Val Ser Asn His Phe Ser
                 85                  90                  95

Leu Trp Leu Ala Thr Ile Leu Ser Ile Phe Tyr Leu Leu Lys Ile Ala
            100                 105                 110

Ser Phe Ser Arg Pro Val Phe Leu Tyr Leu Lys Trp Arg Val Lys Lys
        115                 120                 125

Val Leu Leu Leu Ile Leu Leu Gly Asn Leu Ile Phe Leu Met Phe Asn
    130                 135                 140

Ile Leu Gln Ile Asn Thr His Ile Glu Asp Trp Met Asp Gln Tyr Lys
145                 150                 155                 160

Arg Asn Ile Thr Trp Asp Ser Arg Val Asn Glu Phe Val Gly Phe Ser
                165                 170                 175

Asn Leu Val Leu Leu Glu Met Ile Met Phe Ser Val Thr Pro Phe Thr
            180                 185                 190

Val Ala Leu Val Ser Phe Ile Leu Leu Ile Phe Ser Leu Trp Lys His
        195                 200                 205

Leu Gln Lys Met His Leu Ser Ser Arg Gly Glu Arg Asp Pro Ser Thr
    210                 215                 220

Lys Ala His Val Asn Ala Leu Arg Ile Met Val Ser Phe Leu Leu Leu
225                 230                 235                 240

Tyr Ala Thr Tyr Phe Ile Ser Phe Phe Ile Ser Leu Ile Pro Met Ala
                245                 250                 255

His Lys Lys Gly Leu Asp Leu Met Phe Ser Leu Thr Val Gly Leu Phe
            260                 265                 270

Tyr Pro Ser Ser His Ser Phe Ile Leu Ile Leu Gly His Ser Asn Leu
        275                 280                 285

Arg His Ser Ser Cys Leu Val Ile Thr Tyr Leu Arg Cys Lys Glu Lys
    290                 295                 300

Asp
305
```

<210> SEQ ID NO 90
<211> LENGTH: 3994
<212> TYPE: DNA
<213> ORGANISM: Rattus sp.
<220> FEATURE:

<221> NAME/KEY: modified_base
<222> LOCATION: (1)..(3994)
<223> OTHER INFORMATION: rat T2R07 (rGR07)
<223> OTHER INFORMATION: n = g, a, c or t

<400> SEQUENCE: 90

```
cagtagcaaa attttactat gttcattgat attatgtcan gncactacgt aagaaggaag      60
acttgaaaga aagcttatct gagttttaa gaatacatgg acatttcagc ttggcaaatg      120
acgagctgtg aattttgtc atctggacat gggaagcagc ctgtatgata tcttaactat      180
tgtcatgatt gcagagttta tattcggaaa tgtgaccaat ggattcatag tgctgacaaa      240
ctgtattgct tggctcagta aagaactct ttctttcatt ggttggatcc agcttttctt      300
ggccatttcc agagtggttt tgatatggga atgttactta gcatggctga aatatatgaa      360
gtattcattt tcatatttgg ctggcacaga attaagggtt atgatgttga cctgggtagt      420
ttccaatcac tttagtctct ggcttgccac cattctaagc atcttttatt tgctcaaaat      480
agctagtttc tccagacctg ttttcctgta tctgaagtgg agagtaaaaa aagtgctcct      540
gctgattctt ctcggaaatt taatcttcct gatgttcaat atattacaaa tcaacactca      600
catagaagac tggatggatc aatataagag aaatataacg tgggattcca gagtgaatga      660
atttgtgggg ttttcaaatc tggttttatt ggagatgatt atgttctctg taacaccatt      720
caccgtggct ctggtctcct tcatcctgtt aatcttctct ttatggaaac atctccagaa      780
gatgcatctc agttccagag gggaacgaga ccctagcaca aaagcccatg tgaatgccct      840
gagaattatg gtctccttcc tcttactcta tgccacttac ttcatatcct tttttatatc      900
attaattcct atggcacata aaaaaggact agatcttatg tttagcctaa ctgttggact      960
tttctaccct tcaagccact catttatctt gattttggga cattctaatc taaggcattc    1020
cagttgtctg gtgataacct atctgagatg taaggaaaag gattagaaat tcactattcc    1080
ataaggcagt taaccacat gctattaggt atactcagtg ctagatccct aggcaagcat     1140
taacattaaa aatatataat ttctagattc ttctatttgt gataaaccac tcacttagaa    1200
taatgctaaa gtagcgtgat gttgtatata agtgtaagaa taaatgtaa ttaatttagt     1260
ttaggcacaa taacatatgt ctactaagta aaaactaggc aggctgctac acgcatatta    1320
gaatccaggc tgaggtatat agactcaaga aatactgtgg aataaagatt ttaattttca    1380
ttctattgtg agttatgtga aatcaatgcc attaaaggca tacacaagat tttcacacac    1440
tgaaacaact tcttgcattt tgtcatattg tattggaagt aaattggaga taaacttaat    1500
atcaataaat tacaaaatgt aaacataaac agggtgatta aaattagcc tctaggtcct     1560
ggggaaatga ttcaagtaaa gtgctttctt ttcaaatagg agaatctgat tgtaaatcat    1620
ctaaaagtct ggcataaaat gtcaatgaaa attgtatgta aatatagct atggcmaaga     1680
gcaccmaaga aaagaaaatt tttgcctttg aaacccagta attgatatcc tttaaaaaag    1740
cagttacata tttttctgtt taagattttg tcaagggta gctttgacaa ctaatataag     1800
ctgaggaagg tagcaagtgt gaagtcagct aatggggtca gtcaagtgct gttagcagca    1860
gatggaggcc actgctgaat ttagcaggca atttacaggg tgagcactgc tagtgctgac    1920
agaagaaaaa ctctgaaatt ttaactcttt agggtctggt gagaaagaaa aagagagaaa    1980
atcgcatata tatatatata tatatatata tatatatata tatatatata tatatatata    2040
tcatggaagc tctaacaagt tgactcaaac aactttatga tgttttagg ccctttatt      2100
ttaatgtcag tgaattaggt gtggtacagc aatattgcta cttttaaatt caaagcagtt    2160
```

```
gttttatata ttattcatta tataagctaa ttataagttt aaatcaaaag gtttatttgt    2220
ccatgatttt actttatcat tgggcacacc tgtgctctca tccttgggct tgacctagaa    2280
tgaaagttta tccttgatca tatgtctgtc acaagactac ttctcttcct atagtagttt    2340
atgtacttac aatatacaaa agtttattga attccttta tcacttatgc agccttttct     2400
tactattcta ttctattcta ttctattcta ttctattcta ttctattcta ttctattcta    2460
ttctattcta ttctattcta gaatctaacc tatacattca tttctggcaa aacaacttat   2520
atcatctcct taattatttt atcaattaat ctaacatcct gaagttattt aaatctaata    2580
taaggactct gtaaagtcac aaatttattt atacttcaca aaattcatta ttttatggaa    2640
ctgcagcatt gcctgggcca ggagtcacaa gagttccaga gttgacttta ttggcatctg    2700
cctggctaac tgaaggatca gttttctgtg tacaataatt ttgtgtatct cttttgatgc    2760
aagatatgaa aaataatttc agtctaaaag tgtccttaaa tttgaaactc tctggccaga    2820
atctaactat tgatgaccag tttgcaccat ggactcagtg tcttctattg ctttaaaata    2880
agcaacatct tgaatgcttt tcttgtgtat taggcaaata attaacaaca tgtttctatg    2940
attgtctcaa taacaatact atatttctca cagtttttaa ttttatggc aaagttggct    3000 aataagaatt ttttcaaat tatcaaacgt gaagaaaact tgacatttta tttcatggag    3060
attctaaatg ttttcttagc atattgcctt tttactaact tgattttat catgttttgg    3120 tagtatttct aatttccctt tttttctaag tatgttatgt agtaacacca ggagaatgaa    3180
acaaatgaca tttatactaa ggatgtgaca aataaggccc aaagaaagtt ttgaaaatca    3240
tgatctcatt tctattcttc tttattaagt atagcataag caaaattctg atggtggtct    3300
tggcccatat ctttgaacac agtgtagtgg tgaagacttt ttcaaatatt atgtcatatt    3360
tgtacccatc tctgtaccta tttcttctga tttcatgagg aaaaaatgag gaagggtttg    3420
tttgtgtgct ggagcagctg aagtggacca aggggcagga attctctctg ttcggtccta    3480
gtgtgactga tgatgctctc attgaaaaac aggaagaaga agaaagactt tatatgcacc    3540
attcactcct tcccctcct acattccacc tccctcttga aagagtgtct atctatatag    3600
atatagctat cctgaaatcc attaagtaga cctgactggc ttaaatctca cagaaattca    3660 cctaccttt ccatgattgc tgaaattaaa gacatgtgcc gacatattgg gcacattcag    3720
accttttgcc aactgtcttt caactcattt ggacctactg agaagtattc aaaatatttg    3780
gttgttttaa ataaaaggaa agtgggtcta tattacttga attggataga gaaattttca    3840
cttacaagtg atattgaaaa tggggggagaa tgtatttag cataagcacc agaacacaaa    3900
gcaattcttg ttaaaacttt atcgataaat tggataaatg ttaaaaaaga aaaaataaaa    3960
tatacgaact attatgaaaa aaaaaaaaaa aaaa                                3994
```

<210> SEQ ID NO 91
<211> LENGTH: 314
<212> TYPE: PRT
<213> ORGANISM: Rattus sp.
<220> FEATURE:
<223> OTHER INFORMATION: rat T2R08 (rGR08)

<400> SEQUENCE: 91

Met Glu Pro Val Ile His Val Phe Ala Thr Leu Leu Ile His Val Glu
 1               5                  10                  15

Phe Ile Phe Gly Asn Leu Ser Asn Gly Leu Ile Val Leu Ser Asn Phe
             20                  25                  30

Trp Asp Trp Val Val Lys Arg Lys Leu Ser Thr Ile Asp Lys Ile Leu

```
                35                  40                  45
Leu Thr Leu Ala Ile Ser Arg Ile Thr Leu Ile Trp Glu Met Tyr Ala
     50                  55                  60

Cys Phe Lys Ile Val Tyr Gly Ser Ser Phe Ile Phe Gly Met Lys
 65                  70                  75                  80

Leu Gln Ile Leu Tyr Phe Ala Trp Ile Leu Ser Ser His Phe Ser Leu
                 85                  90                  95

Trp Phe Ala Thr Ala Leu Ser Ile Phe Tyr Leu Leu Arg Ile Ala Asn
                100                 105                 110

Cys Ser Trp Lys Ile Phe Leu Tyr Leu Lys Trp Arg Leu Lys Gln Val
                115                 120                 125

Ile Val Gly Met Leu Leu Ala Ser Leu Val Phe Leu Pro Gly Ile Leu
130                 135                 140

Met Gln Arg Thr Leu Glu Glu Arg Pro Tyr Gln Tyr Gly Gly Asn Thr
145                 150                 155                 160

Ser Glu Asp Ser Met Glu Thr Asp Phe Ala Lys Phe Thr Glu Leu Ile
                165                 170                 175

Leu Phe Asn Met Thr Ile Phe Ser Val Ile Pro Phe Ser Leu Ala Leu
                180                 185                 190

Ile Ser Phe Leu Leu Leu Ile Phe Ser Leu Trp Lys His Leu Gln Lys
                195                 200                 205

Met Gln Leu Ser Ser Arg Gly His Gly Asp Pro Ser Thr Lys Ala His
210                 215                 220

Arg Asn Ala Leu Arg Ile Met Val Ser Phe Leu Leu Leu Tyr Thr Ser
225                 230                 235                 240

Tyr Phe Leu Ser Leu Leu Ile Ser Trp Ile Ala Gln Lys His His Ser
                245                 250                 255

Lys Leu Val Asp Ile Ile Gly Ile Ile Thr Glu Leu Met Tyr Pro Ser
                260                 265                 270

Val His Ser Phe Ile Leu Ile Leu Gly Asn Ser Lys Leu Lys Gln Thr
                275                 280                 285

Ser Leu Trp Ile Leu Ser His Leu Lys Cys Arg Leu Lys Gly Glu Asn
    290                 295                 300

Ile Leu Thr Pro Ser Gly Lys Pro Ile Asn
305                 310

<210> SEQ ID NO 92
<211> LENGTH: 1886
<212> TYPE: DNA
<213> ORGANISM: Rattus sp.
<220> FEATURE:
<221> NAME/KEY: modified_base
<222> LOCATION: (1351)
<223> OTHER INFORMATION: rat T2R08 (rGR08)
<223> OTHER INFORMATION: n = g, a, c or t

<400> SEQUENCE: 92
ctgcaggttg gtgatccagt aatgagcagc actgttatat ctcaggcttt ctaagatcat    60
ggaacctgtc attcacgtct tgccactct actaatacat gtggagttca ttttgggaa    120 tctgagcaat ggattaatag tgttgtcaaa cttctgggac tgggtcgtta aacgaaaact    180
ttccacaatt gataaaattc ttcttacatt ggcaatttca agaatcactc tcatctggga    240
aatgtatgct tgttttaaaa ttgtatatgg ttcatcttca tttatatttg ggatgaagtt    300
acaaattctt tattttgcct ggatcctttc tagtcacttc agcctctggt ttgccacagc    360
tctcagcatc ttttacttac tcagaatagc taactgctcc tggaagatct tcctgtatct    420
```

```
gaaatggaga cttaaacaag tgattgtggg gatgttgctg gcaagcttgg tgttcttgcc      480
tggaatcctg atgcaaagga ctcttgaaga gaggccctat caatatggag gaaacacaag      540
tgaggattcc atggaaactg actttgcaaa gtttacagag ctgattcttt tcaacatgac      600
tatattctct gtaataccat tttcattggc cttgatttct tttctcctgc taatcttctc      660
tttgtggaaa catctccaga agatgcagct cagttccaga ggacatggag acccctagcac     720 caaggcccac agaaatgctt tgagaattat ggtctccttc ctcttgctct acacttcata      780
tttcctgtct cttcttatat catggattgc tcagaagcat cacagtaaac tggttgacat      840
tattggtatt attactgaac tcatgtatcc ttcagtccac tcatttatcc tgattctagg      900
aaattctaaa ttaaagcaga cttctctttg gatactgagt catttgaaat gtagactgaa      960
aggagagaat attttaactc catctggcaa accaattaac tagctgttat atattctgta     1020
ttgcaaacaa atcagtgagt tagtggttca aggattccat ccttgactta ttgtatcatg     1080
gaagtcatat agggagaggc tgaacaagct atcttctgta aattggcaag ggttgcatat     1140
agtactggta ctgggacacc atccaaccat aaaaccttct aaccataacc tacctgactg     1200
caagatatgc tgggacaatg gtggctcaga gattttggga ctggccaacc aatgtctatt     1260
ctttcttgag gctcactcaa taaggaggcc atgcccaact cgtcctggat ggccaggaac     1320
cagaatctct gatggccaa tgatctatgg nagaacccag cattactggg aaaaaagaat      1380
aatcactttg atgaatggtc aaatatttcc taaatatatt ctgatacact tgtacatcat     1440
ttctctttcc caatcatcat cacagggact tctccccagc acctgatggg aacagatacc     1500
aaaatctaca gccaaatact aaatgcaggt tggggaactc cacaaaagac tggaaggaag     1560
tactgtgaga gccagagtgg tccagaacac taggagaaca cagaacatcg aattaactaa     1620
gcagcactca tagggttaat gtaaaataaa gcagcagtca catagactgc acaggtgtac     1680
tctagatcct ctgcatatat gttgtggttg tcaaacttgg gagttttgtt ggactaataa     1740
caatgtgaat aagtaagtct ctgacactta ttcccgctct tggaaccctt ttccacattt     1800
tgtattgtct taccaccttg atatgaaggt ttctgaatag tccaaaaaaa aaaaaaaaa      1860 aaaaaaaaa  aaaaaaaaaa aaaaaa                                          1886
```

<210> SEQ ID NO 93
<211> LENGTH: 309
<212> TYPE: PRT
<213> ORGANISM: Rattus sp.
<220> FEATURE:
<223> OTHER INFORMATION: rat T2R09 (rGR09)

<400> SEQUENCE: 93

```
Met Leu Ser Ala Ala Glu Gly Ile Leu Leu Ser Ile Ala Thr Val Glu
  1               5                  10                  15

Ala Gly Leu Gly Val Leu Gly Asn Thr Phe Ile Ala Leu Val Asn Cys
                 20                  25                  30

Met Asp Trp Ala Lys Asn Lys Lys Leu Ser Lys Ile Gly Phe Leu Leu
             35                  40                  45

Phe Gly Leu Ala Thr Ser Arg Ile Phe Ile Val Trp Ile Leu Ile Leu
         50                  55                  60

Asp Ala Tyr Ala Lys Leu Phe Phe Pro Gly Lys Tyr Leu Ser Lys Ser
 65                  70                  75                  80

Leu Thr Glu Ile Ile Ser Cys Ile Trp Met Thr Val Asn His Met Thr
                 85                  90                  95
```

```
Val Trp Phe Ala Thr Ser Leu Ser Ile Phe Tyr Phe Leu Lys Ile Ala
            100                 105                 110

Asn Phe Ser His Tyr Ile Phe Leu Trp Leu Lys Arg Arg Thr Asp Lys
            115                 120                 125

Val Phe Ala Phe Leu Leu Trp Cys Leu Leu Ile Ser Trp Ala Ile Ser
        130                 135                 140

Phe Ser Phe Thr Val Lys Val Met Lys Ser Asn Pro Lys Asn His Gly
145                 150                 155                 160

Asn Arg Thr Ser Gly Thr His Trp Glu Lys Arg Glu Phe Thr Ser Asn
                165                 170                 175

Tyr Val Leu Ile Asn Ile Gly Val Ile Ser Leu Leu Ile Met Thr Leu
            180                 185                 190

Thr Ala Cys Phe Leu Leu Ile Ile Ser Leu Trp Lys His Ser Arg Gln
        195                 200                 205

Met Gln Ser Asn Val Ser Gly Phe Arg Asp Leu Asn Thr Glu Ala His
        210                 215                 220

Val Lys Ala Ile Lys Phe Leu Ile Ser Phe Ile Ile Leu Phe Ile Leu
225                 230                 235                 240

Tyr Phe Ile Gly Val Ala Val Glu Ile Ile Cys Met Phe Ile Pro Glu
            245                 250                 255

Asn Lys Leu Leu Phe Ile Phe Gly Leu Thr Thr Ala Ser Val Tyr Pro
            260                 265                 270

Cys Cys His Ser Val Ile Leu Ile Leu Thr Asn Ser Gln Leu Lys Gln
        275                 280                 285

Ala Phe Val Lys Val Leu Glu Gly Leu Lys Phe Ser Glu Asn Gly Lys
        290                 295                 300

Asp Leu Arg Ala Thr
305

<210> SEQ ID NO 94
<211> LENGTH: 2596
<212> TYPE: DNA
<213> ORGANISM: Rattus sp.
<220> FEATURE:
<223> OTHER INFORMATION: rat T2R09 (rGR09)

<400> SEQUENCE: 94
ggacactgca gcagatctgc tatagaataa cagatacaaa catagcaacc tgcagagatg      60
ctcagtgcag cagaaggcat ccttctttcc attgcaactg ttgaagctgg gctgggagtt     120
ttagggaaca catttatcgc cctggttaac tgcatggatt gggccaagaa caagaagctc     180
tctaagattg gtttccttct ctttggctta gcaacttcca gaattttat tgtatggata      240 ttaattttag acgcatatgc aaagctattc tttccgggga gtatttgtc taagagtctg      300 actgaaatca tctcttgtat atggatgact gtgaatcaca tgactgtctg gtttgccacc     360
agcctcagca tcttctattt cctaaaaata gcaaattttt cccactatat atttctctgg     420
ttaaagagga gaactgataa agtatttgcc tttctcttgt ggtgtttatt aatttcatgg     480
gcaatctcct tctcattcac tgtgaaagtg atgaagagca tccaaagaa tcatggaaac      540 aggaccagtg ggacacattg ggagaagaga gaattcacaa gtaactatgt tttaatcaat     600
attggagtca tttctctctt gatcatgacc ttaactgcat gtttcttgtt aattatttca     660
ctttggaaac acagcaggca gatgcagtct aatgtttcag gattcagaga tctcaacact     720
gaagctcatg tgaaagccat aaaattttta atttcattta tcatcctttt catcttgtac     780
tttataggtg ttgcagtaga aatcatctgc atgtttatcc cagaaaacaa actgctattt     840
```

```
attttttggtt tgacaactgc atccgtctat ccctgctgtc actcagtcat tctaattcta    900
acaaacagcc agctgaagca agcctttgta aaggtactgg agggattaaa gttctctgag    960
aacggaaaag atctcagggc cacatgagtc tggaacagaa atgggtagtc tggaataatt   1020
gtaaggaagt cgtagaaggt cttttccatt tgtacagtgc tcttaccttg tttttgagga   1080
gatgtaaact tttttatttt tattttttat cctatgtgaa taagtgtgtg tgtgtgtgtg   1140
tgtgtttatg tgtgtgtgta tatatgtcta tgtgtgtttt aggaggttta agagggaaga   1200
gggaatagag gtatgttggt gttttttaaca tggatattca caggccaagg aacttgttct   1260
ctccttttac cttagggtag tgtcctttgt ggctgtcact ctgacagtct acactagttg   1320
aactaagagc ttttagccag ttcacttgtc taaacctccc ttctcatggt agcagtgttc   1380
tgattacaga atcatgctgt cacatacagc tttttaacaa ggttcccata gacagaattc   1440
atgtcaaacg gaatgcacag ctgtcactct tacccaccga tctctcttgc cagcccattc   1500
ctattgactt taaactgtag tattaaactt tactgaaatc ttctgcaacc agtctgacta   1560
tgtctcttga aatcacatga tatggtggaa ttttaatgcc atgtgaaaat ttgtttgttc   1620
agttagtttc ctactctgcc aaatcattct cttacacttg gcagaaaaaa accatcaact   1680
gtagactatt ttgtgtaaag actaatacag atagaataag tatcttaatc aagatgtcat   1740
tgtgattatc ctaatttccc cagagcactg gttcccttttc cccagaaaga ctcacaaagg   1800
aactgaggca aacagttgtg gtcactcttg atatttacca gttgaaactg aagaacagtg   1860
tttcctttct gttcagtttt actacttaca gttactttat ttcatccatt aaatcccaaa   1920
gtgcttatta atagtagata tttgatgaag caacaatggt tataagagtg gatgtggatc   1980
tatgacaaag atctagagaa acagactatt tgtgaaagat ggatgaaagc cctgatgaaa   2040
ggattcttca tggtctttga ccccagggag ttttgaaatc aagcagccac agatcaaaga   2100
gagctgagaa gaggttctcc tgaagaaaat atccaaacac atggtgccag ccaaagcaga   2160
aaatagtgga caattcagtc caggacctga atgaggtaga caatgtcctg ttaagggttg   2220
gaacaaatat atagatatgg tcattcatat acagaaacct acaggcgtgt ttgaactctt   2280
ggtttctcag taatcaattc ttaaatctttt tttagaatgg attttttatc atcattcatg   2340
atctctcagc agagtctgca ggggctaaga gacacactaa gagtatctgg aggggggagt   2400
gtcttcctgc tctatcaacc cctaaagtca tatataacaa tacaaaattc cacattagtt   2460
aagttctttt tttacatct ttattaaatt gggtatttct tatttacatt tcaaatgtga   2520
ttcccttttcc tggtttccag gccaatatcc ccctaacctc tccccttcta tgtgggtatt   2580
ccctcgtgcc gaattc                                                    2596
```

```
<210> SEQ ID NO 95
<211> LENGTH: 137
<212> TYPE: PRT
<213> ORGANISM: Rattus sp.
<220> FEATURE:
<223> OTHER INFORMATION: rat T2R10 (rGR10)

<400> SEQUENCE: 95
```

Met Phe Leu His Thr Ile Lys Gln Arg Asp Ile Phe Thr Leu Ile Ile
 1               5                  10                  15

Ile Phe Phe Val Glu Ile Thr Met Gly Ile Leu Gly Asn Gly Phe Ile
             20                  25                  30

Ala Leu Val Asn Ile Val Asp Trp Ile Lys Arg Arg Ile Ser Ser
         35                  40                  45

```
Val Asp Lys Ile Leu Thr Thr Leu Ala Leu Thr Arg Leu Ile Tyr Ala
 50                  55                  60

Trp Ser Met Leu Ile Phe Ile Leu Leu Phe Ile Leu Gly Pro His Leu
 65                  70                  75                  80

Ile Met Arg Ser Glu Ile Leu Thr Ser Met Gly Val Ile Trp Val Val
                 85                  90                  95

Asn Asn His Phe Ser Ile Trp Leu Ala Thr Cys Leu Gly Val Phe Tyr
                100                 105                 110

Phe Leu Lys Ile Ala Asn Phe Ser Asn Ser Leu Phe Leu Tyr Leu Lys
            115                 120                 125

Trp Arg Val Lys Lys Val Val Leu Met
        130                 135

<210> SEQ ID NO 96
<211> LENGTH: 818
<212> TYPE: DNA
<213> ORGANISM: Rattus sp.
<220> FEATURE:
<223> OTHER INFORMATION: rat T2R10 (rGR10)

<400> SEQUENCE: 96
cccgggctgc aggattcggc acgagaatga aaacttttgc tctactattt tgctgttctg      60
tgataccaca gaccataaaa caatcgagcc aagggatcaa gagctgaaac ttcagaaagt     120
gggaatcaaa tttccttcct gataggttag cttatgagaa ttcagcatct tattcaactt     180
cagaaaattg gatataagat acagtgtctg gatgaagccg aattgatcta tttggggaga     240
aaaaacgcca acatttataa taaggtttta tgagacagtt cctgggaaat ttggatattt     300
cctagttagt aatgtgtaaa tgggatttta aaacatgatt attttgtatt tttaacaacc     360
aacatgagga gcttttttaaa tgccacttag acattataaa ctgaagcatg ttcttacaca     420
caataaagca acgtgatatt tttactttga taatcatatt ttttgtggaa ataacaatgg     480
gaatcttagg aaatggattc atagcactag tgaacattgt ggactggatc aagagaagaa     540
ggatttcttc agtggataag attctcacta ccttggccct taccagactc atttatgcgt     600
ggtctatgct cattttttata ttgttattca tactgggccc gcatttgatt atgagatcag     660
aaatacttac atcaatgggt gttatctggg tggtgaacaa tcacttcagc atctggcttg     720
ctacatgcct cggtgtcttt tatttttctca agatagccaa ttttttctaac tctttgtttc     780 tttacctaaa gtggagagtt aaaaaagtgg ttttaatg                             818

<210> SEQ ID NO 97
<211> LENGTH: 105
<212> TYPE: PRT
<213> ORGANISM: Rattus sp.
<220> FEATURE:
<221> NAME/KEY: MOD_RES
<222> LOCATION: (101)
<223> OTHER INFORMATION: rat T2R11 (rGR11)
<223> OTHER INFORMATION: Xaa = any amino acid

<400> SEQUENCE: 97

Gly Ser Gly Asn Gly Phe Ile Val Ser Val Asn Gly Ser His Trp Phe
  1               5                  10                  15

Lys Ser Lys Lys Ile Ser Leu Ser Asp Phe Ile Ile Thr Ser Leu Ala
             20                  25                  30

Leu Phe Arg Ile Phe Leu Leu Trp Ile Ile Phe Thr Asp Ser Leu Ile
         35                  40                  45
```

```
Ile Val Phe Ser Tyr His Ala His Asp Ser Gly Ile Arg Met Gln Leu
         50                  55                  60

Ile Asp Val Phe Trp Thr Phe Thr Thr His Phe Ser Ile Trp Leu Ile
 65                  70                  75                  80

Ser Cys Leu Ser Val Phe Tyr Cys Leu Lys Ile Ala Thr Phe Ser His
                 85                  90                  95

Pro Ser Phe Leu Xaa Leu Lys Ser Arg
            100                 105
```

```
<210> SEQ ID NO 98
<211> LENGTH: 315
<212> TYPE: DNA
<213> ORGANISM: Rattus sp.
<220> FEATURE:
<223> OTHER INFORMATION: rat T2R11 (rGR11)

<400> SEQUENCE: 98
ggatccggaa acggttttat cgtgtcagtc aatggcagcc attggttcaa gagcaagaag      60
atttctttgt ctgacttcat cattaccagc ttggccctct tcaggatctt tctgctgtgg     120
atcatcttta ctgatagcct cataatagtg ttctcttacc acgcccacga ctcagggata     180
aggatgcaac ttattgatgt tttctggaca tttacaaccc acttcagtat tggcttatc      240 tcctgtctca gtgttttcta ctgcctgaaa atagccactt ctcccacccc tcattcctg      300 tagctcaaat ctaga                                                      315
```

```
<210> SEQ ID NO 99
<211> LENGTH: 308
<212> TYPE: PRT
<213> ORGANISM: Rattus sp.
<220> FEATURE:
<223> OTHER INFORMATION: rat T2R12 (rGR12)

<400> SEQUENCE: 99

Met Leu Ser Thr Val Ser Val Phe Phe Met Ser Ile Phe Val Leu Leu
  1               5                  10                  15

Cys Phe Leu Gly Ile Leu Ala Asn Gly Phe Ile Val Leu Met Leu Ser
                 20                  25                  30

Arg Glu Trp Leu Trp Arg Gly Arg Leu Leu Pro Ser Asp Met Ile Leu
             35                  40                  45

Leu Ser Leu Gly Thr Ser Arg Phe Cys Gln Gln Cys Val Gly Leu Val
 50                  55                  60

Asn Ser Phe Tyr Tyr Ser Leu His Leu Val Glu Tyr Ser Arg Ser Leu
 65                  70                  75                  80

Ala Arg Gln Leu Ile Ser Leu His Met Asp Phe Leu Asn Ser Ala Thr
                 85                  90                  95

Phe Trp Phe Gly Thr Trp Leu Ser Val Leu Phe Cys Ile Lys Ile Ala
            100                 105                 110

Asn Phe Ser His Pro Ala Phe Leu Trp Leu Lys Trp Arg Phe Pro Ala
        115                 120                 125

Leu Val Pro Trp Leu Leu Gly Ser Ile Leu Val Ser Phe Ile Val
130                 135                 140

Thr Leu Met Phe Phe Trp Gly Asn His Thr Val Tyr Gln Ala Phe Leu
145                 150                 155                 160

Arg Arg Lys Phe Ser Gly Asn Thr Thr Phe Lys Glu Trp Asn Arg Arg
                165                 170                 175

Leu Glu Ile Asp Tyr Phe Met Pro Leu Lys Leu Val Thr Thr Ser Ile
            180                 185                 190
```

```
Pro Cys Ser Leu Phe Leu Val Ser Ile Leu Leu Ile Asn Ser Leu
        195                 200                 205

Arg Arg His Ser Gln Arg Met Gln His Asn Ala His Ser Leu Gln Asp
        210                 215                 220

Pro Asn Thr Gln Ala His Ser Arg Ala Leu Lys Ser Leu Ile Ser Phe
225                 230                 235                 240

Leu Val Leu Tyr Ala Leu Ser Tyr Val Ser Met Val Ile Asp Ala Thr
                245                 250                 255

Val Val Ile Ser Ser Asp Asn Val Trp Tyr Trp Pro Trp Gln Ile Ile
            260                 265                 270

Leu Tyr Leu Cys Met Ser Val His Pro Phe Ile Leu Thr Asn Asn
        275                 280                 285

Leu Lys Phe Arg Gly Thr Phe Arg Gln Leu Leu Leu Leu Ala Arg Gly
        290                 295                 300

Phe Trp Val Thr
305

<210> SEQ ID NO 100
<211> LENGTH: 1295
<212> TYPE: DNA
<213> ORGANISM: Rattus sp.
<220> FEATURE:
<223> OTHER INFORMATION: rat T2R12 (rGR12)

<400> SEQUENCE: 100
gtgtgaggga ctgtgggtag gggctgggag gaggccagga accaaggcaa ccagtggtga      60
caggaggggc tgaaatgcta tcaactgtat cagttttctt catgtcgatc tttgttctgc     120
tctgtttcct gggaatcctg gcaaacggct tcattgtgct gatgctgagc agggaatggc     180
tatggcgcgg taggctgctc ccctcagaca tgatcctcct cagtttgggc acctcccgat     240
tctgccagca gtgcgttggg ctggtgaaca gtttctacta tcccctccac cttgttgagt     300
actccaggag ccttgcccgt caactcatta gtcttcacat ggacttcttg aactcagcca     360 cttttctggtt tggcacctgg ctcagcgtcc tgttctgtat caagattgct aacttctccc     420
atcctgcctt cctgtggttg aagtggagat cccagcatt ggtgccttgg ctcctactgg     480
gctctatctt ggtgtccttc atcgtaactc tgatgttctt tggggaaaac cacactgtct     540
atcaggcatt cttaaggaga aagttttctg gaacacaac ctttaaggag tggaacagaa     600
ggctggaaat agactatttc atgcctctga acttgtcac cacgtcaatt ccttgctctc     660
tttttctagt ctcaattttg ctgttgatca attctctcag aaggcattca caagaatgc     720 agcacaatgc tcacagcttg caagacccca cacccaggc tcacagcaga gccctgaagt     780
cactcatctc atttctggtt ctttacgcgc tgtcctatgt gtccatggtc attgacgcta     840
cagttgtcat ctcctcagat aacgtgtggt attggccctg gcaaattata ctttacttgt     900
gcatgtccgt acatccattt atccttatca ctaataatct caagttccga ggcaccttca     960
ggcagctact cctgttggcc agggattct gggtgaccta aaggtttgg tctctttatc     1020 tgtaccctt gaagagactt aggtgagggt gacttcccctt ggaagtgatc tcatctacat     1080
ggaaatgtct ttgtaggctg acatgggtc atactatgtg gttcctcctt gggaaagagg     1140
agaagaaaat acagggattc tgagcgttct tccttatctt gggatattat gaaaatggac     1200
attctgaatc ctgaaccagt attgatctga agtgcaaagt acaatatgcc tgttcccttc     1260
atgtctgcta tcctcttggt acttattaat tccct                              1295
```

<210> SEQ ID NO 101
<211> LENGTH: 332
<212> TYPE: PRT
<213> ORGANISM: Rattus sp.
<220> FEATURE:
<223> OTHER INFORMATION: rat T2R13 (rGR13)

<400> SEQUENCE: 101

```
Met Cys Gly Phe Pro Leu Ser Ile Gln Leu Leu Thr Gly Leu Val Gln
 1               5                  10                  15

Met Tyr Val Ile Leu Ile Ile Ala Val Phe Thr Pro Gly Met Leu Gly
                20                  25                  30

Asn Val Phe Ile Gly Leu Val Asn Tyr Ser Asp Trp Val Lys Asn Lys
            35                  40                  45

Lys Ile Thr Phe Ile Asn Phe Ile Leu Ile Cys Leu Ala Ala Ser Arg
 50                  55                  60

Ile Ser Ser Val Leu Val Val Phe Ile Asp Ala Ile Ile Leu Glu Leu
 65                  70                  75                  80

Thr Pro His Val Tyr His Ser Tyr Ser Arg Val Lys Cys Ser Asp Ile
                85                  90                  95

Phe Trp Val Ile Thr Asp Gln Leu Ser Thr Trp Leu Ala Thr Cys Leu
            100                 105                 110

Ser Ile Phe Tyr Leu Leu Lys Ile Ala His Phe Ser His Pro Leu Phe
        115                 120                 125

Leu Trp Leu Lys Trp Arg Leu Arg Gly Val Leu Val Gly Phe Leu Leu
130                 135                 140

Phe Ser Leu Phe Ser Leu Ile Val Tyr Phe Leu Leu Glu Leu Leu
145                 150                 155                 160

Ser Ile Trp Gly Asp Ile Tyr Val Ile Pro Lys Ser Asn Leu Thr Leu
                165                 170                 175

Tyr Ser Glu Thr Ile Lys Thr Leu Ala Phe Gln Lys Ile Ile Val Phe
            180                 185                 190

Asp Met Leu Tyr Leu Val Pro Phe Leu Val Ser Leu Ala Ser Leu Leu
        195                 200                 205

Leu Leu Phe Leu Ser Leu Val Lys His Ser Gln Asn Leu Asp Arg Ile
210                 215                 220

Ser Thr Thr Ser Glu Asp Ser Arg Ala Lys Ile His Lys Lys Ala Met
225                 230                 235                 240

Lys Met Leu Leu Ser Phe Leu Val Leu Phe Ile Ile His Ile Phe Cys
                245                 250                 255

Met Gln Leu Ser Arg Trp Leu Phe Phe Leu Phe Pro Asn Asn Arg Ser
            260                 265                 270

Thr Asn Phe Leu Leu Leu Thr Leu Asn Ile Phe Pro Leu Ser His Thr
        275                 280                 285

Phe Ile Ile Ile Leu Gly Asn Ser Lys Leu Arg Gln Arg Ala Met Arg
    290                 295                 300

Val Leu Gln His Leu Lys Ser Gln Leu Gln Glu Leu Ile Leu Ser Leu
305                 310                 315                 320

His Arg Leu Ser Arg Val Phe Thr Met Glu Ile Ala
                325                 330
```

<210> SEQ ID NO 102
<211> LENGTH: 1287
<212> TYPE: DNA
<213> ORGANISM: Rattus sp.
<220> FEATURE:

<223> OTHER INFORMATION: rat T2R13 (rGR13)

<400> SEQUENCE: 102

```
gggattcagt tggataagag aaaagtcaaa accctaagac taagaatttc cttaagtaga      60
tatcaatttc tatccattgg aaggagtttc caatcacact gaaattacaa taaaaaagga     120
gcaagataac tatgggaaag gatgattttc ggtggatgtt tgagaactga gcagcaaggc     180
aaattgatag atgtgtggat tccctctttc tattcaactg cttactggat tggttcaaat     240
gtacgtgata ttgataatag cagtgtttac acctggaatg ctggggaatg tgttcattgg     300
actggtaaac tactctgact gggtaaaaaa caagaaaatc accttcatca acttcatcct     360
gatctgtttg gcagcgtcca gaatcagctc tgtgttggtg gtatttattg atgcaatcat     420
cctagaacta actcctcatg tctatcattc ttacagtcga gtgaaatgct ctgatatatt     480
ctgggttata actgaccagc tgtcaacgtg gcttgccacc tgcctcagca ttttctactt     540
actcaaaata gcccacttct cccatcccct tttcctttgg ttgaagtgga gattgagagg     600
agtgcttgtt ggttttcttc tattttcttt gttctcattg attgtttatt ttctactcct     660
ggaattactg tctatttggg gagatattta tgtgatccct aaaagcaatc tgactttata     720
ttcagaaaca attaagaccc ttgcttttca aaagataatt gttttgata tgctatattt      780
agtcccattt cttgtgtccc tagcctcatt gctcctttta tttttatcct tggtgaagca     840
ctcccaaaac cttgacagga tttctaccac ctctgaagat tccagagcca agatccacaa     900
gaaggccatg aaaatgctat tatctttcct cgttctcttt ataattcaca ttttttgcat     960
gcagttgtca cggtggttat tctttttgtt tccaaacaac aggtcaacta attttctttt    1020
gttaacatta aacatcttcc cattatctca tacattcatt atcatcctgg aaacagcaa     1080
gcttcgacaa agagcaatga gggtcctgca acatcttaaa agccaacttc aagagttgat    1140
cctctcccctt catagattgt ccagagtctt cactatggaa atagcttaaa ggggagactt    1200
ggaaggtcac tggtaacttg ttcttccgct gagttctgtt aagtaatgct ggacatatat    1260
gaactatccc tagtgcatac tgatatt                                        1287
```

<210> SEQ ID NO 103
<211> LENGTH: 68
<212> TYPE: PRT
<213> ORGANISM: Rattus sp.
<220> FEATURE:
<223> OTHER INFORMATION: rat T2R14 (rGR14)

<400> SEQUENCE: 103

```
Val Ala Asn Ile Met Asp Trp Val Lys Arg Lys Leu Ser Ala Val
  1               5                  10                  15
Asp Gln Leu Leu Thr Val Leu Ala Ile Ser Arg Ile Thr Leu Leu Trp
             20                  25                  30
Ser Leu Tyr Ile Leu Lys Ser Thr Phe Ser Met Val Pro Asn Phe Glu
         35                  40                  45
Val Ala Ile Pro Ser Thr Arg Leu Thr Asn Leu Val Trp Ile Ile Ser
     50                  55                  60
Asn His Phe Asn
 65
```

<210> SEQ ID NO 104
<211> LENGTH: 206
<212> TYPE: DNA
<213> ORGANISM: Rattus sp.
<220> FEATURE:

-continued

```
<223> OTHER INFORMATION: rat T2R14 (rGR14)

<400> SEQUENCE: 104
ctgtggcaaa cataatggat tgggtcaaga gaaggaagct ctctgcagtg gatcagctcc      60
tcactgtgct ggccatctcc agaatcactc tgttgtggtc attgtacata ctgaaatcaa     120
cattttcaat ggtgccaaac tttgaggtag ctataccgtc aacaagacta actaatcttg    180
tctggataat ttctaaccat tttaat                                          206

<210> SEQ ID NO 105
<211> LENGTH: 327
<212> TYPE: PRT
<213> ORGANISM: Mus sp.
<220> FEATURE:
<223> OTHER INFORMATION: mouse T2R01 (mGR01)

<400> SEQUENCE: 105
```

Met Gln His Leu Leu Lys Thr Ile Phe Val Ile Cys His Ser Thr Leu
 1               5                  10                  15

Ala Ile Ile Leu Ile Phe Glu Leu Ile Ile Gly Ile Leu Gly Asn Gly
            20                  25                  30

Phe Met Ala Leu Val His Cys Met Asp Trp Val Lys Arg Lys Lys Met
        35                  40                  45

Ser Leu Val Asn Lys Ile Leu Thr Ala Leu Ala Ile Ser Arg Ile Phe
    50                  55                  60

His Leu Ser Leu Leu Leu Ile Ser Leu Val Ile Phe Phe Ser Tyr Ser
65                  70                  75                  80

Asp Ile Pro Met Thr Ser Arg Met Thr Gln Val Ser Asn Asn Val Trp
                85                  90                  95

Ile Ile Val Asn His Phe Ser Ile Trp Leu Ser Thr Cys Leu Ser Val
            100                 105                 110

Leu Tyr Phe Leu Lys Ile Ser Asn Phe Ser Asn Ser Phe Phe Leu Tyr
        115                 120                 125

Leu Lys Trp Arg Val Glu Lys Val Val Ser Val Thr Leu Leu Val Ser
    130                 135                 140

Leu Leu Leu Leu Ile Leu Asn Ile Leu Leu Ile Asn Leu Glu Ile Ser
145                 150                 155                 160

Ile Cys Ile Lys Glu Cys Gln Arg Asn Ile Ser Cys Ser Phe Ser Ser
                165                 170                 175

His Tyr Tyr Ala Lys Cys His Arg Gln Val Ile Arg Leu His Ile Ile
            180                 185                 190

Phe Leu Ser Val Pro Val Val Leu Ser Leu Ser Thr Phe Leu Leu Leu
        195                 200                 205

Ile Phe Ser Leu Trp Thr Leu His Gln Arg Met Gln Gln His Val Gln
    210                 215                 220

Gly Gly Arg Asp Ala Arg Thr Thr Ala His Phe Lys Ala Leu Gln Thr
225                 230                 235                 240

Val Ile Ala Phe Phe Leu Leu Tyr Ser Ile Phe Ile Leu Ser Val Leu
                245                 250                 255

Ile Gln Asn Glu Leu Leu Lys Lys Asn Leu Phe Val Val Phe Cys Glu
            260                 265                 270

Val Val Tyr Ile Ala Phe Pro Thr Phe His Ser Tyr Ile Leu Ile Val
        275                 280                 285

Gly Asp Met Lys Leu Arg Gln Ala Cys Leu Pro Leu Cys Ile Ile Ala
    290                 295                 300

Ala Glu Ile Gln Thr Thr Leu Cys Arg Asn Phe Arg Ser Leu Lys Tyr
305                 310                 315                 320

Phe Arg Leu Cys Cys Ile Phe
            325

<210> SEQ ID NO 106
<211> LENGTH: 1374
<212> TYPE: DNA
<213> ORGANISM: Mus sp.
<220> FEATURE:
<223> OTHER INFORMATION: mouse T2R01 (mGR01)

<400> SEQUENCE: 106

| | | | | | |
|---|---|---|---|---|---|
| agctgtgcgt | gagcaaagca | tttcttgtct | gccacttctg | agctgtgtga | ggagacacat | 60 |
| tatcacggaa | agagattcag | actctgtcgc | tgtcaaacct | gtatgtttgc | tcctcttta | 120 |
| ctgtgaaggc | agagttacga | aaaaaaatgt | tatgagaacc | aactcagaaa | ttgacaaaaa | 180 |
| ttttctaaat | gtcatttta | aaattatat | ttcaaatgga | aatgtgagca | aatctttata | 240 |
| actaatatat | aaaatgcagc | atcttttaaa | gacaatattt | gttatctgcc | atagcacact | 300 |
| tgcaatcatt | ttaatctttg | aattaataat | tggaatttta | ggaaatgggt | tcatggccct | 360 |
| ggtgcactgt | atggactggg | ttaagagaaa | gaaaatgtcc | ttagttaata | aaatcctcac | 420 |
| tgctttggca | atctccagaa | tttttcatct | cagtttattg | cttataagtt | tagtcatatt | 480 |
| ctttcatat | tctgatattc | ctatgacttc | aaggatgaca | caagtcagta | ataatgtttg | 540 |
| gattatagtc | aatcatttca | gtatctggct | ttctacatgc | ctcagtgtcc | tttattttct | 600 |
| caagatatcc | aatttttcta | actctttttt | tctttatcta | aagtggagag | ttgaaaaagt | 660 |
| agtttcagtt | acactgttgg | tgtcattgct | cctcctgatt | ttaaatattt | tattaattaa | 720 |
| cttggaaatt | agcatatgca | taaggaatg | tcaaagaaac | atatcatgca | gcttcagttc | 780 |
| tcattactat | gcaaagtgtc | acaggcaggt | gataaggctt | cacattattt | tcctgtctgt | 840 |
| ccccgttgtt | ttgtccctgt | caacttttct | cctgctcatc | ttctccctgt | ggacacttca | 900 |
| ccagaggatg | cagcagcatg | ttcagggagg | cagagatgcc | agaaccacgg | cccacttcaa | 960 |
| agccctacaa | actgtgattg | catttttcct | actatattcc | atttttattc | tgtctgtctt | 1020 |
| aatacaaata | tgaattactg | aagaaaaatc | ttttcgttgt | attttgtgag | ttgtatata | 1080 |
| tagcttttcc | gacattccat | tcatatattc | tgattgtagg | agacatgaag | ctgagacagg | 1140 |
| cctgcctgcc | tctctgtatt | atcgcagctg | aaattcagac | tacactatgt | agaaatttta | 1200 |
| gatcactaaa | gtactttaga | ttatgttgta | tattctagac | aaaaattaac | tgatacaaat | 1260 |
| gtcttttgta | ttttcattt | taaatatcct | ttaattttga | ctgcatgaaa | ttgatttctg | 1320 |
| cttgcaatta | tcactgatta | aaactattaa | taatttaact | agttgtatac | aagg | 1374 |

<210> SEQ ID NO 107
<211> LENGTH: 327
<212> TYPE: PRT
<213> ORGANISM: Mus sp.
<220> FEATURE:
<223> OTHER INFORMATION: mouse T2R02 (mGR02)

<400> SEQUENCE: 107

Met Glu Ser Val Leu His Asn Phe Ala Thr Val Leu Ile Tyr Val Glu
 1               5                  10                  15

Phe Ile Phe Gly Asn Leu Ser Asn Gly Phe Ile Val Leu Ser Asn Phe
             20                  25                  30

Leu Asp Trp Val Ile Lys Gln Lys Leu Ser Leu Ile Asp Lys Ile Leu

```
                 35                  40                  45
Leu Thr Leu Ala Ile Ser Arg Ile Thr Leu Ile Trp Glu Ile Tyr Ala
 50                  55                  60

Trp Phe Lys Ser Leu Tyr Asp Pro Ser Ser Phe Leu Ile Gly Ile Glu
 65                  70                  75                  80

Phe Gln Ile Ile Tyr Phe Ser Trp Val Leu Ser Ser His Phe Ser Leu
                 85                  90                  95

Trp Leu Ala Thr Thr Leu Ser Val Phe Tyr Leu Leu Arg Ile Ala Asn
                100                 105                 110

Cys Ser Trp Gln Ile Phe Leu Tyr Leu Lys Trp Arg Leu Lys Gln Leu
                115                 120                 125

Ile Val Gly Met Leu Leu Gly Ser Leu Val Phe Leu Leu Gly Asn Leu
130                 135                 140

Met Gln Ser Met Leu Glu Glu Arg Phe Tyr Gln Tyr Gly Arg Asn Thr
145                 150                 155                 160

Ser Val Asn Thr Met Ser Asn Asp Leu Ala Met Trp Thr Glu Leu Ile
                165                 170                 175

Phe Phe Asn Met Ala Met Phe Ser Val Ile Pro Phe Thr Leu Ala Leu
                180                 185                 190

Ile Ser Phe Leu Leu Leu Ile Phe Ser Leu Trp Lys His Leu Gln Lys
                195                 200                 205

Met Gln Leu Ile Ser Arg Arg His Arg Asp Pro Ser Thr Lys Ala His
210                 215                 220

Met Asn Ala Leu Arg Ile Met Val Ser Phe Leu Leu Leu Tyr Thr Met
225                 230                 235                 240

His Phe Leu Ser Leu Leu Ile Ser Trp Ile Ala Gln Lys His Gln Ser
                245                 250                 255

Glu Leu Ala Asp Ile Ile Gly Met Ile Thr Glu Leu Met Tyr Pro Ser
                260                 265                 270

Val His Ser Cys Ile Leu Ile Leu Gly Asn Ser Lys Leu Lys Gln Thr
                275                 280                 285

Ser Leu Cys Met Leu Arg His Leu Arg Cys Arg Leu Lys Gly Glu Asn
290                 295                 300

Ile Thr Ile Ala Tyr Ser Asn Gln Ile Thr Ser Phe Cys Val Phe Cys
305                 310                 315                 320

Val Ala Asn Lys Ser Met Arg
                325

<210> SEQ ID NO 108
<211> LENGTH: 1759
<212> TYPE: DNA
<213> ORGANISM: Mus sp.
<220> FEATURE:
<223> OTHER INFORMATION: mouse T2R02 (mGR02)

<400> SEQUENCE: 108
cagcacagtg aaaaactcat gggccacttg gtcacccagg acaggcgac gctgttatat      60 gccaagcttt ctatgaacat ggaatctgtc cttcacaact tgccactgt actaatatac     120 gtggagttta ttttgggaa tttgagcaat ggattcatag tgttgtcaaa cttcttggac     180
tgggtcatta aacaaaagct ttccttaata gataaaattc ttcttacatt ggcaatttca     240
agaatcactc tcatctggga aatatatgct tggtttaaaa gtttatga tccatcttcc      300 tttttaattg gaatagaatt tcaaattatt tattttagct gggtcctttc tagtcacttc     360
agcctctggc ttgccacaac tctcagcgtc ttttatttac tcagaatagc taactgctcc     420
```

-continued

```
tggcagatct ttctctattt gaaatggaga cttaaacaac tgattgtggg gatgttgctg       480
ggaagcttgg tgttcttgct tggaaatctg atgcaaagca tgcttgaaga gaggttctat       540
caatatggaa ggaacacaag tgtgaatacc atgagcaatg accttgcaat gtggaccgag       600
ctgatctttt tcaacatggc tatgttctct gtaataccat ttacattggc cttgatttct       660
tttctcctgc taatcttctc tttgtggaaa catctccaga agatgcagct catttccaga       720
agacacagag accctagcac caaggcccac atgaatgcct gagaattat  ggtgtccttc       780 ctcttgctct ataccatgca tttcctgtct cttcttatat catggattgc tcaaaagcat       840
cagagtgaac tggctgatat tattggtatg ataactgaac tcatgtatcc ttcagtccat       900
tcatgtatcc tgattctagg aaattctaaa ttaaagcaga cttctctttg tatgctgagg       960
catttgagat gtaggctgaa aggagagaat atcacaattg catatagcaa ccaaataact      1020
agcttttgtg tattctgtgt tgcaaacaaa tctatgaggt agttgttcaa ggaatccttc      1080
cttgacttat tgtatcatgg aagtcatatg ggggagtctg aaagagctgt cttctgtaag      1140
caaggtttgt atacactagt ggggctggga caccaaccca agcacaaaac ctagctataa      1200
cctatcctgg ctgcaggata tgctggaaca atggtggctt ggaaattgtg ggactggcaa      1260
agcaatagct agtctaactt gaggcccatt ccacagcagg aagctcatgc ccacctctgc      1320
ctggatggcc aggaagcaaa atcttgatgg ccccaagacc tatggtaaac tgaacactac      1380
tggaaaaaga aagactcgtg ttaatgatct atcaaatatt tcctaatgat attctgataa      1440
actcatatat tagtccctgt cctaatcatc atcactggga ctccttccca gcacctgatg      1500
ggagcagata gagatctaca tccaaatagt aagtgtatct tggggaactc cacttaagaa      1560
tagaaggaac aattatgaga gccagagtga tccagaacac taggatcaca gaatcaacta      1620
agcagcatgc ataggggtta atggagactg aagtggcaat cacagagcct gcataggtct      1680
acactaagtc ctctgtgtat atactgtggc tgtttagctt aggaattttg ttggactcct      1740
aacaatggat aaggaattc                                                   1759
```

<210> SEQ ID NO 109
<211> LENGTH: 312
<212> TYPE: PRT
<213> ORGANISM: Mus sp.
<220> FEATURE:
<223> OTHER INFORMATION: mouse T2R03 (mGR03)

<400> SEQUENCE: 109

```
Met Val Leu Thr Ile Arg Ala Ile Leu Trp Val Thr Leu Ile Thr Ile
  1               5                  10                  15

Ile Ser Leu Glu Phe Ile Ile Gly Ile Leu Gly Asn Val Phe Ile Ala
                 20                  25                  30

Leu Val Asn Ile Ile Asp Trp Val Lys Arg Gly Lys Ile Ser Ala Val
             35                  40                  45

Asp Lys Thr Tyr Met Ala Leu Ala Ile Ser Arg Thr Ala Phe Leu Leu
         50                  55                  60

Ser Leu Ile Thr Gly Phe Leu Val Ser Leu Leu Asp Pro Ala Leu Leu
 65                  70                  75                  80

Gly Met Arg Thr Met Val Arg Leu Leu Thr Ile Ser Trp Met Val Thr
                 85                  90                  95

Asn His Phe Ser Val Trp Phe Ala Thr Cys Leu Ser Ile Phe Tyr Phe
                100                 105                 110

Leu Lys Ile Ala Asn Phe Ser Asn Ser Ile Phe Leu Val Leu Lys Trp
```

```
                115                 120                 125
Glu Ala Lys Lys Val Val Ser Val Thr Leu Val Ser Val Ile Ile
    130                 135                 140
Leu Ile Met Asn Ile Ile Val Ile Asn Lys Phe Thr Asp Arg Leu Gln
145                 150                 155                 160
Val Asn Thr Leu Gln Asn Cys Ser Thr Ser Asn Thr Leu Lys Asp Tyr
                165                 170                 175
Gly Leu Phe Leu Phe Ile Ser Thr Gly Phe Thr Leu Thr Pro Phe Ala
                180                 185                 190
Val Ser Leu Thr Met Phe Leu Leu Leu Ile Phe Ser Leu Trp Arg His
            195                 200                 205
Leu Lys Asn Met Cys His Ser Ala Thr Gly Ser Arg Asp Val Ser Thr
    210                 215                 220
Val Ala His Ile Lys Gly Leu Gln Thr Val Val Thr Phe Leu Leu Leu
225                 230                 235                 240
Tyr Thr Ala Phe Val Met Ser Leu Leu Ser Glu Ser Leu Asn Ile Asn
                245                 250                 255
Ile Gln His Thr Asn Leu Leu Ser His Phe Leu Arg Ser Ile Gly Val
                260                 265                 270
Ala Phe Pro Thr Gly His Ser Cys Val Leu Ile Leu Gly Asn Ser Lys
                275                 280                 285
Leu Arg Gln Ala Ser Leu Ser Val Ile Leu Trp Leu Arg Tyr Lys Tyr
    290                 295                 300
Lys His Ile Glu Asn Trp Gly Pro
305                 310

<210> SEQ ID NO 110
<211> LENGTH: 1484
<212> TYPE: DNA
<213> ORGANISM: Mus sp.
<220> FEATURE:
<223> OTHER INFORMATION: mouse T2R03 (mGR03)

<400> SEQUENCE: 110
ctttaatagc agggtgtgaa tatttaaatt ttctttctgc agcaactact gagggcttca      60
gactgctgta tacagggcat gaagcatctg gatgaagttc agctgtgctg cctttgacaa     120
caatttttg tgtatgtgtg gagaacataa accatttcat tagtgaaatt tggcttttgg     180
gtgacattgt ctatgatagt tctgaaagtg attatgttaa gaatcagaca cagccgtcta     240
gaagattgta ttaacacatc tttggtagtt cagaagaaat tagatcatca tggtgttgac     300
aataagggct attttatggg taacattgat aactattata agtctggagt ttatcatagg     360
aattttagga aatgtattca tagctctcgt gaacatcata gactgggtta aaagaggaaa     420
gatctctgca gtggataaga cctatatggc cctggccatc tccaggactg ctttttatt     480
gtcactaatc acagggttct tggtatcatt attggaccca gctttattgg gaatgagaac     540
gatggtaagg ctccttacta tttcctggat ggtgaccaat catttcagtg tctggtttgc     600
aacatgcctc agtatctttt attttctcaa gatagctaat ttctcaaatt ctattttcct     660
tgttctcaaa tgggaagcta aaaagtggt atcagtgaca ttggtggtat ctgtgataat     720
cttgatcatg aacattatag tcataaacaa attcactgac agacttcaag taaacacact     780
ccagaactgt agtacaagta acactttaaa agattatggg ctctttttat tcattagcac     840
tgggtttaca ctcaccccat tcgctgtgtc tttgacaatg tttcttctgc tcatcttctc     900
cctgtggaga catctgaaga atatgtgtca cagtgccaca ggctccagag atgtcagcac     960
```

-continued

```
agtggcccac ataaaaggct tgcaaactgt ggtaaccttc ctgttactat atactgcttt    1020
tgttatgtca cttctttcag agtctttgaa tattaacatt caacatacaa atcttctttc    1080
tcatttttta cggagtatag gagtagcttt tcccacaggc cactcctgtg tactgattct    1140
tggaaacagt aagctgaggc aagcctctct ttctgtgata ttgtggctga ggtataagta    1200
caaacatata gagaatlggg gcccctaaat catatcaggg atccttttcc acattctaga    1260
aaaaaatcag ttaataagaa caggaattta ggaaggaatc tgaaattatg aatctcatag    1320
gccatgaacc ttcagacaaa ggattcatta gagagataga gagagaacat tgttatctgt    1380
aactcgacag gcaacactgt agattatgaa aataaatgtc agtctgtaat ggaaagcaaa    1440
acatgctata ttttattaat tggttttggt ttaaggtcgg gata                     1484
```

<210> SEQ ID NO 111
<211> LENGTH: 302
<212> TYPE: PRT
<213> ORGANISM: Mus sp.
<220> FEATURE:
<223> OTHER INFORMATION: mouse T2R04 (mGR04)

<400> SEQUENCE: 111

```
Met Leu Ser Ala Leu Glu Ser Ile Leu Leu Ser Val Ala Thr Ser Glu
 1               5                  10                  15

Ala Met Leu Gly Val Leu Gly Asn Thr Phe Ile Val Leu Val Asn Tyr
            20                  25                  30

Thr Asp Trp Val Arg Asn Lys Lys Leu Ser Lys Ile Asn Phe Ile Leu
        35                  40                  45

Thr Gly Leu Ala Ile Ser Arg Ile Phe Thr Ile Trp Ile Ile Thr Leu
    50                  55                  60

Asp Ala Tyr Thr Lys Val Phe Leu Leu Thr Met Leu Met Pro Ser Ser
65                  70                  75                  80

Leu His Glu Cys Met Ser Tyr Ile Trp Val Ile Asn His Leu Ser
                85                  90                  95

Val Trp Phe Ser Thr Ser Leu Gly Ile Phe Tyr Phe Leu Lys Ile Ala
            100                 105                 110

Asn Phe Ser His Tyr Ile Phe Leu Trp Met Lys Arg Arg Ala Asp Lys
        115                 120                 125

Val Phe Val Phe Leu Ile Val Phe Leu Ile Ile Thr Trp Leu Ala Ser
    130                 135                 140

Phe Pro Leu Ala Val Lys Val Ile Lys Asp Val Lys Ile Tyr Gln Ser
145                 150                 155                 160

Asn Thr Ser Trp Leu Ile His Leu Glu Lys Ser Glu Leu Leu Ile Asn
                165                 170                 175

Tyr Val Phe Ala Asn Met Gly Pro Ile Ser Leu Phe Ile Val Ala Ile
            180                 185                 190

Ile Ala Cys Phe Leu Leu Thr Ile Ser Leu Trp Arg His Ser Arg Gln
        195                 200                 205

Met Gln Ser Ile Gly Ser Gly Phe Arg Asp Leu Asn Thr Glu Ala His
    210                 215                 220

Met Lys Ala Met Lys Val Leu Ile Ala Phe Ile Ile Leu Phe Ile Leu
225                 230                 235                 240

Tyr Phe Leu Gly Ile Leu Ile Glu Thr Leu Cys Leu Phe Leu Thr Asn
                245                 250                 255

Asn Lys Leu Leu Phe Ile Phe Gly Phe Thr Leu Ser Ala Met Tyr Pro
            260                 265                 270
```

Cys Cys His Ser Phe Ile Leu Ile Leu Thr Ser Arg Glu Leu Lys Gln
            275                 280                 285

Asp Thr Met Arg Ala Leu Gln Arg Leu Lys Cys Cys Glu Thr
        290                 295                 300

<210> SEQ ID NO 112
<211> LENGTH: 1529
<212> TYPE: DNA
<213> ORGANISM: Mus sp.
<220> FEATURE:
<223> OTHER INFORMATION: mouse T2R04 (mGR04)

<400> SEQUENCE: 112

| | |
|---|---|
| ctgcagcagg taaatcacac cagatccagc agaagccttc ttggaaattg gcagagatgc | 60 |
| tgagtgcact ggaaagcatc ctcctttctg ttgccactag tgaagccatg ctgggagttt | 120 |
| tagggaacac atttattgta cttgtaaact acacagactg ggtcaggaat aagaaactct | 180 |
| ctaagattaa ctttattctc actggcttag caatttccag gatttttacc atatggataa | 240 |
| taactttaga tgcatataca aaggttttcc ttctgactat gcttatgccg agcagtctac | 300 |
| atgaatgcat gagttacata tgggtaatta ttaaccatct gagcgtttgg tttagcacca | 360 |
| gcctcggcat cttttatttt ctgaagatag caaattttc ccactacata tttctctgga | 420 |
| tgaagagaag agctgataaa gttttgtct ttctaattgt attcttaatt ataacgtggc | 480 |
| tagcttcctt tccgctagct gtgaaggtca ttaaagatgt taaatatat cagagcaaca | 540 |
| catcctggct gatccacctg gagaagagtg agttactat aaactatgtt tttgccaata | 600 |
| tggggcccat ttccctcttt attgtagcca taattgcttg tttcttgtta accatttccc | 660 |
| tttggagaca cagcaggcag atgcaatcca ttggatcagg attcagagat ctcaacacag | 720 |
| aagctcacat gaaagccatg aaagtttaa ttgcatttat catcctcttt atcttatatt | 780 |
| ttttgggtat tctcatagaa acattatgct tgtttcttac aaacaataaa cttctctta | 840 |
| ttttggctt cactttgtca gccatgtatc cctgttgcca ttcctttatc ctaattctaa | 900 |
| caagcaggga gctgaagcaa gacactatga gggcactgca gagattaaaa tgctgtgaga | 960 |
| cttgacagag aaatgaatgt tctggcacag ttcagcaggg aatccctgga gcccttcca | 1020 |
| ttcccactat gttctcacac tgtctttagt tgaattgtta aaagttttg aaacctttgg | 1080 |
| caactgattg actgcagcta cgccagtgta agattttcat agtaagagca acattgaaa | 1140 |
| ataagacttc tcagtcttat ttcattgagt ttctaaagca ttgacaccca ttcaccagaa | 1200 |
| aaaccaaagg ggaagagagg agttttcaga catgtgtgat gaatcttgat atttaggaca | 1260 |
| tggaattgag gagccagagg gatgctaccg tgtgtctaca gctttgtttg ttaaatagct | 1320 |
| acttttcctt tcccagttag ttaaagtaga tgcttggagt agtggtgaaa atcatggcag | 1380 |
| tagatgggat ctgtgggaag tggttgagga agcaggctgt ttctgaacga agagaccaga | 1440 |
| ggactgattg aactggtcat tgtgtatatc aaaaatagtg atttcagatg aagccaagtt | 1500 |
| gtagagcaaa gatatctgag gaagaattc | 1529 |

<210> SEQ ID NO 113
<211> LENGTH: 300
<212> TYPE: PRT
<213> ORGANISM: Mus sp.
<220> FEATURE:
<223> OTHER INFORMATION: mouse T2R05 (mGR05)

<400> SEQUENCE: 113

```
Met Leu Ser Ala Ala Glu Gly Ile Leu Leu Ser Ile Ala Thr Val Glu
  1               5                  10                  15

Ala Gly Leu Gly Val Leu Gly Asn Thr Phe Ile Ala Leu Val Asn Cys
             20                  25                  30

Met Asp Trp Ala Lys Asn Asn Lys Leu Ser Met Thr Gly Phe Leu Leu
         35                  40                  45

Ile Gly Leu Ala Thr Ser Arg Ile Phe Ile Val Trp Leu Leu Thr Leu
     50                  55                  60

Asp Ala Tyr Ala Lys Leu Phe Tyr Pro Ser Lys Tyr Phe Ser Ser
 65                  70                  75                  80

Leu Ile Glu Ile Ile Ser Tyr Ile Trp Met Thr Val Asn His Leu Thr
                 85                  90                  95

Val Trp Phe Ala Thr Ser Leu Ser Ile Phe Tyr Phe Leu Lys Ile Ala
                100                 105                 110

Asn Phe Ser Asp Cys Val Phe Leu Trp Leu Lys Arg Arg Thr Asp Lys
            115                 120                 125

Ala Phe Val Phe Leu Leu Gly Cys Leu Leu Thr Ser Trp Val Ile Ser
    130                 135                 140

Phe Ser Phe Val Val Lys Val Met Lys Asp Gly Lys Val Asn His Arg
145                 150                 155                 160

Asn Arg Thr Ser Glu Met Tyr Trp Glu Lys Arg Gln Phe Thr Ile Asn
                165                 170                 175

Tyr Val Phe Leu Asn Ile Gly Val Ile Ser Leu Phe Met Met Thr Leu
                180                 185                 190

Thr Ala Cys Phe Leu Leu Ile Met Ser Leu Trp Arg His Ser Arg Gln
            195                 200                 205

Met Gln Ser Gly Val Ser Gly Phe Arg Asp Leu Asn Thr Glu Ala His
    210                 215                 220

Val Lys Ala Ile Lys Phe Leu Ile Ser Phe Ile Ile Leu Phe Val Leu
225                 230                 235                 240

Tyr Phe Ile Gly Val Ser Ile Glu Ile Cys Ile Phe Ile Pro Glu
                245                 250                 255

Asn Lys Leu Leu Phe Ile Phe Gly Phe Thr Thr Ala Ser Ile Tyr Pro
                260                 265                 270

Cys Cys His Ser Phe Ile Leu Ile Leu Ser Asn Ser Gln Leu Lys Gln
            275                 280                 285

Ala Phe Val Lys Val Leu Gln Gly Leu Lys Phe Phe
    290                 295                 300

<210> SEQ ID NO 114
<211> LENGTH: 903
<212> TYPE: DNA
<213> ORGANISM: Mus sp.
<220> FEATURE:
<223> OTHER INFORMATION: mouse T2R05 (mGR05)

<400> SEQUENCE: 114
atgctgagtg cggcagaagg catcctcctt tccattgcaa ctgttgaagc tgggctggga      60
gttttaggga acacatttat tgcactggta aactgcatgg actgggccaa gaacaataag     120
ctttctatga ctggcttcct tctcatcggc ttagcaactt ccaggatttt tattgtgtgg     180
ctattaactt tagatgcata tgcaaagcta ttctatccaa gtaagtattt ttctagtagt     240
ctgattgaaa tcatctctta tatatggatg actgtgaatc acctgactgt ctggtttgcc     300
accagcctaa gcatcttcta tttcctgaag atagccaatt tttccgactg tgtatttctc     360
```

```
tggttgaaga ggagaactga taaagctttt gttttctct  tggggtgttt gctaacttca    420
tgggtaatct ccttctcatt tgttgtgaag gtgatgaagg acggtaaagt gaatcataga    480
aacaggacct cggagatgta ctgggagaaa aggcaattca ctattaacta cgttttcctc    540
aatattggag tcatttctct ctttatgatg accttaactg catgtttctt gttaattatg    600
tcactttgga gacacagcag gcagatgcag tctggtgttt caggattcag agacctcaac    660
acagaagctc atgtgaaagc cataaaattt ttaatttcat ttatcatcct tttcgtcttg    720
tattttatag gtgtttcaat agaaattatc tgcatattta taccagaaaa caaactgcta    780
tttatttttg gtttcacaac tgcatccata tatccttgct gtcactcatt tattctaatt    840
ctatctaaca gccagctaaa gcaagccttt gtaaaggtac tgcaaggatt aaagttcttt    900
tag                                                                  903
```

<210> SEQ ID NO 115
<211> LENGTH: 308
<212> TYPE: PRT
<213> ORGANISM: Mus sp.
<220> FEATURE:
<223> OTHER INFORMATION: mouse T2R06 (mGR06)

<400> SEQUENCE: 115

```
Met Leu Thr Val Ala Glu Gly Ile Leu Leu Cys Phe Val Thr Ser Gly
  1               5                  10                  15

Ser Val Leu Gly Val Leu Gly Asn Gly Phe Ile Leu His Ala Asn Tyr
             20                  25                  30

Ile Asn Cys Val Arg Lys Lys Phe Ser Thr Ala Gly Phe Ile Leu Thr
         35                  40                  45

Gly Leu Ala Ile Cys Arg Ile Phe Val Ile Cys Ile Ile Ile Ser Asp
     50                  55                  60

Gly Tyr Leu Lys Leu Phe Ser Pro His Met Val Ala Ser Asp Ala His
 65                  70                  75                  80

Ile Ile Val Ile Ser Tyr Ile Trp Val Ile Ile Asn His Thr Ser Ile
                 85                  90                  95

Trp Phe Ala Thr Ser Leu Asn Leu Phe Tyr Leu Leu Lys Ile Ala Asn
            100                 105                 110

Phe Ser His Tyr Ile Phe Phe Cys Leu Lys Arg Arg Ile Asn Thr Val
        115                 120                 125

Phe Ile Phe Leu Leu Gly Cys Leu Phe Ile Ser Trp Ser Ile Ala Phe
    130                 135                 140

Pro Gln Thr Val Lys Ile Phe Asn Val Lys Lys Gln His Arg Asn Val
145                 150                 155                 160

Ser Trp Gln Val Tyr Leu Tyr Lys Asn Glu Phe Ile Val Ser His Ile
                165                 170                 175

Leu Leu Asn Leu Gly Val Ile Phe Phe Phe Met Val Ala Ile Ile Thr
            180                 185                 190

Cys Phe Leu Leu Ile Ile Ser Leu Trp Lys His Asn Arg Lys Met Gln
        195                 200                 205

Leu Tyr Ala Ser Arg Phe Lys Ser Leu Asn Thr Glu Val His Val Lys
    210                 215                 220

Val Met Lys Val Leu Ile Ser Phe Ile Ile Leu Leu Ile Leu His Phe
225                 230                 235                 240

Ile Gly Ile Leu Ile Glu Thr Leu Ser Phe Leu Lys Tyr Glu Asn Lys
                245                 250                 255

Leu Leu Leu Ile Leu Gly Leu Ile Ile Ser Cys Met Tyr Pro Cys Cys
```

```
                260             265              270
His Ser Phe Ile Leu Ile Leu Ala Asn Ser Gln Leu Lys Gln Ala Ser
            275                 280                 285

Leu Lys Ala Leu Lys Gln Leu Lys Cys His Lys Asp Lys Asp Val
        290                 295                 300

Arg Val Thr Trp
305

<210> SEQ ID NO 116
<211> LENGTH: 1242
<212> TYPE: DNA
<213> ORGANISM: Mus sp.
<220> FEATURE:
<223> OTHER INFORMATION: mouse T2R06 (mGR06)

<400> SEQUENCE: 116
tatagttgca gcagaagcaa cgttagggat ctgtagagat gctgactgta gcagaaggaa      60
tcctcctttg ttttgtaact agtggttcag tcctgggagt tctaggaaat ggatttatcc    120
tgcatgcaaa ctacattaac tgtgtcagaa agaagttctc cacagctggc tttattctca    180
caggcttggc tatttgcaga atctttgtca tatgtataat aatctctgat ggatatttaa    240
aattgttttc tccacatatg gttgcctctg atgcccacat tatagtgatt cttacatat     300 gggtaattat caatcataca agtatatggt ttgccaccag cctcaacctc ttctatctcc    360
tgaagatagc aaattttct cactacatct tcttctgctt gaagagaaga atcaatacag     420
tatttatctt tctcctggga tgcttattta tcatggtc aattgctttc ccacaaacag      480
tgaagatatt taatgttaaa aagcagcaca gaaatgtttc ctggcaggtt tacctctata    540
agaatgagtt cattgtaagc cacattcttc tcaacctggg agttatattc ttctttatgg    600
tggctatcat tacatgcttc ctattaatta tttcactttg gaaacataac agaaagatgc    660
agttgtatgc ctcaagattc aaaagcctta acacagaagt acatgtgaaa gtcatgaaag    720
ttttaatttc ttttattatc ctgttaatct tgcatttcat agggattttg atagaaacat    780 tgagctttt aaaatatgaa ataaactgc tacttatttt gggtttgata atttcatgca     840
tgtatccttg ctgtcattca tttatcctaa ttctagcaaa cagtcagctg aagcaggctt    900
ctttgaaggc actgaagcaa ttaaaatgcc ataagaaaga caaggacgtc agagtgacat    960
ggtagactta tggagaaatg aatggtcaca agaaatagcc tggtgtggag atgttgatat   1020
ctctaaagac cgtttcactt ccaaattctt gcaattattt aaaaaaaaaa gtcttgctga   1080
tatcatggaa tcatgggaaa tgttgcaatt gtgttttggg gacagggtga ccagtgaagg   1140
tatggttaag cagcgaaaca ctcatacagc tcgttcgttc ttttgtatt ttattttgtg    1200 ttggtggcct tccaagacat gatttctcta tgtaagtttt gg                     1242

<210> SEQ ID NO 117
<211> LENGTH: 308
<212> TYPE: PRT
<213> ORGANISM: Mus sp.
<220> FEATURE:
<223> OTHER INFORMATION: mouse T2R07 (mGR07)

<400> SEQUENCE: 117

Met Leu Asn Ser Ala Glu Gly Ile Leu Leu Cys Val Val Thr Ser Glu
 1               5                  10                  15

Ala Val Leu Gly Val Leu Gly Asp Thr Tyr Ile Ala Leu Phe Asn Cys
            20                  25                  30
```

```
Met Asp Tyr Ala Lys Asn Lys Lys Leu Ser Lys Ile Gly Phe Ile Leu
             35                  40                  45
Ile Gly Leu Ala Ile Ser Arg Ile Gly Val Val Trp Ile Ile Leu
 50                  55                  60
Gln Gly Tyr Ile Gln Val Phe Phe Pro His Met Leu Thr Ser Gly Asn
 65                  70                  75                  80
Ile Thr Glu Tyr Ile Thr Tyr Ile Trp Val Phe Leu Asn His Leu Ser
                 85                  90                  95
Val Trp Phe Val Thr Asn Leu Asn Ile Leu Tyr Phe Leu Lys Ile Ala
            100                 105                 110
Asn Phe Ser Asn Ser Val Phe Leu Trp Leu Lys Arg Val Asn Ala
            115                 120                 125
Val Phe Ile Phe Leu Ser Gly Cys Leu Leu Thr Ser Trp Leu Leu Cys
130                 135                 140
Phe Pro Gln Met Thr Lys Ile Leu Gln Asn Ser Lys Met His Gln Arg
145                 150                 155                 160
Asn Thr Ser Trp Val His Gln Arg Lys Asn Tyr Phe Leu Ile Asn Gln
                165                 170                 175
Ser Val Thr Asn Leu Gly Ile Phe Phe Phe Ile Ile Val Ser Leu Ile
            180                 185                 190
Thr Cys Phe Leu Leu Ile Val Phe Leu Trp Arg His Val Arg Gln Met
            195                 200                 205
His Ser Asp Val Ser Gly Phe Arg Asp His Ser Thr Lys Val His Val
            210                 215                 220
Lys Ala Met Lys Phe Leu Ile Ser Phe Met Val Phe Phe Ile Leu His
225                 230                 235                 240
Phe Val Gly Leu Ser Ile Glu Val Leu Cys Phe Ile Leu Pro Gln Asn
                245                 250                 255
Lys Leu Leu Phe Ile Thr Gly Leu Thr Ala Thr Cys Leu Tyr Pro Cys
            260                 265                 270
Gly His Ser Ile Ile Val Ile Leu Gly Asn Lys Gln Leu Lys Gln Ala
            275                 280                 285
Ser Leu Lys Ala Leu Gln Gln Leu Lys Cys Cys Glu Thr Lys Gly Asn
290                 295                 300
Phe Arg Val Lys
305

<210> SEQ ID NO 118
<211> LENGTH: 1754
<212> TYPE: DNA
<213> ORGANISM: Mus sp.
<220> FEATURE:
<223> OTHER INFORMATION: mouse T2R07 (mGR07)

<400> SEQUENCE: 118
ttcataatga agaggaggca gggcaatgtt ggtttctgtt gtctgaccag tgtatttgac      60
agtgatacta cacatttgat tgctaaatgc aaatagttcc aaaggaacaa gtaaatttta     120
tgaaatagaa gcttctattt gcttattaac aaactgcaag caaacattag tctgcacaca     180
ttttatagac aagctaaatc ttcaaaagca ataaaaaaga gcacccataa agttctgact     240
ctatcacatg acaataggct tgaaaagatt gtctatgtag ataagaaga tggcataact      300 tctccatcaa gaagccagta tatgggacat tctccagcag ataatttaca atagatgcag     360
cagaagtaac cttagagatc tgtaaagatg ctgaattcag cagaaggcat cctcctttgt     420
gttgtcacta gtgaggctgt gctcggagtt ttaggggaca catatattgc acttttaac      480
```

```
tgcatggact atgctaagaa caagaagctc tctaagatcg gtttcattct cattggcttg      540
gcgatttcca gaattggtgt tgtatggata ataattttac aagggtatat acaagtattt      600
tttccacaca tgcttacctc tggaaacata actgaatata ttacttacat atgggtattt      660
ctcaatcact taagtgtctg gtttgtcacc aacctcaaca tcctctactt tctaaagata      720
gctaattttt ccaactctgt atttctctgg ctgaaaagga gagtcaatgc agtttttatc      780
tttctgtcag gatgcttact tacctcatgg ttactatgtt ttccacaaat gacaaagata      840
cttcaaaata gtaaaatgca ccagagaaac acatcttggg tccaccagcg gaaaaattac      900
tttcttatta ccaaagtgtg gaccaatctg ggaatctttt tcttcattat tgtatccctg      960
attacctgct ttctgttgat tgttttcctc tggagacatg tcagacaaat gcactcagat     1020
gtttcaggat tcagagacca cagcacaaaa gtacatgtga aagctatgaa atttctaata     1080
tcttttatgg tcttctttat tctgcatttt gtaggccttt ccatagaagt gctatgcttt     1140
attctgccac aaaataaact gctctttata actggtttga cagccacatg cctctatccc     1200
tgcggtcact caatcatcgt aattttagga aataagcagt taaagcaagc tctctttgaag    1260 gcactgcagc aactaaaatg ctgtgagaca aaaggaaatt tcagagtcaa ataaatgggt     1320
ttgcaaataa atagctgcct tgttcttcca ctggttttta ccctgttagt tgatgttatg     1380
aaaagttcct gctatggttg atgacatctc aaggaatcta ttttctggt ggcatgttaa      1440 gtccacgtga agcctcactt catactgtga cttgactatg caattctttt ccacaaaata     1500
accagataac attcagcctg gagataaatt catttaaagg cttttatggt gaggataaac     1560
aaaaaaaaaa aatcattttt ctgtgattca ctgtaactcc caggatgagt aaaagaaaac     1620
aagacaaatg gttgtgatca gcctttgtgt gtctagacag agctagggac cagatgttga     1680
tgcttgtgtg tggttttgag ttctttaaga agttattgcc tctctgccat tcggtattcc     1740
tcaggtgaga attc                                                        1754
```

<210> SEQ ID NO 119  
<211> LENGTH: 297  
<212> TYPE: PRT  
<213> ORGANISM: Mus sp.  
<220> FEATURE:  
<223> OTHER INFORMATION: mouse T2R08 (mGR08)

<400> SEQUENCE: 119

```
Met Leu Trp Glu Leu Tyr Val Phe Val Phe Ala Ala Ser Val Phe Leu
  1               5                  10                  15

Asn Phe Val Gly Ile Ala Asn Leu Phe Ile Ile Val Ile Ile Ile
             20                  25                  30

Lys Thr Trp Val Asn Ser Arg Arg Ile Ala Ser Pro Asp Arg Ile Leu
         35                  40                  45

Phe Ser Leu Ala Ile Thr Arg Phe Leu Thr Leu Gly Leu Phe Leu Leu
     50                  55                  60

Asn Ser Val Tyr Ile Ala Thr Asn Thr Gly Arg Ser Val Tyr Phe Ser
 65                  70                  75                  80

Thr Phe Phe Leu Leu Cys Trp Lys Phe Leu Asp Ala Asn Ser Leu Trp
                 85                  90                  95

Leu Val Thr Ile Leu Asn Ser Leu Tyr Cys Val Lys Ile Thr Asn Phe
            100                 105                 110

Gln His Pro Val Phe Leu Leu Leu Lys Arg Thr Ile Ser Met Lys Thr
        115                 120                 125
```

```
Thr Ser Leu Leu Leu Ala Cys Leu Leu Ile Ser Ala Leu Thr Thr Leu
    130                 135                 140

Leu Tyr Tyr Met Leu Ser Gln Ile Ser Arg Phe Pro Glu His Ile Ile
145                 150                 155                 160

Gly Arg Asn Asp Thr Ser Phe Asp Leu Ser Asp Gly Ile Leu Thr Leu
                165                 170                 175

Val Ala Ser Leu Val Leu Asn Ser Leu Leu Gln Phe Met Leu Asn Val
                180                 185                 190

Thr Phe Ala Ser Leu Leu Ile His Ser Leu Arg Arg His Ile Gln Lys
            195                 200                 205

Met Gln Arg Asn Arg Thr Ser Phe Trp Asn Pro Gln Thr Glu Ala His
    210                 215                 220

Met Gly Ala Met Arg Leu Met Ile Cys Phe Leu Val Leu Tyr Ile Pro
225                 230                 235                 240

Tyr Ser Ile Ala Thr Leu Leu Tyr Leu Pro Ser Tyr Met Arg Lys Asn
                245                 250                 255

Leu Arg Ala Gln Ala Ile Cys Met Ile Ile Thr Ala Ala Tyr Pro Pro
            260                 265                 270

Gly His Ser Val Leu Leu Ile Ile Thr His His Lys Leu Lys Ala Lys
            275                 280                 285

Ala Lys Lys Ile Phe Cys Phe Tyr Lys
    290                 295
```

<210> SEQ ID NO 120
<211> LENGTH: 1475
<212> TYPE: DNA
<213> ORGANISM: Mus sp.
<220> FEATURE:
<223> OTHER INFORMATION: mouse T2R08 (mGR08)

<400> SEQUENCE: 120

```
aagcttgttt gtaattaggc attcctaaga aaataagaac aggagtgaag aaatagtaat      60
ttaatccttg aaagatttgc atctcagtaa aagcagctgc ctcttagacc agaaatggtg     120
tttgccatgc tggaaaataa aaaggagacc tctttccagg ctgcatcctg tgtctgctta     180
cttatttcag tttgttttca tcggcaccaa acgaggaaag atgctctggg aactgtatgt     240
atttgtgttt gctgcctcgg ttttttaaa ttttgtagga atcattgcaa atctatttat      300
tatagtgata attattaaga cttgggtcaa cagtcgcaga attgcctctc cggataggat     360
cctgttcagc ttggccatca ctagattcct gactttgggg ttgtttctac tgaacagtgt     420
ctacattgct acaaatactg gaaggtcagt ctactttttcc acattttttc tattgtgttg    480
gaagtttctg gatgcaaaca gtctctggtt agtgaccatt ctgaacagct tgtattgtgt     540
gaagattact aattttcaac acccagtgtt tctcctgttg aaacggacta tctctatgaa     600
gaccaccagc tgctgttggg cctgtcttct gatttcagcc ctcaccactc tcctatatta     660
tatgctctca cagatatcac gttttcctga acacataatt gggagaaatg acacgtcatt     720
tgacctcagt gatggtatct tgacgttagt agcctctttg gtcctgaact cacttctaca     780
gtttatgctc aatgtgactt tgcttccctt gttaatacat tccttgagaa gacatataca     840
gaagatgcag agaaacagga ccagcttttg gaatccccag acggaggctc acatgggtgc     900
tatgaggctg atgatctgtt cctcgtgct ctacattcca tattcaattg ctaccctgct      960
ctatcttcct tcctatatga ggaagaatct gagagcccag gccatttgca tgattattac   1020
tgctgcttac cctccaggac attctgtcct cctcattatc acacatcata aactgaaagc   1080
```

```
taaagcaaag aagatttct gtttctacaa gtagcagaat ttcattagta gttaacagca    1140
tcaattcatg gtttggttgc attagaaatg tctcagtgat ctaaggactt aattttgtga    1200
tcttgtatct ggcatcctga ccctgagact aagtgcttat atttttggtca atacagcatc   1260 ttttggctaa tattttaaag taaatcacat tccataagaa attgtttaag ggatttacgt    1320
atttttcatg gctatcacat tcctagacaa tggaaatcac catactgttt cgctagctac    1380
tgaagtacca ggggaaagtc catgaatgaa ggccacattg tgatgttctt ggttagcaca    1440
gattagagaa tttggcctca actgagcaag atatc                                1475
```

<210> SEQ ID NO 121
<211> LENGTH: 316
<212> TYPE: PRT
<213> ORGANISM: Mus sp.
<220> FEATURE:
<223> OTHER INFORMATION: mouse T2R09 (mGR09)

<400> SEQUENCE: 121

```
Met Glu His Leu Leu Lys Arg Thr Phe Asp Ile Thr Glu Asn Ile Leu
  1               5                  10                  15

Leu Ile Ile Leu Phe Ile Glu Leu Ile Ile Gly Leu Ile Gly Asn Gly
                 20                  25                  30

Phe Thr Ala Leu Val His Cys Met Asp Trp Val Lys Arg Lys Lys Met
         35                  40                  45

Ser Leu Val Asn Lys Ile Leu Thr Ala Leu Ala Thr Ser Arg Ile Phe
     50                  55                  60

Leu Leu Trp Phe Met Leu Val Gly Phe Pro Ile Ser Ser Leu Tyr Pro
 65                  70                  75                  80

Tyr Leu Val Thr Thr Arg Leu Met Ile Gln Phe Thr Ser Thr Leu Trp
                 85                  90                  95

Thr Ile Ala Asn His Ile Ser Val Trp Phe Ala Thr Cys Leu Ser Val
            100                 105                 110

Phe Tyr Phe Leu Lys Ile Ala Asn Phe Ser Asn Ser Pro Phe Leu Tyr
        115                 120                 125

Leu Lys Arg Arg Val Glu Lys Val Val Ser Val Thr Leu Leu Val Ser
    130                 135                 140

Leu Val Leu Leu Phe Leu Asn Ile Leu Leu Asn Leu Glu Ile Asn
145                 150                 155                 160

Met Cys Ile Asn Glu Tyr His Gln Ile Asn Ile Ser Tyr Ile Phe Ile
                165                 170                 175

Ser Tyr Tyr His Leu Ser Cys Gln Ile Gln Val Leu Gly Ser His Ile
            180                 185                 190

Ile Phe Leu Ser Val Pro Val Val Leu Ser Leu Ser Thr Phe Leu Leu
        195                 200                 205

Leu Ile Phe Ser Leu Trp Thr Leu His Lys Arg Met Gln Gln His Val
    210                 215                 220

Gln Gly Gly Arg Asp Ala Arg Thr Thr Ala His Phe Lys Ala Leu Gln
225                 230                 235                 240

Ala Val Ile Ala Phe Leu Leu Tyr Ser Ile Phe Ile Leu Ser Leu
                245                 250                 255

Leu Leu Gln Phe Trp Ile His Gly Leu Arg Lys Lys Pro Pro Phe Ile
            260                 265                 270

Ala Phe Cys Gln Val Val Asp Thr Ala Phe Pro Ser Phe His Ser Tyr
        275                 280                 285

Val Leu Ile Leu Arg Asp Arg Lys Leu Arg His Ala Ser Leu Ser Val
```

```
        290                 295                 300
Leu Ser Trp Leu Lys Cys Arg Pro Asn Tyr Val Lys
305                 310                 315

<210> SEQ ID NO 122
<211> LENGTH: 1339
<212> TYPE: DNA
<213> ORGANISM: Mus sp.
<220> FEATURE:
<223> OTHER INFORMATION: mouse T2R09 (mGR09)

<400> SEQUENCE: 122
gaattcagaa atcatcaaaa aatcttcaaa actacatgtt taaaatagca cttcaaatga      60
atacatttgc aaatctttac aactaataca taaaatggag catcttttga agagaacatt     120
tgatatcacc gagaacatac ttctaattat tttattcatt gaattaataa ttggacttat     180
aggaaacgga ttcacagcct tggtgcactg catggactgg gttaagagaa aaaaaatgtc     240
attagttaat aaaatcctca ccgctttggc aacttctaga attttcctgc tctggttcat     300
gctagtaggg tttccaatta gctcactgta cccatattta gttactacta gactgatgat     360
acagttcact agtactctat ggactatagc taaccatatt agtgtctggt ttgctacatg     420
cctcagtgtc ttttattttc tcaagatagc caatttttct aattctcctt ttctctatct     480
aaagaggaga gttgaaaaag tagtttcagt tacattactg gtgtctctgg tcctcttgtt     540
tttaaatatt ttactactta atttggaaat taacatgtgt ataaatgaat atcatcaaat     600
aaacatatca tacatcttca tttcttatta ccatttaagt tgtcaaattc aggtgttagg     660
aagtcacatt attttcctgt ctgtccccgt tgttttgtcc ctgtcaactt ttctcctgct     720
catcttctcc ctgtggacac ttcacaagag gatgcagcag catgttcagg gaggcagaga     780
tgccagaacc acggcccact tcaaagcctt gcaagcagtg attgcctttc cctactata     840
ctccattttt atcctgtcac tgttactaca attttggatc catggattaa ggaagaaacc     900
tcctttcatt gcattttgtc aggttgtaga tacagctttt ccttcattcc attcatatgt     960
cttgattctg agagacagga agctgagaca cgcctctctc tctgtgttgt cgtggctgaa    1020
atgcaggcca aattatgtga ataatatttt ctttgtattt tcattttcaa ttttaaaata    1080
ttcttagaat ttgactgcat gtatttcatc ttttatttga acaaccact aattaaagct     1140
attactaatt tagcaagtcg tatacaaggt tatttttaa tacacatatc aaaaactgac     1200
atgtttatgt tctacaaaaa cctgaatata tcaaaattat ataaatttg tatcaacgat      1260
taacaatgga gttttttat ttatgacctg tcacgggact ccggtggagt cagcttgtca     1320
gatgaaagtc tgaaagctt                                                1339

<210> SEQ ID NO 123
<211> LENGTH: 333
<212> TYPE: PRT
<213> ORGANISM: Mus sp.
<220> FEATURE:
<223> OTHER INFORMATION: mouse T2R10 (mGR10)

<400> SEQUENCE: 123

Met Phe Ser Gln Ile Ile Ser Thr Ser Asp Ile Phe Thr Phe Thr Ile
  1               5                  10                  15

Ile Leu Phe Val Glu Leu Val Ile Gly Ile Leu Gly Asn Gly Phe Ile
             20                  25                  30

Ala Leu Val Asn Ile Met Asp Trp Thr Lys Arg Arg Ser Ile Ser Ser
         35                  40                  45
```

```
Ala Asp Gln Ile Leu Thr Ala Leu Ala Ile Thr Arg Phe Leu Tyr Val
        50                  55                  60

Trp Phe Met Ile Ile Cys Ile Leu Leu Phe Met Leu Cys Pro His Leu
 65                  70                  75                  80

Leu Thr Arg Ser Glu Ile Val Thr Ser Ile Gly Ile Ile Trp Ile Val
                85                  90                  95

Asn Asn His Phe Ser Val Trp Leu Ala Thr Cys Leu Gly Val Phe Tyr
            100                 105                 110

Phe Leu Lys Ile Ala Asn Phe Ser Asn Ser Leu Phe Leu Tyr Leu Lys
        115                 120                 125

Trp Arg Val Lys Lys Val Val Leu Met Ile Ile Gln Val Ser Met Ile
130                 135                 140

Phe Leu Ile Leu Asn Leu Leu Ser Leu Ser Met Tyr Asp Gln Phe Ser
145                 150                 155                 160

Ile Asp Val Tyr Glu Gly Asn Thr Ser Tyr Asn Leu Gly Asp Ser Thr
                165                 170                 175

Pro Phe Pro Thr Ile Ser Leu Phe Ile Asn Ser Ser Lys Val Phe Val
            180                 185                 190

Ile Thr Asn Ser Ser His Ile Phe Leu Pro Ile Asn Ser Leu Phe Met
        195                 200                 205

Leu Ile Pro Phe Thr Val Ser Leu Val Ala Phe Leu Met Leu Ile Phe
    210                 215                 220

Ser Leu Trp Lys His His Lys Lys Met Gln Val Asn Ala Lys Pro Pro
225                 230                 235                 240

Arg Asp Ala Ser Thr Met Ala His Ile Lys Ala Leu Gln Thr Gly Phe
                245                 250                 255

Ser Phe Leu Leu Leu Tyr Ala Val Tyr Leu Leu Phe Ile Val Ile Gly
            260                 265                 270

Met Leu Ser Leu Arg Leu Ile Gly Gly Lys Leu Ile Leu Leu Phe Asp
        275                 280                 285

His Ile Ser Gly Ile Gly Phe Pro Ile Ser His Ser Phe Val Leu Ile
    290                 295                 300

Leu Gly Asn Asn Lys Leu Arg Gln Ala Ser Leu Ser Val Leu His Cys
305                 310                 315                 320

Leu Arg Cys Arg Ser Lys Asp Met Asp Thr Met Gly Pro
                325                 330

<210> SEQ ID NO 124
<211> LENGTH: 1371
<212> TYPE: DNA
<213> ORGANISM: Mus sp.
<220> FEATURE:
<223> OTHER INFORMATION: mouse T2R10 (mGR10)

<400> SEQUENCE: 124
gaattcaaca tcttattcaa cttcagaaaa ctggatatta gacacagtgt ctggatgaag      60
cagaggtgat ctctttggga aaaaagcca  agtagtcata aagaatttat gaaacaattc     120
ctgggattgt ttatatttgt tacaaacaaa tttatatgtt tgttagtcag taatgtataa    180
gtgggatttt aaagcatgat tatcttgaat ttttaacaaa aaacatgtag tgcttttttaa   240 atgtagcaga aacattaaaa attgaagcat gttctcacag ataataagca ccagtgatat    300
ttttactttt acaataatat tatttgtgga attagtaata ggaattttag gaaatggatt    360
catagcacta gtgaatatca tggactggac caagagaaga agcatttcat cagcggatca    420
```

-continued

```
gattctcact gctttggcca ttaccagatt tctctatgtg tggtttatga tcatttgtat    480
attgttattc atgctgtgcc cacatttgct tacaagatca gaaatagtaa catcaattgg    540
tattatttgg atagtgaata accatttcag cgtttggctt gccacatgcc tcggtgtctt    600 ttatttctg aagatagcca attttctaa ctctttgttt ctttacctaa agtggagagt      660
taaaaaagta gttttaatga taatacaggt atcaatgatt ttcttgattt taaacctgtt    720
atctctaagc atgtatgatc agttctcaat tgatgtttat gaaggaaata catcttataa    780
tttaggggat tcaaccccat ttcccacaat ttccttattc atcaattcat caaaagtttt    840
cgtaatcacc aactcatccc atattttctt acccatcaac tccctgttca tgctcatacc    900
cttcacagtg tccctggtag cctttctcat gctcatcttc tcactgtgga agcatcacaa    960
aaagatgcag gtcaatgcca aaccacctag agatgccagc accatggccc acattaaagc    1020
cttgcaaaca gggttctcct tcctgctgct gtatgcagta tacttacttt ttattgtcat    1080
aggaatgttg agcctaggt tgataggagg aaaattaata cttttatttg accacatttc     1140
tggaataggt tttcctataa gccactcatt tgtgctgatt ctgggaaata acaagctgag    1200
acaagccagt ctttcagtgt tgcattgtct gaggtgccga tccaaagata tggacaccat    1260
gggtccataa aaaatttcag aggtcattgg gaaacatttt gagatcttat aggggaaaaa    1320
gaaaatgtgg ggcttcaaag ctggtaggag taatatagag aaggatagga g             1371
```

<210> SEQ ID NO 125
<211> LENGTH: 303
<212> TYPE: PRT
<213> ORGANISM: Mus sp.
<220> FEATURE:
<221> NAME/KEY: MOD_RES
<222> LOCATION: (169)
<223> OTHER INFORMATION: mouse T2R11 (mGR11)
<223> OTHER INFORMATION: Xaa = any amino acid

<400> SEQUENCE: 125

```
Met Glu His Pro Leu Arg Arg Thr Phe Asp Phe Ser Gln Ser Ile Leu
  1               5                  10                  15

Leu Thr Ile Leu Phe Ile Glu Leu Ile Ile Gly Leu Ile Arg Asn Gly
             20                  25                  30

Leu Met Val Leu Val His Cys Ile Asp Trp Val Lys Arg Lys Lys Phe
         35                  40                  45

His Leu Leu Ile Lys Ser Ser Pro Leu Trp Gln Thr Ser Arg Ile Cys
     50                  55                  60

Leu Leu Trp Phe Met Leu Ile His Leu Leu Ile Thr Leu Leu Tyr Ala
 65                  70                  75                  80

Asp Leu Ala Ser Thr Arg Thr Met Met Gln Phe Ala Ser Asn Pro Trp
                 85                  90                  95

Thr Ile Ser Asn His Ile Ser Ile Trp Leu Ala Thr Cys Leu Gly Val
            100                 105                 110

Phe Tyr Phe Leu Lys Ile Ala Asn Phe Ser Asn Ser Thr Phe Leu Tyr
        115                 120                 125

Leu Lys Trp Arg Val Gln Phe Leu Leu Leu Asn Ile Leu Val Lys
    130                 135                 140

Phe Glu Ile Asn Met Trp Ile Asn Glu Tyr His Gln Ile Asn Ile Pro
145                 150                 155                 160

Tyr Ser Phe Ile Ser Tyr Tyr Gln Xaa Cys Gln Ile Gln Val Leu Ser
                165                 170                 175

Leu His Ile Ile Phe Leu Ser Val Pro Phe Ile Leu Ser Leu Ser Thr
```

-continued

```
                    180                 185                 190
Phe Leu Leu Leu Ile Phe Ser Leu Trp Thr Leu His Gln Arg Met Gln
            195                 200                 205

Gln His Val Gln Gly Tyr Arg Asp Ala Ser Thr Met Ala His Phe Lys
    210                 215                 220

Ala Leu Gln Ala Val Ile Ala Phe Leu Leu Ile His Ser Ile Phe Ile
225                 230                 235                 240

Leu Ser Leu Leu Leu Gln Leu Trp Lys His Glu Leu Arg Lys Lys Pro
                245                 250                 255

Pro Phe Val Val Phe Cys Gln Val Ala Tyr Ile Ala Phe Pro Ser Ser
            260                 265                 270

His Ser Tyr Val Phe Ile Leu Gly Asp Arg Lys Leu Arg Gln Ala Cys
        275                 280                 285

Leu Ser Val Leu Trp Arg Leu Lys Cys Arg Pro Asn Tyr Val Gly
    290                 295                 300
```

<210> SEQ ID NO 126
<211> LENGTH: 1108
<212> TYPE: DNA
<213> ORGANISM: Mus sp.
<220> FEATURE:
<223> OTHER INFORMATION: mouse T2R11 (mGR11)

<400> SEQUENCE: 126

```
aataatgtat gtggaagagt taagtataaa tgttgtatga gaatgaactc agaaatcatc      60
aaaaatcttt aaaactgcat gttaaaaatc acacttcaaa tgaatatatt tgtaattctt     120
tagaactaat aaataaaatg gagcatcctt tgaggagaac atttgatttc tcccagagca     180
tacttctaac cattttattc attgaattaa taattggact tataagaaat ggattaatgg     240
tattggtgca ctgcatagat tgggttaaga gaaaaaaatt tcatttgtta atcaaatcct     300
caccactttg gcaaacttcc agaatttgtc tgctctggtt catgctaata catctcctga     360
ttactttatt gtatgcagat ttagctagta ctagaacgat gatgcaattc gctagcaatc     420
catggactat atctaaccat atcagcatct ggcttgctac atgccttggt gtctttattt     480
ttctcaagat agccaattt tctaactcta cttttctcta tctaaaatgg cgagttcagt     540
tcctcttgtt aaatatttta ctggttaaat ttgagattaa catgtggata aatgaatatc     600
atcaaataaa cataccatac agcttcattt cttattacca aattgtcaaa tacaggtgtt     660
aagtcttcac attattttcc tgtctgtccc ctttatttg tccctgtcaa cttttctcct     720
gctcatcttc tccctgtgga cacttcacca gaggatgcag cagcatgttc aaggatacag     780
agatgccagc acaatggccc acttcaaagc cttgcaagca gtgattgcct ttctcttaat     840
acactccatt tttatcctgt cactgttact acaactttgg aaacatgaat taaggaagaa     900
acctcctttt gttgtatttt gtcaggttgc atatatagct tttccttcat cccattcata     960
tgtcttcatt ctgggagaca gaaagctgag acaggcttgt ctctctgtgt tgtggaggct    1020
gaaatgcagg ccaaattatg tgggataaaa tctctttgtg ctttcatttc caattcttaa    1080
atattctttg attttgactg cataaatt                                       1108
```

<210> SEQ ID NO 127
<211> LENGTH: 150
<212> TYPE: PRT
<213> ORGANISM: Mus sp.
<220> FEATURE:
<223> OTHER INFORMATION: mouse T2R12 (mGR12)

-continued

<400> SEQUENCE: 127

| Gly | Ala | Ile | Val | Asn | Val | Asp | Phe | Leu | Ile | Gly | Asn | Val | Gly | Asn | Gly |
| 1 | | | | 5 | | | | | 10 | | | | | 15 | |

| Phe | Ile | Val | Val | Ala | Asn | Ile | Met | Asp | Leu | Val | Lys | Arg | Arg | Lys | Leu |
| | | | 20 | | | | | 25 | | | | | 30 | | |

| Ser | Ser | Val | Asp | Gln | Leu | Leu | Thr | Ala | Leu | Ala | Val | Ser | Arg | Ile | Thr |
| | | 35 | | | | | 40 | | | | | 45 | | | |

| Leu | Leu | Trp | Tyr | Leu | Tyr | Ile | Met | Lys | Arg | Thr | Phe | Leu | Val | Asp | Pro |
| | 50 | | | | | 55 | | | | | 60 | | | | |

| Asn | Ile | Gly | Ala | Ile | Met | Gln | Ser | Thr | Arg | Leu | Thr | Asn | Val | Ile | Trp |
| 65 | | | | | 70 | | | | | 75 | | | | | 80 |

| Ile | Ile | Ser | Asn | His | Phe | Ser | Ile | Trp | Leu | Ala | Thr | Thr | Leu | Ser | Ile |
| | | | | 85 | | | | | 90 | | | | | 95 | |

| Phe | Tyr | Phe | Leu | Lys | Ile | Ala | Asn | Phe | Ser | Asn | Ser | Ile | Phe | Cys | Tyr |
| | | | 100 | | | | | 105 | | | | | 110 | | |

| Leu | Arg | Trp | Arg | Phe | Glu | Lys | Val | Ile | Leu | Met | Ala | Leu | Leu | Val | Ser |
| | | | 115 | | | | | 120 | | | | | 125 | | |

| Leu | Val | Leu | Leu | Phe | Ile | Asp | Ile | Leu | Val | Thr | Asn | Met | Tyr | Ile | Asn |
| | 130 | | | | | 135 | | | | | 140 | | | | |

| Ile | Trp | Thr | Asp | Glu | Phe |
| 145 | | | | | 150 |

<210> SEQ ID NO 128
<211> LENGTH: 520
<212> TYPE: DNA
<213> ORGANISM: Mus sp.
<220> FEATURE:
<223> OTHER INFORMATION: mouse T2R12 (mGR12)

<400> SEQUENCE: 128

```
ttttcagcag tgactttggg aagcagaacg tcctcttaga dacagtgggt gctgctatcc      60
tagttaatgt ggagcaatag ttaatgtgga tttcctaatt ggaaatgttg ggaatggatt     120
cattgttgtg gcaaacataa tggacttggt caagagaaga aagctttctt cagtggatca     180
gctgctcact gcactggccg tctccagaat cactttgctg tggtacctgt acataatgaa     240
acgaacattt ttagtggatc caaacattgg tgcaattatg caatcaacaa gactgactaa     300
tgttatctgg ataatttcta accattttag tatatggctg gccaccaccc tcagcatctt     360
ttattttctc aagatagcaa attttttctaa ctctattttc tgttacctga ggtggagatt     420
tgaaaaggtg attttgatgg cattgctggt gtccctggtc ctcttgttta tagatatttt     480
agtaacaaac atgtacatta atatttggac tgatgaattc                           520
```

<210> SEQ ID NO 129
<211> LENGTH: 309
<212> TYPE: PRT
<213> ORGANISM: Mus sp.
<220> FEATURE:
<223> OTHER INFORMATION: mouse T2R13 (mGR13)

<400> SEQUENCE: 129

| Met | Val | Ala | Val | Leu | Gln | Ser | Thr | Leu | Pro | Ile | Ile | Phe | Ser | Met | Glu |
| 1 | | | | 5 | | | | | 10 | | | | | 15 | |

| Phe | Ile | Met | Gly | Thr | Leu | Gly | Asn | Gly | Phe | Ile | Phe | Leu | Ile | Val | Cys |
| | | | 20 | | | | | 25 | | | | | 30 | | |

| Ile | Asp | Trp | Val | Gln | Arg | Arg | Lys | Ile | Ser | Leu | Val | Asp | Gln | Ile | Arg |
| | | 35 | | | | | 40 | | | | | 45 | | | |

Thr Ala Leu Ala Ile Ser Arg Ile Ala Leu Ile Trp Leu Ile Phe Leu
    50                  55                  60

Asp Trp Trp Val Ser Val His Tyr Pro Ala Leu His Glu Thr Gly Lys
65                  70                  75                  80

Met Leu Ser Thr Tyr Leu Ile Ser Trp Thr Val Ile Asn His Cys Asn
                85                  90                  95

Phe Trp Leu Thr Ala Asn Leu Ser Ile Leu Tyr Phe Leu Lys Ile Ala
            100                 105                 110

Asn Phe Ser Asn Ile Ile Phe Leu Tyr Leu Lys Phe Arg Ser Lys Asn
        115                 120                 125

Val Val Leu Val Thr Leu Leu Val Ser Leu Phe Leu Phe Leu Asn
    130                 135                 140

Thr Val Ile Ile Lys Ile Phe Ser Asp Val Cys Phe Asp Ser Val Gln
145                 150                 155                 160

Arg Asn Val Ser Gln Ile Phe Ile Met Tyr Asn His Glu Gln Ile Cys
                165                 170                 175

Lys Phe Leu Ser Phe Thr Asn Pro Met Phe Thr Phe Ile Pro Phe Val
            180                 185                 190

Met Ser Thr Val Met Phe Ser Leu Leu Ile Phe Ser Leu Trp Arg His
        195                 200                 205

Leu Lys Asn Met Gln His Thr Ala Lys Gly Cys Arg Asp Ile Ser Thr
    210                 215                 220

Thr Val His Ile Arg Ala Leu Gln Thr Ile Ile Val Ser Val Val Leu
225                 230                 235                 240

Tyr Thr Ile Phe Phe Leu Ser Phe Phe Val Lys Val Trp Ser Phe Val
                245                 250                 255

Ser Pro Glu Arg Tyr Leu Ile Phe Leu Phe Val Trp Ala Leu Gly Asn
            260                 265                 270

Ala Val Phe Ser Ala His Pro Phe Val Met Ile Leu Val Asn Arg Arg
        275                 280                 285

Leu Arg Leu Ala Ser Leu Ser Leu Ile Phe Trp Leu Trp Tyr Arg Phe
    290                 295                 300

Lys Asn Ile Glu Val
305

<210> SEQ ID NO 130
<211> LENGTH: 1199
<212> TYPE: DNA
<213> ORGANISM: Mus sp.
<220> FEATURE:
<223> OTHER INFORMATION: mouse T2R13 (mGR13)

<400> SEQUENCE: 130
aagcttgttt gtgtttggat gaattctatt tatgtctatc aatttaagat tttcatatga      60
atcattaaga atcttgata gttgtttgtg agatatcact tctgcaattt ttaaatgaaa     120
ttacactcat attttgaagg aacaatatgt tttaaaggaa tatattaaca aatcttcagc     180
agttacctca gaagtttggg tattgtttta cagaaaatgg tggcagttct acagagcaca     240
cttccaataa ttttcagtat ggaattcata atgggaacct taggaaatgg attcattttt     300
ctgatagtct gcatagactg ggtccaaaga agaaaaatct ctttagtgga tcaaatccgc     360
actgctctgg caattagcag aatcgctcta atttggttga tattcctaga ttggtgggtg     420
tctgttcatt acccagcatt acatgaaact ggtaagatgt tatcaacata tttgatttcc     480
tggacggtga tcaatcattg taacttttgg cttactgcaa acttgagcat cctttatttt     540

-continued

```
ctcaagatag ccaacttttc taacattatt tttctttatc taaagtttag atctaaaaat    600
gtggtattag tgaccctgtt agtgtctcta tttttcttgt tcttaaatac tgtaattata    660
aaaatatttt ctgatgtgtg ttttgatagt gttcaaagaa atgtgtctca aattttcata    720
atgtataacc atgaacaaat ttgtaaattt cttttccttta ctaaccctat gttcacattc    780
ataccttttg ttatgtccac ggtaatgttt tctttgctca tcttctccct gtggagacat    840
ctgaagaata tgcagcacac cgccaaagga tgcagagaca tcagcaccac agtgcacatc    900
agagccctgc aaaccatcat tgtgtctgta gtgctataca ctattttttt tctatcattt    960
tttgttaaag tttggagttt tgtgtcacca gagagatacc tgatcttttt gtttgtctgg   1020
gctctgggaa atgctgtttt ttctgctcac ccatttgtca tgattttggt aaacagaaga   1080
ttgagattgg cttctctctc tctgattttt tggctctggt acaggtttaa aaatatagaa   1140
gtatagggtc caaagaccac caaggaatca ttttccttat cctaaagaaa aatcaggag    1199
```

<210> SEQ ID NO 131
<211> LENGTH: 309
<212> TYPE: PRT
<213> ORGANISM: Mus sp.
<220> FEATURE:
<223> OTHER INFORMATION: mouse T2R14 (mGR14)

<400> SEQUENCE: 131

```
Met Leu Ser Thr Met Glu Gly Val Leu Leu Ser Val Ser Thr Ser Glu
  1               5                  10                  15

Ala Val Leu Gly Ile Val Gly Asn Thr Phe Ile Ala Leu Val Asn Cys
             20                  25                  30

Met Asp Tyr Asn Arg Asn Lys Lys Leu Ser Asn Ile Gly Phe Ile Leu
         35                  40                  45

Thr Gly Leu Ala Ile Ser Arg Ile Cys Leu Val Leu Ile Leu Ile Thr
     50                  55                  60

Glu Ala Tyr Ile Lys Ile Phe Tyr Pro Gln Leu Ser Pro Val Asn
 65                  70                  75                  80

Ile Ile Glu Leu Ile Ser Tyr Leu Trp Ile Ile Cys Gln Leu Asn
                 85                  90                  95

Val Trp Phe Ala Thr Ser Leu Ser Ile Phe Tyr Phe Lys Ile Ala
            100                 105                 110

Asn Phe Ser His Tyr Ile Phe Val Trp Leu Lys Arg Ile Asp Leu
        115                 120                 125

Val Phe Phe Leu Ile Gly Cys Leu Leu Ile Ser Trp Leu Phe Ser
    130                 135                 140

Phe Pro Val Val Ala Lys Met Val Lys Asp Asn Lys Met Leu Tyr Ile
145                 150                 155                 160

Asn Thr Ser Trp Gln Ile His Met Lys Lys Ser Glu Leu Ile Ile Asn
                165                 170                 175

Tyr Val Phe Thr Asn Gly Gly Val Phe Leu Phe Met Ile Met Leu
            180                 185                 190

Ile Val Cys Phe Leu Leu Ile Ile Ser Leu Trp Arg His Arg Arg Gln
        195                 200                 205

Met Glu Ser Asn Lys Leu Gly Phe Arg Asp Leu Asn Thr Glu Val His
    210                 215                 220

Val Arg Thr Ile Lys Val Leu Leu Ser Phe Ile Ile Leu Phe Ile Leu
225                 230                 235                 240

His Phe Met Gly Ile Thr Ile Asn Val Ile Cys Leu Leu Ile Pro Glu
                245                 250                 255
```

Ser Asn Leu Leu Phe Met Phe Gly Leu Thr Thr Ala Phe Ile Tyr Pro
        260                 265                 270

Gly Cys His Ser Leu Ile Leu Ile Leu Ala Asn Ser Arg Leu Lys Gln
    275                 280                 285

Cys Ser Val Met Ile Leu Gln Leu Leu Lys Cys Cys Glu Asn Gly Lys
    290                 295                 300

Glu Leu Arg Asp Thr
305

<210> SEQ ID NO 132
<211> LENGTH: 1535
<212> TYPE: DNA
<213> ORGANISM: Mus sp.
<220> FEATURE:
<223> OTHER INFORMATION: mouse T2R14 (mGR14)

<400> SEQUENCE: 132

| | | | | | | |
|---|---|---|---|---|---|---|
| ctgcaggtat | atacctaccc | tgaaggcttc | atctagagta | acaaagtag | tctgtatagt | 60 |
| ctgccattcc | tcagattctc | ctcaacttcc | caccctccag | tgacctttct | ccttttctac | 120 |
| agtcaaacta | tggacctcac | aacctgacac | ttcttcagat | gcaaatatt | ctcacagaga | 180 |
| caagtaaaac | atacaaaaca | aatactttaa | tttgcctatt | aacaaatggc | aagaaaagat | 240 |
| tcaggcttga | acatcctgta | gacaagctaa | ggacaggagc | aactgaaggg | atctccatga | 300 |
| agacctttca | gatttctacc | aaaagtaatt | tttaactata | tttaagtctt | taagaaaaga | 360 |
| aagtaaagcc | actcttttat | tgaacagcaa | tagattggaa | tcttaaacaa | ctgcaacaga | 420 |
| agccatttta | aagatcaaca | aagatgctga | gcacaatgga | aggtgtcctc | ctttcagttt | 480 |
| caactagtga | ggctgtgctg | ggcattgtag | ggaacacatt | cattgcactt | gtaaactgta | 540 |
| tggactataa | caggaacaag | aagctctcta | atattggctt | tattctcact | ggcttggcaa | 600 |
| tttccagaat | ttgccttgtg | ttgatcttaa | tcacagaggc | atacataaaa | atattctatc | 660 |
| cacagttgct | gtctcctgtc | aacataattg | agctcatcag | ttatctatgg | ataattatct | 720 |
| gtcaattgaa | tgtctggttt | gccactagtc | tcagtatttt | ttatttcctg | aagatagcaa | 780 |
| atttttccca | ctacatattt | gtctggttaa | aagaagaat | tgatttagtt | ttttttcttcc | 840 |
| tgatagggtg | cttgcttatc | tcatggctat | tttctttccc | agttgttgcg | aagatggtta | 900 |
| aagataataa | aatgctgtat | ataaacacat | cttggcagat | ccacatgaag | aaaagtgagt | 960 |
| taatcattaa | ctatgttttc | accaatgggg | gagtattttt | attttttatg | ataatgttaa | 1020 |
| ttgtatgttt | cctgttaatc | atttcacttt | ggagacatcg | caggcagatg | gaatcaaata | 1080 |
| aattaggatt | cagagatctc | aacacagaag | ttcatgtgag | aacaataaaa | gttttattgt | 1140 |
| cttttattat | ccttttttata | ttgcatttca | tgggtattac | cataaatgta | atttgtctgt | 1200 |
| taatcccaga | aagcaacttg | ttattcatgt | ttggtttgac | aactgcattc | atctatcccg | 1260 |
| gctgccactc | acttatccta | attctagcaa | acagtcggct | gaagcagtgc | tctgtaatga | 1320 |
| tactgcaact | attaaagtgc | tgtgagaatg | gtaaagaact | cagagacaca | tgacagtctg | 1380 |
| gaacacatgc | aatctggaat | tgtcagtgga | aaaagttact | gaagatcttt | tcacttgcac | 1440 |
| tatgctcttt | tattgatttg | gcatcattat | caaacactgt | tggagccttg | tgaactcttg | 1500 |
| ttcagagtct | tctgcctctc | aaggaatcac | actcc | | | 1535 |

<210> SEQ ID NO 133
<211> LENGTH: 310
<212> TYPE: PRT

<213> ORGANISM: Mus sp.
<220> FEATURE:
<223> OTHER INFORMATION: mouse T2R15 (mGR15)

<400> SEQUENCE: 133

| | | | | | | | | | | | | | | |
|---|---|---|---|---|---|---|---|---|---|---|---|---|---|---|
| Met | Cys | Ala | Val | Leu | Arg | Ser | Ile | Leu | Thr | Ile | Ile | Phe | Ile | Leu | Glu |
| 1 | | | | 5 | | | | | 10 | | | | | 15 | |
| Phe | Phe | Ile | Gly | Asn | Leu | Gly | Asn | Gly | Phe | Ile | Ala | Leu | Val | Gln | Cys |
| | | | 20 | | | | | 25 | | | | | 30 | | |
| Met | Asp | Leu | Arg | Lys | Arg | Arg | Thr | Phe | Pro | Ser | Ala | Asp | His | Phe | Leu |
| | | 35 | | | | | 40 | | | | | 45 | | | |
| Thr | Ala | Leu | Ala | Ile | Ser | Arg | Leu | Ala | Leu | Ile | Trp | Val | Leu | Phe | Leu |
| | 50 | | | | | 55 | | | | | 60 | | | | |
| Asp | Ser | Phe | Leu | Phe | Ile | Gln | Ser | Pro | Leu | Leu | Met | Thr | Arg | Asn | Thr |
| 65 | | | | | 70 | | | | | 75 | | | | | 80 |
| Leu | Arg | Leu | Ile | Gln | Thr | Ala | Trp | Asn | Ile | Ser | Asn | His | Phe | Ser | Ile |
| | | | | 85 | | | | | 90 | | | | | 95 | |
| Trp | Phe | Ala | Thr | Ser | Leu | Ser | Ile | Phe | Tyr | Leu | Phe | Lys | Ile | Ala | Ile |
| | | | 100 | | | | | 105 | | | | | 110 | | |
| Phe | Ser | Asn | Tyr | Leu | Phe | Phe | Tyr | Leu | Lys | Arg | Arg | Val | Lys | Arg | Val |
| | | | 115 | | | | | 120 | | | | | 125 | | |
| Val | Leu | Val | Ile | Leu | Leu | Ser | Met | Ile | Leu | Leu | Phe | Phe | Asn | Ile |
| | 130 | | | | | 135 | | | | | 140 | | | | |
| Phe | Leu | Glu | Ile | Lys | His | Ile | Asp | Val | Trp | Ile | Tyr | Gly | Thr | Lys | Arg |
| 145 | | | | | 150 | | | | | 155 | | | | | 160 |
| Asn | Ile | Thr | Asn | Gly | Leu | Ser | Ser | Asn | Ser | Phe | Ser | Glu | Phe | Ser | Arg |
| | | | | 165 | | | | | 170 | | | | | 175 | |
| Leu | Ile | Leu | Ile | Pro | Ser | Leu | Met | Phe | Thr | Leu | Val | Pro | Phe | Gly | Val |
| | | | 180 | | | | | 185 | | | | | 190 | | |
| Ser | Leu | Ile | Ala | Phe | Leu | Leu | Ile | Phe | Ser | Leu | Met | Lys | His | Val |
| | 195 | | | | | 200 | | | | | 205 | | | | |
| Arg | Lys | Met | Gln | Tyr | Tyr | Thr | Lys | Gly | Cys | Lys | Asp | Val | Arg | Thr | Met |
| | 210 | | | | | 215 | | | | | 220 | | | | |
| Ala | His | Thr | Thr | Ala | Leu | Gln | Thr | Val | Val | Ala | Phe | Leu | Leu | Leu | Tyr |
| 225 | | | | | 230 | | | | | 235 | | | | | 240 |
| Thr | Thr | Phe | Phe | Leu | Ser | Leu | Val | Val | Glu | Val | Ser | Thr | Leu | Glu | Met |
| | | | | 245 | | | | | 250 | | | | | 255 | |
| Asp | Glu | Ser | Leu | Met | Leu | Leu | Phe | Ala | Lys | Val | Thr | Ile | Met | Ile | Phe |
| | | | 260 | | | | | 265 | | | | | 270 | | |
| Pro | Ser | Ile | His | Ser | Cys | Ile | Phe | Ile | Leu | Lys | His | Asn | Lys | Leu | Arg |
| | | 275 | | | | | 280 | | | | | 285 | | | |
| Gln | Asp | Leu | Leu | Ser | Val | Leu | Lys | Trp | Leu | Gln | Tyr | Trp | Cys | Lys | Arg |
| | 290 | | | | | 295 | | | | | 300 | | | | |
| Glu | Lys | Thr | Leu | Asp | Ser |
| 305 | | | | | 310 |

<210> SEQ ID NO 134
<211> LENGTH: 1482
<212> TYPE: DNA
<213> ORGANISM: Mus sp.
<220> FEATURE:
<223> OTHER INFORMATION: mouse T2R15 (mGR15)

<400> SEQUENCE: 134

```
aataatagat ttttaatat tcagaatttt taagtaatgt agtattgtta gcagcatagc    60
ttataggaaa agttccaagt aatttgatt ttgtaattct gattccccca aatcaagtat   120
```

```
caagtttacc tgcacagaca agggaagaag tggcaaaatg tgcaaatgag agcaacttta    180
tttgactgtc agtacgttga aattcagtgt tccttaatc agttatggat tgacatttat     240
gtgcacagaa cctggaagaa tttcagccaa gctggaggta aaaatccaaa attctgatga   300
taaaaccaaa agtaaatcac aggtaaatct tctttatttt tctttttaa tactgtatat    360
ggacatttt taatacagca tatttttttt ttgaaattta gaaaaaaacc actaagaaat    420
attccaccaat ggaatagact ttaaagtcac ttagagaatg tgtgctgttc tacgtagcat  480
actgacaatc atttcattt tggagttctt cattggaaat ctggggaatg gattcatagc    540
tctggtacaa tgcatggact tacgaaagag aagaacgttc ccttcagcag atcatttcct   600
cactgctctg gccatctcca ggcttgctct gatatgggtt ttatttctag attcatttct  660
gtttatacaa tccccattac tgatgactag aaatacatta agactgattc agactgcctg   720
gaatataagc aatcatttca gtatatggtt tgctaccagc ctcagcatct tttatctctt   780
caagatagcc attttttcta actatctttt cttctacctg aagcggagag ttaaaagggg   840
ggttttggtg atactgctgc tatccatgat ccttttgttt tttaatatat ttttagaaat  900
caaacatatt gatgtctgga tctatggaac caaaagaaac ataactaatg gtttgagttc   960
aaacagtttt tcagagtttt ccaggcttat tttaattcca agtttaatgt tcacattagt  1020
acccttggt gtatccttga tagctttcct cctcctaatc ttttccctta tgaaacatgt   1080
aaggaagatg cagtactaca ccaaaggat caaagatgtc agaaccatgg cccacaccac    1140
agccctgcag actgtggttg ccttcctcct attatatact actttctttc tgtctctagt   1200
tgtggaagtt tcaacacttg aaatggatga agtctgatg cttctgtttg caaaagttac    1260
tataatgatt tttccttcca tccactcctg tattttcatt ttgaaacata ataagttgag   1320
acaggacttg ctttcagtac tgaagtggct acagtattgg tgcaagcgtg agaaaacctt   1380
ggattcatag accattgtat gcatcacctt gaatattcta gaggggtgta ggttcatatg   1440
aaagtattga atttttaaat ttgagccttt tgtatatttt ct                      1482
```

<210> SEQ ID NO 135
<211> LENGTH: 305
<212> TYPE: PRT
<213> ORGANISM: Mus sp.
<220> FEATURE:
<223> OTHER INFORMATION: mouse T2R16 (mGR16)

<400> SEQUENCE: 135

Met Asn Gly Val Leu Gln Val Thr Phe Ile Val Ile Leu Ser Val Glu
1               5                   10                  15

Phe Ile Ile Gly Ile Phe Gly Asn Gly Phe Ile Ala Val Val Asn Ile
            20                  25                  30

Lys Asp Leu Val Lys Gly Arg Lys Ile Ser Ser Val Asp Gln Ile Leu
        35                  40                  45

Thr Ala Leu Ala Ile Ser Arg Ile Ala Leu Leu Trp Leu Ile Leu Val
    50                  55                  60

Ser Trp Trp Ile Phe Val Leu Tyr Pro Gly Gln Trp Met Thr Asp Arg
65                  70                  75                  80

Arg Val Ser Ile Met His Ser Ile Trp Thr Thr Phe Asn Gln Ser Ser
                85                  90                  95

Leu Trp Phe Ala Thr Ser Leu Ser Ile Phe Tyr Phe Lys Ile Ala
            100                 105                 110

Asn Phe Ser Asn Pro Ile Phe Leu Tyr Leu Lys Val Arg Leu Lys Lys

```
                    115                 120                 125
Val Met Ile Gly Thr Leu Ile Met Ser Leu Ile Leu Phe Cys Leu Asn
        130                 135                 140

Ile Ile Ile Met Asn Ala Pro Glu Asn Ile Leu Ile Thr Glu Tyr Asn
145                 150                 155                 160

Val Ser Met Ser Tyr Ser Leu Ile Leu Asn Asn Thr Gln Leu Ser Met
                165                 170                 175

Leu Phe Pro Phe Ala Asn Thr Met Phe Gly Phe Ile Pro Phe Ala Val
            180                 185                 190

Ser Leu Val Thr Phe Val Leu Val Phe Ser Leu Trp Lys His Gln
        195                 200                 205

Arg Lys Met Gln His Ser Ala His Gly Cys Arg Asp Ala Ser Thr Lys
    210                 215                 220

Ala His Ile Arg Ala Leu Gln Thr Leu Ile Ala Ser Leu Leu Leu Tyr
225                 230                 235                 240

Ser Ile Phe Phe Leu Ser His Val Met Lys Val Trp Ser Ala Leu Leu
                245                 250                 255

Leu Glu Arg Thr Leu Leu Leu Ile Thr Gln Val Ala Arg Thr Ala
            260                 265                 270

Phe Pro Ser Val His Ser Trp Val Leu Ile Leu Gly Asn Ala Lys Met
        275                 280                 285

Arg Lys Ala Ser Leu Tyr Val Phe Leu Trp Leu Arg Cys Arg His Lys
    290                 295                 300

Glu
305

<210> SEQ ID NO 136
<211> LENGTH: 1316
<212> TYPE: DNA
<213> ORGANISM: Mus sp.
<220> FEATURE:
<223> OTHER INFORMATION: mouse T2R16 (mGR16)

<400> SEQUENCE: 136
tttatgatgg aaagaataaa accattagca aggcttaatg gcttgtttgg tattagacct      60
gtacattgtt tatggaacat gatatggagc tttgtttatt gaatatgcac aatattttag     120
aagcatgttt caaagaatct taagtaatta caatagaaat tgaagcatcc aagtgaagat     180
gaatggtgtc ctacaggtta catttatagt cattttgagt gtggaattta taattggcat     240
ctttggcaat ggattcatag cggtggtgaa cataaaggac ttggtcaagg aaggaagat      300 ctcttcagtg gatcagatcc tcactgctct ggccatctcc agaattgcac tgctgtggtt     360
aatattagta agttggtgga tatttgtgct ttacccagga caatggatga ctgatagaag     420
agttagcata atgcacagta tatggacaac attcaaccag gtagtctct ggtttgctac      480 aagtctcagc atcttttatt ttttcaagat agcaaatttt tccaacccta ttttctttta    540
tttaaaggtc agacttaaaa aagtcatgat agggacattg ataatgtctt tgattctctt     600
ttgtttaaat attatcatta tgaatgcacc tgagaacatt ttaatcactg aatataatgt     660
atctatgtct tacagcttga ttttgaataa cacacagctt tctatgctgt tccatttgc     720 caacaccatg tttgggttca taccttttgc tgtgtcactg gtcacttttg tccttccttg     780
tttctcccct ggaaacatca gagaaagat gcaacacagt gcccatggat gcagagatgc      840
cagcactaag gcccacatca gagccttgca gacattgatt gcctccctcc tcctgtattc     900
cattttcttc ctgtctcatg ttatgaaggt ttggagtgct ctgcttctgg agaggacact     960
```

-continued

```
cctgcttttg atcacacagg ttgcaagaac agcttttccg tcagtgcact cctgggtcct    1020
gattctgggc aatgctaaga tgagaaaggc ttctctctat gtattcctgt ggctgaggtg    1080
caggcacaaa gaatgaaacc ctacagtgta cagacctggg gtatatttat gtggatgatc    1140
ttacatatct tagaggaaaa tggattaaaa gaaattctca tatttataaa ttttaggtc     1200 tgaattacat aaaaatgtat ataatatttt caaagtacaa gatagtagtt tataacttac    1260
atgataaata ctgtctatgc atcttctagt ctttgtagaa tatgtaaaaa catgtt        1316
```

<210> SEQ ID NO 137
<211> LENGTH: 330
<212> TYPE: PRT
<213> ORGANISM: Mus sp.
<220> FEATURE:
<223> OTHER INFORMATION: mouse T2R17 (mGR17)

<400> SEQUENCE: 137

```
Met Lys His Phe Trp Lys Ile Leu Ser Val Ile Ser Gln Ser Thr Leu
  1               5                  10                  15

Ser Val Ile Leu Ile Val Glu Leu Val Ile Gly Ile Ile Gly Asn Gly
             20                  25                  30

Phe Met Val Leu Val His Cys Met Asp Trp Val Lys Lys Lys Lys Met
         35                  40                  45

Ser Leu Val Asn Gln Ile Leu Thr Ala Leu Ser Ile Ser Arg Ile Phe
     50                  55                  60

Gln Leu Cys Leu Leu Phe Ile Ser Leu Val Ile Asn Phe Ser Tyr Thr
 65                  70                  75                  80

Asp Leu Thr Thr Ser Ser Arg Met Ile Gln Val Met Tyr Asn Ala Trp
                 85                  90                  95

Ile Leu Ala Asn His Phe Ser Ile Trp Ile Ala Thr Cys Leu Thr Val
            100                 105                 110

Leu Tyr Phe Leu Lys Ile Ala Asn Phe Ser Asn Ser Phe Phe Leu Tyr
        115                 120                 125

Leu Lys Trp Arg Val Glu Lys Val Val Ser Val Thr Leu Leu Val Ser
    130                 135                 140

Leu Leu Leu Leu Ile Leu Asn Ile Leu Leu Thr Asn Leu Glu Thr Asp
145                 150                 155                 160

Met Trp Thr Asn Glu Tyr Gln Arg Asn Ile Ser Cys Ser Phe Ser Ser
                165                 170                 175

His Tyr Tyr Ala Lys Cys His Arg Gln Val Leu Arg Leu His Ile Ile
            180                 185                 190

Phe Leu Ser Val Pro Val Val Leu Ser Leu Ser Thr Phe Leu Leu Leu
        195                 200                 205

Ile Phe Ser Leu Trp Thr His His Lys Arg Met Gln Gln His Val Gln
    210                 215                 220

Gly Gly Arg Asp Ala Arg Thr Thr Ala His Phe Lys Ala Leu Gln Thr
225                 230                 235                 240

Val Ile Ala Phe Phe Leu Leu Tyr Ser Ile Phe Ile Leu Ser Val Leu
                245                 250                 255

Ile Gln Ile Trp Lys Tyr Glu Leu Leu Lys Lys Asn Leu Phe Val Val
            260                 265                 270

Phe Cys Glu Val Val Tyr Ile Ala Phe Pro Thr Phe His Ser Tyr Ile
        275                 280                 285

Leu Ile Val Gly Asp Met Lys Leu Arg Gln Ala Cys Leu Pro Leu Cys
    290                 295                 300
```

Ile Ile Ala Ala Glu Ile Gln Thr Thr Leu Cys Arg Asn Phe Arg Ser
305                 310                 315                 320

Leu Lys Tyr Phe Arg Leu Cys Cys Ile Phe
            325                 330

<210> SEQ ID NO 138
<211> LENGTH: 1354
<212> TYPE: DNA
<213> ORGANISM: Mus sp.
<220> FEATURE:
<223> OTHER INFORMATION: mouse T2R17 (mGR17)

<400> SEQUENCE: 138

```
gaattctggt ctggcacccc tgagctgtgt gagtagacac attatcatgg aaagagattc      60
agaatctgtc actgtcaaaa ctgcatgttt gctcctctgt tagtgtgttg gggaaagtta     120
agaaaaatac attttatgag aatcaactca gaggttgtca gaattgtcg  aaacagcatt     180
ttaaaatttt acatctcaac tggatatatg agcaagtctt tataactgat atataaaatg     240
aagcactttt ggaagatatt atctgttatc tcccagagca cactttcagt cattttaatc     300
gtggaattag taattggaat tataggaaat gggttcatgg tcctggtcca ctgtatggac     360
tgggttaaga aaaagaaaat gtccctagtt aatcaaattc ttactgcttt gtcaatctcc     420
agaattttc  agctctgttt attgtttata agtttagtaa tcaactttc  atatacagat     480
ttaactacaa gttcaaggat gatacaagtc atgtacaatg cttggatttt agccaaccat     540
ttcagcatct ggattgctac atgcctcact gtcctttatt ttctaaagat agccaatttt     600
tctaactctt tttttcttta tctaaagtgg agagttgaaa agtagtttc  agttacactg     660
ttggtgtcat tgctcctcct gatttaaat  attttactaa ctaacttgga aaccgacatg     720
tggacaaatg aatatcaaag aaacatatca tgcagcttca gttctcatta ctatgcaaag     780
tgtcacaggc aggtgttaag gcttcacatt attttcctgt ctgtccccgt tgttttgtcc     840
ctgtcaactt ttctcctgct catcttctcc ctgtggacac atcacaagag gatgcagcag     900
catgttcagg gaggcagaga tgccagaacc acggcccact tcaaagccct acaaactgtg     960
attgcatttt tcctactata ttccattttt attctgtctg tcttaataca aatttggaaa    1020
tatgaattac tgaagaaaaa tcttttcgtt gtattttgtg aggttgtata tatagctttt    1080
ccgacattcc attcatatat tctgattgta ggagacatga agctgagaca ggcctgcctg    1140
cctctctgta ttatcgcagc tgaaattcag actacactat gtagaaattt tagatcacta    1200
aagtacttta gattatgttg tatattctag acaaaaatta actgatacaa atgtcttttg    1260
tattttcat  tttaaatatc ctttaatttt gactgcatga aattgatttc tgcttgcaat    1320
tatcactgat taaaactatt aataatttaa ctag                                1354
```

<210> SEQ ID NO 139
<211> LENGTH: 299
<212> TYPE: PRT
<213> ORGANISM: Mus sp.
<220> FEATURE:
<223> OTHER INFORMATION: mouse T2R18 (mGR18)

<400> SEQUENCE: 139

Met Val Pro Thr Gln Val Thr Ile Phe Ser Ile Ile Met Tyr Val Leu
 1               5                  10                  15

Glu Ser Leu Val Ile Ile Val Gln Ser Cys Thr Thr Val Ala Val Leu
            20                  25                  30

```
Phe Arg Glu Trp Met His Phe Gln Arg Leu Ser Pro Val Glu Thr Ile
         35                  40                  45

Leu Ile Ser Leu Gly Ile Ser His Phe Cys Leu Gln Trp Thr Ser Met
 50                  55                  60

Leu Tyr Asn Phe Gly Thr Tyr Ser Arg Pro Val Leu Leu Phe Trp Lys
 65                  70                  75                  80

Val Ser Val Val Trp Glu Phe Met Asn Ile Leu Thr Phe Trp Leu Thr
                 85                  90                  95

Ser Trp Leu Ala Val Leu Tyr Cys Val Lys Val Ser Ser Phe Thr His
            100                 105                 110

Pro Ile Phe Leu Trp Leu Arg Met Lys Ile Leu Lys Leu Val Leu Trp
        115                 120                 125

Leu Ile Leu Gly Ala Leu Ile Ala Ser Cys Leu Ser Ile Ile Pro Ser
130                 135                 140

Val Val Lys Tyr His Ile Gln Met Glu Leu Val Thr Leu Asp Asn Leu
145                 150                 155                 160

Pro Lys Asn Asn Ser Leu Ile Leu Arg Leu Gln Gln Phe Glu Trp Tyr
                165                 170                 175

Phe Ser Asn Pro Leu Lys Met Ile Gly Phe Gly Ile Pro Phe Phe Val
            180                 185                 190

Phe Leu Ala Ser Ile Ile Leu Leu Thr Val Ser Leu Val Gln His Trp
        195                 200                 205

Val Gln Met Lys His Tyr Ser Ser Ser Asn Ser Ser Leu Lys Ala Gln
    210                 215                 220

Phe Thr Val Leu Lys Ser Leu Ala Thr Phe Phe Thr Phe Phe Thr Ser
225                 230                 235                 240

Tyr Phe Leu Thr Ile Val Ile Ser Phe Ile Gly Thr Val Phe Asp Lys
                245                 250                 255

Lys Ser Trp Phe Trp Val Cys Glu Ala Val Ile Tyr Gly Leu Val Cys
            260                 265                 270

Ile His Phe Thr Ser Leu Met Met Ser Asn Pro Ala Leu Lys Lys Ala
        275                 280                 285

Leu Lys Leu Gln Phe Trp Ser Pro Glu Pro Ser
290                 295

<210> SEQ ID NO 140
<211> LENGTH: 2887
<212> TYPE: DNA
<213> ORGANISM: Mus sp.
<220> FEATURE:
<221> NAME/KEY: modified_base
<222> LOCATION: (1083)
<223> OTHER INFORMATION: mouse T2R18 (mGR18)
<223> OTHER INFORMATION: n = g, a, c or t

<400> SEQUENCE: 140
gcgtgcttca cagagcagta tactacaaag caaatgtcat tgctgccatt gtatatttct      60
ctaaagacat ttcacatttt atctccctgt cccattgtgt gcagagccca cacttcaatc    120
aatcaattcc ttaattataa gctattgttt cattatttca tttcctacgt ttttttgcat    180
ttttactaaa actccaaagc agacattttc taattataat cctacatgta gttagaattt    240
taaaaattat atactatttt ctttgcacca ctgagttcag taggttttga aggtttatgc    300
ttaacaattg aacatttcat gttagattat tcctgccttc ctaatcttga ataattaaat    360
gtccatccag gcttagaatt cacagagtca acagctttca ccttgattct ctcactatct    420
atcaatgact agaatctgtc tgtcactttt gaaaccgcta attaaatagt tggtgcttat    480
```

-continued

```
ttaaagggtg ccccatgcca agagaaaatg tatttcttct ctagatgcct tcgtccttta    540
caagttacat gctttactga tggtgaattg gttttcttcc agttcatctg ggttaagtga    600
cctaagaacc tagccatgga aggagaaaca gaagcaaata ttaacgatac aagaacaagt    660
tccagaacat tggaaagtac ttagtaaagg cattggaatt agcaaaagaa tagtagcgaa    720
gcaaaaaata cttcatctcc attgggaggt caagaaagac tatgcagtgt ttttgatgca    780
acttgtcatc tctgagttag acgattcagc acacactttt gagattgaac ttcaacaggt    840
ggagccagca gacctgagct ttaggaatga tggtggaatt tccaagcaaa gacttccgtt    900
acctttttga tgtcccctaa caattcggtt gcaatgctca caccgcccaa ctgttgaaat    960
gcttgggaaa agggattctg agactggcat tagtatgtca tttgacagaa tggaaacatt   1020
gcccagggca ttaatgcaca gtaaaggatt cacctttttct aagtgctcaa atttttaaatt  1080 tgnatatttt tagaagacat tatttaaaag aaaggtggag aggatatcca acagcaccta   1140
tgagcagata aagaggtgaa gaagaaaaaa caacatgcgt acatgatgga tttctcttta   1200
tgaaaatgat caaatgatct taggatcaag aatccacacc tgaatgagat ttgcttgtat   1260
ccctgtgtga atttgaccta acaagcaaag cacagacaaa tgctgtagat agggaaatgt   1320
ctatgtcaaa tgtgtgtaag gaggatttgc atccacaaag aagtgccctc ttatactgag   1380
agtgctaaga acacatgtcc gtttcatatt cggaaagtgg tatagagctg ttgagtcttt   1440
ggctaggaag agacttcaga gtggaagcat ggtgccaacg caagtcacca tcttctccat   1500
catcatgtat gtgcttgagt ccttagtaat aattgtgcaa agttgcacaa cggttgcagt   1560
gctattcaga gagtggatgc actttcaaag actgtcaccg gtggagacga ttctcatcag   1620
cctgggcatc tcacatttct gtctacagtg gacatcaatg ctatacaact ttggtactta   1680
ttctaggcct gtccttttat tttggaaggt atcagtcgtc tgggagttca tgaacatttt   1740
gacattctgg ttaaccagtt ggcttgctgt cctctactgt gtcaaggtct cttccttcac   1800 tcacccccatc ttcctctggc tgaggatgaa atcttgaaa ctggttctct ggttgatact   1860
gggtgctctg atagcttctt gtttgtcaat catcccttct gttgttaaat atcacatcca   1920
gatggaatta gtcaccctag ataatttacc caagaacaat tctttgattc taagactaca   1980
acagtttgaa tggtatttttt ctaatccttt aaaaatgatt ggctttggta ttcctttctt   2040
cgtgttcctg gcttctatca tcttactcac agtctcattg gtccaacact gggtgcagat   2100
gaaacactac agcagcagca actccagcct gaaagctcag ttcactgttc tgaagtctct   2160
tgctaccttc ttcaccttct tcacatccta ttttctgact atagtcatct cctttattgg   2220
cactgtgttt gataagaaat cttggttctg ggtctgcgaa gctgtcatct atggtttagt   2280
ctgtattcac ttcacttcac tgatgatgag caaccctgca ttgaaaaagg cactgaagct   2340
gcagttctgg agcccagagc cttcctgagg caggaaacac agttaagcct ctagggtaag   2400
gagactttgc attggcacag tccctatagt gtaatgcaaa cttgaacaca aacttcatcc   2460
cttttcacat ccacaaatgg ctgcatctat acatcatcac cagtcttccc tgtattctga   2520
cccattctct tcctgtccta tccatagtcc ccaggttggt tttgattttt tcatgatca    2580 caccaactct gcttagcttt tgccaccact gtaaatagtaa acatggggtg ttctatatat   2640
tacagtcaaa atcattctca cattgttgat tgcctcacaa attcatataa atccccctc    2700 ctgtcaggaa tttattgtct gctcacttaa tgctcaccat atattaaagc cattaattcc   2760
cccttcctac cttgagttta agaaggaaaa tgtcttacca ttgcccacaa cctattctgc   2820
```

```
tgcttctaga cttttatgca agtgatttat acacacacac acacacacac acacacatac    2880
aaacaac                                                              2887
```

<210> SEQ ID NO 141
<211> LENGTH: 335
<212> TYPE: PRT
<213> ORGANISM: Mus sp.
<220> FEATURE:
<223> OTHER INFORMATION: mouse T2R19 (mGR19)

<400> SEQUENCE: 141

```
Met Met Glu Gly His Met Leu Phe Phe Leu Leu Val Val Val Gln
 1               5                  10                  15

Phe Leu Thr Gly Val Leu Ala Asn Gly Leu Ile Val Val Asn Ala
                20                  25                  30

Ile Asp Leu Ile Met Trp Lys Lys Met Ala Pro Leu Asp Leu Leu
                35                  40                  45

Phe Cys Leu Ala Thr Ser Arg Ile Ile Leu Gln Leu Cys Ile Leu Phe
 50                  55                      60

Ala Gln Leu Gly Leu Ser Cys Leu Val Arg His Thr Leu Phe Ala Asp
 65                  70                      75                  80

Asn Val Thr Phe Val Tyr Ile Ile Asn Glu Leu Ser Leu Trp Phe Ala
                    85                      90                      95

Thr Trp Leu Gly Val Phe Tyr Cys Ala Lys Ile Ala Thr Ile Pro His
                    100                     105                     110

Pro Leu Phe Leu Trp Leu Lys Met Arg Ile Ser Arg Leu Val Pro Trp
                    115                     120                     125

Leu Ile Leu Ala Ser Val Val Tyr Val Thr Val Thr Thr Phe Ile His
 130                     135                     140

Ser Arg Glu Thr Ser Glu Leu Pro Lys Gln Ile Phe Ile Ser Phe Phe
 145                     150                     155                     160

Ser Lys Asn Thr Thr Arg Val Arg Pro Ala His Ala Thr Leu Leu Ser
                    165                     170                     175

Val Phe Val Phe Gly Leu Thr Leu Pro Phe Leu Ile Phe Thr Val Ala
                    180                     185                     190

Val Leu Leu Leu Ser Ser Leu Trp Asn His Ser Arg Gln Met Arg
                    195                     200                     205

Thr Met Val Gly Thr Arg Glu Pro Ser Arg His Ala Leu Val Ser Ala
 210                     215                     220

Met Leu Ser Ile Leu Ser Phe Leu Ile Leu Tyr Leu Ser His Asp Met
 225                     230                     235                     240

Val Ala Val Leu Ile Cys Thr Gln Gly Leu His Phe Gly Ser Arg Thr
                    245                     250                     255

Phe Ala Phe Cys Leu Leu Val Ile Gly Met Tyr Pro Ser Leu His Ser
                    260                     265                     270

Ile Val Leu Ile Leu Gly Asn Pro Lys Leu Lys Arg Asn Ala Lys Thr
                    275                     280                     285

Phe Ile Val His Cys Lys Cys Cys His Cys Ala Arg Ala Trp Val Thr
                    290                     295                     300

Ser Arg Asn Pro Arg Leu Ser Asp Leu Pro Val Pro Ala Thr His His
 305                     310                     315                     320

Ser Ala Asn Lys Thr Ser Cys Ser Glu Ala Cys Ile Met Pro Ser
                    325                     330                     335
```

<210> SEQ ID NO 142

<211> LENGTH: 1698
<212> TYPE: DNA
<213> ORGANISM: Mus sp.
<220> FEATURE:
<223> OTHER INFORMATION: mouse T2R19 (mGR19)

<400> SEQUENCE: 142

```
ctgcagccta gagaactaat gcataggaaa cttatattcc cacctccgtg acgtcactct      60
gacagaagtg aacttatatt cccacctccg tgacgtcact ctgacagaag tgacttgttt     120
ttgtatgatg ctccaggatg cctcattagc attgaggaca atcataatta agtaaggcaa     180
ggcatgaagg tggtcctcac taggtacctg gaggcttctg gttgcatgat ttacttgtga     240
tgactctgac acttaagaag acctgaaaaa tgcaaaagct gtcataaggc acagttcgtt     300
tctatggtat ctcttcctta tttgactgac attgagttga aaggcagca  ctataaacaa     360
atgggcccca ccttcctctt ccattgtctt tgggttggca tcatctccaa aggaaccttg     420
gtctagttga aagaagccag aaatcataca tggctgagac tgtgcataac tctatgtatc     480
atttaaagaa gtcattggtt cttcttattt taaaatgatg aaggtcata  tgctcttctt     540
ccttctggtc gtggtagtgc agttttaac tggggtcttg gcaaatggcc tcattgtggt      600
tgtcaatgcc atcgacttga tcatgtggaa gaaaatggcc ccactggatc tgcttctttt     660
ttgcctggcg acttctcgga tcattcttca attgtgtata ttgtttgcac agctgggtct     720
atcctgtttg gtgagacaca cgttatttgc tgacaatgtt acctttgtct acattataaa     780
cgaactgagt ctctggtttg ccacatggct tggtgtttc  tactgtgcca agattgctac     840
catccctcac ccactctttc tgtggctgaa gatgaggata tccaggttgg tgccatggct     900
gatcctggca tctgtggtct atgtaactgt tactactttc atccatagca gagagacttc     960
agaacttcct aagcaaatct ttataagctt ttttttctaaa atacaactc  gggtcagacc    1020
agcgcatgcc acactactct cagtctttgt ctttgggctc acactaccat ttctcatctt    1080
cactgttgct gttctgctct tgttgtcctc cctgtggaac cacagccggc agatgaggac    1140
tatggtggga actagggaac ctagcagaca tgccctcgtc agtgcgatgc tctccattct    1200
gtcattcctc atcctctatc tctcccatga catggtagct gttctgatct gtacccaagg    1260
cctccacttt ggaagcagaa cctttgcatt ctgcttattg gttattggta tgtacccctc    1320
cttacactcg attgtcttaa ttttaggaaa ccctaagctg aaacgaaatg caaaaacgtt    1380
cattgtccat tgtaagtgtt gtcattgtgc aagagcttgg gtcacctcaa ggaacccaag    1440
actcagcgac ttgccagtgc ctgctactca tcactcagcc aacaagacat cctgctcaga    1500
agcctgtata atgccatctt aattgtccaa cctgaggctt aatcatttca aagggtaaat    1560
tgatgatcaa agcccaacac atgatatgac atcaaggtcc atatcccagt agtcatgtgg    1620
aaataccacc ttgcaaaatg atgtcattga gaaccaggg  caaatggagt ctaggtcttt    1680
cagtatgatt tgctgcag                                                   1698
```

<210> SEQ ID NO 143
<211> LENGTH: 295
<212> TYPE: PRT
<213> ORGANISM: Mus sp.
<220> FEATURE:
<223> OTHER INFORMATION: mouse T2R20 (mGR20)

<400> SEQUENCE: 143

Met Asn Leu Val Glu Trp Ile Val Thr Ile Ile Met Met Thr Glu Phe
1               5                   10                  15

```
Leu Leu Gly Asn Cys Ala Asn Val Phe Ile Thr Ile Val Asn Phe Ile
         20                  25                  30

Asp Cys Val Lys Arg Lys Ile Ser Ser Ala Asp Arg Ile Ile Thr
     35                  40                  45

Ala Ile Ala Ile Phe Arg Ile Gly Leu Leu Trp Ala Met Leu Thr Asn
 50                  55                  60

Trp His Ser His Val Phe Thr Pro Asp Thr Asp Asn Leu Gln Met Arg
 65                  70                  75                  80

Val Phe Gly Gly Ile Thr Trp Ala Ile Thr Asn His Phe Thr Thr Trp
                 85                  90                  95

Leu Gly Thr Ile Leu Ser Met Phe Tyr Leu Phe Lys Ile Ala Asn Phe
             100                 105                 110

Ser Asn Ser Leu Phe Leu His Leu Lys Arg Lys Leu Asp Asn Val Leu
         115                 120                 125

Leu Val Ile Phe Leu Gly Ser Ser Leu Phe Leu Val Ala Tyr Leu Gly
 130                 135                 140

Met Val Asn Ile Lys Lys Ile Ala Trp Met Ser Ile His Glu Gly Asn
145                 150                 155                 160

Val Thr Thr Lys Ser Lys Leu Lys His Val Thr Ser Ile Thr Asn Met
                165                 170                 175

Leu Leu Phe Ser Leu Ile Asn Ile Val Pro Phe Gly Ile Ser Leu Asn
            180                 185                 190

Cys Val Leu Leu Ile Tyr Ser Leu Ser Lys His Leu Lys Asn Met
        195                 200                 205

Lys Phe Tyr Gly Lys Gly Cys Gln Asp Gln Ser Thr Met Val His Ile
    210                 215                 220

Lys Ala Leu Gln Thr Val Val Ser Phe Leu Leu Leu Tyr Ala Thr Tyr
225                 230                 235                 240

Ser Ser Cys Val Ile Ile Ser Gly Trp Ser Leu Gln Asn Ala Pro Val
                245                 250                 255

Phe Leu Phe Cys Val Thr Ile Gly Ser Phe Tyr Pro Ala Gly His Ser
            260                 265                 270

Cys Ile Leu Ile Trp Gly Asn Gln Lys Leu Lys Gln Val Phe Leu Leu
        275                 280                 285

Leu Leu Arg Gln Met Arg Cys
    290                 295

<210> SEQ ID NO 144
<211> LENGTH: 1394
<212> TYPE: DNA
<213> ORGANISM: Mus sp.
<220> FEATURE:
<223> OTHER INFORMATION: mouse T2R20 (mGR20)

<400> SEQUENCE: 144
ctagatgggc tgtttcatat aatgactgga actccctaca tgctccacgt cttgagttct      60
aaaatttcac taacaaattt ttgactgcca taataatga aggtttaaag aaagaacaac     120
atttgaagca atggaccaga attcctcttt atttgactct tagcaaattg gaatgcagca     180
tcctttcaag agcagcactg aaatatacca gtcaatggca gagagtaaaa agtatgcaa     240 ttggagacat tatggtaata taaatttcca ttaaaaatga gactgcattc acctattaca     300
acacattgct attctgctca acacagagtt aaaagaaac aagaactctt gtatacattc      360
agttagtcac aagtataatt atgttcacat attttaaaaa aatgaatcat gatctgtgaa     420
ttgagcctgg cttttttgt ctctctcttt ttattctttt cctttagaca gacacaatga     480
```

-continued

```
atttggtaga atgqattgtt accatcataa tgatgacaga atttctctta ggaaactgtg      540
ccaatgtctt cataaccata gtgaacttca tcgactgtgt gaagagaaga aagatctcct      600
cagctgatcg aattataact gctattgcca tcttcagaat tggtttgttg tgggcaatgt      660
taacgaactg gcattcacat gtgtttactc cagacacaga caatttacaa atgagagttt      720
tcggtggaat tacctgggct ataaccaacc attttaccac ttggctgggg accatactga      780
gcatgtttta tttattcaag atagccaatt tttccaacag tctatttctt catctaaaaa      840
gaaaacttga caatgttcta cttgtgattt tcctgggatc gtctctgttt ttggttgcat      900
atcttgggat ggtgaacatc aagaagattg cttggatgag tattcatgaa ggaaatgtga      960
ccacaaagag caaactgaag catgtaacaa gcatcacaaa tatgcttctc ttcagcctga     1020
taaacattgt accatttggt atatcactga actgtgttct gctcttaatc tattccctga     1080
gtaaacatct caagaatatg aaattctatg gcaaaggatg tcaagatcag agcaccatgg     1140
tccacataaa ggccttgcaa actgtggtct cttttctctt gttatatgcc acatactctt     1200
cctgtgtcat tatatcaggt tggagtttgc aaaatgcacc agtcttcctg tttgtgtga      1260
caattggatc cttctaccca gcaggtcatt cttgtatctt gatttgggga aaccagaaac     1320
ttaaacaggt cttctgttg ttgctgaggc agatgagatg ctgactgaaa aaatgaaagt      1380
ccccctgtct ctag                                                      1394
```

<210> SEQ ID NO 145
<211> LENGTH: 305
<212> TYPE: PRT
<213> ORGANISM: Mus sp.
<220> FEATURE:
<223> OTHER INFORMATION: mouse T2R21 (mGR21)

<400> SEQUENCE: 145

```
Met Gly Ser Asn Val Tyr Gly Ile Leu Thr Met Val Met Ile Ala Glu
 1               5                  10                  15

Phe Val Phe Gly Asn Met Ser Asn Gly Phe Ile Val Leu Ile Asn Cys
            20                  25                  30

Ile Asp Trp Val Arg Lys Gly Thr Leu Ser Ser Ile Gly Trp Ile Leu
        35                  40                  45

Leu Phe Leu Ala Ile Ser Arg Met Val Leu Ile Trp Glu Met Leu Ile
    50                  55                  60

Thr Trp Ile Lys Tyr Met Lys Tyr Ser Phe Ser Phe Val Thr Gly Thr
65                  70                  75                  80

Glu Leu Arg Gly Ile Met Phe Thr Trp Val Ile Ser Asn His Phe Ser
                85                  90                  95

Leu Trp Leu Ala Thr Ile Leu Ser Ile Phe Tyr Leu Leu Lys Ile Ala
            100                 105                 110

Ser Phe Ser Lys Pro Val Phe Leu Tyr Leu Lys Trp Arg Glu Lys Lys
        115                 120                 125

Val Leu Leu Ile Val Leu Leu Gly Asn Leu Ile Phe Leu Met Leu Asn
    130                 135                 140

Ile Leu Gln Ile Asn Lys His Ile Glu His Trp Met Tyr Gln Tyr Glu
145                 150                 155                 160

Arg Asn Ile Thr Trp Ser Ser Arg Val Ser Asp Phe Ala Gly Phe Ser
                165                 170                 175

Asn Leu Val Leu Leu Glu Met Ile Val Phe Ser Val Thr Pro Phe Thr
            180                 185                 190
```

```
Val Ala Leu Val Ser Phe Ile Leu Leu Ile Phe Ser Leu Trp Lys His
        195                 200                 205

Leu Gln Lys Met His Leu Asn Ser Arg Gly Glu Arg Asp Pro Ser Thr
    210                 215                 220

Lys Ala His Val Asn Ala Leu Arg Ile Met Val Ser Phe Leu Leu Leu
225                 230                 235                 240

Tyr Ala Thr Tyr Phe Ile Ser Phe Phe Leu Ser Leu Ile Pro Met Ala
                245                 250                 255

His Lys Thr Arg Leu Gly Leu Met Phe Ser Ile Thr Val Gly Leu Phe
            260                 265                 270

Tyr Pro Ser Ser His Ser Phe Ile Leu Ile Leu Gly His Ser Asn Leu
        275                 280                 285

Arg Gln Ala Ser Leu Trp Val Met Thr Tyr Leu Lys Cys Gly Gln Lys
    290                 295                 300

His
305

<210> SEQ ID NO 146
<211> LENGTH: 2567
<212> TYPE: DNA
<213> ORGANISM: Mus sp.
<220> FEATURE:
<223> OTHER INFORMATION: mouse T2R21 (mGR21)

<400> SEQUENCE: 146
ctcttttgaa gacaatagtt gttctactag ctattgatag catgtttaca tttgtcattt      60
tcaagtatgt tcagaaacaa agctacatat tgtggggagt atataaaata tgaaagcatg     120
ccattcccag gcatccaagg atccctgtgt attaaaaggc aacaaagcag aaccaaatgt     180
tctgttttgg acatgagctt cttccaattc aactgctgaa aaatttggat aactacatat     240
aaaactaaga acacagagtg tcacagagca gtctctgctc tccaattcac caggattaat     300
attgacagac ccaaaagatg tcatttaggt aaattttgga tgaatcatat tgttgtcacc     360
tttgtgctct agaacataag ctgatagaat caaattttct ttagcagaga caatgcaaat     420
tgatataaca gtgaaagaga atatatcttt atttgcatgt tagcaaatga cagctggatg     480
cacttcatga ttttctgcaa tctagttcag tctttagaag gatatatata tatatatata     540
tatatatata tatatatata tatatatata tataaacctt agtcttgaaa gatatcagaa     600
agaaggattt cacaagaatg tacagagcca ttagcaaaat tttaatatac tcatcgacat     660
taggtcagtc actacataag aaggacttga atgaaagctt atcttagttt ttgagactac     720
agggacattt caccttgcca aatgagaagc agtgagtctt ctttgtctgg acatgggaag     780
caatgtgtat ggtatcttaa ctatggttat gattgcagag tttgtatttg gaaatatgag     840
caatggattc atagtgctga taaactgcat tgattgggtc aggaaaggaa ctctttcttc     900
cattggttgg atcctgcttt tcttggccat ttcaagaatg tgttgatat  gggaaatgtt     960 ataacatgg ataaaatata tgaagtattc attttcattt gtgactggaa cagaattacg    1020
gggtatcatg tttacctggg taatttccaa tcacttcagt ctctggcttg ccactattct    1080
cagcatcttt tatttgctca aaatagccag tttctccaaa ccggttttc  tctatttgaa    1140 gtggagagag aagaaagtgc ttctgattgt ccttctggga aatttgatct tcttgatgct    1200
caacatatta caaataaaca aacatataga acactggatg tatcaatatg agagaaatat    1260
aacttggagt tctagagtga gtgactttgc agggttttca aatctggtct tattggagat    1320
gattgtgttc tctgtaacac cattcacagt ggccctggtc tccttcatcc tgttaatctt    1380
```

-continued

```
ctccttgtgg aaacatctac agaaaatgca tctcaattct agaggggaac gagacccag      1440 cactaaagcc catgtgaatg ccttgagaat tatggtctcc ttcctcttac tctatgccac      1500
ttacttcata tcttttttc tatcattgat tcccatggca cataaaacac gactgggtct      1560
tatgtttagc ataactgttg ggcttttcta cccttcaagc cactcattta tcttaatttt      1620
gggacattct aatttaaggc aagccagtct ttgggtgatg acatatctta aatgtgggca      1680
aaagcattag aatttcacta ttccataagg cagccaaacc acgtgctact aggtatatga      1740
tactactcag tggtaaagcc ctaggcaaac attaacctta gaaaatatat aattttgtga      1800
ctcttctgta tttgataaat cactcacata tttagaagaa tgctacagta gtgtgatctt      1860
gtacatgatt gtaacaattc aattttatta atatagttca ggcatgataa catacccctg      1920
ataactgaaa agtaagtagg atgctacata tatatttaga tctagactta ggggcaaaga      1980
gagacccagc tgatagctgt gcaataaaga ttttaatttt catcctgttg tgagttatct      2040
gaaatctatg tcactgaagg cataagcaag attttcacac actgaaacaa tctcttatgc      2100
tttcttatat tgttttaaaa gtaaattaga aaatttaaat aaacttaatg gcaattgaaa      2160
ttacaaaagc taaacacatg tggttattag aaattagact gtatgtaggt cctaggggat      2220
ggcttagtaa agtgctttgt tgcaagcttc aggatatgat tctaaatccc tagattcaat      2280
taaaaacctg gcataaatag ccaatgtaaa atttgtctgt aaaatgtaac cagtgctaag      2340
agtaccaaga caacaaaatg tttacttta aaccattta ttgatattct tttaaaaata      2400
ggtatgtatt ttactattta aataagattt tgtcaaaagc tagtcttgac accttaggta      2460
aacataggaa ggcaacaagt ttgaagtcag ctactgggga cagtgctgct agcagctgac      2520
agaggccact gctgactaca gcagatcatt tacaggttca gcactag                   2567
```

<210> SEQ ID NO 147
<211> LENGTH: 309
<212> TYPE: PRT
<213> ORGANISM: Mus sp.
<220> FEATURE:
<223> OTHER INFORMATION: mouse T2R22 (mGR22)

<400> SEQUENCE: 147

```
Met Ser Ser Leu Leu Glu Ile Phe Phe Val Ile Ile Ser Val Val Glu
  1               5                  10                  15

Phe Ile Ile Gly Thr Leu Gly Asn Gly Phe Ile Val Leu Ile Asn Ser
             20                  25                  30

Thr Ser Trp Phe Lys Asn Gln Lys Ile Ser Val Ile Asp Phe Ile Leu
         35                  40                  45

Thr Trp Leu Ala Ile Ser Arg Met Cys Val Leu Trp Thr Thr Ile Ala
     50                  55                  60

Gly Ala Ser Leu Arg Lys Phe Tyr Lys Thr Leu Ser Tyr Ser Lys Asn
 65                  70                  75                  80

Phe Lys Phe Cys Phe Asp Ile Ile Trp Thr Gly Ser Asn Tyr Leu Cys
                 85                  90                  95

Ile Ala Cys Thr Thr Cys Ile Ser Val Phe Tyr Leu Phe Lys Ile Ala
            100                 105                 110

Asn Phe Ser Asn Ser Ile Phe Phe Trp Ile Lys Gln Arg Ile His Ala
        115                 120                 125

Val Leu Leu Ala Ile Val Leu Gly Thr Leu Met Tyr Phe Ile Leu Phe
    130                 135                 140

Leu Ile Phe Met Lys Met Ile Ala Asn Asn Phe Ile Tyr Lys Trp Thr
```

```
                145                 150                 155                 160
Lys Leu Glu Gln Asn Thr Thr Phe Pro Val Leu Asp Thr Leu Ser Gly
                165                 170                 175
Phe Leu Val Tyr His Ser Leu Tyr Asn Gly Ile Leu Ile Phe Phe Phe
            180                 185                 190
Ile Val Ser Leu Thr Ser Phe Leu Leu Ile Phe Ser Leu Trp Ser
        195                 200                 205
His Leu Arg Arg Met Lys Leu Gln Gly Ile His Thr Lys Asp Ile Ser
        210                 215                 220
Thr Glu Ala His Ile Lys Ala Met Lys Thr Met Met Ser Phe Leu Leu
225                 230                 235                 240
Phe Phe Ile Ile Tyr Tyr Ile Ser Asn Ile Met Leu Ile Val Ala Ser
                245                 250                 255
Ser Ile Leu Asp Asn Val Val Ala Gln Ile Phe Ser Tyr Asn Leu Ile
                260                 265                 270
Phe Leu Tyr Leu Ser Val His Pro Phe Leu Leu Val Leu Trp Asn Ser
            275                 280                 285
Lys Leu Lys Trp Thr Phe Gln His Val Leu Arg Lys Leu Val Cys His
        290                 295                 300
Cys Gly Gly Tyr Ser
305

<210> SEQ ID NO 148
<211> LENGTH: 1488
<212> TYPE: DNA
<213> ORGANISM: Mus sp.
<220> FEATURE:
<223> OTHER INFORMATION: mouse T2R22 (mGR22)

<400> SEQUENCE: 148
aaatgaataa tttcatgcaa aggataccat tagaatatga tcactattta aattttagca      60
aatacatatt caaataccag cacaatgttt caaatttaaa atataaacat tataaaaccc     120
agcagagaac aaaatgatag ccttgataat tgttggtttg ctcaagaaaa atgggtgtat     180
actttaacat ttaattggga actcagttga gagcatacat ttagggtttt acagaggtat     240
tcattgccca tttaagattt ggattcacac atctacatca atgtggctgt aatccatttt     300
cccatgatga aataaggtag agactgccta ttaaacgaca tgtcgagcct actggagatt     360
ttctttgtga tcatttcggt tgtagaattc ataataggaa cttttgggaaa tggatttatt     420
gtcctgataa acagtacttc ttggttcaag aatcagaaaa tctctgtaat tgatttcatt     480
cttacttggt tggccatctc cagaatgtgt gttctatgga caacaattgc tggtgcctct     540
ctcaggaaat tctacaagac gttaagttac tctaagaatt caaattttg ttttgacatt      600
atctggacag gatccaacta tttatgcata gcctgtacaa cgtgcatcag tgtcttctac     660
tgttcaaga ttgccaactt ttctaattcc attttcttct ggattaaaca gagaattcat      720
gcagtacttc tggctattgt cctaggcaca ctcatgtatt tcattttatt tctcattttt     780
atgaaaatga tagctaataa ttttatctac aaatggacaa aattggaaca aaacacaaca     840
ttccctgttt tagatactct aagtggtttc ttagtctacc atagcctcta caatgggatt     900
ctcatttct ttttatagt gtctctgacc tcatttcttc ttttaatctt ctctttatgg       960
agccacctta ggaggatgaa actacagggc atacatacca aagacataag cacagaagca    1020
cacataaaag ctatgaaaac tatgatgtca ttccttttgt tcttcatcat atattatatt    1080
agcaacatta tgcttattgt ggcaagctcc attcttgaca atgtggttgc acaaattttc    1140
```

```
tcttataacc taatatttct gtatttatct gttcatcctt ttcttctggt tttatggaac    1200
agcaaattga aatggacatt ccagcatgta ttgagaaagc tggtgtgtca ttgtggaggt    1260
tattcttgat ttcagtaaat acactcaata taactgatgg atttctaagg taagaaaaat    1320
ggaacaagga ataaagagga gaaatatatt cctttcaga tcatctgctc tgtcattctg     1380
tccttagcat gctattaaga attgttgact aaatccagtc atttttaaca tgaggaaagg    1440
atgtttcaat ccaacttaga gagggtacaa aatagtccta ggaggcag                 1488
```

<210> SEQ ID NO 149
<211> LENGTH: 333
<212> TYPE: PRT
<213> ORGANISM: Mus sp.
<220> FEATURE:
<223> OTHER INFORMATION: mouse T2R23 (mGR23)

<400> SEQUENCE: 149

```
Met Phe Ser Gln Lys Ile Asn Tyr Ser His Leu Phe Thr Phe Ser Ile
 1               5                  10                  15

Thr Leu Tyr Val Glu Ile Val Thr Gly Ile Leu Gly His Gly Phe Ile
            20                  25                  30

Ala Leu Val Asn Ile Met Asp Trp Val Lys Arg Arg Ile Ser Ser
        35                  40                  45

Val Asp Gln Ile Leu Thr Ala Leu Ala Leu Thr Arg Phe Ile Tyr Val
    50                  55                  60

Leu Ser Met Leu Ile Cys Ile Leu Leu Phe Met Leu Cys Pro His Leu
65                  70                  75                  80

Pro Arg Arg Ser Glu Met Leu Ser Ala Met Gly Ile Phe Trp Val Val
                85                  90                  95

Asn Ser His Phe Ser Ile Trp Leu Thr Thr Cys Leu Gly Val Phe Tyr
            100                 105                 110

Phe Leu Lys Ile Ala Asn Phe Ser Asn Ser Phe Phe Leu Tyr Leu Lys
        115                 120                 125

Trp Arg Val Lys Lys Val Ile Leu Ile Ile Leu Ala Ser Leu Ile
    130                 135                 140

Phe Leu Thr Leu His Ile Leu Ser Leu Gly Ile Tyr Asp Gln Phe Ser
145                 150                 155                 160

Ile Ala Ala Tyr Val Gly Asn Met Ser Tyr Ser Leu Thr Asp Leu Thr
                165                 170                 175

Gln Phe Ser Ser Thr Phe Leu Phe Ser Asn Ser Ser Asn Val Phe Leu
            180                 185                 190

Ile Thr Asn Ser Ser His Val Phe Leu Pro Ile Asn Ser Leu Phe Met
        195                 200                 205

Leu Ile Pro Phe Thr Val Ser Leu Val Ala Phe Leu Met Leu Ile Phe
    210                 215                 220

Ser Leu Trp Lys His His Lys Lys Met Gln Val Asn Ala Lys Gln Pro
225                 230                 235                 240

Arg Asp Val Ser Thr Met Ala His Ile Lys Ala Leu Gln Thr Val Phe
                245                 250                 255

Ser Phe Leu Leu Leu Tyr Ala Ile Tyr Leu Leu Phe Leu Ile Ile Gly
            260                 265                 270

Ile Leu Asn Leu Gly Leu Met Glu Lys Ile Val Ile Leu Ile Phe Asp
        275                 280                 285

His Ile Ser Gly Ala Val Phe Pro Ile Ser His Ser Phe Val Leu Ile
    290                 295                 300
```

Leu Gly Asn Ser Lys Leu Arg Gln Ala Ser Leu Ser Val Leu Pro Cys
305                 310                 315                 320

Leu Arg Cys Gln Ser Lys Asp Met Asp Thr Met Gly Leu
            325                 330

<210> SEQ ID NO 150
<211> LENGTH: 1442
<212> TYPE: DNA
<213> ORGANISM: Mus sp.
<220> FEATURE:
<223> OTHER INFORMATION: mouse T2R23 (mGR23)

<400> SEQUENCE: 150
aattttcagc aaccaatatg tagactgctt aaatgcatca gaaacattat aaattgaagc      60
atgttttcac agaaaataaa ctacagccat ttgtttactt tttcaatcac cttgtatgtg     120
gaaatagtaa cgggaatctt aggacatgga ttcatagcat tagtgaacat catggactgg     180
gtcaaaagaa gaaggatctc ttcagtggat cagattctca ctgctttggc ccttaccaga     240
ttcatttatg tcttgtctat gctgatttgc atattgttat tcatgctgtg cccacatttg     300
cctaggagat cagaaatgct ttcagcaatg ggtatttttct gggtagtcaa cagccatttt     360
agcatctggc ttactacatg cctcggtgtc ttttattttc tcaagatagc caattttttct     420
aactcttttt ttctttatct aaagtggaga gttaaaaaag tgattttaat aataatcctg     480
gcatcactga ttttcttgac tttacacatt ttatctttag ggatatatga tcagttctca     540
attgctgctt atgtaggaaa tatgtcttat agtttgacag atttaacaca attttccagt     600
actttcttat tctccaactc atccaatgtt tccttaatca ccaactcatc ccatgttttc     660
ttacccatca actccctgtt catgctcata cccttcacag tgtccctggt agcctttctc     720
atgctcatct tctcactgtg gaagcatcac aaaaagatgc aggtcaatgc caaacaacct     780
agagatgtca gtactatggc ccacattaaa gccttgcaaa ctgtgttctc cttcctgctg     840
ctgtatgcca tatacttact tttccttatc ataggaattt tgaaccttgg attgatggag     900
aaaatagtga tactgatatt tgaccacatt tctggagcag ttttttcctat aagccactca     960
tttgtactga ttctgggaaa cagtaagctg agacaagcca gtctttctgt gttgccttgt    1020
ctaaggtgcc agtccaaaga tatggacacc atgggtctct agtaaattcc agagtacatt    1080
ttgtaaaaat cttgaggatg atcagttcat agaaaaaagt taccttatgg gggaaaataa    1140
aaagtggggc ttcaatcctg ggagtaataa tacacaggag ggtaggacag catgaaggag    1200
actagcacta tataagtggt ctcatacagg atatgggaaa ggaaagattt atgcaataaa    1260
gagggagatc atattggagg atgaggaggc attacatatg taaatgact ataagaatgg     1320
aatcatgcta atctaaaaaa atctgtaatg catttcattc agactatata catatatgcc    1380
tatatatgga tatatgggga tatatattct atacatattt taaagaacc tttcttatat     1440
ag                                                                   1442

<210> SEQ ID NO 151
<211> LENGTH: 309
<212> TYPE: PRT
<213> ORGANISM: Mus sp.
<220> FEATURE:
<223> OTHER INFORMATION: mouse T2R24 (mGR24)

<400> SEQUENCE: 151

Met Val Pro Val Leu His Ser Leu Ser Thr Ile Ile Leu Ile Ala Glu
1               5                   10                  15

Phe Val Trp Gly Asn Leu Ser Asn Gly Leu Ile Val Leu Lys Asn Cys
            20                  25                  30

Ile Asp Trp Ile Asn Lys Lys Glu Leu Ser Thr Val Asp Gln Ile Leu
        35                  40                  45

Ile Val Leu Ala Ile Ser Arg Ile Ser Leu Ile Trp Glu Thr Leu Ile
    50                  55                  60

Ile Trp Val Lys Asp Gln Leu Ser Ser Ile Thr Ile Glu Glu Leu
65                  70                  75                  80

Lys Ile Ile Val Phe Ser Phe Ile Leu Ser Ser His Phe Ser Leu Trp
                85                  90                  95

Leu Ala Thr Ala Leu Ser Ile Phe Tyr Leu Phe Arg Ile Pro Asn Cys
            100                 105                 110

Tyr Trp Gln Ile Phe Leu Tyr Leu Lys Trp Arg Ile Lys Gln Leu Ile
        115                 120                 125

Val His Met Leu Leu Gly Ser Leu Val Phe Leu Val Ala Asn Met Ile
    130                 135                 140

Gln Ile Thr Ile Thr Leu Glu Glu Arg Phe Tyr Gln Tyr Gly Gly Asn
145                 150                 155                 160

Thr Ser Val Asn Ser Met Glu Thr Glu Phe Ser Ile Leu Ile Glu Leu
                165                 170                 175

Met Leu Phe Asn Met Thr Met Phe Ser Ile Ile Pro Phe Ser Leu Ala
            180                 185                 190

Leu Ile Ser Phe Leu Leu Leu Ile Phe Ser Leu Trp Lys His Leu Gln
        195                 200                 205

Lys Met Pro Leu Asn Ser Arg Gly Asp Arg Asp Pro Ser Ala Thr Ala
    210                 215                 220

His Arg Asn Ala Leu Arg Ile Leu Val Ser Phe Leu Leu Leu Tyr Thr
225                 230                 235                 240

Ile Tyr Phe Leu Ser Leu Leu Ile Ser Trp Val Ala Gln Lys Asn Gln
                245                 250                 255

Ser Glu Leu Val His Ile Ile Cys Met Ile Thr Ser Leu Val Tyr Pro
            260                 265                 270

Ser Phe His Ser Tyr Ile Leu Ile Leu Gly Asn Tyr Lys Leu Lys Gln
        275                 280                 285

Thr Ser Leu Trp Val Met Arg Gln Leu Gly Cys Arg Met Lys Arg Gln
    290                 295                 300

Asn Thr Pro Thr Thr
305

<210> SEQ ID NO 152
<211> LENGTH: 1465
<212> TYPE: DNA
<213> ORGANISM: Mus sp.
<220> FEATURE:
<223> OTHER INFORMATION: mouse T2R24 (mGR24)

<400> SEQUENCE: 152
caaagaggag aaatatttag ctacacagtg taccacatac aagccgttca atcagtataa      60
ggggagcagt catatagaat ttgggctttc tttcttttaa tatggtacct gttctgcaca     120
gtctctccac catcatacta attgcagagt ttgtttgggg aaatttgagc aatggtttga     180
tagtgttgaa gaactgcatt gactggatca ataaaaaga gctctccaca gttgatcaaa      240
tactcattgt cttggcaatt tcaagaatta gtctcatctg ggaaacacta attatatggg     300
ttaaagatca actaatttca tctattacta ttgaagaatt aaaaataatt gtgttcagct     360

-continued

```
ttatactatc tagccacttc agtctctggc ttgctacagc tctcagcatc ttctatttat    420
tcagaatacc taattgctac tggcagatct ttctctactt gaaatggaga ataaagcaac    480
tgattgtcca catgcttctg ggaagcttgg tgttcttggt tgcaaatatg atacagataa    540
ccatcactct tgaagagagg ttctatcaat atggaggaaa tacaagtgta aattccatgg    600
agactgagtt ctcaattttg atagagctga tgttatttaa catgactatg ttctccatta    660
taccattttc attggcctta atttcttttc ttctgctaat cttctcttta tggaaacatc    720
tccagaagat gccactcaat tctagaggag atagagaccc tagtgctacg cccacagaa     780
atgccttgag aattttggtc tccttcctct tgctctatac tatatatttc ctgtctcttc    840
ttatatcatg ggttgctcag aagaatcaaa gtgaactggt tcacattatt tgtatgataa    900
cttcactcgt gtatccttca ttccactcat atatcctgat tctgggaaat tataaattaa    960
agcagacctc tctttgggta atgaggcagc tgggatgtag gatgaaaaga cagaatacac   1020
caactacata aggcagccaa acagtctatt gggttttaga taacaaatct aaatctatga   1080
ggaagtagtt caataacatt tttcccttg acatggagta gcagggtttt tttttattag    1140
atattttctt tacttacatt tcaaatgcta tcccgaaaat tccctgtacc ctctccctgt   1200
cctgttcccc tacccaccca ctcccacttc ttggccctgg cattcccctg gagtatcagt   1260
ttttattag tcaaactatc tcactgacta agggtcataa aacaagttat tttaacacta    1320
atttcaatta aatcaaaggt aaagtgtcag cacatgcctt taatcacaca attccatcaa   1380
attcagcact caggagaggg tgatctctgt gaattccagc acactggcgg ccgttactag   1440
tggatccgag ctcggtacca agctt                                         1465
```

<210> SEQ ID NO 153
<211> LENGTH: 311
<212> TYPE: PRT
<213> ORGANISM: Mus sp.
<220> FEATURE:
<223> OTHER INFORMATION: mouse T2R25 (mGR25)

<400> SEQUENCE: 153

```
Met Met Gly Ile Ala Ile Asp Ile Leu Trp Ala Ile Ile Ile Val
 1               5                  10                  15

Gln Phe Ile Ile Gly Asn Ile Ala Asn Gly Phe Ile Ala Leu Val Asn
                20                  25                  30

Ile Ile Asp Trp Val Lys Arg Arg Lys Ile Ser Leu Met Asp Lys Ile
            35                  40                  45

Ile Thr Ala Leu Ala Ile Ser Arg Ile Tyr Leu Leu Trp Ser Thr Phe
        50                  55                  60

Leu Ile Thr Leu Thr Ser Ser Leu Asp Pro Asp Ile Lys Met Ala Val
 65                  70                  75                  80

Lys Ile Ile Arg Ile Ser Asn Asn Thr Trp Ile Ala Asn His Phe
                85                  90                  95

Ser Ile Trp Phe Ala Thr Cys Leu Ser Ile Phe Tyr Phe Leu Lys Ile
                100                 105                 110

Ala Asn Phe Ser Asn Tyr Ile Phe Leu Tyr Leu Arg Trp Arg Phe Lys
            115                 120                 125

Lys Val Val Ser Val Thr Leu Ile Ser Leu Ile Phe Leu Leu Leu
        130                 135                 140

Asn Ile Leu Leu Met Asn Met His Ile Asp Ile Trp Ser Asp Lys Ser
145                 150                 155                 160
```

```
Lys Arg Asn Leu Ser Phe Ser Val Arg Ser Asn Asn Cys Thr Gln Phe
                165                 170                 175

Pro Arg Leu Val Leu Leu Ile Asn Thr Met Phe Thr Ser Ile Pro Phe
            180                 185                 190

Thr Val Ser Leu Leu Ala Phe Leu Leu Leu Ile Phe Ser Leu Trp Arg
        195                 200                 205

His Leu Lys Thr Met Gln Tyr Tyr Ala Lys Gly Ser Glu Asp Thr Thr
    210                 215                 220

Thr Ala Ala His Ile Lys Ala Leu His Met Val Val Ala Phe Leu Leu
225                 230                 235                 240

Phe Tyr Thr Val Phe Phe Leu Ser Leu Ala Ile Gln Tyr Trp Thr Ser
                245                 250                 255

Gly Ser Gln Glu Asn Asn Asn Leu Phe Tyr Ala Thr Ile Val Ile Thr
            260                 265                 270

Phe Pro Ser Val His Ser Cys Ile Leu Ile Leu Arg Asn Ser Gln Leu
        275                 280                 285

Arg Gln Ala Ser Leu Leu Val Leu Trp Trp Leu Leu Cys Lys Ser Lys
    290                 295                 300

Asp Val Arg Met Leu Val Pro
305                 310

<210> SEQ ID NO 154
<211> LENGTH: 1103
<212> TYPE: DNA
<213> ORGANISM: Mus sp.
<220> FEATURE:
<223> OTHER INFORMATION: mouse T2R25 (mGR25)

<400> SEQUENCE: 154
aaaactattc gaattgaaca cagtaaccaa ttcttcagcg gacttacaca aatcaagcta      60
ttatcttatg gatgatgggt attgccatag atatcttatg ggcagctatt atcattgtgc     120
aattcataat tgggaatatt gcaaatggat tcatagcatt ggtgaacatc atagactggg     180
tgaagagaag aaaaatctct taatggata agatcattac tgctttggca atctctagga     240
tttatctgct gtggtctaca ttcttaatta cactaacatc ttcactggat ccagatatta     300
aaatggctgt gaaaatcatt agaataagca ataacacctg gattattgca atcatttca      360
gcatttggtt tgctacatgt ctcagcatct tttattttct caagatagcc aattttcta      420
actatatttt tctctactta aggtggagat ttaagaaggt ggtttcagtg acattgctaa     480
tctctcttat cttcctgctt ttaaatattt tactgatgaa catgcatatt gatatctgga     540
gtgataagtc caaagaaaac ctttctttta gtgtcagatc aaataattgc actcagtttc     600
ccagacttgt ccttttaatc aacacaatgt tcacatcaat cccctttcact gtgtccctgt     660
tggctttct gcttctcatc ttctccctgt ggagacacct gaaaaccatg caatactatg     720
ctaaaggctc cgaagacacc accacagctg cacatataaa ggccttgcac atggtagtgg     780
cctttctcct gttctacaca gttttctttt tgtctcttgc catacaatat tggacctctg     840
ggtctcaaga gaataacaac ctgttttatg ccacaattgt aattactttc ccttcagtcc     900
attcatgtat cctgattctg agaaacagcc agctgaggca ggcatctctg ttggtgctgt     960
ggtggctgct gtgcaagtcc aaagatgtac ggatgttggt ccctgaaaat actctgtcaa    1020
tgctctttag tagtgaagaa gaaaatagct tagttaagga aattcttgtt cattaccgaa    1080
gtatactttc aagtttatgt atc                                            1103
```

<210> SEQ ID NO 155
<211> LENGTH: 308
<212> TYPE: PRT
<213> ORGANISM: Mus sp.
<220> FEATURE:
<223> OTHER INFORMATION: mouse T2R26 (mGR26)

<400> SEQUENCE: 155

```
Met Leu Pro Thr Leu Ser Val Phe Phe Met Leu Thr Phe Val Leu Leu
 1               5                  10                  15

Cys Phe Leu Gly Ile Leu Ala Asn Gly Phe Ile Val Leu Met Leu Ser
             20                  25                  30

Arg Glu Trp Leu Leu Arg Gly Arg Leu Leu Pro Ser Asp Met Ile Leu
         35                  40                  45

Phe Ser Leu Gly Thr Ser Arg Phe Phe Gln Gln Cys Val Gly Leu Val
     50                  55                  60

Asn Ser Phe Tyr Tyr Phe Leu His Leu Val Glu Tyr Ser Gly Ser Leu
 65                  70                  75                  80

Ala Arg Gln Leu Ile Ser Leu His Trp Asp Phe Leu Asn Ser Ala Thr
                 85                  90                  95

Phe Trp Phe Cys Thr Trp Leu Ser Val Leu Phe Cys Ile Lys Ile Ala
            100                 105                 110

Asn Phe Ser His Pro Ala Phe Leu Trp Leu Lys Trp Arg Phe Pro Ala
        115                 120                 125

Leu Val Pro Trp Phe Leu Leu Gly Ser Ile Leu Val Ser Val Ile Val
    130                 135                 140

Thr Leu Leu Phe Phe Trp Gly Asn His Thr Ile Tyr Gln Ala Phe Leu
145                 150                 155                 160

Arg Arg Lys Phe Thr Gly Asn Thr Thr Phe Lys Glu Trp Asn Arg Arg
                165                 170                 175

Leu Glu Ile Asp Tyr Phe Met Pro Leu Lys Val Val Thr Met Ser Ile
            180                 185                 190

Pro Cys Ser Leu Phe Leu Val Ser Ile Leu Leu Ile Ser Ser Leu
        195                 200                 205

Arg Arg His Ser Leu Arg Met Gln His Asn Thr His Ser Leu Gln Asp
    210                 215                 220

Pro Asn Val Gln Ala His Ser Arg Ala Leu Lys Ser Leu Ile Ser Phe
225                 230                 235                 240

Leu Val Leu Tyr Ala Val Ser Phe Val Ser Met Ile Ile Asp Ala Thr
                245                 250                 255

Val Phe Ile Ser Ser Asp Asn Val Trp Tyr Trp Pro Trp Gln Ile Ile
            260                 265                 270

Leu Tyr Phe Cys Met Ser Val His Pro Phe Ile Leu Ile Thr Asn Asn
        275                 280                 285

Leu Arg Phe Arg Gly Thr Phe Arg Gln Leu Leu Leu Leu Ala Arg Gly
    290                 295                 300

Phe Trp Val Ala
305
```

<210> SEQ ID NO 156
<211> LENGTH: 3437
<212> TYPE: DNA
<213> ORGANISM: Mus sp.
<220> FEATURE:
<223> OTHER INFORMATION: mouse T2R26 (mGR26)

<400> SEQUENCE: 156

| | |
|---|---|
| gaattctaga caaggaaaga cacacactaa atgactttac ttgtgggacc taaaataacc | 60 |
| aaaataagtc aaaatcacag tgatgttact agggatctag gataagggaa tgaagagaaa | 120 |
| gatgttggtc atagagtaca aaaattcagc taagaactca gtcctggagg ctgaatgtat | 180 |
| agctgtgtga cagacagcag ctagccatac cagagtatac acttgcctct tgctgaaaga | 240 |
| gtagatctta tgtgtccttg tcacacataa agtaattga aaaagtaact ctctgagatg | 300 |
| acagatacgt taaaatggtt ttactttca acctgctcca gtaggggtcc ctttaatgtt | 360 |
| tgtgctagta gatggggggac tctcaagtat ctttgtggta gacaaatcta aggtggcctt | 420 |
| catgaatacc aacccagact tttgtgactt tgtgatcccc cacttttgaa gtggataaga | 480 |
| gctgtgactt gagtctaatc aaaggagtcc aacgtgttgt ttattctgta acagtgcttt | 540 |
| gtgtttctag ttaataacac aggcaaagaa ggctagggtg acattcctag gattgtgtta | 600 |
| tttctatctt gctcatgcct ccctctgctg gtctaatgaa ataagtcagt ggccatattt | 660 |
| aaatatgact acgtggcaaa tactgatgat agcctgtgtg ttccaacaaa tatccagtag | 720 |
| gagacctagg cattcagtcc tgcagccaca aggaaatagg ttctttcact ggaaaaagag | 780 |
| cagtttagat ggttataaat tacttaatcc atagaagcca tagggctttt atgtagagat | 840 |
| ttgggtagag aggtagacct agatattgac ttaggagtgg ctattcctga gtgggggtag | 900 |
| atatatggca gggaaactca gataagaaag acttctttag tgtcacgatt tttcctaggt | 960 |
| atctccttgt gccagatatc tatgcgtcta tgtacctacc tacctaccta cctacctacc | 1020 |
| tacctaccta cctactgaca cctaatagga agaggcaagt ggtcacaacc tgcaatgatg | 1080 |
| ggataagaat gatggaactc agttaccaag attaaaatac cttccccact gatgttattg | 1140 |
| caagcatggc agcatgtagg caaaatcaga gaaggcaaat catgagcagc tgctgcccca | 1200 |
| tggtacccga gcccgggaaa tatttgcatc atatctgagc caaaagcaca ccttttatct | 1260 |
| actgcctgag cattttttcac attgaagttc tggctcacat gcagaatcca accatttatc | 1320 |
| tcctgtctcc agaagggagt gtcagggact gtgggtaggg gcagggagga ggccaggaac | 1380 |
| caaggcaatc agtggtgaca ggaggaggga ctgaaatgct accaacatta tcagttttct | 1440 |
| tcatgttgac cttttgttctg ctctgtttcc tggggatcct ggccaacggc ttcattgtgc | 1500 |
| tgatgctgag cagggaatgg ctactgcgtg gtaggctgct cccctcggac atgatcctct | 1560 |
| tcagtttggg cacctcccga ttcttccagc agtgtgtggg attggtcaac agtttctatt | 1620 |
| acttcctcca tctggttgag tactccggga gccttgcccg gcagctcatt agtcttcact | 1680 |
| gggacttctt gaactcagcc actttctggt tttgtacctg gctcagcgtc ctgttctgta | 1740 |
| tcaagattgc taacttctcc catcctgcct tcctgtggtt gaagtggaga ttcccagcgt | 1800 |
| tggtgccctg gttcttgttg ggctctatct tggtgtccgt cattgtaact ctgctgttct | 1860 |
| tttgggaaa ccacactata tatcaggcat tcttaaggag aaagtttact gggaacacaa | 1920 |
| cctttaagga gtgaacagaa aggctggaaa tagactattt catgcctctg aaagttgtca | 1980 |
| ccatgtcaat tccttgttct cttttttctgg tctcaatttt gctgttgatc agttctctca | 2040 |
| gaaggcattc gctaagaatg cagcacaata cccacagctt gcaagacccc aacgtccagg | 2100 |
| ctcacagcag agccctgaag tcactcatct cattcctggt tctttatgcg gtgtcctttg | 2160 |
| tgtccatgat cattgatgct acagtcttca tctcctcaga taatgtgtgg tattggccct | 2220 |
| ggcaaattat actttacttt tgcatgtctg tacatccatt tatcctcatc accaataatc | 2280 |
| tcaggttccg cggcaccttc aggcagctac tcctgttggc caggggattc tgggtggcct | 2340 |
| agaaggcttg gtctctttat ctagagcctt tgaagagact caggtgaggg taacttcact | 2400 |

```
tggaagtgag ctcatctacg tggaaatgtc tttgtaggca ggcatggggt catactgtga    2460
ggttcctcat tgggaaagag gagaagaaaa tacagagtgt ccttccttac cttaggatat    2520
tatgaaagtg gaaattccga atcctggacc agtattgatc taagtgcaaa gtacaatatg    2580
tcctgttcct ttcatgtctg ttttcctttt gttactgatt cattctctag ggaatagtct    2640
tgatcaactg aatcatctca tctggctggc cactggggag gtaaaagaac tttgtgtcac    2700
tgctgcattg ggatatacat gggtgggaag caagtgtccc tgaggcagag tagcactcag    2760
tatgagaacc tcaaagagca ggtggctgtg catgcagggg ctggggcaag gagtcctgat    2820
cactcttcac tgtatgggga ttatttgtct cttgccaaaa tttggagact tggctttag     2880 ttttgtgaag atgactggaa aaattcttaa tgctaccctg tatcatttct caataatatt    2940
ttccttttcc tgcctttaat tttctcctat ctgcagcgcc ccttgcttgt tatccgtaaa    3000
taaataaata aataaataaa taagcccaat cctcattttc ctgtctttgg gaacccttt    3060 acttccccag gtatacgcta caaagccact tctgcattga ataaacatta tctttcattc    3120
agaaaaagac ttaagaatct caccttaca aaaaaaaaa aaaagaatc tcacttattt      3180 tatattcaaa ttccattttt aaaagaaaa gcacagcatt aattttcta aatactgttt     3240 ataaaaataa cttgctctaa gaattataca aatgttttga aaggtaactt tggaaaaaaa    3300
gtgtgattag acatggatgt tgtaagaca gaacaaagag ctcttggaag tccatggcag    3360
ctcattggtc ttgccttcag tagagcctgt ctgaatcctg taacctctta tgcccttttg   3420
tagcttttct gcagatc                                                  3437

<210> SEQ ID NO 157
<211> LENGTH: 340
<212> TYPE: DNA
<213> ORGANISM: Mus sp.
<220> FEATURE:
<223> OTHER INFORMATION: mouse T2R27 (mGR27)

<400> SEQUENCE: 157
gaattcgccc ttgcgggatc cgggaacgga ttcatagcac tggtaaactt catgggctgg      60
atgaagaata ggaagattgc ctccattgat ttaatcctca caagtctggc catatccaga    120
atttgtctat tgtgcgtaat actattagat tgttttatat tggtgctata tccagatgtc    180
tatgccactg gtaaagaaat gagaatcatt gacttcttct ggacactaac caatcactta    240
agtatctggt ttgcaacctg cctcagcatt tactatttct tcaagatagg taatttcttt    300
cacccacttt tcctatgcct caagtctaga cgccaagggc                         340

<210> SEQ ID NO 158
<211> LENGTH: 82
<212> TYPE: PRT
<213> ORGANISM: Mus sp.
<220> FEATURE:
<223> OTHER INFORMATION: mouse T2R28 (mGR28)

<400> SEQUENCE: 158

Gly Arg Glu Trp Leu Arg Tyr Gly Arg Leu Leu Pro Leu Asp Met Ile
 1               5                   10                  15

Leu Ile Ser Leu Gly Ala Ser Arg Phe Cys Leu Gln Leu Val Gly Thr
                20                  25                  30

Val His Asn Phe Tyr Tyr Ser Ala Gln Lys Val Glu Tyr Ser Gly Gly
            35                  40                  45

Leu Gly Arg Gln Phe Phe His Leu His Trp His Phe Leu Asn Ser Ala
```

-continued

```
                    50                    55                      60
Thr Phe Trp Phe Cys Ser Trp Leu Ser Val Leu Phe Cys Val Lys Ile
 65                    70                      75                  80

Ala Asn

<210> SEQ ID NO 159
<211> LENGTH: 341
<212> TYPE: DNA
<213> ORGANISM: Mus sp.
<220> FEATURE:
<223> OTHER INFORMATION: mouse T2R28 (mGR28)

<400> SEQUENCE: 159
gaattcgccc ttgcgggatc cgggaacggg tttattgtgc tggtgctggg cagggagtgg      60
ctgcgatatg gcaggttgct gcccttggat atgatcctca ttagcttggg tgcctcccgc     120
ttctgcctgc agttggttgg gacggtgcac aacttctact actctgccca gaaggtcgag     180
tactctgggg gtctcggccg acagttcttc catctacact ggcacttcct gaactcagcc     240
accttctggt tttgcagctg gctcagtgtc ctgttctgtg tgaagattgc taacatcaca     300
cactccacct tcctgtgtct caagtctaga cgccaagggc g                         341

<210> SEQ ID NO 160
<211> LENGTH: 320
<212> TYPE: PRT
<213> ORGANISM: Mus sp.
<220> FEATURE:
<223> OTHER INFORMATION: mouse T2R29 (mGR29)

<400> SEQUENCE: 160

Met Asp Gly Ile Val Gln Asn Met Phe Thr Phe Ile Val Ile Val Glu
  1               5                  10                  15

Ile Ile Ile Gly Trp Ile Gly Asn Gly Phe Ile Ala Leu Val Asn Cys
                 20                  25                  30

Ile His Trp Tyr Lys Arg Arg Lys Ile Ser Ala Leu Asn Gln Ile Leu
             35                  40                  45

Thr Ala Leu Ala Phe Ser Arg Ile Tyr Leu Leu Leu Thr Val Phe Thr
         50                  55                  60

Val Ile Ala Val Ser Thr Leu Tyr Thr His Val Leu Val Thr Arg Arg
 65                  70                  75                  80

Val Val Lys Leu Ile Asn Phe His Leu Leu Phe Ser Asn His Phe Ser
                 85                  90                  95

Met Trp Leu Ala Ala Cys Leu Gly Leu Tyr Tyr Phe Leu Lys Ile Ala
            100                 105                 110

His Phe Pro Asn Ser Ile Phe Val Tyr Leu Lys Met Arg Ile Asn Gln
            115                 120                 125

Val Val Ser Gly Thr Leu Leu Met Ser Leu Gly Leu Leu Phe Leu Asn
        130                 135                 140

Thr Leu Leu Ile Asn Ser Tyr Ile Asp Thr Lys Ile Asp Asp Tyr Arg
145                 150                 155                 160

Glu His Leu Leu Tyr Asp Phe Thr Ser Asn Asn Thr Ala Ser Phe Tyr
                165                 170                 175

Arg Val Ile Leu Val Ile Asn Asn Cys Ile Phe Thr Ser Ile Pro Phe
                180                 185                 190

Thr Leu Ser Gln Ser Thr Phe Leu Leu Leu Ile Phe Ser Leu Trp Arg
            195                 200                 205

His Tyr Lys Lys Met Gln Gln His Ala Gln Arg Cys Arg Asp Val Leu
```

-continued

```
            210                 215                 220
Ala Asp Ala His Ile Arg Val Leu Gln Thr Met Val Thr Tyr Val Leu
225                 230                 235                 240

Leu Cys Ala Ile Phe Phe Leu Ser Leu Ser Met Gln Ile Leu Arg Ser
                245                 250                 255

Glu Leu Leu Lys Asn Ile Leu Tyr Val Arg Phe Cys Glu Ile Val Ala
            260                 265                 270

Ala Val Phe Pro Ser Gly His Ser Cys Val Leu Ile Cys Arg Asp Thr
        275                 280                 285

Asn Leu Arg Gly Thr Phe Leu Ser Val Leu Ser Trp Leu Lys Gln Arg
    290                 295                 300

Phe Thr Ser Trp Ile Pro Asn Ile Asn Cys Arg Ser Ser Cys Ile Phe
305                 310                 315                 320
```

<210> SEQ ID NO 161
<211> LENGTH: 1108
<212> TYPE: DNA
<213> ORGANISM: Mus sp.
<220> FEATURE:
<223> OTHER INFORMATION: mouse T2R29 (mGR29)

<400> SEQUENCE: 161

| | | | | |
|---|---|---|---|---|
| agcttgatat | ttcctatttg | ttactgcaca | gagttttttt | taaaaattga gtttgttatg | 60 |
| tggattcaat | actcagatag | agctctttaa | tttttttaca | gtgacctcat gaatcataac | 120 |
| ttgccttaca | gacaatggat | ggaatcgtac | agaacatgtt | tacattcatt gtaattgtgg | 180 |
| aaataataat | aggatggatt | ggaaatggat | tcatagctct | ggtgaactgc atacactggt | 240 |
| acaagagaag | aaagatctct | gcactgaatc | aaatactcac | agccttggct ttctccagaa | 300 |
| tctaccttct | tttaacagta | ttcactgtta | tagcagtgtc | tacgctatac acacacgtgt | 360 |
| tggtaactag | aagagtggta | aaactgatta | atttccattt | gcttttcagc aatcatttta | 420 |
| gcatgtggct | tgctgcatgc | cttggccttt | attattttct | taaaatagct cattttccta | 480 |
| actctatttt | tgtttactta | aagatgagaa | ttaaccaggt | ggtttcaggg actttgctca | 540 |
| tgtctttggg | cctcttgttt | ctaaacactc | tgctgataaa | ctcatacatt gataccaaga | 600 |
| tagatgacta | cagagaacat | ctactgtatg | atttcacttc | gaataatact gcttcatttt | 660 |
| acagggttat | tttagtcatt | aacaactgta | ttttcacatc | tatacccttt acactttccc | 720 |
| agtccacttt | tctcctgctc | atcttctccc | tgtggagaca | ttacaagaag atgcaacagc | 780 |
| atgcacaaag | atgcagagat | gtccttgcag | atgcccacat | cagagtcttg caaaccatgg | 840 |
| tcacctatgt | cctactctgt | gccatttttct | ttctgtctct | ttccatgcaa attttgagga | 900 |
| gtgagttgtt | gaagaacatt | ctttacgtta | ggttctgcga | gattgttgca gcagtttttc | 960 |
| cttcaggaca | ctcctgtgtc | ttaatctgta | gagacacaaa | cctgagaggg acctttcttt | 1020 |
| ctgtgctatc | gtggctgaag | cagaggttta | catcatggat | tcctaacata aattgcagat | 1080 |
| catcttgcat | attctaaaag | aaactgag | | | 1108 |

<210> SEQ ID NO 162
<211> LENGTH: 312
<212> TYPE: PRT
<213> ORGANISM: Mus sp.
<220> FEATURE:
<223> OTHER INFORMATION: mouse T2R30 (mGR30)

<400> SEQUENCE: 162

Met Thr Tyr Glu Thr Asp Thr Thr Leu Met Leu Val Ala Val Gly Glu

```
                1               5              10              15
Ala Leu Val Gly Ile Leu Gly Asn Ala Phe Ile Ala Leu Val Asn Phe
                       20                  25                  30

Met Gly Trp Met Lys Asn Arg Lys Ile Ala Ser Ile Asp Leu Ile Leu
                35                  40                  45

Ser Ser Val Ala Met Ser Arg Ile Cys Leu Gln Cys Ile Ile Leu Leu
         50                  55                  60

Asp Cys Ile Ile Leu Val Gln Tyr Pro Asp Thr Tyr Asn Arg Gly Lys
 65                  70                  75                  80

Glu Met Arg Thr Val Asp Phe Phe Trp Thr Leu Thr Asn His Leu Ser
                 85                  90                  95

Val Trp Phe Ala Thr Cys Leu Ser Ile Phe Tyr Leu Phe Lys Ile Ala
                100                 105                 110

Asn Phe Phe His Pro Leu Phe Leu Trp Ile Lys Trp Arg Ile Asp Lys
            115                 120                 125

Leu Ile Leu Arg Thr Leu Leu Ala Cys Val Ile Ile Ser Leu Cys Phe
        130                 135                 140

Ser Leu Pro Val Thr Glu Asn Leu Ser Asp Asp Phe Arg Arg Cys Val
145                 150                 155                 160

Lys Thr Lys Glu Arg Ile Asn Ser Thr Leu Arg Cys Lys Val Asn Lys
                165                 170                 175

Ala Gly His Ala Ser Val Lys Val Asn Leu Asn Leu Val Met Leu Phe
            180                 185                 190

Pro Phe Ser Val Ser Leu Val Ser Phe Leu Leu Ile Leu Ser Leu
        195                 200                 205

Trp Arg His Thr Arg Gln Ile Gln Leu Ser Val Thr Gly Tyr Lys Asp
    210                 215                 220

Pro Ser Thr Thr Ala His Val Lys Ala Met Lys Ala Val Ile Ser Phe
225                 230                 235                 240

Leu Ala Leu Phe Val Val Tyr Cys Leu Ala Phe Leu Ile Ala Thr Ser
                245                 250                 255

Ser Tyr Phe Met Pro Glu Ser Glu Leu Ala Val Ile Trp Gly Glu Leu
            260                 265                 270

Ile Ala Leu Ile Tyr Pro Ser Ser His Ser Phe Ile Leu Ile Leu Gly
        275                 280                 285

Ser Ser Lys Leu Lys Gln Ala Ser Val Arg Val Leu Cys Arg Val Lys
    290                 295                 300

Thr Met Leu Lys Gly Lys Lys Tyr
305                 310
```

<210> SEQ ID NO 163
<211> LENGTH: 3775
<212> TYPE: DNA
<213> ORGANISM: Mus sp.
<220> FEATURE:
<223> OTHER INFORMATION: mouse T2R30 (mGR30)

<400> SEQUENCE: 163

| | | | | | |
|---|---|---|---|---|---|
| aaaaatgttc | attgtttatc | taaaattcaa | atttaactga | gtgccctaca | ttttatttta | 60 |
| ttcaatctag | tagctgtact | gaggttatta | gtgtgatttc | tgaagcccaa | atttgtaaaa | 120 |
| cttagcctca | gataaacagc | ttgagaccat | ggaaagtaat | ttggtaaatt | tgcatcttag | 180 |
| caaatagtag | ctcagcctaa | attaactgtg | tgtagaaaag | aatgacctgc | ggagaagata | 240 |
| aatggacata | caatatccag | gctaaggatt | gccaaacaca | ctgttttta | gactaattga | 300 |

-continued

```
gatttagata aactatctac agtcttcatg tataattctc atcttcatca caagacagac      360
ttcaacttaa ggaggtaaag acaaggacag cgaaccctaa acagccaagt gtagaaacca      420
aactgcatca aatcagccag aaactaattg gatacttctc tactttaaaa tgacatacga      480
aacagatact accttaatgc ttgtagctgt tggtgaggcc ttagtaggga ttttaggaaa      540
tgcattcatt gcactggtaa acttcatggg ctggatgaag aataggaaga ttgcctctat      600
tgatttaatc ctctcaagtg tggccatgtc cagaatttgt ctacagtgta taatcctatt      660
agattgtatt atattggtgc agtatccaga cacctacaac agaggtaaag aaatgaggac      720
cgttgacttc ttctggacac ttaccaacca tttaagtgtc tggtttgcca cctgcctcag      780
cattttctat ttattcaaga tagcaaactt cttccaccct cttttcctct ggataaagtg      840
gagaattgac aagctaattc tcagaactct actggcatgt gtgattatct ccctgtgttt      900
tagcctccca gtcactgaaa atctgagtga tgatttcaga cgttgtgtta agacaaagga      960
gagaataaac tctactttga gatgcaaagt aaataaagct ggacatgcct ctgtcaaggt     1020
aaatctcaac ttggtcatgc tgttcccctt ttctgtgtct ctggtctcct ttctcctctt     1080
gatcctctcc ctgtggagac acaccaggca gatacaactc agtgtaacag ggtacaaaga     1140
tcccagcaca acagctcatg tgaaagccat gaaagcagta atttccttcc tggccctgtt     1200
tgttgtctac tgcctagcct ttctcatagc cacctccagc tacttatgc cagagagtga      1260 attagctgta atatggggtg agctgatagc tctaatctat ccttcaagcc attcatttat     1320
cctcatcctg gggagtagta aactaaaaca agcatctgtg agggtgcttt gtagagtaaa     1380
gaccatgtta aagggaaaaa aatattagca tcatgagcat atctgaagaa aaactatcac     1440
tttctaagag aaaggaagac acgatcatta tccgtccttt tcacatgaat attgatttca     1500
tgcagtgaca tcctcttaac aaacttaaat tgaaccttga gaaatctcat atacagcaac     1560
tttgcatgtc tctatctctg cttttctct cctttcaat atgagttgac ataaaaaata      1620
attttcagaa caaattataa cagaagaaag gcatttttca taatcagttc tgaatcactc     1680
ctccaaatgc aaagctgcct gacaaattca aaacaattgt aacagcatct cactgtcgtt     1740
tgcattcttt ggaaaagcag gtggtttgtt cttggagcct ggcttagagt tttcttctta     1800
gaccattgaa ttatgttcat gattggagaa gagtcaagta ccaagtaaca attttttattg    1860 tgaagatggg tgttcatcat gtgatttttgg ctggcctgga acttgttatg tagactagtc    1920
tgtcatcaaa cacacaaaga tctgcctgcc tcacctgcca gttctaggat tcaaggaatg     1980
caccaccaca gcttgttcaa gtgacaattc ttacaaatgt tttagaaata aataatatac     2040
tagaaattaa cactgaatgt aagtgctgtt taggtataaa ttatgattaa atgttatagt     2100
tagaaaatta tttaagatta tagatcagtg atgaaaatat tctagaataa gttttatgaa     2160
gaaactttta taagaaact ggaaaaaaat ctcttgattg catattgaaa caaatttctc      2220 caaaagaac acctacaaat ttgctctaga catctagact gtatcaaaca gtgaatatga      2280
aaatatcata acaggatata gcctttagta ttgaagacag gttcatctat attaaacctg     2340
catacatacc taaaagacta agtcaatatc ccacaaacat atttgcacta tcatgtctat     2400
tgaaacacta ttcatagtag ctaaaatatg gcacaaaact agacattcat caatagatga     2460
atcaataaag caaatgtaca tacacaagat gaaattgtat tcaggcataa agaagaatgc     2520
agtcatgtca ttagcaaaaa cataaacaga attggaggtc attgtgataa ttgaaataaa     2580
ccagacctgg aaaaaacaaa acctgtgtaa ttttctgaa gtagagaata tactcttgga      2640
tggatagatg ggtactgtta tagtataaaa tgtgtgtgtg tgtgtgtgtg tgtgtgtgtg     2700
```

-continued

```
tatttcatga aagcaagaat gggactgctt agagaaagaa aaggacaaac aggtgaaggg    2760
gtgaaagaaa aaggcaatga caaggagtaa tgatatgagc aaagtaccat tattaaacat    2820
gtgacaatat tatatagaaa cacatgattt tgtgtgccta ccaaaactgg ataataattt    2880
ttaaaatgta tctattaaaa ggaaagaaaa gaaagtgcaa gcccaggaaa gggagaaaag    2940
gaaacaatga gagagaaatg gaaaatggtg agaagtgaag agaacaaaaa gaaatggagt    3000
aagtgtggcc aggaatgaag gatctcagct atagttatcc cagtacggta atacaaatct    3060
gtgactccag cacttgacaa ggctgagaga tgtgagagag gccagttaa caaccagtct    3120 gggcttattc caagagataa aagattgggg ggaaagtatg tagaagggtt tggagggaag    3180
agagagaaga gggaaatgat gtaatgatag tacaaatcaa aagttatttt ttctaaaaaa    3240
gcaatgggac aggaaaccaa cctaacaagt aaaggtgctt ggttcacaag accagcaacc    3300
tgagtgcatc cttgctagaa tgaaattggc cttactctgg aaagcttact tcctcagtgt    3360
attcattgtt aaaattcatg tggagatttt aaagaaaaaa ggaaaaaaaa agttaaatgg    3420
tagatttgtg taggggaata ttcccctaat taattgatta gataataaag atgacaagca    3480
aattgctgtg caaaaaggaa gacaaggtct aagaggggaa gaggggacac gggaggaaaa    3540
aaaacggccc ttttaaagc aaggtgggga gtgagggaag cgagatgtag acagggaact    3600
gttagacctg gtggcagctt ctgccacctg aagattttca acatagtata gttcatgagt    3660
ttaggaagat atgttccctg cccagcggtt gtatcatctg ttgattttaa actaagattg    3720
tctggtgttt tccatttgcg gagactcaag tagaccaaag ggaaagaatg aattc         3775
```

<210> SEQ ID NO 164
<211> LENGTH: 310
<212> TYPE: PRT
<213> ORGANISM: Mus sp.
<220> FEATURE:
<223> OTHER INFORMATION: mouse T2R31 (mGR31)

<400> SEQUENCE: 164

```
Met Tyr Met Ile Leu Val Arg Ala Val Phe Ile Thr Gly Met Leu Gly
 1               5                  10                  15

Asn Met Phe Ile Gly Leu Ala Asn Cys Ser Asp Trp Val Lys Asn Gln
                20                  25                  30

Lys Ile Thr Phe Ile Asn Phe Ile Met Val Cys Leu Ala Ala Ser Arg
            35                  40                  45

Ile Ser Ser Val Leu Met Leu Phe Ile Asp Ala Thr Ile Gln Glu Leu
        50                  55                  60

Ala Pro His Phe Tyr Tyr Ser Tyr Arg Leu Val Lys Cys Ser Asp Ile
 65                  70                  75                  80

Phe Trp Val Ile Thr Asp Gln Leu Ser Thr Trp Leu Ala Thr Cys Leu
                85                  90                  95

Ser Ile Phe Tyr Leu Phe Lys Val Ala His Ile Ser His Pro Leu Phe
               100                 105                 110

Leu Trp Leu Lys Trp Arg Leu Arg Gly Val Leu Val Val Phe Leu Val
           115                 120                 125

Phe Ser Leu Phe Leu Leu Ile Ser Tyr Phe Leu Leu Leu Glu Thr Leu
       130                 135                 140

Pro Ile Trp Gly Asp Ile Tyr Val Thr Leu Lys Asn Asn Leu Thr Leu
145                 150                 155                 160

Phe Ser Gly Thr Ile Lys Thr Thr Ala Phe Gln Lys Ile Ile Val Phe
               165                 170                 175
```

```
Asp Ile Ile Tyr Leu Val Pro Phe Leu Val Ser Leu Ala Ser Leu Leu
            180                 185                 190

Leu Leu Phe Leu Ser Leu Val Lys His Ser Arg Ser Leu Asp Leu Ile
        195                 200                 205

Ser Thr Thr Ser Glu Asp Ser Arg Thr Lys Ile His Lys Lys Ala Met
    210                 215                 220

Lys Met Leu Val Ser Phe Leu Ile Leu Phe Ile Ile His Ile Phe Phe
225                 230                 235                 240

Met Gln Leu Ala Arg Trp Leu Leu Phe Leu Phe Pro Met Ser Arg Pro
                245                 250                 255

Ile Asn Phe Ile Leu Thr Leu Asn Ile Phe Ala Leu Thr His Ser Phe
            260                 265                 270

Ile Leu Ile Leu Gly Asn Ser Asn Leu Arg Gln Arg Ala Met Arg Ile
        275                 280                 285

Leu Gln His Leu Lys Ser Gln Leu Gln Glu Leu Ile Leu Ser Leu His
    290                 295                 300

Arg Phe Ser Ser Leu Tyr
305             310

<210> SEQ ID NO 165
<211> LENGTH: 4675
<212> TYPE: DNA
<213> ORGANISM: Mus sp.
<220> FEATURE:
<221> NAME/KEY: modified_base
<222> LOCATION: (1)..(4675)
<223> OTHER INFORMATION: mouse T2R31 (mGR31)
<223> OTHER INFORMATION: n = g, a, c or t

<400> SEQUENCE: 165
ctgcagcttt ctagaaatct caccagaatg tctttgtgca gctttaatag ttcctggtta     60
taccttgtca cattataagc taagacatct ttggtgccac aatatactct cactaatcag    120
agagattaga cagaaaaata agtttcttaa caactgtttt agatagggtc atgaaatgac    180
ataaaacacc aatgctaagg caatccatta tgttttctca tgaggagccc atatgtacac    240
ttgagtgtgt cttattattt ccctgagtga ttttgtaatt ttattaaaca cttaactgtg    300
attcatacta gttagttctg aaattctttt cttcatcaaa gccattaatc ctggggtttt    360
ttaaatggag aaccccaaaa caaagtgaaa tgttgtgtgt ggagcaggct gtcttcccac    420
acactaccat gagatgctca ttctgtaatt gttccccgga ataggaaatg ccctgaattc    480
aggcacacaa gagctagtct gtgcaccatg tctggttctt gcattaatac ccacttttgt    540
cacgaagctt cattgattcg catcttcaga agctggtatc attattagtt tctttcctca    600
ggtgactctg gnccaaaata ttanggcgcc ctttaaaaaa gtaaaactac aaaatttctt    660
tataattttc tttaagtttg ttataatata gcatgaccta cacacacaca cacacacaca    720
cacacacaca cacacacaca agtatgcctc tcctttcctt ctaaaaatct cacttaaagc    780
aattgtttag ctgtcttcga agtctagact gccactgtcg tgcttctagc caaacaaat     840
gcaacacata aaatgataga gctcaaaact taggaatcta tttaactgtg aagatcacgc    900
aagcaaacct gagaaacctc tagaaggaaa ccacagcaaa tcactggaga gaaggtgtta    960
atctagtaag aatagttttt attttgggta tcctttgta gattggttag ttcatccaaa   1020
atccaacttg ttagttcttc ataaattgta agtgtctcca acatcaaagc accacttctc   1080
tcttttcccc tgtatgaaga tgctttaagt acagagttac tcttttctg tactgacagt   1140
```

-continued

```
aatttaaaaa aattgttcac tcattctttt ttggtgttgt tattctgtgt tcctcaatgt    1200
tatctttttt ttttcaaaac tttcttttat aaaaagtcat acacatagca aatgcagtgc    1260
atgtttatgg aatccataac taacttattg agacttctcc tagtactttc tttgaacagt    1320
aacaaagata tctgcttcta cagagtgcag tgtttcaggt gaggaggaac atattataca    1380
aatcagtgaa aaaaaaatct gattcaaatt tgtattttaa tatatttgac tttatcactt    1440
cagatattac atcaatggga attttgaagg cacacaagtg atgatgtggg catagagact    1500
gtctgtacta gaatttaata tttcttttaa atatctttaa ataaaaatat gatgctgtat    1560
tcataaacag atctttatag attaagtatg agattaaagt tggaaaaaca aaagacaaaa    1620
acctaggact aagaatttcc ttaagtatgt gtgaatatca acctaatgga ggaagtttcc    1680
aatcaaagct gaaattacag taaaaaggag gaagataaat atggaaaagg atgattttct    1740
gtggaagttt gtttgagaac tgatccacga gacaaattgc tagaagtgtg gattcccttt    1800
tactattcaa ctgcttatag gactggatca aatgtatatg atactggtaa gagcagtatt    1860
tataactgga atgctgggaa atatgttcat tggactggca aactgctctg actgggtcaa    1920
gaaccagaaa atcaccttca tcaacttcat catggtctgt ttggcagctt ccagaatcag    1980
ctctgtgctg atgttattta ttgatgcaac catacaagaa ctagcgcctc atttctatta    2040
ttcttaccgt ctagtaaaat gctctgatat attctgggtt ataactgatc aactatcaac    2100
atggcttgcc acctgcctga gcatattcta cttattcaaa gtagcccaca tttcccatcc    2160
cctttcctc tggttgaagt ggagattgag aggtgtgctt gttgttttc ttgtattttc       2220
tttgttctta ttgatttctt atttctact gcttgaaaca cttcctattt ggggagatat      2280
ttatgtaacc cttaaaaaca atctgacctt attttcaggt acaattaaga ccactgcttt    2340
tcaaaagata attgttttg atataatata tttagtccca tttcttgtgt ccctagcatc      2400
attgctcctt ttattttgt ccttggtgaa acactcccga agccttgacc tgatttctac      2460
cacttctgaa gattccagaa ccaagattca taagaaggcc atgaaaatgc tggtgtcttt    2520
cctcattctc tttataattc acattttttt catgcagtta gcacggtggt tattattttt    2580
gtttccaatg agcaggccaa ttaatttcat cttaacatta aatatctttg ccttaactca    2640
ctcatttatt ctcatcctgg gaaatagcaa tcttcgacag agagcaatga ggatcctgca    2700
acatcttaaa agccagcttc aagagctgat cctctccctt catagattct ccagtcttta    2760
ctagaggaac agcttaacag ggagacttgg aaggtcactg gcaaattatt cttctttgat    2820
ttctttaag tactgctgaa catatatgaa ctgtccccag agcatagtgc tatcttatga    2880
gaaggatatc atctcacagt ctggttataa aacacaaacc aatctttta taatttcttt     2940
acagcattgc taataaaaga cttgtagtct caaatatttt aaagagaata attaatttta    3000
taggcaaaag gtatgaaatt acaattcaca gggaaggttc atgactcctt agatattaaa    3060
gttaattgta agccacaata ggcagaagat gagcaaaatg ttgataggag ataaataaaa    3120
tctaaagtta cggagaaaaa aaacatcaac ttgccttta gattacttta aagctctctc     3180
tctcgctctc tctctctgta tctacttact ttatatatac aaatgttttg tctgcatgta    3240
tttctttgca ccatataaat gtctaagtat ccagaangtc agcagagggc atcaaattct    3300
ctggaaagag agttacaaat tgctgtgggt aacactgggt gctgggaact aacctgagtc    3360
ctctgccaca gcaactgctc ttccctgctg agtcatgttt taagtctcca caacttaaac    3420
tcattgttga tgtggtcatt gcataatgat gaatttacat tctaaggttt gtatcatagg    3480
taggagggct ggttttaatc atattctaat gttcttatac aaacccaggt tttgtaagag    3540
```

```
actgtattct atcatgagac tctttcccca caccgccaat gtaacatttt tattaatttt    3600
gaggggaatt ttatacagtg taccctgatc acccttgctt cccactcctt gcaggtctac    3660
cctcccacca ttgctcaatc cccctaaaa gagagagaaa caaaccatgt ccaatttgtg     3720
ttggacacat actcagtgga acatggccaa accctagtg agcagttcct taaagaaaac    3780
taagctgcct ccccaccact accaccatag ggcattaact gtgaagagct acactttagc    3840
tattttatca ccaatttaaa agactgtctt caatagcttc ctctatggac tgtttctggt    3900
tttagtggga cagggagaag gggtcaagag gttgtcacag aaactttga tgtctcttat     3960 tctcagttaa agtccactgc aaaagaagtc tgctggctct aataaagctt gcaacagcat    4020
gggccagtga catcatcatg atttctggca acaatatgga ccacaaatat catggctcag    4080
gtggcattac ggaccacaga catcaacatg gtctctggca gcaagaacca gaatcttttg    4140
aggaggcttc attcagaaaa tgaattttc ttcatcccag atatactgat gttgctcaat     4200
cagagtatta gtatggttgg gcaccatatt tggggacagg accttcaata tttccaggct    4260
gctgtgtaac acattatctt tagtgtcagg tgcccttagt gtcaggacat gaccatcatg    4320
tatgcgcctg tgggcagaaa tacatctttg tactttctta cacctagcag ggtgagtagc    4380
aggagcagcg gcattaatac ttccataccct ctgggcagcc tatcaggtat catctaggca    4440
aggtaagccc agtagtggcc caaggctcct ggtgtctact tggcaacaac atgctccttt    4500
gtctgcactg ccatatctat ggctggttct ccatccctag ttctgcttct ctcaggtttt    4560
atacgactct attccacatt ctattttcc agttccatga aaccagtgtt taaaagtatc     4620
atcccataag accggccttt taaaggttat tctggagata ttgcagagtc tgcag          4675
```

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence:T2R family
      consensus sequence 1, T2R transmembrane region 1
<220> FEATURE:
<221> NAME/KEY: MOD_RES
<222> LOCATION: (2)
<223> OTHER INFORMATION: Xaa = Phe or Ala
<220> FEATURE:
<221> NAME/KEY: MOD_RES
<222> LOCATION: (3)
<223> OTHER INFORMATION: Xaa = Ile, Val or Leu
<220> FEATURE:
<221> NAME/KEY: MOD_RES
<222> LOCATION: (4)
<223> OTHER INFORMATION: Xaa = Val or Leu
<220> FEATURE:
<221> NAME/KEY: MOD_RES
<222> LOCATION: (6)
<223> OTHER INFORMATION: Xaa = Ile or Val
<220> FEATURE:
<221> NAME/KEY: MOD_RES
<222> LOCATION: (7)
<223> OTHER INFORMATION: Xaa = Leu or Val
<220> FEATURE:
<221> NAME/KEY: MOD_RES
<222> LOCATION: (10)
<223> OTHER INFORMATION: Xaa = Gly or Thr
<220> FEATURE:
<221> NAME/KEY: MOD_RES
<222> LOCATION: (13)
<223> OTHER INFORMATION: Xaa = Val or Ala
<220> FEATURE:
<221> NAME/KEY: MOD_RES
<222> LOCATION: (18)
<223> OTHER INFORMATION: Xaa = Ile or Met

```
<400> SEQUENCE: 166

Glu Xaa Xaa Xaa Gly Xaa Xaa Gly Asn Xaa Phe Ile Xaa Leu Val Asn
 1               5                  10                  15

Cys Xaa Asp Trp
            20

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence:T2R family
      consensus sequence 2, T2R transmembrane region 2
<220> FEATURE:
<221> NAME/KEY: MOD_RES
<222> LOCATION: (1)
<223> OTHER INFORMATION: Xaa = Asp or Gly
<220> FEATURE:
<221> NAME/KEY: MOD_RES
<222> LOCATION: (2)
<223> OTHER INFORMATION: Xaa = Phe or Leu
<220> FEATURE:
<221> NAME/KEY: MOD_RES
<222> LOCATION: (3)
<223> OTHER INFORMATION: Xaa = Ile or Leu
<220> FEATURE:
<221> NAME/KEY: MOD_RES
<222> LOCATION: (5)
<223> OTHER INFORMATION: Xaa = Thr or Ile
<220> FEATURE:
<221> NAME/KEY: MOD_RES
<222> LOCATION: (6)
<223> OTHER INFORMATION: Xaa = Gly, Ala or Ser
<220> FEATURE:
<221> NAME/KEY: MOD_RES
<222> LOCATION: (13)
<223> OTHER INFORMATION: Xaa = Cys, Gly or Phe

<400> SEQUENCE: 167

Xaa Xaa Xaa Leu Xaa Xaa Leu Ala Ile Ser Arg Ile Xaa Leu
 1               5                  10

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence:T2R family
      consensus sequence 3, T2R transmembrane region 3
<220> FEATURE:
<221> NAME/KEY: MOD_RES
<222> LOCATION: (3)
<223> OTHER INFORMATION: Xaa = Leu or Phe
<220> FEATURE:
<221> NAME/KEY: MOD_RES
<222> LOCATION: (4)
<223> OTHER INFORMATION: Xaa = Ser, Thr or Asn
<220> FEATURE:
<221> NAME/KEY: MOD_RES
<222> LOCATION: (5)
<223> OTHER INFORMATION: Xaa = Leu, Ile or Val
<220> FEATURE:
<221> NAME/KEY: MOD_RES
<222> LOCATION: (7)
<223> OTHER INFORMATION: Xaa = Phe or Leu
<220> FEATURE:
<221> NAME/KEY: MOD_RES
<222> LOCATION: (8)
<223> OTHER INFORMATION: Xaa = Ala or Thr
<220> FEATURE:
<221> NAME/KEY: MOD_RES
<222> LOCATION: (10)
<223> OTHER INFORMATION: Xaa = Cys, Ser or Asn
```

```
<220> FEATURE:
<221> NAME/KEY: MOD_RES
<222> LOCATION: (12)
<223> OTHER INFORMATION: Xaa = Ser, Asn or Gly
<220> FEATURE:
<221> NAME/KEY: MOD_RES
<222> LOCATION: (13)
<223> OTHER INFORMATION: Xaa = Ile or Val

<400> SEQUENCE: 168

Asn His Xaa Xaa Xaa Trp Xaa Xaa Thr Xaa Leu Xaa Xaa
 1               5                  10

<210> SEQ ID NO 169
<211> LENGTH: 18
<212> TYPE: PRT
<213> ORGANISM: Artificial Sequence
<220> FEATURE:
<223> OTHER INFORMATION: Description of Artificial Sequence:T2R family
      consensus sequence 4, T2R transmembrane region 4
<220> FEATURE:
<221> NAME/KEY: MOD_RES
<222> LOCATION: (3)
<223> OTHER INFORMATION: Xaa = Phe or Cys
<220> FEATURE:
<221> NAME/KEY: MOD_RES
<222> LOCATION: (8)
<223> OTHER INFORMATION: Xaa = Asn or Ser
<220> FEATURE:
<221> NAME/KEY: MOD_RES
<222> LOCATION: (11)
<223> OTHER INFORMATION: Xaa = His or Asn
<220> FEATURE:
<221> NAME/KEY: MOD_RES
<222> LOCATION: (12)
<223> OTHER INFORMATION: Xaa = Pro or Ser
<220> FEATURE:
<221> NAME/KEY: MOD_RES
<222> LOCATION: (13)
<223> OTHER INFORMATION: Xaa = Leu, Ile or Val
<220> FEATURE:
<221> NAME/KEY: MOD_RES
<222> LOCATION: (16)
<223> OTHER INFORMATION: Xaa = Trp or Tyr

<400> SEQUENCE: 169

Phe Tyr Xaa Leu Lys Ile Ala Xaa Phe Ser Xaa Xaa Xaa Phe Leu Xaa
 1               5                  10                  15

Leu Lys

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence:T2R family
      consensus sequence 5, T2R transmembrane region 5
<220> FEATURE:
<221> NAME/KEY: MOD_RES
<222> LOCATION: (4)
<223> OTHER INFORMATION: Xaa = Ile, Phe or Val
<220> FEATURE:
<221> NAME/KEY: MOD_RES
<222> LOCATION: (8)
<223> OTHER INFORMATION: Xaa = Lys or Arg
<220> FEATURE:
<221> NAME/KEY: MOD_RES
<222> LOCATION: (10)
<223> OTHER INFORMATION: Xaa = Ser or Thr
<220> FEATURE:
<221> NAME/KEY: MOD_RES
<222> LOCATION: (11)
<223> OTHER INFORMATION: Xaa = Lys or Arg
<220> FEATURE:
```

```
<221> NAME/KEY: MOD_RES
<222> LOCATION: (12)
<223> OTHER INFORMATION: Xaa = Gln or Lys
<220> FEATURE:
<221> NAME/KEY: MOD_RES
<222> LOCATION: (13)
<223> OTHER INFORMATION: Xaa = Met or Ile
<220> FEATURE:
<221> NAME/KEY: MOD_RES
<222> LOCATION: (14)
<223> OTHER INFORMATION: Xaa = Gln or Lys

<400> SEQUENCE: 170

Leu Leu Ile Xaa Ser Leu Trp Xaa His Xaa Xaa Xaa Xaa Xaa
 1               5                  10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence:T2R family
      consensus sequence 6, T2R transmembrane region 7
<220> FEATURE:
<221> NAME/KEY: MOD_RES
<222> LOCATION: (3)
<223> OTHER INFORMATION: Xaa = Phe or Leu
<220> FEATURE:
<221> NAME/KEY: MOD_RES
<222> LOCATION: (4)
<223> OTHER INFORMATION: Xaa = Ile or Val
<220> FEATURE:
<221> NAME/KEY: MOD_RES
<222> LOCATION: (7)
<223> OTHER INFORMATION: Xaa = Leu or Met
<220> FEATURE:
<221> NAME/KEY: MOD_RES
<222> LOCATION: (8)
<223> OTHER INFORMATION: Xaa = Gly, Ser or Thr
<220> FEATURE:
<221> NAME/KEY: MOD_RES
<222> LOCATION: (10)
<223> OTHER INFORMATION: Xaa = Pro, Ser or Asn
<220> FEATURE:
<221> NAME/KEY: MOD_RES
<222> LOCATION: (13)
<223> OTHER INFORMATION: Xaa = Lys or Arg
<220> FEATURE:
<221> NAME/KEY: MOD_RES
<222> LOCATION: (14)
<223> OTHER INFORMATION: Xaa = Gln or Arg

<400> SEQUENCE: 171

His Ser Xaa Xaa Leu Ile Xaa Xaa Asn Xaa Lys Leu Xaa Xaa
 1               5                  10

<210> SEQ ID NO 172
<211> LENGTH: 300
<212> TYPE: PRT
<213> ORGANISM: Mus sp.
<220> FEATURE:
<221> NAME/KEY: MOD_RES
<222> LOCATION: (44)
<223> OTHER INFORMATION: mT2R5
<220> FEATURE:
<221> NAME/KEY: MOD_RES
<222> LOCATION: (85)
<223> OTHER INFORMATION: Xaa = Ile or Thr
<220> FEATURE:
<221> NAME/KEY: MOD_RES
<222> LOCATION: (101)
<223> OTHER INFORMATION: Xaa = Val or Ile
<220> FEATURE:
<221> NAME/KEY: MOD_RES
<222> LOCATION: (155)
```

```
<223> OTHER INFORMATION: Xaa = Ala or Thr
<220> FEATURE:
<221> NAME/KEY: MOD_RES
<222> LOCATION: (294)
<223> OTHER INFORMATION: Xaa = Asp or Gly
<223> OTHER INFORMATION: Xaa = Arg or Leu

<400> SEQUENCE: 172

Met Leu Ser Ala Ala Glu Gly Ile Leu Leu Ser Ile Ala Thr Val Glu
  1               5                  10                  15

Ala Gly Leu Gly Val Leu Gly Asn Thr Phe Ile Ala Leu Val Asn Cys
             20                  25                  30

Met Asp Trp Ala Lys Asn Asn Lys Leu Ser Met Xaa Gly Phe Leu Leu
         35                  40                  45

Ile Gly Leu Ala Thr Ser Arg Ile Phe Ile Val Trp Leu Leu Thr Leu
     50                  55                  60

Asp Ala Tyr Ala Lys Leu Phe Tyr Pro Ser Lys Tyr Phe Ser Ser
 65                  70                  75                  80

Leu Ile Glu Ile Xaa Ser Tyr Ile Trp Met Thr Val Asn His Leu Thr
                 85                  90                  95

Val Trp Phe Ala Xaa Ser Leu Ser Ile Phe Tyr Phe Leu Lys Ile Ala
                100                 105                 110

Asn Phe Ser Asp Cys Val Phe Leu Trp Leu Lys Arg Arg Thr Asp Lys
            115                 120                 125

Ala Phe Val Phe Leu Leu Gly Cys Leu Leu Thr Ser Trp Val Ile Ser
130                 135                 140

Phe Ser Phe Val Val Lys Val Met Lys Asp Xaa Lys Val Asn His Arg
145                 150                 155                 160

Asn Arg Thr Ser Glu Met Tyr Trp Glu Lys Arg Gln Phe Thr Ile Asn
                165                 170                 175

Tyr Val Phe Leu Asn Ile Gly Val Ile Ser Leu Phe Met Met Thr Leu
                180                 185                 190

Thr Ala Cys Phe Leu Leu Ile Met Ser Leu Trp Arg His Ser Arg Gln
            195                 200                 205

Met Gln Ser Gly Val Ser Gly Phe Arg Asp Leu Asn Thr Glu Ala His
        210                 215                 220

Val Lys Ala Ile Lys Phe Leu Ile Ser Phe Ile Ile Leu Phe Val Leu
225                 230                 235                 240

Tyr Phe Ile Gly Val Ser Ile Glu Ile Cys Ile Phe Ile Pro Glu
                245                 250                 255

Asn Lys Leu Leu Phe Ile Phe Gly Phe Thr Thr Ala Ser Ile Tyr Pro
            260                 265                 270

Cys Cys His Ser Phe Ile Leu Ile Leu Ser Asn Ser Gln Leu Lys Gln
        275                 280                 285

Ala Phe Val Lys Val Xaa Gln Leu Leu Lys Phe Phe
        290                 295                 300
```

METHODS OF SCREENING MODULATORS OF T2R TASTE RECEPTORS

CROSS-REFERENCES TO RELATED APPLICATIONS

This application claims priority to and is a continuation of U.S. Ser. No. 10/962,365, filed Oct. 7, 2004, now U.S. Pat. No. 7,465,550 which is a continuation of U.S. Ser. No. 09/510,332 (now U.S. Pat. No. 7,244,584), filed Feb. 22, 2000, which is a continuation-in-part of U.S. Ser. No. 09/393,634 (now U.S. Pat. No. 6,558,910), filed Sep. 10, 1999, all of which are herein incorporated by reference in their entireties.

STATEMENT AS TO FEDERALLY SPONSORED RESEARCH AND DEVELOPMENT

This invention was made with government support under Grant No. 5R01 DC03160, awarded by the National Institutes of Health. The government has certain rights in this invention.

FIELD OF THE INVENTION

The invention provides isolated nucleic acid and amino acid sequences of taste cell specific G-protein coupled receptors, antibodies to such receptors, methods of detecting such nucleic acids and receptors, and methods of screening for modulators of taste cell specific G-protein coupled receptors.

BACKGROUND OF THE INVENTION

Taste transduction is one of the most sophisticated forms of chemotransduction in animals (see, e.g., Margolskee, *BioEssays* 15:645-650 (1993); Avenet & Lindemann, *J. Membrane Biol.* 112:1-8 (1989)). Gustatory signaling is found throughout the animal kingdom, from simple metazoans to the most complex of vertebrates; its main purpose is to provide a reliable signaling response to non-volatile ligands. Each of these modalities is though to be mediated by distinct signaling pathways mediated by receptors or channels, leading to receptor cell depolarization, generation of a receptor or action potential, and release of neurotransmitter at gustatory afferent neuron synapses (see, e.g., Roper, *Ann. Rev. Neurosci.* 12:329-353 (1989)).

Mammals are believed to have five basic taste modalities: sweet, bitter, sour, salty, and umami (the taste of monosodium glutamate) (see, e.g., Kawamura & Kare, *Introduction to Umami: A Basic Taste* (1987); Kinnamon & Cummings, *Ann. Rev. Physiol.* 54:715-731 (1992); Lindemann, *Physiol. Rev.* 76:718-766 (1996); Stewart et al., *Am. J. Physiol.* 272:1-26 (1997)). Extensive psychophysical studies in humans have reported that different regions of the tongue display different gustatory preferences (see, e.g., Hoffmann, *Menchen. Arch. Path. Anat. Physiol.* 62:516-530 (1875); Bradley et al., *Anatomical Record* 212: 246-249 (1985); Miller & Reedy, *Physiol. Behav.* 47:1213-1219 (1990)). Also, numerous physiological studies in animals have shown that taste receptor cells may selectively respond to different tastants (see, e.g., Akabas et al., *Science* 242:1047-1050 (1988); Gilbertson et al., *J. Gen. Physiol.* 100:803-24 (1992); Bernhardt et al., *J. Physiol.* 490:325-336 (1996); Cummings et al., *J. Neurophysiol.* 75:1256-1263 (1996)).

In mammals, taste receptor cells are assembled into taste buds that are distributed into different papillae in the tongue epithelium. Circumvallate papillae, found at the very back of the tongue, contain hundreds (mice) to thousands (human) of taste buds and are particularly sensitive to bitter substances. Foliate papillae, localized to the posterior lateral edge of the tongue, contain dozens to hundreds of taste buds and are particularly sensitive to sour and bitter substances. Fungiform papillae containing a single or a few taste buds are at the front of the tongue and are thought to mediate much of the sweet taste modality.

Each taste bud, depending on the species, contains 50-150 cells, including precursor cells, support cells, and taste receptor cells (see, e.g., Lindemann, *Physiol. Rev.* 76:718-766 (1996)). Receptor cells are innervated at their base by afferent nerve endings that transmit information to the taste centers of the cortex through synapses in the brain stem and thalamus. Elucidating the mechanisms of taste cell signaling and information processing is critical for understanding the function, regulation, and "perception" of the sense of taste.

Although much is known about the psychophysics and physiology of taste cell function, very little is known about the molecules and pathways that mediate these sensory signaling responses (reviewed by Gilbertson, *Current Opin. Neurobiol.* 3:532-539 (1993)). Electrophysiological studies suggest that sour and salty tastants modulate taste cell function by direct entry of $H^+$ and $Na^+$ ions through specialized membrane channels on the apical surface of the cell. In the case of sour compounds, taste cell depolarization is hypothesized to result from $H^+$ blockage of $K^+$ channels (see, e.g., Kinnamon et al., *Proc. Nat'l Acad. Sci. USA* 85: 7023-7027 (1988)) or activation of pH-sensitive channels (see, e.g., Gilbertson et al., *J. Gen. Physiol.* 100:803-24 (1992)); salt transduction may be partly mediated by the entry of $Na^+$ via amiloride-sensitive $Na^+$ channels (see, e.g., Heck et al., *Science* 223:403-405 (1984); Brand et al., *Brain Res.* 207-214 (1985); Avenet et al., *Nature* 331: 351-354 (1988)).

Sweet, bitter, and umami transduction are believed to be mediated by G-protein-coupled receptor (GPCR) signaling pathways (see, e.g., Striem et al., *Biochem. J.* 260:121-126 (1989); Chaudhari et al., *J. Neuros.* 16:3817-3826 (1996); Wong et al., *Nature* 381: 796-800 (1996)). Confusingly, there are almost as many models of signaling pathways for sweet and bitter transduction as there are effector enzymes for GPCR cascades (e.g., G protein subunits, cGMP phosphodiesterase, phospholipase C, adenylate cyclase; see, e.g., Kinnamon & Margolskee, *Curr. Opin. Neurobiol.* 6:506-513 (1996)). However, little is known about the specific membrane receptors involved in taste transduction, or many of the individual intracellular signaling molecules activated by the individual taste transduction pathways. Identification of such molecules is important given the numerous pharmacological and food industry applications for bitter antagonists, sweet agonists, and other modulators of taste.

One taste-cell specific G protein that has been identified is called Gustducin (McLaughin et al., *Nature* 357:563-569 (1992)). This protein is proposed to be involved in the detection of certain bitter and sweet tastes since gustducin knockout mice show decreased sensitivity to some sweet and bitter tastants (Wong et al., *Nature* 381:796-800 (1996)), and because gustducin is expressed in a significant subset of cells from all types of taste papillae (McLaughlin et al., *Nature* 357:563-569 (1992)). In addition, gustducin can be activated in vitro by stimulating taste membranes with bitter compounds, likely through the activation of bitter receptors (Ming et al, *PNAS* 95:8933-8938 (1998)).

Recently, two novel GPCRs were identified and found to be specifically expressed in taste cells. While these receptor proteins, called TR1 and TR2, appear to be directly involved in taste reception (Hoon et al., *Cell* 96:541-551 (1999)), they are only expressed in a fraction of mammalian taste receptor cells. For example, neither of the genes are extensively expressed in Gustducin-expressing cells. Thus, it is clear that additional taste-involved GPCRs remain to be discovered.

Genetic studies in mammals have identified numerous loci that are involved in the detection of taste. For example, psychophysical tasting studies have shown that humans can be categorized as tasters, non-tasters, and super-tasters for the bitter substance PROP (6-n-propylthiouracil), and that PROP tasting may be conferred by a dominant allele, with non-tasters having two recessive alleles and tasters having at least one dominant allele (see Bartoshuk et al., *Physiol Behav* 56(6):1165-71; 58:203-204 (1994)). Recently, a locus involved in PROP tasting has been mapped to human interval 5p15 (Reed et al., *Am. J. Hum. Genet.*, 64(5):1478-80 (1999)). The PROP tasting gene present at the 5p15 locus has yet to be described, however.

In addition, a number of genes involved in taste have been mapped in mice. For example, a cluster of genes involved in bitter-taste detection has been mapped to a region of chromosome 6 in mice (Lush et al., *Genet Res.* 66:167-174 (1995)).

The identification and isolation of novel taste receptors and taste signaling molecules would allow for new methods of pharmacological and genetic modulation of taste transduction pathways. For example, the availability of receptor and channel molecules would permit the screening for high affinity agonists, antagonists, inverse agonists, and modulators of taste cell activity. Such taste modulating compounds would be useful in the pharmaceutical and food industries to customize taste. In addition, such taste cell specific molecules can serve as invaluable tools in the generation of taste topographic maps that elucidate the relationship between the taste cells of the tongue and taste sensory neurons leading to taste centers in the brain.

SUMMARY OF THE INVENTION

The present invention thus provides novel nucleic acids encoding a family of taste-cell specific G-protein coupled receptors. These nucleic acids and the polypeptides that they encode are referred to as the "T2R" family of G-protein coupled taste receptors. These receptors are also referred to as the "SF" family of G-protein coupled taste receptors. This novel family of GPCRs includes components of the taste transduction pathway. In particular, members of this family are involved in the detection of bitter tastes.

In one aspect, the present invention provides a method for identifying a compound that modulates taste signaling in taste cells, the method comprising the steps of: (i) contacting a taste transduction G-protein coupled receptor polypeptide with the compound, the polypeptide comprising at least about 50% amino acid identity to a sequence selected from the group consisting of SEQ ID NO:166, SEQ ID NO:167, SEQ ID NO:168, SEQ ID NO:169, SEQ ID NO:170, and SEQ ID NO:171; and (ii) determining the functional effect of the compound upon the polypeptide.

In another aspect, the present invention provides a method for identifying a compound that modulates taste signaling in taste cells, the method comprising the steps of: (i) contacting a taste transduction G-protein coupled receptor polypeptide with the compound, the polypeptide comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164; and (ii) determining the functional effect of the compound upon the polypeptide.

In another aspect, the present invention provides a method for identifying a compound that modulates taste signaling in taste cells, the method comprising the steps of: (i) contacting a polypeptide comprising an extracellular domain or transmembrane region, or combination thereof, of a taste transduction G-protein coupled receptor with the compound, the extracellular domain or transmembrane region comprising greater than about 60% amino acid sequence identity to the extracellular domain or transmembrane region of a polypeptide comprising a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ D NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ D NO:97, SEQ ID NO:99, SEQ ID NO:101, SEQ ID NO:103, SEQ ID NO:105, SEQ ID NO:107, SEQ ID NO:109, SEQ ID NO:11, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164; and (ii) determining the functional effect of the compound upon the extracellular domain or transmembrane region.

In one embodiment, the polypeptide has G-protein coupled receptor activity. In another embodiment, the functional effect is a chemical effect. In another embodiment, the functional effect is a physical effect. In another embodiment, the functional effect is determined by measuring binding of the compound to an extracellular domain of the polypeptide. In another embodiment, the functional effect is determined by measuring radiolabeled GTP binding to the polypeptide. In another embodiment, the polypeptide is recombinant. In another embodiment, the polypeptide comprises an extracellular domain or transmembrane region or a combination of an extracellular domain and transmembrane region that is covalently linked to a heterologous polypeptide, forming a chimeric polypeptide. In another embodiment, the polypeptide is linked to a solid phase, either covalently or non-covalently. In another embodiment, the polypeptide is from a rat, a mouse, or a human.

In another embodiment, the polypeptide is expressed in a cell or a cell membrane. In another embodiment, the cell is a eukaryotic cell. In another embodiment, the functional effect is measured by determining changes in the electrical activity of a cell expressing the polypeptide. In another embodiment, the functional effect of the compound upon the polypeptide is determined by measuring changes in intracellular cAMP, cGMP, IP3, or $Ca^{2+}$ in a cell expressing the polypeptide. In another embodiment, a change in intracellular $Ca^{2+}$ in the cell is detected by detecting FURA-2 dependent fluorescence in the cell. In another embodiment, the cell is a eukaryotic cell. In another embodiment, the cell is an HEK-293 cell. In another embodiment, the polypeptide is a fusion protein comprising at least about 20 consecutive N-terminal amino acids of a rhodopsin protein. In another embodiment, the rhodopsin protein is a bovine rhodopsin. In another embodiment, the cell comprises Gal 5. In another embodiment, the polypeptide is expressed in a cell, and the polypeptide is contacted with the compound in the presence of a bitter tastant, wherein a difference in the functional effect of the bitter tastant on the cell in the presence of the compound and the functional effect of the bitter tastant on the cell in the absence of the compound indicates that the compound is capable of modulating taste signaling in taste cells.

In another embodiment, the polypeptide comprises an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In another aspect, the present invention provides an isolated nucleic acid encoding a taste transduction G-protein coupled receptor, the receptor comprising greater than about 50% amino acid sequence identity to a sequence selected from the group consisting of SEQ ID NO:166, SEQ ID NO:167, SEQ ID NO:168, SEQ ID NO:169, SEQ ID NO:170, and SEQ ID NO:171.

In another aspect, the present invention provides an isolated nucleic acid encoding a taste transduction G-protein coupled receptor, wherein the nucleic acid is amplified by primers that selectively hybridize to the same sequence as degenerate primer sets encoding amino acid sequences selected from the group consisting of SEQ ID NO:166, SEQ ID NO:167, SEQ ID NO:168, SEQ ID NO:169, SEQ ID NO:170, and SEQ ID NO:171.

In another aspect, the present invention provides an isolated nucleic acid encoding a taste transduction G-protein coupled receptor, the receptor comprising greater than about 60% amino acid sequence identity to a sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In another aspect, the present invention provides an isolated nucleic acid encoding a taste transduction G-protein coupled receptor, wherein the nucleic acid specifically hybridizes under highly stringent conditions to a nucleic acid having a nucleotide sequence selected from the group consisting of SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ D NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ D NO:159, SEQ ID NO:161, SEQ ID NO:163, and SEQ ID NO:165, but not to a nucleic acid having a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, and SEQ ID NO:63.

In another aspect, the present invention provides an isolated nucleic acid encoding a taste transduction G-protein coupled receptor, the receptor comprising greater than about 60% amino acid identity to a polypeptide having an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164, wherein the nucleic acid selectively hybridizes under moderately stringent hybridization conditions to a nucleotide sequence having a nucleotide sequence selected from the group consisting of SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ ID NO:159, SEQ ID NO:161, SEQ ID NO:163, and SEQ ID NO:165 but not to a nucleic acid having a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ D NO:43, SEQ ID NO:45, SEQ ID NO:52, SEQ ID NO:54, SEQ ID NO:57, SEQ ID NO:61, and SEQ ID NO:63.

In another aspect, the present invention provides an isolated nucleic acid encoding an extracellular domain or transmembrane region or a combination thereof of a taste transduction G-protein coupled receptor, the extracellular domain or transmembrane region having greater than about 60% amino acid sequence identity to the extracellular domain or transmembrane region of a polypeptide comprising an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In one embodiment, the nucleic acid encodes a receptor that specifically binds to polyclonal antibodies generated against a polypeptide having an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164, but not to polyclonal antibodies generated against a polypeptide having an amino acid sequence selected from the group consisting of SEQ ID NO:1, SEQ ID NO:3, SEQ ID NO:5; SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, and SEQ ID NO:76.

In another embodiment, the nucleic acid encodes a receptor comprising an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, SEQ ID NO:164, SEQ ID NO:166, SEQ ID NO:167, SEQ ID NO:168, SEQ ID NO:169, SEQ ID NO:170, and SEQ ID NO:171.

In another embodiment, the nucleic acid comprises a nucleotide sequence selected from the group consisting of SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ ID NO:159, SEQ ID NO:161, SEQ ID NO:163, and SEQ ID NO:165.

In another embodiment, the nucleic acid encodes a receptor that has G-protein coupled receptor activity. In another embodiment, the nucleic acid is from a rat or a mouse.

In another embodiment, the nucleic acid encodes an extracellular domain or transmembrane region or combination thereof linked to a heterologous polypeptide, forming a chimeric polypeptide. In another embodiment, the nucleic acid encodes the extracellular domain of a polypeptide comprising an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, SEQ ID NO:164, SEQ ID NO:166, SEQ ID NO:167, SEQ ID NO:168, SEQ ID NO:169, SEQ ID NO:170, and SEQ ID NO:171.

In another aspect, the present invention provides an expression vector comprising any of the above nucleic acids. In another aspect, the present invention provides isolated cells comprising the expression vector.

In another aspect, the present invention provides an isolated taste transduction G-protein coupled receptor, the receptor comprising greater than about 50% amino acid sequence identity to a sequence selected from the group consisting of SEQ ID NO:166, SEQ ID NO:167, SEQ ID NO:168, SEQ ID NO:169, SEQ ID NO:170, and SEQ ID NO:171.

In another aspect, the present invention provides an isolated taste transduction G-protein coupled receptor, the receptor comprising greater than about 60% amino acid sequence identity to a sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:11, SEQ ID NO:113, SEQ D NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In one embodiment, the receptor comprises an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, SEQ ID NO:164, SEQ ID NO:166, SEQ ID NO:167, SEQ ID NO:168, SEQ ID NO:169, SEQ ID NO:170, and SEQ ID NO:171.

In another embodiment, the receptor specifically binds to polyclonal antibodies generated against a polypeptide having an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164, but not to polyclonal antibodies generated against a polypeptide having an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, and SEQ ID NO:76. In another embodiment, the receptor has G-protein coupled receptor activity. In another embodiment, the receptor is from a rat or a mouse.

In another aspect, the present invention provides an isolated polypeptide comprising an extracellular domain or a transmembrane region or a combination thereof of a taste transduction G-protein coupled receptor, the extracellular domain or transmembrane region comprising greater than about 60% amino acid sequence identity to the extracellular domain or transmembrane region of a polypeptide comprising an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In one embodiment, the polypeptide encodes the extracellular domain or transmembrane region of a polypeptide comprising an amino acid sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:107, SEQ ID NO:109, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, SEQ ID NO:164, SEQ ID NO:166, SEQ ID NO:167, SEQ ID NO:168, SEQ ID NO:169, SEQ ID NO:170, and SEQ ID NO:171. In another embodiment, the extracellular domain or transmembrane region is covalently linked to a heterologous polypeptide, forming a chimeric polypeptide.

In one aspect, the present invention provides an antibody that selectively binds to the receptor comprising greater than about 60% amino acid sequence identity to a sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In another aspect, the present invention provides an expression vector comprising a nucleic acid encoding a taste transduction G-protein coupled receptor, wherein the receptor is expressed in a taste cell, the receptor comprising greater than about 60% amino acid sequence identity to a sequence selected from the group consisting of SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164.

In another aspect, the present invention provides a host cell transfected with the expression vector.

In another aspect, the present invention provides an expression cassette comprising a polynucleotide sequence that encodes a human taste transduction G protein coupled receptor, operably linked to a heterologous promoter, wherein the receptor comprises an amino acid sequence comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, and SEQ ID NO:76.

In one embodiment, the receptor comprises an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, and SEQ ID NO:76.

In another aspect, the present invention provides an isolated eukaryotic cell comprising the expression cassette.

BRIEF DESCRIPTION OF THE DRAWINGS

Figure 8:
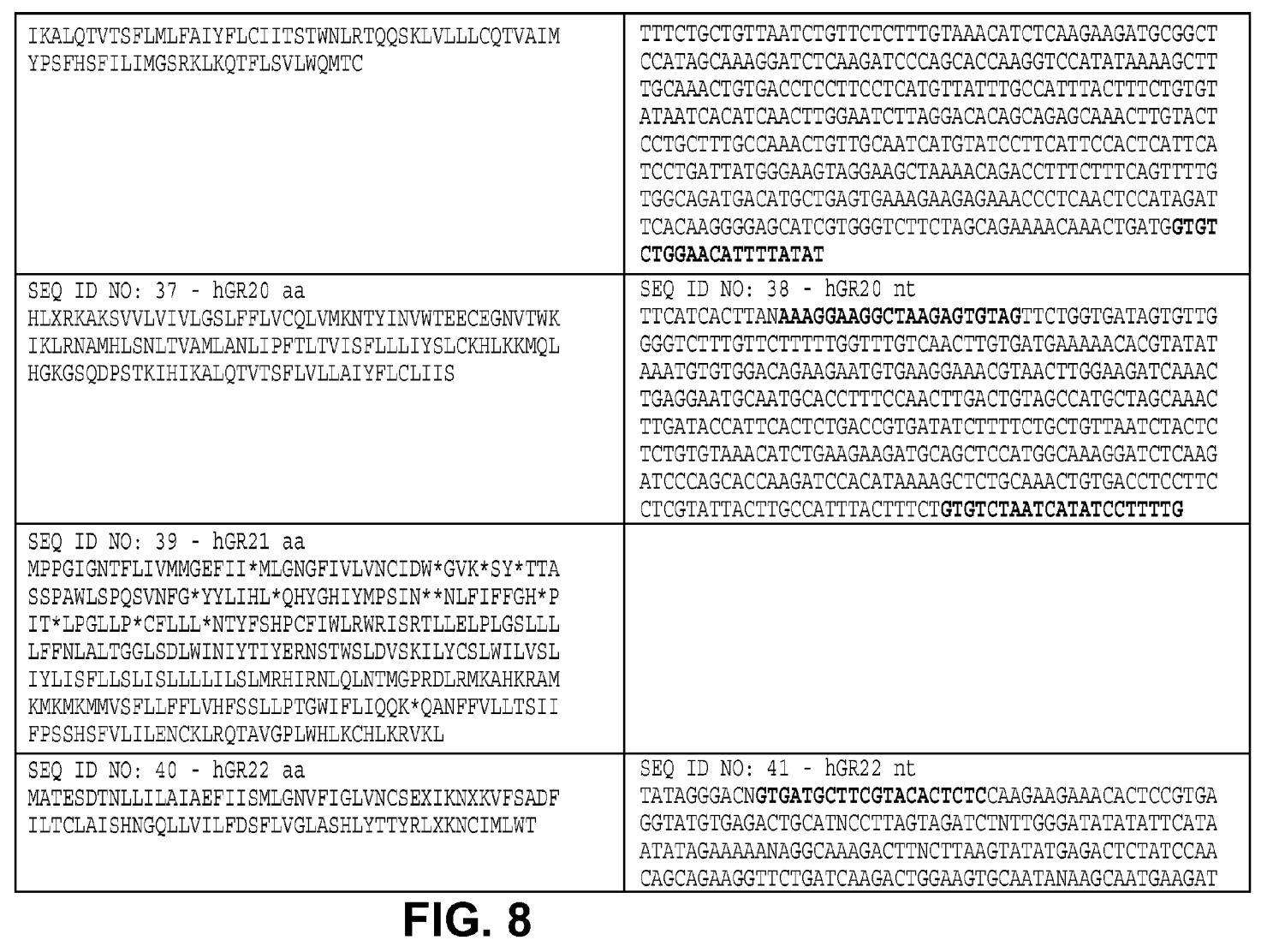

FIG. 8 provides a table including nucleic acid and protein sequences for a number of human, rat, and mouse T2R family members.

DETAILED DESCRIPTION OF THE INVENTION

I. Introduction

Figure 1:
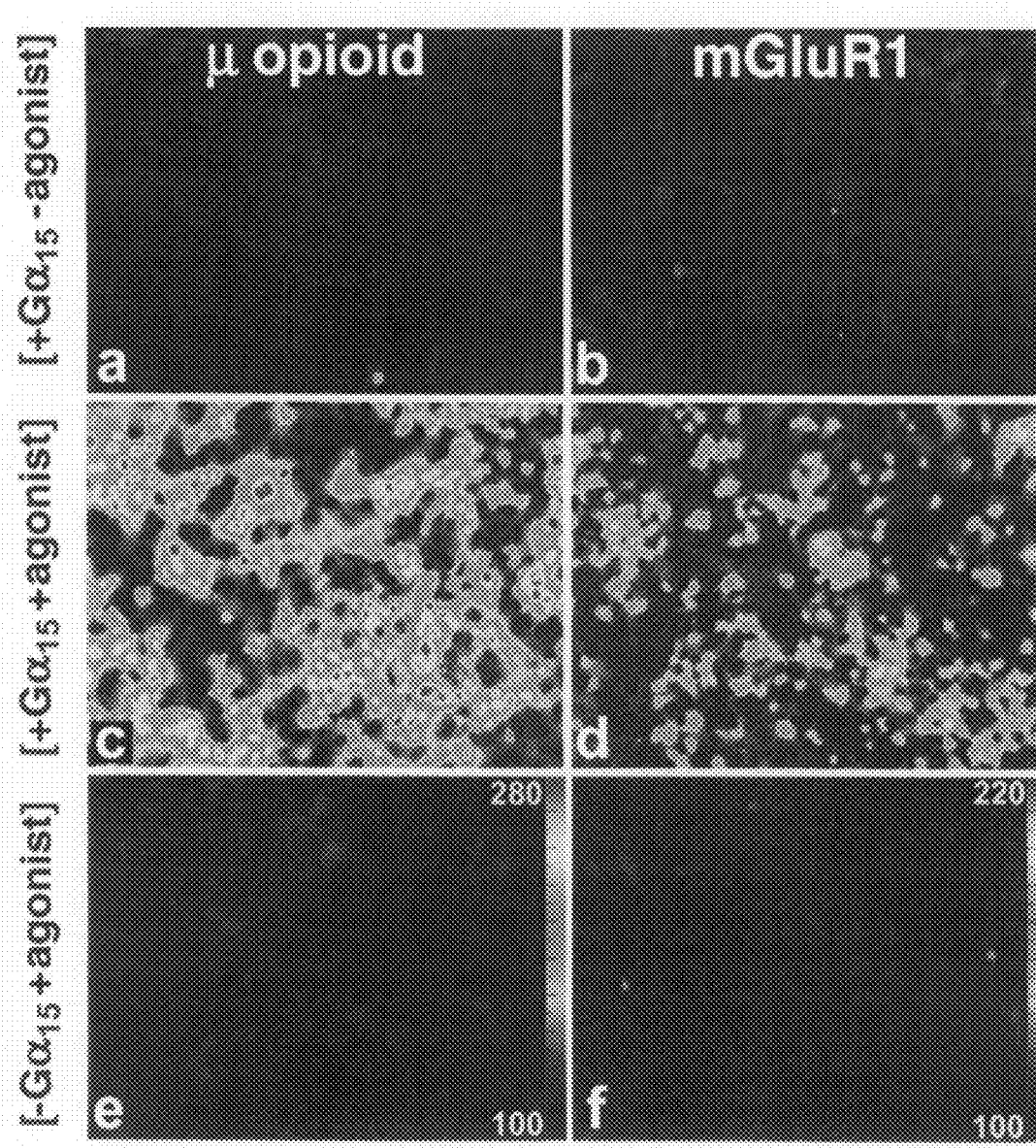
FIG. 1a-1f demonstrate that Gα15 couples the activation of μ opioid receptor and mG1R1 receptor to the release of intracellular calcium. HEK-293 cells were transiently transfected with the Gαi coupled μ opioid receptor or the Gαq coupled mG1uR1 receptor. Transfected cells containing Gα15 were assayed for increases in [Ca2+]i before (a, b) and after (c, d) the addition of receptor agonists: (c) 10 μM DAMGO and (d) 20 μM trans (±) 1-amino-1,3 cyclopentane dicarboxylic acid, (ACPD). Ligand- and receptor-dependent increase in [Ca2+]i were dependent on Gα15 (panels e, f). Scales indicate [Ca2+]i (nM) determined from FURA-2 emission ratios.

The present invention provides nucleic acids encoding a novel family of taste cell specific G-protein coupled receptors. These nucleic acids and the receptors that they encode are referred to as members of the "T2R" family of taste cell specific G protein coupled receptors. These taste cell specific GPCRs are components of the taste transduction pathway, e.g., the bitter taste transduction pathway, and are involved in the taste detection of substances such as the bitter substances 6-n-propylthiouracil (PROP), sucrose octaacetate (soa), raffinose undecaacetate (roa), cycloheximide (cyx), denatonium, copper glycinate (Glb), and quinine (qui).

These nucleic acids provide valuable probes for the identification of taste cells, as the nucleic acids are specifically expressed in taste cells. For example, probes for T2R polypeptides and proteins can be used to identity taste cells present in foliate, circumvallate, and fungiform papillae, as well as taste cells present in the geschmackstreifen and epiglottis. In particular, T2R probes are useful to identify bitter sensing, gustducin expressing taste cells. They also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors.

The invention also provides methods of screening for modulators, e.g., activators, inhibitors, stimulators, enhancers, agonists, and antagonists, of these novel taste cell GPCRs. Such modulators of taste transduction are useful for pharmacological and genetic modulation of taste signaling pathways. These methods of screening can be used to identify high affinity agonists and antagonists of taste cell activity. These modulatory compounds can then be used in the food and pharmaceutical industries to customize taste, for example, to decrease the bitter taste of foods or drugs. Thus, the invention provides assays for taste modulation, where members of the T2R family act as direct or indirect reporter molecules for the effect of modulators on taste transduction. GPCRs can be used in assays, e.g., to measure changes in ligand binding, ion concentration, membrane potential, current flow, ion flux, transcription, signal transduction, receptor-ligand interactions, second messenger concentrations, in vitro, in vivo, and ex vivo. In one embodiment, members of the T2R family can be used as indirect reporters via attachment to a second reporter molecule such as green fluorescent protein (see, e.g., Mistili & Spector, Nature Biotechnology 15:961-964 (1997)). In another embodiment, T2R family members are recombinantly expressed in cells, and modulation of taste transduction via GPCR activity is assayed by measuring changes in $Ca^{2+}$ levels and other intracellular messages such as cAMP, cGMP, and IP3.

In a preferred embodiment, a T2R polypeptide is expressed in a eukaryotic cell as a chimeric receptor with a heterologous, chaperone sequence that facilitates its maturation and targeting through the secretory pathway. In a preferred embodiment, the heterologous sequence is a rhodopsin sequence, such as an N-terminal fragment of a rhodopsin. Such chimeric T2R receptors can be expressed in any eukaryotic cell, such as HEK-293 cells. Preferably, the cells comprise a functional G protein, e.g., Gα15, that is capable of coupling the chimeric receptor to an intracellular signaling pathway or to a signaling protein such as phospholipase Cβ. Activation of such chimeric receptors in such cells can be detected using any standard method, such as by detecting changes in intracellular calcium by detecting FURA-2 dependent fluorescence in the cell.

Methods of assaying for modulators of taste transduction include in vitro ligand binding assays using T2R polypeptides, portions thereof such as the extracellular domain or transmembrane region or combination thereof, or chimeric proteins comprising one or more domains of a T2R family member; oocyte or tissue culture cell T2R gene expression, or expression of T2R fragments or fusion proteins, such as rhodopsin fusion proteins; transcriptional activation of T2R genes; phosphorylation and dephosphorylation of T2R family members; G-protein binding to GPCRs; ligand binding assays; voltage, membrane potential and conductance changes; ion flux assays; changes in intracellular second messengers such as cGMP, cAMP and inositol triphosphate; changes in intracellular calcium levels; and neurotransmitter release.

Finally, the invention provides methods of detecting T2R nucleic acid and protein expression, allowing investigation of taste transduction regulation and specific identification of taste receptor cells. T2R family members also provide useful nucleic acid probes for paternity and forensic investigations. T2R genes are also useful as a nucleic acid probe for identifying taste receptor cells, such as foliate, fungiform, circumvallate, geschmackstreifen, and epiglottis taste receptor cells, in particular bitter-taste receptive, gustducin expressing cells. T2R receptors can also be used to generate monoclonal and polyclonal antibodies useful for identifying taste receptor cells. Taste receptor cells can be identified using techniques such as reverse transcription and amplification of mRNA, isolation of total RNA or poly A$^+$ RNA, northern blotting, dot blotting, in situ hybridization, RNase protection, S1 digestion, probing DNA microchip arrays, western blots, and the like.

The T2R genes comprise a large family of related taste cell specific G-protein coupled receptors. Within the genome, these genes are present either alone or within one of several gene clusters. One gene cluster, located at human genomic region 12p13, comprises at least 9 genes, and a second cluster, located at 7q31, comprises at least 4 genes. In total, more than 50 distinct T2R family members have been identified, including several putative pseudogenes. It is estimated that the human genome may contain as many as 80-120 distinct T2R genes, encoding as many as 40-80 functional human receptors.

Some of the T2R genes have been associated with previously mapped mammalian taste-specific loci. For example, the human T2R01 is located at human interval 5p15, precisely where the locus underlying the ability to taste the substance PROP has previously been mapped. In addition, the human gene cluster found at genomic region 12p13 corresponds to a region of mouse chromosome 6 that has been shown to contain numerous bitter-tasting genes, including sucrose octaacetate, ruffinose acetate, cycloheximide, and quinine (see, e.g., Lush et al., *Genet. Res.* 6:167-174 (1995)). These associations indicate that the T2R genes are involved in the taste detection of various substances, in particular bitter substances. In addition, as shown in Example 7, infra, mouse T2R5 is specifically receptive to cycloheximide, and mutations in the mT2R5 gene produce a Cyx phenotype. Similarly, human T2R 4 and mouse T2R8 are specifically receptive to both denatonium and PROP).

Functionally, the T2R genes comprise a family of related seven transmembrane G-protein coupled receptors involved in taste transduction, which interact with a G-protein to mediate taste signal transduction (see, e.g., Fong, *Cell Signal* 8:217 (1996); Baldwin, *Curr. Opin. Cell Biol.* 6:180 (1994)). In particular, T2Rs interact in a ligand-specific manner with the G protein Gustducin.

Structurally, the nucleotide sequence of T2R family members (see, e.g., SEQ ID NOS:2, 4, 6, 8, 10, 12, 14, 16, 18, 20, 23, 25, 27, 29, 31, 34, 36, 38, 41, 43, 45, 52, 54, 57, 61, 63, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 157, 159, 161, 163, and 165, isolated from rats, mice, and humans) encodes a family of related polypeptides comprising an extracellular domain, seven transmembrane domains, and a cytoplasmic domain. Related T2R family genes from other species share at least about 60% nucleotide sequence identity over a region of at least about 50 nucleotides in length, optionally 100, 200, 500, or more nucleotides in length, to SEQ ID NO: 2, 4, 6, 8, 10, 12, 14, 16, 18, 20, 23, 25, 27, 29, 31, 34, 36, 38, 41, 43, 45, 52, 54, 57, 61, 63, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 157, 159, 161, 163, or 165, or encode polypeptides sharing at least about 60% amino acid sequence identity over an amino acid region at least about 25 amino acids in length, optionally 50 to 100 amino acids in length to SEQ ID NO:1, 3, 5, 7, 9, 11, 13, 15, 17, 19, 21, 22, 24, 26, 28, 30, 32, 33, 35, 37, 39, 40, 42, 44, 46-51, 53, 55, 56, 58-60, 62, 64-77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 158, 160, 162, or 164. T2R genes are specifically expressed in taste cells.

Several consensus amino acid sequences or domains have also been identified that are characteristic of T2R family members. For example, T2R family members typically comprise a sequence having at least about 50%, optionally 55%, 60%, 65%, 70%, 75%, 80%, 85%, 90%, 95%, or higher, identity to SEQ ID NO:166 (corresponding, e.g., to amino acid positions 16-35 in SEQ ID NO:1, and to T2R transmembrane region 1), SEQ ID NO:167 (corresponding, e.g., to amino acid positions 45-58 in SEQ ID NO:1, and to T2R transmembrane region 2), SEQ ID NO:168 (corresponding, e.g., to amino acid positions 89-101 in SEQ ID NO:1, and to T2R transmembrane region 3), SEQ ID NO:169 (corresponding, e.g., to amino acid positions 102-119 in SEQ ID NO:1, and to T2R transmembrane region 3), SEQ ID NO:170 (corresponding, e.g., to amino acid positions 196-209 in SEQ ID NO:1, and to T2R transmembrane region 5), or SEQ ID NO:171 (corresponding, e.g., to amino acid positions 273-286 in SEQ ID NO:35, and to T2R transmembrane region 7). These conserved domains thus can be used to identify members of the T2R family, by % identity, specific hybridization or amplification, or specific binding by antibodies raised against a domain.

Several T2R genes represent apparent orthologs of each other. For example, human T2R01 (SEQ ID NOs:1, 2), rat T2R01 (SEQ ID NOs:77, 78), and mouse T2R19 (SEQ ID NOs:141, 142), are apparent orthologs. In addition, rat T2R08 (SEQ ID NOs:91, 92) and mouse T2R02 (SEQ ID NOs:107, 108) are about 74% identical at the amino acid sequence level, and are each at least about 50% identical to human T2R13 (SEQ ID NOs:24, 25). Rat T2R03 (SEQ ID NOs:81, 82) and mouse T2R18 (SEQ ID NOs:139, 140) are about 92% identical, and are each at least about 50% identical to human T2R16 (SEQ ID NOs:30, 31). Finally, human T2R04 (SEQ ID NOs:7, 8) and mouse T2R08 (SEQ ID NOs: 119, 120) are about 67% identical to each other.

The present invention also provides polymorphic variants of the T2R proteins provided herein. For example, in the rat T2R depicted in SEQ ID NO:77: variant #1, in which an isoleucine residue is substituted for a leucine residue at amino acid position 7; and variant #2, in which an alanine residue is substituted for a glycine residue at amino acid position 20.

The present invention also provides polymorphic variants of the T2R protein depicted in SEQ ID NO:79: variant #1, in which a tyrosine residue is substituted for a phenylalanine residue at amino acid position 2; and variant #2, in which a valine residue is substituted for an isoleucine residue at amino acid position 62.

The present invention also provides polymorphic variants of the T2R protein depicted in SEQ ID NO:81: variant #1, in which a glutamine residue is substituted for an asparagine residue at amino acid position 179; and variant #2, in which a cysteine residue is substituted for a methionine residue at amino acid position 183.

The present invention also provides polymorphic variants of the T2R protein depicted in SEQ ID NO:83: variant #1, in which a glycine residue is substituted for an alanine residue at amino acid position 4; and variant #2, in which a leucine residue is substituted for an isoleucine residue at amino acid position 63.

The present invention also provides polymorphic variants of the T2R protein depicted in SEQ ID NO:85: variant #1, in which a valine residue is substituted for an isoleucine residue at amino acid position 56; and variant #2, in which a methionine residue is substituted for a cysteine residue at amino acid position 57.

The present invention also provides polymorphic variants of the T2R protein depicted in SEQ ID NO:87: variant #1, in which an isoleucine residue is substituted for a valine residue at amino acid position 4; and variant #2, in which an alanine residue is substituted for a glycine residue at amino acid position 5.

The present invention also provides polymorphic variants of the T2R protein depicted in SEQ ID NO:89: variant #1, in which an alanine residue is substituted for a glycine residue at amino acid position 79; and variant #2, in which an arginine residue is substituted for a lysine residue at amino acid position 127.

The present invention also provides polymorphic variants of the T2R protein depicted in SEQ ID NO:91: variant #1, in which a leucine residue is substituted for a valine residue at amino acid position 28; and variant #2, in which an arginine residue is substituted for a lysine residue at amino acid position 80.

The present invention also provides polymorphic variants of the T2R protein depicted in SEQ ID NO:93: variant #1, in which an arginine residue is substituted for a lysine residue at amino acid position 75; and variant #2, in which a methionine residue is substituted for a cysteine residue at amino acid position 251.

The present invention also provides polymorphic variants of the T2R protein depicted in SEQ ID NO:95: variant #1, in which a threonine residue is substituted for a serine residue at amino acid position 48; and variant #2, in which an isoleucine residue is substituted for a valine residue at amino acid position 49.

The present invention also provides polymorphic variants of the T2R protein depicted in SEQ ID NO:97: variant #1, in which a glutamic acid residue is substituted for an aspartic acid residue at amino acid position 25; and variant #2, in which an isoleucine residue is substituted for a leucine residue at amino acid position 100.

The present invention also provides polymorphic variants of the T2R protein depicted in SEQ ID NO:99: variant #1, in which a serine residue is substituted for a threonine residue at amino acid position 4; and variant #2, in which an isoleucine residue is substituted for a valine residue at amino acid position 74;

The present invention also provides polymorphic variants of the T2R protein depicted in SEQ ID NO:101: variant #1, in which an asparagine residue is substituted for a glutamine residue at amino acid position 9; and variant #2, in which a tryptophan residue is substituted for a tyrosine residue at amino acid position 18.

The present invention also provides polymorphic variants of the T2R protein depicted in SEQ ID NO:103: variant #1, in which a threonine residue is substituted for a serine residue at amino acid position 26; and variant #2, in which an isoleucine residue is substituted for a valine residue at amino acid position 8.

The present invention also provides polymorphic variants of the T2R protein depicted in SEQ ID NO:105: variant #1, in which an isoleucine residue is substituted for a leucine residue at amino acid position 4; and variant #2, in which an arginine residue is substituted for a lysine residue at amino acid position 46.

The present invention also provides polymorphic variants of the T2R protein depicted in SEQ ID NO:107: variant #1, in which a threonine residue is substituted for a serine residue at amino acid position 3; and variant #2, in which an isoleucine residue is substituted for a valine residue at amino acid position 28.

The present invention also provides polymorphic variants of the T2R protein depicted in SEQ ID NO:109: variant #1, in which an isoleucine residue is substituted for a leucine residue at amino acid position 26; and variant #2, in which an arginine residue is substituted for a lysine residue at amino acid position 50.

The present invention also provides polymorphic variants of the T2R protein depicted in SEQ ID NO:111: variant #1, in which a glycine residue is substituted for an alanine residue at amino acid position 4; and variant #2, in which a phenylalanine residue is substituted for a tryptophan residue at amino acid position 60.

The present invention also provides polymorphic variants of the T2R protein depicted in SEQ ID NO:113: variant #1, in which an isoleucine residue is substituted for a leucine residue at amino acid position 62; and variant #2, in which an alanine residue is substituted for a glycine residue at amino acid position 244.

The present invention also provides polymorphic variants of the T2R protein depicted in SEQ ID NO:115: variant #1, in which a serine residue is substituted for a threonine residue at amino acid position 3; and variant #2, in which a lysine residue is substituted for an arginine residue at amino acid position 123.

The present invention also provides polymorphic variants of the T2R protein depicted in SEQ ID NO:117: variant #1, in which an asparagine residue is substituted for a glutamine residue at amino acid position 65; and variant #2, in which a leucine residue is substituted for an isoleucine residue at amino acid position 68.

The present invention also provides polymorphic variants of the T2R protein depicted in SEQ ID NO:119: variant #1, in which an isoleucine residue is substituted for a leucine residue at amino acid position 2; and variant #2, in which an aspartic acid residue is substituted for a glutamic acid residue at amino acid position 4.

The present invention also provides polymorphic variants of the T2R protein depicted in SEQ ID NO:121: variant #1, in which an isoleucine residue is substituted for a leucine residue at amino acid position 16; and variant #2, in which an arginine residue is substituted for a lysine residue at amino acid position 46.

The present invention also provides polymorphic variants of the T2R protein depicted in SEQ ID NO:123: variant #1, in which a threonine residue is substituted for a serine residue at amino acid position 9; and variant #2, in which a tryptophan residue is substituted for a phenylalanine residue at amino acid position 14.

The present invention also provides polymorphic variants of the T2R protein depicted in SEQ ID NO:125: variant #1, in which an isoleucine residue is substituted for a leucine residue at amino acid position 24; and variant #2, in which an arginine residue is substituted for a lysine residue at amino acid position 53.

The present invention also provides polymorphic variants of the T2R protein depicted in SEQ ID NO:127: variant #1, in which a phenylalanine residue is substituted for a tryptophan residue at amino acid position 51; and variant #2, in which an arginine residue is substituted for a lysine residue at amino acid position 101.

The present invention also provides polymorphic variants of the T2R protein depicted in SEQ ID NO:129: variant #1, in which an isoleucine residue is substituted for a valine residue at amino acid position 4; and variant #2, in which a glycine residue is substituted for an alanine residue at amino acid position 52.

The present invention also provides polymorphic variants of the T2R protein depicted in SEQ ID NO:131: variant #1, in which an arginine residue is substituted for a lysine residue at amino acid position 150; and variant #2, in which a leucine residue is substituted for a valine residue at amino acid position 225.

The present invention also provides polymorphic variants of the T2R protein depicted in SEQ ID NO:133: variant #1, in which a leucine residue is substituted for an isoleucine residue at amino acid position 27; and variant #2, in which a lysine residue is substituted for an arginine residue at amino acid position 127.

The present invention also provides polymorphic variants of the T2R protein depicted in SEQ ID NO:135: variant #1, in which a threonine residue is substituted for a serine residue at amino acid position 102; and variant #2, in which a glutamic acid residue is substituted for an aspartic acid residue at amino acid position 220.

The present invention also provides polymorphic variants of the T2R protein depicted in SEQ ID NO:137: variant #1, in which an isoleucine residue is substituted for a leucine residue at amino acid position 24; and variant #2, in which an arginine residue is substituted for a lysine residue at amino acid position 45.

The present invention also provides polymorphic variants of the T2R protein depicted in SEQ ID NO:139: variant #1, in which a leucine residue is substituted for an isoleucine residue at amino acid position 50; and variant #2, in which an alanine residue is substituted for a glycine residue at amino acid position 53.

The present invention also provides polymorphic variants of the T2R protein depicted in SEQ ID NO:141: variant #1, in which a serine residue is substituted for a threonine residue at amino acid position 76; and variant #2, in which an isoleucine residue is substituted for a leucine residue at amino acid position 131.

The present invention also provides polymorphic variants of the T2R protein depicted in SEQ ID NO:143: variant #1, in which an alanine residue is substituted for a glycine residue at amino acid position 98; and variant #2, in which a phenylalanine residue is substituted for a tryptophan residue at amino acid position 153.

The present invention also provides polymorphic variants of the T2R protein depicted in SEQ ID NO:145: variant #1, in which a leucine residue is substituted for an isoleucine residue at amino acid position 8; and variant #2, in which a glycine residue is substituted for an alanine residue at amino acid position 100.

The present invention also provides polymorphic variants of the T2R protein depicted in SEQ ID NO:147: variant #1, in which a glycine residue is substituted for an alanine residue at amino acid position 52; and variant #2, in which a valine residue is substituted for a leucine residue at amino acid position 75.

The present invention also provides polymorphic variants of the T2R protein depicted in SEQ ID NO:149: variant #1, in which a lysine residue is substituted for an arginine residue at amino acid position 44; and variant #2, in which a leucine residue is substituted for a valine residue at amino acid position 49.

The present invention also provides polymorphic variants of the T2R protein depicted in SEQ ID NO:151: variant #1, in which an isoleucine residue is substituted for a leucine residue at amino acid position 5; and variant #2, in which an alanine residue is substituted for a glycine residue at amino acid position 25.

The present invention also provides polymorphic variants of the T2R protein depicted in SEQ ID NO:153: variant #1, in which a glutamic acid residue is substituted for an aspartic acid residue at amino acid position 7; and variant #2, in which an isoleucine residue is substituted for a leucine residue at amino acid position 60.

The present invention also provides polymorphic variants of the T2R protein depicted in SEQ ID NO:155: variant #1, in which an isoleucine residue is substituted for a valine residue at amino acid position 7; and variant #2, in which a glycine residue is substituted for an alanine residue at amino acid position 23.

The present invention also provides polymorphic variants of the T2R protein depicted in SEQ ID NO:158: variant #1, in which an isoleucine residue is substituted for a leucine residue at amino acid position 5; and variant #2, in which an alanine residue is substituted for a glycine residue at amino acid position 21.

The present invention also provides polymorphic variants of the T2R protein depicted in SEQ ID NO:160: variant #1, in which a leucine residue is substituted for a valine residue at amino acid position 5; and variant #2, in which an alanine residue is substituted for a glycine residue at amino acid position 23.

The present invention also provides polymorphic variants of the T2R protein depicted in SEQ ID NO:162: variant #1, in which an isoleucine residue is substituted for a leucine residue at amino acid position 22; and variant #2, in which an alanine residue is substituted for a glycine residue at amino acid position 34.

The present invention also provides polymorphic variants of the T2R protein depicted in SEQ ID NO:164: variant #1, in which a leucine residue is substituted for an isoleucine residue at amino acid position 49; and variant #2, in which an arginine residue is substituted for a lysine residue at amino acid position 76.

Specific regions of the T2R nucleotide and amino acid sequences may be used to identify polymorphic variants, interspecies homologs, and alleles of T2R family members. This identification can be made in vitro, e.g., under stringent hybridization conditions or PCR (e.g., using primers encoding SEQ ID NOS:166-171) and sequencing, or by using the sequence information in a computer system for comparison with other nucleotide sequences. Typically, identification of polymorphic variants and alleles of T2R family members is made by comparing an amino acid sequence of about 25 amino acids or more, e.g., 50-100 amino acids. Amino acid identity of approximately at least 60% or above, optionally 65%, 70%, 75%, 80%, 85%, or 90-95% or above typically demonstrates that a protein is a polymorphic variant, interspecies homolog, or allele of a T2R family member. Sequence comparison can be performed using any of the sequence comparison algorithms discussed below. Antibodies that bind specifically to T2R polypeptides or a conserved region thereof can also be used to identify alleles, interspecies homologs, and polymorphic variants.

Polymorphic variants, interspecies homologs, and alleles of T2R genes are confirmed by examining taste cell specific expression of the putative T2R polypeptide. Typically, T2R polypeptides having an amino acid sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, or SEQ ID NO:164 is used as a positive control in comparison to the putative T2R protein to demonstrate the identification of a polymorphic variant or allele of the T2R family member. The polymorphic variants, alleles and interspecies homologs are expected to retain the seven transmembrane structure of a G-protein coupled receptor.

The present invention also provides nucleotide sequences for T2R promoters, which can be used to drive taste cell-specific expression of polynucleotides, especially in gustducin expressing taste cells that are receptive to bitter tastants.

Nucleotide and amino acid sequence information for T2R family members may also be used to construct models of taste cell specific polypeptides in a computer system. These models are subsequently used to identify compounds that can activate or inhibit T2R receptor proteins. Such compounds that modulate the activity of T2R family members can be used to investigate the role of T2R genes in taste transduction.

The isolation of T2R family members provides a means for assaying for inhibitors and activators of G-protein coupled receptor taste transduction. Biologically active T2R proteins are useful for testing inhibitors and activators of T2R as taste transducers, especially bitter taste transducers, using in vivo and in vitro assays that measure, e.g., transcriptional activation of T2R-dependent genes; ligand binding; phosphorylation and dephosphorylation; binding to G-proteins; G-protein activation; regulatory molecule binding; voltage, membrane potential and conductance changes; ion flux; intracellular second messengers such as cGMP, cAMP and inositol triphosphate; intracellular calcium levels; and neurotransmitter release. Such activators and inhibitors identified using T2R family members can be used to further study taste transduction and to identify specific taste agonists and antagonists. Such activators and inhibitors are useful as pharmaceutical and food agents for customizing taste, for example to decrease the bitter taste of foods or pharmaceuticals.

The present invention also provides assays, preferably high throughput assays, to identify molecules that interact with and/or modulate a T2R polypeptide. In numerous assays, a particular domain of a T2R family member is used, e.g., an extracellular, transmembrane, or intracellular domain or region. In numerous embodiments, an extracellular domain or transmembrane region or combination thereof is bound to a solid substrate, and used, e.g., to isolate ligands, agonists, antagonists, or any other molecule that can bind to and/or modulate the activity of an extracellular domain or transmembrane region of a T2R polypeptide. In certain embodiments, a domain of a T2R polypeptide, e.g., an extracellular, transmembrane, or intracellular domain, is fused to a heterologous polypeptide, thereby forming a chimeric polypeptide, e.g., a chimeric polypeptide with G protein coupled receptor activity. Such chimeric polypeptides are useful, e.g., in assays to identify ligands, agonists, antagonists, or other modulators of a T2R polypeptide. In addition, such chimeric polypeptides are useful to create novel taste receptors with novel ligand binding specificity, modes of regulation, signal transduction pathways, or other such properties, or to create novel taste receptors with novel combinations of ligand binding specificity, modes of regulation, signal transduction pathways, etc.

Methods of detecting T2R nucleic acids and expression of T2R polypeptides are also useful for identifying taste cells and creating topological maps of the tongue and the relation of tongue taste receptor cells to taste sensory neurons in the brain. In particular, methods of detecting T2R can be used to identify taste cells sensitive to bitter tastants. Chromosome localization of the genes encoding human T2R genes can be used to identify diseases, mutations, and traits caused by and associated with T2R family members.

II. Definitions

As used herein, the following terms have the meanings ascribed to them unless specified otherwise.

"Taste cells" include neuroepithelial cells that are organized into groups to form taste buds of the tongue, e.g., foliate, fungiform, and circumvallate cells (see, e.g., Roper et al., *Ann. Rev. Neurosci.* 12:329-353 (1989)). Taste cells also include cells of the palate, and other tissues that may contain taste cells such as the esophagus and the stomach.

"T2R" refers to one or more members of a family of G-protein coupled receptors that are expressed in taste cells such as foliate, fungiform, and circumvallate cells, as well as cells of the palate, esophagus, and stomach (see, e.g., Hoon et al., *Cell* 96:541-551 (1999), herein incorporated by reference in its entirety). This family is also referred to as the "SF family" (see, e.g., U.S. Ser. No. 09/393,634). Such taste cells can be identified because they express specific molecules such as Gustducin, a taste cell specific G protein, or other taste specific molecules (McLaughin et al., *Nature* 357:563-569 (1992)). Taste receptor cells can also be identified on the basis of morphology (see, e.g., Roper, supra). T2R family members have the ability to act as receptors for taste transduction. T2R family members are also referred to as the "GR" family, for gustatory receptor, or "SF" family.

"T2R" nucleic acids encode a family of GPCRs with seven transmembrane regions that have "G-protein coupled receptor activity," e.g., they bind to G-proteins in response to extracellular stimuli and promote production of second messengers such as IP3, cAMP, cGMP, and $Ca^{2+}$ via stimulation of enzymes such as phospholipase C and adenylate cyclase (for a description of the structure and function of GPCRs, see, e.g., Fong, supra, and Baldwin, supra). A dendogram providing the relationship between certain T2R family members is provided as FIG. 2. These nucleic acids encode proteins that are expressed in taste cells, in particular Gustducin-expressing taste cells that are responsive to bitter tastants. A single taste cell may contain many distinct T2R polypeptides.

The term "T2R" family therefore refers to polymorphic variants, alleles, mutants, and interspecies homologs that: (1) have about 60% amino acid sequence identity, optionally about 75, 80, 85, 90, or 95% amino acid sequence identity to SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, or SEQ ID NO:164 over a window of about 25 amino acids, optionally 50-100 amino acids; (2) specifically bind to antibodies raised against an immunogen comprising an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47; SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, and SEQ ID NO:164, and conservatively modified variants thereof; (3) specifically hybridize (with a size of at least about 100, optionally at least about 500-1000 nucleotides) under stringent hybridization conditions to a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, SEQ ID NO:63, SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO: 100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO: 152, SEQ ID NO:154, SEQ ID NO:156, SEQ ID NO:157, SEQ ID NO:159, SEQ ID NO:161, SEQ ID NO:163, and SEQ ID NO:165, and conservatively modified variants thereof; (4) comprise a sequence at least about 50% identical to an amino acid sequence selected from the group consisting of SEQ ID NO:166, SEQ ID NO:167, SEQ ID NO:168, SEQ ID NO:169, SEQ ID NO:170, and SEQ ID NO:171; or (5) are amplified by primers that specifically hybridize under stringent hybridization conditions to the same sequence as a degenerate primer sets encoding SEQ ID NO:166, SEQ ID NO:167, SEQ ID NO:168, SEQ ID NO:169, SEQ ID NO:170, or SEQ ID NO:171.

Topologically, sensory GPCRs have an "N-terminal domain" "extracellular domains," a "transmembrane domain" comprising seven transmembrane regions, cytoplasmic, and extracellular loops, "cytoplasmic domains," and a "C-terminal domain" (see, e.g., Hoon et al., *Cell* 96:541-551 (1999); Buck & Axel, *Cell* 65:175-187 (1991)). These domains can be structurally identified using methods known to those of skill in the art, such as sequence analysis programs that identify hydrophobic and hydrophilic domains (see, e.g., Stryer, *Biochemistry* (3rd ed. 1988); see also any of a number of Internet based sequence analysis programs, such as those found at dot.imgen.bcm.tmc.edu). Such domains are useful for making chimeric proteins and for in vitro assays of the invention, e.g., ligand binding assays.

"Extracellular domains" therefore refers to the domains of T2R polypeptides that protrude from the cellular membrane and are exposed to the extracellular face of the cell. Such domains would include the "N terminal domain" that is exposed to the extracellular face of the cell, as well as the extracellular loops of the transmembrane domain that are exposed to the extracellular face of the cell, i.e., the loops between transmembrane regions 2 and 3, and between transmembrane regions 4 and 5. The "N terminal domain" region starts at the N-terminus and extends to a region close to the start of the transmembrane domain. These extracellular domains are useful for in vitro ligand binding assays, both soluble and solid phase. In addition, transmembrane regions, described below, can also bind ligand either in combination with the extracellular domain or alone, and are therefore also useful for in vitro ligand binding assays.

"Transmembrane domain," which comprises the seven transmembrane "regions," refers to the domain of T2R polypeptides that lies within the plasma membrane, and may also include the corresponding cytoplasmic (intracellular) and extracellular loops, also referred to as transmembrane domain "regions." The seven transmembrane regions and extracellular and cytoplasmic loops can be identified using standard methods, as described in Kyte & Doolittle, *J. Mol. Biol.* 157:105-132 (1982)), or in Stryer, supra.

"Cytoplasmic domains" refers to the domains of T2R proteins that face the inside of the cell, e.g., the "C terminal domain" and the intracellular loops of the transmembrane domain, e.g., the intracellular loops between transmembrane regions 1 and 2, and the intracellular loops between transmembrane regions 3 and 4. "C terminal domain" refers to the region that spans the end of the last transmembrane domain and the C-terminus of the protein, and which is normally located within the cytoplasm.

"Biological sample" as used herein is a sample of biological tissue or fluid that contains one or more T2R nucleic acids encoding one or more T2R proteins. Such samples include, but are not limited to, tissue isolated from humans, mice, and rats, in particular, tongue, palate, and other tissues that may contain taste cells such as the esophagus and the stomach. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans.

"GPCR activity" refers to the ability of a GPCR to transduce a signal. Such activity can be measured in a heterologous cell, by coupling a GPCR (or a chimeric GPCR) to either a G-protein or promiscuous G-protein such as Gal 5, and an enzyme such as PLC, and measuring increases in intracellular calcium using (Offermans & Simon, *J. Biol. Chem.* 270: 15175-15180 (1995)). Receptor activity can be effectively measured by recording ligand-induced changes in $[Ca^{2+}]i$ using fluorescent $Ca^{2+}$-indicator dyes and fluorometric imaging. Optionally, the polypeptides of the invention are involved in sensory transduction, optionally taste transduction in taste cells.

The phrase "functional effects" in the context of assays for testing compounds that modulate T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G-protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T2R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T2R gene expression; tissue culture cell T2R expression; transcriptional activation of T2R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T2R genes or proteins are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G-proteins; kinases (e.g., homologs of rhodopsin kinase and beta adrenergic receptor kinases that are involved in deactivation and desensitization of a receptor); and arrestin-like proteins, which also deactivate and desensitize receptors. Modulators include genetically modified versions of T2R family members, e.g., with altered activity, as well as naturally occurring and synthetic ligands, antagonists, agonists, small chemical molecules and the like. Such assays for inhibitors and activators include, e.g., expressing T2R family members in cells or cell membranes, applying putative modulator compounds, in the presence or absence of tastants, e.g., bitter tastants, and then determining the functional effects on taste transduction, as described above. Samples or assays comprising T2R family members that are treated with a potential activator, inhibitor, or modulator are compared to control samples without the inhibitor, activator, or modulator to examine the extent of inhibition. Control samples (untreated with inhibitors) are assigned a relative T2R activity value of 100%. Inhibition of a T2R is achieved when the T2R activity value relative to the control is about 80%, optionally 50% or 25-0%. Activation of a T2R is achieved when the T2R activity value relative to the control is 110%, optionally 150%, optionally 200-500%, or 1000-3000% higher.

"Biologically active" T2R refers to a T2R having GPCR activity as described above, involved in taste transduction in taste receptor cells, in particular bitter taste transduction.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated T2R nucleic acid is separated from open reading frames that flank the T2R gene and encode proteins other than a T2R. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3d ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably-linked to a promoter.

The terms "identical" or percent "identity," in the context of two or more nucleic acids or polypeptide sequences, refer to two or more sequences or subsequences or domains that are the same or have a specified percentage of amino acid residues or nucleotides that are the same (i.e., 50% identity, optionally 55%, 60%, 65%, 70%, 75%, 80%, 85%, 90%, 95% or higher identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Nati. Acad. Sci. USA 89:10915 (1989)) alignments (B) of 50, expectation (E) of 10, M=5, N=−4, and a comparison of both strands.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment (see, e.g., FIG. 2). PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T2R" antibody is an antibody or antibody fragment that specifically binds a polypeptide encoded by a T2R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a T2R family member from specific species such as rat, mouse, or human can be selected to obtain only those polyclonal antibodies that are specifically immunoreactive with the T2R protein or an immunogenic portion thereof and not with other proteins, except for orthologs or polymorphic variants and alleles of the T2R protein. This selection may be achieved by subtracting out antibodies that cross-react with T2R molecules from other species or other T2R molecules. Antibodies can also be selected that recognize only T2R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

In one embodiment, immunogenic domains corresponding to SEQ ID NOs:166-171 can be used to raise antibodies that specifically bind to polypeptides of the T2R family.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

III. Isolation of Nucleic Acids Encoding T2R Family Members

A. General Recombinant DNA Methods

This invention relies on routine techniques in the field of recombinant genetics. Basic texts disclosing the general methods of use in this invention include Sam brook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding T2R Family Members In general, the nucleic acid sequences encoding T2R family members and related nucleic acid sequence homologs are cloned from cDNA and genomic DNA libraries by hybridization with probes, or isolated using amplification techniques with oligonucleotide primers. For example, T2R sequences are typically isolated from mammalian nucleic acid (genomic or cDNA) libraries by hybridizing with a nucleic acid probe, the sequence of which can be derived from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, SEQ ID NO:63, SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ ID NO:159, SEQ ID NO:161, SEQ ID NO:163, or SEQ ID NO:165. A suitable tissue from which RNA and cDNA for T2R family members can be isolated is tongue tissue, optionally taste bud tissues or individual taste cells.

Amplification techniques using primers can also be used to amplify and isolate T2R sequences from DNA or RNA. For example, degenerate primers encoding the following amino acid sequences can be used to amplify a sequence of a T2R gene: SEQ ID NOS: 166, 167, 168, 169, 170, or 171 (see, e.g., Dieffenfach & Dveksler, *PCR Primer: A Laboratory Manual* (1995)). These primers can be used, e.g. to amplify either the full length sequence or a probe of one to several hundred nucleotides, which is then used to screen a mammalian library for full-length T2R clones. As described above, such primers can be used to isolate a full length sequence, or a probe which can then be used to isolated a full length sequence, e.g., from a library.

Nucleic acids encoding T2R can also be isolated from expression libraries using antibodies as probes. Such polyclonal or monoclonal antibodies can be raised using the sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:11, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, or SEQ ID NO:164.

Polymorphic variants, alleles, and interspecies homologs that are substantially identical to a T2R family member can be isolated using T2R nucleic acid probes, and oligonucleotides under stringent hybridization conditions, by screening libraries. Alternatively, expression libraries can be used to clone T2R family members and T2R family member polymorphic variants, alleles, and interspecies homologs, by detecting expressed homologs immunologically with antisera or purified antibodies made against a T2R polypeptide, which also recognize and selectively bind to the T2R homolog.

To make a cDNA library, one should choose a source that is rich in T2R mRNA, e.g., tongue tissue, or isolated taste buds. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.,* 72:3961-3965 (1975).

An alternative method of isolating T2R nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of T2R genes directly from mRNA, from cDNA, from genomic libraries or cDNA libraries. Degenerate oligonucleotides can be designed to amplify T2R family member homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of T2R-encoding mRNA in physiological samples, for nucleic acid sequencing, or for other purposes. Genes amplified by the PCR reaction can be purified from agarose gels and cloned into an appropriate vector.

Gene expression of T2R family members can also be analyzed by techniques known in the art, e.g., reverse transcription and amplification of mRNA, isolation of total RNA or poly $A^+$ RNA, northern blotting, dot blotting, in situ hybridization, RNase protection, probing DNA microchip arrays, and the like. In one embodiment, high density oligonucleotide analysis technology (e.g., GeneChip™) is used to identify homologs and polymorphic variants of the GPCRs of the invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

Synthetic oligonucleotides can be used to construct recombinant T2R genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the T2R nucleic acid. The specific subsequence is then ligated into an expression vector.

The nucleic acid encoding a T2R gene is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising a T2R polypeptide or domains thereof can be made according to standard techniques. For example, a domain such as a ligand binding domain (e.g., an extracellular domain alone, an extracellular domain plus a transmembrane region, or a transmembrane region alone), an extracellular domain, a transmembrane domain (e.g., one comprising up to seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, β-gal, glutamate receptor, and the rhodopsin presequence.

C. Expression in Prokaryotes and Eukaryotes

To obtain high level expression of a cloned gene or nucleic acid, such as those cDNAs encoding a T2R family member, one typically subclones the T2R sequence into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. *Bacterial expression systems for expressing the T*2R protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the T2R-encoding nucleic acid in host cells. A typical expression cassette thus contains a promoter operably linked to the nucleic acid sequence encoding a T2R and signals required for efficient polyadenylation of the transcript, ribosome binding sites, and translation termination. The nucleic acid sequence encoding a T2R may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as neomycin, hymidine kinase, hygromycin B phosphotransferase, and dihydrofolate reductase. Alternatively, high yield expression systems not involving gene amplification are also suitable, such as using a baculovirus vector in insect cells, with a sequence encoding a T2R family member under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of a T2R protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a T2R gene.

In one preferred embodiment, a polynucleotide encoding a T2R is operably linked to a EF-1α promoter, e.g., using a pEAK10 mammalian expression vector (Edge Biosystems, MD) is used. Such vectors can be introduced into cells, e.g., HEK-293 cells using any standard method, such as transfection using LipofectAMINE (Lifetechnologies).

After the expression vector is introduced into the cells, the transfected cells are cultured under conditions favoring expression of the T2R family member, which is recovered from the culture using standard techniques identified below.

IV. Purification of T2R Polypeptides

Either naturally occurring or recombinant T2R polypeptides can be purified for use in functional assays. Optionally, recombinant T2R polypeptides are purified. Naturally occurring T2R polypeptides are purified, e.g., from mammalian tissue such as tongue tissue, and any other source of a T2R homolog. Recombinant T2R polypeptides are purified from any suitable bacterial or eukaryotic expression system, e.g., CHO cells or insect cells.

T2R proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant T2R family members are being purified. For example, proteins having established molecular adhesion properties can be reversibly fused to the T2R polypeptide. With the appropriate ligand, a T2R can be selectively adsorbed to a purification column and then freed from the column in a relatively pure form. The fused protein is then removed by enzymatic activity. Finally T2R proteins can be purified using immunoaffinity columns.

A. Purification of T2R Protein from Recombinant Cells

Recombinant proteins are expressed by transformed bacteria or eukaryotic cells such as CHO cells or insect cells in large amounts, typically after promoter induction; but expression can be constitutive. Promoter induction with IPTG is a one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of T2R inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. T2R polypeptides are separated from other bacterial proteins by standard separation techniques, e.g., with Ni-NTA agarose resin.

Alternatively, it is possible to purify T2R polypeptides from bacteria periplasm. After lysis of the bacteria, when a T2R protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying T2R Polypeptides

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of a T2R protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

T2R proteins can also be separated from other proteins on the basis of its size, net surface charge, hydrophobicity, and affinity for ligands. In addition, antibodies raised against proteins can be conjugated to column matrices and the proteins immuno purified. All of these methods are well known in the art. It will be apparent to one of skill that chromatographic techniques can be performed at any scale and using equipment from many different manufacturers (e.g., Pharmacia Biotech).

V. Immunological Detection of T2R Polypeptides

In addition to the detection of T2R genes and gene expression using nucleic acid hybridization technology, one can also use immunoassays to detect T2R, e.g., to identify taste receptor cells, especially bitter taste receptor cells, and variants of T2R family members. Immunoassays can be used to qualitatively or quantitatively analyze the T2R. A general overview of the applicable technology can be found in Harlow & Lane, *Antibodies: A Laboratory Manual* (1988).

A. Antibodies to T2R Family Members

Methods of producing polyclonal and monoclonal antibodies that react specifically with a T2R family member are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of T2R-comprising immunogens may be used to produce antibodies specifically reactive with a T2R family member. For example, a recombinant T2R protein, or an antigenic fragment thereof, is isolated as described herein. Suitable antigenic regions include, e.g., the conserved motifs that are used to identify members of the T2R family, i.e., SEQ ID NOS:166, 167, 168, 169, 170, and 171. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the T2R. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-T2R proteins, or even other T2R family members or other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Once T2R family member specific antibodies are available, individual T2R proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

T2R proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case a T2R family member or an antigenic subsequence thereof). The antibody (e.g., anti-T2R) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled T2R polypeptide or a labeled anti-T2R antibody. Alternatively, the labeling agent may be a third moiety, such a secondary antibody, that specifically binds to the antibody/T2R complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting a T2R protein in a sample may be either competitive or noncompetitive. Noncompetitive immunoassays are assays in which the amount of antigen is directly measured. In one preferred "sandwich" assay, for example, the anti-T2R antibodies can be bound directly to a solid substrate on which they are immobilized. These immobilized antibodies then capture the T2R protein present in the test sample. The T2R protein is thus immobilized is then bound by a labeling agent, such as a second T2R antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of T2R protein present in the sample is measured indirectly by measuring the amount of a known, added (exogenous) T2R protein displaced (competed away) from an anti-T2R antibody by the unknown 12R protein present in a sample. In one competitive assay, a known amount of T2R protein is added to a sample and the sample is then contacted with an antibody that specifically binds to the T2R. The amount of exogenous T2R protein bound to the antibody is inversely proportional to the concentration of T2R protein present in the sample. In a particularly preferred embodiment, the antibody is immobilized on a solid substrate. The amount of T2R protein bound to the antibody may be determined either by measuring the amount of T2R protein present in a T2R/antibody complex, or alternatively by measuring the amount of remaining uncomplexed protein. The amount of T2R protein may be detected by providing a labeled T2R molecule:

A hapten inhibition assay is another preferred competitive assay. In this assay the known T2R protein is immobilized on a solid substrate. A known amount of anti-T2R antibody is added to the sample, and the sample is then contacted with the immobilized T2R. The amount of anti-T2R antibody bound to the known immobilized T2R protein is inversely proportional to the amount of T2R protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, SEQ ID NO:63, SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ ID NO:159, SEQ ID NO:161, SEQ ID NO:163, or SEQ ID NO:165, can be immobilized to a solid support. Proteins (e.g., T2R proteins and homologs) are added to the assay that compete for binding of the antisera to the immobilized antigen. The ability of the added proteins to compete for binding of the antisera to the immobilized protein is compared to the ability of the T2R polypeptide encoded by SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, SEQ ID NO:63, SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ ID NO:159, SEQ ID NO:161, SEQ ID NO:163, or SEQ ID NO:165 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. In addition, peptides comprising amino acid sequences representing conserved motifs that are used to identify members of the T2R family can be used in cross-reactivity determinations, i.e., SEQ ID NO:166, SEQ ID NO:167, SEQ ID NO:168; SEQ ID NO:169, SEQ ID NO:170, or SEQ D NO:171.

The immunoabsorbed and pooled antisera are then used in a competitive binding immunoassay as described above to compare a second protein, thought to be perhaps an allele or polymorphic variant of a T2R family member, to the immunogen protein (i.e., T2R protein encoded by SEQ ID NO:2, SEQ. ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, SEQ ID NO:63, SEQ ID NO:78, SEQ ID NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ D NO:112, SEQ D NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ. ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ D NO:152, SEQ ID NO:154, SEQ ID NO:156, SEQ ID NO:157, SEQ ID NO:159, SEQ ID NO:161, SEQ ID NO:163, or SEQ ID NO:165). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:23, SEQ ID NO:25, SEQ ID NO:27, SEQ ID NO:29, SEQ ID NO:31, SEQ ID NO:34, SEQ ID NO:36, SEQ ID NO:38, SEQ ID NO:41, SEQ ID NO:43, SEQ ID NO:45, SEQ ID NO:52, SEQ ID NO:54, SEQ ID NO:57, SEQ ID NO:61, SEQ ID NO:63, SEQ ID NO:78, SEQ 1D NO:80, SEQ ID NO:82, SEQ ID NO:84, SEQ ID NO:86; SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ D NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:157, SEQ ID NO:159, SEQ ID NO:161, SEQ ID NO:163, or SEQ ID NO:165 that is required to inhibit 50% of binding, then the second protein is said to specifically bind to the polyclonal antibodies generated to a T2R immunogen.

Antibodies raised against SEQ ID NOs:166-171 can also be used to prepare antibodies that specifically bind only to GPCRs of the T2R family, but not to GPCRs from other families.

Polyclonal antibodies that specifically bind to a particular member of the T2R family, e.g., T2R01, can be make by subtracting out cross-reactive antibodies using other T2R family members. Species-specific polyclonal antibodies can be made in a similar way. For example, antibodies specific to human T2R01 can be made by subtracting out antibodies that are cross-reactive with orthologous sequences, e.g., rat T2R01 or mouse T2R19.

Other Assay Formats

Western blot (immunoblot) analysis is used to detect and quantify the presence of T2R protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the T2R protein. The anti-T2R polypeptide antibodies specifically bind to the T2R polypeptide on the solid support. These antibodies may be directly labeled or alternatively may be subsequently detected using labeled antibodies (e.g., labeled sheep anti-mouse antibodies) that specifically bind to the anti-T2R antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:3441 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g. horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a T2R protein, or secondary antibodies that recognize anti-T2R.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of T2R Family Members

A. Assays for T2R Protein Activity

T2R family members and their alleles and polymorphic variants are G-protein coupled receptors that participate in taste transduction, e.g., bitter taste transduction. The activity of T2R polypeptides can be assessed using a variety of in vitro and in vivo assays to determine functional, chemical, and physical effects, e.g., measuring ligand binding (e.g., radioactive ligand binding), second messengers (e.g., cAMP, cGMP, IP$_3$, DAG, or Ca$^{2+}$), ion flux, phosphorylation levels, transcription levels, neurotransmitter levels, and the like. Furthermore, such assays can be used to test for inhibitors and activators of T2R family members. Modulators can also be genetically altered versions of T2R receptors. Such modulators of taste transduction activity are useful for customizing taste, for example to modify the detection of bitter tastes.

The T2R protein of the assay will typically be selected from a polypeptide having a sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:19, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, or SEQ ID NO:164 or conservatively modified variant thereof.

Alternatively, the T2R protein of the assay will be derived from a eukaryote and include an amino acid subsequence having amino acid sequence identity to SEQ ID NO:1, SEQ ID NO:3, SEQ ID NO:5; SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:22, SEQ ID NO:24, SEQ ID NO:26, SEQ ID NO:28, SEQ ID NO:30, SEQ ID NO:32, SEQ ID NO:33, SEQ ID NO:35, SEQ ID NO:37, SEQ ID NO:39, SEQ ID NO:40, SEQ ID NO:42, SEQ ID NO:44, SEQ ID NO:46, SEQ ID NO:47, SEQ ID NO:48, SEQ ID NO:49, SEQ ID NO:50, SEQ ID NO:51, SEQ ID NO:53, SEQ ID NO:55, SEQ ID NO:56, SEQ ID NO:58, SEQ ID NO:59, SEQ ID NO:60, SEQ ID NO:62, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:158, SEQ ID NO:160, SEQ ID NO:162, or SEQ ID NO:164. Generally, the amino acid sequence identity will be at least 60%, optionally at least 70% to 85%, optionally at least 90-95%. Optionally, the polypeptide of the assays will comprise a domain of a T2R protein, such as an extracellular domain, transmembrane region, transmembrane domain, cytoplasmic domain, ligand binding domain, subunit association domain, active site, and the like. Either the T2R protein or a domain thereof can be covalently linked to a heterologous protein to create a chimeric protein used in the assays described herein.

Modulators of T2R receptor activity are tested using T2R polypeptides as described above, either recombinant or naturally occurring. The protein can be isolated, expressed in a cell, expressed in a membrane derived from a cell, expressed in tissue or in an animal, either recombinant or naturally occurring. For example, tongue slices, dissociated cells from a tongue, transformed cells, or membranes can b used. Modulation is tested using one of the in vitro or in vivo assays described herein. Taste transduction can also be examined in vitro with soluble or solid state reactions, using a full-length T2R-GPCR or a chimeric molecule such as an extracellular domain or transmembrane region, or combination thereof, of a T2R receptor covalently linked to a heterologous signal transduction domain, or a heterologous extracellular domain and/or transmembrane region covalently linked to the transmembrane and/or cytoplasmic domain of a T2R receptor. Furthermore, ligand-binding domains of the protein of interest can be used in vitro in soluble or solid state reactions to assay for ligand binding. In numerous embodiments, a chimeric receptor will be made that comprises all or part of a T2R polypeptide as well an additional sequence that facilitates the localization of the T2R to the membrane, such as a rhodopsin, e.g. an N-terminal fragment of a rhodopsin protein.

Ligand binding to a T2R protein, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors, e.g., by adding an activator to the receptor and G protein in the absence of GTP, which form a tight complex, and then screen for inhibitors by looking at dissociation of the receptor-G protein complex. In the presence of GTP, release of the alpha subunit of the G protein from the other two G protein subunits serves as a criterion of activation.

In particularly preferred embodiments, T2R-Gustducin interactions are monitored as a function of T2R receptor activation. As shown in Example IX, mouse T2R5 shows strong cycloheximide-dependent coupling with Gustducin. Such ligand dependent coupling of T2R receptors with Gustducin can be used as a marker to identify modifiers of any member of the T2R family.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

In a preferred embodiment, a T2R polypeptide is expressed in a eukaryotic cell as a chimeric receptor with a heterologous, chaperone sequence that facilitates its maturation and targeting through the secretory pathway. In a preferred embodiment, the heterologous sequence is a rhodopsin sequence, such as an N-terminal fragment of a rhodopsin. Such chimeric T2R receptors can be expressed in any eukaryotic cell, such as HEK-293 cells. Preferably, the cells comprise a functional G protein, e.g., Gα15, that is capable of coupling the chimeric receptor to an intracellular signaling pathway or to a signaling protein such as phospholipase Cβ. Activation of such chimeric receptors in such cells can be detected using any standard method, such as by detecting changes in intracellular calcium by detecting FURA-2 dependent fluorescence in the cell.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

Samples or assays that are treated with a potential T2R protein inhibitor or activator are compared to control samples without the test compound, to examine the extent of modulation. Such assays may be carried out in the presence of a bitter tastant that is known to activate the particular receptor, and modulation of the bitter-tastant-dependent activation monitored. Control samples (untreated with activators or inhibitors) are assigned a relative T2R activity value of 100. Inhibition of a T2R protein is achieved when the T2R activity value relative to the control is about 90%, optionally 50%, optionally 25-0%. Activation of a T2R protein is achieved when the T2R activity value relative to the control is 110%, optionally 150%, 200-500%, or 1000-2000%.

Changes in ion flux may be assessed by determining changes in polarization (i.e., electrical potential) of the cell or membrane expressing a T2R protein. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336: 1575-1595 (1997)). Whole cell currents are conveniently determined using the standard methodology (see; e.g., Hamil et al., *PFlugers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J. Membrane Biology* 137:59-70 (1994)). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al., *Proc. Nat'l Acad. Sci. USA* 88:10049-10053 (1991)). Such promiscuous G-proteins allow coupling of a wide range of receptors.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868-9872 (1991) and Dhallan et al., *Nature* 347: 184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a preferred embodiment, T2R protein activity is measured by expressing a T2R gene in a heterologous cell with a promiscuous G-protein that links the receptor to a phospholipase C signal transduction pathway (see Offermanns & Simon, *J. Biol. Chem.* 270:15175-15180 (1995)). Optionally the cell line is HEK-293 (which does not naturally express T2R genes) and the promiscuous G-protein is $G\alpha15$ (Offermanns & Simon, supra). Modulation of taste transduction is assayed by measuring changes in intracellular $Ca^{2+}$ levels, which change in response to modulation of the T2R signal transduction pathway via administration of a molecule that associates with a T2R protein. Changes in $Ca^{2+}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon, *J. Biol. Chem.* 270:15175-15180 (1995) may be used to determine the level of cAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436, 128, herein incorporated by reference. Briefly, the assay involves labeling of cells with $^3H$-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing a T2R protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of a T2R family member can be any small chemical compound, or a biological entity, such as a protein, sugar, nucleic acid or lipid. Alternatively, modulators can be genetically altered versions of a T2R gene. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc;* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provide soluble assays using molecules such as a domain such as ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a T2R protein; or a cell or tissue expressing a T2R protein, either naturally occurring or recombinant. In another embodiment, the invention provides solid phase based in vitro assays in a high throughput format, where the domain, chimeric molecule, T2R protein, or cell or tissue expressing the T2R is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate T2R protein activity involves computer assisted drug design, in which a computer system is used to generate a three-dimensional structure of a T2R protein based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a T2R polypeptide into the computer system. The nucleotide sequence encoding the polypeptide, or the amino acid sequence thereof, can be any of SEQ ID NO:1-165, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the T2R protein to identify ligands that bind to the protein. Binding affinity between the protein and ligands is determined using energy terms to determine which ligands have an enhanced probability of binding to the protein.

Computer systems are also used to screen for mutations, polymorphic variants, alleles and interspecies homologs of T2R genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated T2R genes involves receiving input of a first nucleic acid or amino acid sequence of a T2R gene, e.g., any of SEQ ID NO:1-165, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various T2R genes, and mutations associated with disease states and genetic traits.

IX. Administration and Pharmaceutical Compositions

Taste modulators can be administered directly to the mammalian subject for modulation of taste, e.g., modulation of bitter taste, in vivo. Administration is by any of the routes normally used for introducing a modulator compound into ultimate contact with the tissue to be treated, optionally the tongue or mouth. The taste modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The taste modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Optionally, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part of prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the LD-50 of the modulator, and the side-effects of the inhibitor at various concentrations, as applied to the mass and overall health of the subject. Administration can be accomplished via single or divided doses.

VIII. Kits

T2R genes and their homologs are useful tools for identifying taste receptor cells, for forensics and paternity determinations, and for examining taste transduction. T2R family member-specific reagents that specifically hybridize to T2R nucleic acids, such as T2R probes and primers, and T2R specific reagents that specifically bind to a T2R protein, e.g., T2R antibodies are used to examine taste cell expression and taste transduction regulation.

Nucleic acid assays for the presence of DNA and RNA for a T2R family member in a sample include numerous techniques are known to those skilled in the art, such as Southern analysis, northern analysis, dot blots, RNase protection, SI analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, a T2R protein can be detected with the various immunoassay techniques described above. The test sample is typically compared to both a positive control (e.g. a sample expressing a recombinant T2R protein) and a negative control.

The present invention also provides for kits for screening for modulators of T2R family members. Such kits can be prepared from readily available materials and reagents. For example, such kits can comprise any one or more of the following materials: T2R nucleic acids or proteins, reaction tubes, and instructions for testing T2R activity. Optionally, the kit contains a biologically active T2R receptor. A wide variety of kits and components can be prepared according to the present invention, depending upon the intended user of the kit and the particular needs of the user.

EXAMPLES

The following examples are provided by way of illustration only and not by way of limitation. Those of skill in the art will readily recognize a variety of noncritical parameters that could be changed or modified to yield essentially similar results.

Example I

Identification of the T2R Gene Family

Recent genetic linkage studies in humans identified a locus at 5p15 that is associated with the ability to respond to the bitter substance 6-n-propyl-2-thiouracil (PROP; Reed et al., *Am. J. Hum. Genet.* 64:1478-1480 (1999)). To determine whether differences in PROP sensitivity reflected functional differences in a bitter taste receptor, DNA sequence databases were searched for genes encoding candidate transmembrane proteins at this location. Analysis of open reading frames in 450 kb of DNA spanning six sequenced human genomic BAC clones (see, e.g., accession number AC003015) from this interval identified a novel GPCR (T2R1) at 5p15.2. T2R1 has seven putative transmembrane segments as well as several conserved residues often present in GPCRs (Probst et al., *DNA Cell. Biol.* 11:1-20 (1992)).

Computer searches using T2R1, and reiterated with T2R1-related sequences, revealed 19 additional human receptors (12 full-length and 7 pseudogenes). Full-length hT2Rs were isolated by PCR amplification of genomic DNA. Full-length hT2Rs were used to probe a rat circumvallate cDNA library (Hoon et al., *Cell*, 96:541-551 (1999)) and mouse BAC filter arrays (Genome Systems) at low stringency (50-55° C. wash in 1×SSC). Southern hybridization experiments were used to identify a non-redundant set of positive BACs and to order overlapping BACs.

These new receptors, referred to as T2Rs (also known as "SF"), define a novel family of GPCRs that are distantly related to V1R vomeronasal receptors and opsins. In contrast to T1Rs, which belong to the superfamily of GPCRs characterized by a large N-terminal domain (Hoon et al., *Cell*, 96:541-551 (1999)), the T2Rs have only a short extracellular N-terminus. Individual members of the T2R-family exhibit 30-70% amino acid identity, and most share highly conserved sequence motifs in the first three and last transmembrane segments, and also in the second cytoplasmic loop. The most divergent regions between T2Rs are the extracellular segments, extending partway into the transmembrane helices. Presumably, the high degree of variability between T2Rs reflects the need to recognize many structurally diverse ligands. Like many other GPCR genes, T2Rs do not contain introns that interrupt coding regions.

Example II

Organization of Human T2R Genes

The identified human T2R genes are localized on three chromosomes, and are often organized as head-to-tail arrays. For example, four receptor genes are clustered within a single PAC clone from 7q31 and nine in a BAC clone from 12p13. There may be more human T2Rs in these arrays, as several additional human T2Rs were found within partially sequenced BAC clones that overlap the 9 gene T2R cluster. Within a given array, the similarity of receptors is highly variable, including both relatively related (e.g. hT2R13, hT2R14 and hT2R15), and highly divergent receptors (e.g. hT2R3 and hT2R4). This type of organization is mirrored in the mouse (see below), and resembles the genomic organization that has been observed for olfactory receptor genes in humans, mice, flies and worms (Rouquier et al., *Nat. Genet.* 18:243-250 (1998)); Sullivan et al., *PNAS* 93:884-888 (1996)); Clyne et al., *Neuron* 22:327-388 (1999)); Vosshall et al., *Cell* 96:725-736 (1999)); Troemel et al., *Cell* 83:207-218 (1995)).

To obtain estimates of the size of this gene family, various genomic resources were examined. Analysis of the Genome Sequence Survey database (gss) yielded 12 partial T2R sequences. Because this database represents an essentially random sampling of ~14% of the human genome, this number suggests that there may be ~90 T2R genes in the human genome. Similar searches of the finished (nr) and unfinished high-throughput human genomic sequence databases (htgs) produced 36 full-length and 15 partial T2R sequences. These databases contain ~50% of the genome sequence, also pointing to ~100 T2R genes in the genome. Recognizing that this analysis may be inaccurate due to the quality of the available databases, and the clustered, non-random distribution of T2Rs in the human genome, it is estimated that the T2R family consists of between 80 to 120 members. However, more than ⅓ of the full-length human T2Rs are pseudogenes; thus, the final number of functional human receptors may be significantly smaller (i.e., 40-80). This is similar to what has been observed for human olfactory receptors, where many of the genes appear to be pseudogenes (Rouquier et al., *Nat. Genet.* 18:243-250 (1998)).

Example III

T2R Genes are Linked to Loci Involved in Bitter Taste

The genetics of sweet and bitter tasting has been extensively studied in mice, where a number of loci influencing responses to sweet and bitter tastants have been mapped by behavioral taste-choice assays (Warren and Lewis, *Nature* 227:77-78 (1970)); Fuller, *J. Hered.* 65:33-66 (1974)). The distal end of mouse chromosome 6 contains a cluster of bitter genes that includes Soa (for sucrose octaacetate; Capeless et al., *Behav. Genet.* 22:655-663 (1992)), Rua (raffinose undecaacetate; Lush, *Genet. Res.* 47:117-123 (1986)), Cyx (cycloheximide; Lush and Holland, *Genet. Res.* 52:207-212 (1988)) and Qui (quinine; Lush, *Genet. Res.* 44:151-160 (1984)). Recombination studies indicated that these four loci are closely linked to each other, and to Prp (salivary proline rich protein; Azen et al., *Trends Genet.* 2:199-200 (1986)). The human 9 gene T2R cluster contains three interspersed PRP genes, and maps to an interval that is homologous with the mouse chromosome 6 bitter cluster.

To define the relationship between the mouse chromosome 6 bitter cluster and T2Rs, a large number of mouse T2R genes were isolated and their genomic organization and physical and genetic map locations were determined. By screening mouse genomic libraries with human T2Rs, 61 BAC-clones containing 28 mouse T2Rs were isolated. The mouse and human receptors display significant amino acid sequence divergence, but share the sequence motifs common to members of this novel family of receptors. Mouse T2Rs were mapped using a mouse/hamster radiation hybrid panel (Research Genetics), and by examining the strain distribution pattern of single nucleotide polymorphisms in a panel of C57BL/6J×DBA/2J recombinant inbred lines (Jackson Laboratory). These studies showed that the mouse genes are clustered at only a few genomic locations. Each genomic interval containing mouse T2Rs is homologous to one containing its closest human counterpart: mT2R8 and hT2R4, mT2R18 and hT2R16, and mT2 μg and hT2R1. Of these 3 sets of potentially orthologous pairs of human/mouse receptors, both the human T2R1 and T2R16 genes map to locations implicated in human bitter perception (Conneally et al., *Hum. Hered.* 26:267-271 (1976); Reed et al., *Am. J. Hum. Genet.* 64:1478-

1480 (1999)). The remaining 25 mT2Rs all map to the distal end of chromosome 6, and are represented by 3 BAC contigs spanning at least 400 kb.

Since Prp and the bitter-cluster also map to the distal end of mouse chromosome 6, it was determined whether they localize within this array of T2Rs. Analysis of a DBA/2×C57BL/6 recombinant inbred panel revealed that receptors within all 3 BAC-contigs co-segregate with Prp and the bitter cluster. Further, the mouse Prp gene was isolated (accession number M23236, containing D6Mit13) and shown that it lies within the large chromosome 6 T2R cluster. These results demonstrate that T2Rs are intimately linked to loci implicated in bitter perception.

Example IV

T2Rs are Expressed in Taste Receptor Cells

The lingual epithelium contains taste buds in three types of papillae: circumvallate papillae at the very back of the tongue, foliate papillae at the posterior lateral edge of the tongue, and fungiform papillae dispersed throughout the front half of the tongue surface. Other parts of the oral cavity also have taste buds; these are particularly prominent in the palate epithelium in an area known as the geschmackstreifen and in the epiglottis. To examine the patterns of expression of T2Rs, in situ hybridizations were performed using sections of various taste papillae. To ensure that the probes used were expressed in taste tissue, a rat circumvallate cDNA library was screened, leading to the isolation of 14 rat T2Rs cDNAs, each of which is an ortholog of a mouse genomic clone.

To carry out the in situ hybridization, tissue was obtained from adult rats and mice. No sex-specific differences of expression patterns were observed, therefore male and female animals were used interchangeably. Fresh frozen sections (16 μm) were attached to silanized slides and prepared for in situ hybridization as described previously (Hoon et al., *Cell*, 96:541-551 (1999)). All in situ hybridizations were carried out at high stringency (hybridization, 5×SSC, 50% formamide, 65-72° C.; washing, 0.2×SSC, 72° C.). Signals were developed using alkaline-phosphatase conjugated antibodies to digoxigenin and standard chromogenic substrates (Boehringer Mannheim). Where possible, probes contained extensive 3'-non translated sequence to minimize potential cross-hybridization between T2Rs, which was not observed at the stringency used for in situ hybridization.

These experiments demonstrated that T2Rs are selectively expressed in subsets of taste receptor cells of the tongue and palate epithelium. Each receptor hybridizes to an average of 2 cells per taste bud per section. Since the sections used in these experiments contain ⅕-⅓ the depth of a taste bud, this reflects a total of 6-10 positive cells/taste bud/probe (or about 15% of the cells in a taste bud). Examination of serial sections demonstrated that all of the taste buds of the circumvallate papilla contain cells that are positive for each of these probes. Thus far, comparable results have been observed with 11 rat T2Rs, and in mouse sections hybridized with 17 different mT2R probes.

Similar studies in foliate, geschmackstreifen and epiglottis taste buds demonstrated that each receptor probe also labels approximately 15% of the cells in every taste bud. In contrast, T2Rs are rarely expressed in fungiform papillae. Examination of hundreds of fungiform taste buds using 11 different T2R probes demonstrated that less than 10% of all fungiform papillae contain T2R-expressing cells. Interestingly, the few fungiform taste buds that do express T2Rs regularly contain multiple positive cells. In fact, the number of positive cells in these papillae is not significantly different from that seen in taste buds from other regions of the oral cavity. Furthermore, fungiform papillae that contain T2R-expressing cells generally appear clustered. This unexpected finding may provide an important clue about the logic of taste coding. It is known that single fibers of the chorda tympani nerve innervate multiple cells in a fungiform taste bud, and that the same fiber often projects to neighboring papillae (Miller, *J. Comp. Neurol.* 158:155-166 (1974)). Perhaps the non-random distribution of T2R-positive taste receptor cells and taste buds in fungiform papillae reflect a map of connectivity between similar cells.

Northern analysis and in situ hybridization demonstrated that T2Rs are not widely expressed outside taste tissue.

Example V

Individual Receptor Cells Express Multiple T2R Receptors

The above-described results demonstrated that any given T2R is expressed in ~15% of the cells of circumvallate, foliate and palate taste buds. Given that there are over 30 T2Rs in the rodent genome, a taste cell must express more than one receptor. To determine how many receptors are expressed in any cell, and what fraction of taste receptor cells express T2Rs, the number of circumvallate cells labeled with various mixes of 2, 5 or 10 receptors was compared with those labeled with the corresponding individual probes. By counting positive cells in multiple serial sections, it was determined that the number of taste cells labeled with the mixed probes (~20%) was only slightly larger than that labeled by any individual receptor (~15%). Not surprisingly, the signal intensity was significantly enhanced in the mixed probe hybridizations. Similar results were observed in taste buds from other regions of the oral cavity including the fungiform papillae. To directly demonstrate co-expression, double labeling experiments were carried out using a collection of differentially labeled cRNA probes. For double-label fluorescent detection, probes were labeled either with fluorescein or with digoxigenin. An alkaline-phosphatase conjugated anti-fluorescein antibody (Amersham) and a horseradish-peroxidase conjugated anti-digoxigenin antibody were used in combination with fast-red and tyramide fluorogenic substrates (Boehringer Mannheim and New England Nuclear). In these experiments, the majority of cells were found to express multiple receptors.

Example VI

T2R Genes are Selectively Expressed in Gustducin-Expressing Cells

Previous results had shown that T1Rs are expressed in ~30% of taste receptor cells. In situ hybridizations with differentially labeled T1R and T2R probes showed that there is no overlap in the expression of these two classes of receptors. Gustducin is also expressed in a large subset of taste receptor cells, but for the most part is not co-expressed with T1Rs (Hoon et al., *Cell*, 96:541-551 (1999)). To determine if T2Rs are expressed in gustducin cells, in situ hybridizations were performed using differentially labeled T2Rs and gustducin riboprobes. These experiments demonstrated that T2Rs are exclusively expressed in gustducin-positive cells of the tongue and palate taste buds.

Approximately ⅓ of the gustducin cells in the circumvallate, foliate and palate taste buds did not label with a mix of 10 T2R probes, suggesting that not all gustducin-expressing cells express T2Rs. These cells may express other, perhaps more distantly related receptors, or could be at a different developmental stage. In fungiform taste buds the situation is quite different. Since only 10% of fungiform taste buds contain T2R positive cells, the great majority of gustducin-positive cells in the front of the tongue do not appear to co-express members of the T2R family of receptors. Therefore, there is likely to be an additional set of receptors expressed in the gustducin-positive cells of fungiform papillae.

Example VII

Functional Expression of T2Rs

T2Rs were expressed in conjunction with Gα15, a G-protein α-subunit that has been shown to couple a wide range of receptors to phospholipase Cβ (Offermanns and Simon, *J Biol Chem*, 270:15175-80 (1995); Krautwurst et al., *Cell* 95:917-926 (1998)). In this system, receptor activation leads to increases in intracellular calcium [Ca2+]i, which can be monitored at the single cell level using the FURA-2 calcium-indicator dye (Tsien et al., *Cell Calcium* 6:145-157 (1985)). To test and optimize Gα15 coupling, two different GPCRs, a Gαi-coupled μ-opioid receptor (Reisine, *Neuropharm.* 34:463-472 (1995)) and a Gαq-coupled mGluR1 receptor (Masu et al., *Nature* 349:760-765 (1991)), were used. Transfection of these receptors into HEK-293 cell produced robust, agonist-selective, and Gα15-dependent $Ca^{2+}$ responses (FIG. 1).

Figure 2:
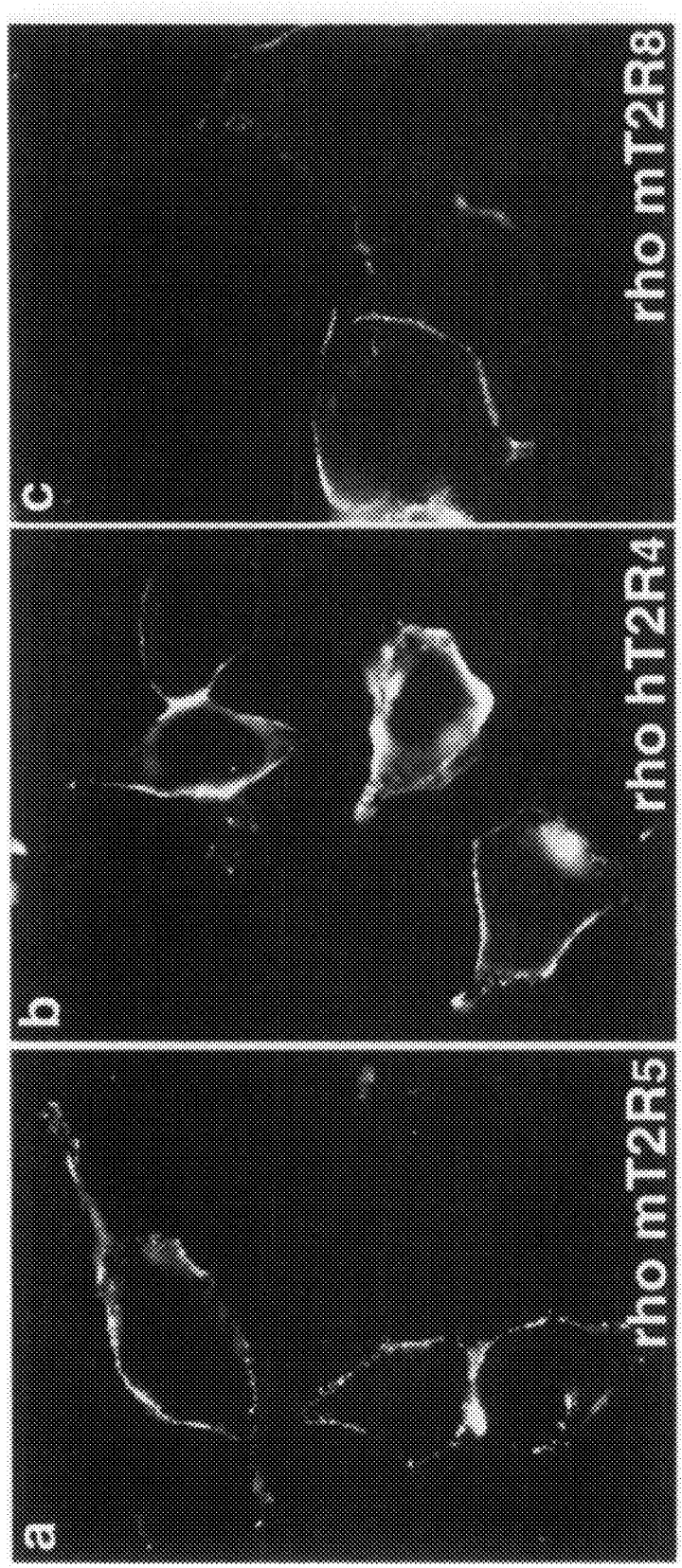
FIG. 2a-2c show that the first 39 amino acids of bovine rhodopsin effectively targets T2Rs to the plasma membrane of HEK-293 cells. Immunofluorescence staining of non-permeabilized cells transfected with representative rho-T2R fusions was detected using an anti-rhodopsin mAb B6-30.

A number of studies have shown that many GPCRs, in particular sensory receptors, require specific "chaperones" for maturation and targeting through the secretory pathway (Baker et al., *Embo J* 13:4886-4895 (1994); Dwyer et al., *Cell* 93:455-466 (1998)). Recently, Krautwurst et al. (*Cell* 95:917-926 (1998)) generated chimeric receptors consisting of the first 20 amino acids of rhodopsin and various rodent olfactory receptors. These were targeted to the plasma membrane and functioned as odorant receptors in HEK-293 cells. To determine whether rhodopsin sequences can also help target T2Rs to the plasma membra, rhodopsin-T2R chimeras (rho-T2Rs) were constructed. Expression of these fusion proteins demonstrated that the first 39 amino acids of bovine rhodopsin are very effective in targeting T2Rs to the plasma membrane of HEK-293 cells (FIG. 2). Similar results were obtained with 11 human and 16 rodent T2Rs (see below). To further enhance the level of T2R expression, rho-T2Rs were placed under the control of a strong EF-1a promoter, and introduced as episomal plasmids into modified HEK-293 cells expressing Gα15 (pEAKrapid cells).

A bridge overlap PCR extension technique was used to generate rho-T2R chimeras, which contain the first 39 amino acids of bovine rhodopsin in frame with human and rodent T2R coding sequences (Mehta and Singh, *Biotechniques* 26:1082-1086 (1999). All receptors were cloned into a pEAK10 mammalian expression vector (Edge Biosystems, MD). Modified HEK-293 cells (PEAK$^{rapid}$ cells; Edge BioSystems, MD) were grown and maintained at 37° C. in UltraCulture medium (Bio Whittaker) supplemented with 5% fetal bovine serum, 100 μg/ml Gentamycin sulphate (Fisher), 1 μg/ml Amphotericin B and 2 mM GlutaMax I (Lifetechnologies). For transfection, cells were seeded onto matrigel coated 24-well culture plates or 35 mm recording chambers. After 24 h at 37° C., cells were washed in OptiMEM medium (Lifetechnologies) and transfected using LipofectAMINE reagent (Lifetechnologies). Transfection efficiencies were estimated by co-transfection of a GFP reporter plasmid, and were typically >70%. Immunofluoresence staining, and activity assays were performed 36-48 h after transfection.

For immunostaining, transfected cells were grown on coated glass coverslips, fixed for 20 min in ice-cold 2% paraformaldehyde, blocked with 1% BSA, and incubated for 4-6 h at 4° C. in blocking buffer containing a 1:1000 dilution of anti-rhodopsin mAb B6-30 (Hargrave, et al. *Exp Eye Res* 42:363-373 (1986)). Chimeric receptor expression was visualized using FITC-coupled donkey anti-mouse secondary antibodies (Jackson Immunochemical).

Two parallel strategies were employed to identify ligands for T2Rs. In one, a random set of human, rat and mouse T2R receptors were selected and individually tested against a collection of 55 bitter and sweet tastants, including (shown with maximum concentrations tested): 5 mM aristolochic acid, 5 mM atropine, 5 mM brucine, 5 mM caffeic acid, 10 mM caffeine, 1 mM chloroquine, 5 mM cycloheximide, 10 mM denatonium benzoate, 5 mM (−) epicatechin, 10 mM L-leucine, 10 mM L-lysine, 10 mM $MgCl_2$, 5 mM naringin, 10 mM nicotine, 2.5 mM papavarine hydrochloride, 3 mM phenyl thiocarbamide, 10 mM 6-n-propyl thiouracil, 1 mM quinacrine, 1 mM quinine hydrochloride, 800 μM raffinose undecaacetate, 3 mM salicin, 5 mM sparteine, 5 mM strychnine nitrate, 3 mM sucrose octaacetate, 2 mM tetraethyl ammonium chloride, 10 mM L-tyrosine, 5 mM yohimbine, 10 mM each of L-glycine, L-alanine, D-tryptophan, L-phenylalanine, L-arginine, sodium saccharin, aspartame, sodium cyclamate, acesulfame K, 150 mM each of sucrose, lactose, maltose, D-glucose, D-fructose, D-galactose, D-sorbitol, 0.1% monellin, 0.1% thaumatin. Additional sweet tastants were 150 μM alitame, 1.8 mM dulcin, 800 μM stevioside, 1.9 mM cyanosusan, 600 μM neohesperidin dihydrochalcone, 10 mM xylitol, 9.7 mM H-Asp-D-Ala-OTMCP, 70 μM N-Dmb-L-Asp-L-Phe-Ome, and 12 μM N-Dmb-L-Asp-D-Val-(S)-α methylbenzylamide. In these assays, functional coupling was assessed based on four criteria: tastant selectivity, temporal specificity, and receptor- and G protein-dependence. The second strategy relied upon data on the genetics of bitter perception in mice to link candidate receptors with specific tastants.

Nearly 30 years ago, it was first reported that various inbred strains of mice differ in their sensitivity to the bitter compound sucrose-octaacetate (Warren and Lewis, *Nature* 227:77-78 (1970)). Subsequently, a number of studies demonstrated that this strain difference was due to allelic variation at a single genetic locus (Soa) (Whitney and Harder, *Behav Genet* 16:559-574 (1986); Capeless et al., *Behav Genet.* 22:655-663 (1992)). These findings were extended to additional loci influencing sensitivity to various bitter tastants, including raffinose undecaacetate (Rua), cycloheximide (Cyx), copper glycinate (Gib), and quinine (Qui) (Lush, *Genet. Res.* 44:151-160 (1984); Lush, *Genet. Res.* 47:117-123 (1986), Lush and Holland, (1988)). Genetic mapping experiments showed that the Soa, Rua, Cyx, Qui and Glb loci are clustered at the distal end of chromosome 6 (Lush and Holland, *Genet. Res.* 52:207-212 (1988); Capeless et al., *Behav Genet.* 22:655-663 (1992)). In view of the above-described localization of various T2R genes to bitter-associated loci in mice, T2R receptors from this array were constructed as corresponding rho-mT2R chimeras and individually transfected into HEK-293 cells expressing the promiscuous Gα15 protein. After loading the cells with FURA-2, responses to sucrose octaacetate, raffinose undecaacetate, copper glycinate, quinine, and cycloheximide were assayed.

Transfected cells were washed once in Hank's balanced salt solution with 1 mM sodium pyruvate and 10 mM HEPES, pH 7.4 (assay buffer), and loaded with 2 μM FURA-2 AM (Molecular Probes) for 1 h at room temperature. The loading solution was removed and cells were incubated in 200 μl of assay buffer for 1 h to allow the cleavage of the AM ester. For most experiments, 24-well tissue culture plates containing cells expressing a single rho-T2R were stimulated with 200 μl of a 2× tastant solution (see next section). [Ca$^{2+}$]i changes were monitored using a Nikon Diaphot 200 microscope equipped with a 10x/0.5 fluor objective with the TILL imaging system (T.I.L.L Photonics GmbH). Acquisition and analysis of the fluorescence images used TILL-Vision software. Generally, [Ca$^{2+}$]i was measured for 80-120 s by sequentially illuminating cells for 200 ms at 340 nm and 380 nm and monitoring the fluorescence emission at 510 nm using a cooled CCD camera. The $F_{340}/F_{380}$ ratio was analyzed to measure [Ca$^{2+}$]i.

Kinetics of activation and deactivation were measured using a bath perfusion system. Cells were seeded onto a 150 μl microperfusion chamber, and test solutions were pressure-ejected with a picospritzer apparatus (General Valve, Inc.). Flow-rate was adjusted to ensure complete exchange of the bath solution within 4-5 s. In the case of mT2R5, the entire camera field was measured since >70% of the cells responded to cycloheximide. For mT2R8 and hT2R4, 100 areas of interest in each were averaged for each experiment.

Figure 3:
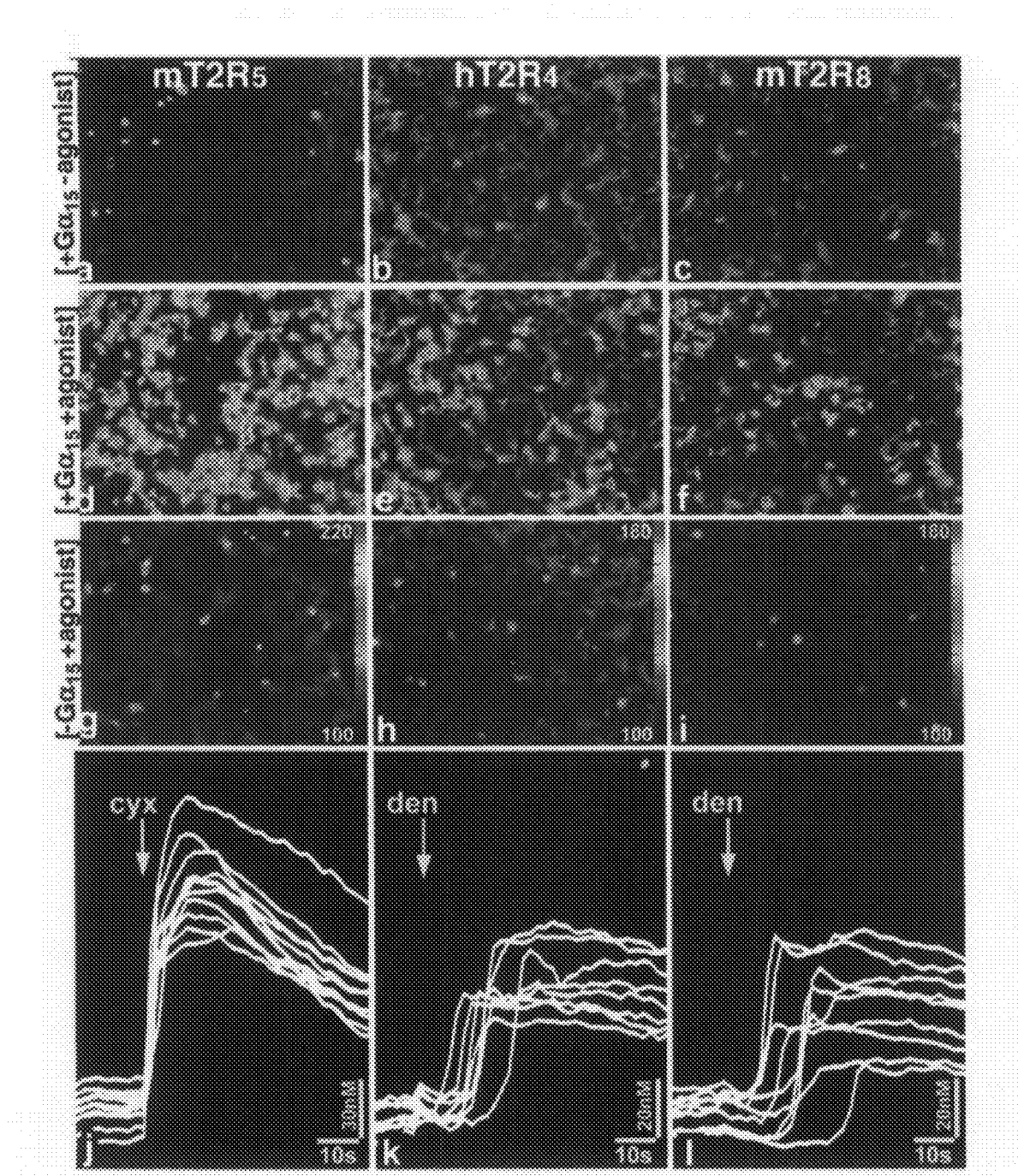
FIG. 3a-3l demonstrate that T2R receptors are stimulated by bitter compounds. HEK-293 cells were transfected with rho-mT2R5 (a, d, g), rho-hT2R4 (b, e, h), and rho-mT2R8 (c, f, i). Cells expressing mT2R5 were stimulated using 1.5 μM cycloheximide (d, g) and those expressing hT2R4 and mT2R8 with 1.5 mM denatonium (e, f, h, i). No increase in [Ca2+]i was observed in the absence of Gα15 (g-i); in contrast robust Gα15 dependent responses were observed in the presence of tastants (d-f); scales indicate [Ca2+]i (nM) determined from FURA-2 emission ratios. Line traces (j-l) show the kinetics of the [Ca2+]i changes for representative cells from nanels (d-f): arrows indicate addition of tastants.
Figure 4:
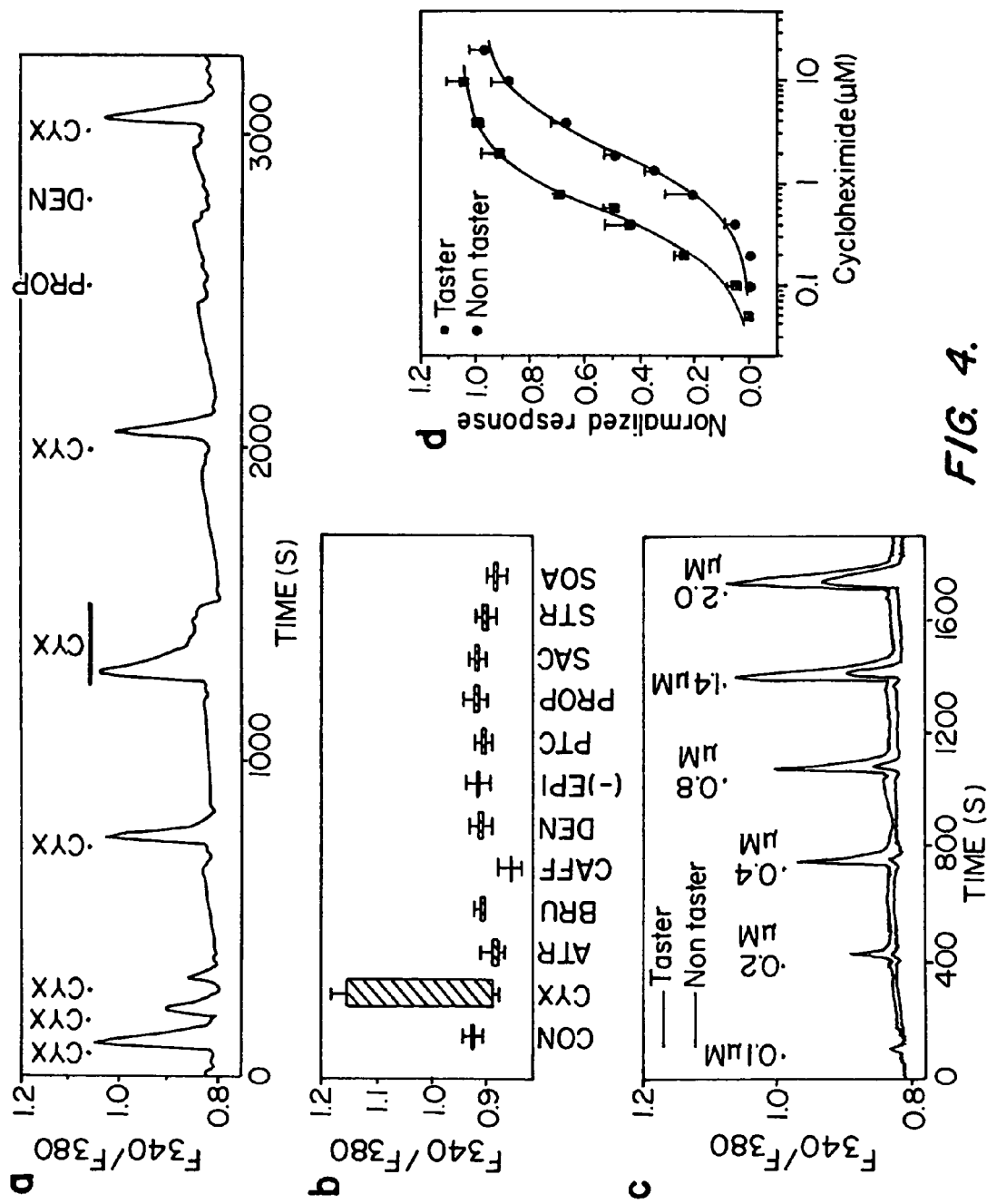
FIG. 4a-4d show that mT2R5 is a taste receptor for cycloheximide. (a) HEK-293 cells expressing Gα15 and rhomT2R5 were challenged with multiple pulses of 2 µM cycloheximide (CYX), 3 mM 6-n-propyl thiouracil (PROP) or 5 mM denatonium (DEN); dots and horizontal bars above the traces indicate the time and duration of tastant pulses. Cycloheximide triggers robust receptor activation. This experiment also illustrates desensitization to repeated stimulation or during sustained application of the stimulus. (b) Responses to cycloheximide are highly specific and are not observed after addition of buffer (CON) or high concentrations of other tastants. Abbreviations and concentrations used are: cycloheximide, CYX (5 µM); atropine, ATR (5 mM); brucine, BRU (5 mM); caffeic acid, CAFF (2 mM); denatonium, DEN (5 mM); epicatechin, (−) EPI (3 mM); phenyl thiocarbamide, PTC (3 mM); 6-n-propyl thiouracil, PROP (10 mM); saccharin, SAC (10 mM); strychnine, STR (5 mM); sucrose octaacetate, SOA (3 mM). Columns represent the mean ±s.e of at least six independent experiments. (c) The mT2R5 gene from taster (DBA/2-allele) and non-taster (C57BL/6-allele) strains mediate differential [Ca2+]i changes to pulses of cycloheximide. Horizontal bars depict the time and duration of the stimulus. 200 s was allowed to elapse between stimuli to ensure that cells were not desensitized due to the successive application of cycloheximide. (d) Cycloheximide dose-response of mT2R5. Changes in [Ca2+]i are shown as FURA-2 (F340/F380) ratios normalized to the response at 30 µM cycloheximide; points represent the mean ±s.e. of at least six determinations. The non-taster allele shows a marked decrease in cycloheximide sensitivity relative to the taster allele (EC50s of ~2.3 µM versus 0.5 µM, respectively).

Cells expressing mT2R5 specifically responded to cycloheximide (FIG. 3). The response occurred in nearly all transfected cells and was receptor- and Gα15-dependent because cells lacking either of these components did not trigger [Ca2+]i changes, even at 5000-fold higher cycloheximide concentration. As expected for this coupling system, the tastant-induced increase in [Ca2+]i was due to release from internal stores, since analogous results were obtained in nominally zero [Ca2+]out. The activation of mT2R5 by cycloheximide is very selective, as this receptor did not respond to any other tastants, even at concentrations that far exceeded their biologically relevant range of action (Saroli, *Naturwissenschaften* 71:428-9 (1984); Glendinning, *Behav Neurosci* 113:840-854 (1994))(FIG. 4a,b). While cycloheximide is only moderately bitter to humans, it is strongly aversive to rodents with a sensitivity threshold of ~0.25 μM (Kusano et al., *Appl. Exptl. Zool.* 6:40-50 (1971); Lush and Holland, *Genet. Res.* 52:207-212 (1988)). In the cell-based assay described herein, the concentration of cycloheximide required to induce half-maximal response of mT2R5 was 0.5 μM, and the threshold was ~0.2 μM (FIG. 4c,d). Notably, this dose-response closely matches the sensitivity range of cycloheximide tasting in mice.

To examine the kinetics of the cycloheximide response, rho-mT2R5 transfected cells were placed on a microperfusion chamber and superfused with test solutions under various conditions. The cells showed robust transient responses to micromolar concentrations of cycloheximide that closely follow application of the stimulus (latency<1 s). As expected, when the tastant was removed, [Ca2+]i returned to baseline. A prolonged exposure to cycloheximide (>10 s) resulted in adaptation: a fast increase of [Ca2+]i followed by a gradual, but incomplete decline to the resting level (FIG. 4a). Similarly, successive applications of cycloheximide led to significantly reduced responses, indicative of desensitization (Lefkowitz et al., *Cold Spring Harb Symp Quant Biol* 57:127-133 (1992)). This is likely to occur at the level of the receptor, since responses of a control, co-transfected mGluR1 were not altered during the period of cycloheximide desensitization.

Figure 5:
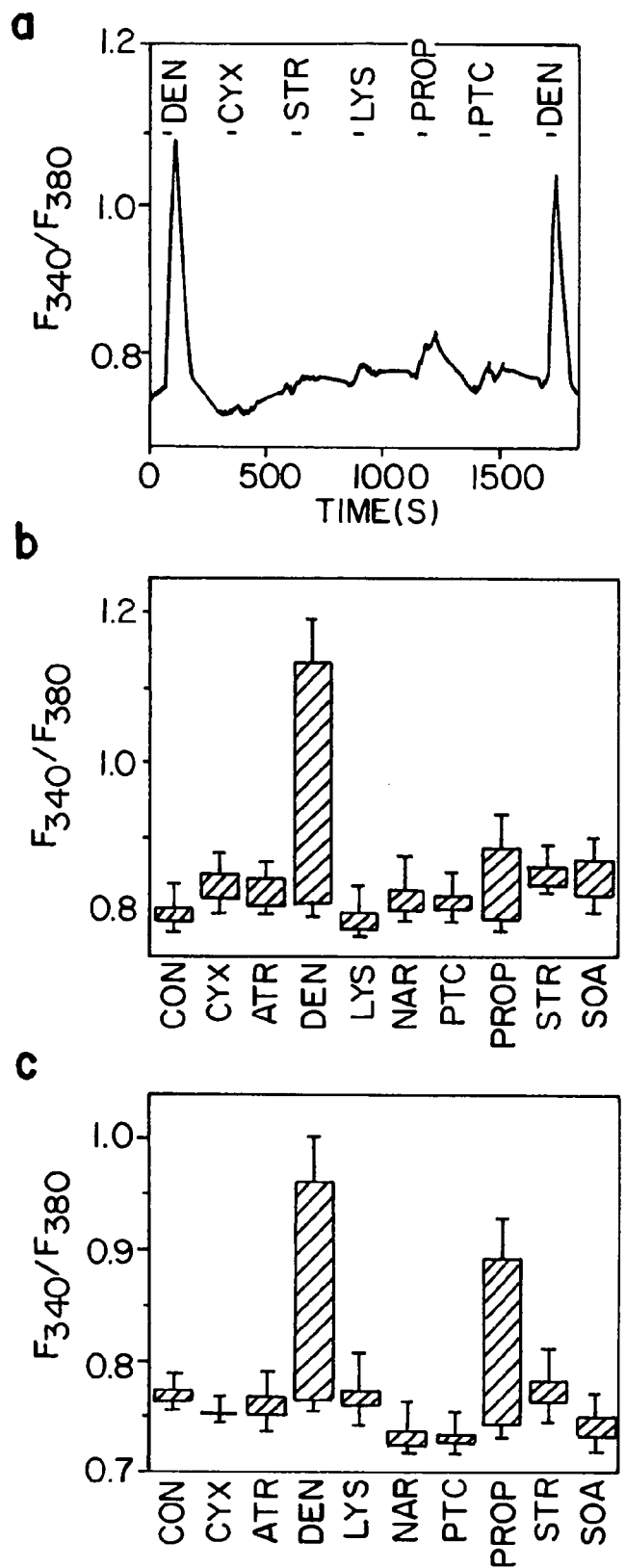
FIG. 5a-5c show that hT2R4 and mT2R8 respond to denatonium. HEK-293 cells expressing Gα15 were transiently transfected with hT2R4 or mT2R8 receptors and [Ca2+]i was monitored as shown in FIG. 3. (a) An increase in [Ca2+]i could be induced by stimulation with denatonium but not by various other bitter compounds. Response profiles of (b) hT2R4 and (c) mT2R8 to a set of nine out of 55 different bitter and sweet tastants (see Experimental Procedures) are shown. CON refers to control buffer addition, NAR to 2 mM naringin and LYS to 5 mM lysine. Other abbreviations and concentrations are as reported in FIG. 4. The mean FURA-2 fluorescence ratio (F340/F380) before and after ligand addition was obtained from 100 equal sized areas that included all responding cells. The values represent the mean ±s.e. of at least 6 experiments.

To determine whether other T2Rs are also activated by bitter compounds, 1 rhodopsin-tagged human T2R receptors were assayed by individually transfecting them into HEK-293 cells expressing Gα15. Each transfected line was tested against a battery of bitter and sweet tastants, including amino acids, peptides, and other natural and synthetic compounds. These experiments demonstrated that the intensely bitter tastant denatonium induced a significant transient increase in [Ca2+]i in cells transfected with one of the human candidate taste receptors, hT2R4, but not in control untransfected cells (FIG. 3), or in cells transfected with other hT2Rs. The denatonium response had a strong dose-dependency with a threshold of ~100 μM. Interestingly, hT2R4 displayed a limited range of promiscuity since it also responded to high concentrations of the bitter tastant 6-n-propyl-2-thiouracil (PROP) (FIG. 5).

If the responses of hT2R4 reflect the in vivo function of this receptor, it was hypothesized that similarly tuned receptors might be found in other species. The mouse receptor mT2R8 is a likely ortholog of hT2R4: they share ~70% identity, while the next closest receptor is only 40% identical; these two genes are contained in homologous genomic intervals. A rho-mT2R8 chimeric receptor was generated and examined for its response to a wide range of tastants. Indeed, mT2R8, like its human counterpart, is activated by denatonium and by high concentrations of PROP (FIGS. 3 and 5). No other tastants elicited significant responses from cells expressing mT2R8. Because these two receptors share only 70% identity, the similarity in their responses to bitter compounds attests to their role as orthologous bitter taste receptors.

Example VIII

Cycloheximide Non-Taster Mice Have Mutations in the mT2R5 Taste Receptor

Figure 6:
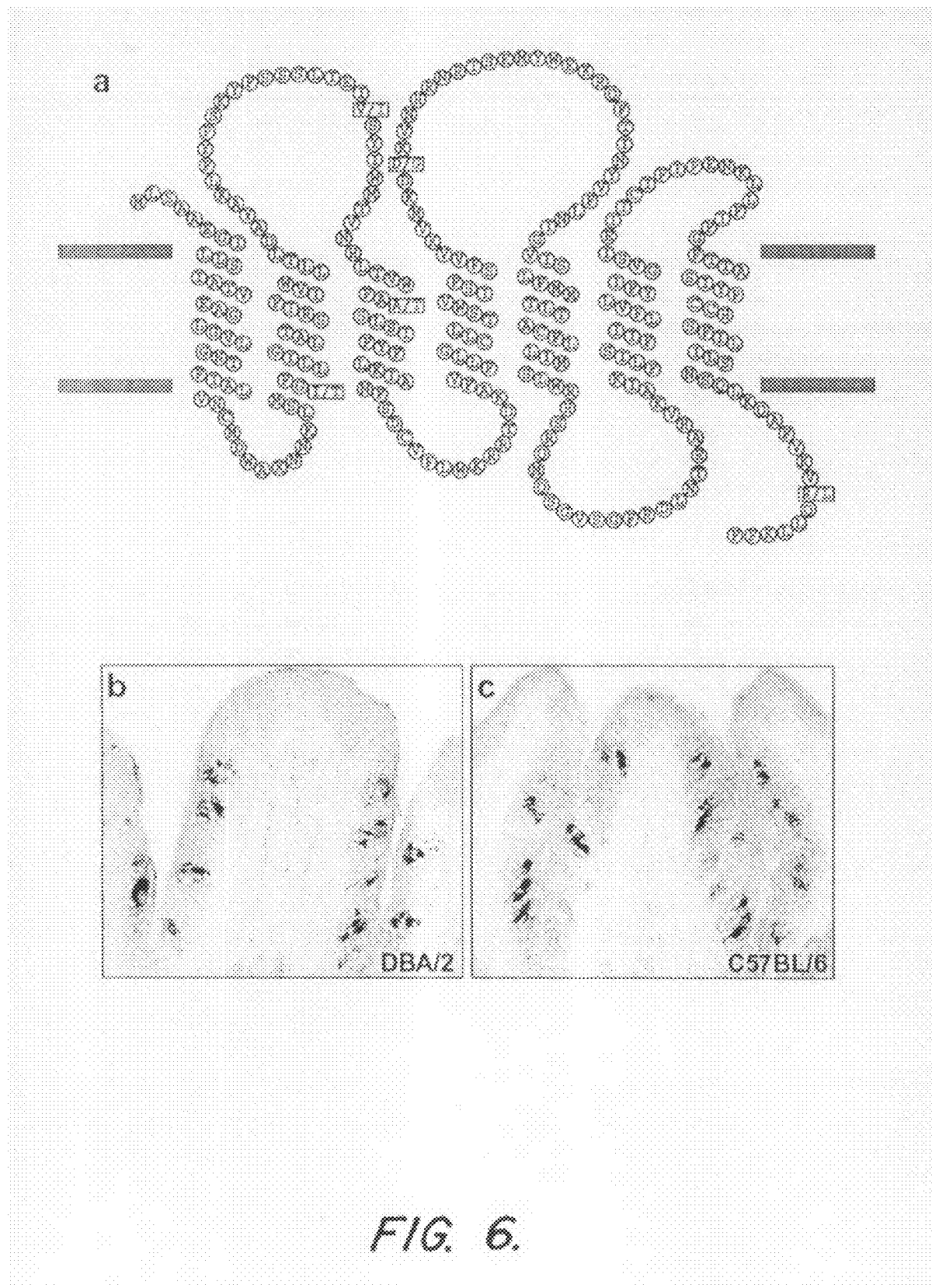
FIG. 6a-6c demonstrate that cycloheximide taster and non-taster strains express different alleles of mT2R5. (a) Predicted transmembrane topology of mT2R5; amino-acid substitutions in the allele from non-taster strains are highlighted in red. The presence of only two alleles at this locus is not unexpected because the strains that share the same polymorphisms were derived from a common founder (Beck et al., Nat Genet. 24:23-55 (2000)). In situ hybridization showing expression of mT2R5 in subsets of cells in the circumvallate papilla of (b) a cycloheximide taster strain (DBA/2) and (c) a non-taster strain (C57BL/6); no strain specific differences in expression pattern were detected in taste buds from other regions of the oral cavity.

The demonstration that mT2R5 functions as a high affinity receptor for cycloheximide suggested that the mT2R5 gene might correspond to the Cyx locus. In situ hybridization to tissue sections demonstrated that the expression profile of mT2R5 is indistinguishable between taster and non-taster strains (FIG. 6). To determine the linkage between mT2R5 and the Cyx locus, polymorphisms in the mT2R5 gene were identified and their distribution in a recombinant inbred panel from a C57BL/6J (non-taster)×DBA/2J (taster) cross was determined. Tight linkage was found between mT2R5 and the Cyx locus. To test the possibility that mutations in the mT2R5 gene were responsible for the Cyx phenotype, the mT2R5 gene was isolated from several additional well-characterized cycloheximide taster (CBA/Ca, BALB/c, C3H/He) and non-taster (129/Sv) strains and their nucleotide sequences determined. Indeed, as would be expected if mT2R5 functions as the cycloheximide receptor in these strains, all the tasters share the same mT2R5 allele as DBA/2J, while the non-tasters share the C57BL/6 allele, which carries missense mutations (FIG. 6), including 3 non-conservative amino acid substitutions (T44I, G155D and L294R).

If the mT2R5 C57BL/6 allele is responsible for the taste deficiency of Cyx mutants, its cycloheximide dose-response might recapitulate the sensitivity shift seen in Cyx mutant strains. Two-bottle preference tests have shown that Cyx taster strains avoid cycloheximide with a threshold of 0.25 μM, while non-tasters have a ~8-fold decrease in sensitivity (e.g. they, are non-tasters at 1 μM, but strongly avoid cycloheximide at 8 μM). A rho-mT2R5 fusion was constructed with the mT2R5 gene from a non-taster strain, and its dose response compared with that of the receptor from taster strains. Remarkably, mT2R5 from the non-taster strains displays a shift in cycloheximide sensitivity (FIG. 4d) that resembles the sensitivity of these strains to this bitter tastant.

Taken together, these results validate mT2R5 as a cycloheximide receptor, and strongly suggest that mT2R5 corresponds to the Cyx locus.

Example IX

T2Rs Couple to Gustducin

The above-described demonstration that T2Rs are co-expressed with gustducin suggests that T2Rs activate this G-protein in response to bitter tastants. To investigate the selectivity of T2R—G-protein coupling, mT2R5 was chosen for study because its activation by cycloheximide recapitulates mouse taste responses. Rho-tagged mT2R5 and gustducin were prepared using a baculovirus expression system. mT2R5-containing membranes were incubated with various purified G-proteins, including gustducin, and measured tastant-induced GTP-γS binding (Hoon et al., *Biochem J* 309: 629-636 (1995)). Specifically, infectious Bacmid containing rhodopsin tagged mT2R5 (DBA/2-allele) was produced using the Bac-to-Bac system (Lifetechnologies, MD). Insect larval cells were infected for 60 h with recombinant Bacmid and membranes were prepared as described previously (Ryba and Tirindelli, *J Biol Chem*, 270:6757-6767 (1995)). Peripheral proteins were removed by treatment with 8 M urea and membranes were resuspended in 10 mM HEPES pH7.5, 1 mM EDTA and 1 mM DTT. The expression of rho-mT2R5 was assessed by Western blot using mAb B6-30 and quantitated by comparison with known amounts of rhodopsin. Approximately 300 pmol of rho-mT2R5 could be obtained from $2\times10^8$ infected cells. Gustducin and $G\beta_1\gamma_8$ heterodimers were isolated as described previously (Hoon et al., *Biochem J* 309:629-636 (1995); Ryba and Tirindelli, *J Biol Chem*, 270: 6757-6767 (1995)). Receptor-catalyzed exchange of GDP for GTPγS on gustducin and other G-protein α-subunits was measured in the presence of 10 nM rho-mT2R5, 100 μM GDP, and 20 μM $G\beta_1\gamma_8$. All measurements were made at 15-minute time points, and reflect the initial rate of GTPγS binding.

Figure 7:
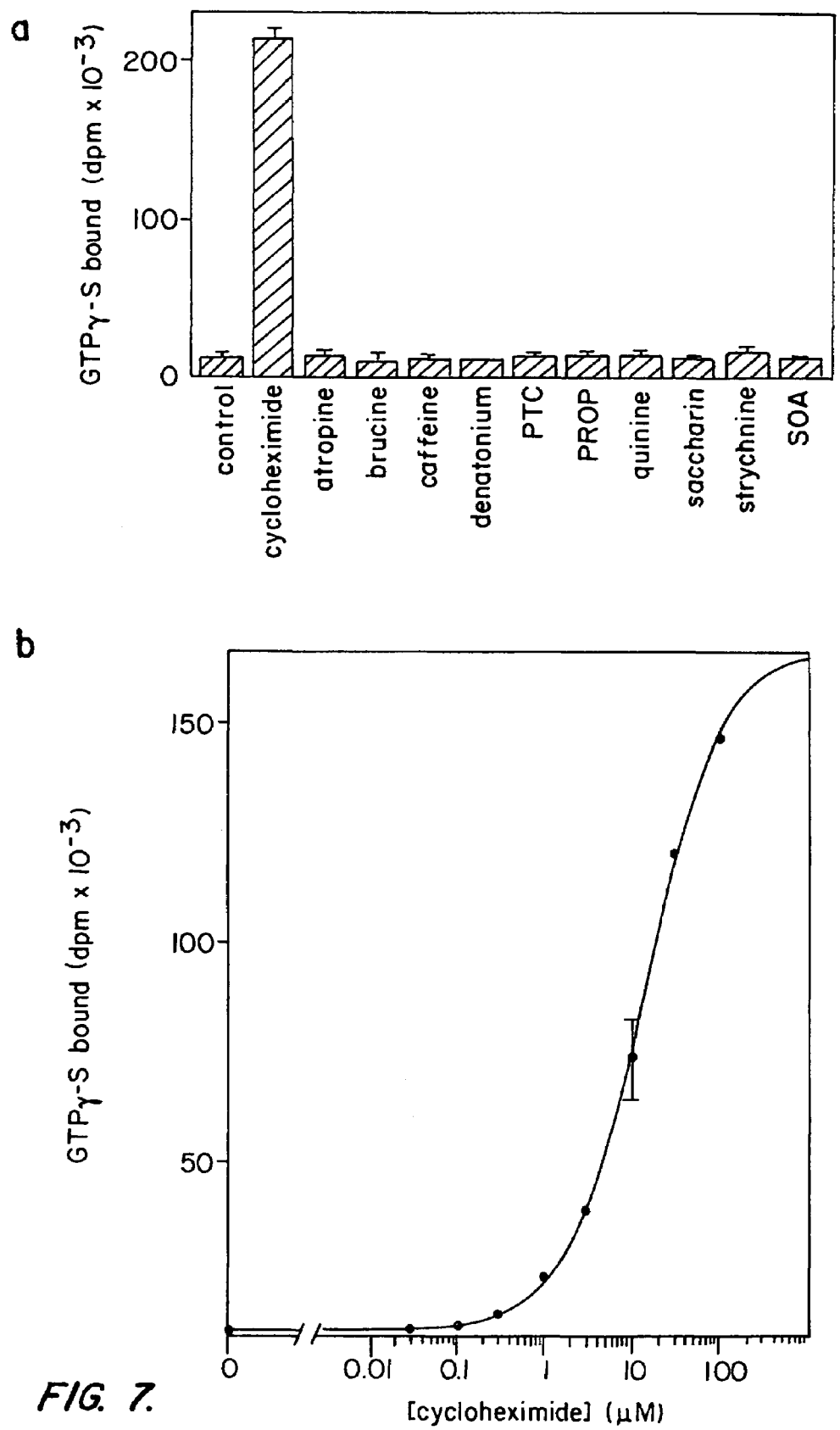
FIG. 7a-7b show that mT2R5 activates gustducin in response to cycloheximide. (a) Insect larval cell membranes containing mT2R5 activate gustducin in the presence 300 µM cycloheximide but not without ligand (control) or in the presence of 1 mM atropine, brucine, caffeine, denatonium, phenylthiocarbamide, 6-n-propyl thiouracil, quinine, saccharin, strychnine, sucrose octaacetate. (b) Cycloheximide concentration dependence of gustducin activation by mT2R5 was fitted by single-site binding (Kd=14.8+0.9 µM).

These GTP-γS binding assays revealed exquisite cycloheximide-dependent coupling of mT2R5 to gustducin (FIG. 7). In contrast, no coupling was seen with Gαs, Gαi, Gαq or Gαo. No significant GTPγS binding was observed in the absence of receptor, gustducin or βγ-heterodimers. The high selectivity of T2R5 for gustducin, and the exclusive expression of T2Rs in taste receptor cells that contain gustducin, affirm the hypothesis that T2Rs function as gustducin-linked taste receptors.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

---

What is claimed is:

1. A method for identifying a compound that modulates taste signaling in taste cells, the method comprising the steps of:
   (i) contacting a taste transduction G-protein coupled receptor polypeptide with the compound, the polypeptide comprising greater than 90% amino acid sequence identity to SEQ ID NO:7, wherein said polypeptide specifically binds to ligands that specifically bind to an endogenous G-protein coupled receptor having the sequence of SEQ ID NO:7; and
   (ii) determining the functional effect of the compound upon the polypeptide, thereby identifying a compound that modulates taste signaling in taste cells.

2. The method of claim 1, wherein the polypeptide has G-protein coupled receptor activity.

3. The method of claim 1, wherein the functional effect is a physical effect.

4. The method of claim 1, wherein the functional effect is determined by measuring binding of radiolabeled GTP to the polypeptide.

5. The method of claim 1, wherein the polypeptide is recombinant.

6. The method of claim 1, wherein the polypeptide is from a rat, a mouse, or a human.

7. The method of claim 1, wherein the polypeptide is expressed in a cell or cell membrane.

8. The method of claim 7, wherein the functional effect is measured by determining changes in the electrical activity of a cell expressing the polypeptide.

9. The method of claim 7, wherein the functional effect is determined by measuring changes in intracellular cAMP, cGMP, IP3, or $Ca^{2+}$.

10. The method of claim 9, wherein a change in intracellular $Ca^{2+}$ is detected by detecting a change in FURA-2 dependent fluorescence in the cell.

11. The method of claim 7, wherein the cell is a eukaryotic cell.

12. The method of claim 11, wherein the cell is an HEK-293 cell.

13. The method of claim 7, wherein the polypeptide is a fusion protein comprising at least about 20 consecutive N-terminal amino acids of a rhodopsin protein.

14. The method of claim 13, wherein the rhodopsin protein is a bovine rhodopsin.

15. The method of claim 7, wherein the cell comprises Gα15.

16. The method of claim 7, wherein the polypeptide is contacted with the compound in the presence of a bitter tastant, and wherein a difference in the functional effect of the bitter tastant on the cell in the presence of the compound and the functional effect of the bitter tastant on the cell in the absence of the compound indicates that the compound is capable of modulating taste signaling in taste cells.

17. The method of claim 1, wherein the polypeptide comprises the amino acid sequence of SEQ ID NO:7.

18. The method of claim 1, wherein the polypeptide is covalently linked to a heterologous polypeptide, forming a chimeric polypeptide.

19. The method of claim 18, wherein the polypeptide is linked to a solid phase.

20. The method of claim 19, wherein the polypeptide is covalently linked to a solid phase.

21. The method of claim 1, wherein said polypeptide comprises a sequence with at least 95% identity to SEQ ID NO:7.

* * * * *